United States Patent
Castro et al.

(10) Patent No.: US 11,608,329 B2
(45) Date of Patent: Mar. 21, 2023

(54) ARYL HYDROCARBON RECEPTOR (AHR) AGONISTS AND USES THEREOF

(71) Applicant: Ikena Oncology, Inc., Boston, MA (US)

(72) Inventors: Alfredo C. Castro, Somerville, MA (US); Karen J. McGovern, Groton, MA (US); Michael Burke, Melrose, MA (US)

(73) Assignee: IKENA ONCOLOGY, INC., Boston, MA (US)

( * ) Notice: Subject to any disclaimer, the term of this patent is extended or adjusted under 35 U.S.C. 154(b) by 0 days.

(21) Appl. No.: 17/126,279

(22) Filed: Dec. 18, 2020

(65) Prior Publication Data
US 2021/0230153 A1    Jul. 29, 2021

Related U.S. Application Data

(60) Provisional application No. 62/951,089, filed on Dec. 20, 2019, provisional application No. 63/122,075, filed on Dec. 7, 2020.

(51) Int. Cl.
| | | |
|---|---|---|
| *C07D 277/42* | (2006.01) | |
| *C07D 417/04* | (2006.01) | |
| *A61P 1/00* | (2006.01) | |
| *A61P 29/00* | (2006.01) | |
| *C07D 235/00* | (2006.01) | |
| *C07D 249/14* | (2006.01) | |
| *C07D 263/48* | (2006.01) | |
| *C07D 271/07* | (2006.01) | |
| *C07D 271/113* | (2006.01) | |
| *C07D 277/48* | (2006.01) | |
| *C07D 285/135* | (2006.01) | |
| *C07D 333/36* | (2006.01) | |
| *C07D 417/12* | (2006.01) | |

(52) U.S. Cl.
CPC ............ *C07D 417/04* (2013.01); *A61P 1/00* (2018.01); *A61P 29/00* (2018.01); *C07D 235/00* (2013.01); *C07D 249/14* (2013.01); *C07D 263/48* (2013.01); *C07D 271/07* (2013.01); *C07D 271/113* (2013.01); *C07D 277/42* (2013.01); *C07D 277/48* (2013.01); *C07D 285/135* (2013.01); *C07D 333/36* (2013.01); *C07D 417/12* (2013.01)

(58) Field of Classification Search
CPC ................................................. C07D 277/42
See application file for complete search history.

(56) References Cited

U.S. PATENT DOCUMENTS

| | | | |
|---|---|---|---|
| 7,244,739 B2 * | 7/2007 | Cheng | ..................... A61P 43/00 548/255 |
| 7,419,992 B2 | 9/2008 | DeLuca et al. | |
| 8,604,067 B2 | 12/2013 | Song | |
| 2014/0343051 A1 | 11/2014 | Sauvageau et al. | |

FOREIGN PATENT DOCUMENTS

| | | | | |
|---|---|---|---|---|
| KR | 20080109206 A | 12/2008 | | |
| KR | 20110116488 A | 10/2011 | | |
| WO | WO-99/32466 A1 * | 7/1999 | .......... | C07D 277/42 |
| WO | 2001064674 A1 | 9/2001 | | |
| WO | WO-01/74793 A2 * | 10/2001 | .......... | C07D 277/00 |
| WO | 2003063871 A1 | 8/2003 | | |
| WO | 2016040553 A1 | 3/2016 | | |
| WO | 2018121434 A1 | 7/2018 | | |
| WO | 2018218143 A1 | 11/2018 | | |
| WO | 2019099977 A2 | 5/2019 | | |
| WO | 2021127301 A1 | 6/2021 | | |

OTHER PUBLICATIONS

Chemical Abstracts Registry No. 515867-95-5, indexed in the Registry file on STN CAS Online May 15, 2003. (Year: 2003).*
Pesce et al., European Journal of Medicinal Chemistry (2015), 99, pp. 14-35. (Year: 2015).*
Chemical Abstracts 708996-12-7, indexed in the Registry file on STN CAS Online Jul. 13, 2004. (Year: 2004).*
Chemical Abstracts 1170626-88-6 {indexed in the Registry file on STN CAS Online Jul. 30, 2009. (Year: 2009).*
Baek et al., "Inhibitory Effect of 4-Aryl 2-Substituted Aniline-Thiazole Analogs on Growth of Human Prostate Cancer LNCap Cells," Bulletin of the Korean Chemical Society 2012; 33(1):111-114.
Berge, et al., "Pharmaceutical salts," J Pharm Sci. 1977; 66(1):1-19.
Cheng, et al., "Tryptophan derivatives regulate the transcription of Oct4 in stem-like cancer cells," Nat Commun. 2015;6:7209.
Nugent et al., "ITE, a novel endogenous nontoxic aryl hydrocarbon receptor ligand, efficiently suppresses EAU and T-cell-mediated immunity," Invest Ophthalmol Vis Sci. 2013; 54(12):7463-9.
PCT International Search Report for PCT Application No. PCT/US2020/065785, mailed by the European Patent Office dated Jun. 2, 2021, 9 Pages.
Quintana et al., "An endogenous aryl hydrocarbon receptor ligand acts on dendritic cells and T cells to suppress experimental autoimmune encephalomyelitis," PNAS. 2010; 107(48):20768-20773.
Rothhammer et al., "The aryl hydrocarbon receptor: an environmental sensor integrating immune responses in health and disease," Nat Rev Immunol. 2019; 19(3):194-197.
Lamas et al., "Caspase recruitment domain 9, microbiota, and tryptophan metabolism: dangerous liaisons in inflammatory bowel diseases," Curr Opin Clin Nutr Metab Care. 2017;20(4):243-247.
Metidji et al., "The Environmental Sensor AHR Protects from Inflammatory Damage by Maintaining Intestinal Stem Cell Homeostasis and Barrier Integrity," Immunity. 2018;49(2):353-362.

(Continued)

*Primary Examiner* — Laura L Stockton
(74) *Attorney, Agent, or Firm* — Dechert LLP; Andrea L. C. Reid; Gang Wang

(57) ABSTRACT

The present invention provides AHR agonists, compositions thereof, and methods of using the same.

20 Claims, 21 Drawing Sheets

(56) References Cited

OTHER PUBLICATIONS

Muku, et al., "Activation of the Ah Receptor Modulates Gastrointestinal Homeostasis and the Intestinal Microbiome," Curr Pharmacol Rep 5. 2019;319-331.
Gutiérrez-Vázquez et al., "Regulation of the Immune Response by the Aryl Hydrocarbon Receptor," Immunity. 2018; 48(1):19-33.

* cited by examiner

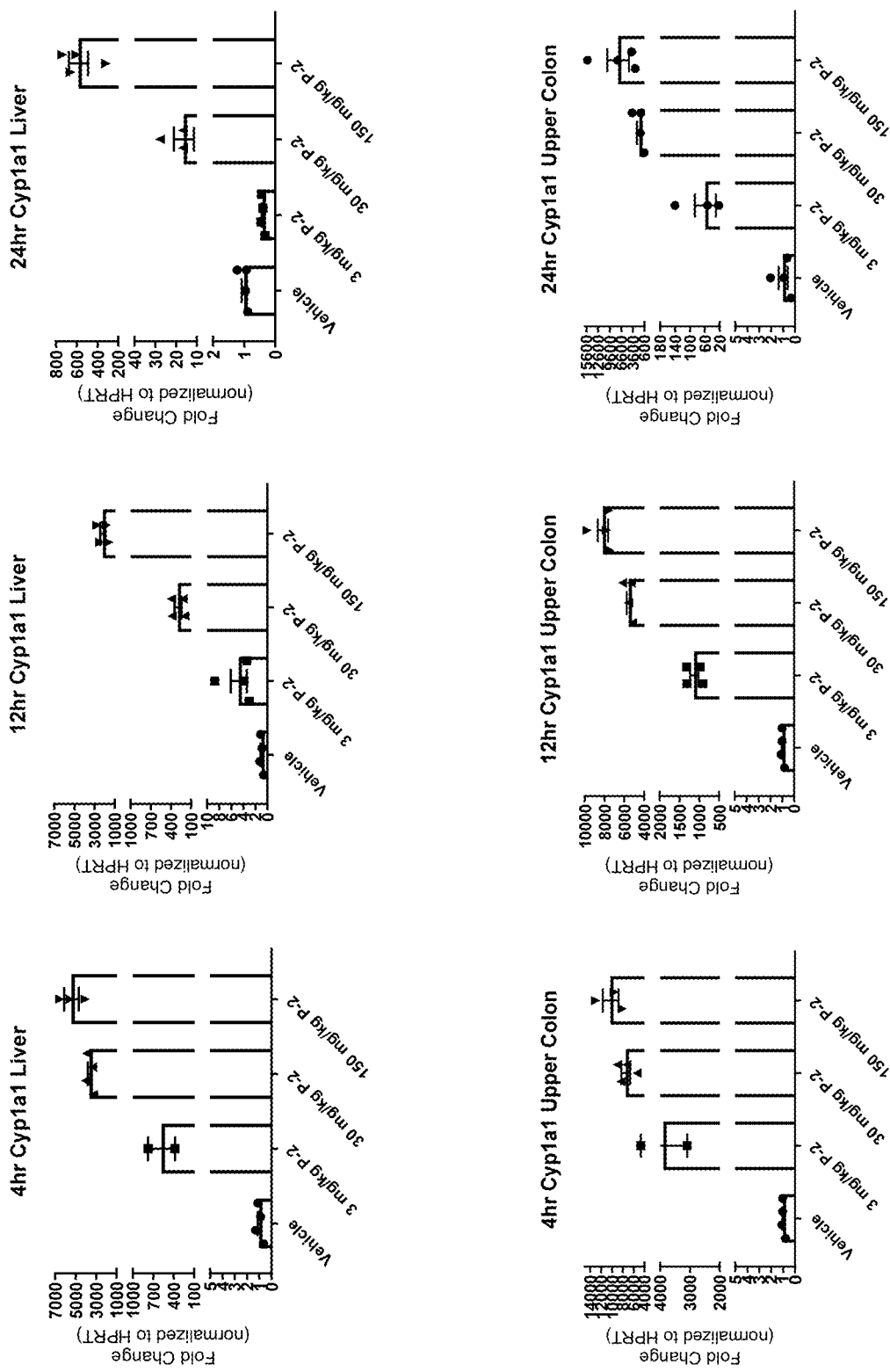
Figure 1 (contd.)

ARYL HYDROCARBON RECEPTOR (AHR) AGONISTS AND USES THEREOF

CROSS-REFERENCE TO RELATED APPLICATIONS

This application claims the benefit under 35 U.S.C. § 119(e) of U.S. Provisional Patent Application No. 62/951,089, filed Dec. 20, 2019, and U.S. Provisional Patent Application No. 63/122,075, filed Dec. 7, 2020, the contents of each of which are herein incorporated by reference in their entireties.

TECHNICAL FIELD OF THE INVENTION

The present invention relates to compounds and methods useful for activating aryl hydrocarbon receptor (AHR). The invention also provides pharmaceutically acceptable compositions comprising compounds of the present invention and methods of using said compositions in the treatment of various disorders.

BACKGROUND

The aryl hydrocarbon receptor (AHR) is a ligand-inducible transcription factor that mediates a number of important biological and pharmacological processes. AHR agonists have been shown to be potentially useful for treating disorders such as cancer (U.S. Pat. No. 8,604,067, Wang et al., 2013, Cheng et al., 2015), obesity (U.S. Pat. No. 7,419,992), and conditions related to imbalanced actions of the immune system (Quintana et al., 2010, Nugent et al., 2013). AHR has also been shown to be involved in immune regulation, hematopoiesis, cell cycle, carcinogenesis and in the maintenance of intestinal barrier integrity and homeostasis.

SUMMARY OF THE INVENTION

It has now been found that compounds of the present invention, and pharmaceutically acceptable compositions thereof, are effective as AHR agonists. In one aspect, the instant invention provides a compound of formula (I):

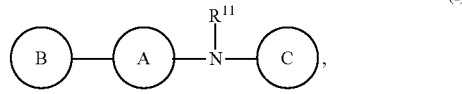

(I)

or a pharmaceutically acceptable salt thereof, wherein each variable is as defined and described herein.

Compounds of the present invention, and pharmaceutically acceptable compositions thereof, are useful for treating a variety of diseases, disorders or conditions, associated with AHR. Such diseases, disorders, or conditions include, for example, cancer, obesity, and inflammatory disorders as described herein.

BRIEF DESCRIPTION OF THE DRAWINGS

FIG. 18A. I-161 results in similar body weight changes and recovery as administration of Cyclosporine A (CSA, positive control) in a DSS model of IBD. FIG. 18B. I-161 demonstrates activity at all doses that is comparable or better than CSA, and histopathology data shows activity comparable to CSA as well.

DETAILED DESCRIPTION OF CERTAIN EMBODIMENTS

Figure 1:
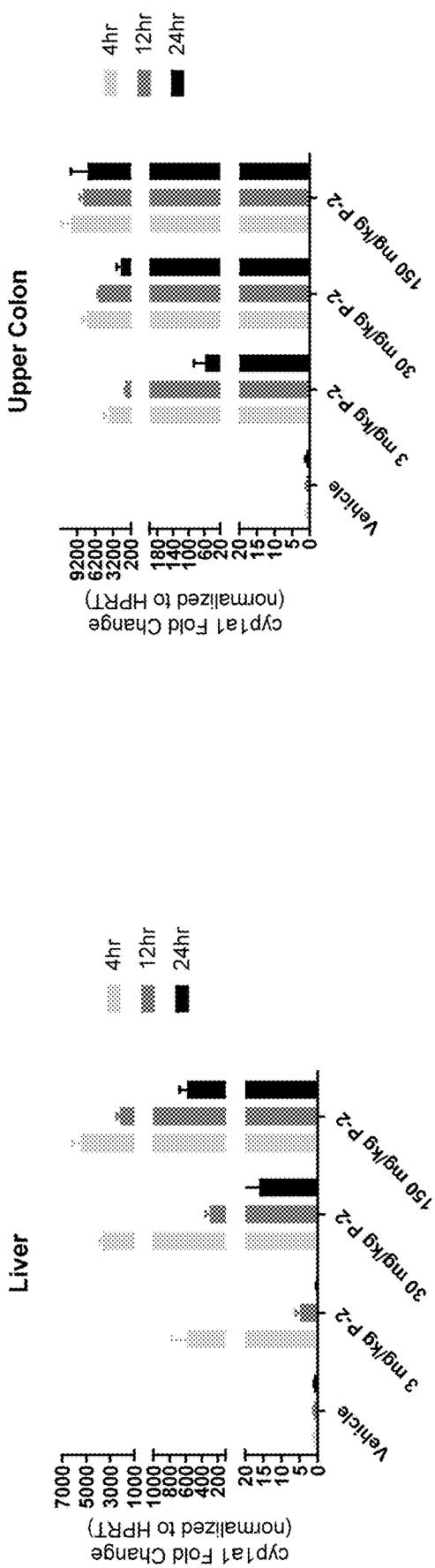
FIG. 1 depicts exemplary pharmacodynamic (PD) data in the liver and colon for AHR agonist compound P-2 at 4 hours, 12 hours, and 24 hours.

1. General Description of Certain Embodiments of the Invention

Compounds of the present invention, and pharmaceutical compositions thereof, are useful as AHR agonists. Without wishing to be bound by any particular theory, it is believed that compounds of the present invention, and pharmaceutical compositions thereof, may activate AHR and thus treat certain diseases, disorders, or conditions associated with AHR, such as those described herein.

It has now been found that compounds of this invention, and pharmaceutically acceptable compositions thereof, are effective as AHR agonists. In one aspect, the present invention provides a compound of Formula (I):

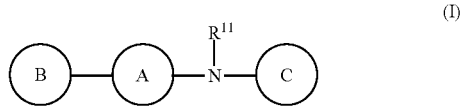

(I)

or a pharmaceutically acceptable salt thereof, wherein:

Ring A is an optionally substituted 5-membered heteroaromatic ring having 1-3 heteroatoms independently selected from N, O, or S;

Ring B is an optionally substituted ring selected from phenyl, a 6-membered heteroaromatic ring having 1-3 N, a 8-10 membered bicyclic aromatic ring, and a 8-10 membered bicyclic heteroaromatic ring having 1-5 heteroatoms independently selected from N, O, or S;

Ring C is optionally substituted phenyl or 6-membered heteroaromatic ring having 1-3 N;

$R^{11}$ is —R, —C(O)—$R^W$, —C(=N$R^W$)—$R^W$, —S(O)$_2$—$R^W$, or —S(O)—$R^W$;

$R^W$ is —R, —N(R)$_2$, —NR—OR, —N(R)—N(R)$_2$, —N(OR)—N(R)$_2$, —N(R)—N(OR)R, —OR, —O—N(R)$_2$, or —SR; and R is hydrogen, optionally substituted $C_{1-6}$ aliphatic, an optionally substituted 3-7 membered carbocyclic ring, or an optionally substituted 3-7 membered heterocyclic ring having 1-3 heteroatoms independently selected from N, O, or S, or two R's together with the nitrogen to which they attach form an optionally substituted 5-7 membered heterocyclic ring having 0-2 heteroatoms independently selected from N, O, or S in addition to the nitrogen to which the two R's attach.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bicyclic ring" or "bicyclic ring system" refers to any bicyclic ring system, i.e. carbocyclic or heterocyclic, saturated or having one or more units of unsaturation, having one or more atoms in common between the two rings of the ring system. Thus, the term includes any permissible ring fusion, such as ortho-fused or spirocyclic. As used herein, the term "heterobicyclic" is a subset of "bicyclic" that requires that one or more heteroatoms are present in one or both rings of the bicycle. Such heteroatoms may be present at ring junctions and are optionally substituted, and may be selected from nitrogen (including N-oxides), oxygen, sulfur (including oxidized forms such as sulfones and sulfonates), phosphorus (including oxidized forms such as phosphates), boron, etc. In some embodiments, a bicyclic group has 7-12 ring members and 0-4 heteroatoms independently selected from nitrogen, oxygen, or sulfur. As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur.

Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bicyclic rings include:

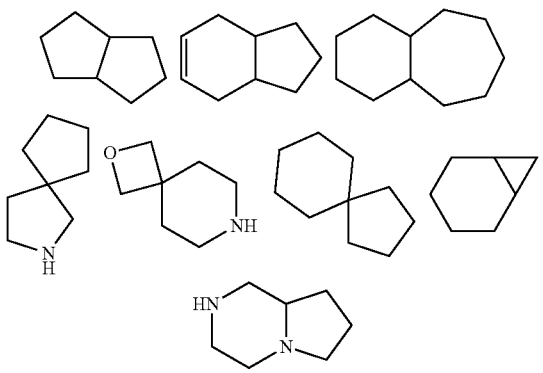

Exemplary bridged bicyclics include:

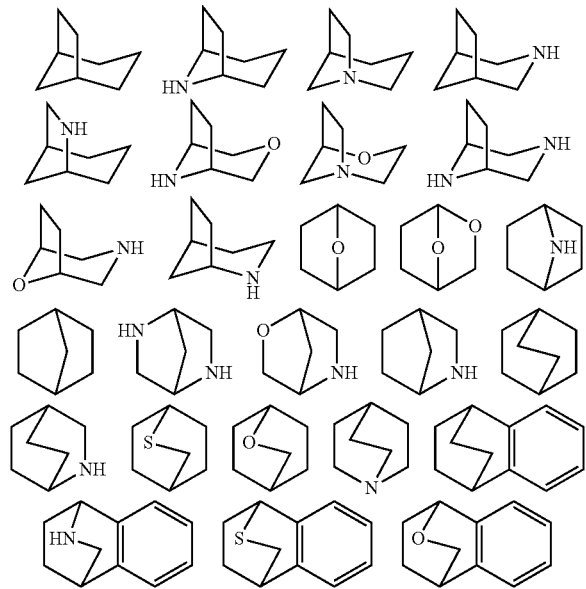

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

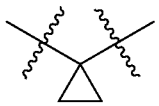

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more nonaromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Each optional substituent on a substitutable carbon is a monovalent substituent independently selected from halogen; —$(CH_2)_{0-4}R^\circ$; —$(CH_2)_{0-4}OR^\circ$; —$O(CH_2)_{0-4}R^\circ$, —O—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —CH=CHPh, which may be substituted with $R^\circ$; —$(CH_2)_{0-4}O(CH_2)_{0-1}$-pyridyl which may be substituted with $R^\circ$; —$NO_2$; —CN; —$N_3$; —$(CH_2)_{0-4}N(R^\circ)_2$; —$(CH_2)_{0-4}N(R^\circ)C(O)R^\circ$; —$(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR$—, $SC(S)SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —$SC(S)SR^\circ$, —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; $(CH_2)_{0-4}S(O)_{20}R^\circ$; —$(CH_2)_{0-4}OS(O)_2R^\circ$; —$S(O)_2NR^\circ_2$; —$S(O)(NR^\circ)R^\circ$; —$S(O)_2N=C(NR^\circ_2)_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; —$OP(O)(OR^\circ)_2$; $SiR^\circ_3$; —$(C_{1-4}$ straight or branched alkylene)O—$N(R^\circ)_2$; or —$(C_{1-4}$ straight or branched alkylene)C)(O)O—$N(R^\circ)_2$.

Each $R^\circ$ is independently hydrogen, $C_{1-6}$ aliphatic, —$CH_2Ph$, —$O(CH_2)_{0-1}Ph$, —$CH_2$—(5-6 membered heteroaryl ring), or a 5-6 membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12 membered saturated, partially unsaturated, or aryl mono- or bicyclic ring having 0-4 heteroatoms independently selected from nitrogen, oxygen, or sulfur, which may be substituted by a divalent substituent on a saturated carbon atom of $R^\circ$ selected from =O and =S; or each $R^\circ$ is optionally substituted with a monovalent substituent independently selected from halogen, —$(CH_2)_{0-2}R^\bullet$, -(haloR$^\bullet$), —$(CH_2)_{0-2}$OH, —$(CH_2)_{0-2}OR^\bullet$, —$(CH_2)_{0-2}CH(OR^\bullet)_2$; —O(haloR$^\bullet$), —CN, —$N_3$, —$(CH_2)_{0-2}C(O)R^\bullet$, —$(CH_2)_{0-2}C(O)OH$, —$(CH_2)_{0-2}C(O)OR^\bullet$, —$(CH_2)_{0-2}SR^\bullet$, —$(CH_2)_{0-2}SH$, —$(CH_2)_{0-2}NH_2$, —$(CH_2)_{0-2}NHR^\bullet$, —$(CH_2)_{0-2}NR^\bullet_2$, —$NO_2$, —$SiR^\bullet_3$, —$OSiR^\bullet_3$, —$C(O)SR^\bullet$, $C_{1-4}$ straight or branched alkylene)C(O)OR$^\bullet$, or —SSR$^\bullet$.

Each R$^\bullet$ is independently selected from $C_{1-4}$ aliphatic, —$CH_2Ph$, —$O(CH_2)_{0-1}Ph$, or a 5-6 membered saturated, partially unsaturated, or aryl ring having 0-4 heteroatoms independently selected from nitrogen, oxygen, or sulfur, and wherein each R$^\bullet$ is unsubstituted or where preceded by halo is substituted only with one or more halogens; or wherein an optional substituent on a saturated carbon is a divalent substituent independently selected from =O, =S, =NNR*$_2$, =NNHC(O)R*, =NNHC(O)PR*, =NNHS(O)$_2$R*, =NR*, =NOR*, —O(C(R*$_2$))$_{2-3}$O—, or —S(C(R*$_2$))$_{2-3}$S—, or a divalent substituent bound to vicinal substitutable carbons of an "optionally substituted" group is —O(CR*$_2$)$_{2-3}$O—, wherein each independent occurrence of R* is selected from hydrogen, $C_{1-6}$ aliphatic or an unsubstituted 5-6 membered saturated, partially unsaturated, or aryl ring having 0-4 heteroatoms independently selected from nitrogen, oxygen, or sulfur.

When R* is $C_{1-6}$ aliphatic, R* is optionally substituted with halogen, —R$^\bullet$, -(haloR$^\bullet$), —OH, OR$^\bullet$, —OR(haloR$^\bullet$), —CN, —C(O)OH, —C(O)OR˙, —NH₂, —NHR˙, —NR˙₂, or —NO₂, wherein each R˙ is independently selected from C₁₋₄ aliphatic, —CH₂Ph, —O(CH₂)₀₋₁Ph, or a 5-6 membered saturated, partially unsaturated, or aryl ring having 0-4 heteroatoms independently selected from nitrogen, oxygen, or sulfur, and wherein each R˙ is unsubstituted or where preceded by halo is substituted only with one or more halogens.

An optional substituent on a substitutable nitrogen is independently R†, —NR†₂, —C(O)R†, —C(O)OR†, —C(O)C(O)R†, —C(O)CH₂C(O)R†, —S(O)₂R†, —S(O)₂NR†₂, —C(S)NR†₂, —C(NH)NR†₂, or N(R†)S(O)₂R†; wherein each R† is independently hydrogen, C₁₋₆ aliphatic, unsubstituted —OPh, or an unsubstituted 5-6 membered saturated, partially unsaturated, or aryl ring having 0-4 heteroatoms independently selected from nitrogen, oxygen, or sulfur, or, two independent occurrences of R†, taken together with their intervening atom(s) form an unsubstituted 3-12 membered saturated, partially unsaturated, or aryl mono or bicyclic ring having 0-4 heteroatoms independently selected from nitrogen, oxygen, or sulfur; wherein when R† is C₁₋₆ aliphatic, R† is optionally substituted with halogen, R˙, -(haloR˙), —OH, —OR˙, —O(haloR˙), —CN, —C(O)OH, —C(O)OR˙, NH₂, NHR˙, NR˙₂, or —NO₂, wherein each R˙ is independently selected from C₁₋₄ aliphatic, —CH₂Ph, —O(CH₂)₀₋₁Ph, or a 5-6 membered saturated, partially unsaturated, or aryl ring having 0-4 heteroatoms independently selected from nitrogen, oxygen, or sulfur, and wherein each R˙ is unsubstituted or where preceded by halo is substituted only with one or more halogens.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N⁺(C₁₋₄alkyl)₄ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a ¹³C- or ¹⁴C-enriched carbon are within the scope of this invention. Such compounds are useful, for example, as analytical tools, as probes in biological assays, or as therapeutic agents in accordance with the present invention.

As used herein, the term "agonist" is defined as a compound that binds to and/or activates AHR with measurable affinity. In certain embodiments, an agonist has an IC₅₀ and/or binding constant of less than about 100 μM, less than about 50 μM, less than about 1 μM, less than about 500 nM, less than about 100 nM, less than about 10 nM, or less than about 1 nM.

The terms "measurable affinity" and "measurably activate," as used herein, means a measurable change in AHR activity between a sample comprising a compound of the present invention, or composition thereof, and AHR, and an equivalent sample comprising AHR, in the absence of said compound, or composition thereof.

3. Description of Exemplary Embodiments

In one aspect, the present invention provides a compound of Formula (I):

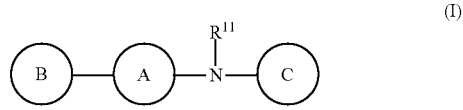

or a pharmaceutically acceptable salt thereof, wherein:
Ring A is an optionally substituted 5-membered heteroaromatic ring having 1-3 heteroatoms independently selected from N, O, or S;
Ring B is an optionally substituted ring selected from phenyl, a 6-membered heteroaromatic ring having 1-3 N, a 8-10 membered bicyclic aromatic ring, and a 8-10 membered bicyclic heteroaromatic ring having 1-5 heteroatoms independently selected from N, O, or S;
Ring C is optionally substituted phenyl or 6-membered heteroaromatic ring having 1-3 N;
R¹¹ is —R, —C(O)—Rᵂ, —C(=NRᵂ)—Rᵂ, —S(O)₂—Rᵂ, or —S(O)—Rᵂ;
Rᵂ is —R, —N(R)₂, —NR—OR, —N(R)—N(R)₂, —N(OR)—N(R)₂, —N(R)—N(OR)R, —OR, —O—N(R)₂, or —SR; and R is hydrogen, optionally substituted $C_{1-6}$ aliphatic, an optionally substituted 3-7 membered carbocyclic ring, or an optionally substituted 3-7 membered heterocyclic ring having 1-3 heteroatoms independently selected from N, O, or S, or two R's together with the nitrogen to which they attach form an optionally substituted 5-7 membered heterocyclic ring having 0-2 heteroatoms independently selected from N, O, or S in addition to the nitrogen to which the two R's attach.

As defined generally above, Ring A is an optionally substituted 5-membered heteroaromatic ring having 1-3 heteroatoms independently selected from N, O, or S.

In some embodiments, Ring A is an unsubstituted 5-membered heteroaromatic ring having 1-3 heteroatoms independently selected from N, O, or S. In some embodiments, Ring A is a 5-membered heteroaromatic ring having 1-3 heteroatoms independently selected from N, O, or S, which is substituted 1 or 2 times by $R^{12}$, wherein each $R^{12}$ is independently an optional substituent as defined above and described in embodiments herein.

In some embodiments, Ring A is an unsubstituted 5-membered heteroaromatic ring having 1, 2, or 3 heteroatoms independently selected from N or S. In some embodiments, Ring A is a 5-membered heteroaromatic ring having 1, 2, or 3 heteroatoms independently selected from N or S, which is substituted 1 or 2 times by $R^{12}$, wherein each $R^{12}$ is independently an optional substituent as defined above and described in embodiments herein.

In some embodiments, Ring A is an unsubstituted 5-membered heteroaromatic ring having 1, 2, or 3 heteroatoms independently selected from N or O. In some embodiments, Ring A is a 5-membered heteroaromatic ring having 1, 2, or 3 heteroatoms independently selected from N or O, which is substituted 1 or 2 times by $R^{12}$, wherein each $R^{12}$ is independently an optional substituent as defined above and described in embodiments herein.

In some embodiments, Ring A is optionally substituted

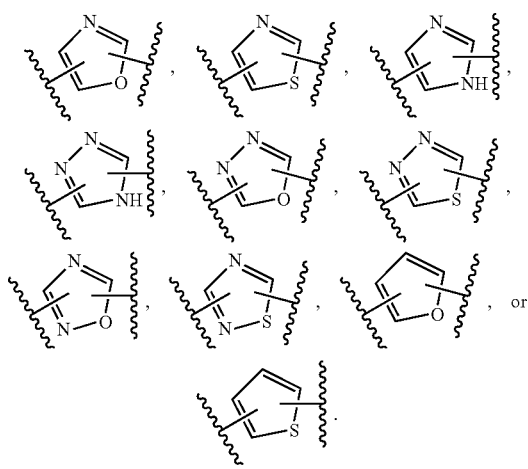

In some embodiments, Ring A is unsubstituted

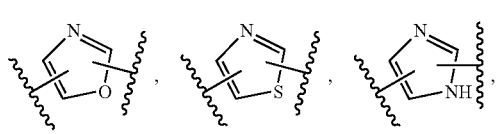

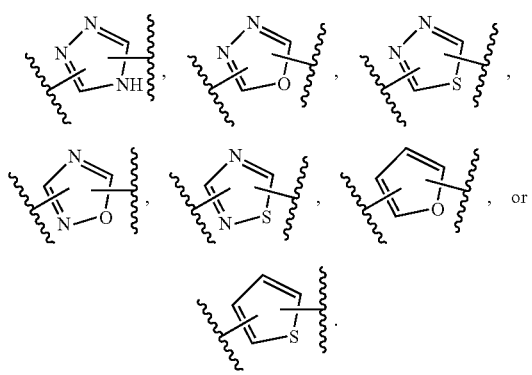

In some embodiments, Ring A is

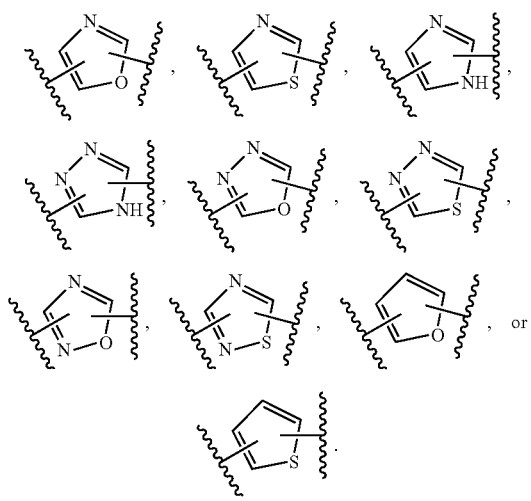

each of which is substituted 1 or 2 times by $R^{12}$, wherein each $R^{12}$ is independently an optional substituent as defined above and described in embodiments herein.

In some embodiments, Ring A is

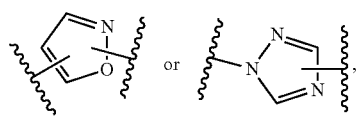

each of which is substituted 1 or 2 times by $R^{12}$, wherein each $R^{12}$ is independently an optional substituent as defined above and described in embodiments herein.

In some embodiments, Ring A is

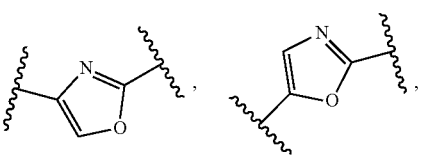

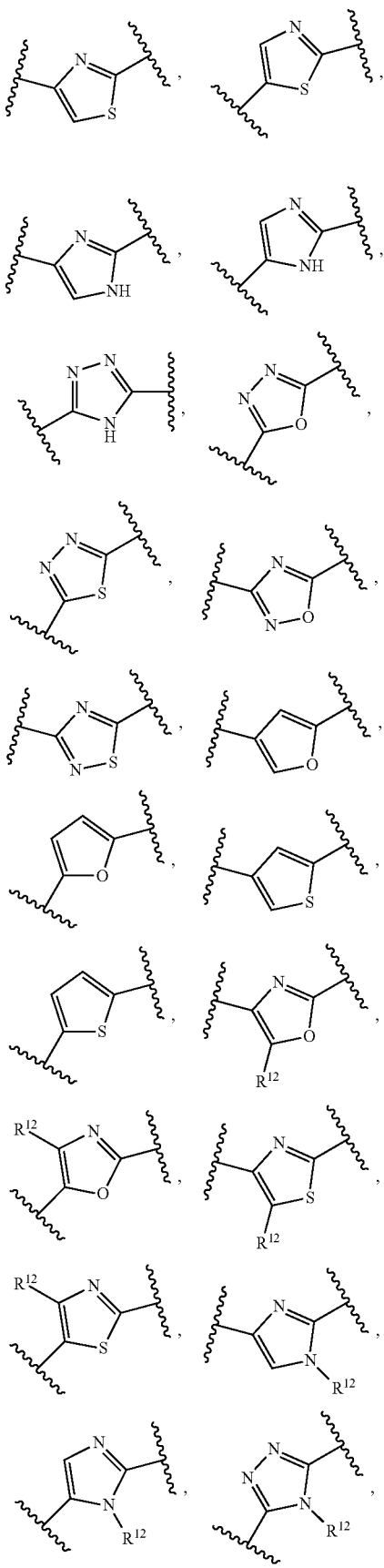

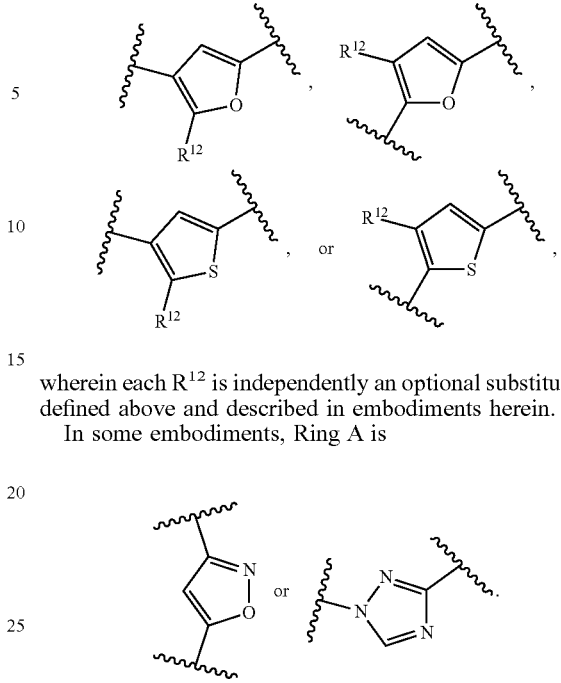

wherein each $R^{12}$ is independently an optional substituent as defined above and described in embodiments herein.

In some embodiments, Ring A is

In some embodiments, $R^{12}$ is halogen, —CN, —NO$_2$, $R^W$, —C(O)—$R^W$, —C(=NR$^W$)—$R^W$, —N(R$^W$)—C(O)—$R^W$, —N(R$^W$)—C(=NR$^W$)—$R^W$, —OC(O)—$R^W$, —OC(=NR$^W$)—$R^W$, —S(O)$_2$—$R^W$, —N(R$^W$)—S(O)$_2$—$R^W$, —OS(O)$_2$—$R^W$, —S(O)—$R^W$, —N(R$^W$)—S(O)—$R^W$, or —OS(O)—$R^W$, wherein each $R^W$ is independently as defined below and described in embodiments herein.

In some embodiments, $R^{12}$ is halogen. In some embodiments, $R^{12}$ is —CN. In some embodiments, $R^{12}$ is —NO$_2$. In some embodiments, $R^{12}$ is $R^W$ as defined below and described in embodiments herein. In some embodiments, $R^{12}$ is —C(O)—$R^W$, wherein $R^W$ is as defined below and described in embodiments herein. In some embodiments, $R^{12}$ is —C(=NR$^W$)—$R^W$, wherein each $R^W$ is independently as defined below and described in embodiments herein. In some embodiments, $R^{12}$ is —N(R$^W$)—C(O)—$R^W$, wherein each $R^W$ is independently as defined below and described in embodiments herein. In some embodiments, $R^{12}$ is —N(R$^W$)—C(=NR$^W$)—$R^W$, wherein each $R^W$ is independently as defined below and described in embodiments herein. In some embodiments, $R^{12}$ is —OC(O)—$R^W$, wherein each $R^W$ is independently as defined below and described in embodiments herein. In some embodiments, $R^{12}$ is —OC(=NR$^W$)—$R^W$, wherein each $R^W$ is independently as defined below and described in embodiments herein. In some embodiments, $R^{12}$ is —S(O)$_2$—$R^W$, wherein $R^W$ is as defined below and described in embodiments herein. In some embodiments, $R^{12}$ is —N(R$^W$)—S(O)$_2$—$R^W$, wherein each $R^W$ is independently as defined below and described in embodiments herein. In some embodiments, $R^{12}$ is —OS(O)$_2$—$R^W$, wherein $R^W$ is as defined below and described in embodiments herein. In some embodiments, $R^{12}$ is —S(O)—$R^W$, wherein $R^W$ is as defined below and described in embodiments herein. In some embodiments, $R^{12}$ is —N(R$^W$)—S(O)—$R^W$, wherein each $R^W$ is independently as defined below and described in embodiments herein. In some embodiments, $R^{12}$ is —OS(O)—$R^W$, wherein $R^W$ is as defined below and described in embodiments herein.

In some embodiments, $R^{12}$ is F. In some embodiments, $R^{12}$ is Cl. In some embodiments, $R^{12}$ is Br. In some embodiments, $R^{12}$ is optionally substituted —$C_{1-6}$ aliphatic. In some embodiments, $R^{12}$ is unsubstituted —$C_{1-6}$ aliphatic. In some embodiments, $R^{12}$ is unsubstituted —$C_{1-6}$ alkyl. In some embodiments, $R^{12}$ is —$C_{1-6}$ aliphatic substituted 1-6 times by halogen. In some embodiments, $R^{12}$ is —$C_{1-6}$ alkyl substituted 1-6 times by halogen. In some embodiments, $R^{12}$ is —$C_{1-6}$ alkyl substituted 1-6 times by F. In some embodiments, $R^{12}$ is —$CF_3$.

In some embodiments, Ring A is selected from those depicted in Table 1-a, below.

As defined generally above, Ring B is an optionally substituted ring selected from phenyl, a 6-membered heteroaromatic ring having 1-3 N, a 8-10 membered bicyclic aromatic ring, and a 8-10 membered bicyclic heteroaromatic ring having 1-5 heteroatoms independently selected from N, O, or S.

In some embodiments, Ring B is optionally substituted phenyl. In some embodiments, Ring B is an optionally substituted 6-membered heteroaromatic ring having 1, 2, or 3 N. In some embodiments, Ring B is an optionally substituted 8-10 membered bicyclic aromatic ring. In some embodiments, Ring B is an optionally substituted 8-10 membered bicyclic heteroaromatic ring having 1-5 heteroatoms independently selected from N, O, or S.

In some embodiments, Ring B is an optionally substituted 6-membered heteroaromatic ring having 1, 2, or 3 N. In some embodiments, Ring B is an optionally substituted 6-membered heteroaromatic ring having 1, 2, or 3 N. In some embodiments, Ring B is optionally substituted pyridyl.

In some embodiments, Ring B is an optionally substituted 8-, 9-, or 10-membered bicyclic heteroaromatic ring having 1, 2, 3, 4, or 5 heteroatoms independently selected from N, O, or S. In some embodiments, Ring B is an optionally substituted 8-, 9-, or 10-membered bicyclic heteroaromatic ring having 1, 2, 3, or 4 heteroatoms independently selected from N or O. In some embodiments, Ring B is an optionally substituted 8-, 9-, or 10-membered bicyclic heteroaromatic ring having 1, 2, 3, or 4 heteroatoms independently selected from N or S. In some embodiments, Ring B is optionally substituted

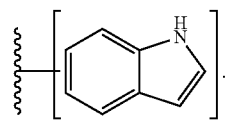

In some embodiments, Ring B is optionally substituted

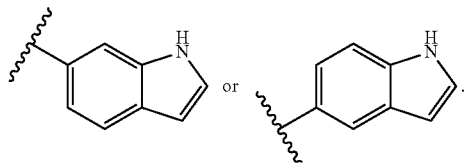 [SMILES: *c1ccc2cc[nH]c2c1 ; *c1ccc2[nH]ccc2c1]

In some embodiments, Ring B is substituted 1-5 times by halogen, —CN, —$NO_2$, $R^W$, —C(O)—$R^W$, —C(=$NR^W$)—$R^W$, —N($R^W$)—C(O)—$R^W$, —N($R^W$)—C(=$NR^W$)—$R^W$, —OC(O)—$R^W$, —OC(=$NR^W$)—$R^W$, —S(O)$_2$—$R^W$, —N($R^W$)—S(O)$_2$—$R^W$, —OS(O)$_2$—$R^W$, —S(O)—$R^W$, —N($R^W$)—S(O)—$R^W$, or —OS(O)—$R^W$, wherein each $R^W$ is independently as defined below and described in embodiments herein.

In some embodiments, Ring B is

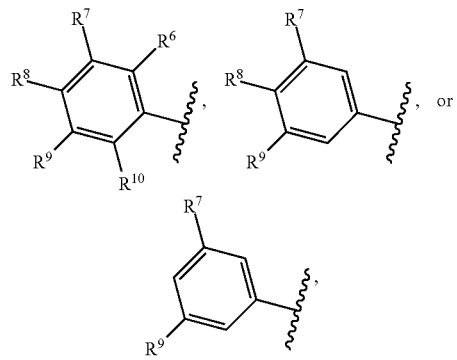

wherein each of $R^6$, $R^7$, $R^8$, $R^9$, and $R^{10}$ is an optional substituent as defined above and described in embodiments herein, both singly and in combination.

In some embodiments, Ring B is

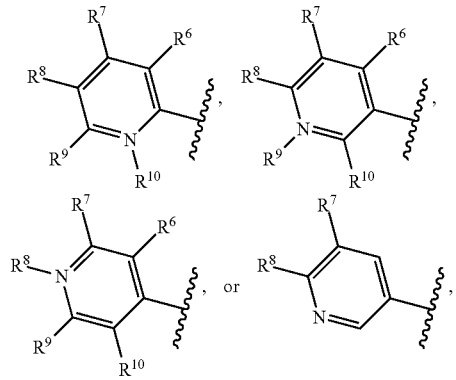

wherein each of $R^6$, $R^7$, $R^8$, $R^9$, and $R^{10}$ is an optional substituent as defined above and described in embodiments herein, both singly and in combination.

In some embodiments, Ring B is

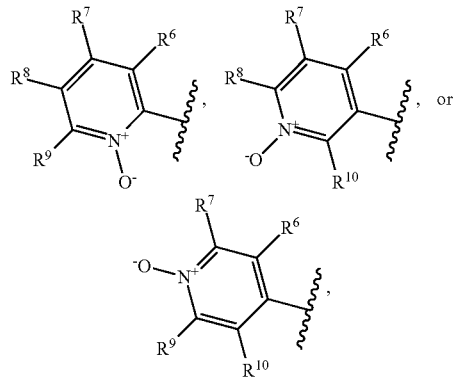

wherein each of $R^6$, $R^7$, $R^8$, $R^9$, and $R^{10}$ is an optional substituent as defined above and described in embodiments herein, both singly and in combination.

In some embodiments, each of $R^6$, $R^7$, $R^8$, $R^9$, and $R^{10}$ is independently halogen, —CN, —NO$_2$, $R^W$, —C(O)—$R^W$, —C(=NR$^W$)—$R^W$, —N(R$^W$)—C(O)—$R^W$, —N(R$^W$)—C(=NR$^W$)—$R^W$, —OC(O)—$R^W$, —OC(=NR$^W$)—$R^W$, —S(O)$_2$—$R^W$, —N(R$^W$)—S(O)$_2$—$R^W$, —OS(O)$_2$—$R^W$, —S(O)—$R^W$, —N(R$^W$)—S(O)—$R^W$, or —OS(O)—$R^W$, wherein each $R^W$ is independently as defined below and described in embodiments herein.

In some embodiments, $R^6$ is halogen. In some embodiments, $R^6$ is —CN. In some embodiments, $R^6$ is —NO$_2$. In some embodiments, $R^6$ is $R^W$ as defined below and described in embodiments herein. In some embodiments, $R^6$ is —C(O)—$R^W$, wherein $R^W$ is as defined below and described in embodiments herein. In some embodiments, $R^6$ is —C(=NR$^W$)—$R^W$, wherein each $R^W$ is independently as defined below and described in embodiments herein. In some embodiments, $R^6$ is —N(R$^W$)—C(O)—$R^W$, wherein each $R^W$ is independently as defined below and described in embodiments herein. In some embodiments, $R^6$ is —N(R$^W$)—C(=NR$^W$)—$R^W$, wherein each $R^W$ is independently as defined below and described in embodiments herein. In some embodiments, $R^6$ is —OC(O)—$R^W$, wherein each $R^W$ is independently as defined below and described in embodiments herein. In some embodiments, $R^6$ is —OC(=NR$^W$)—$R^W$, wherein each $R^W$ is independently as defined below and described in embodiments herein. In some embodiments, $R^6$ is —S(O)$_2$—$R^W$, wherein $R^W$ is as defined below and described in embodiments herein. In some embodiments, $R^6$ is —N(R$^W$)—S(O)$_2$—$R^W$, wherein each $R^W$ is independently as defined below and described in embodiments herein. In some embodiments, $R^6$ is —OS(O)$_2$—$R^W$, wherein $R^W$ is as defined below and described in embodiments herein. In some embodiments, $R^6$ is —S(O)—$R^W$, wherein $R^W$ is as defined below and described in embodiments herein. In some embodiments, $R^6$ is —N(R$^W$)—S(O)—$R^W$, wherein each $R^W$ is independently as defined below and described in embodiments herein. In some embodiments, $R^6$ is —OS(O)—$R^W$, wherein $R^W$ is as defined below and described in embodiments herein.

In some embodiments, $R^7$ is halogen. In some embodiments, $R^7$ is —CN. In some embodiments, $R^7$ is —NO$_2$. In some embodiments, $R^7$ is $R^W$ as defined below and described in embodiments herein. In some embodiments, $R^7$ is —C(O)—$R^W$, wherein $R^W$ is as defined below and described in embodiments herein. In some embodiments, $R^7$ is —C(=NR$^W$)—$R^W$, wherein each $R^W$ is independently as defined below and described in embodiments herein. In some embodiments, $R^7$ is —N(R$^W$)—C(O)—$R^W$, wherein each $R^W$ is independently as defined below and described in embodiments herein. In some embodiments, $R^7$ is —N(R$^W$)—C(=NR$^W$)—$R^W$, wherein each $R^W$ is independently as defined below and described in embodiments herein. In some embodiments, $R^7$ is —OC(O)—$R^W$, wherein each $R^W$ is independently as defined below and described in embodiments herein. In some embodiments, $R^7$ is —OC(=NR$^W$)—$R^W$, wherein each $R^W$ is independently as defined below and described in embodiments herein. In some embodiments, $R^7$ is —S(O)$_2$—$R^W$, wherein $R^W$ is as defined below and described in embodiments herein. In some embodiments, IC is —N(R$^W$)—S(O)$_2$—$R^W$, wherein each $R^W$ is independently as defined below and described in embodiments herein. In some embodiments, $R^7$ is —OS(O)$_2$—$R^W$, wherein $R^W$ is as defined below and described in embodiments herein. In some embodiments, $R^7$ is —S(O)—$R^W$, wherein $R^W$ is as defined below and described in embodiments herein. In some embodiments, $R^7$ is —N(R$^W$)—S(O)—$R^W$, wherein each $R^W$ is independently as defined below and described in embodiments herein. In some embodiments, $R^7$ is —OS(O)—$R^W$, wherein $R^W$ is as defined below and described in embodiments herein.

In some embodiments, $R^7$ is independently

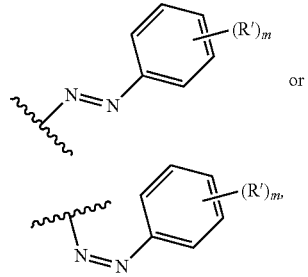

wherein each R' is independently halogen, —CN, —NO$_2$, R, —OR, —SR, —N(R)$_2$, —C(O)OR, —C(O)N(R)$_2$, and m is 0, 1, 2, 3, 4, or 5, wherein each R is independently as defined and described in embodiments herein. In some embodiments, R' is —OH. In some embodiments, R' is —COOH.

In some embodiments, $R^7$ is

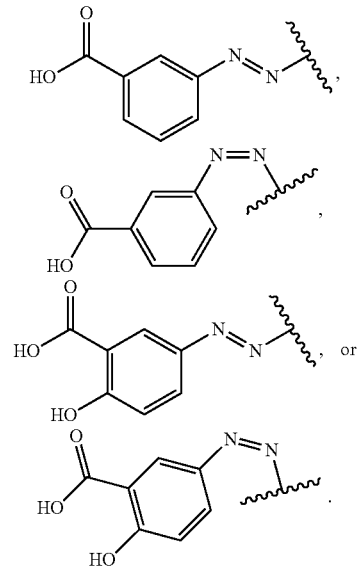

In some embodiments, $R^8$ is halogen. In some embodiments, $R^8$ is —CN. In some embodiments, $R^8$ is —NO$_2$. In some embodiments, $R^8$ is $R^W$ as defined below and described in embodiments herein. In some embodiments, $R^8$ is —C(O)—$R^W$, wherein $R^W$ is as defined below and described in embodiments herein. In some embodiments, $R^8$ is —C(=NR$^W$)—$R^W$, wherein each $R^W$ is independently as defined below and described in embodiments herein. In some embodiments, $R^8$ is —N(R$^W$)—C(O)—$R^W$, wherein each $R^W$ is independently as defined below and described in embodiments herein. In some embodiments, $R^8$ is —N(R$^W$)—C(=NR$^W$)—$R^W$, wherein each $R^W$ is independently as defined below and described in embodiments herein. In some embodiments, $R^8$ is —OC(O)—$R^W$, wherein each $R^W$ is independently as defined below and described in embodiments herein. In some embodiments, $R^8$ is —OC(=NR$^W$)—$R^W$, wherein each $R^W$ is independently as defined below and described in embodiments herein. In some embodiments, $R^8$ is —S(O)$_2$—$R^W$, wherein $R^W$ is as defined below and described in embodiments herein. In some embodiments, $R^8$ is —N($R^W$)—S(O)$_2$—$R^W$, wherein each $R^W$ is independently as defined below and described in embodiments herein. In some embodiments, $R^8$ is —OS(O)$_2$—$R^W$, wherein $R^W$ is as defined below and described in embodiments herein. In some embodiments, $R^8$ is —S(O)—$R^W$, wherein $R^W$ is as defined below and described in embodiments herein. In some embodiments, $R^8$ is —N($R^W$)—S(O)—$R^W$, wherein each $R^W$ is independently as defined below and described in embodiments herein. In some embodiments, $R^8$ is —OS(O)—$R^W$, wherein $R^W$ is as defined below and described in embodiments herein.

In some embodiments, $R^9$ is halogen. In some embodiments, $R^9$ is —CN. In some embodiments, $R^9$ is —NO$_2$. In some embodiments, $R^9$ is $R^W$ as defined below and described in embodiments herein. In some embodiments, $R^9$ is —C(O)—$R^W$, wherein $R^W$ is as defined below and described in embodiments herein. In some embodiments, $R^9$ is —C(=N$R^W$)—$R^W$, wherein each $R^W$ is independently as defined below and described in embodiments herein. In some embodiments, $R^9$ is —N($R^W$)—C(O)—$R^W$, wherein each $R^W$ is independently as defined below and described in embodiments herein. In some embodiments, $R^9$ is —N($R^W$)—C(=N$R^W$)—$R^W$, wherein each $R^W$ is independently as defined below and described in embodiments herein. In some embodiments, $R^9$ is —OC(O)—$R^W$, wherein each $R^W$ is independently as defined below and described in embodiments herein. In some embodiments, $R^9$ is —OC(=N$R^W$)—$R^W$, wherein each $R^W$ is independently as defined below and described in embodiments herein. In some embodiments, $R^9$ is —S(O)$_2$—$R^W$, wherein $R^W$ is as defined below and described in embodiments herein. In some embodiments, $R^9$ is —N($R^W$)—S(O)$_2$—$R^W$, wherein each $R^W$ is independently as defined below and described in embodiments herein. In some embodiments, $R^9$ is —OS(O)$_2$—$R^W$, wherein $R^W$ is as defined below and described in embodiments herein. In some embodiments, $R^9$ is —S(O)—$R^W$, wherein $R^W$ is as defined below and described in embodiments herein. In some embodiments, $R^9$ is —N($R^W$)—S(O)—$R^W$, wherein each $R^W$ is independently as defined below and described in embodiments herein. In some embodiments, $R^9$ is —OS(O)—$R^W$, wherein $R^W$ is as defined below and described in embodiments herein. In some embodiments, $R^9$ is independently

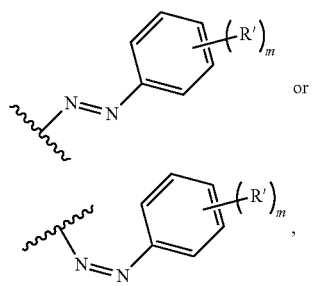

wherein each R' is independently halogen, —CN, —NO$_2$, R, —OR, —SR, —N(R)$_2$, —C(O)OR, —C(O)N(R)$_2$, and m is 0, 1, 2, 3, 4, or 5, wherein each R is independently as defined and described in embodiments herein. In some embodiments, R' is —OH. In some embodiments, R' is —COOH.

In some embodiments, $R^9$ is

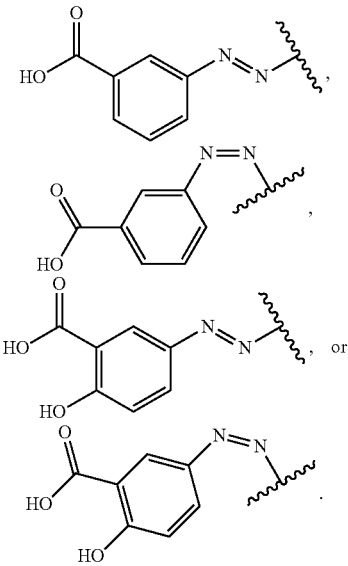

In some embodiments, $R^{10}$ is halogen. In some embodiments, $R^{10}$ is —CN. In some embodiments, $R^{10}$ is —NO$_2$. In some embodiments, $R^{10}$ is $R^W$ as defined below and described in embodiments herein. In some embodiments, $R^{10}$ is —C(O)—$R^W$, wherein $R^W$ is as defined below and described in embodiments herein. In some embodiments, $R^{10}$ is —C(=N$R^W$)—$R^W$, wherein each $R^W$ is independently as defined below and described in embodiments herein. In some embodiments, $R^{10}$ is —N($R^W$)—C(O)—$R^W$, wherein each $R^W$ is independently as defined below and described in embodiments herein. In some embodiments, $R^{10}$ is —N($R^W$)—C(=N$R^W$)—$R^W$, wherein each $R^W$ is independently as defined below and described in embodiments herein. In some embodiments, $R^{10}$ is —OC(O)—$R^W$, wherein each $R^W$ is independently as defined below and described in embodiments herein. In some embodiments, $R^{10}$ is —OC(=N$R^W$)—$R^W$, wherein each $R^W$ is independently as defined below and described in embodiments herein. In some embodiments, $R^{10}$ is —S(O)$_2$—$R^W$, wherein $R^W$ is as defined below and described in embodiments herein. In some embodiments, $R^{10}$ is —N($R^W$)—S(O)$_2$—$R^W$, wherein each $R^W$ is independently as defined below and described in embodiments herein. In some embodiments, $R^{10}$ is —OS(O)$_2$—$R^W$, wherein $R^W$ is as defined below and described in embodiments herein. In some embodiments, $R^{10}$ is —S(O)—$R^W$, wherein $R^W$ is as defined below and described in embodiments herein. In some embodiments, $R^{10}$ is —N($R^W$)—S(O)—$R^W$, wherein each $R^W$ is independently as defined below and described in embodiments herein. In some embodiments, $R^{10}$ is —OS(O)—$R^W$, wherein $R^W$ is as defined below and described in embodiments herein.

In some embodiments, each of $R^6$, $R^7$, $R^8$, $R^9$, and $R^{10}$ is independently hydrogen, —Cl, —Br, —CN, —NO$_2$, —NH$_2$, —N(CH$_3$)$_2$, —N$^+$(CH$_3$)$_3$, —OH, —O(CH$_2$)$_2$N(CH$_3$)$_2$, —O(CH$_2$)$_2$—N$^+$(CH$_3$)$_3$, —OCH$_3$, —OCF$_3$, —CF$_3$, —CH$_3$, —C(O)NH$_2$, —C(O)N(CH$_3$)$_2$, —COOH, —NH—C(O)—(CH$_2$)$_2$—N$^+$(CH$_3$)$_3$, —NH—C(O)—(CH$_2$)$_3$—N$^+$(CH$_3$)$_3$, —NH—C(O)O—(CH$_2$)$_2$—N$^+$(CH$_3$)$_3$, —C(=NH)NH$_2$, —S(O)$_2$—N(CH$_3$)$_2$,

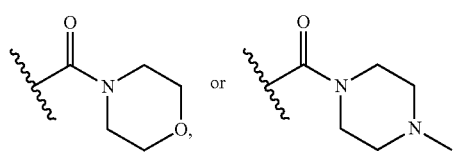

In some embodiments, Ring B is optionally substituted

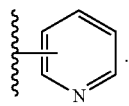

In some embodiments, Ring B is optionally substituted

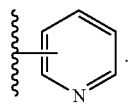

In some embodiments, Ring B is optionally substituted

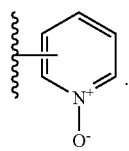

In some embodiments, Ring B is unsubstituted

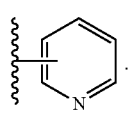

In some embodiments, Ring B is unsubstituted

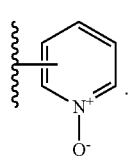

In some embodiments, Ring B is

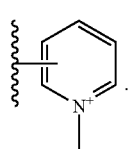

In some embodiments, Ring B is phenyl,

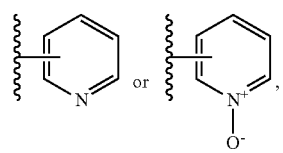

each of which is substituted 1-5 times by halogen, —CN, —NO$_2$, —N(R)$_2$, R, —OR, —SR, —C(O)—R, —C(O)OR, —C(O)—N(R)$_2$, —C(=NR)—N(R)$_2$, —N(R)—C(O)—R, —N(R)—C(O)OR, —N(R)—C(O)—N(R)$_2$, —OC(O)—R, —OC(O)OR, —OC(O)—N(R)$_2$, —S(O)$_2$—R, —S(O)$_2$OR, —S(O)$_2$—N(R)$_2$, —N(R)—S(O)$_2$—R, —N(R)—S(O)$_2$OR, —N(R)—S(O)$_2$—N(R)$_2$, —OS(O)$_2$—R, —OS(O)$_2$OR, or —OS(O)$_2$—N(R)$_2$, wherein each R is independently as defined below and described in embodiments herein.

In some embodiments, Ring B is

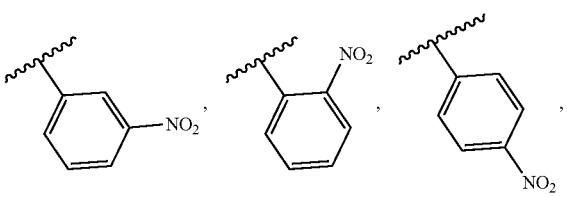

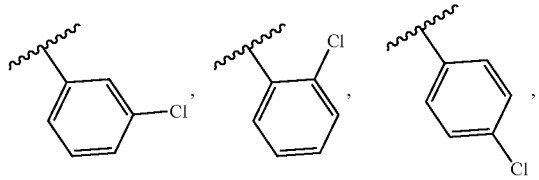

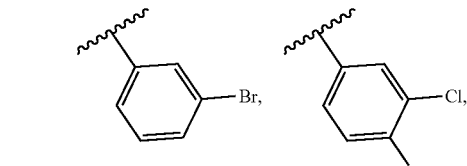

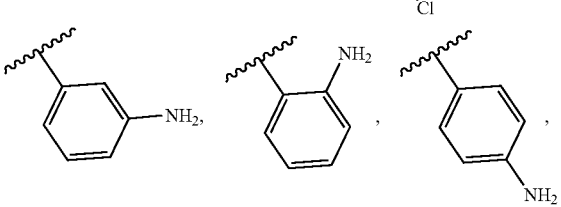

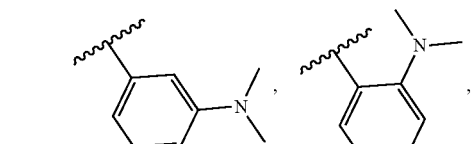

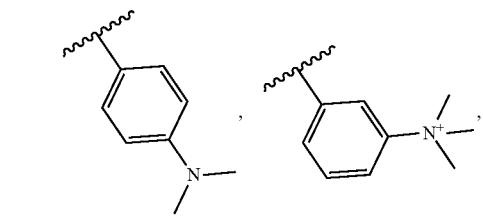

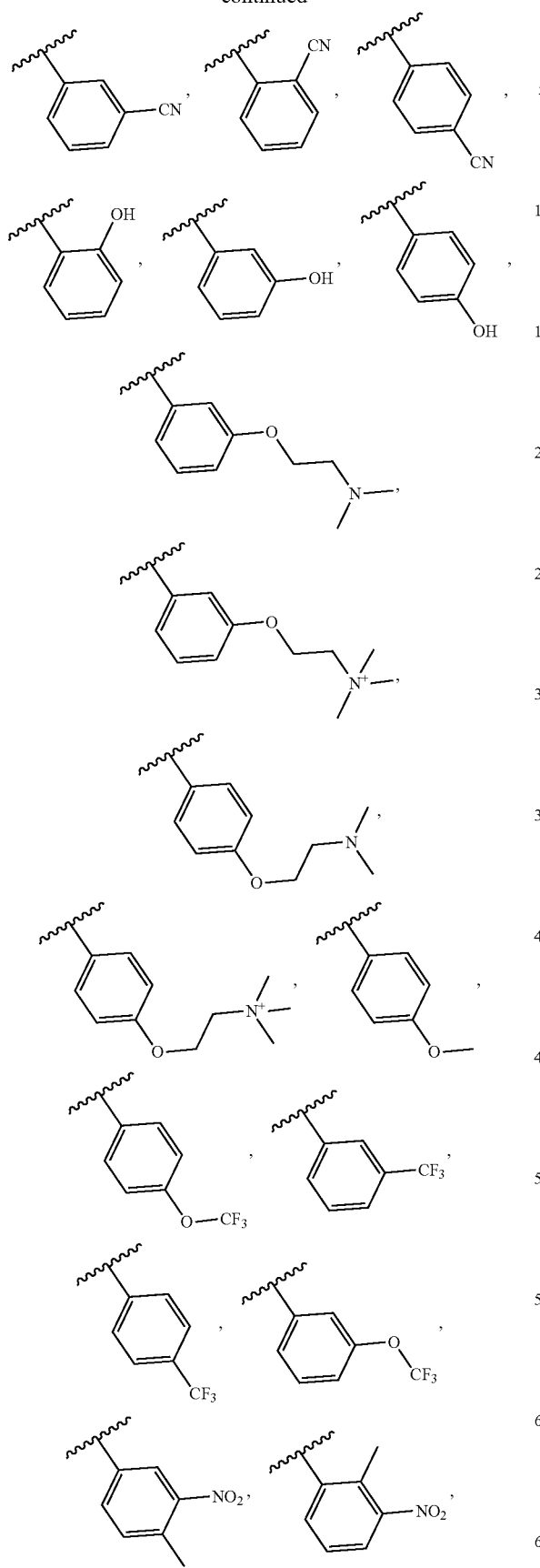
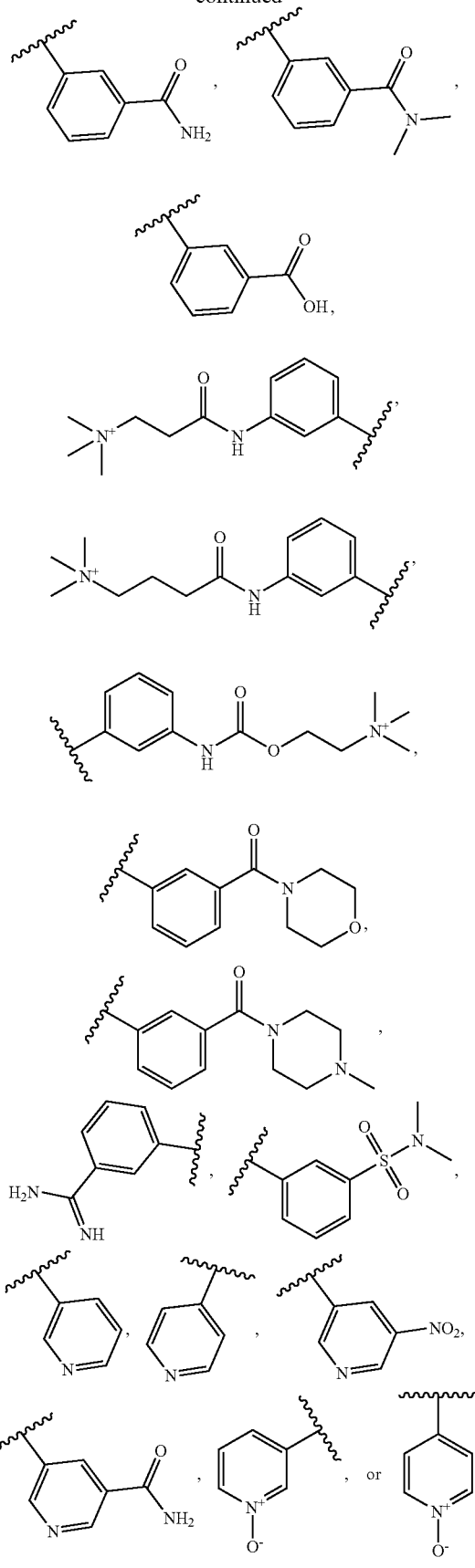

In some embodiments, Ring B is
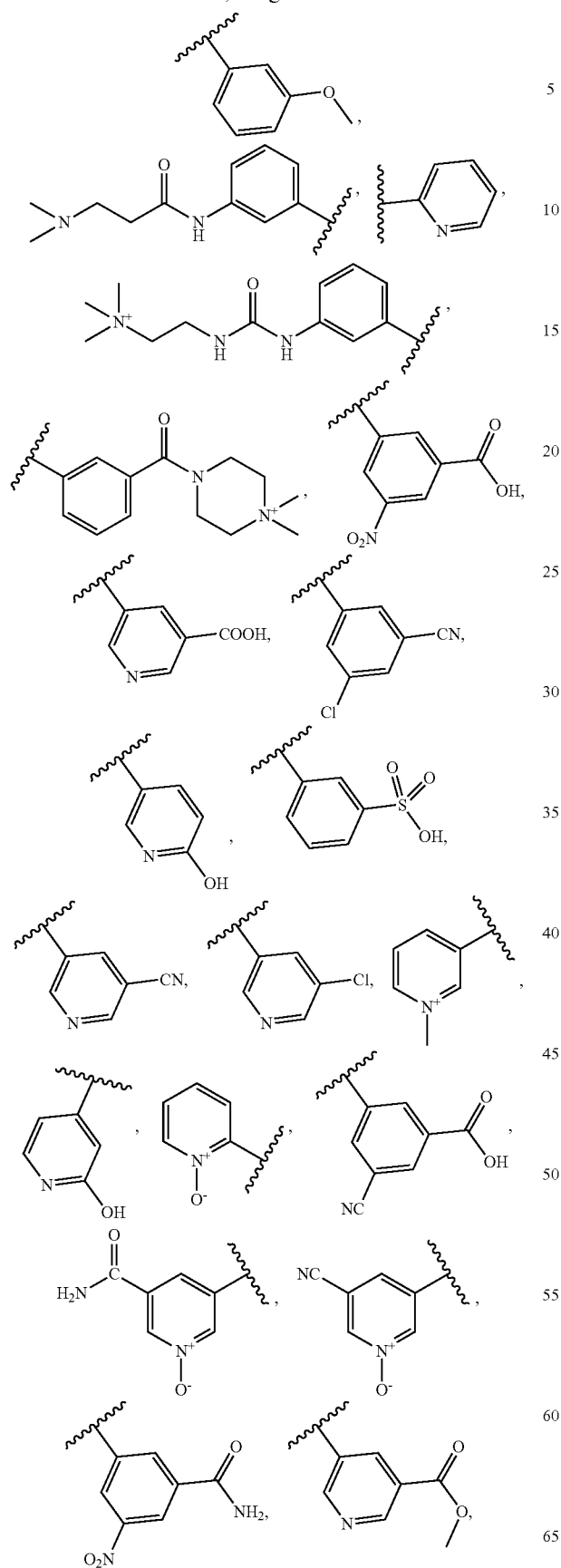
-continued
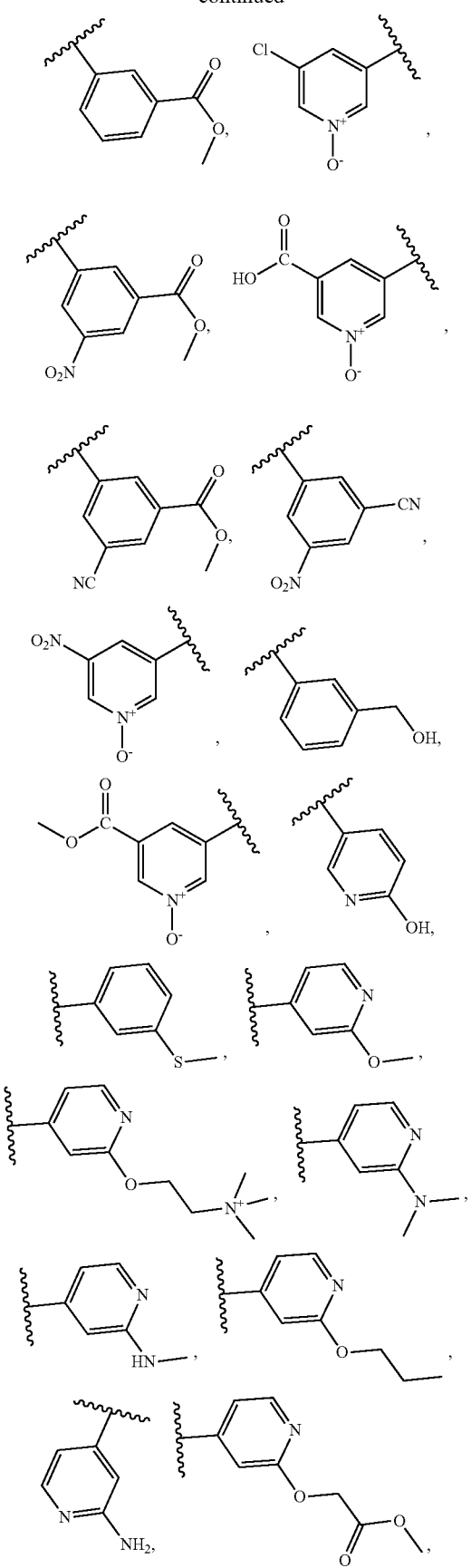

-continued
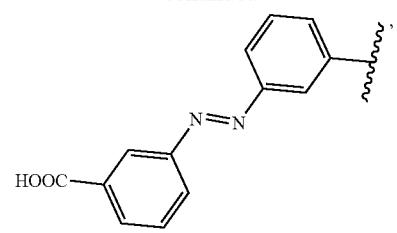
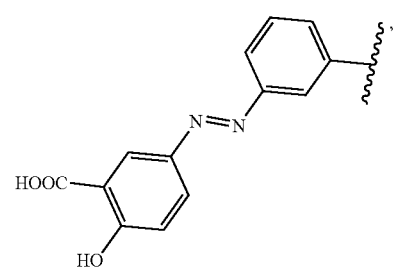
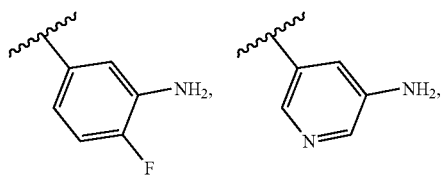
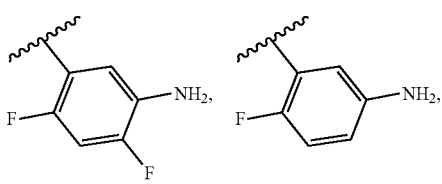
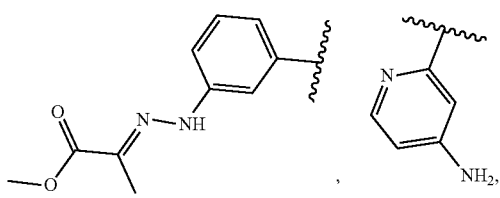
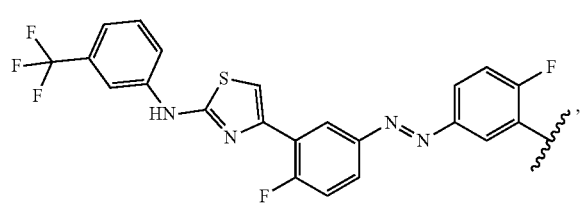
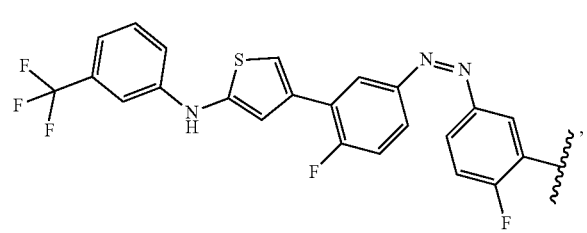
-continued
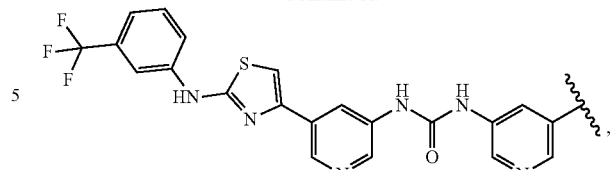
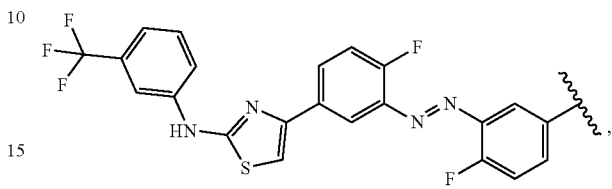
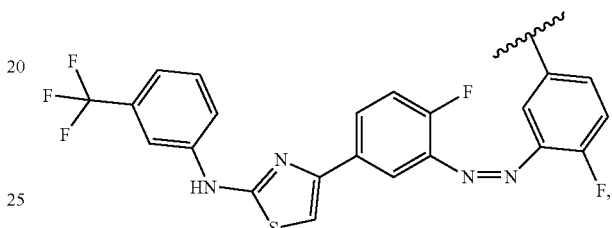
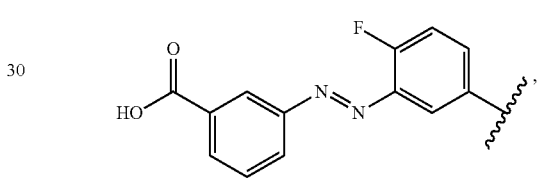
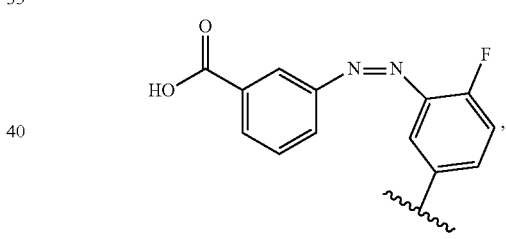
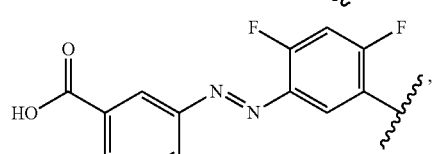
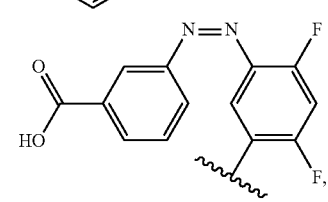
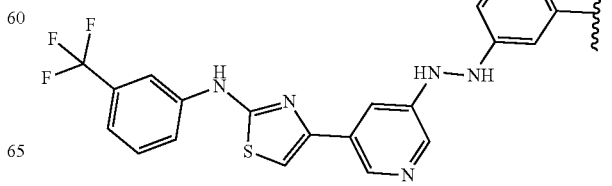

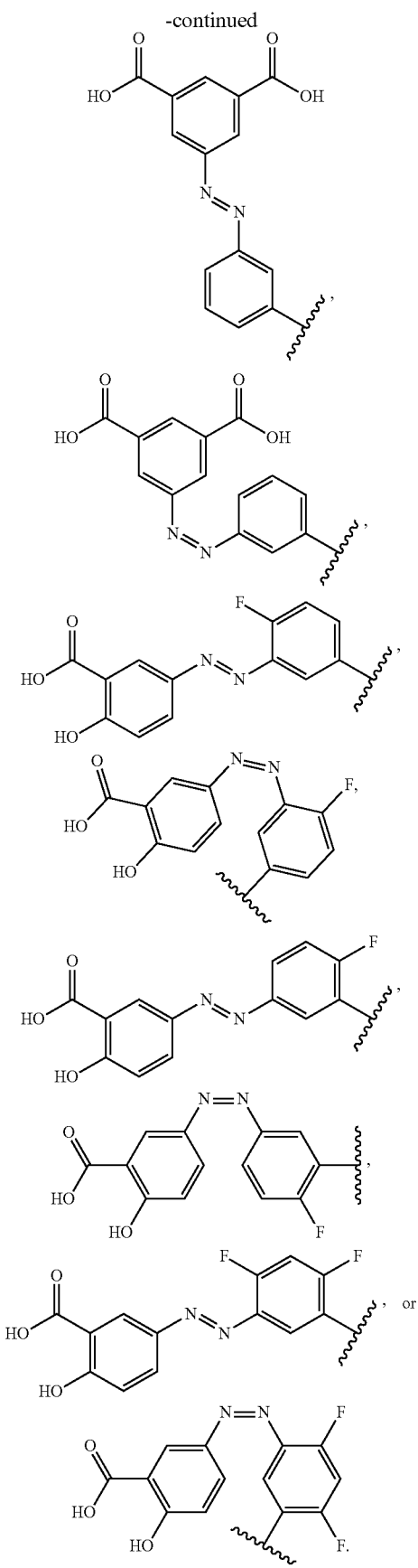

As described herein, structures depicted herein are also meant to include all isomeric forms. Accordingly, in some embodiments, Ring B is

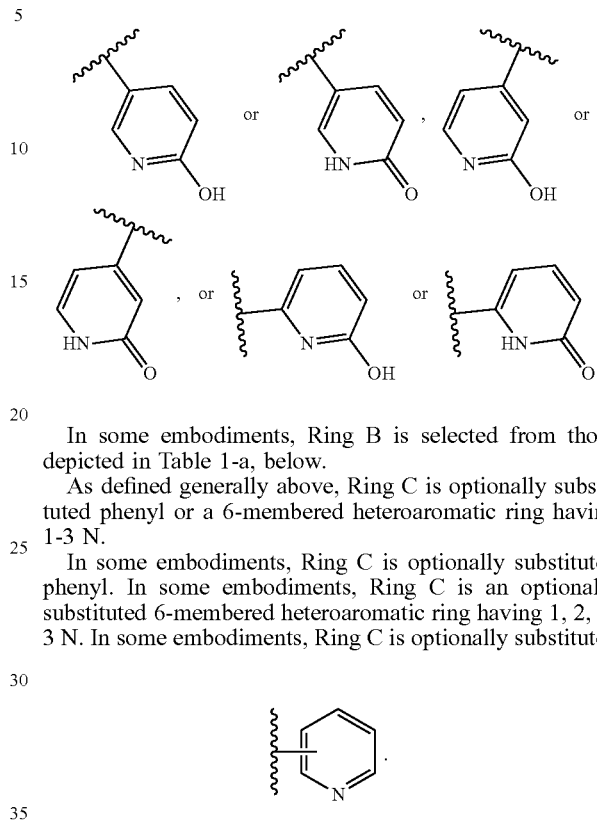

In some embodiments, Ring B is selected from those depicted in Table 1-a, below.

As defined generally above, Ring C is optionally substituted phenyl or a 6-membered heteroaromatic ring having 1-3 N.

In some embodiments, Ring C is optionally substituted phenyl. In some embodiments, Ring C is an optionally substituted 6-membered heteroaromatic ring having 1, 2, or 3 N. In some embodiments, Ring C is optionally substituted

In some embodiments, Ring C is substituted 1-5 times by halogen, —CN, —NO$_2$, R$^W$, —C(O)—R$^W$, —C(=NR$^W$)—R$^W$, —N(R$^W$)—C(O)—R$^W$, —N(R$^W$)—C(=NR$^W$)—R$^W$, —OC(O)—R$^W$, —OC(=NR$^W$)—R$^W$, —S(O)$_2$—R$^W$, —N(R$^W$)—S(O)$_2$—R$^W$, —OS(O)$_2$—R$^W$, —S(O)—R$^W$, —N(R$^W$)—S(O)—R$^W$, or —OS(O)—R$^W$, wherein each R$^W$ is independently as defined below and described in embodiments herein.

In some embodiments, Ring C is

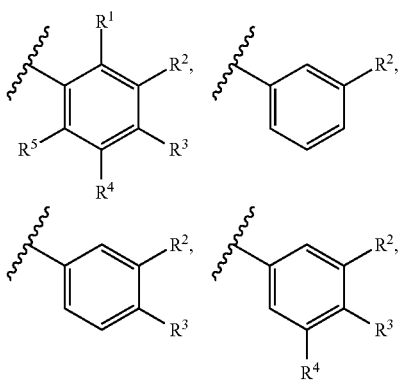

wherein each of R$^1$, R$^2$, R$^3$, R$^4$, and R$^5$ is an optional substituent as defined above and as described in embodiments herein, both singly and in combination.

In some embodiments, each of R$^1$, R$^2$, R$^3$, R$^4$, and R$^5$ is independently halogen, —CN, —NO$_2$, R$^W$, —C(O)—R$^W$, —C(=NR$^W$)—R$^W$, —N(R$^W$)—C(O)—R$^W$, —N(R$^W$)—C(=NR$^W$)—R$^W$, —OC(O)—R$^W$, —OC(=NR$^W$)—R$^W$, —S(O)$_2$—R$^W$, —N(R$^W$)—S(O)$_2$—R$^W$, —OS(O)$_2$—R$^W$, —S(O)—R$^W$, —N(R$^W$)—S(O)—R$^W$, or —OS(O)—R$^W$, wherein each R$^W$ is independently as defined below and described in embodiments herein.

In some embodiments, R$^1$ is halogen. In some embodiments, R$^1$ is —CN. In some embodiments, R$^1$ is —NO$_2$. In some embodiments, R$^1$ is R$^W$ as defined below and described in embodiments herein. In some embodiments, R$^1$ is —C(O)—R$^W$, wherein R$^W$ is as defined below and described in embodiments herein. In some embodiments, R$^1$ is —C(=NR$^W$)—R$^W$, wherein each R$^W$ is independently as defined below and described in embodiments herein. In some embodiments, R$^1$ is —N(R$^W$)—C(O)—R$^W$, wherein each R$^W$ is independently as defined below and described in embodiments herein. In some embodiments, R$^1$ is —N(R$^W$)—C(=NR$^W$)—R$^W$, wherein each R$^W$ is independently as defined below and described in embodiments herein. In some embodiments, R$^1$ is —OC(O)—R$^W$, wherein each R$^W$ is independently as defined below and described in embodiments herein. In some embodiments, R$^1$ is —OC(=NR$^W$)—R$^W$, wherein each R$^W$ is independently as defined below and described in embodiments herein. In some embodiments, R$^1$ is —S(O)$_2$—R$^W$, wherein R$^W$ is as defined below and described in embodiments herein. In some embodiments, R$^1$ is —N(R$^W$)—S(O)$_2$—R$^W$, wherein each R$^W$ is independently as defined below and described in embodiments herein. In some embodiments, R$^1$ is —OS(O)$_2$—R$^W$, wherein R$^W$ is as defined below and described in embodiments herein. In some embodiments, r$^1$ is —S(O)—R$^W$, wherein R$^W$ is as defined below and described in embodiments herein. In some embodiments, R$^1$ is —N(R$^W$)—S(O)—R$^W$, wherein each R$^W$ is independently as defined below and described in embodiments herein. In some embodiments, R$^1$ is —OS(O)—R$^W$, wherein R$^W$ is as defined below and described in embodiments herein.

In some embodiments, R$^2$ is halogen. In some embodiments, R$^2$ is —CN. In some embodiments, R$^2$ is —NO$_2$. In some embodiments, R$^2$ is R$^W$ as defined below and described in embodiments herein. In some embodiments, R$^2$ is —C(O)—R$^W$, wherein R$^W$ is as defined below and described in embodiments herein. In some embodiments, R$^2$ is —C(=NR$^W$)—R$^W$, wherein each R$^W$ is independently as defined below and described in embodiments herein. In some embodiments, R$^2$ is —N(R$^W$)—C(O)—R$^W$, wherein each R$^W$ is independently as defined below and described in embodiments herein. In some embodiments, R$^2$ is —N(R$^W$)—C(=NR$^W$)—R$^W$, wherein each R$^W$ is independently as defined below and described in embodiments herein. In some embodiments, R$^2$ is —OC(O)—R$^W$, wherein each R$^W$ is independently as defined below and described in embodiments herein. In some embodiments, R$^2$ is —OC(=NR$^W$)—R$^W$, wherein each R$^W$ is independently as defined below and described in embodiments herein. In some embodiments, R$^2$ is —S(O)$_2$—R$^W$, wherein R$^W$ is as defined below and described in embodiments herein. In some embodiments, R$^2$ is —N(R$^W$)—S(O)$_2$—R$^W$, wherein each R$^W$ is independently as defined below and described in embodiments herein. In some embodiments, R$^2$ is —OS(O)$_2$—R$^W$, wherein R$^W$ is as defined below and described in embodiments herein. In some embodiments, R$^2$ is —S(O)—R$^W$, wherein R$^W$ is as defined below and described in embodiments herein. In some embodiments, R$^2$ is —N(R$^W$)—S(O)—R$^W$, wherein each R$^W$ is independently as defined below and described in embodiments herein. In some embodiments, R$^2$ is —OS(O)—R$^W$, wherein R$^W$ is as defined below and described in embodiments herein.

In some embodiments, R$^3$ is halogen. In some embodiments, R$^3$ is —CN. In some embodiments, R$^3$ is —NO$_2$. In some embodiments, R$^3$ is R$^W$ as defined below and described in embodiments herein. In some embodiments, R$^3$ is —C(O)—R$^W$, wherein R$^W$ is as defined below and described in embodiments herein. In some embodiments, R$^3$ is —C(=NR$^W$)—R$^W$, wherein each R$^W$ is independently as defined below and described in embodiments herein. In some embodiments, R$^3$ is —N(R$^W$)—C(O)—R$^W$, wherein each R$^W$ is independently as defined below and described in embodiments herein. In some embodiments, R$^3$ is —N(R$^W$)—C(=NR$^W$)—R$^W$, wherein each R$^W$ is independently as defined below and described in embodiments herein. In some embodiments, R$^3$ is —OC(O)—R$^W$, wherein each R$^W$ is independently as defined below and described in embodiments herein. In some embodiments, R$^3$ is —OC(=NR$^W$)—R$^W$, wherein each R$^W$ is independently as defined below and described in embodiments herein. In some embodiments, R$^3$ is —S(O)$_2$—R$^W$, wherein R$^W$ is as defined below and described in embodiments herein. In some embodiments, R$^3$ is —N(R$^W$)—S(O)$_2$—R$^W$, wherein each R$^W$ is independently as defined below and described in embodiments herein. In some embodiments, R$^3$ is —OS(O)$_2$—R$^W$, wherein R$^W$ is as defined below and described in embodiments herein. In some embodiments, R$^3$ is —S(O)—R$^W$, wherein R$^W$ is as defined below and described in embodiments herein. In some embodiments, R$^3$ is —N(R$^W$)—S(O)—R$^W$, wherein each R$^W$ is independently as defined below and described in embodiments herein. In some embodiments, R$^3$ is —OS(O)—R$^W$, wherein R$^W$ is as defined below and described in embodiments herein.

In some embodiments, R$^4$ is halogen. In some embodiments, R$^4$ is —CN. In some embodiments, R$^4$ is —NO$_2$. In some embodiments, R$^4$ is R$^W$ as defined below and described in embodiments herein. In some embodiments, R$^4$ is —C(O)—R$^W$, wherein R$^W$ is as defined below and described in embodiments herein. In some embodiments, R$^4$ is —C(=NR$^W$)—R$^W$, wherein each R$^W$ is independently as defined below and described in embodiments herein. In some embodiments, R$^4$ is —N(R$^W$)—C(O)—R$^W$, wherein each R$^W$ is independently as defined below and described in embodiments herein. In some embodiments, R$^4$ is —N(R$^W$)—C(=NR$^W$)—R$^W$, wherein each R$^W$ is independently as defined below and described in embodiments herein. In some embodiments, R$^4$ is —OC(O)—R$^W$, wherein each R$^W$ is independently as defined below and described in embodiments herein. In some embodiments, R$^4$ is —OC(=NR$^W$)—R$^W$, wherein each R$^W$ is independently as defined below and described in embodiments herein. In some embodiments, R$^4$ is —S(O)$_2$—R$^W$, wherein R$^W$ is as defined below and described in embodiments herein. In some embodiments, R$^4$ is —N(R$^W$)—S(O)$_2$—R$^W$, wherein each R$^W$ is independently as defined below and described in embodiments herein. In some embodiments, R$^4$ is —OS(O)$_2$—R$^W$, wherein R$^W$ is as defined below and described in embodiments herein. In some embodiments, R$^4$ is —S(O)—R$^W$, wherein R$^W$ is as defined below and described in embodiments herein. In some embodiments, R$^4$ is —N(R$^W$)—S(O)—R$^W$, wherein each R$^W$ is independently as defined below and described in embodiments herein. In some embodiments, R$^4$ is —OS(O)—R$^W$, wherein R$^W$ is as defined below and described in embodiments herein.

In some embodiments, R$^5$ is halogen. In some embodiments, R$^5$ is —CN. In some embodiments, R$^5$ is —NO$_2$. In some embodiments, R$^5$ is R$^W$ as defined below and described in embodiments herein. In some embodiments, $R^5$ is —C(O)—$R^W$, wherein $R^W$ is as defined below and described in embodiments herein. In some embodiments, $R^5$ is —C(=N$R^W$)—$R^W$, wherein each $R^W$ is independently as defined below and described in embodiments herein. In some embodiments, $R^5$ is —N($R^W$)—C(O)—$R^W$, wherein each $R^W$ is independently as defined below and described in embodiments herein. In some embodiments, $R^5$ is —N($R^W$)—C(=N$R^W$)—$R^W$, wherein each $R^W$ is independently as defined below and described in embodiments herein. In some embodiments, $R^5$ is —OC(O)—$R^W$, wherein each $R^W$ is independently as defined below and described in embodiments herein. In some embodiments, $R^5$ is —OC(=N$R^W$)—$R^W$, wherein each $R^W$ is independently as defined below and described in embodiments herein. In some embodiments, $R^5$ is —S(O)$_2$—$R^W$, wherein $R^W$ is as defined below and described in embodiments herein. In some embodiments, $R^5$ is —N($R^W$)—S(O)$_2$—$R^W$, wherein each $R^W$ is independently as defined below and described in embodiments herein. In some embodiments, $R^5$ is —OS(O)$_2$—$R^W$, wherein $R^W$ is as defined below and described in embodiments herein. In some embodiments, $R^5$ is —S(O)—$R^W$, wherein $R^W$ is as defined below and described in embodiments herein. In some embodiments, $R^5$ is —N($R^W$)—S(O)—$R^W$, wherein each $R^W$ is independently as defined below and described in embodiments herein. In some embodiments, $R^5$ is —OS(O)—$R^W$, wherein $R^W$ is as defined below and described in embodiments herein.

In some embodiments, each of $R^1$, $R^2$, $R^3$, $R^4$, and $R^5$ is independently hydrogen, —Cl, —Br, —CN, —NO$_2$, —NH$_2$, —N(CH$_3$)$_2$, —N$^+$(CH$_3$)$_3$, —OH, —O(CH$_2$)$_2$N(CH$_3$)$_2$, —O(CH$_2$)$_2$—N$^+$(CH$_3$)$_3$, —OCH$_3$, —OCF$_3$, —CF$_3$, —CH$_3$, —C(O)NH$_2$, —C(O)N(CH$_3$)$_2$, —COOH, —NH—C(O)—(CH$_2$)$_2$—N$^+$(CH$_3$)$_3$, —NH—C(O)—(CH$_2$)$_3$—N$^+$(CH$_3$)$_3$, —NH—C(O)O—(CH$_2$)$_3$—N$^+$(CH$_3$)$_3$, —C(=NH)NH$_2$, —S(O)$_2$—N(CH$_3$)$_2$,

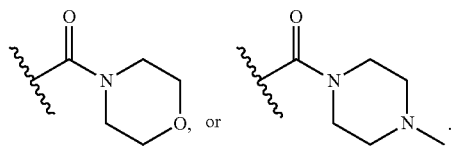

In some embodiments, Ring C is

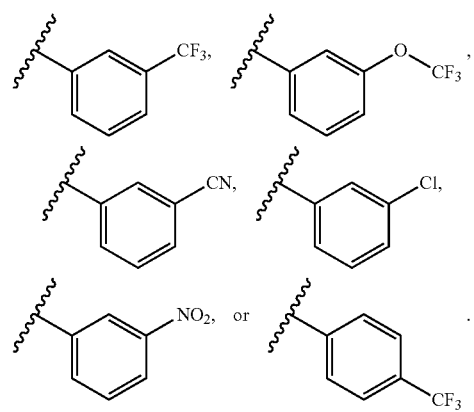

In some embodiments, Ring C is

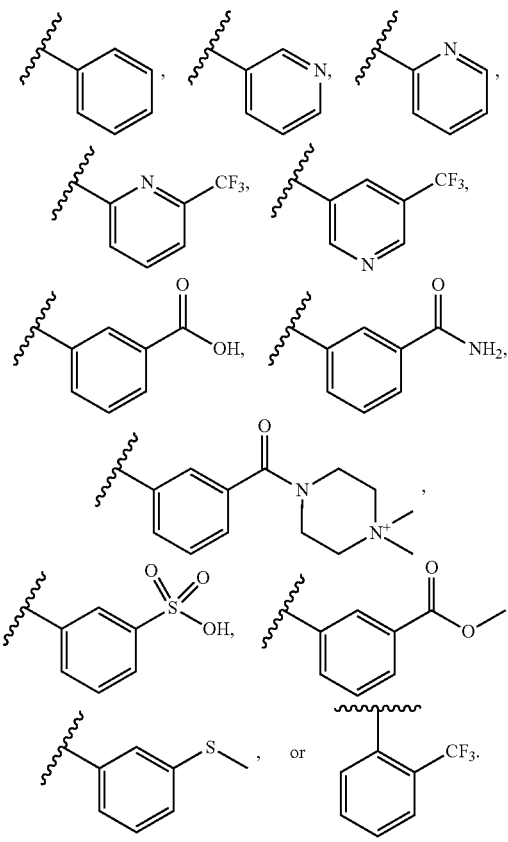

In some embodiments, Ring C is selected from those depicted in Table 1-a, below.

As defined generally above, $R^{11}$ is —R, —C(O)—$R^W$, —C(=N$R^W$)—$R^W$, —S(O)$_2$—$R^W$, or —S(O)—$R^W$, wherein each $R^W$ is independently as defined below and described in embodiments herein.

In some embodiments, $R^{11}$ is —R, wherein R is as defined below and described in embodiments herein. In some embodiments, $R^{11}$ is —C(O)—$R^W$, wherein $R^W$ is as defined below and described in embodiments herein. In some embodiments, $R^{11}$ is —C(=N$R^W$)—$R^W$, wherein each $R^W$ is independently as defined below and described in embodiments herein. In some embodiments, $R^{11}$ is —S(O)$_2$—$R^W$, wherein $R^W$ is as defined below and described in embodiments herein. In some embodiments, $R^{11}$ is —S(O)—$R^W$, wherein $R^W$ is as defined below and described in embodiments herein.

In some embodiments, $R^{11}$ is H. In some embodiments, $R^{11}$ is optionally substituted $C_{1-6}$ aliphatic. In some embodiments, $R^{11}$ is optionally substituted $C_{1-6}$ alkyl.

In some embodiments, $R^{11}$ is —OR, —SR, —C(O)—R, —C(O)OR, —C(O)—N(R)$_2$, —C(=NR)—N(R)$_2$, —S(O)$_2$—R, —S(O)$_2$OR, or —S(O)$_2$—N(R)$_2$, wherein R is optionally substituted $C_{1-6}$ alkyl. In some embodiments, $R^{11}$ is —OR, —SR, —C(O)—R, —C(O)OR, —C(O)—N(R)$_2$, —C(=NR)—N(R)$_2$, —S(O)$_2$—R, —S(O)$_2$OR, or —S(O)$_2$—N(R)$_2$, wherein R is $C_{1-6}$ alkyl substituted by

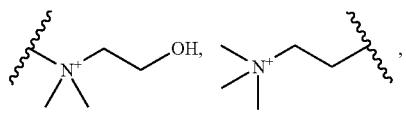

-continued

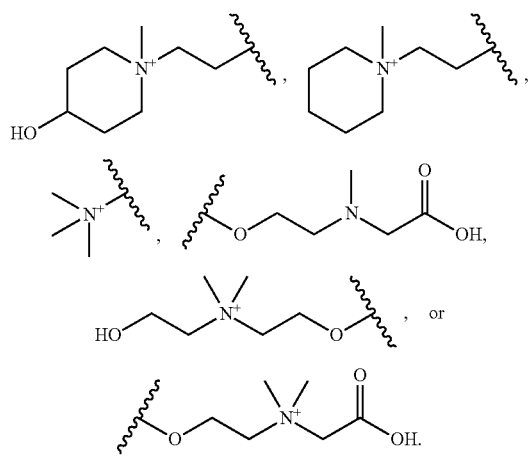

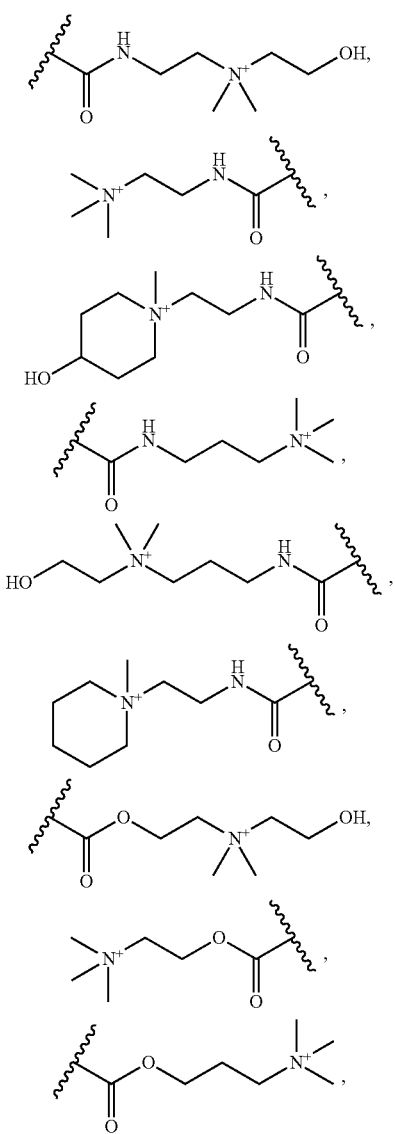

In some embodiments, R[11] is

-continued

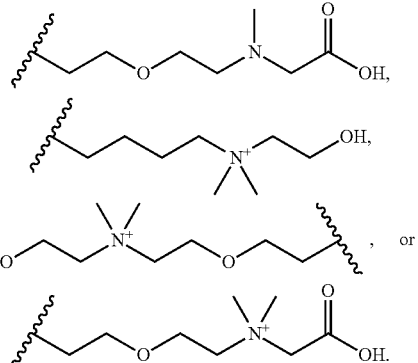

In some embodiments, R[11] is

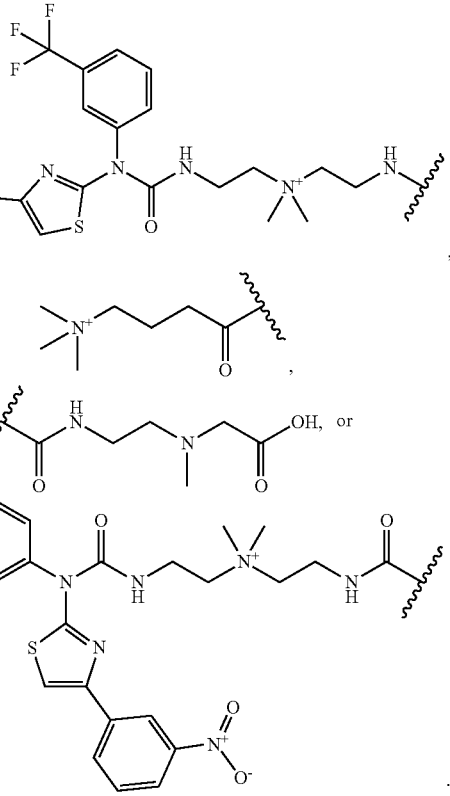

In some embodiments, R[11] is not —C(O)H.

In some embodiments, R[11] is selected from those depicted in Table 1-a, below.

As defined generally above, R[W] is —R, —N(R)$_2$, —NR—OR, —N(R)—N(R)$_2$, —N(OR)—N(R)$_2$, —N(R)—N(OR)R, —OR, —O—N(R)$_2$, or SR.

In some embodiments, R[W] is —R, wherein R is as defined below and described in embodiments herein. In some embodiments, R[W] is —N(R)$_2$, wherein each R is independently as defined below and described in embodiments herein. In some embodiments, R[W] is —NR—OR, wherein each R is independently as defined below and described in embodiments herein. In some embodiments, R[W] is —N(R)—N(R)$_2$, wherein each R is independently as defined below and described in embodiments herein. In some embodiments, R[W] is —N(OR)—N(R)$_2$, wherein each R is independently as defined below and described in embodiments herein. In some embodiments, $R^W$ is —N(R)—N(OR)R, wherein each R is independently as defined below and described in embodiments herein. In some embodiments, $R^W$ is —OR, wherein R is as defined below and described in embodiments herein. In some embodiments, $R^W$ is —O—N(R)$_2$, wherein each R is independently as defined below and described in embodiments herein. In some embodiments, $R^W$ is —SR, wherein R is as defined below and described in embodiments herein.

In some embodiments, $R^W$ is selected from those depicted in Table 1-a, below.

As defined generally above, R is hydrogen, optionally substituted $C_{1-6}$ aliphatic, an optionally substituted 3-7 membered carbocyclic ring, or an optionally substituted 3-7 membered heterocyclic ring having 1-3 heteroatoms independently selected from N, O, or S, or two R's together with the nitrogen to which they attach form an optionally substituted 5-7 membered heterocyclic ring having 0-2 heteroatoms independently selected from N, O, or S in addition to the nitrogen to which the two R's attach.

In some embodiments, R is hydrogen. In some embodiments, R is optionally substituted $C_{1-6}$ aliphatic. In some embodiments, R is optionally substituted $C_{1-6}$ alkyl. In some embodiments, R is unsubstituted —$C_{1-6}$ aliphatic. In some embodiments, R is unsubstituted —$C_{1-6}$ alkyl. In some embodiments, R is —$C_{1-6}$ aliphatic which is substituted by —CH$_3$, —CF$_3$, —OH, —OCH$_3$, —OCF$_3$, —N(CH$_3$)$_2$, —N$^+$(CH$_3$)$_3$,

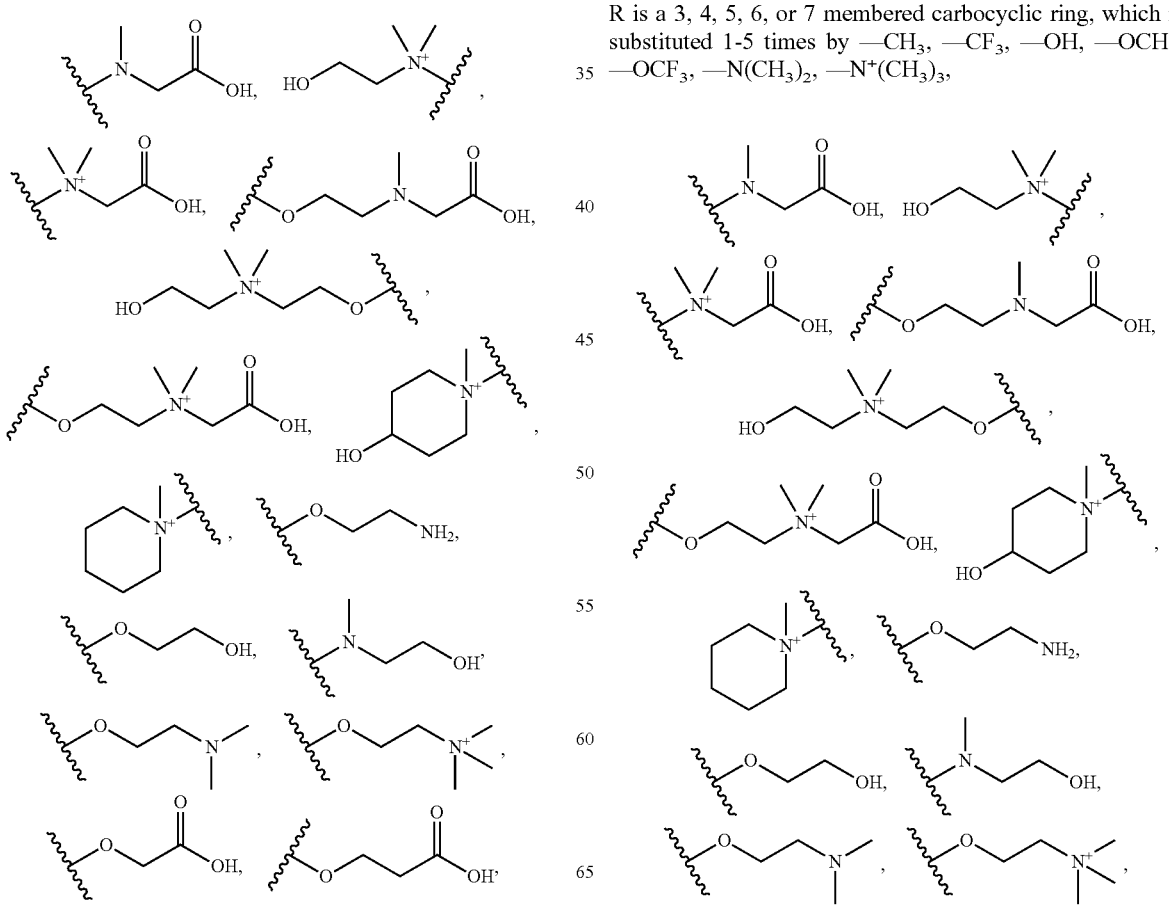

In some embodiments, R is —$C_{1-6}$ aliphatic substituted 1-6 times by halogen. In some embodiments, R is —$C_{1-6}$ alkyl substituted 1-6 times by halogen. In some embodiments, R is —$C_{1-6}$ alkyl substituted 1-6 times by F. In some embodiments, R is —CH$_3$. In some embodiments, R is —CH$_2$CH$_3$. In some embodiments, R is —CH$_2$CH$_2$CH$_3$. In some embodiments, R is —CH(CH$_3$)$_2$. In some embodiments, R is —CH$_2$CH$_2$CH$_2$CH$_3$. In some embodiments, R is —CH$_2$CH(CH$_3$)$_2$. In some embodiments, R is —C(CH$_3$)$_3$. In some embodiments, R is —CF$_3$.

In some embodiments, R is an optionally substituted 3, 4, 5, 6, or 7 membered carbocyclic ring. In some embodiments, R is a 3, 4, 5, 6, or 7 membered carbocyclic ring, which is substituted 1-5 times by —CH$_3$, —CF$_3$, —OH, —OCH$_3$, —OCF$_3$, —N(CH$_3$)$_2$, —N$^+$(CH$_3$)$_3$,

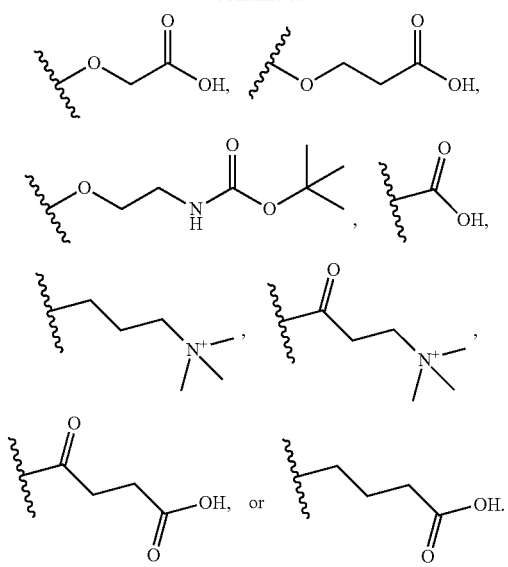

In some embodiments, R is an optionally substituted

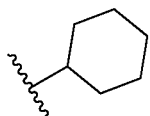

In some embodiments, R is an optionally substituted 3, 4, 5, 6, or 7 membered heterocyclic ring having 1, 2, or 3 heteroatoms independently selected from N, O, or S. In some embodiments, R is a 3, 4, 5, 6, or 7 membered heterocyclic ring having 1, 2, or 3 heteroatoms independently selected from N, O, or S, which is substituted 1-5 times by —CH$_3$, —CF$_3$, —OH, —OCH$_3$, —OCF$_3$, —N(CH$_3$)$_2$, —N$^+$(CH$_3$)$_3$,

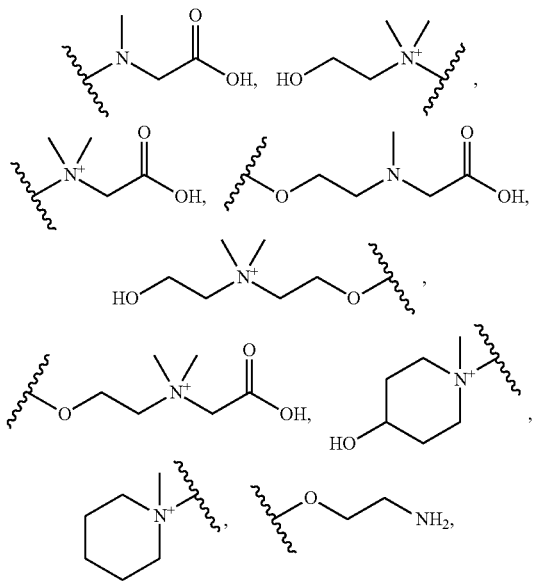

In some embodiments, R is an optionally substituted 5, 6, or 7 membered heterocyclic ring having 1, 2, or 3 heteroatoms independently selected from N, O, or S. In some embodiments, R is an optionally substituted 6-membered heterocyclic ring having 1 or 2 heteroatoms independently selected from N, O, or S.

In some embodiments, R is optionally substituted

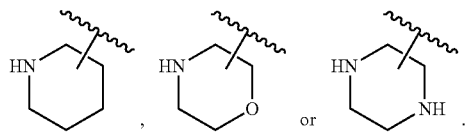

In some embodiments, R is optionally substituted

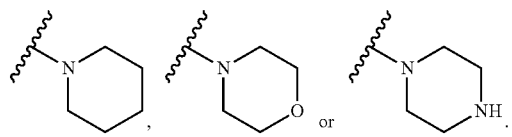

In some embodiments, R is

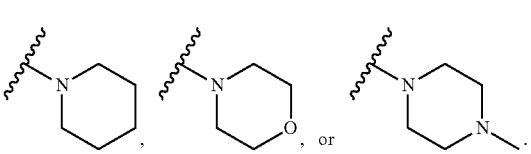

In some embodiments, two R's together with the nitrogen to which they attach form an optionally substituted 5-7 membered heterocyclic ring having 0-2 heteroatoms independently selected from N, O, or S in addition to the nitrogen to which the two R's attach. In some embodiments, two R's together with the nitrogen to which they attach form an optionally substituted 5-7 membered heterocyclic ring having 0 or 1 heteroatom selected from N, O, or S in addition to the nitrogen to which the two R's attach. In some embodiments, —N(R)₂ is optionally substituted

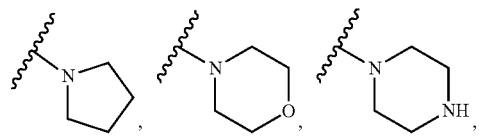

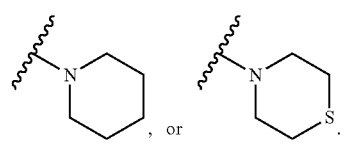

In some embodiments, R is selected from those depicted in Table 1-a, below.

In some embodiments, the present invention provides a compound of Formula (I-a):

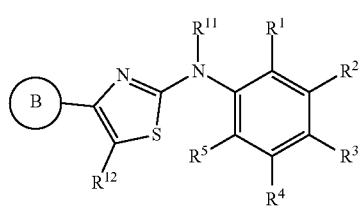

(I-a)

or a pharmaceutically acceptable salt thereof, wherein each variable is as defined above and described in embodiments herein, both singly and in combination.

In some embodiments, the present invention provides a compound of Formula (II):

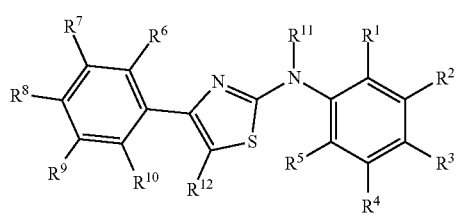

(II)

or a pharmaceutically acceptable salt thereof, wherein each variable is as defined above and described in embodiments herein, both singly and in combination.

In some embodiments, the present invention provides a compound of Formula (III)

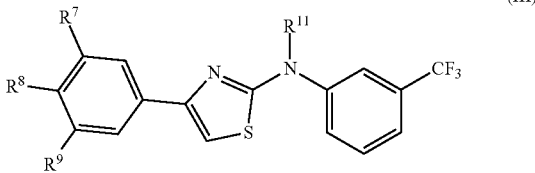

(III)

or a pharmaceutically acceptable salt thereof, wherein each variable is as defined above and described in embodiments herein, both singly and in combination.

In some embodiments, the present invention provides a compound of Formula (IV):

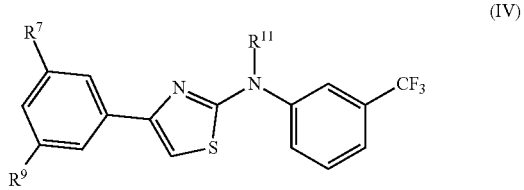

(IV)

or a pharmaceutically acceptable salt thereof, wherein each variable is as defined above and described in embodiments herein, both singly and in combination.

In some embodiments, the present invention provides a compound of Formula (V):

(V)

or a pharmaceutically acceptable salt thereof, wherein each variable is as defined above and described in embodiments herein, both singly and in combination.

In some embodiments, the present invention provides a compound of Formula (VI):

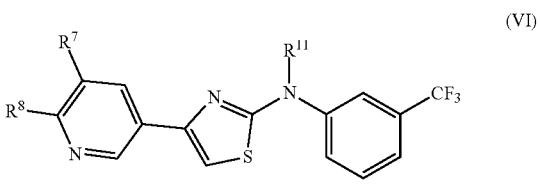

(VI)

or a pharmaceutically acceptable salt thereof, wherein each variable is as defined above and described in embodiments herein, both singly and in combination.

In some embodiments, the present invention provides a compound of Formula (VII):

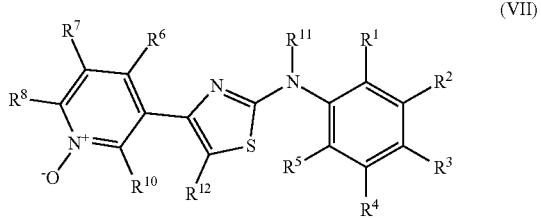

(VII)

or a pharmaceutically acceptable salt thereof, wherein each variable is as defined above and described in embodiments herein, both singly and in combination.

In some embodiments, the present invention provides a compound of Formula (VIII):

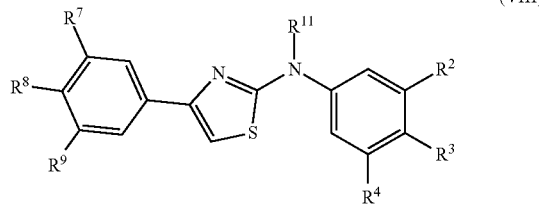

(VIII)

or a pharmaceutically acceptable salt thereof, wherein $R^{11}$ is —C(O)—$R^W$, except that $R^{11}$ is not —C(O)H; and each of $R^W$, $R^2$, $R^3$, $R^4$, $R^7$, $R^8$, and $R^9$ is as defined above and described in embodiments herein, both singly and in combination.

In some embodiments, the present invention provides a compound of Formula (VIII), or a pharmaceutically acceptable salt thereof, wherein $R^{11}$ is —C(O)—N(R)$_2$, —C(O)—NR—OR, —C(O)—N(R)—N(R)$_2$, —C(O)—N(OR)—N(R)$_2$, —C(O)—N(R)—N(OR)R, wherein each of R, $R^2$, $R^3$, $R^4$, $R^7$, $R^8$, and $R^9$ is as defined above and described in embodiments herein, both singly and in combination.

In some embodiments, the present invention provides a compound of Formula (VIII), or a pharmaceutically acceptable salt thereof, wherein $R^{11}$ is —C(O)OR or —C(O)O—N(R)$_2$, and each of R, $R^2$, $R^3$, $R^4$, $R^7$, $R^8$, and $R^9$ is as defined above and described in embodiments herein, both singly and in combination.

In some embodiments, the present invention provides a compound of Formula (IX):

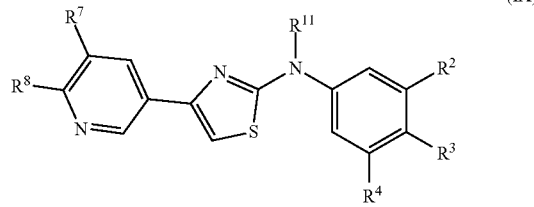

(IX)

or a pharmaceutically acceptable salt thereof, wherein $R^{11}$ is —C(O)—$R^W$, and each of $R^W$, $R^2$, $R^3$, $R^4$, $R^7$, and $R^8$ is as defined above and described in embodiments herein, both singly and in combination.

In some embodiments, the present invention provides a compound of Formula (IX), or a pharmaceutically acceptable salt thereof, wherein:

$R^{11}$ is —C(O)—$R^W$, except that $R^{11}$ is not —C(O)H; and
each of $R^W$, $R^2$, $R^3$, $R^4$, $R^7$, and $R^8$ is as defined above and described in embodiments herein, both singly and in combination.

In some embodiments, the present invention provides a compound of Formula (VI):

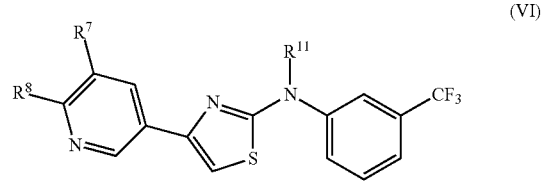

(VI)

or a pharmaceutically acceptable salt thereof, wherein:
$R^{11}$ is —C(O)—$R^W$, except that $R^{11}$ is not —(O)H; and
each of $R^W$, $R^7$ and $R^8$ is as defined above and described in embodiments herein, both singly and in combination.

In some embodiments, the present invention provides a compound of Formula (X):

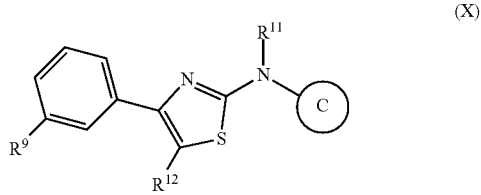

(X)

or a pharmaceutically acceptable salt thereof, wherein each of $R^9$, $R^{11}$, $R^{12}$ and Ring C is as defined above and described in embodiments herein, both singly and in combination.

In some embodiments, the present invention provides a compound selected from Formulas (X-1) to (X-10):

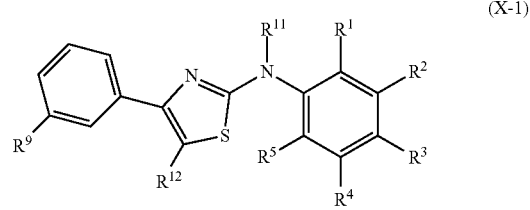

(X-1)

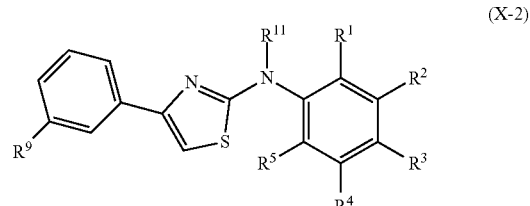

(X-2)

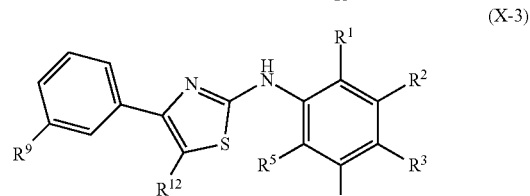

(X-3)

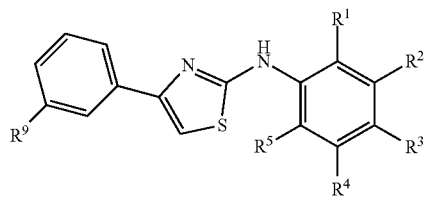
(X-4)

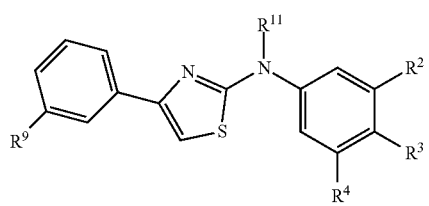
(X-5)

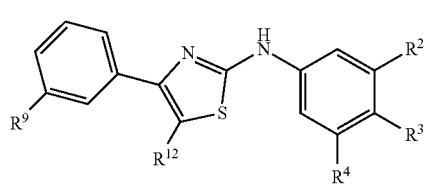
(X-6)

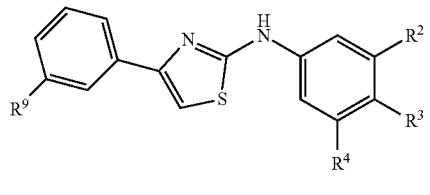
(X-7)

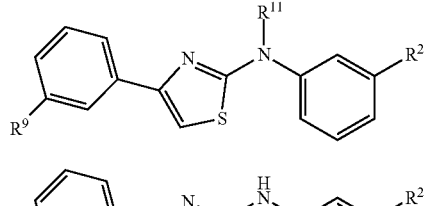
(X-8)

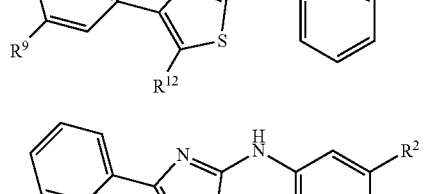
(X-9)

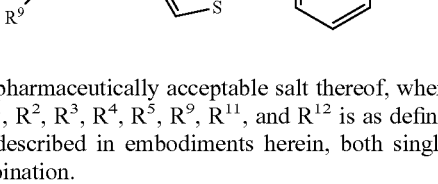
(X-10)

or a pharmaceutically acceptable salt thereof, wherein each of $R^1$, $R^2$, $R^3$, $R^4$, $R^5$, $R^9$, $R^{11}$, and $R^{12}$ is as defined above and described in embodiments herein, both singly and in combination.

In some embodiments, the present invention provides a dimerized compound, or a pharmaceutically acceptable salt thereof, wherein one compound of formulas (I)-(IX) attaches to another compound of formulas (I)-(IX) via a covalent linker $L^1$, as defined below and described in embodiments. In some embodiments, a covalent linker $L^1$ attaches to Ring A of a compound of formulas (I)-(IX). In some embodiments, a covalent linker $L^1$ attaches to Ring B of a compound of formulas (I)-(IX). In some embodiments, a covalent linker $L^1$ attaches to Ring C of a compound of formulas (I)-(IX). In some embodiments, a covalent linker $L^1$ attaches to the N between Ring A and Ring C of a compound of formulas (I)-(IX). In some embodiments, the present invention provides a compound of formulas (DI) to (D4):

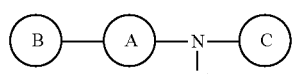
(D1)

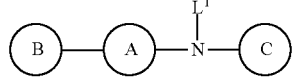
(D2)

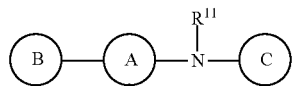
(D3)

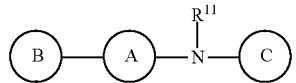
(D4)

or a pharmaceutically acceptable salt thereof, wherein each variable is as defined below and described in embodiments herein, both singly and in combination.

In some embodiments, the present invention provides a compound of formulas (D5):

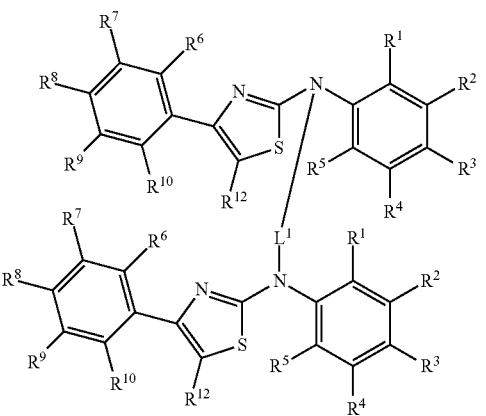
(D5)

or a pharmaceutically acceptable salt thereof, wherein each variable is as defined below and described in embodiments herein, both singly and in combination.

In some embodiments, the present invention provides a compound of formula (D6):

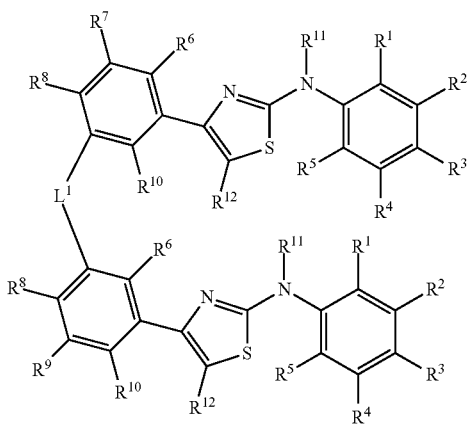

(D6)

or a pharmaceutically acceptable salt thereof, wherein each variable is as defined below and described in embodiments herein, both singly and in combination, and wherein at least one of $R^6$, $R^7$, $R^8$, $R^9$, and 10 is absent to accommodate the linkage $L^1$.

In some embodiments, the present invention provides a compound selected from Formulas (D6-a) to (D6-j):

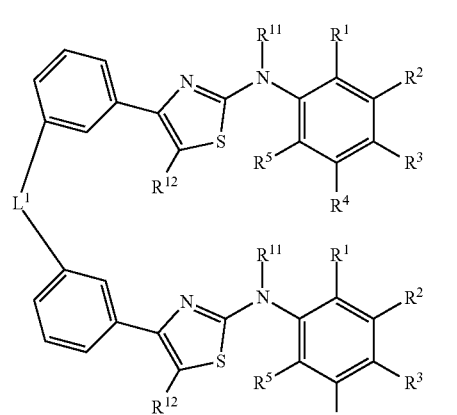

(D6-a)

(D6-b)

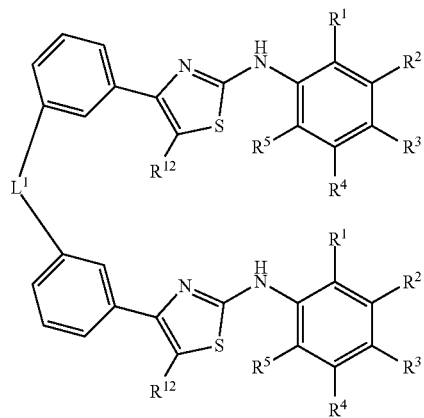

(D6-c)

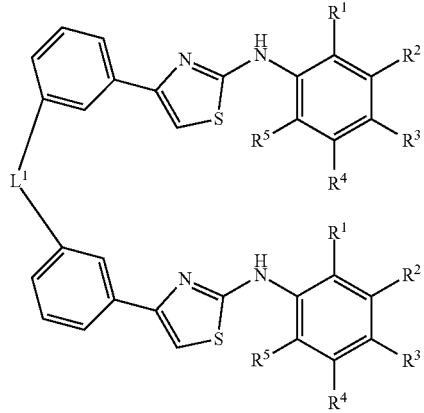

(D6-d)

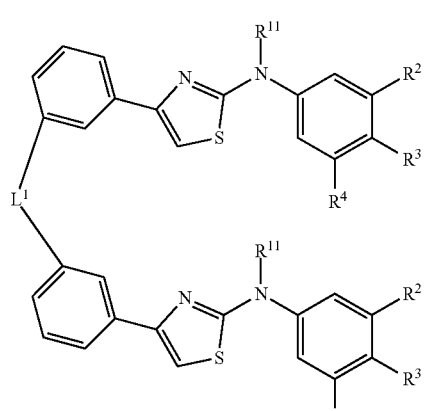

(D6-e)

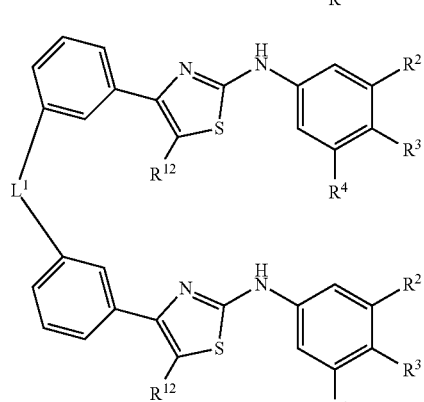

(D6-f)

(D6-g)
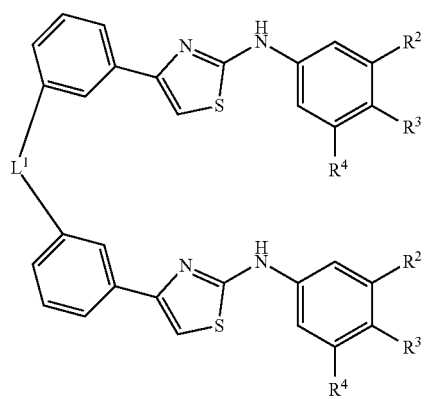

(D6-h)
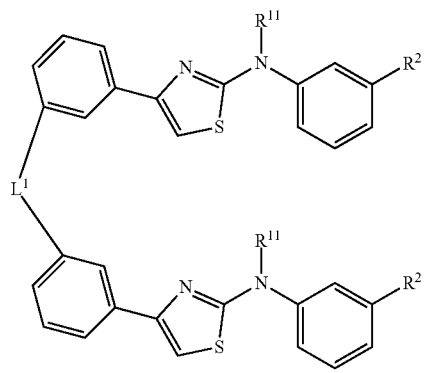

(D6-i)
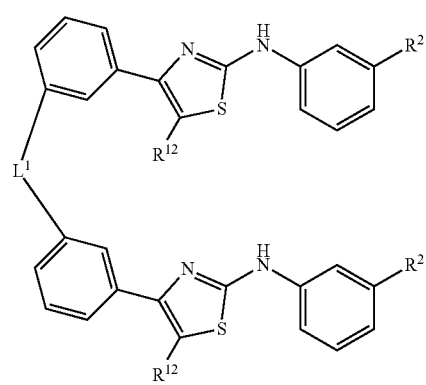

(D6-j)
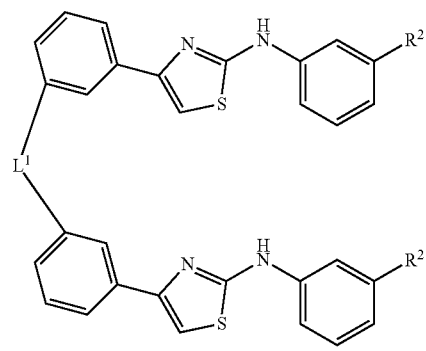

or a pharmaceutically acceptable salt thereof, wherein each of $R^1$, $R^2$, $R^3$, $R^4$, $R^5$, $R^9$, $R^{11}$, $R^{12}$, and $L^1$ is as defined and described in embodiments herein, both singly and in combination.

In some embodiments, $L^1$ is a $C_{1-10}$ bivalent straight or branched hydrocarbon chain wherein 1, 2, or 3 methylene units of the chain are independently and optionally replaced with —O—, —CH(OR)—, —CH(SR)—, —CH(N(R)$_2$)—, —C(O)—, —C(O)O—, —OC(O)—, —N(R)—, —N$^+$(R)$_2$—, —N=N—, —C(O)N(R)—, —(R)NC(O)—, —OC(O)N(R)—, —(R)NC(O)O—, —N(R)C(O)N(R)—, —S—, —SO—, —SO$_2$—, —SO$_2$N(R)—, —(R)NSO$_2$—, —C(S)—, —C(S)O—, —OC(S)—, —C(S)N(R)—, —(R)NC(S)—, or —(R)NC(S)N(R)—, wherein each R is independently as defined below and described in embodiments herein.

In some embodiments, $L^1$ is —N=N— or

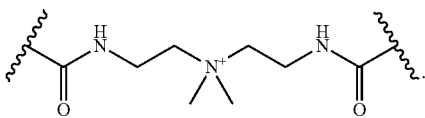 [SMILES: *C(=O)NCC[N+](C)(C)CCNC(*)=O]

In some embodiments, $L^1$ is —N=N—, which can be a Z isomer

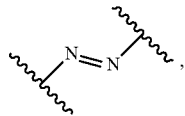 [SMILES: */N=N/*]

an E isomer

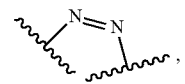

or a mixture of the Z and E isomers.

In some embodiments, $L^1$ is

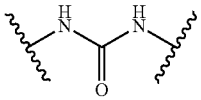 [SMILES: *NC(=O)N*]

or —NH—NH—.

Exemplary compounds of the invention are set forth in Table 1-a, below.

TABLE 1-a
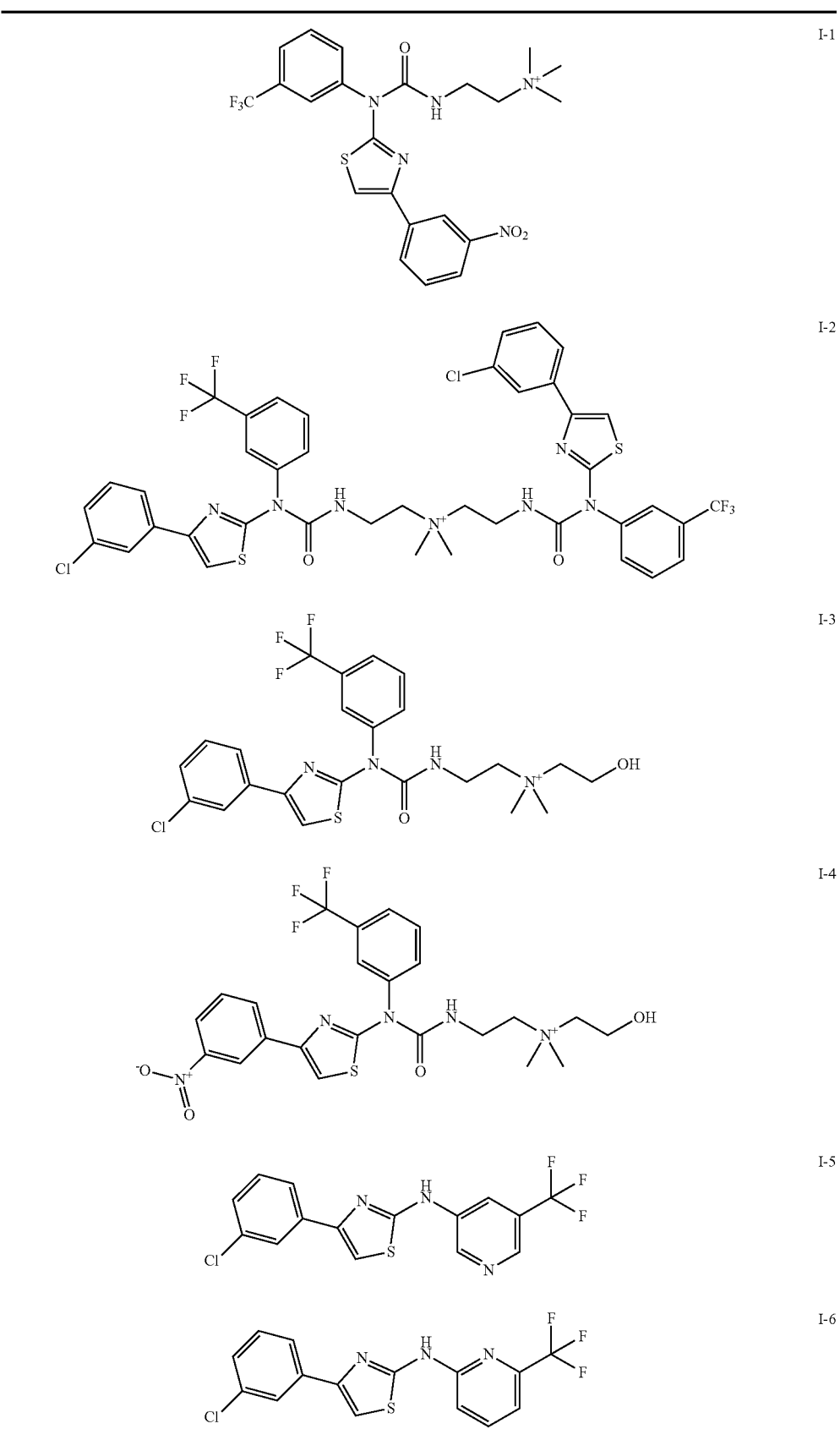

TABLE 1-a-continued
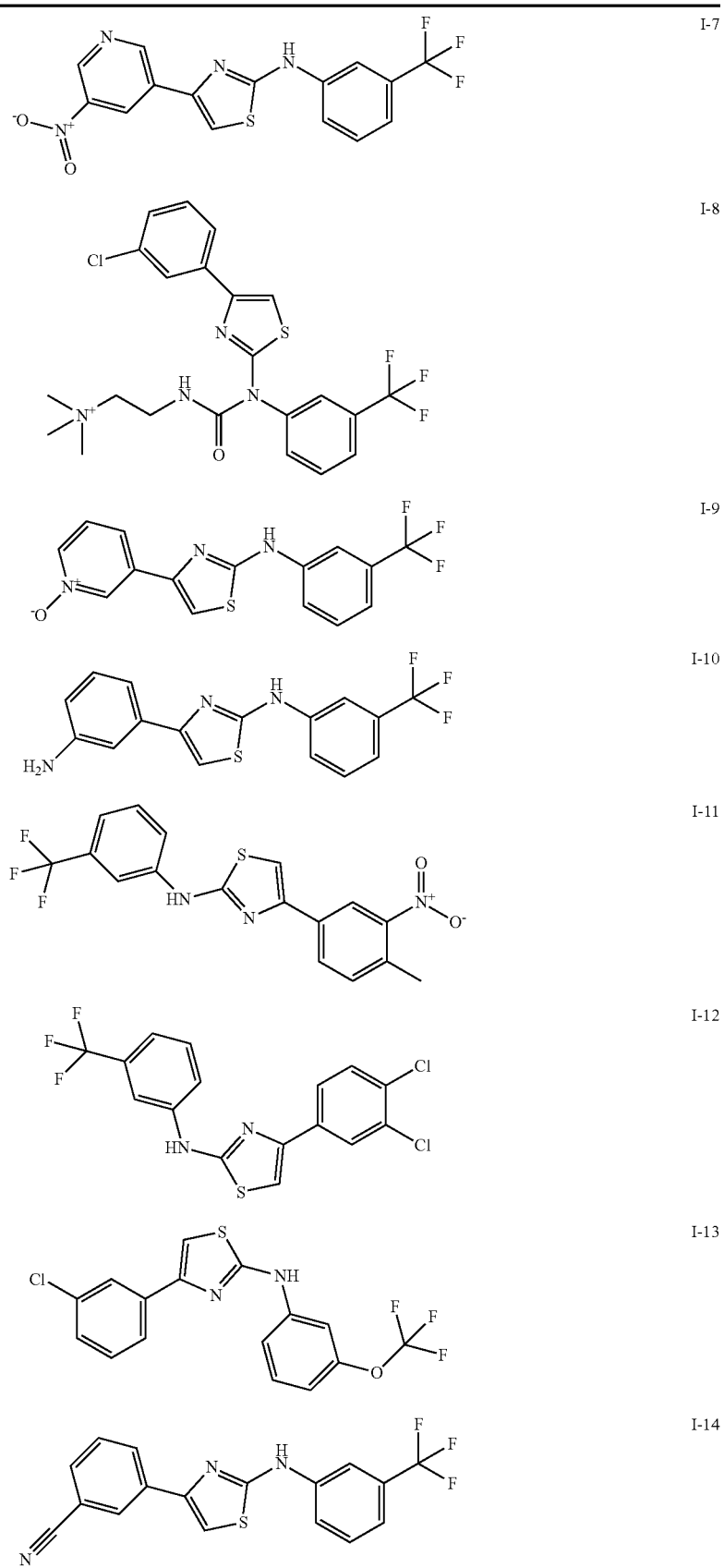

TABLE 1-a-continued
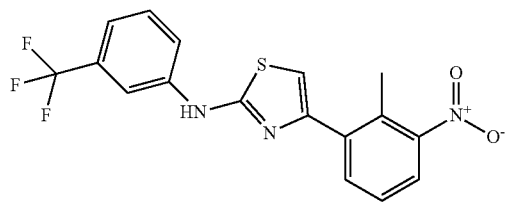 [SMILES: Cc1c(-c2csc(Nc3cccc(C(F)(F)F)c3)n2)cccc1[N+](=O)[O-]]
I-15
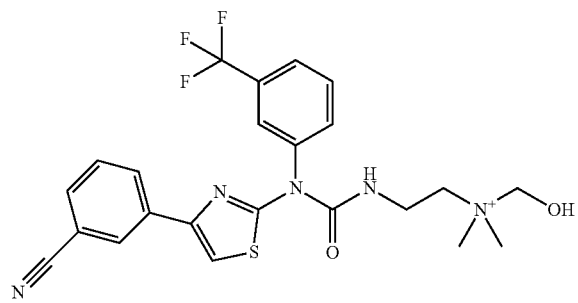 [SMILES: C[N+](C)(CO)CCNC(=O)N(c1cccc(C(F)(F)F)c1)c1nc(-c2cccc(C#N)c2)cs1]
I-16
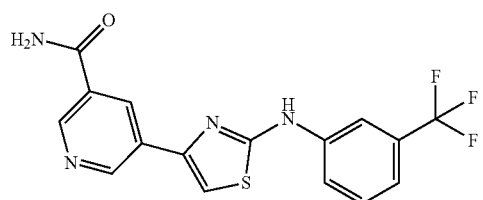
I-17
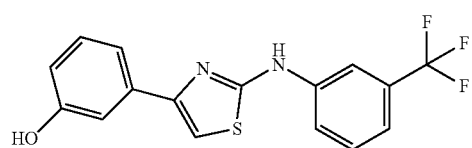
I-18
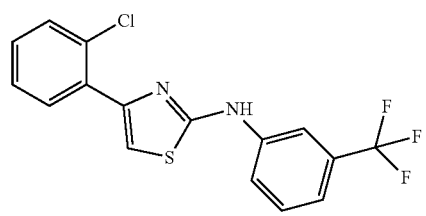 [SMILES: FC(F)(F)c1cccc(Nc2nc(-c3ccccc3Cl)cs2)c1]
I-19
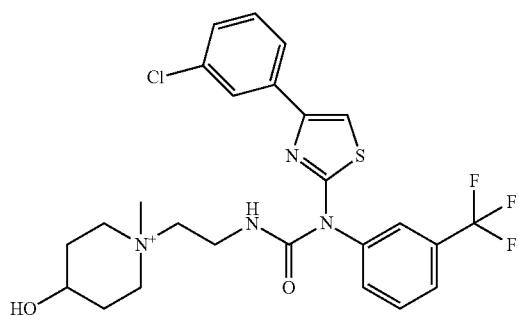 [SMILES: C[N+]1(CCNC(=O)N(c2cccc(C(F)(F)F)c2)c2nc(-c3cccc(Cl)c3)cs2)CCC(O)CC1]
I-20
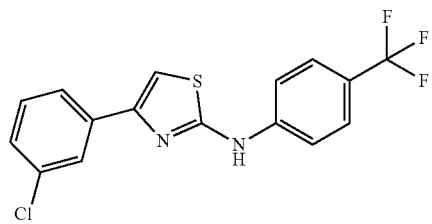
I-21

TABLE 1-a-continued
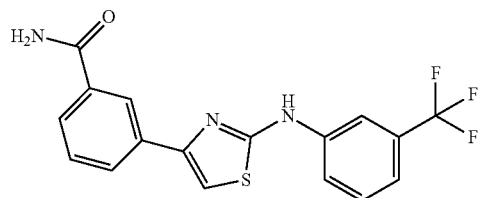 I-22
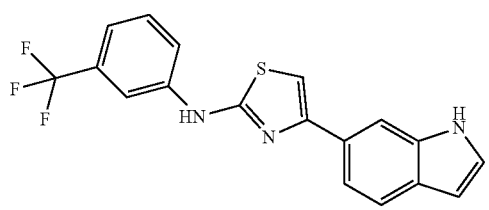 [SMILES: FC(F)(F)c1cccc(Nc2nc(-c3ccc4cc[nH]c4c3)cs2)c1] I-23
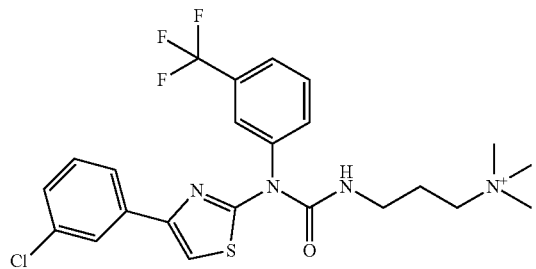 [SMILES: C[N+](C)(C)CCCNC(=O)N(c1cccc(C(F)(F)F)c1)c1nc(-c2cccc(Cl)c2)cs1] I-24
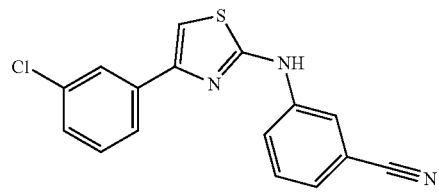 [SMILES: N#Cc1cccc(Nc2nc(-c3cccc(Cl)c3)cs2)c1] I-25
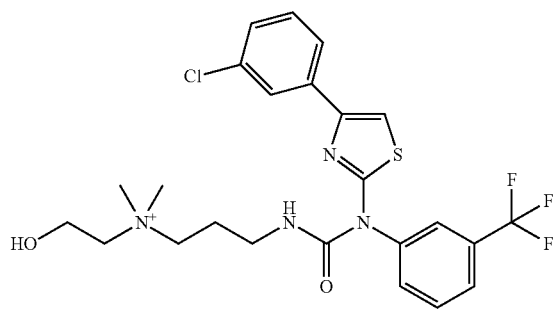 [SMILES: C[N+](C)(CCO)CCCNC(=O)N(c1cccc(C(F)(F)F)c1)c1nc(-c2cccc(Cl)c2)cs1] I-26
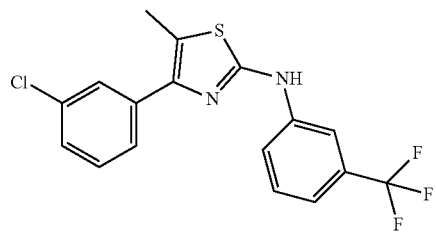 [SMILES: Cc1sc(Nc2cccc(C(F)(F)F)c2)nc1-c1cccc(Cl)c1] I-27

TABLE 1-a-continued
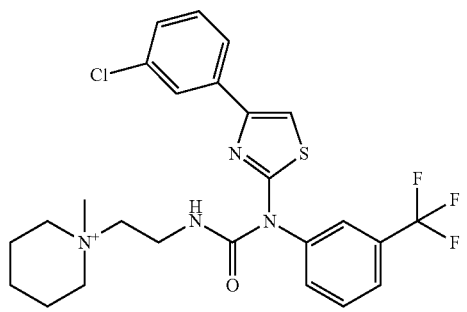 [SMILES: C[N+]1(CCNC(=O)N(c2cccc(C(F)(F)F)c2)c2nc(-c3cccc(Cl)c3)cs2)CCCCC1]
I-28
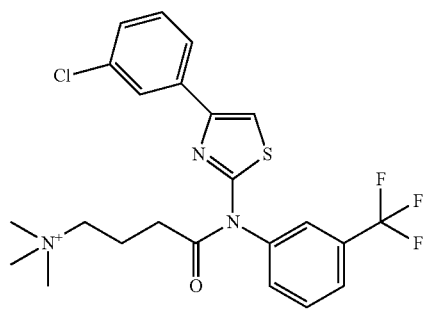 [SMILES: C[N+](C)(C)CCCC(=O)N(c1cccc(C(F)(F)F)c1)c1nc(-c2cccc(Cl)c2)cs1]
I-29
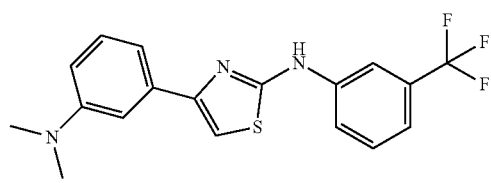 [SMILES: CN(C)c1cccc(-c2csc(Nc3cccc(C(F)(F)F)c3)n2)c1]
I-30
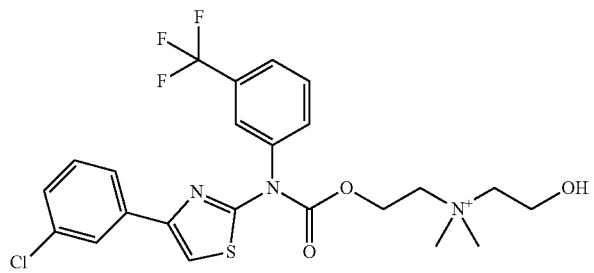 [SMILES: C[N+](C)(CCO)CCOC(=O)N(c1cccc(C(F)(F)F)c1)c1nc(-c2cccc(Cl)c2)cs1]
I-31
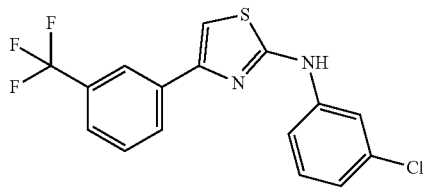 [SMILES: FC(F)(F)c1cccc(-c2csc(Nc3cccc(Cl)c3)n2)c1]
I-32
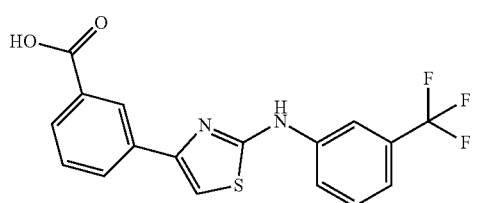
I-33

TABLE 1-a-continued
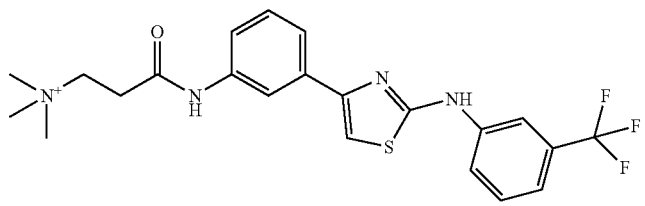 [SMILES: C[N+](C)(C)CCC(=O)Nc1cccc(-c2csc(Nc3cccc(C(F)(F)F)c3)n2)c1]
I-34
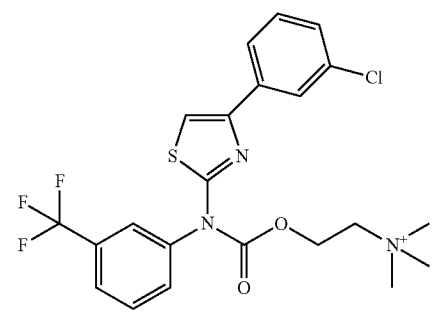 [SMILES: C[N+](C)(C)CCOC(=O)N(c1cccc(C(F)(F)F)c1)c1nc(-c2cccc(Cl)c2)cs1]
I-35
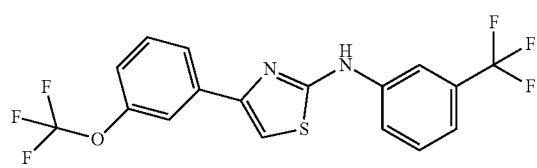 [SMILES: FC(F)(F)Oc1cccc(-c2csc(Nc3cccc(C(F)(F)F)c3)n2)c1]
I-36
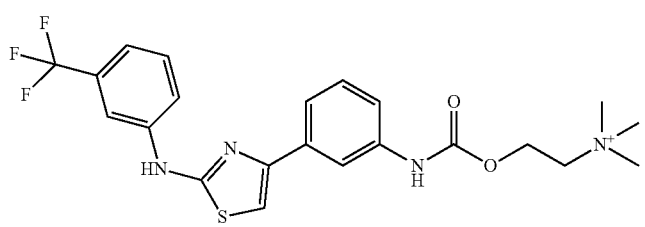 [SMILES: C[N+](C)(C)CCOC(=O)Nc1cccc(-c2csc(Nc3cccc(C(F)(F)F)c3)n2)c1]
I-37
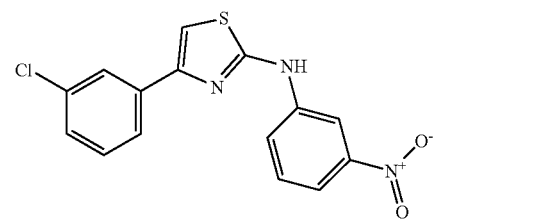 [SMILES: O=[N+]([O-])c1cccc(Nc2nc(-c3cccc(Cl)c3)cs2)c1]
I-38
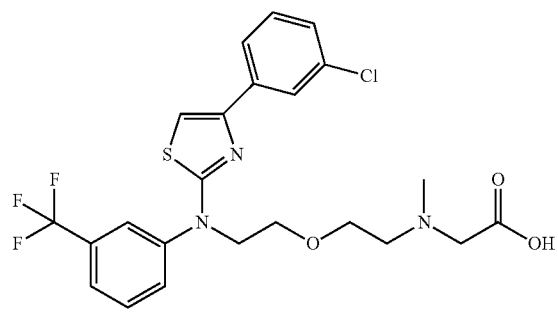 [SMILES: CN(CCOCCN(c1cccc(C(F)(F)F)c1)c1nc(-c2cccc(Cl)c2)cs1)CC(=O)O]
I-39

TABLE 1-a-continued
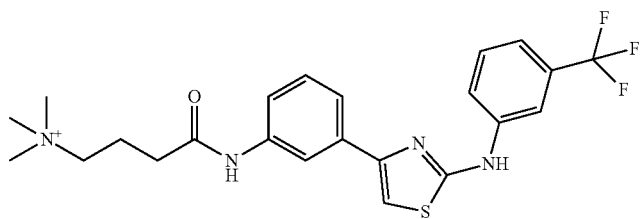 [SMILES: C[N+](C)(C)CCCC(=O)Nc1cccc(-c2csc(Nc3cccc(C(F)(F)F)c3)n2)c1]
I-40
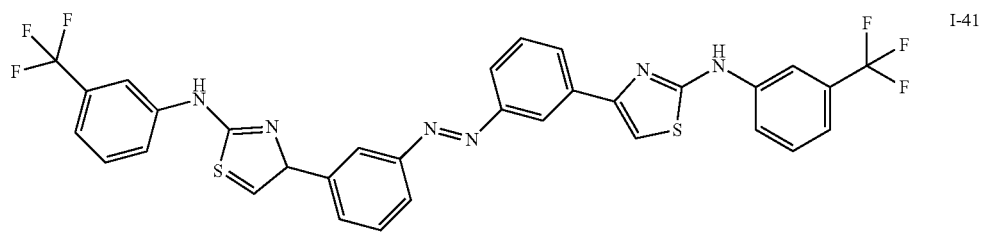
I-41
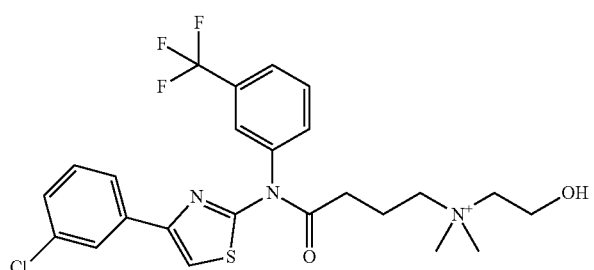
I-42
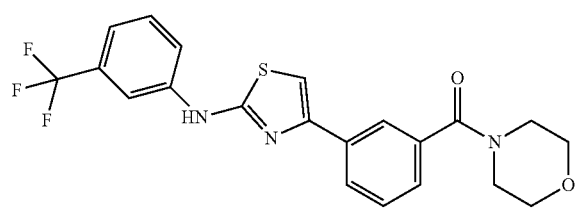 [SMILES: O=C(c1cccc(-c2csc(Nc3cccc(C(F)(F)F)c3)n2)c1)N1CCOCC1]
I-43
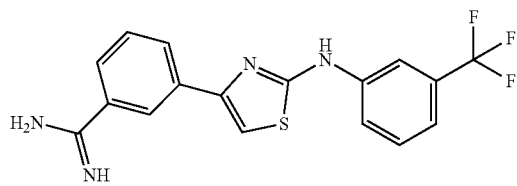 [SMILES: N=C(N)c1cccc(-c2csc(Nc3cccc(C(F)(F)F)c3)n2)c1]
I-44
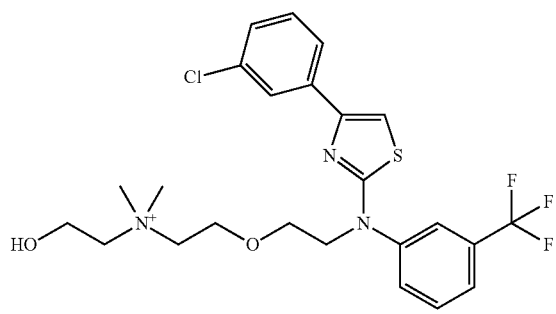 [SMILES: C[N+](C)(CCO)CCOCCN(c1cccc(C(F)(F)F)c1)c1nc(-c2cccc(Cl)c2)cs1]
I-45
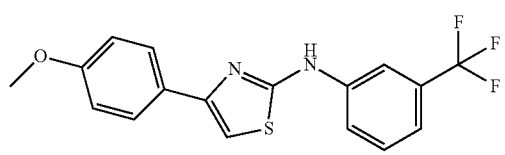 [SMILES: COc1ccc(-c2csc(Nc3cccc(C(F)(F)F)c3)n2)cc1]
I-46

TABLE 1-a-continued
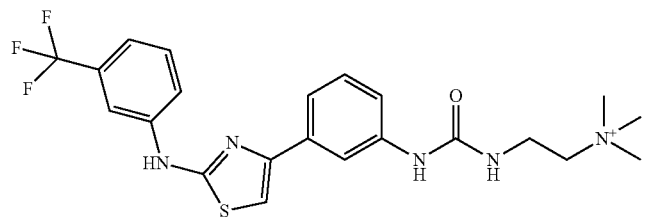 [SMILES: C[N+](C)(C)CCNC(=O)Nc1cccc(-c2csc(Nc3cccc(C(F)(F)F)c3)n2)c1]
I-47
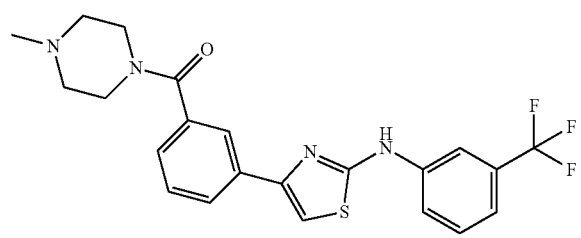 [SMILES: CN1CCN(C(=O)c2cccc(-c3csc(Nc4cccc(C(F)(F)F)c4)n3)c2)CC1]
I-48
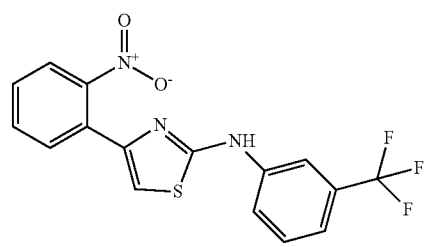 [SMILES: O=[N+]([O-])c1ccccc1-c1csc(Nc2cccc(C(F)(F)F)c2)n1]
I-49
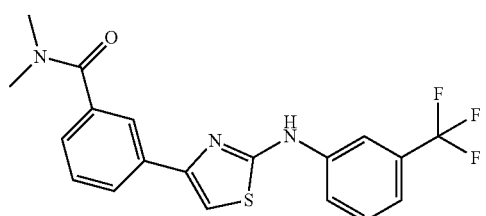
I-50
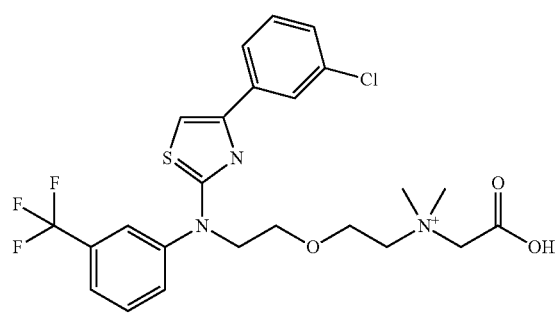
I-51
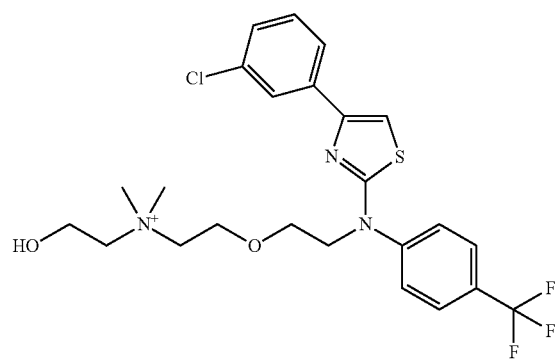 [SMILES: C[N+](C)(CCO)CCOCCN(c1ccc(C(F)(F)F)cc1)c1nc(-c2cccc(Cl)c2)cs1]
I-52

TABLE 1-a-continued
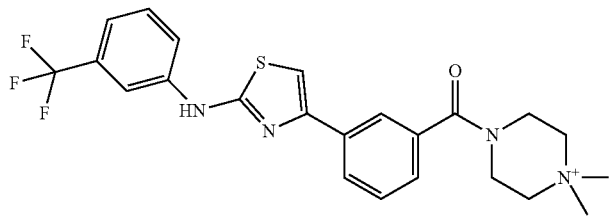 [SMILES: C[N+]1(C)CCN(C(=O)c2cccc(-c3csc(Nc4cccc(C(F)(F)F)c4)n3)c2)CC1]
I-53
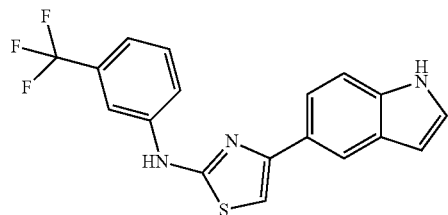 [SMILES: FC(F)(F)c1cccc(Nc2nc(-c3ccc4[nH]ccc4c3)cs2)c1]
I-54
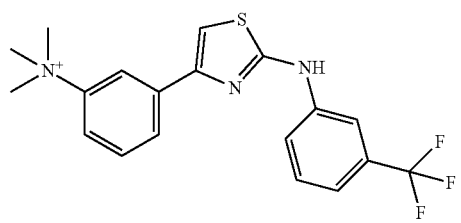 [SMILES: C[N+](C)(C)c1cccc(-c2csc(Nc3cccc(C(F)(F)F)c3)n2)c1]
I-55
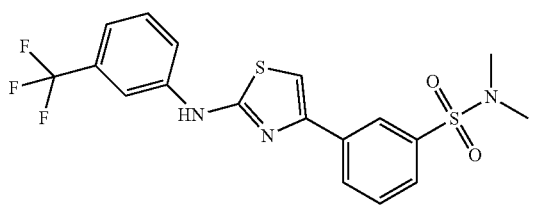 [SMILES: CN(C)S(=O)(=O)c1cccc(-c2csc(Nc3cccc(C(F)(F)F)c3)n2)c1]
I-56
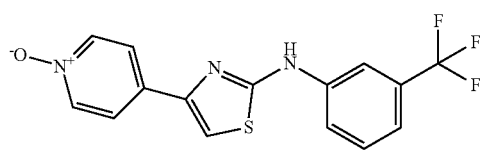
I-57
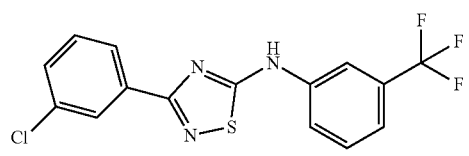 [SMILES: FC(F)(F)c1cccc(Nc2nc(-c3cccc(Cl)c3)ns2)c1]
I-58
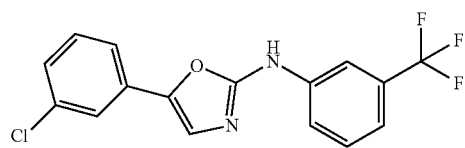 [SMILES: FC(F)(F)c1cccc(Nc2ncc(-c3cccc(Cl)c3)o2)c1]
I-59
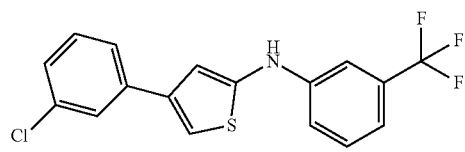 [SMILES: FC(F)(F)c1cccc(Nc2cc(-c3cccc(Cl)c3)cs2)c1]
I-60

TABLE 1-a-continued
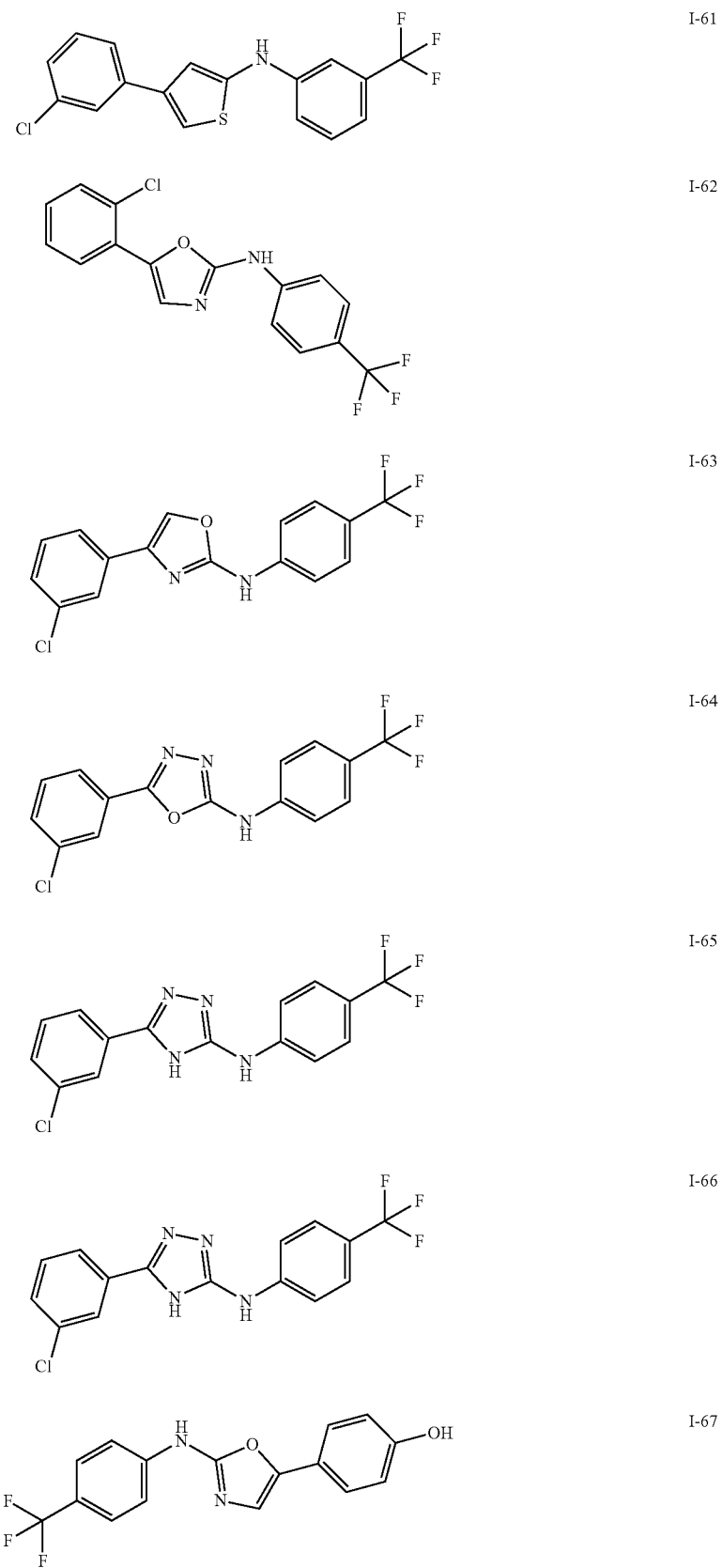

TABLE 1-a-continued
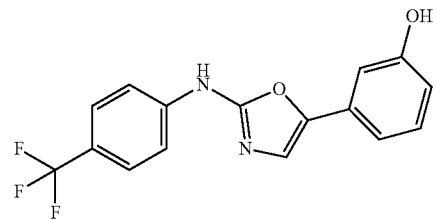 [SMILES: Oc1cccc(-c2cnc(Nc3ccc(C(F)(F)F)cc3)o2)c1]
I-68
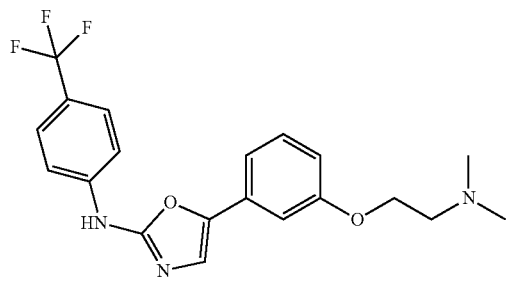 [SMILES: CN(C)CCOc1cccc(-c2cnc(Nc3ccc(C(F)(F)F)cc3)o2)c1]
I-69
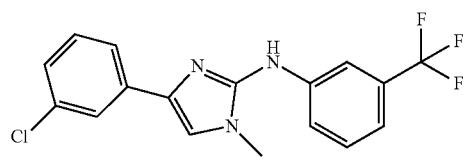 [SMILES: Cn1cc(-c2cccc(Cl)c2)nc1Nc1cccc(C(F)(F)F)c1]
I-70
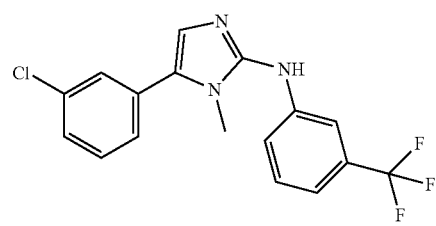 [SMILES: Cn1c(-c2cccc(Cl)c2)cnc1Nc1cccc(C(F)(F)F)c1]
I-71
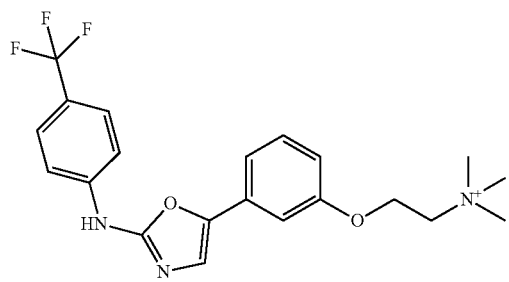 [SMILES: C[N+](C)(C)CCOc1cccc(-c2cnc(Nc3ccc(C(F)(F)F)cc3)o2)c1]
I-72
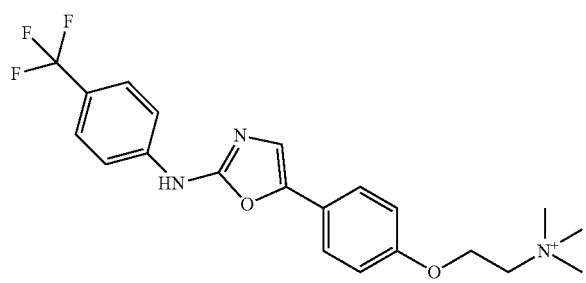 [SMILES: C[N+](C)(C)CCOc1ccc(-c2cnc(Nc3ccc(C(F)(F)F)cc3)o2)cc1]
I-73

TABLE 1-a-continued
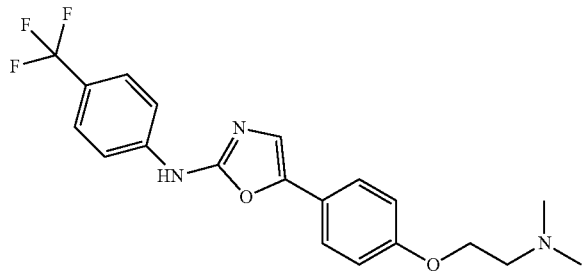 [SMILES: CN(C)CCOc1ccc(-c2cnc(Nc3ccc(C(F)(F)F)cc3)o2)cc1]
I-74
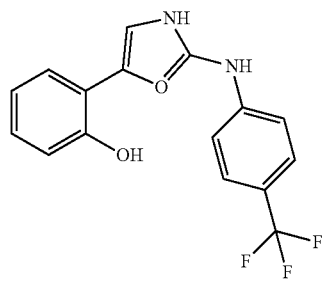
I-75
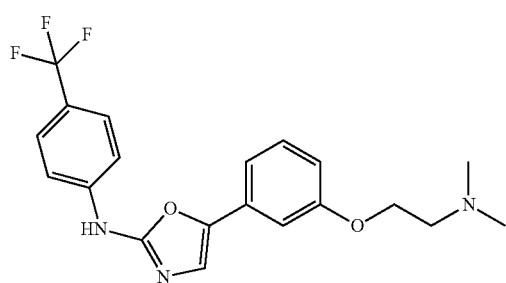 [SMILES: CN(C)CCOc1cccc(-c2cnc(Nc3ccc(C(F)(F)F)cc3)o2)c1]
I-76
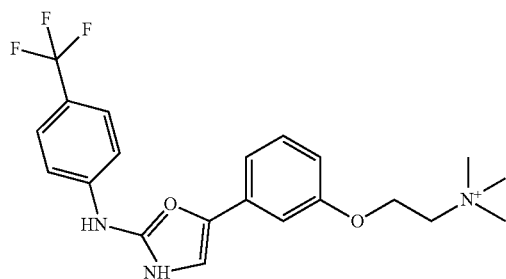
I-77
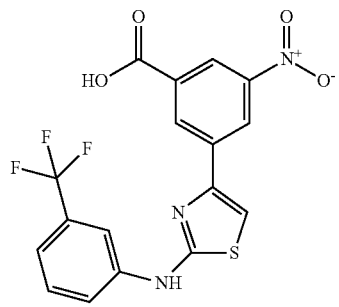 [SMILES: O=C(O)c1cc(-c2csc(Nc3cccc(C(F)(F)F)c3)n2)cc([N+](=O)[O-])c1]
I-78
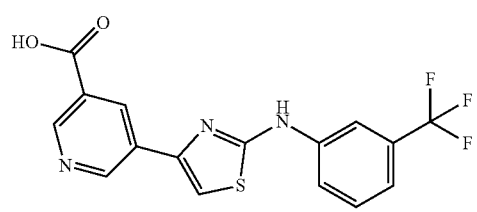 [SMILES: O=C(O)c1cncc(-c2csc(Nc3cccc(C(F)(F)F)c3)n2)c1]
I-79

TABLE 1-a-continued
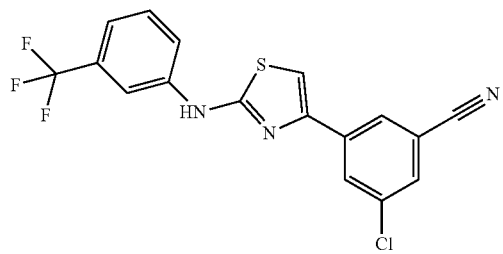 [SMILES: N#Cc1cc(Cl)cc(-c2csc(Nc3cccc(C(F)(F)F)c3)n2)c1]
I-80
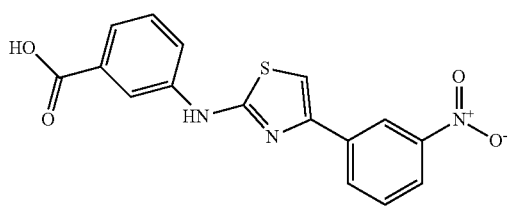 [SMILES: O=C(O)c1cccc(Nc2nc(-c3cccc([N+](=O)[O-])c3)cs2)c1]
I-81
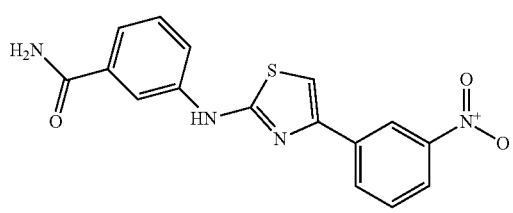
I-82
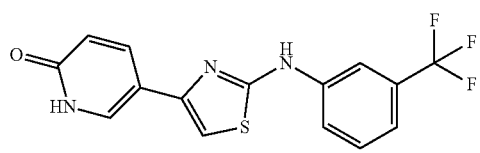 [SMILES: O=c1ccc(-c2csc(Nc3cccc(C(F)(F)F)c3)n2)c[nH]1]
I-83
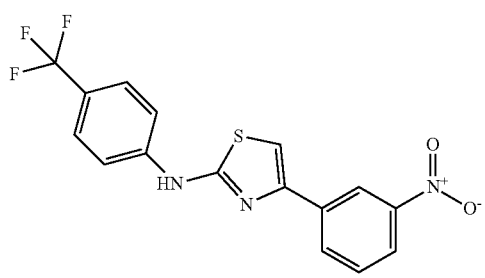 [SMILES: O=[N+]([O-])c1cccc(-c2csc(Nc3ccc(C(F)(F)F)cc3)n2)c1]
I-84
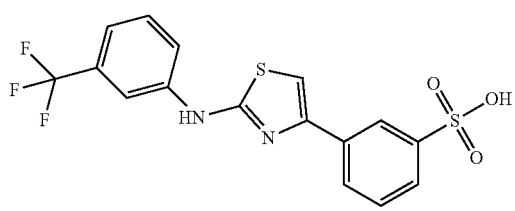 [SMILES: O=S(=O)(O)c1cccc(-c2csc(Nc3cccc(C(F)(F)F)c3)n2)c1]
I-85

TABLE 1-a-continued
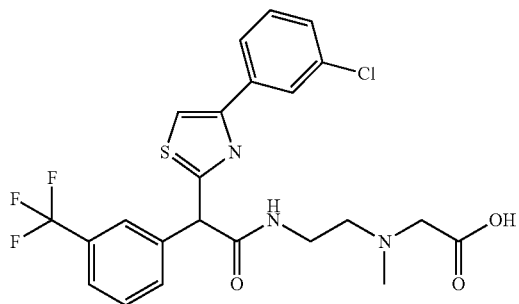
I-86
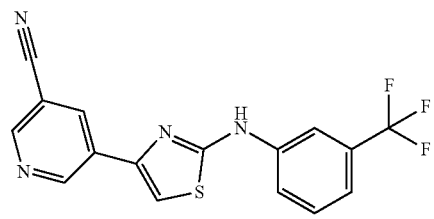 [SMILES: N#Cc1cncc(-c2csc(Nc3cccc(C(F)(F)F)c3)n2)c1]
I-87
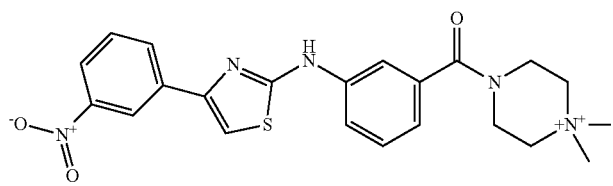
I-88
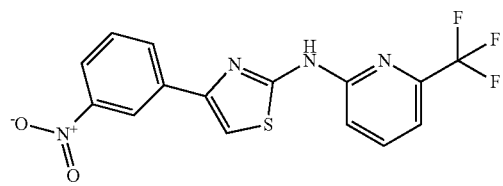
I-89
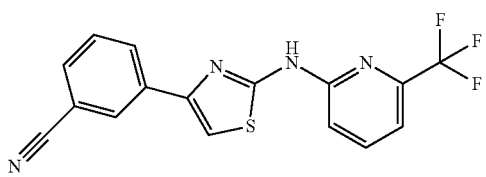 [SMILES: N#Cc1cccc(-c2csc(Nc3cccc(C(F)(F)F)n3)n2)c1]
I-90
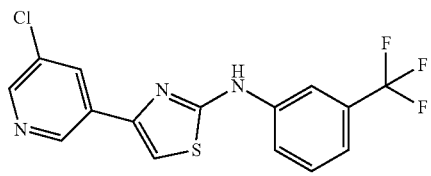 [SMILES: FC(F)(F)c1cccc(Nc2nc(-c3cncc(Cl)c3)cs2)c1]
I-91
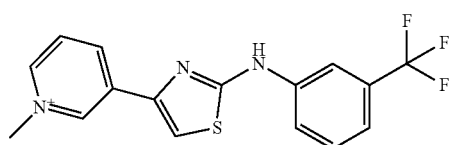
I-92
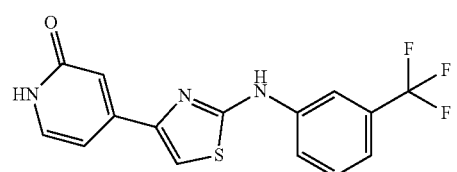
I-93

TABLE 1-a-continued
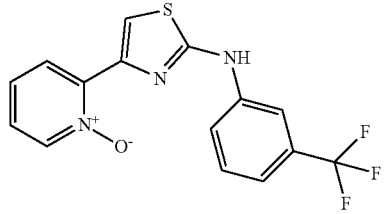 [SMILES: [O-][n+]1ccccc1-c1csc(Nc2cccc(C(F)(F)F)c2)n1]
I-94
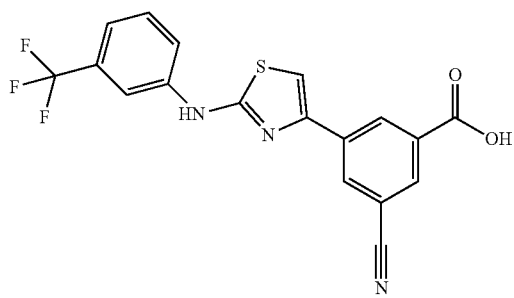 [SMILES: N#Cc1cc(C(=O)O)cc(-c2csc(Nc3cccc(C(F)(F)F)c3)n2)c1]
I-95
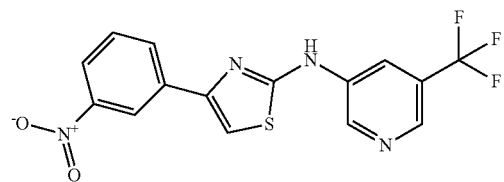
I-96
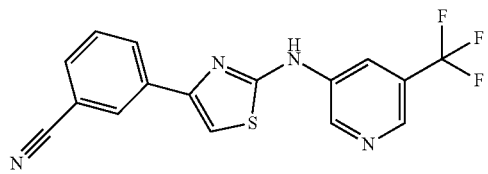 [SMILES: N#Cc1cccc(-c2csc(Nc3cncc(C(F)(F)F)c3)n2)c1]
I-97
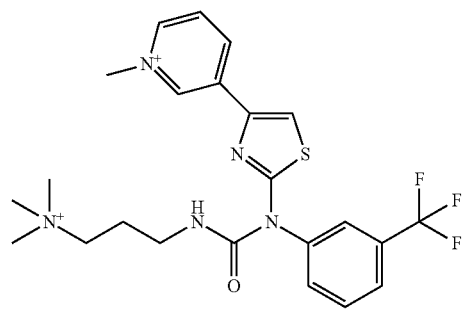 [SMILES: C[n+]1cccc(-c2csc(N(C(=O)NCCC[N+](C)(C)C)c3cccc(C(F)(F)F)c3)n2)c1]
I-98
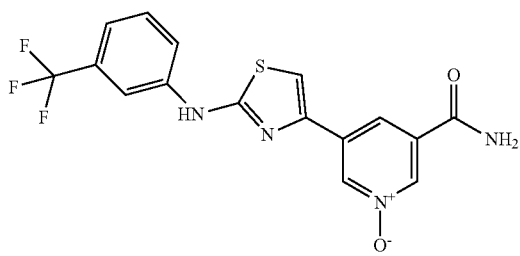 [SMILES: NC(=O)c1cc(-c2csc(Nc3cccc(C(F)(F)F)c3)n2)c[n+]([O-])c1]
I-99

TABLE 1-a-continued
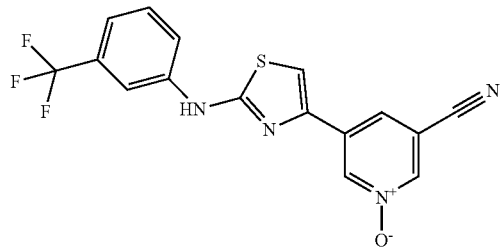 [SMILES: N#Cc1cc(-c2csc(Nc3cccc(C(F)(F)F)c3)n2)c[n+]([O-])c1]
I-100
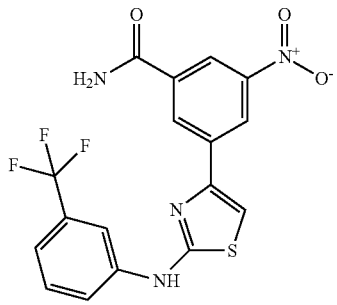 [SMILES: NC(=O)c1cc(-c2csc(Nc3cccc(C(F)(F)F)c3)n2)cc([N+](=O)[O-])c1]
I-101
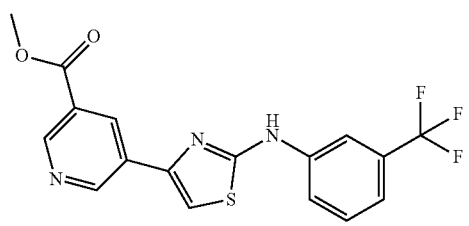 [SMILES: COC(=O)c1cncc(-c2csc(Nc3cccc(C(F)(F)F)c3)n2)c1]
I-102
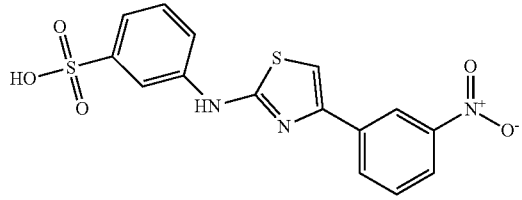 [SMILES: O=[N+]([O-])c1cccc(-c2csc(Nc3cccc(S(=O)(=O)O)c3)n2)c1]
I-103
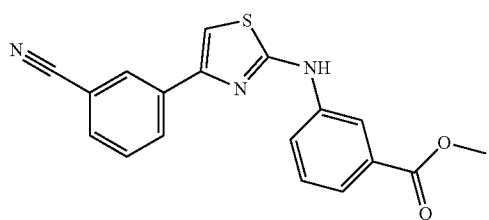 [SMILES: COC(=O)c1cccc(Nc2nc(-c3cccc(C#N)c3)cs2)c1]
I-104
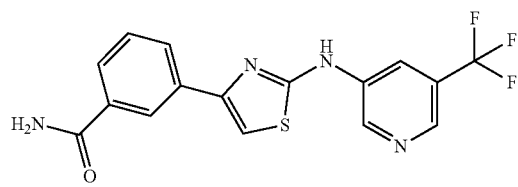 [SMILES: NC(=O)c1cccc(-c2csc(Nc3cncc(C(F)(F)F)c3)n2)c1]
I-105
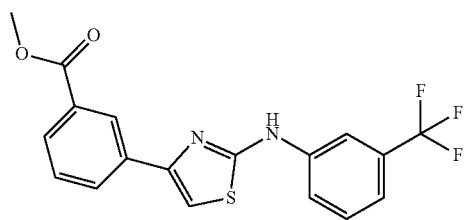 [SMILES: COC(=O)c1cccc(-c2csc(Nc3cccc(C(F)(F)F)c3)n2)c1]
I-106

TABLE 1-a-continued
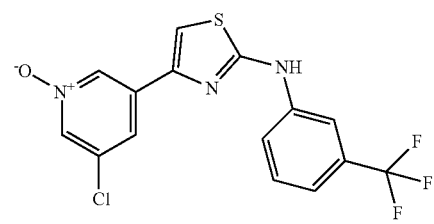
I-107
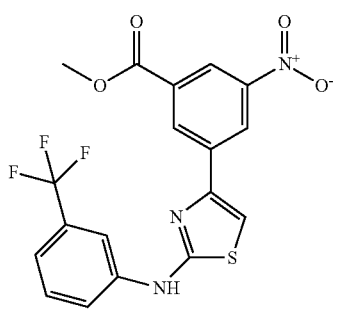 [SMILES: COC(=O)c1cc(-c2csc(Nc3cccc(C(F)(F)F)c3)n2)cc([N+](=O)[O-])c1]
I-108
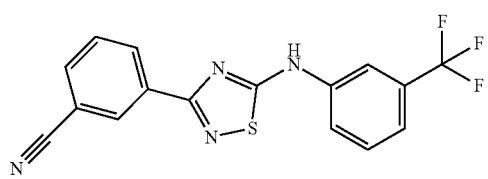 [SMILES: N#Cc1cccc(-c2nsc(Nc3cccc(C(F)(F)F)c3)n2)c1]
I-109
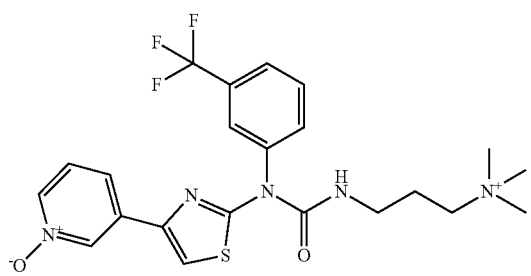
I-110
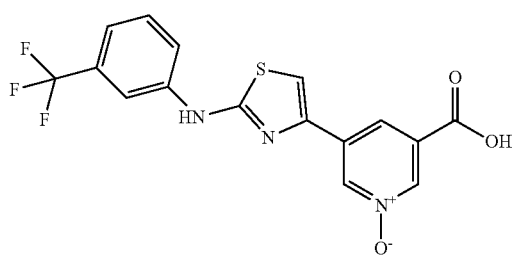 [SMILES: O=C(O)c1cc(-c2csc(Nc3cccc(C(F)(F)F)c3)n2)c[n+]([O-])c1]
I-111
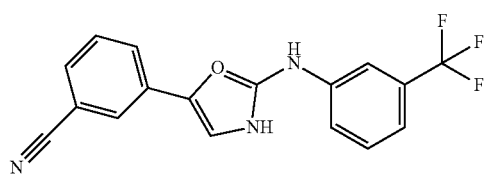
I-112

TABLE 1-a-continued
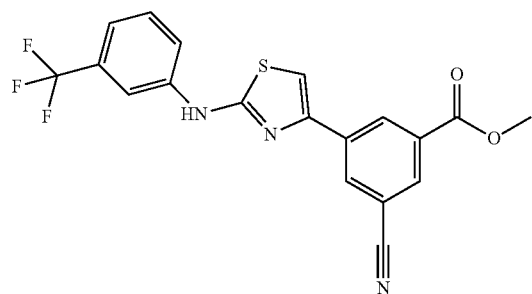 [SMILES: COC(=O)c1cc(C#N)cc(-c2csc(Nc3cccc(C(F)(F)F)c3)n2)c1] I-113
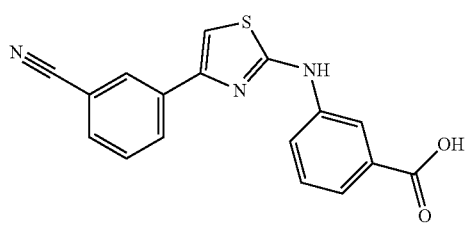 [SMILES: N#Cc1cccc(-c2csc(Nc3cccc(C(=O)O)c3)n2)c1] I-114
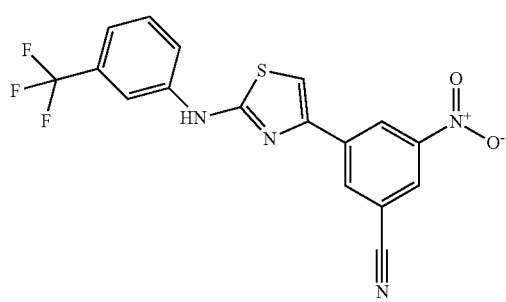 [SMILES: N#Cc1cc(-c2csc(Nc3cccc(C(F)(F)F)c3)n2)cc([N+](=O)[O-])c1] I-115
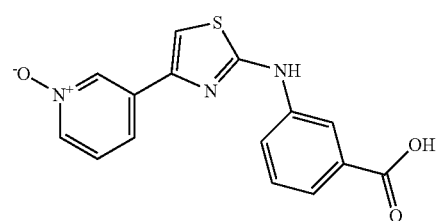 I-116
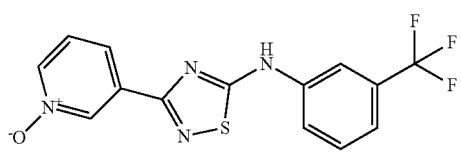 I-117
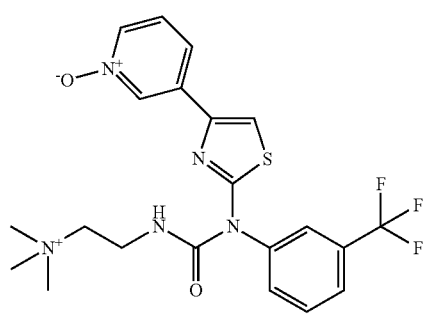 I-118

TABLE 1-a-continued
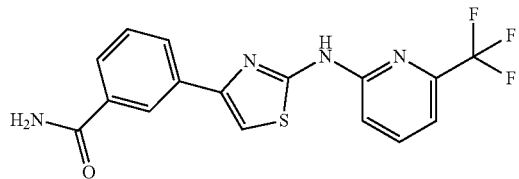 [SMILES: NC(=O)c1cccc(-c2csc(Nc3cccc(C(F)(F)F)n3)n2)c1] I-119
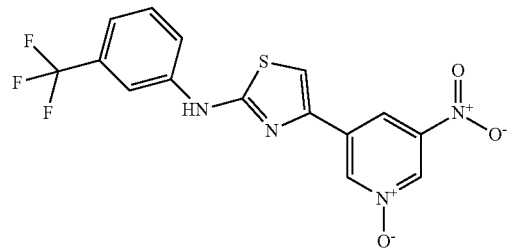 [SMILES: O=[N+]([O-])c1cc(-c2csc(Nc3cccc(C(F)(F)F)c3)n2)c[n+]([O-])c1] I-120
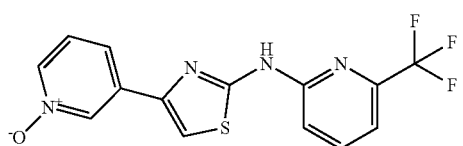 I-121
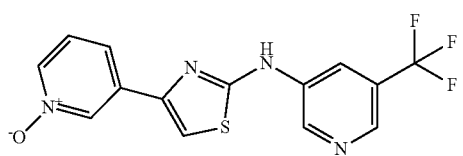 I-122
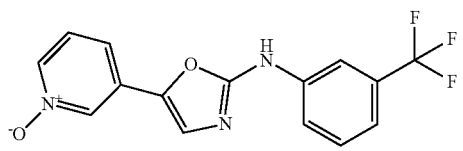 I-123
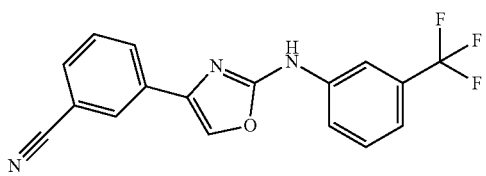 [SMILES: N#Cc1cccc(-c2coc(Nc3cccc(C(F)(F)F)c3)n2)c1] I-124
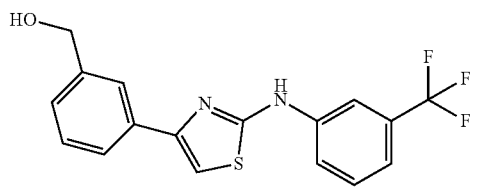 [SMILES: OCc1cccc(-c2csc(Nc3cccc(C(F)(F)F)c3)n2)c1] I-125
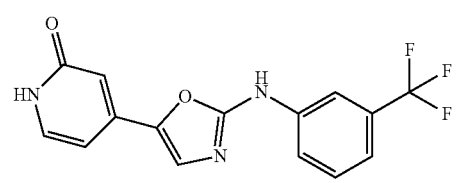 [SMILES: O=c1cc(-c2cnc(Nc3cccc(C(F)(F)F)c3)o2)cc[nH]1] I-126

TABLE 1-a-continued
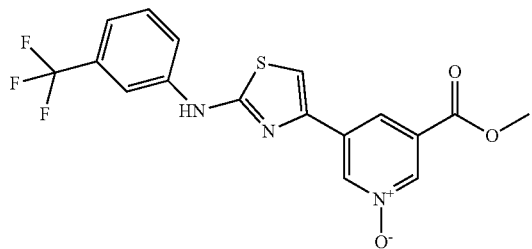 [SMILES: COC(=O)c1cc(-c2csc(Nc3cccc(C(F)(F)F)c3)n2)c[n+]([O-])c1] I-127
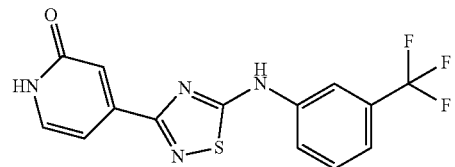 I-128
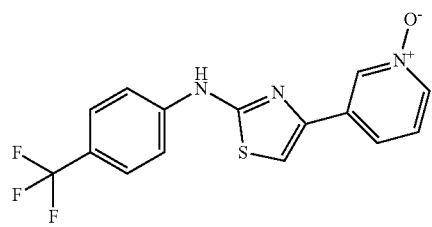 [SMILES: [O-][n+]1cccc(-c2csc(Nc3ccc(C(F)(F)F)cc3)n2)c1] I-129
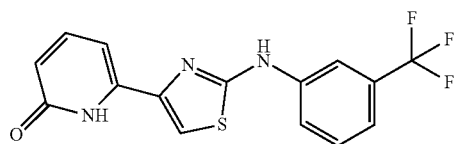 I-130
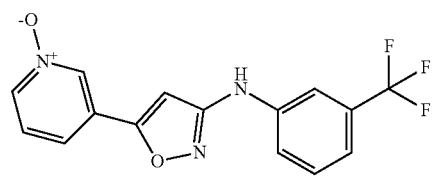 I-131
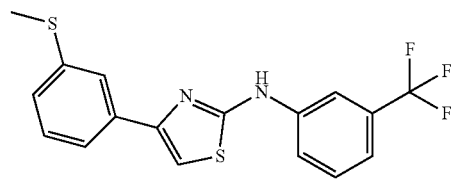 [SMILES: CSc1cccc(-c2csc(Nc3cccc(C(F)(F)F)c3)n2)c1] I-132
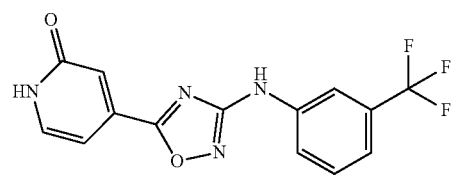 [SMILES: O=c1cc(-c2nc(Nc3cccc(C(F)(F)F)c3)no2)cc[nH]1] I-133
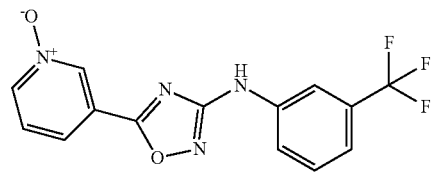 I-134

TABLE 1-a-continued
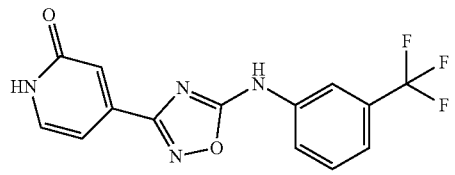
I-135
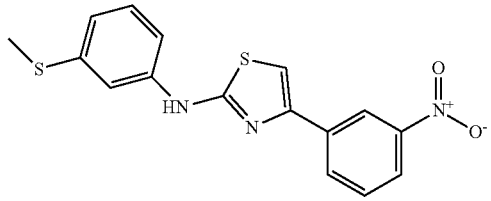 [SMILES: CSc1cccc(Nc2nc(-c3cccc([N+](=O)[O-])c3)cs2)c1]
I-136
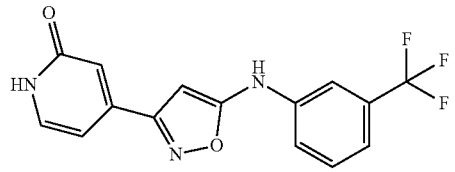 [SMILES: O=c1cc(-c2cc(Nc3cccc(C(F)(F)F)c3)on2)cc[nH]1]
I-137
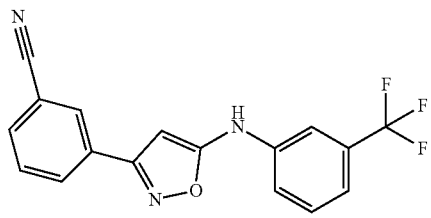 [SMILES: N#Cc1cccc(-c2cc(Nc3cccc(C(F)(F)F)c3)on2)c1]
I-138
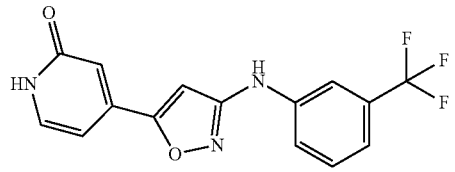 [SMILES: O=c1cc(-c2cc(Nc3cccc(C(F)(F)F)c3)no2)cc[nH]1]
I-139
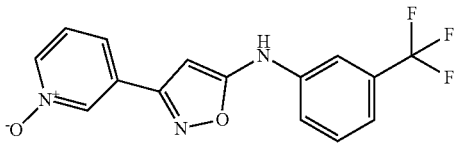
I-140
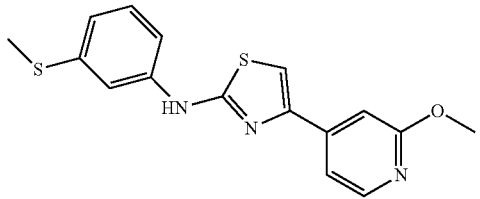
I-141
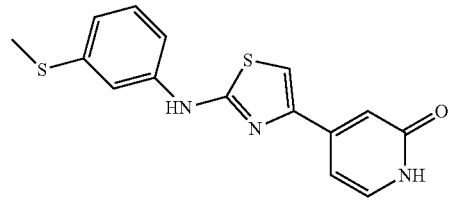 [SMILES: CSc1cccc(Nc2nc(-c3cc[nH]c(=O)c3)cs2)c1]
I-142

TABLE 1-a-continued
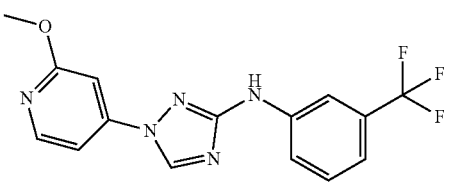 [SMILES: COc1cc(-n2cnc(Nc3cccc(C(F)(F)F)c3)n2)ccn1]
I-143
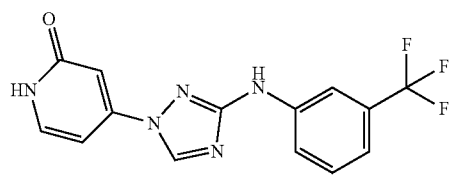 [SMILES: O=c1cc(-n2cnc(Nc3cccc(C(F)(F)F)c3)n2)cc[nH]1]
I-144
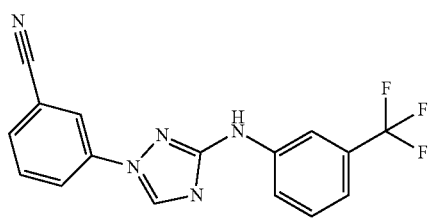
I-145
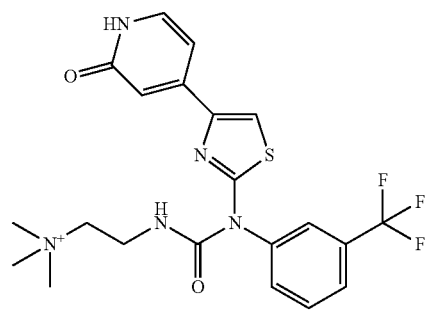 [SMILES: C[N+](C)(C)CCNC(=O)N(c1cccc(C(F)(F)F)c1)c1nc(-c2cc[nH]c(=O)c2)cs1]
I-146
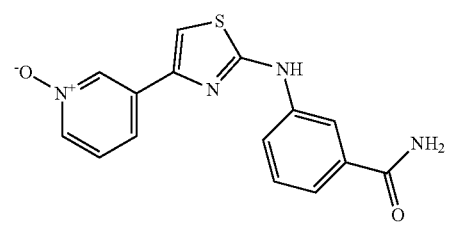
I-147
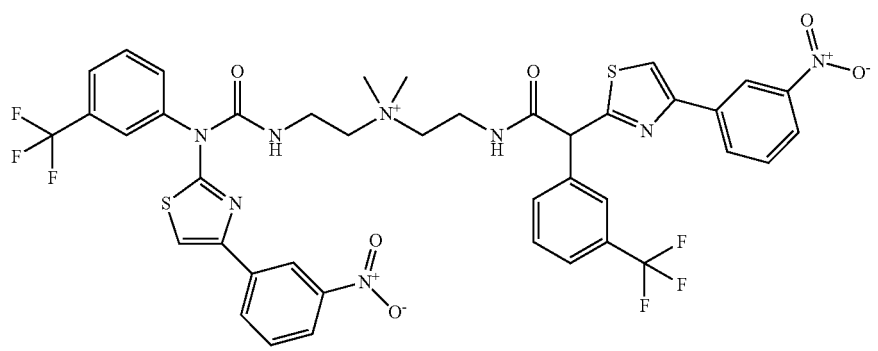 [SMILES: C[N+](C)(CCNC(=O)C(c1cccc(C(F)(F)F)c1)c1nc(-c2cccc([N+](=O)[O-])c2)cs1)CCNC(=O)N(c1cccc(C(F)(F)F)c1)c1nc(-c2cccc([N+](=O)[O-])c2)cs1]
I-148

TABLE 1-a-continued
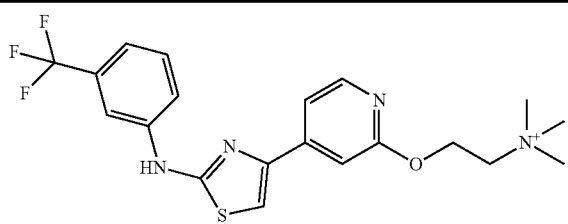 I-149
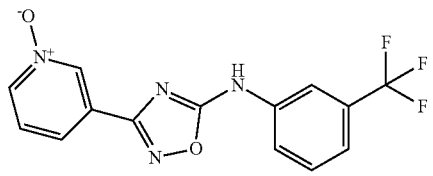 I-150
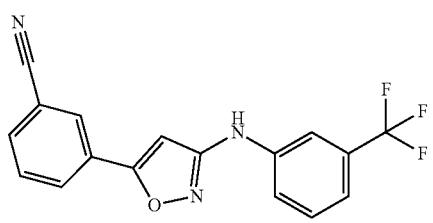 [SMILES: N#Cc1cccc(-c2cc(Nc3cccc(C(F)(F)F)c3)no2)c1] I-151
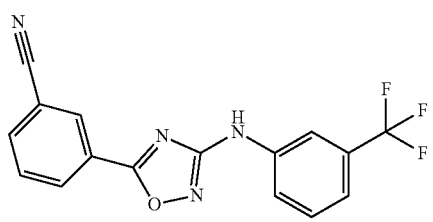 [SMILES: N#Cc1cccc(-c2nc(Nc3cccc(C(F)(F)F)c3)no2)c1] I-152
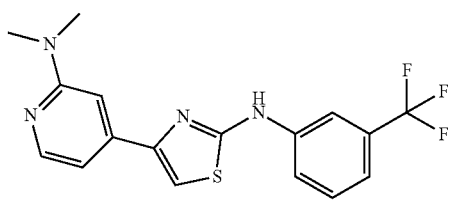 [SMILES: CN(C)c1cc(-c2csc(Nc3cccc(C(F)(F)F)c3)n2)ccn1] I-153
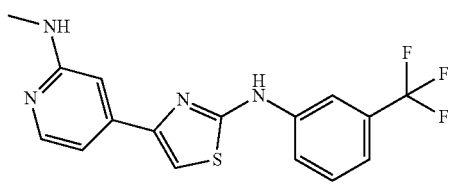 [SMILES: CNc1cc(-c2csc(Nc3cccc(C(F)(F)F)c3)n2)ccn1] I-154
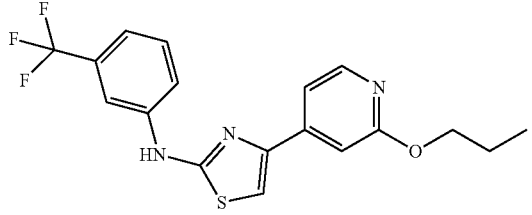 [SMILES: CCCOc1cc(-c2csc(Nc3cccc(C(F)(F)F)c3)n2)ccn1] I-155
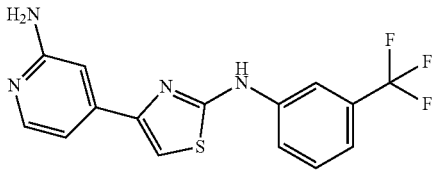 [SMILES: Nc1cc(-c2csc(Nc3cccc(C(F)(F)F)c3)n2)ccn1] I-156

TABLE 1-a-continued
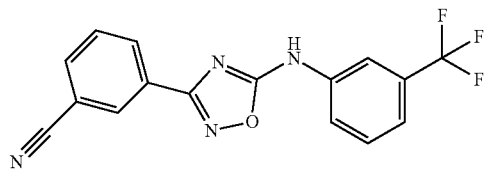 [SMILES: N#Cc1cccc(-c2noc(Nc3cccc(C(F)(F)F)c3)n2)c1] I-157
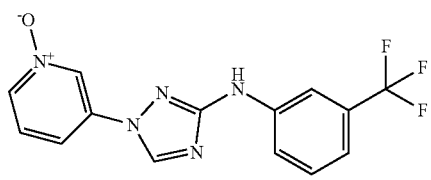 I-158
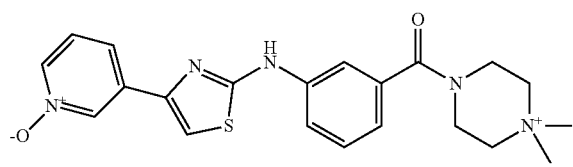 I-159
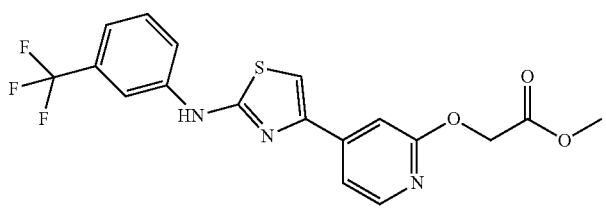 [SMILES: COC(=O)COc1cc(-c2csc(Nc3cccc(C(F)(F)F)c3)n2)ccn1] I-160
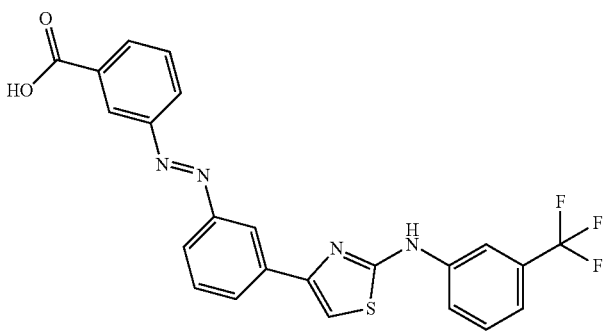 [SMILES: O=C(O)c1cccc(/N=N/c2cccc(-c3csc(Nc4cccc(C(F)(F)F)c4)n3)c2)c1] I-161
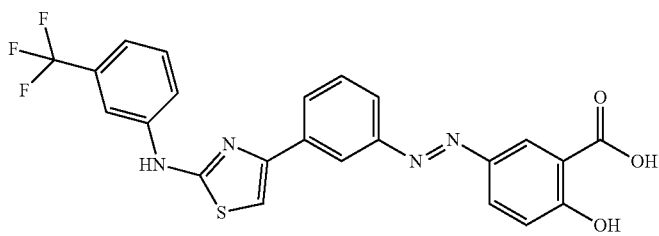 [SMILES: O=C(O)c1cc(/N=N/c2cccc(-c3csc(Nc4cccc(C(F)(F)F)c4)n3)c2)ccc1O] I-162
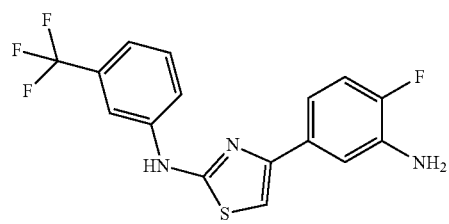 [SMILES: Nc1cc(-c2csc(Nc3cccc(C(F)(F)F)c3)n2)ccc1F] I-163

TABLE 1-a-continued
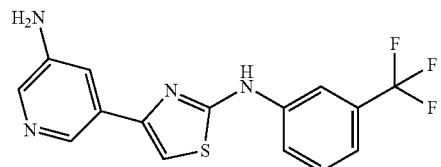
I-164
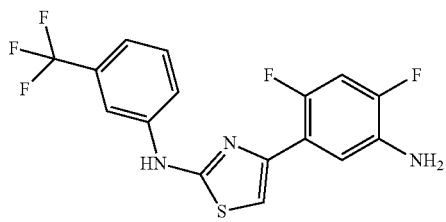 [SMILES: Nc1cc(-c2csc(Nc3cccc(C(F)(F)F)c3)n2)c(F)cc1F]
I-165
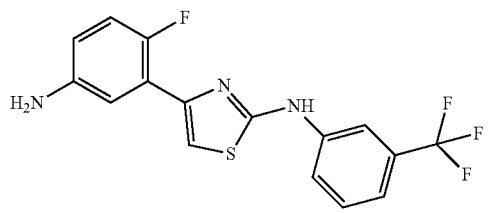 [SMILES: Nc1ccc(F)c(-c2csc(Nc3cccc(C(F)(F)F)c3)n2)c1]
I-166
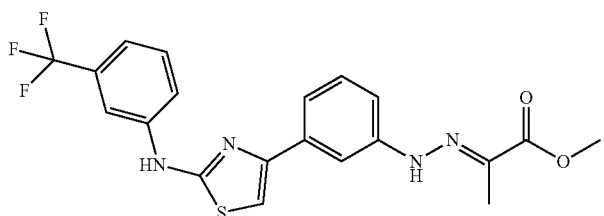
I-167
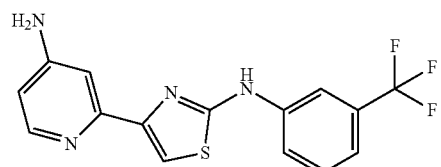
I-168
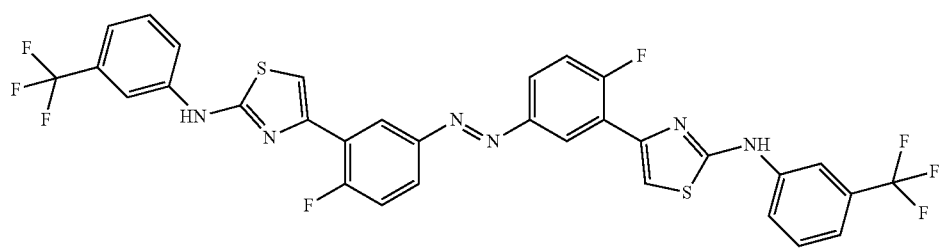 [SMILES: Fc1ccc(/N=N/c2ccc(F)c(-c3csc(Nc4cccc(C(F)(F)F)c4)n3)c2)cc1-c1csc(Nc2cccc(C(F)(F)F)c2)n1]
I-169
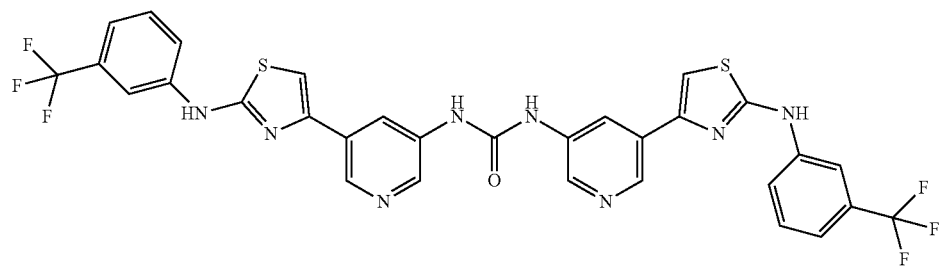 [SMILES: O=C(Nc1cncc(-c2csc(Nc3cccc(C(F)(F)F)c3)n2)c1)Nc1cncc(-c2csc(Nc3cccc(C(F)(F)F)c3)n2)c1]
I-170

TABLE 1-a-continued
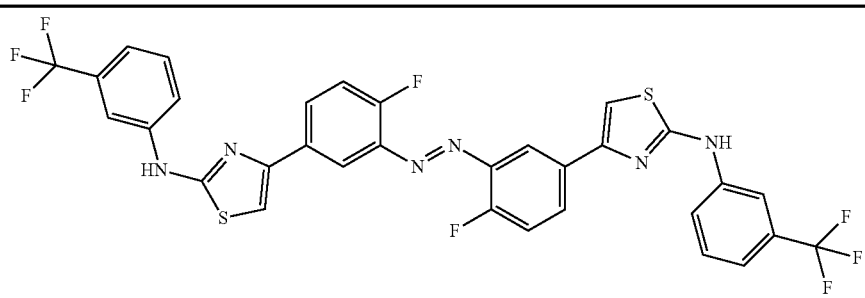
I-171
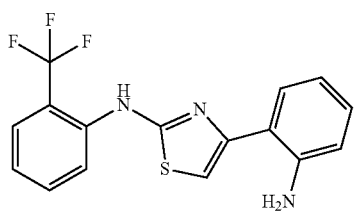 [SMILES: Nc1ccccc1-c1csc(Nc2ccccc2C(F)(F)F)n1]
I-172
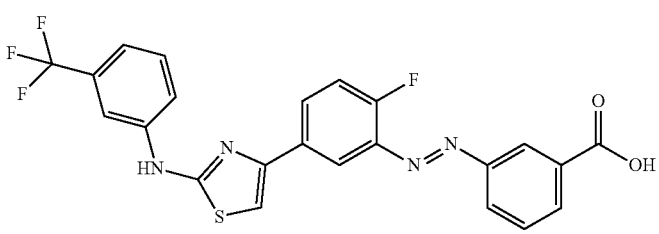 [SMILES: O=C(O)c1cccc(/N=N/c2cc(-c3csc(Nc4cccc(C(F)(F)F)c4)n3)ccc2F)c1]
I-173
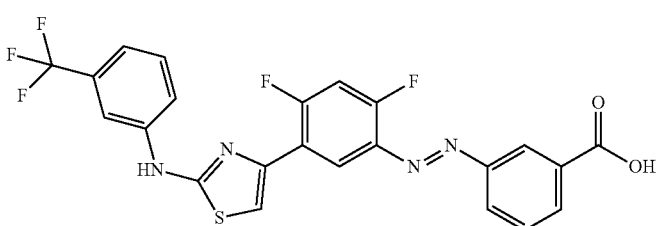
I-174
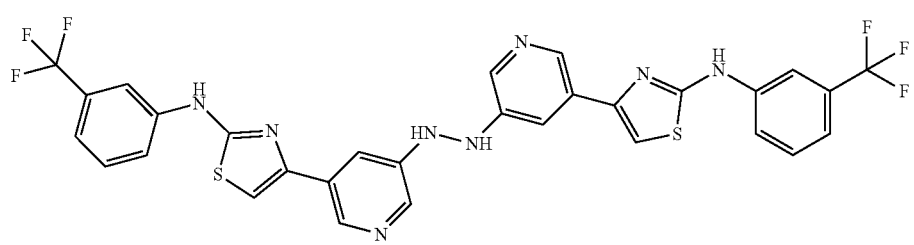 [SMILES: FC(F)(F)c1cccc(Nc2nc(-c3cncc(NNc4cncc(-c5csc(Nc6cccc(C(F)(F)F)c6)n5)c4)c3)cs2)c1]
I-175
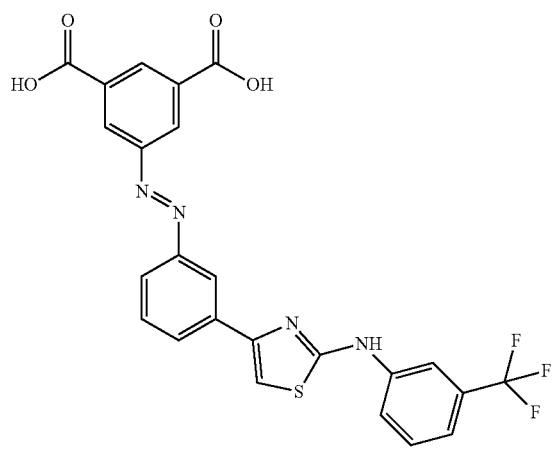 [SMILES: O=C(O)c1cc(/N=N/c2cccc(-c3csc(Nc4cccc(C(F)(F)F)c4)n3)c2)cc(C(=O)O)c1]
I-176

TABLE 1-a-continued
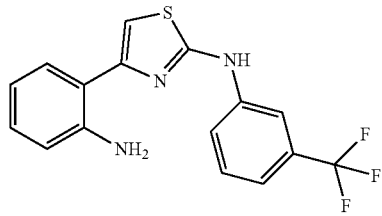 [SMILES: Nc1ccccc1-c1csc(Nc2cccc(C(F)(F)F)c2)n1] I-177
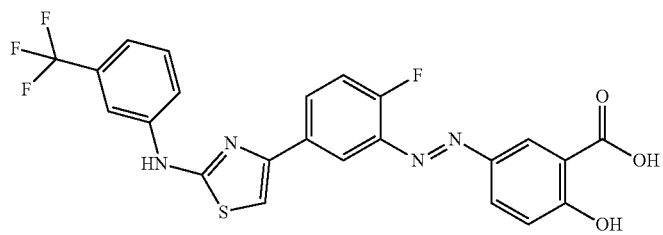 [SMILES: O=C(O)c1cc(/N=N/c2cc(-c3csc(Nc4cccc(C(F)(F)F)c4)n3)ccc2F)ccc1O] I-178
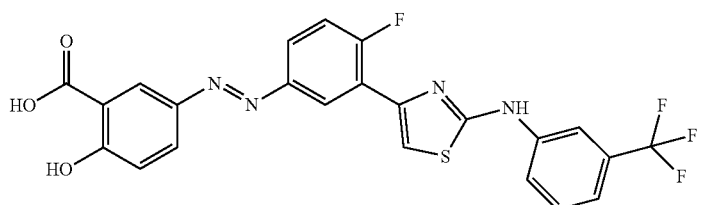 I-179
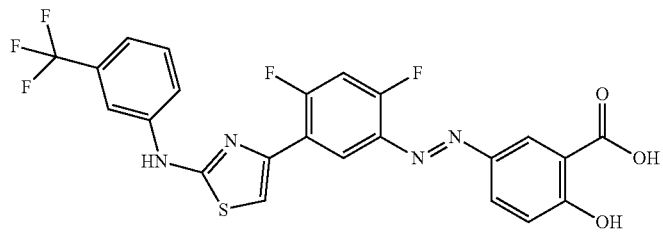 [SMILES: O=C(O)c1cc(/N=N/c2cc(-c3csc(Nc4cccc(C(F)(F)F)c4)n3)c(F)cc2F)ccc1O] I-180
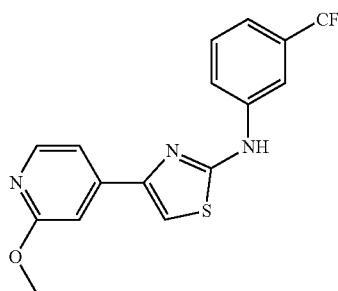 I-181
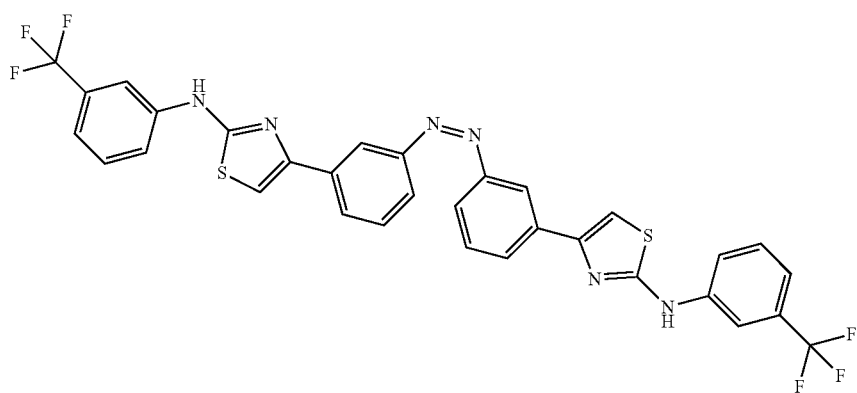 [SMILES: FC(F)(F)c1cccc(Nc2nc(-c3cccc(/N=N\c4cccc(-c5csc(Nc6cccc(C(F)(F)F)c6)n5)c4)c3)cs2)c1] I-182

TABLE 1-a-continued
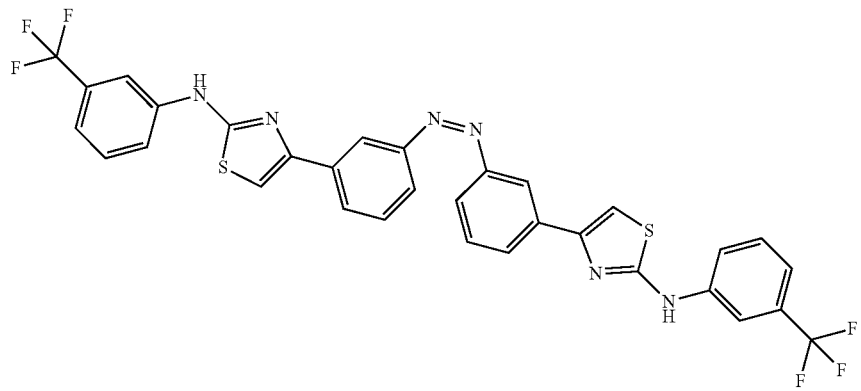 [SMILES: FC(F)(F)c1cccc(Nc2nc(-c3cccc(/N=N\c4cccc(-c5csc(Nc6cccc(C(F)(F)F)c6)n5)c4)c3)cs2)c1]
I-183
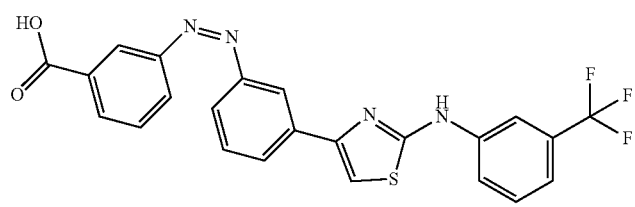 [SMILES: O=C(O)c1cccc(/N=N\c2cccc(-c3csc(Nc4cccc(C(F)(F)F)c4)n3)c2)c1]
I-184
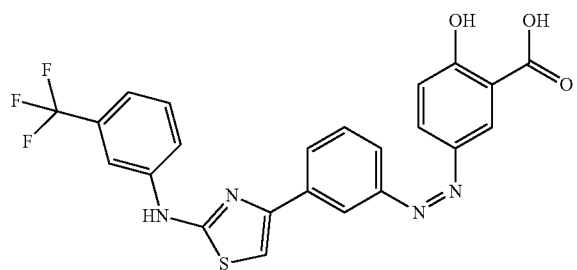 [SMILES: O=C(O)c1cc(/N=N\c2cccc(-c3csc(Nc4cccc(C(F)(F)F)c4)n3)c2)ccc1O]
I-185
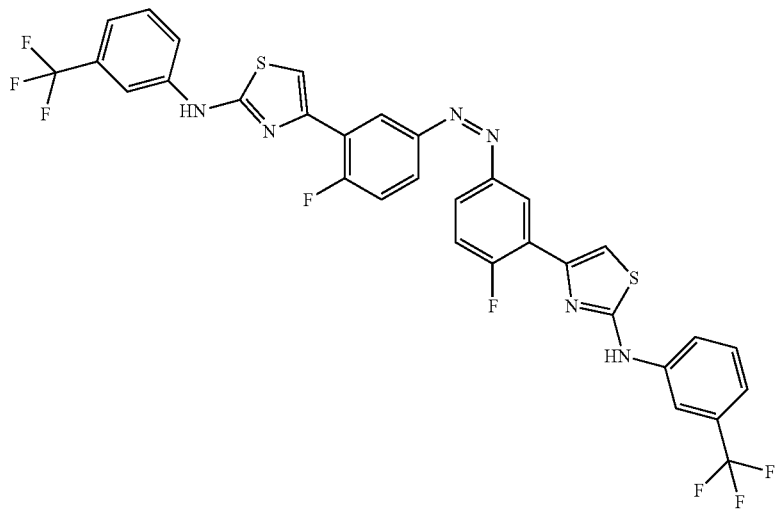 [SMILES: Fc1ccc(/N=N\c2ccc(F)c(-c3csc(Nc4cccc(C(F)(F)F)c4)n3)c2)cc1-c1csc(Nc2cccc(C(F)(F)F)c2)n1]
I-186

TABLE 1-a-continued
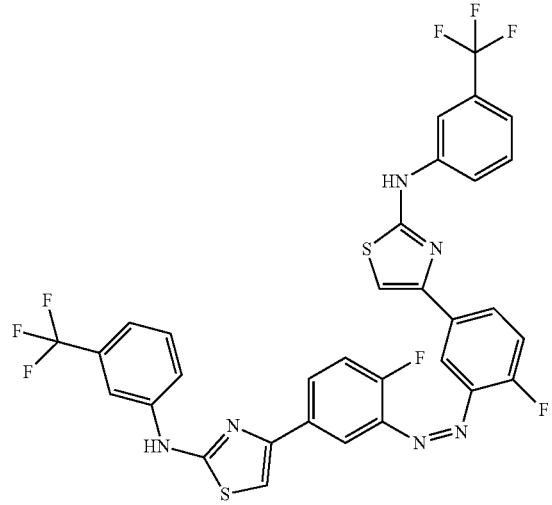 [SMILES: Fc1ccc(-c2csc(Nc3cccc(C(F)(F)F)c3)n2)cc1/N=N\c1cc(-c2csc(Nc3cccc(C(F)(F)F)c3)n2)ccc1F]
I-187
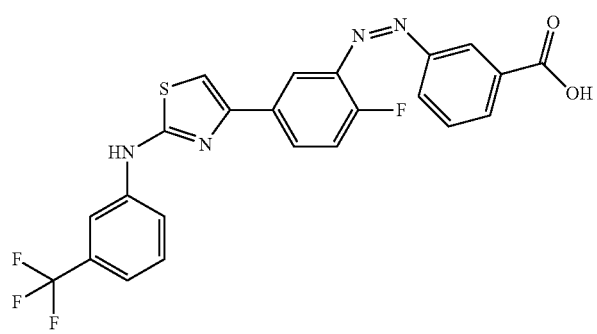 [SMILES: O=C(O)c1cccc(/N=N\c2cc(-c3csc(Nc4cccc(C(F)(F)F)c4)n3)ccc2F)c1]
I-188
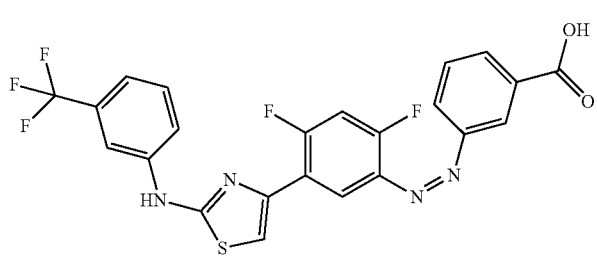 [SMILES: O=C(O)c1cccc(/N=N\c2cc(-c3csc(Nc4cccc(C(F)(F)F)c4)n3)c(F)cc2F)c1]
I-189
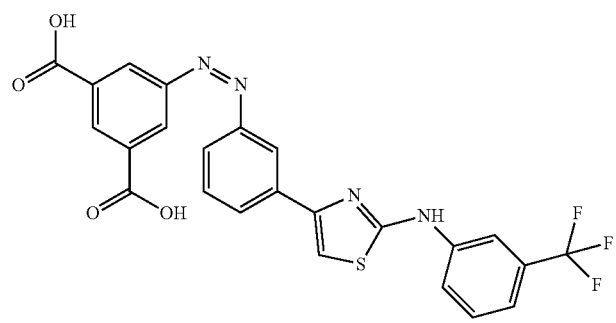 [SMILES: O=C(O)c1cc(/N=N\c2cccc(-c3csc(Nc4cccc(C(F)(F)F)c4)n3)c2)cc(C(=O)O)c1]
I-190

TABLE 1-a-continued
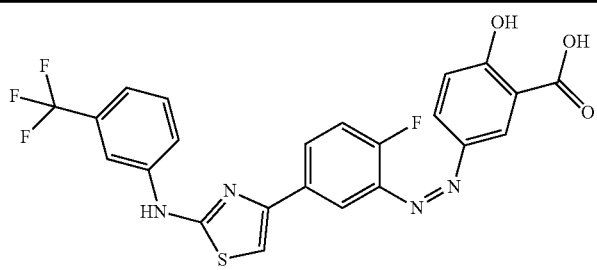
I-191
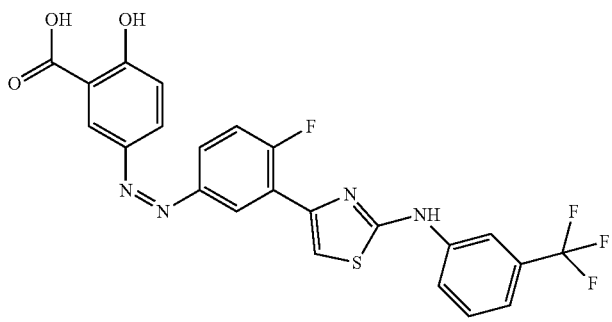 [SMILES: O=C(O)c1cc(/N=N\c2ccc(F)c(-c3csc(Nc4cccc(C(F)(F)F)c4)n3)c2)ccc1O]
I-192
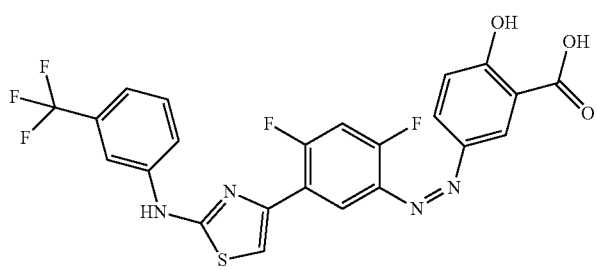 [SMILES: O=C(O)c1cc(/N=N\c2cc(-c3csc(Nc4cccc(C(F)(F)F)c4)n3)c(F)cc2F)ccc1O]
I-193
In some embodiments, the present invention provides a compound set forth in Table 1-a above, or a pharmaceutically acceptable salt thereof.
In some embodiments, a compound of the present invention is not
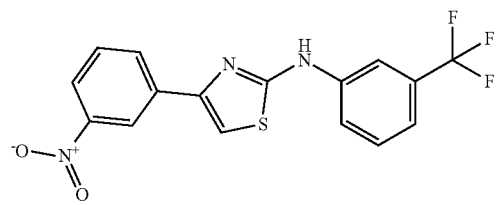
P-1
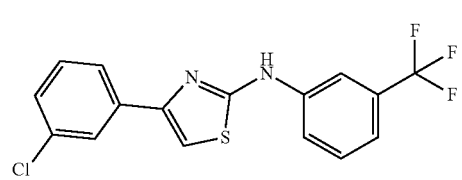
P-2
P-3
-continued
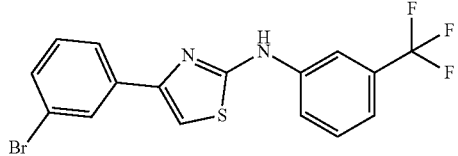
P-4
P-5
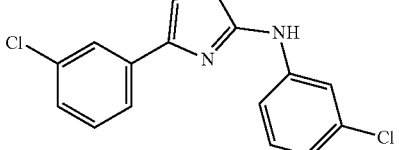
P-6
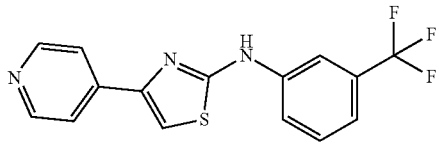
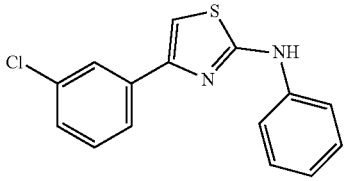
P-7

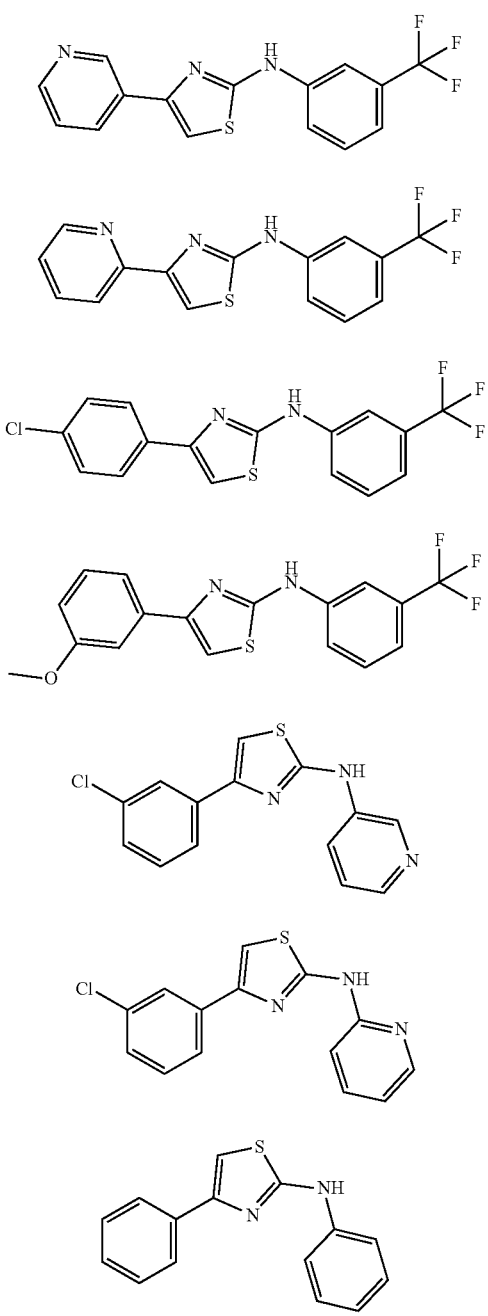
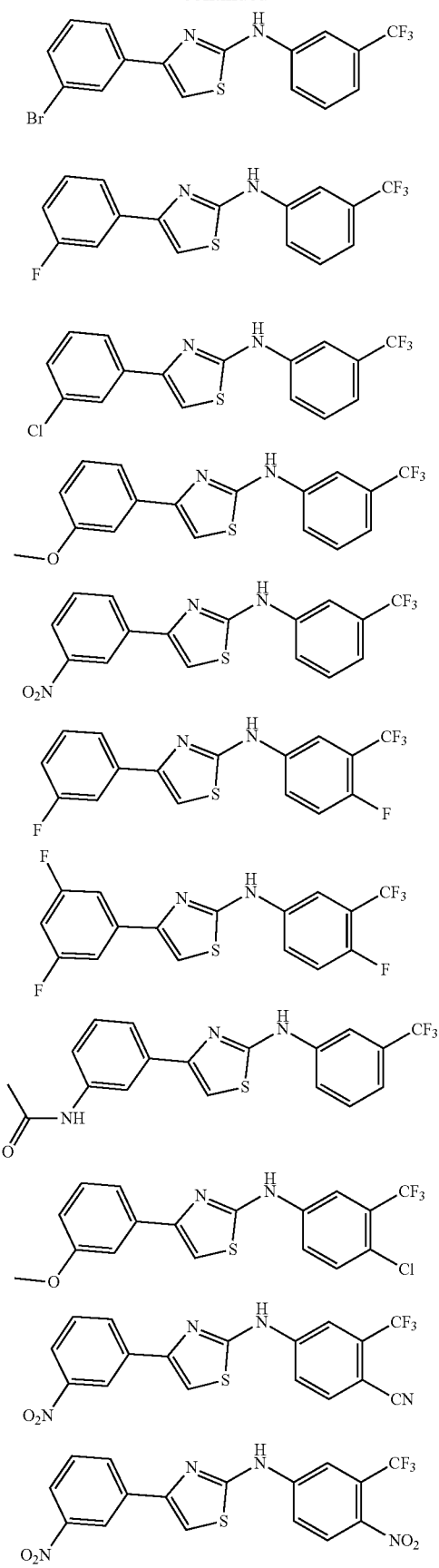
In some embodiments, a compound of the present invention is not
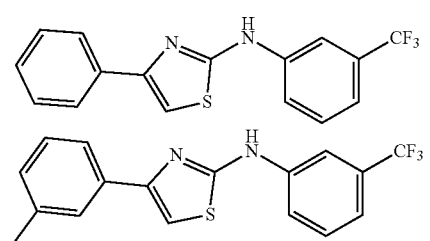

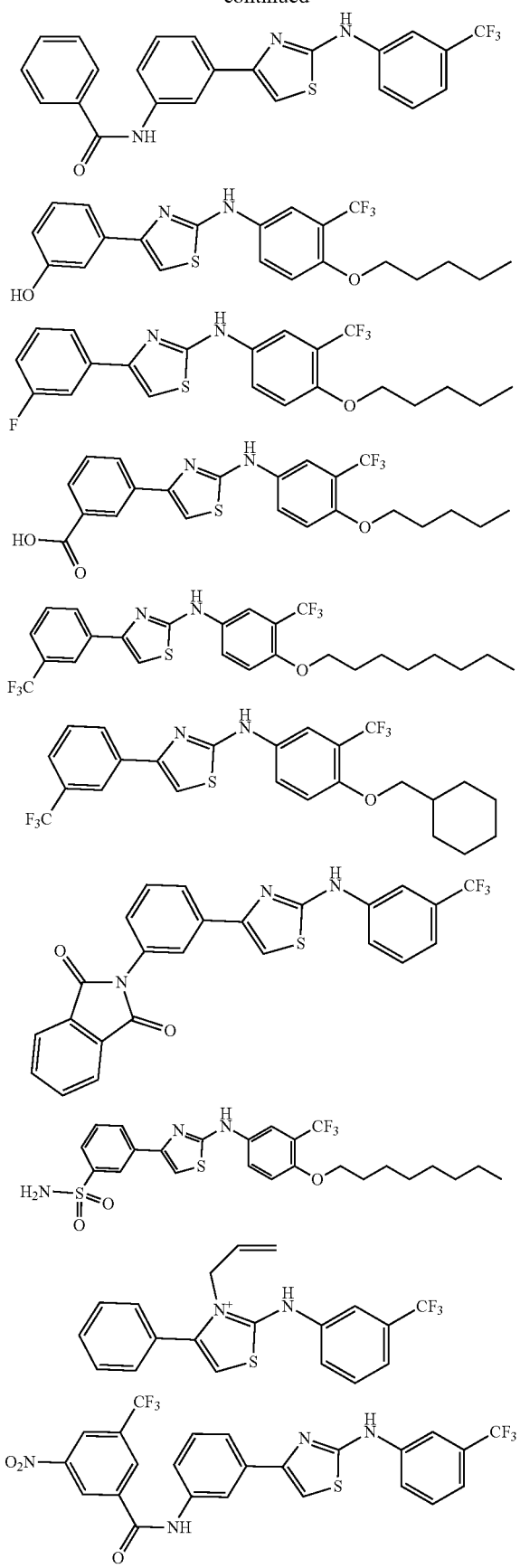
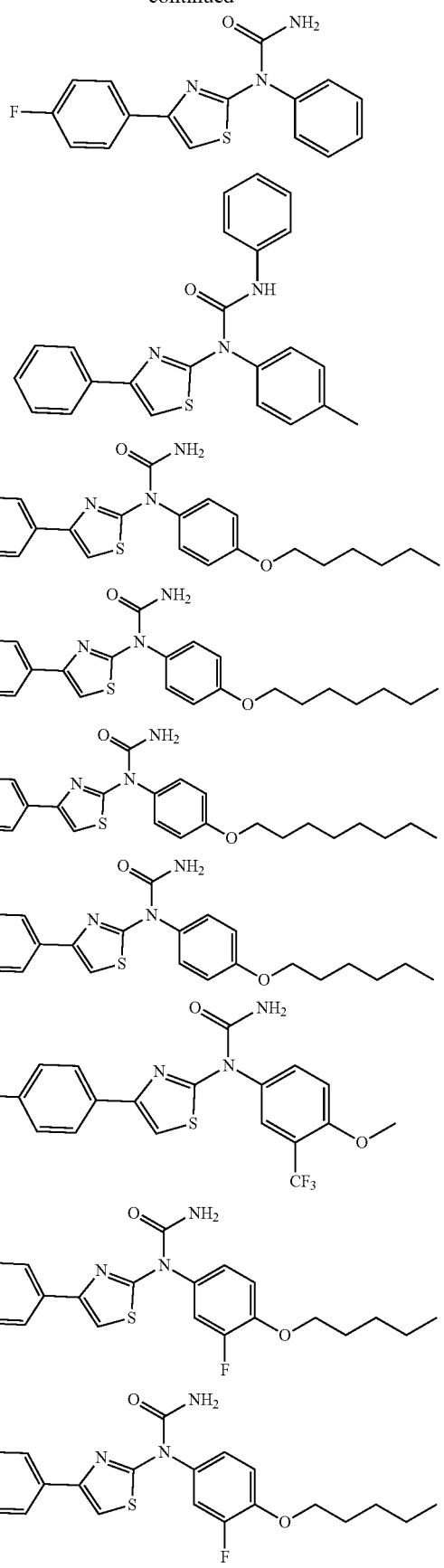

-continued
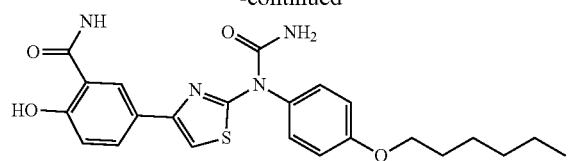
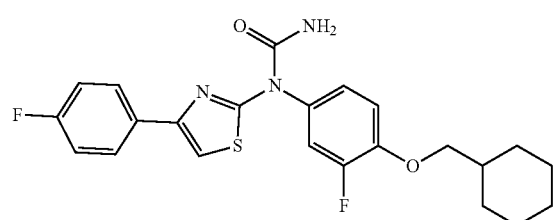
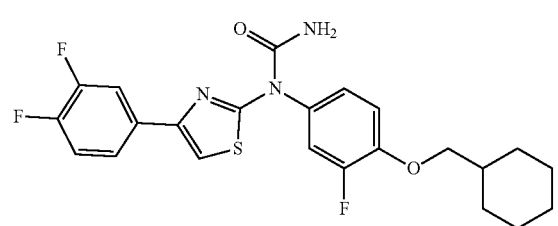
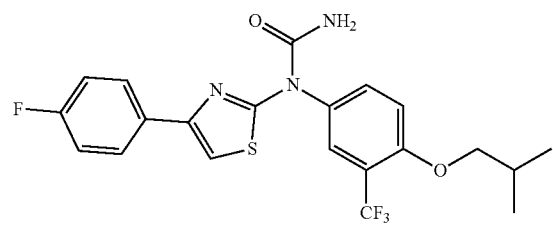
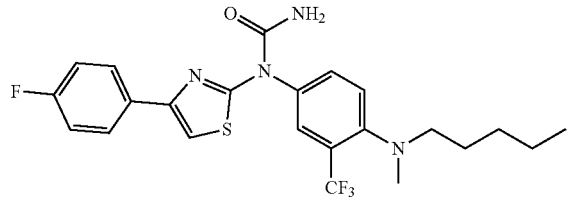
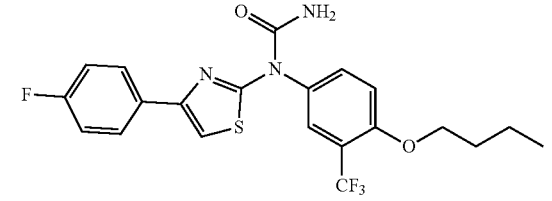
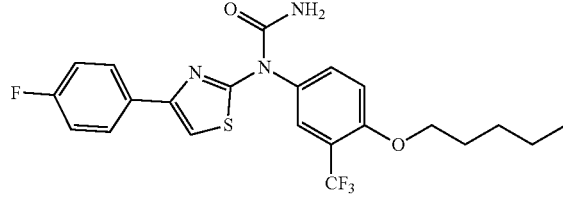
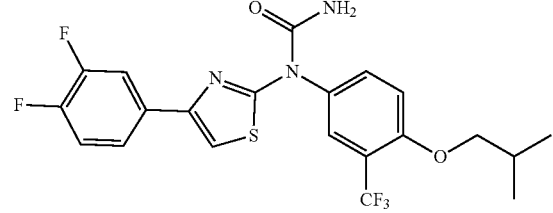
-continued
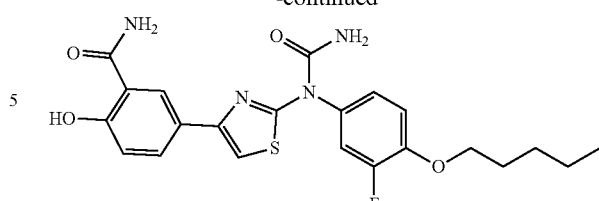
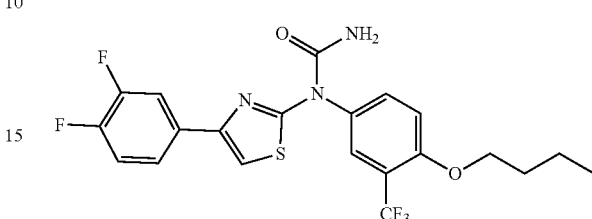
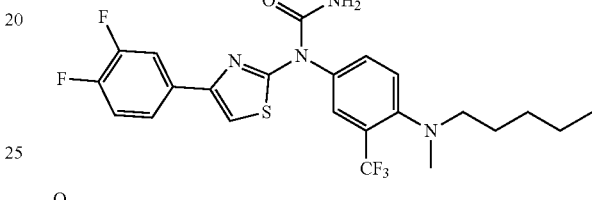

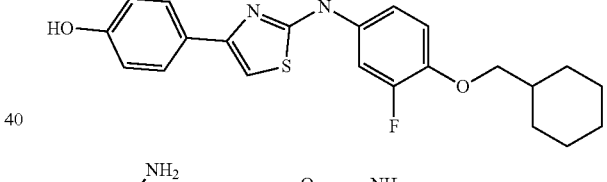
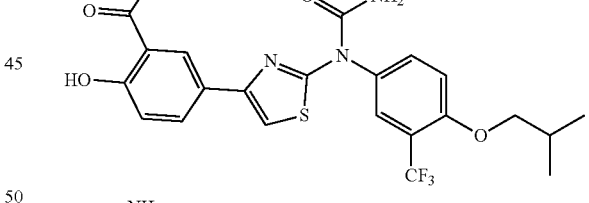
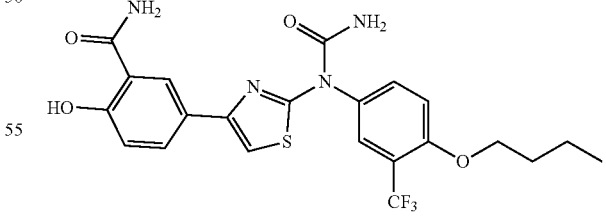
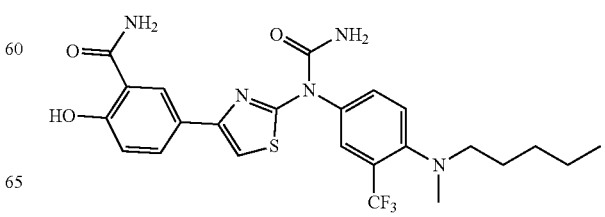

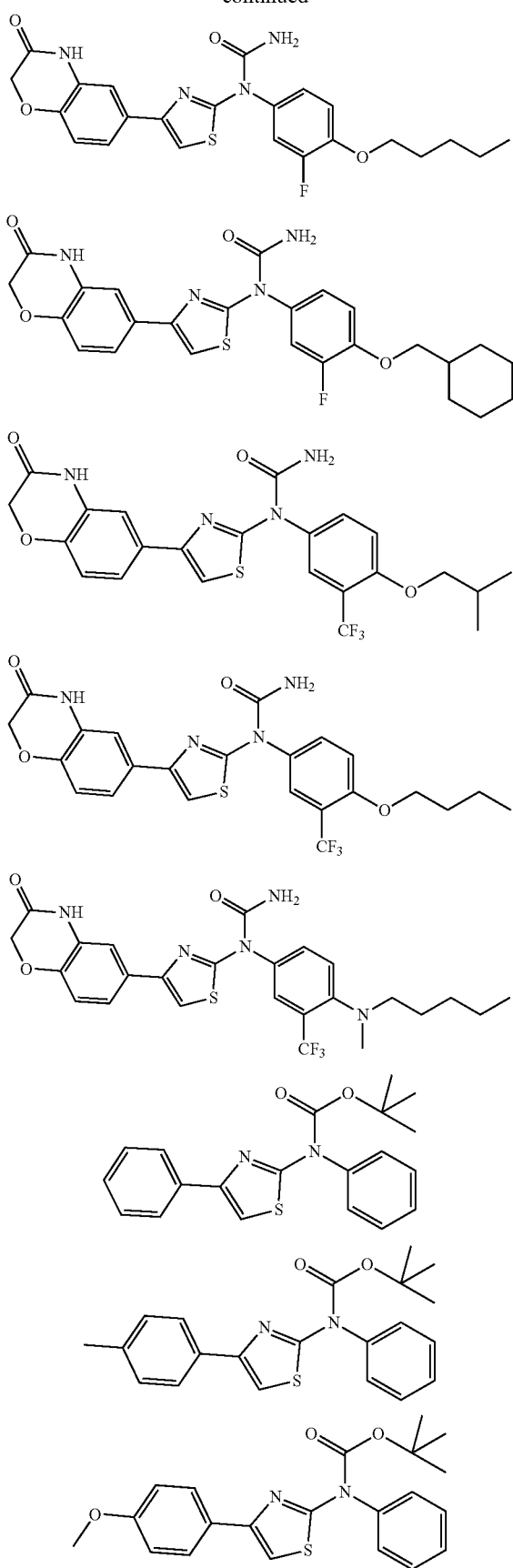
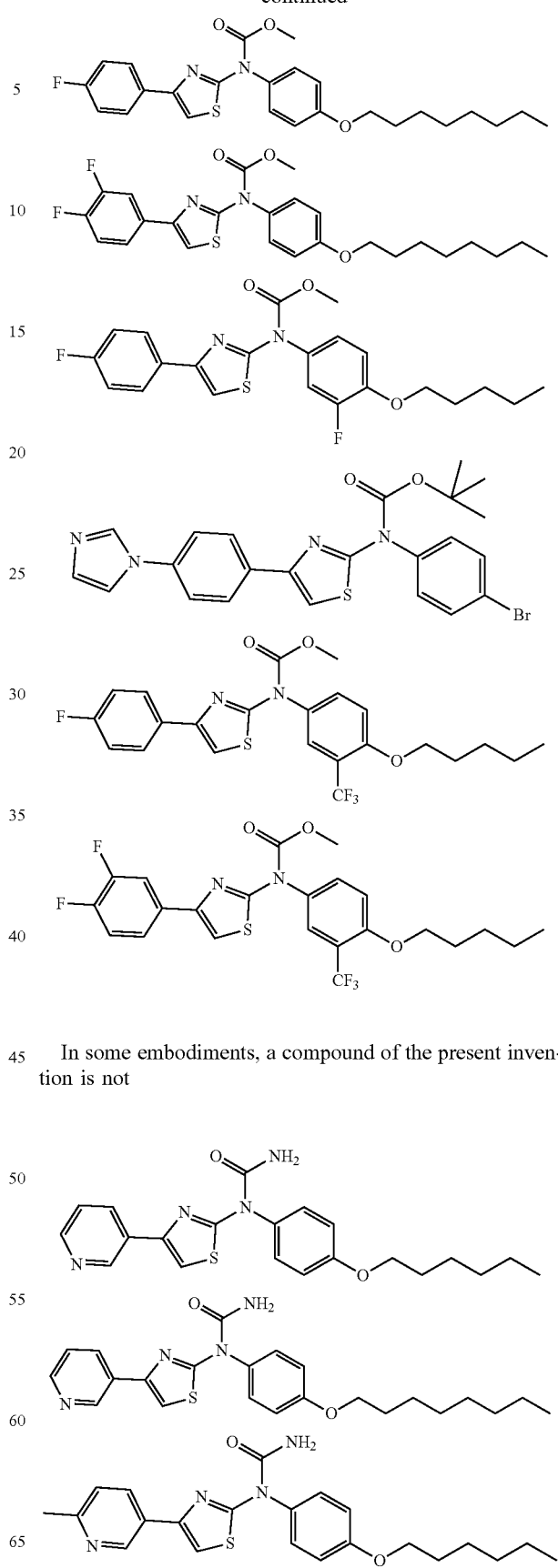
In some embodiments, a compound of the present invention is not -continued
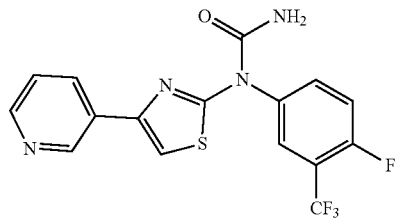
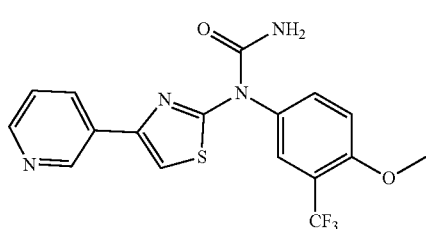
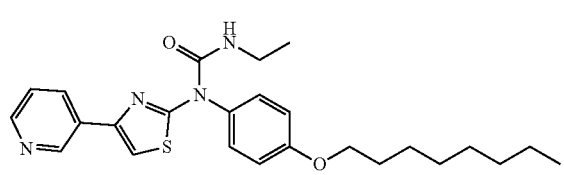
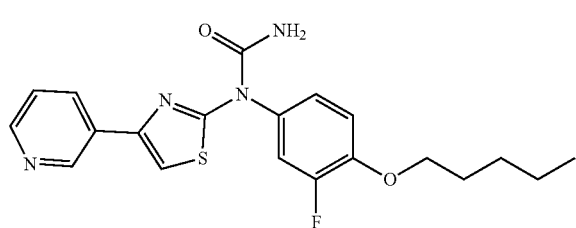
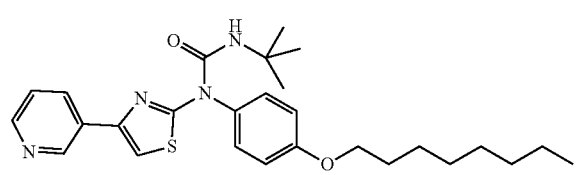
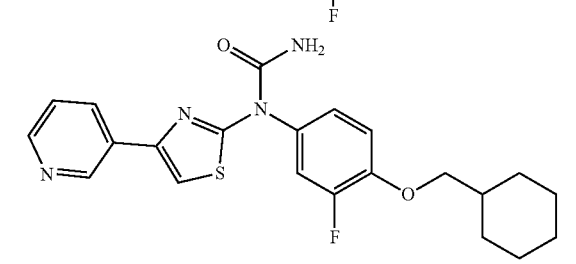
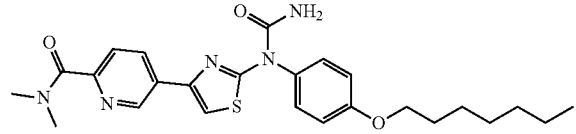
-continued
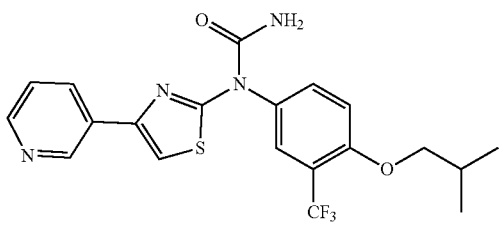
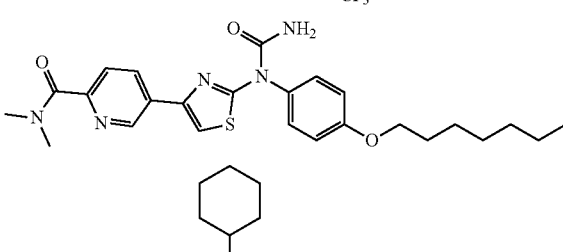
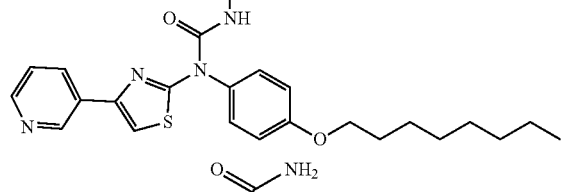
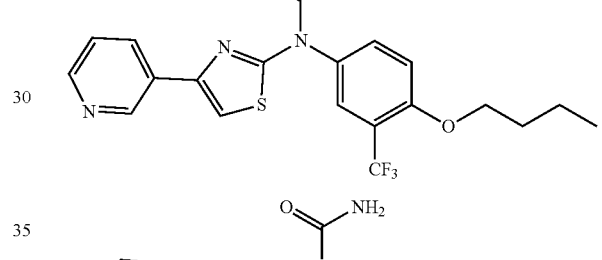
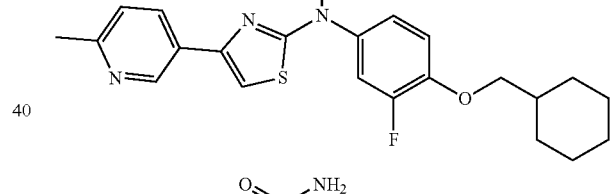
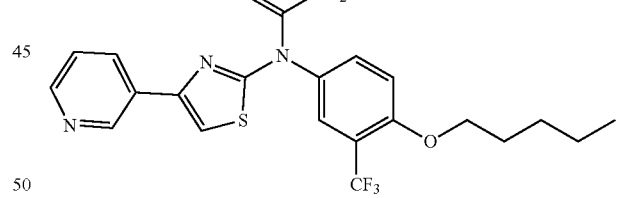
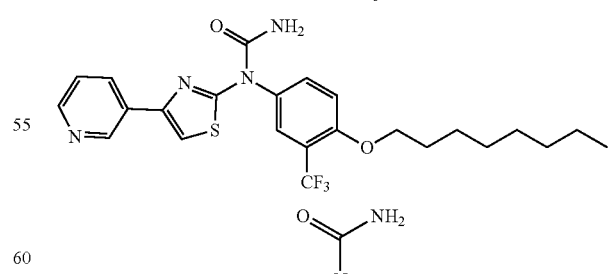
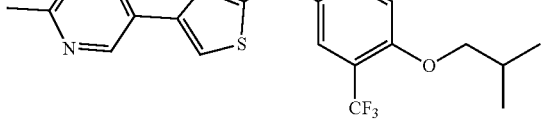

121
-continued
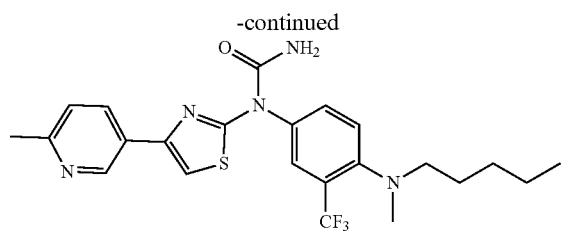
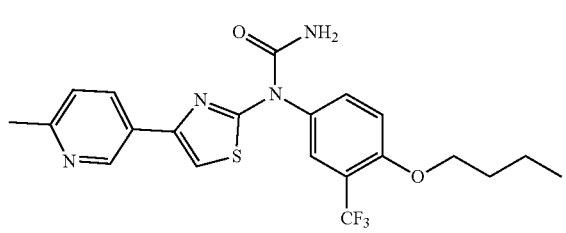
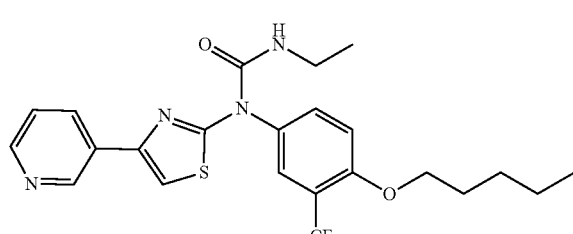
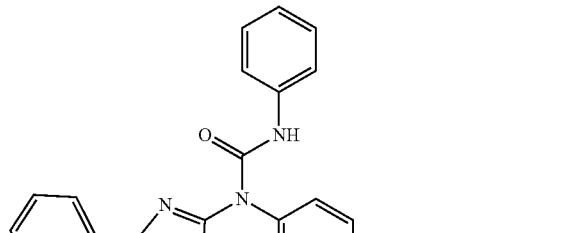
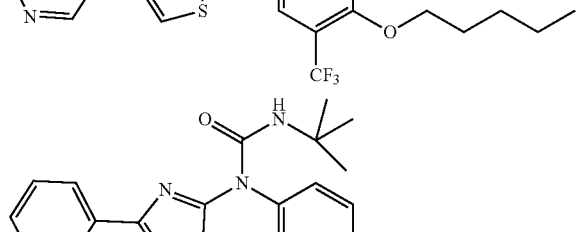
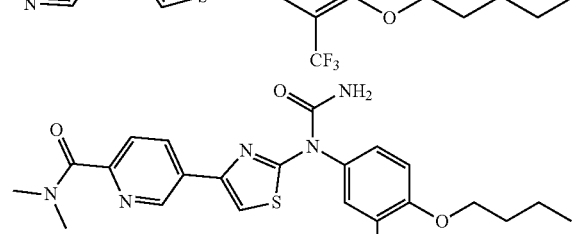
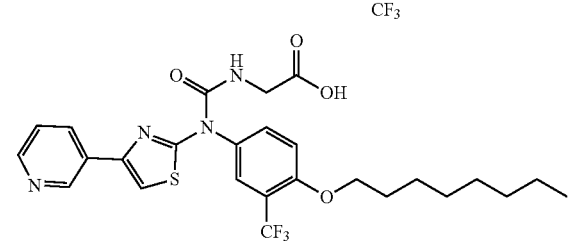
122
-continued
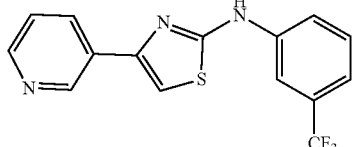
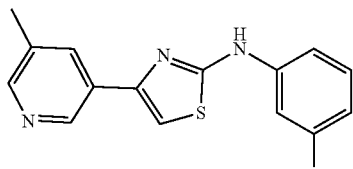
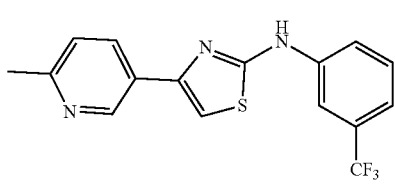
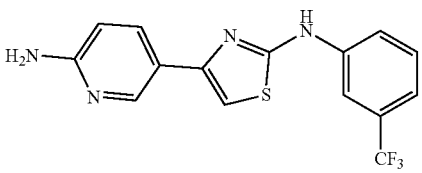
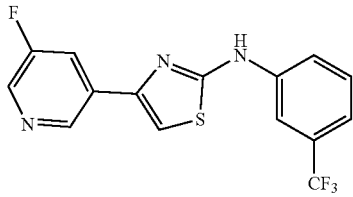
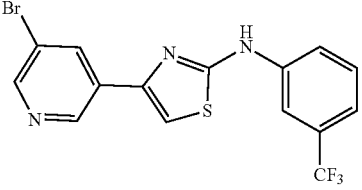
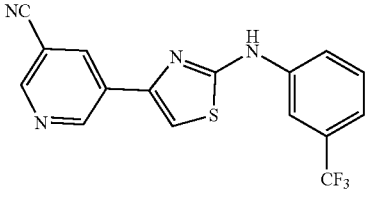
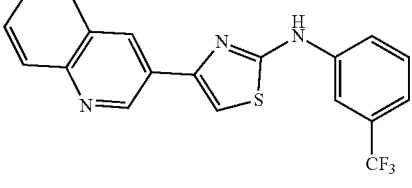
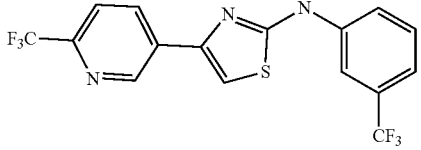

-continued

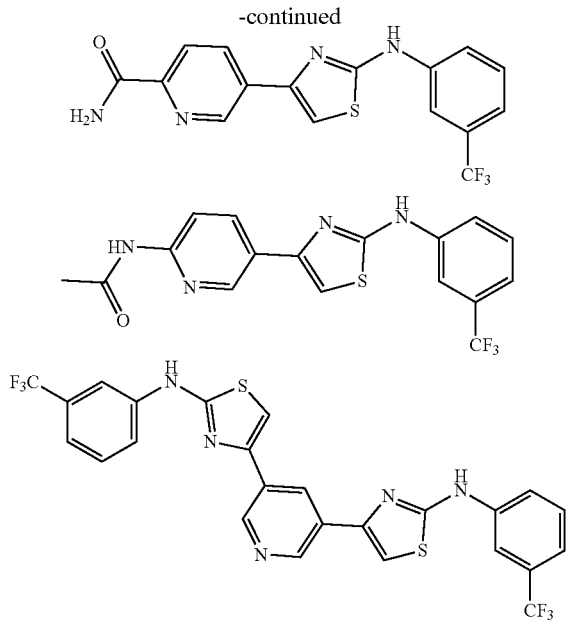

The compounds of this invention may be prepared or isolated in general by synthetic and/or semi-synthetic methods known to those skilled in the art for analogous compounds and by methods described in detail in the Examples, herein. In some embodiments, the present invention provides a compound or an intermediate compound as described in the Examples, or a salt thereof 4. Uses, Formulation and Administration Pharmaceutically Acceptable Compositions According to another embodiment, the invention provides a pharmaceutical composition comprising a compound of this invention or a pharmaceutically acceptable derivative thereof and a pharmaceutically acceptable carrier, adjuvant, or vehicle. The amount of compound in compositions of this invention is such that is effective to measurably activate AHR, or a mutant thereof, in a biological sample or in a patient. The amount of compound in compositions of this invention is such that is effective to measurably activate AHR, or a variant or mutant thereof, in a biological sample or in a patient. In certain embodiments, the amount of compound in compositions of this invention is such that is effective to measurably activate AHR, or a mutant thereof, in a biological sample or in a patient. In certain embodiments, the amount of compound in compositions of this invention is such that is effective to measurably activate AHR, or a variant or mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an active metabolite or residue thereof.

As used herein, the term "active metabolite or residue thereof" means that a metabolite or residue thereof also activates AHR, or a mutant thereof. The term "active metabolite or residue thereof" also means that a metabolite or residue thereof activates AHR, or a variant or mutant thereof.

Compositions of the present invention can be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions can be formulated according to techniques known in the art using suitable dispersing or wetting agents and suspending agents. The sterile injectable preparation can also be a sterile injectable solution or suspension in a non-toxic parenterally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium.

For this purpose, any bland fixed oil can be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention can be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch.

When aqueous suspensions are required for oral use, the active ingredient is combined with emulsifying and suspending agents. If desired, certain sweetening, flavoring or coloring agents can also be added.

Alternatively, pharmaceutically acceptable compositions of this invention can be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention can also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches can also be used.

For topical applications, provided pharmaceutically acceptable compositions can be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions can be formulated in an ointment such as petrolatum.

Pharmaceutically acceptable compositions of this invention can also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that can be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient depends upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition also depends upon the particular compound in the composition.

Uses of Compounds and Pharmaceutically Acceptable Compositions

In some embodiments, the present invention provides a method of using a compound as described herein for treating a disease or disorder associated with AHR. In some embodiments, a disease or disorder associated with AHR is an angiogenesis implicated disorder as described herein. In some embodiments, a disease or disorder associated with AHR is a cancer as described herein. In some embodiments, a disease or disorder associated with AHR is an inflammatory disorder as described herein. In some embodiments, a disease or disorder associated with AHR is a disease or disorder as described in Gutiérrez-Vázquez C. et al., *Immunity* 2018, 48(1):19-33, and Rothhammer V., et al., *Nat Rev Immunol.* 2019; 19(3):184-197, each of which is incorporated herein by reference in its entirety.

Angiogenesis Implicated Disorders

In one aspect, the present invention provides a method for treating or preventing or reducing the risk of an angiogenesis implicated disorder in a patient comprising administering to the patient a compound of the invention, or a pharmaceutically acceptable salt thereof, or a pharmaceutical composition thereof. In some embodiments, an angiogenesis implicated disorder is associated with a reduced expression or activation of an AHR.

In some embodiments, an angiogenesis implicated disorder is a retinopathy, psoriasis, rheumatoid arthritis, obesity, or cancer (for example, as described below).

Cancer

In some embodiments, the present invention provides a method for treating or preventing or reducing the risk of cancer in patient comprising administering to the patient a compound of the invention, or a pharmaceutically acceptable salt thereof, or a pharmaceutical composition thereof. In some embodiments, a cancer is associated with a reduced expression or activation of an aryl hydrocarbon receptor (AHR).

The cancer or proliferative disorder or tumor to be treated using the compounds and methods and uses described herein include, but are not limited to, a hematological cancer, a lymphoma, a myeloma, a leukemia, a neurological cancer, skin cancer, breast cancer, a prostate cancer, a colorectal cancer, lung cancer, head and neck cancer, a gastrointestinal cancer, a liver cancer, a pancreatic cancer, a genitourinary cancer, a bone cancer, renal cancer, and a vascular cancer.

In some embodiments, a cancer includes, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia, polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, and retinoblastoma).

In some embodiments, a cancer is glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, or retinoblastoma.

In some embodiments, a cancer is acoustic neuroma, astrocytoma (e.g. Grade I—Pilocytic Astrocytoma, Grade II—Low-grade Astrocytoma, Grade III—Anaplastic Astrocytoma, or Grade IV Glioblastoma (GBM)), chordoma, CNS lymphoma, craniopharyngioma, brain stem glioma, ependymoma, mixed glioma, optic nerve glioma, subependymoma, medulloblastoma, meningioma, metastatic brain tumor, oligodendroglioma, pituitary tumors, primitive neuroectodermal (PNET) tumor, or schwannoma. In some embodiments, the cancer is a type found more commonly in children than adults, such as brain stem glioma, craniopharyngioma, ependymoma, juvenile pilocytic astrocytoma (JPA), medulloblastoma, optic nerve glioma, pineal tumor, primitive neuroectodermal tumors (PNET), or rhabdoid tumor. In some embodiments, the patient is an adult human. In some embodiments, the patient is a child or pediatric patient.

Cancer includes, in another embodiment, without limitation, mesothelioma, hepatobilliary (hepatic and billiary duct), bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, non-Hodgkins's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

In some embodiments, a cancer is a solid tumor, such as a sarcoma, carcinoma, or lymphoma. Solid tumors generally comprise an abnormal mass of tissue that typically does not include cysts or liquid areas. In some embodiments, the cancer is selected from renal cell carcinoma, or kidney cancer; hepatocellular carcinoma (HCC) or hepatoblastoma, or liver cancer; melanoma; breast cancer; colorectal carcinoma, or colorectal cancer; colon cancer; rectal cancer; anal cancer; lung cancer, such as non-small cell lung cancer (NSCLC) or small cell lung cancer (SCLC); ovarian cancer, ovarian epithelial cancer, ovarian carcinoma, or fallopian tube cancer; papillary serous cystadenocarcinoma or uterine papillary serous carcinoma (UPSC); prostate cancer; testicular cancer; gallbladder cancer; hepatocholangiocarcinoma; soft tissue and bone synovial sarcoma; rhabdomyosarcoma; osteosarcoma; chondrosarcoma; Ewing sarcoma; anaplastic thyroid cancer; adrenocortical carcinoma; pancreatic cancer; pancreatic ductal carcinoma or pancreatic adenocarcinoma; gastrointestinal/stomach (GIST) cancer; lymphoma; squamous cell carcinoma of the head and neck (SCCHN); salivary gland cancer; glioma, or brain cancer; neurofibromatosis-1 associated malignant peripheral nerve sheath tumors (MPNST); Waldenstrom's macroglobulinemia; or medulloblastoma.

In some embodiments, a cancer is hepatocellular carcinoma (HCC). In some embodiments, the cancer is hepatoblastoma. In some embodiments, the cancer is colon cancer. In some embodiments, the cancer is rectal cancer. In some embodiments, the cancer is ovarian cancer, or ovarian carcinoma. In some embodiments, the cancer is ovarian epithelial cancer. In some embodiments, the cancer is fallopian tube cancer. In some embodiments, the cancer is papillary serous cystadenocarcinoma. In some embodiments, the cancer is uterine papillary serous carcinoma (UPSC). In some embodiments, the cancer is hepatocholangiocarcinoma. In some embodiments, the cancer is soft tissue and bone synovial sarcoma. In some embodiments, the cancer is rhabdomyosarcoma. In some embodiments, the cancer is osteosarcoma. In some embodiments, the cancer is anaplastic thyroid cancer. In some embodiments, the cancer is adrenocortical carcinoma. In some embodiments, the cancer is pancreatic cancer, or pancreatic ductal carcinoma. In some embodiments, the cancer is pancreatic adenocarcinoma. In some embodiments, the cancer is glioma. In some embodiments, the cancer is malignant peripheral nerve sheath tumors (MPNST). In some embodiments, the cancer is neurofibromatosis-1 associated MPNST. In some embodiments, the cancer is Waldenstrom's macroglobulinemia. In some embodiments, the cancer is medulloblastoma.

In some embodiments, a cancer is a viral-associated cancer, including human immunodeficiency virus (HIV) associated solid tumors, human papilloma virus (HPV)-16 positive incurable solid tumors, and adult T-cell leukemia, which is caused by human T-cell leukemia virus type I (HTLV-I) and is a highly aggressive form of CD4+ T-cell leukemia characterized by clonal integration of HTLV-I in leukemic cells (See clinicaltrials.gov, study NCT02631746); as well as virus-associated tumors in gastric cancer, nasopharyngeal carcinoma, cervical cancer, vaginal cancer, vulvar cancer, squamous cell carcinoma of the head and neck, and Merkel cell carcinoma. (See clinicaltrials.gov, studies NCT02488759, NCT0240886, NCT02426892)

In some embodiments, a cancer is melanoma cancer. In some embodiments, a cancer is breast cancer. In some embodiments, a cancer is lung cancer. In some embodiments, a cancer is small cell lung cancer (SCLC). In some embodiments, a cancer is non-small cell lung cancer (NSCLC). In some embodiments, a cancer is selected from prostate cancer, liver cancer, and ovarian cancer.

Inflammatory Disorders

In some embodiments, the present invention provides a method for treating or preventing or reducing the risk of an inflammatory disorder in patient comprising administering to the patient a compound of the invention, or a pharmaceutically acceptable salt thereof, or a pharmaceutical composition thereof. In some embodiments, an inflammatory disorder is associated with a reduced expression or activation of an aryl hydrocarbon receptor (AHR). In some embodiments, an inflammatory disorder is associated with a reduced expression or reduced activation of an aryl hydrocarbon receptor (AHR).

Inflammatory disorders include a large number of disorders or conditions that are involved in a variety of diseases, including those involving the immune system, including those demonstrated in allergic reactions and myopathies, or non-immune diseases with causal origins in inflammatory processes including, but not limited to cancer, atherosclerosis, and ischemic heart disease. Non-limiting examples of disorders associated with inflammation include, but are not limited to, acne vulgaris, asthma, autoimmune diseases, autoinflammatory diseases, celiac disease, chronic prostatitis, diverticulitis, glomerulonephritis, hidradenitis suppurativa, hypersensitivities, inflammatory bowel diseases (IBDs), interstitial cystitis, otitis, pelvic inflammatory disease, reperfusion injury, rheumatic fever, rheumatoid arthritis, sarcoidosis, transplant rejection, and vasculitis.

In some embodiments, an inflammatory disorder is necrotizing enterocolitis, inflammatory bowel disease (IBD), autoimmune diseases Crohn's disease, celiac disease, ulcerative colitis, cardiovascular disease, ocular Behcet's disease, breast cancer, and others.

Other non-limiting examples of inflammatory disease include, without limitation, acne, acid-induced lung injury, Addison's disease, adrenal hyperplasia, adrenocortical insufficiency, adult-onset Still's disease, adult respiratory distress syndrome (ARDS), age-related macular degeneration, aging, alcoholic hepatitis, alcoholic liver disease, allergen-induced asthma, allergic bronchopulmonary, allergic conjunctivitis, allergic contact dermatitis, allergies, allergic encephalomyelitis, allergic neuritis, allograft rejection, alopecia, alopecia areata, Alzheimer's disease, amyloidosis, amyotrophic lateral sclerosis, angina pectoris, angioedema, angiofibroma, anhidrotic ectodermal dysplasia-ill, anti-glomerular basement membrane disease, antigen-antibody complex mediated diseases, ankylosing spondylitis, antiphospholipid syndrome, aphthous stomatitis, appendicitis, arthritis, ascites, aspergillosis, asthma, atherosclerosis, atherosclerotic plaques, atopic dermatitis, atrophic thyroiditis, autoimmune diseases, autoimmune hemolytic anemia (immune pancytopenia, paroxysmal nocturnal hemoglobinuria), autoimmune polyendocrinopathies, autoimmune thrombocytopenia (idiopathic thrombocytopenic purpura, immune-mediated thrombocytopenia), autoimmune hepatitis, autoimmune thyroid disorders, autoinflammatory diseases, back pain, Bacillus anthracis infection, Bechet's disease, bee sting-induced inflammation, Behget's syndrome, Bell's palsy, berylliosis, Blau syndrome, bone pain, bronchiolitis, bullous pemphigoid (BP) asthma, burns, bursitis, cardiac hypertrophy, carpal tunnel syndrome, Castleman's disease, catabolic disorders, cataracts, Celiac disease, cerebral aneurysm, chemical irritant-induced inflammation, chorioretinitis, chronic atypical neutrophilic dermatosis with lipodystrophy and elevated temperature (CANDLE) syndrome, chronic heart failure, chronic lung disease of prematurity, chronic obstructive pulmonary disease (COPD), chronic pancreatitis, chronic prostatitis, chronic recurrent multifocal osteomyelitis, cicatricial alopecia, colitis, complex regional pain syndrome, complications of organ transplantation, conjunctivitis, connective tissue disease, contact dermatitis, corneal graft neovascularization, corneal ulcer, Crohn's disease, cryopyrin-associated periodic syndromes, cutaneous lupus erythematosus (CLE), cryptococcosis, cystic fibrosis, deficiency of the interleukin-1 receptor antagonist (DIRA), dermatitis, dermatitis endotoxemia, dermatomyositis, diabetic macular edema, diverticulitis, eczema, encephalitis, endometriosis, endotoxemia, eosinophilic pneumonias, epicondylitis, epidermolysis bullosa, erythema multiforme, erythroblastopenia, esophagitis, familial amyloidotic polyneuropathy, familial cold urticarial, familial Mediterranean fever, fetal growth retardation, fibromyalgia, fistulizing Crohn's disease, food allergies, giant cell arteritis, glaucoma, glioblastoma, glomerular disease, glomerular nephritis, glomerulonephritis, gluten-sensitive enteropathy, gout, gouty arthritis, graft-versus-host disease (GVHD), granulomatous hepatitis, Graves' disease, growth plate injuries, Guillain-Barre syndrome, gut diseases, hair loss, Hashimoto's thyroiditis, head injury, headache, hearing loss, heart disease, hemangioma, hemolytic anemia, hemophilic joints, Henoch-Scholein purpura, hepatitis, hereditary periodic fever syndrome, heritable disorders of connective tissue, herpes zoster and simplex, hidradenitis suppurativa (HS), hip replacement, Hodgkin's disease, Huntington's disease, hyaline membrane disease, hyperactive inflammatory response, hyperammonemia, hypercalcemia, hypercholesterolemia, hypereosinophilic syndrome (HES), hyperimmunoglobulinemia D with recurrent fever (HIDS), hypersensitivity pneumonitis, hypertropic bone formation, hypoplastic and other anemias, hypoplastic anemia, ichthyosis, idiopathic demyelinating polyneuropathy, Idiopathic inflammatory myopathies (dermatomyositis, polymyositis), idiopathic pulmonary fibrosis, idiopathic thrombocytopenic purpura, immunoglobulin nephropathies, immune complex nephritis, immune thrombocytopenic purpura (ITP), incontinentia pigmenti (IP, Bloch-Siemens syndrome), infectious mononucleosis, infectious diseases including viral diseases such as AIDS (HIV infection), hepatitis A, B, C, D, and E, herpes; inflammation, inflammation of the CNS, inflammatory bowel disease (IBD), inflammatory disease of the lower respiratory tract including bronchitis or chronic obstructive pulmonary diseases, inflammatory disease of the upper respiratory tract including the nose and sinuses such as rhinitis or sinusitis, inflammatory diseases of the respiratory tract, inflammatory ischemic event such as stroke or cardiac arrest, inflammatory lung disease, inflammatory myopathy such as myocarditis, inflammatory liver disease, inflammatory neuropathy, inflammatory pain, insect bite-induced inflammation, interstitial cystitis, interstitial lung disease, iritis, irritant-induced inflammation, ischemia/reperfusion, joint replacement, juvenile arthritis, juvenile rheumatoid arthritis, keratitis, kidney injury caused by parasitic infections, kidney transplant rejection, leptospirosis, leukocyte adhesion deficiency, lichen sclerosus (LS), Lambert-Eaton myasthenic syndrome, Loeffler's syndrome, lupus, lupus nephritis, Lyme disease, Marfan syndrome (MFS), mast cell activation syndrome, mastocytosis, meningitis, meningioma, mesothelioma, mixed connective tissue disease, Muckle-Wells syndrome (urticaria deafness amyloidosis), mucositis, multiple organ injury syndrome, multiple sclerosis, muscle wasting, muscular dystrophy, myasthenia gravis (MG), myelodysplastic syndrome, myocarditis, myositis, nasal sinusitis, necrotizing enterocolitis, neonatal onset multisystem inflammatory disease (NOMID), neovascular glaucoma, nephrotic syndrome, neuritis, neuropathological diseases, non-allergen induced asthma, obesity, ocular allergy, optic neuritis, organ transplant rejection, Osier-Weber syndrome, osteoarthritis, osteogenesis imperfecta, osteonecrosis, osteoporosis, osterarthritis, otitis, pachyonychia congenita, Paget's disease, Paget's disease of bone, pancreatitis, Parkinson's disease, pediatric rheumatology, pelvic inflammatory disease, pemphigus, pemphigus vulgaris (PV), bullous pemphigoid (BP), pericarditis, periodic fever, periodontitis, peritoneal endometriosis, pernicious anemia (Addison's disease), pertussis, PFAPA (periodic fever aphthous pharyngitis and cervical adenopathy), pharyngitis and adenitis (PFAPA syndrome), plant irritant-induced inflammation, pneumocystis infection, pneumonia, pneumonitis, poison ivy/urushiol oil-induced inflammation, polyarthritis nodosa, polychondritis, polycystic kidney disease, polymyalgia rheumatic, giant cell arteritis, polymyositis, pouchitis, reperfusion injury and transplant rejection, primary biliary cirrhosis, primary pulmonary hypertension, primary sclerosing cholangitis (PSC), proctitis, psoriasis, psoriasis vulgaris, psoriatic arthritis, psoriatic epidermis, psychosocial stress diseases, pulmonary disease, pulmonary fibrosis, pulmonary hypertension, pyoderma gangrenosum, pyogenic granuloma retrolental fibroplasias, pyogenic sterile arthritis, Raynaud's syndrome, Reiter's disease, reactive arthritis, renal disease, renal graft rejection, reperfusion injury, respiratory distress syndrome, retinal disease, retrolental fibroplasia, Reynaud's syndrome, rheumatic carditis, rheumatic diseases, rheumatic fever, rheumatoid arthritis, rhinitis, rhinitis psoriasis, rosacea, sarcoidosis, Schnitzler syndrome, scleritis, sclerosis, scleroderma, scoliosis, seborrhea, sepsis, septic shock, severe pain, Sezary syndrome, sickle cell anemia, silica-induced disease (Silicosis), Sjogren's syndrome, skin diseases, skin irritation, skin rash, skin sensitization (contact dermatitis or allergic contact dermatitis), sleep apnea, spinal cord injury, spinal stenosis, spondyloarthropathies, sports injuries, sprains and strains, Stevens-Johnson syndrome (SJS), stroke, subarachnoid hemorrhage, sunburn, synovial inflammation, systemic inflammatory response syndrome (SIRS), systemic lupus erythematosus, systemic mast cell disease (SMCD), systemic vasculitis, systemic-onset juvenile idiopathic arthritis, temporal arteritis, tendinitis, tenosynovitis, thrombocytopenia, thyroditis, thyroiditis, tissue transplant, toxoplasmosis, trachoma, transplantation rejection, traumatic brain injury, tuberculosis, tubulointerstitial nephritis, tumor necrosis factor (TNF) receptor associated periodic syndrome (TRAPS), type 1 diabetes, type 2 diabetes, complications from type 1 or type 2 diabetes, ulcerative colitis, urticaria, uterine fibroids, uveitis, uveoretinitis, vascular restenosis, vasculitis, vasculitis (NHLBI), vitiligo, Wegener's granulomatosis, and Whipple's disease.

The term "inflammatory bowel disease" or "IBD" as used herein is a collective term describing inflammatory disorders of the gastrointestinal tract, the most common forms of which are ulcerative colitis and Crohn's disease. Other forms of IBD that can be treated with the presently disclosed compounds, compositions and methods include diversion colitis, ischemic colitis, infectious colitis, chemical colitis, microscopic colitis (including collagenous colitis and lymphocytic colitis), atypical colitis, pseudomembranous colitis, fulminant colitis, autistic enterocolitis, indeterminate colitis, Behget's disease, gastroduodenal CD, jejunoileitis, ileitis, ileocolitis, Crohn's (granulomatous) colitis, irritable bowel syndrome, mucositis, radiation induced enteritis, short bowel syndrome, celiac disease, stomach ulcers, diverticulitis, pouchitis, proctitis, and chronic diarrhea.

As used herein, treating or preventing an inflammatory disease also includes ameliorating or reducing one or more symptoms of the inflammatory disease. Where the inflammatory disease or disorder is IBD, the term "symptoms of IBD" can refer to detected symptoms such as abdominal pain, diarrhea, rectal bleeding, weight loss, fever, loss of appetite, and other more serious complications, such as dehydration, anemia and malnutrition. A number of such symptoms are subject to quantitative analysis (e.g., weight loss, fever, anemia, etc.). Some symptoms are readily determined from a blood test (e.g., anemia) or a test that detects the presence of blood (e.g., rectal bleeding). The term "wherein said symptoms are reduced" refers to a qualitative or quantitative reduction in detectable symptoms, including but not limited to, a detectable impact on the rate of recovery from disease (e.g., rate of weight gain). The diagnosis is typically determined by way of an endoscopic observation of the mucosa, and pathologic examination of endoscopic biopsy specimens. The course of IBD varies, and is often associated with intermittent periods of disease remission and disease exacerbation. Various methods have been described for characterizing disease activity and severity of IBD as well as response to treatment in subjects having IBD. Treatment according to the present methods is generally applicable to a subject having IBD of any level or degree of disease activity.

In some embodiments, the present invention provides a method for treating or preventing or reducing the risk of an angiogenesis implicated disorder, cancer, or an inflammatory disorder, such as those described above, comprising administering to the patient a compound selected from:

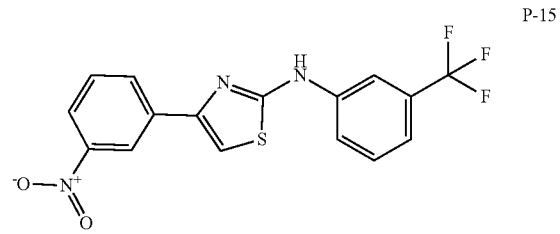

P-15

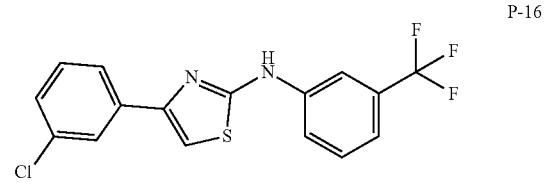

P-16

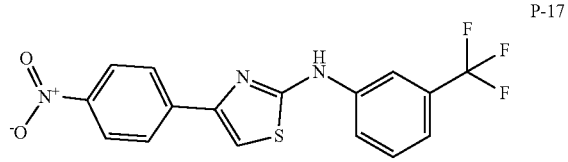

P-17

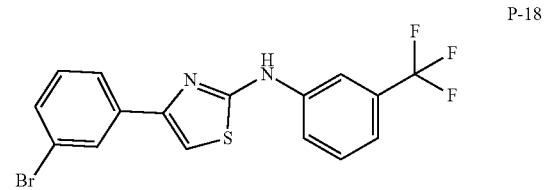

P-18

-continued

P-19 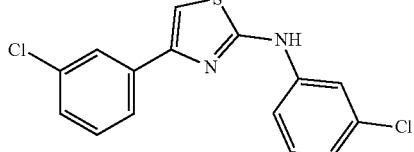

P-20 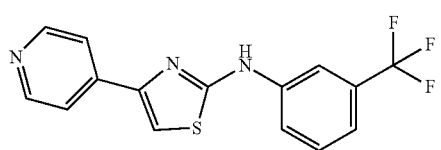

P-21 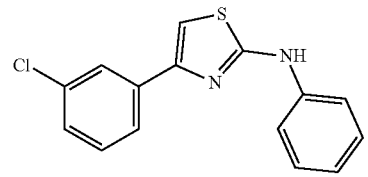

P-22 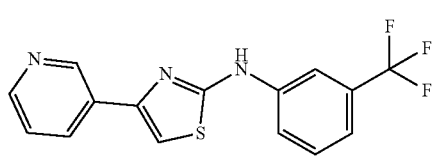

P-23 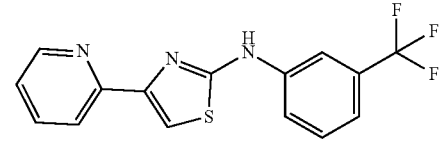

P-24 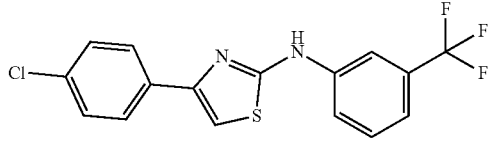

P-25 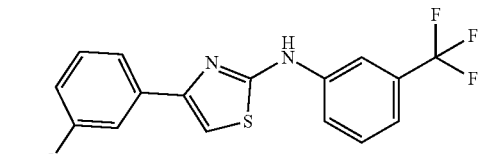

P-26 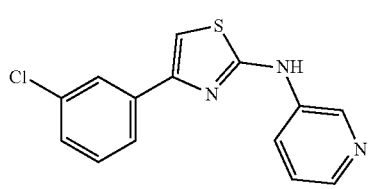

P-27 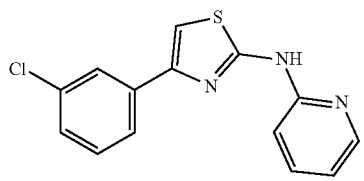

-continued

P-28 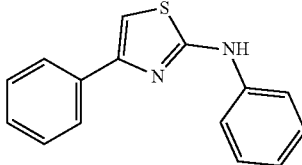

or a pharmaceutically acceptable salt thereof, or a pharmaceutical composition thereof.

The compounds and compositions, according to the method of the present invention, may be administered using any amount and any route of administration effective for activating AHR and treating or lessening the severity of a disease, for example, as those described herein. The exact amount required will vary from subject to subject, depending on the species, age, and general condition of the subject, the severity of the disease or condition, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the disease or disorder being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention.

Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Co-Administration with One or More Other Therapeutic Agent(s)

Depending upon the particular condition, or disease, to be treated, additional therapeutic agents that are normally administered to treat that condition, can also be present in the compositions of this invention. As used herein, additional therapeutic agents that are normally administered to treat a particular disease, or condition, are known as "appropriate for the disease, or condition, being treated."

In some embodiments, the present invention provides a method of treating a disclosed disease or condition comprising administering to a patient in need thereof an effective amount of a compound disclosed herein or a pharmaceutically acceptable salt thereof and co-administering simultaneously or sequentially an effective amount of one or more additional therapeutic agents, such as those described herein. In some embodiments, the method includes co-administering one additional therapeutic agent. In some embodiments, the method includes co-administering two additional therapeutic agents. In some embodiments, the combination of the disclosed compound and the additional therapeutic agent or agents acts synergistically.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds.

One or more other therapeutic agent(s) can be administered separately from a compound or composition of the invention, as part of a multiple dosage regimen. Alternatively, one or more other therapeutic agent(s) may be part of a single dosage form, mixed together with a compound of this invention in a single composition. If administered as a multiple dosage regime, one or more other therapeutic agent(s) and a compound or composition of the invention can be administered simultaneously, sequentially or within a period of time from one another, for example within 1, 2, 3, 4, 5, 6, 7, 8, 9, 10, 11, 12, 13, 14, 15, 16, 17, 18, 18, 20, 21, 22, 23, or 24 hours from one another. In some embodiments, one or more other therapeutic agent(s) and a compound or composition of the invention are administered as a multiple dosage regimen within greater than 24 hours apart.

As used herein, the term "combination," "combined," and related terms refers to the simultaneous or sequential administration of therapeutic agents in accordance with this invention. For example, a compound of the present invention can be administered with one or more other therapeutic agent(s) simultaneously or sequentially in separate unit dosage forms or together in a single unit dosage form. Accordingly, the present invention provides a single unit dosage form comprising a compound of the current invention, one or more other therapeutic agent(s), and a pharmaceutically acceptable carrier, adjuvant, or vehicle.

The amount of a compound of the invention and one or more other therapeutic agent(s) (in those compositions which comprise an additional therapeutic agent as described above) that can be combined with the carrier materials to produce a single dosage form varies depending upon the host treated and the particular mode of administration. Preferably, a composition of the invention should be formulated so that a dosage of between 0.01-100 mg/kg body weight/day of a compound of the invention can be administered.

In those compositions which comprise one or more other therapeutic agent(s), the one or more other therapeutic agent(s) and a compound of the invention can act synergistically. Therefore, the amount of the one or more other therapeutic agent(s) in such compositions may be less than that required in a monotherapy utilizing only that therapeutic agent. In such compositions a dosage of between 0.01-1,000 g/kg body weight/day of the one or more other therapeutic agent(s) can be administered.

The amount of one or more other therapeutic agent(s) present in the compositions of this invention may be no more than the amount that would normally be administered in a composition comprising that therapeutic agent as the only active agent. Preferably the amount of one or more other therapeutic agent(s) in the presently disclosed compositions ranges from about 50% to 100% of the amount normally present in a composition comprising that agent as the only therapeutically active agent. In some embodiments, one or more other therapeutic agent(s) is administered at a dosage of about 50%, about 55%, about 60%, about 65%, about 70%, about 75%, about 80%, about 85%, about 90%, or about 95% of the amount normally administered for that agent. As used herein, the phrase "normally administered" means the amount an FDA approved therapeutic agent is approved for dosing per the FDA label insert.

The compounds of this invention, or pharmaceutical compositions thereof, can also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

Exemplary Other Therapeutic Agents

In some embodiments, provided herein are methods of treatment in which an AHR agonist compound described herein is administered in combination with an agent for treatment of an inflammatory disease or condition. Examples of agents for treatment of an inflammatory disease or condition that can be used in combination with compounds described herein, include alpha-fetoprotein modulators; adenosine A3 receptor antagonist; adrenomedullin ligands; AKT1 gene inhibitors; antibiotics; antifungals; ASK1 inhibitors; ATPase inhibitors; beta adrenoceptor antagonists; BTK inhibitors; calcineurin inhibitors; carbohydrate metabolism modulators; cathepsin S inhibitors; CCR9 chemokine antagonists; CD233 modulators; CD29 modulators; CD3 antagonists; CD40 ligand inhibitors; CD40 ligand receptor antagonists; chemokine CXC ligand inhibitors; CHST15 gene inhibitors; collagen modulators; CSF-1 antagonists; CX3CR1 chemokine modulators; eco-biotics; eotaxin ligand inhibitors; EP4 prostanoid receptor agonists; FI FO ATP synthase modulators; farnesoid X receptor (FXR and NR1H4) agonists or modulators; fecal microbiota transplantation (FMT); fractalkine ligand inhibitors; free fatty acid receptor 2 antagonists; GATA 3 transcription factor inhibitors; glucagon-like peptide 2 agonists; glucocorticoid agonists; Glucocorticoid receptor modulators; guanylate cyclase receptor agonists; HIF prolyl hydroxylase inhibitors; histone deacetylase inhibitors; HLA class II antigen modulators; hypoxia inducible factor-1 stimulator; ICAM1 gene inhibitors; IL-1 beta ligand modulators; IL-12 antagonists; IL-13 antagonists; IL-18 antagonists; IL-22 agonists; IL-23 antagonists; IL-23A inhibitors; IL-6 antagonists; IL-7 receptor antagonists; IL-8 receptor antagonists; integrin alpha-4/beta-1 antagonists; integrin alpha-4/beta-7 antagonists; integrin antagonists; interleukin ligand inhibitors; interleukin receptor 17A antagonists; interleukin-1 beta ligands; interleukin 1 like receptor 2 inhibitors; IL-6 receptor modulators; JAK tyrosine kinase inhibitors; Jak1 tyrosine kinase inhibitors; Jak3 tyrosine kinase inhibitors; lactoferrin stimulators; LanC like protein 2 modulators; leukocyte elastase inhibitors; leukocyte proteinase-3 inhibitors; MAdCAM inhibitors; melanin concentrating hormone (MCH-1) antagonist; melanocortin agonists; metalloprotease-9 inhibitors; microbiome-targeting therapeutics; natriuretic peptide receptor C agonists; neuregulin-4 ligands; NLPR3 inhibitors; NKG2 D activating NK receptor antagonists; nuclear factor kappa B inhibitors; opioid receptor antagonists; 0×40 ligand inhibitors; oxidoreductase inhibitors; P2X7 purinoceptor modulators; PDE 4 inhibitors; Pellino homolog 1 inhibitors; PPAR alpha/delta agonists; PPAR gamma agonists; protein fimH inhibitors; P-selectin glycoprotein ligand-1 inhibitors; Ret tyrosine kinase receptor inhibitors; RIP-1 kinase inhibitors; RIP-2 kinase inhibitors; RNA polymerase inhibitors; sphingosine 1 phosphate phosphatase 1 stimulators; sphingosine-1-phosphate receptor-1 agonists; sphingosine-1-phosphate receptor-5 agonists; sphingosine-1-phosphate receptor-1 antagonists; sphingosine-1-phosphate receptor-1 modulators; stem cell antigen-1 inhibitors; superoxide dismutase modulators; SYK inhibitors; tissue transglutaminase inhibitor; TLR-3 antagonists; TLR-4 antagonists; Toll-like receptor 8 (TLR8) inhibitors; TLR-9 agonists; TNF alpha ligand inhibitors; TNF ligand inhibitors; TNF alpha ligand modulators; TNF antagonists; TPL-2 inhibitors; tumor necrosis factor 14 ligand modulators; tumor necrosis factor 15 ligand inhibitors; Tyk2 tyrosine kinase inhibitors; type I IL-1 receptor antagonists; vanilloid VR1 agonists; and zonulin inhibitors, and combinations thereof.

In some embodiments, the one or more other therapeutic agents is an anti-inflammatory agent. Anti-inflammatory agents include but are not limited to NSAIDs, non-specific and COX-2 specific cyclooxgenase enzyme inhibitors, gold compounds, corticosteroids, methotrexate, tumor necrosis factor receptor (TNF) receptors antagonists, immunosuppressants and methotrexate. Non-limiting examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors (i.e., a compound that inhibits COX-2 with an IC50 that is at least 50-fold lower than the IC50 for COX-1) such as celecoxib, valdecoxib, lumiracoxib, etoricoxib and/or rofecoxib.

In a further embodiment, the anti-inflammatory agent is a salicylate. Salicylates include, but are not limited to, acetylsalicylic acid or aspirin, sodium salicylate, and choline and magnesium salicylates.

The anti-inflammatory agent can also be a corticosteroid. For example, the corticosteroid can be chosen from cortisone, dexamethasone, methylprednisolone, prednisolone, prednisolone sodium phosphate, and prednisone. In some embodiments, the anti-inflammatory therapeutic agent is a gold compound such as gold sodium thiomalate or auranofin.

In some embodiments, the anti-inflammatory agent is a metabolic inhibitor such as a dihydrofolate reductase inhibitor, such as methotrexate or a dihydroo rotate dehydrogenase inhibitor, such as leflunomide.

In some embodiments, the anti-inflammatory compound is an anti-CS monoclonal antibody (such as eculizumab or pexelizumab), a TNF antagonist, such as entanercept, or infliximab, which is an anti-TNF alpha monoclonal antibody.

Included herein are methods of treatment in which a compound described herein, is administered in combination with an immunosuppressant. In some embodiments, the immunosuppressant is methotrexate, leflunomide, cyclosporine, tacrolimus, azathioprine, or mycophenolate mofetil.

Included herein are methods of treatment in which an AHR agonist compound described herein, is administered in combination with a class of agent for treatment of IBD. Examples of classes of agents for treatment of IBD that can be used in combination with a compound described herein include ASK1 inhibitors, beta adrenoceptor antagonists, BTK inhibitors, beta-glucuronidase inhibitors, bradykinin receptor modulators, calcineurin inhibitors, calcium channel inhibitors, cathepsin S inhibitors, CCR3 chemokine antagonists, CD40 ligand receptor antagonists, chemokine CXC ligand inhibitors, CHST15 gene inhibitors, collagen modulators, CSF-1 antagonists, cyclooxygenase inhibitors, cytochrome P450 3A4 inhibitors, eotaxin ligand inhibitors, EP4 prostanoid receptor agonists, erythropoietin receptor agonists, fractalkine ligand inhibitors, free fatty acid receptor 2 antagonists, GATA 3 transcription factor inhibitors, glucagon-like peptide 2 agonists, glucocorticoid agonists, guanylate cyclase receptor agonists, histone deacetylase inhibitors, HLA class II antigen modulators, IL-12 antagonists, IL-13 antagonists, IL-23 antagonists, IL-6 antagonists, IL-6 receptor modulators, interleukin-7 receptor modulators, IL-7 antagonists, IL-8 antagonists, integrin alpha-4/beta-1 antagonists, integrin alpha-4/beta-7 antagonists, integrin alpha-E antagonists, integrin antagonists, integrin beta-7 antagonists, interleukin ligand inhibitors, interleukin-2 ligand, interleukin receptor 17A antagonists, interleukin-1 beta ligands, interleukin-1 beta ligand modulators, IRAK4 inhibitors, JAK tyrosine kinase inhibitors, Jak1 tyrosine kinase inhibitors, Jak3 tyrosine kinase inhibitors, LanC like protein 2 modulators, lipoxygenase modulators, MAdCAM inhibitors, matrix metalloprotease inhibitors, melanocortin agonists, metalloprotease-9 inhibitors, natriuretic peptide receptor C agonists, neuregulin-4 ligands, NKG2 D activating NK receptor antagonists, opioid receptor antagonists, opioid receptor delta antagonists, oxidoreductase inhibitors, P2X7 purinoceptor agonists, PDE 4 inhibitors, phagocytosis stimulating peptide modulators, potassium channel inhibitors, PPAR alpha agonists, PPAR delta agonists, PPAR gamma agonists, protein fimH inhibitors, P-selectin glycoprotein ligand-1 inhibitors, RNA polymerase inhibitors, sphingosine 1 phosphate phosphatase 1 stimulators, sphingosine 1 phosphate phosphatase modulators, sphingosine-1-phosphate receptor-1 agonists, sphingosine-1-phosphate receptor-1 antagonists, sphingosine-1-phosphate receptor-1 modulators, sphingosine-1-phosphate receptor-5 modulators, STAT3 gene inhibitors, stem cell antigen-1 inhibitors, superoxide dismutase modulators, superoxide dismutase stimulators, SYK inhibitors, TGF beta 1 ligand inhibitors, thymulin agonists, TLR antagonists, TLR agonists, TNF alpha ligand inhibitors, TNF antagonists, tumor necrosis factor 14 ligand modulators, type II TNF receptor modulators, Tpl 2 inhibitors, and Zonulin inhibitors.

Included herein are methods of treatment in which a compound described herein is administered in combination with an agent for treatment of IBD. Examples of agents for treatment of IBD that can be used in combination with a compound described herein, or a pharmaceutically acceptable salt, stereoisomer, mixture of stereoisomers, tautomer, or deuterated analog thereof, include those provided herein for the treatment of an inflammatory disease or condition, and ABX-464, adalimumab; alicaforsen, ALLO-ASC-CD, AMG-966, anakinra, apremilast; Alequel; AMG-139; amiselimod, ASD-003, ASP-3291, AX-1505, BBT-401, balsalazide; beclomethasone dipropionate; BI-655130, BMS-986184; budesonide; CEQ-508; certolizumab; ChAdOx2-HAV, dexamethasone sodium phosphate, DNVX-078, etanercept; cibinetide; Clostridium butyricum; ETX-201, golimumab; GS-4997, GS-9876, GS-4875, GS-4059, infliximab; mesalazine, HLD-400, LYC-30937 EC; IONIS-JBI1-2.5Rx, JNJ-64304500, JNJ-4447, naltrexone; natalizumab; neihulizumab, olsalazine; PH-46-A, propionyl-L-carnitine; PTG-100; remestemcel-L; tacrolimus; teduglutide; tofacitinib; ASP-1002; ustekinumab; vedolizumab; AVX-470; INN-108; SGM-1019; PF-06480605; PF-06651600; PF-06687234; RBX-8225, SER-287; Thetanix; TOP-1288; VBY-129; 99mTc-annexin V-128; bertilimumab; DLX-105; dolcanatide; FFP-104; filgotinib; foralumab; GED-0507-34-Levo; givinostat; GLPG-0974; iberogast; JNJ-40346527; K(D)PT; KAG–308; KHK-4083; KRP-203; larazotide acetate; LY–3074828, midismase; olokizumab; OvaSave; P-28-GST; PF-547659; prednisolone; QBECO; RBX-2660, RG–7835; JKB-122; SB-012; STNM-01; Debio-0512; TRK-170; zucapsaicin; ABT-494; Ampion; BI-655066; carotegast methyl; cobitolimod; elafibranor; etrolizumab; GS-5745; HMPL-004; LP-02, ozanimod; peficitinib; quetmolimab (E-6011); RHB-104; rifaximin; tildrakizumab; tralokinumab; brodalumab; laquinimod; plecanatide; vidofludimus; and AZD-058.

EXEMPLIFICATION

The following examples are intended to illustrate the invention and are not to be construed as being limitations thereon. Unless otherwise stated, one or more tautomeric forms of compounds of the examples described hereinafter may be prepared in situ and/or isolated. All tautomeric forms of compounds of the examples described hereafter should be considered to be disclosed. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art. Further, the compounds of the present invention can be produced by organic synthesis methods known to one of ordinary skill in the art as shown in the following examples.

Example 1: Synthesis of Exemplary Compounds

Certain exemplary compounds are prepared following the following schemes.

I-61

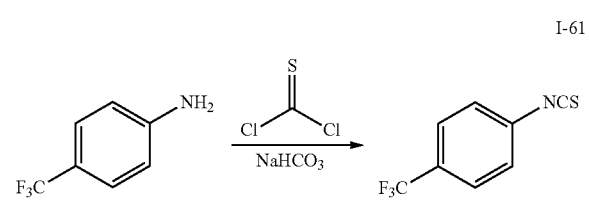

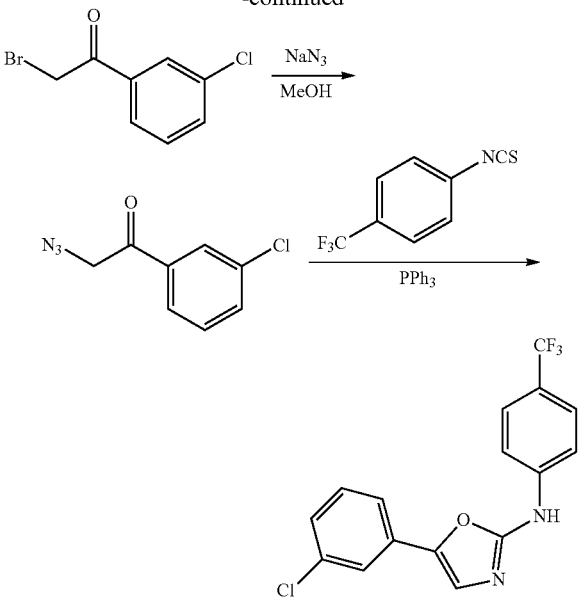

Step 1: 1-Isothiocyanato-4-(trifluoromethyl)benzene

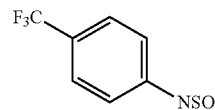

To a solution of NaHCO$_3$ (521.38 mg, 6.20 mmol, 2 eq) in H$_2$O (5 mL) was added a solution of 4-(trifluoromethyl)aniline (500 mg, 3.10 mmol, 384.62 µL, 1 eq) in DCM (5 mL). The reaction mixture was cooled to 0° C. and thiocarbonyl dichloride (356.44 mg, 3.10 mmol, 237.63 µL, 1 eq) was added dropwise over 0.5 h. The reaction was stirred at 25° C. for 12 h. TLC (PE/EtOAc=1/0, R$_f$=0.8) indicated starting material was consumed completely and one new spot formed. The reaction mixture was diluted with H$_2$O (50 mL) and extracted with DCM (30 mL×2). The combined organic layers were washed with brine (30 mL), dried over Na$_2$SO$_4$, filtered and concentrated under reduced pressure to yield 1-isothiocyanato-4-(trifluoromethyl)benzene (500 mg, 2.34 mmol, 75.4% yield, 95.0% purity) as a brown solid, which was used in the next step without further purification. $^1$H NMR (500 MHz, CDCl$_3$) δ ppm 7.62 (d, J=8.5 Hz, 2H), 7.32 (d, J=8.0 Hz, 2H).

Step 2: 2-Azido-1-(3-chlorophenyl)ethanone

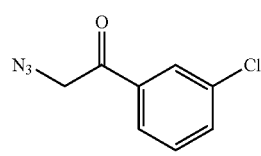 [SMILES: [N-]=[N+]=NCC(=O)c1cccc(Cl)c1]

To a solution of 2-bromo-1-(3-chlorophenyl)ethanone (500 mg, 2.14 mmol, 1 eq) in MeCN (5 mL) was added NaN$_3$ (167.06 mg, 2.57 mmol, 1.2 eq). The mixture was stirred at 25° C. for 4 h. TLC (PE/EtOAc=10/1, $R_f$=0.4) indicated starting material was consumed completely and one new spot formed. The reaction mixture was concentrated under reduced pressure to remove solvent. The residue was diluted with $H_2O$ (50 mL) and extracted with DCM (30 mL×2). The combined organic layers were washed with brine (30 mL), dried over $Na_2SO_4$, filtered and concentrated under reduced pressure to yield 2-azido-1-(3-chlorophenyl) ethanone (400 mg, 1.84 mmol, 86.0% yield, 90.0% purity) as a brown solid. $^1$H NMR (500 MHz, CDCl$_3$) δ ppm 7.87 (d, J=2.0 Hz, 1H), 7.76 (d, J=7.5 Hz, 1H), 7.58 (d, J=8.0 Hz, 1H), 7.44 (t, J=7.5 Hz, 1H), 4.53 (s, 2H).

Step 3: 5-(3-Chlorophenyl)-N-[4-(trifluoromethyl) phenyl]oxazol-2-amine

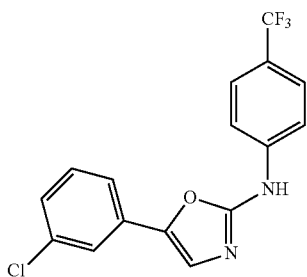 [SMILES: FC(F)(F)c1ccc(Nc2ncc(-c3cccc(Cl)c3)o2)cc1]

To a mixture of 2-azido-1-(3-chlorophenyl)ethanone (300 mg, 1.38 mmol, 1 eq) and 1-isothiocyanato-4-(trifluoromethyl)benzene (350 mg, 1.64 mmol, 1.19 eq) in DCM (5 mL) was added PPh$_3$ (543.07 mg, 2.07 mmol, 1.5 eq). The mixture was stirred at 30° C. for 12 h. TLC (PE/EtOAc=3/1, $R_f$=0.40) showed starting material was remained, and many new spots was detected. The reaction mixture was concentrated to yield a residue which was purified by flash silica gel chromatography (from pure PE to PE/EtOAc=3/2, TLC: PE/EtOAc=3/1, $R_f$=0.40). The residue was purified by preparative HPLC (HCl condition; column: Phenomenex Synergi C18 150*30 mm*4 μm; mobile phase: [water (0.05% HCl)-ACN]; B %: 70%-90%, 10 min) and lyophilized to yield a residue which was purified by preparative HPLC (condition; column: Agela DuraShell C18 250*25 mm*10 μm; mobile phase: [water (0.04% NH$_3$H$_2$O+10 mM NH$_4$HCO$_3$)-ACN]; B %: 58%-88%, 10 min]; B %: 65%-95%, 8 min) and lyophilized to yield 5-(3)-chlorophenyl)-N-[4-(trifluoromethyl)phenyl]oxazol-2-amine (30.88 mg, 89.09 μmol, 6.4% yield, 97.7% purity) as a white solid. $^1$H NMR (500 MHz, CD$_3$OD) δ ppm 7.74 (d, J=8.7 Hz, 2H), 7.64-7.58 (m, 3H), 7.54 (d, J=7.9 Hz, 1H), 7.41-7.36 (m, 2H), 7.27 (dd, J=1.0, 8.0 Hz, 1H); ES-LCMS m/z 339.0, 341.0 [M+H]$^+$.

I-63

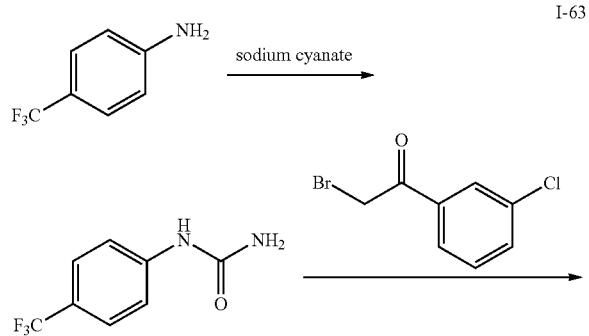

-continued

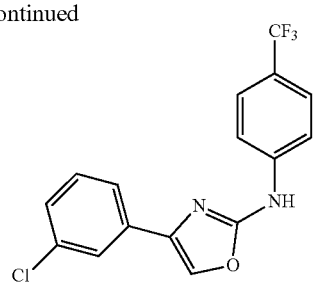

Step 1: [4-(Trifluoromethyl)phenyl]urea

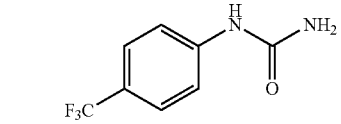

To a mixture of 4-(trifluoromethyl)aniline (4.08 g, 25.33 mmol, 3.14 mL, 1 eq) in AcOH (7 mL) and H$_2$O (7 mL) was added sodium; cyanate (3.29 g, 50.67 mmol, 2 eq). After being stirred at 40° C. for 4 h, 30 mL water was added to the above mixture, stirred at 25° C. for 0.5 h. The mixture was filtered and the solid was dried under reduce pressure to yield a residue which was purified by flash silica gel chromatography (from PE/EtOAc=100/1 to 1/1, TLC: PE/EtOAc=0/1, $R_f$=0.33) to yield [4-(trifluoromethyl)phenyl]urea (2.5 g, 12.25 mmol, 48.3% yield, 100% purity) as a white solid. $^1$H NMR (500 MHz, DMSO-d$_6$) δ ppm 8.94 (s, 1H), 7.62-7.53 (m, 4H), 6.03 (br s, 2H); ES-LCMS m/z 205.0 [M+H]$^+$.

Step 2: 4-(3-Chlorophenyl)-N-[4-(trifluoromethyl) phenyl]oxazol-2-amine

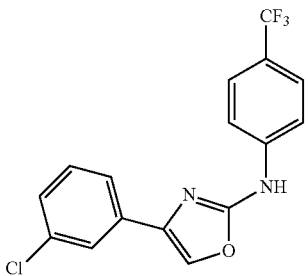 [SMILES: FC(F)(F)c1ccc(Nc2nc(-c3cccc(Cl)c3)co2)cc1]

A mixture of [4-(trifluoromethyl)phenyl]urea (500 mg, 2.45 mmol, 1 eq), 2-bromo-1-(3-chlorophenyl)ethanone (514.67 mg, 2.20 mmol, 0.9 eq) in ethylene glycol (5 mL) was stirred at 150° C. for 1 h under N$_2$ atmosphere in microwave. The reaction mixture was quenched by addition of water (50 mL), extracted with EtOAc (80 mL×3). The combined organic layers were washed with brine (50 mL), dried over Na$_2$SO$_4$, filtered and concentrated under reduced pressure to yield a residue which was purified twice by preparative HPLC (column: Phenomenex Gemini 150*25 mm*10 μm; mobile phase: [water (0.05% HCl)-ACN]; B %: 51%-81%, 10 min; column: Agela DuraShell C18 250*25 mm*10 μm; mobile phase: [water (0.04% NH$_3$H$_2$O+10 mM NH₄HCO₃)-ACN]; B %: 37%-67%, 10 min), followed by lyophilization to yield 4-(3-chlorophenyl)-N-[4-(trifluoromethyl)phenyl]oxazol-2-amine (23.7 mg, 69.97 µmol, 2.8% yield, 100% purity) as a white solid. ¹H NMR (500 MHz, CD₃OD) δ ppm 7.72 (d, J=8.2 Hz, 2H), 7.41 (d, J=8.4 Hz, 2H), 7.27-7.19 (m, 2H), 7.16 (s, 1H), 6.96 (d, J=7.3 Hz, 1H), 6.84 (s, 1H); ES-LCMS m/z 339.0, 341.0 [M+H]⁺.

I-64

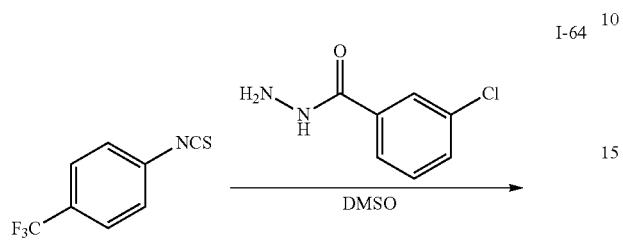

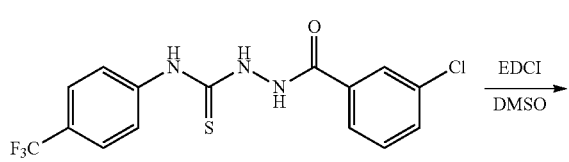

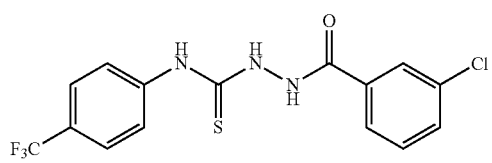 [SMILES: O=C(NNC(=S)Nc1ccc(C(F)(F)F)cc1)c1cccc(Cl)c1]

Step 1: 1-[(3-Chlorobenzoyl)amino]-3-[4-(trifluoromethyl)phenyl]thiourea

To a solution of 1-isothiocyanato-4-(trifluoromethyl)benzene (450 mg, 1.99 mmol, 1 eq) in DMSO (1 mL) was added 3-chlorobenzohydrazide (374.05 mg, 2.19 mmol, 1.1 eq). The mixture was stirred at 20° C. for 12 h. The mixture was added H₂O (10 mL) and filtered. The filtered cake was collected to yield 1-[(3-chlorobenzoyl)amino]-3-[4-(trifluoromethyl)phenyl]thiourea (700 mg, 1.69 mmol, 84.6% yield, 90.0% purity) as a yellow solid. ¹H NMR (500 MHz, DMSO-d₆) δ ppm 10.74 (br s, 1H), 10.02 (br s, 2H), 8.01 (s, 1H), 7.90 (d, J=7.6 Hz, 1H), 7.78-7.74 (m, 2H), 7.72-7.66 (m, 3H), 7.59-7.53 (m, 1H); ES-LCMS m/z 374.0 [M+H]⁺.

Step 2: 5-(3-Chlorophenyl)-N-[4-(trifluoromethyl)phenyl]-1,3,4-oxadiazol-2-amine

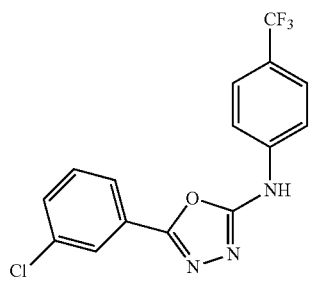 [SMILES: FC(F)(F)c1ccc(Nc2nnc(-c3cccc(Cl)c3)o2)cc1]

To a solution of 1-[(3-chlorobenzoyl)amino]-3-[4-(trifluoromethyl)phenyl]thiourea (370 mg, 890.90 µmol, 1 eq) in DMSO (2 mL) was added EDCI (204.94 mg, 1.07 mmol, 1.2 eq). The mixture was stirred at 60° C. for 12 h. The mixture was added H₂O (10 mL) and filtered, then the filtered cake was collected which was purified by flash silica gel chromatography (from pure PE to PE/EtOAc=4/1, TLC: PE/EtOAc=1/1, R_f=0.6) to yield 5-(3-chlorophenyl)-N-[4-(trifluoromethyl)phenyl]-1,3,4-oxadiazol-2-amine (75.81 mg, 220.80 µmol, 24.8% yield, 98.9% purity) as a white solid. ¹H NMR (400 MHz, DMSO-d₆) δ ppm 11.26 (br s, 1H), 7.90-7.84 (m, 2H), 7.83-7.78 (m, 2H), 7.77-7.71 (m, 2H), 7.69-7.59 (m, 2H); ES-LCMS m/z 340.1 [M+H]⁺.

I-65

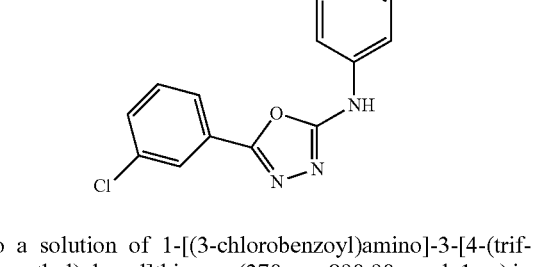

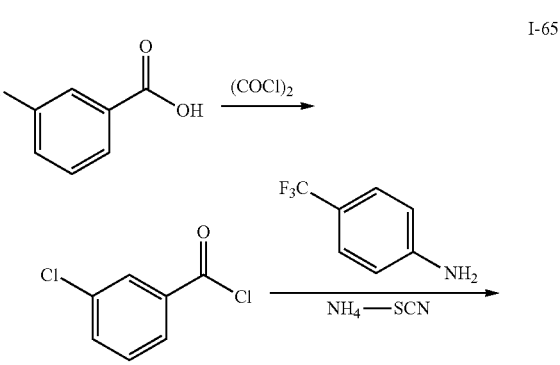

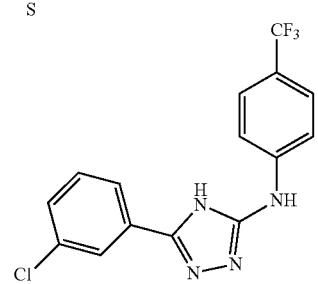

Step 1: 3-Chlorobenzoyl Chloride

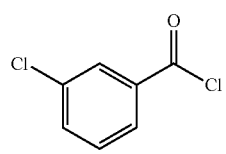

To a solution of 3-chlorobenzoic acid (1 g, 6.39 mmol, 1 eq) in DCM (20 mL) was added (COCl)$_2$ (972.82 mg, 7.66 mmol, 670.91 µL, 1.2 eq) and DMF (466.86 mg, 6.39 mmol, 491.43 µL, 1 eq). The mixture was stirred at 15° C. for 1 h. TLC (PE/EtOAc=3/1, R$_f$=0.72, in MeOH) indicated the starting material was consumed, and one major new spot was formed. The reaction mixture was concentrated to yield 3-chlorobenzoyl chloride (1.1 g, crude) as colorless oil which was used in the next step without further purification.

Step 2: 3-Chloro-N-[[4-(trifluoromethyl)phenyl] carbamothioyl]benzamide

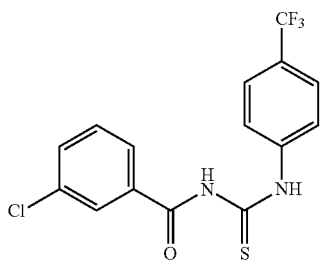 [SMILES: O=C(NC(=S)Nc1ccc(C(F)(F)F)cc1)c1cccc(Cl)c1]

To a solution of ammonia; thiocyanic acid (566.92 mg, 7.45 mmol, 566.92 µL, 1.5 eq) in acetone (20 mL) was added in one portion 3-chlorobenzoyl chloride (1.04 g, 5.96 mmol, 761.13 µL, 1.2 eq). The reaction was warmed to 50° C. for 30 min, then cooled to 15° C., slowly added 4-(trifluoromethyl)aniline (800 mg, 4.97 mmol, 615.38 µL, eq). The resulting mixture was stirred at 15° C. for 1 h. The reaction mixture was poured into ice-water (100 g), extracted with EtOAc (80 mL×3). The combined organic layers were washed with brine (30 mL), dried over Na$_2$SO$_4$, filtered and concentrated under reduced pressure to yield a residue which was purified by flash silica gel chromatography (from PE/EtOAc=1/0 to 5/1, TLC: PE/EtOAc=5/1, R$_f$=0.28) to yield 3-chloro-N-[[4-(trifluoromethyl)phenyl]carbamothioyl]benzamide (1 g, 2.65 mmol, 53.3% yield, 95% purity) as a yellow solid. $^1$H NMR (400 MHz, CDCl$_3$) δ ppm 12.70 (br s, 1H), 9.06 (br s, 1H), 7.97-7.87 (m, 3H), 7.79-7.75 (m, 1H), 7.72-7.64 (m, 3H), 7.55-7.49 (m, 1H); ES-LCMS m/z 358.9, 360.9 [M+H]$^+$.

Step 3: 5-(3-Chlorophenyl)-N-[4-(trifluoromethyl)phenyl]-4H-1,2,4-triazol-3-amine

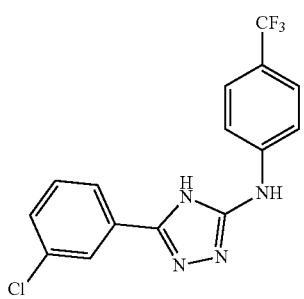 [SMILES: FC(F)(F)c1ccc(Nc2nnc(-c3cccc(Cl)c3)[nH]2)cc1]

To a solution of 3-chloro-N-[[4-(trifluoromethyl)phenyl] carbamothioyl]benzamide (300 mg, 794.39 µmol, 1 eq) in toluene (35 mL) was added NH$_2$NH$_2$.H$_2$O (233.92 mg, 3.97 mmol, 227.11 µL, 85%, 5 eq). The mixture was stirred at 130° C. for 12 h under Dean-Stark trap. The reaction mixture was concentrated to yield a residue which was purified by flash silica gel chromatography (from PE/EtOAc=1/0 to 1/1, TLC: PE/EtOAc=1/1, R$_f$=0.32) to yield 5-(3-chlorophenyl)-N-[4-(trifluoromethyl)phenyl]-4H-1,2,4-triazol-3-amine (88.39 mg, 260.96 µmol, 32.8% yield, 100% purity) as a white solid. $^1$H NMR (400 MHz, DMSO-d$_6$) δ ppm 9.91 (br s, 1H), 8.01 (s, 1H), 7.97-7.92 (m, 1H), 7.76 (d, J=8.6 Hz, 2H), 7.66-7.52 (m, 4H); ES-LCMS m/z 339.0, 341.0 [M+H]$^+$.

I-59

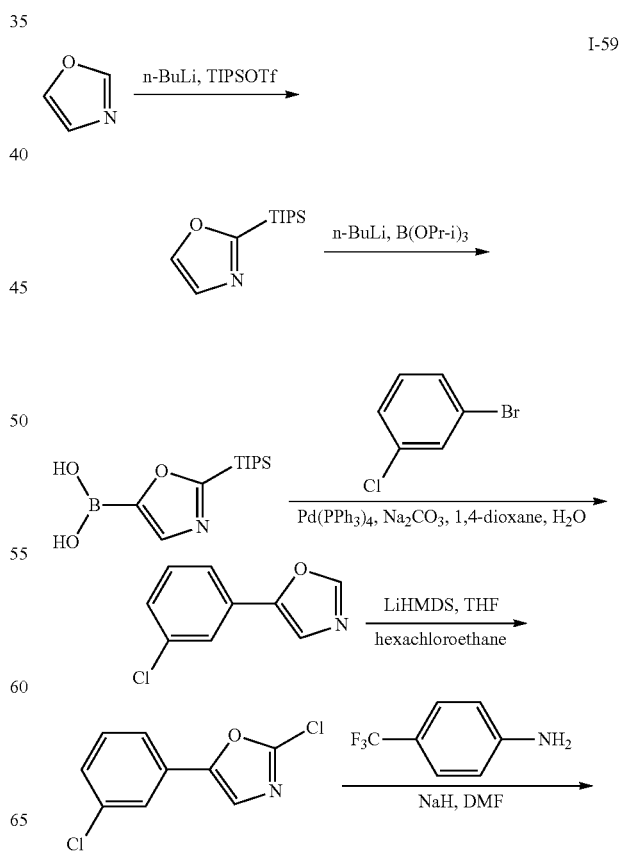

-continued

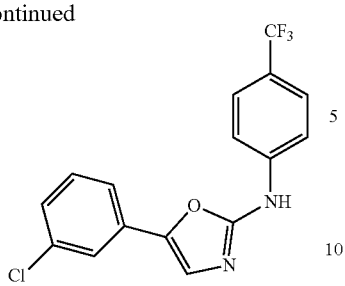

Step 1: Triisopropyl(oxazol-2-yl)silane

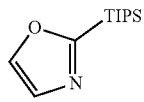

To a solution of oxazole (1 g, 14.48 mmol, 925.93 µL, 1 eq) in THF (30 mL) was added n-BuLi (2.5 M, 6.08 mL, 1.05 eq) under $N_2$ atmosphere. The mixture was stirred under $N_2$ atmosphere at −30° C. for 0.5 h. To the mixture was added TIPS-OTf (5.02 g, 16.37 mmol, 4.4 mL, 1.13 eq). The mixture was stirred under $N_2$ atmosphere at −30° C. for 1.5 h. TLC (PE/EtOAc=5:1, $R_f$=0.55) showed the starting material was consumed completely and one major new spot was detected. The mixture was quenched with $H_2O$ (30 mL) and extracted with EtOAc (40 mL×3). The combine organic layers were dried over anhydrous $Na_2SO_4$, filtered and concentrated to yield triisopropyl(oxazol-2-yl)silane (3.8 g, crude) as yellow oil, which was used in the next step without further purification. $^1H$ NMR (400 MHz, $CDCl_3$) δ ppm 7.82 (d, J=2.0 Hz, 1H), 7.22 (d, J=2.0 Hz, 1H), 1.46-1.40 (m, 3H), 1.14 (d, J=7.2 Hz, 18H).

Step 2: (2-Triisopropylsilyloxazol-5-yl)boronic acid

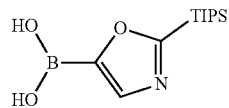

To a solution of triisopropyl(oxazol-2-yl)silane (2 g, 8.87 mmol, 1 eq) in THF (80 mL) was added n-BuLi (2.5 M, 4.26 mL, 1.2 eq) dropwise under $N_2$ atmosphere at −30° C. The mixture was stirred under $N_2$ atmosphere at −30° C. for 0.5 h. Triisopropyl borate (2.00 g, 10.65 mmol, 2.45 mL, 1.2 eq) was added. The mixture was stirred under $N_2$ atmosphere at −30° C. for 1 h. TLC (PE/EtOAc=5/1, $R_f$=0.05) showed the starting material was consumed completely and one spot formed. The mixture was quenched with water (20 mL), acidified with aqueous HCl (1 M) until pH=2 and extracted with EtOAc (50 mL×3). The organic layer was dried over $Na_2SO_4$, filtered and concentrated under reduced pressure to yield (2-triisopropylsilyloxazol-5-yl)boronic acid (2.4 g, crude) as a colorless gum, which was used in the next step without further purification. $^1H$ NMR (500 MHz, DMSO-$d_6$) δ ppm 8.54 (br s, 1H), 8.42 (br s, 1H), 7.68 (s, 1H), 1.37-1.32 (m, 3H), 0.99-0.97 (m, 18H).

Step 3: 5-(3-Chlorophenyl)oxazole

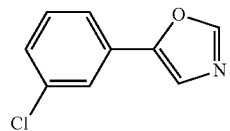 [SMILES: Clc1cccc(-c2cnco2)c1]

A mixture of (2-triisopropylsilyloxazol-5-yl)boronic acid (2.4 g, 8.91 mmol, 1 eq), 1-bromo-3-chloro-benzene (2 g, 10.45 mmol, 1.23 mL, 1.17 eq), Pd(PPh$_3$)$_4$ (500 mg, 432.69 µmol, 4.85e-2 eq) and $Na_2CO_3$ (3 g, 28.30 mmol, 3.18 eq) in 1,4-dioxane (60 mL) and $H_2O$ (20 mL) was stirred under $N_2$ atmosphere at 80° C. for 1 h. TLC (PE/EtOAc=10/1, $R_f$=0.40) showed the starting material was consumed completely. The reaction mixture was diluted with $H_2O$ (50 mL) and extracted with EtOAc (50 mL×3). The organic layer was dried over $Na_2SO_4$, filtered and concentrated under reduced pressure to yield a residue which was purified by flash silica gel chromatography (from PE/EtOAc=100/1 to 10/1, TLC: PE/EtOAc=10/1, $R_f$=0.40) to yield 5-(3-chlorophenyl)oxazole (1 g, 5.21 mmol, 58.4% yield, 93.5% purity) as a white solid. $^1H$ NMR (400 MHz, $CDCl_3$) δ ppm 7.94 (s, 1H), 7.65 (s, 1H), 7.54 (s, 1H), 7.40-7.32 (m, 3H); ES-LCMS m/z 180.0 [M+H]$^+$.

Step 4: 2-Chloro-5-(3-chlorophenyl)oxazole

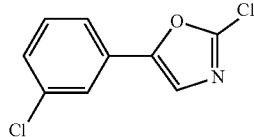 [SMILES: Clc1cccc(-c2cnc(Cl)o2)c1]

To a solution of 5-(3-chlorophenyl)oxazole (1 g, 5.21 mmol, 1 eq) in THF (20 mL) was added LiHMDS (1 M, 6.25 mL, 1.2 eq) dropwise under $N_2$ atmosphere at −70° C. The mixture was stirred under $N_2$ atmosphere at −70° C. for 0.5 h. A solution of hexachloroethane (1.40 g, 5.92 mmol, 1.14 eq) in THF (5 mL) was added under $N_2$ atmosphere at −70° C. The mixture was stirred under $N_2$ atmosphere at −70° C. for 0.5 h and then at 20° C. for 3 h. TLC (PE/EtOAc=10/1, $R_f$=0.60) showed the starting material was consumed completely. The mixture was quenched with $H_2O$ (50 mL) and extracted with EtOAc (50 mL×3). The organic layer was dried over $Na_2SO_4$, filtered and concentrated under reduced pressure to yield a residue which was purified by flash silica gel chromatography (from PE/EtOAc=100/1 to 30/1, TLC: PE/EtOAc=10/1, $R_f$=0.60) to yield 2-chloro-5-(3-chlorophenyl)oxazole (430 mg, 2.01 mmol, 38.6% yield, 100.0% purity) as a white solid. $^1H$ NMR (500 MHz, $CDCl_3$) δ ppm 7.60 (s, 1H), 7.48 (d, J=7.5 Hz, 1H), 7.38 (t, J=7.5 Hz, 1H), 7.35-7.33 (m, 1H), 7.32 (s, 1H); ES-LCMS m/z 213.9 [M+H]$^+$.

151

Step 5: 5-(3-Chlorophenyl)-N-[3-(trifluoromethyl)phenyl]oxazol-2-amine

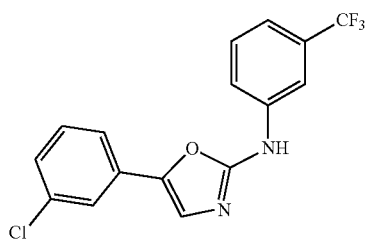 [SMILES: FC(F)(F)c1cccc(Nc2ncc(-c3cccc(Cl)c3)o2)c1]

To a solution of 3-(trifluoromethyl)aniline (45.16 mg, 280.31 μmol, 35.01 μL, 1 eq) in DMF (2 mL) was added NaH (19.96 mg, 498.95 μmol, 60% purity, 1.78 eq). The mixture was stirred at 20° C. for 0.5 h. 2-Chloro-5-(3-chlorophenyl)oxazole (60 mg, 280.31 μmol, 1 eq) was added. The mixture was stirred at 60° C. for 12 h. TLC (PE/EtOAc=5/1, $R_f$=0.35) showed the starting material was consumed completely. The reaction mixture was diluted with H₂O (20 mL) and extracted with EtOAc (20 mL×3). The organic layer was dried over Na₂SO₄, filtered and concentrated under reduced pressure to yield a residue which was purified by preparative HPLC (column: Agela DuraShell C18 150*25 mm*5 um; mobile phase: [water (0.04% NH₃.H₂O+10 mM NH₄HCO₃)-ACN]; B %: 60%-90%, 10 min), followed by lyophilization to yield 5-(3-chlorophenyl)-N-[3-(trifluoromethyl)phenyl]oxazol-2-amine (17.92 mg, 52.91 μmol, 18.9% yield, 100.0% purity) as a yellow solid. ¹H NMR (400 MHz, CD₃OD) δ ppm 7.99 (s, 1H), 7.74 (d, J=8.3 Hz, 1H), 7.60 (s, 1H), 7.54-7.45 (m, 2H), 7.40-7.34 (m, 2H), 7.25 (d, J=7.8 Hz, 2H); ES-LCMS m/z 339.0 [M+H]⁺.

I-21

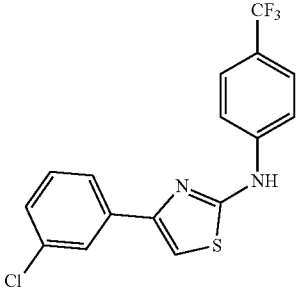

152

Step 1: [4-(Trifluoromethyl)phenyl]thiourea

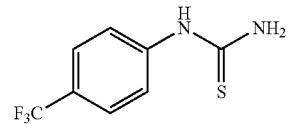 [SMILES: NC(=S)Nc1ccc(C(F)(F)F)cc1]

To a solution of 1-isothiocyanato-4-(trifluoromethyl)benzene (630 mg, 3.10 mmol, 1 eq) in MeCN (10 mL) was added NH₃.H₂O (582.20 mg, 4.65 mmol, 639.78 μL, 28%, 1.5 eq). The mixture was stirred at 15° C. for 3 h. TLC (PE/EtOAc=1/1, $R_f$=0.08) indicated the starting material was consumed, one major new spot was detected. The reaction mixture was concentrated to yield a residue which was added PE/EA (10/1, 50 mL), and stirred at 15° C. for 1 h. The slurry was filtered, rinsed with PE (2×10 mL). The solid was collected, dried to yield [4-(trifluoromethyl)phenyl]thiourea (500 mg, 2.16 mmol, 69.5% yield, 95.0% purity) as a white solid which was used in the next step without further purification. ¹H NMR (400 MHz, DMSO-d₆) δ ppm 10.58 (s, 1H), 7.83 (d, J=8.6 Hz, 2H), 7.64 (d, J=8.6 Hz, 2H); ES-LCMS m/z 221.0 [M+H]⁺.

Step 2: 4-(3-Chlorophenyl)-N-[4-(trifluoromethyl)phenyl]thiazol-2-amine

A mixture of [4-(trifluoromethyl)phenyl]thiourea (100 mg, 431.40 μmol, 1 eq), KF (25.06 mg, 431.40 μmol, 10.11 μL, 1 eq) and 2-bromo-1-(3-chlorophenyl)ethanone (100.73 mg, 431.40 μmol, 1 eq) in MeOH (2 mL) and H₂O (2 mL) was stirred at 25° C. for 12 h. The reaction mixture was concentrated to yield a residue which was purified by preparative HPLC (column: Agela DuraShell C18 150*25 mm*5 μm; mobile phase: [water (0.04% NH₃H₂O+10 mM NH₄HCO₃)-ACN]; B %: 65%-95%, 10 min), followed by lyophilization to yield 4-(3-chlorophenyl)-N-[4-(trifluoromethyl)phenyl]thiazol-2-amine (131.72 mg, 371.28 μmol, 86.0% yield, 100% purity) as colorless oil. ¹H NMR (500 MHz, CD₃OD) δ ppm 7.95-7.92 (m, 1H), 7.89 (d, J=8.5 Hz, 2H), 7.86 (d, J=7.9 Hz, 1H), 7.62 (d, J=8.7 Hz, 2H), 7.42-7.37 (m, 1H), 7.31 (dd, J=1.1, 8.0 Hz, 1H), 7.25 (s, 1H); ES-LCMS m/z 355.0, 357.0 [M+H]⁺.

I-62

Step 1: 5-(2-Chlorophenyl)oxazole

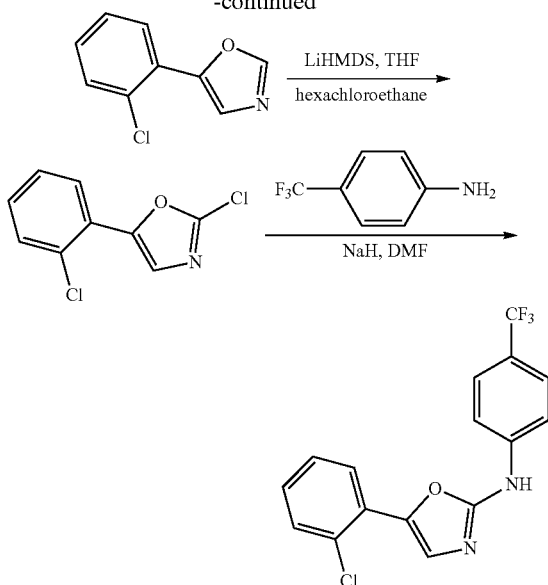

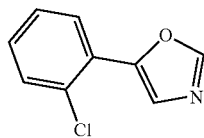 [SMILES: Clc1ccccc1-c1cnco1]

A mixture of 2-chlorobenzaldehyde (5 g, 35.57 mmol, 4.00 mL, 1 eq), Tos-MIC (7.64 g, 39.13 mmol, 1.1 eq) and K$_2$CO$_3$ (4.92 g, 35.57 mmol, 1 eq) in MeOH (50 mL) was stirred at 90° C. for 3 h. TLC (PE/EtOAc=10/1, R$_f$=0.25) showed the starting material was consumed completely. The reaction mixture was diluted with H$_2$O (150 mL) and extracted with EtOAc (100 mL×3). The organic layer was dried over Na$_2$SO$_4$, filtered and concentrated under reduced pressure to yield a residue which was purified by flash silica gel chromatography (from PE/EtOAc=100/1 to 8/1, TLC: PE/EtOAc=10/1, R$_f$=0.25) to yield 5-(2-chlorophenyl)oxazole (5.2 g, 28.95 mmol, 81.4% yield, 100.0% purity) as colorless oil. $^1$H NMR (400 MHz, CDCl$_3$) δ ppm 7.98 (s, 1H), 7.83 (dd, J=1.6, 7.9 Hz, 1H), 7.81 (s, 1H), 7.49 (dd, J=1.0, 8.1 Hz, 1H), 7.37 (dt, J=1.1, 7.6 Hz, 1H), 7.32-7.27 (m, 1H); ES-LCMS m/z 180.0 [M+H]$^+$.

Step 2: 2-Chloro-5-(2-chlorophenyl)oxazole

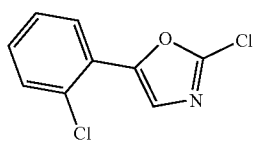 [SMILES: Clc1ncc(-c2ccccc2Cl)o1]

To a solution of 5-(2-chlorophenyl)oxazole (1 g, 5.57 mmol, 1 eq) in THF (20 mL) was added LiHMDS (1 M, 7 mL, 1.26 eq) dropwise under N$_2$ atmosphere at −70° C. The mixture was stirred under N$_2$ atmosphere at −70° C. for 0.5 h. A solution of hexachloroethane (1.45 g, 6.12 mmol, 1.1 eq) in THF (5 mL) was added dropwise under N$_2$ atmosphere at −70° C. The mixture was stirred under N$_2$ atmosphere at −70° C. for 0.5 h and then at 20° C. for 1 h. TLC (PE/EtOAc=10/1, R$_f$=0.5) showed the starting material was consumed completely. The reaction mixture was quenched with H$_2$O (100 mL) and extracted with EtOAc (100 mL×3). The organic layer was dried over Na$_2$SO$_4$, filtered and concentrated under reduced pressure to yield a residue which was purified by flash silica gel chromatography (from PE/EtOAc=100/1 to 10/1, TLC: PE/EtOAc=10/1, R$_f$=0.50) to yield 2-chloro-5-(2-chlorophenyl)oxazole (900 mg, 4.20 mmol, 75.5% yield, 100.0% purity) as a white solid. $^1$H NMR (400 MHz, CDCl$_3$) δ ppm 7.74 (dd, J=1.3, 7.9 Hz, 1H), 7.70 (s, 1H), 7.45 (d, J=8.1 Hz, 1H), 7.37-7.32 (m, 1H), 7.30-7.24 (m, 1H); ES-LCMS m/z 213.9 [M+H]$^+$.

Step 3: 5-(2-Chlorophenyl)-N-[4-(trifluoromethyl)phenyl]oxazol-2-amine

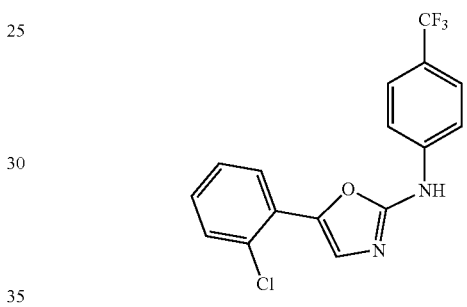

To a solution of 4-(trifluoromethyl)aniline (120 mg, 744.77 μmol, 92.31 μL, 1.06 eq) in DMF (2 mL) was added NaH (45 mg, 1.13 mmol, 60% purity, 1.61 eq) partwise at 20° C. The mixture was stirred at 20° C. for 0.5 h. 2-Chloro-5-(2-chlorophenyl)oxazole (150 mg, 700.78 μmol, 1 eq) was added. The mixture was stirred at 60° C. for 12 h. TLC (PE/EtOAc=3/1, R$_f$=0.33) showed the starting material was consumed completely. The mixture was quenched with water (5 mL), stirred at 20° C. for 10 minutes and filtered. To the solid was added MeOH (20 mL). The mixture was stirred at 20° C. for 0.5 h and filtered. The solid was washed with MeOH (10 mL) to yield a residue which was dissolved in MeCN (5 mL) and water (15 mL) and lyophilized to yield 5-(2-chlorophenyl)-N-[4-(trifluoromethyl)phenyl]oxazol-2-amine (33.50 mg, 98.90 μmol, 14.1% yield, 100.0% purity) as a white solid. $^1$H NMR (500 MHz, DMSO-d$_6$) δ ppm 10.90 (br s, 1H), 7.85 (d, J=8.1 Hz, 2H), 7.76-7.65 (m, 4H), 7.60 (d, J=8.1 Hz, 1H), 7.49 (t, J=7.5 Hz, 1H), 7.40-7.32 (m, 1H); ES-LCMS m/z 339.0 [M+H]$^+$.

I-66

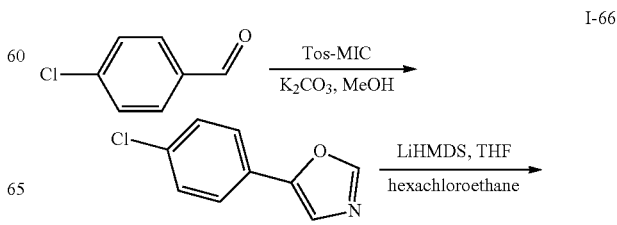

Step 1: 5-(4-Chlorophenyl)oxazole

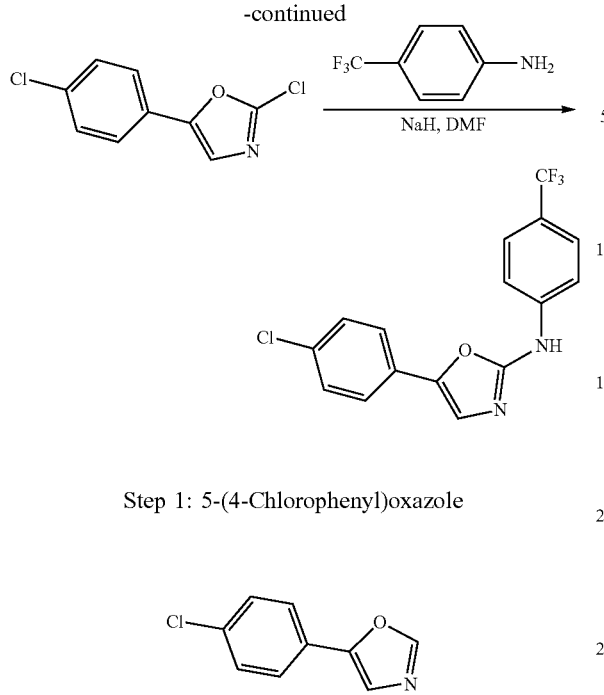

To a stirred solution of 4-chlorobenzaldehyde (2 g, 14.23 mmol, 1 eq) in MeOH (30 mL) was added Tos-MIC (3.06 g, 15.65 mmol, 1.1 eq) and K$_2$CO$_3$ (2.36 g, 17.07 mmol, 1.2 eq). The reaction mixture was stirred at 90° C. for 3 h. TLC (PE/EtOAc=3/1, R$_f$=0.50) showed the starting material was consumed completely and one new spot was detected. The reaction mixture was concentrated to remove MeOH. The residue was added to water (150 mL) and extracted with EtOAc (150 mL×3). The combined organic layers were dried over Na$_2$SO$_4$, filtered and the filtrate was concentrated to yield a residue which was purified by preparative TLC (PE/EtOAc=3/1, TLC: PE/EtOAc=3/1, R$_f$=0.50) to yield 5-(4-chlorophenyl)oxazole (1.8 g, 10.02 mmol, 70.4% yield, 100.0% purity) as a yellow solid. $^1$H NMR (400 MHz, CDCl$_3$) δ ppm 7.95-7.90 (m, 1H), 7.63-7.57 (m, 2H), 7.44-7.38 (m, 2H), 7.37-7.34 (m, 1H); ES-LCMS m/z 180.0, 182.0 [M+H]$^+$.

Step 2: 2-Chloro-5-(4-chlorophenyl)oxazole

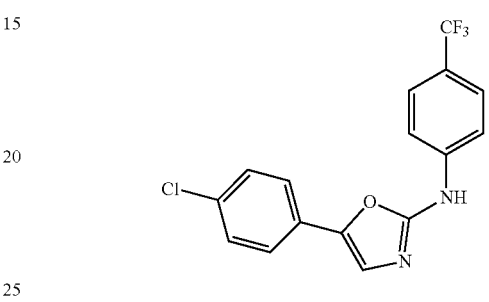

To a solution of 5-(4-chlorophenyl)oxazole (0.9 g, 5.01 mmol, 1 eq) in THF (20 mL) was added LiHMDS (1 M, 6.01 mL, 1.2 eq) dropwise under N$_2$ atmosphere at −70° C. The mixture was stirred under N$_2$ atmosphere at −70° C. for 0.5 h. A solution of hexachloroethane (1.30 g, 5.51 mmol, 1.1 eq) in THF (5 mL) was added under N$_2$ atmosphere at −70° C. The mixture was stirred under N$_2$ atmosphere at −70° C. for 0.5 h and then at 20° C. for 1.5 h. TLC (PE/EtOAc=3/1, R$_f$=0.65) showed the starting material was consumed completely and one new spot was detected. The mixture was quenched with water (150 mL) and extracted with EtOAc (150 mL×3). The combined organic layers were dried over Na$_2$SO$_4$, filtered and the filtrate was concentrated to yield a residue which was purified by preparative TLC (PE/EtOAc=3/1, TLC: PE/EtOAc=3/1, R$_f$=0.65) to yield 2-chloro-5-(4-chlorophenyl)oxazole (900 mg, 4.18 mmol, 83.3% yield, 99.3% purity) as a white solid. $^1$H NMR (400 MHz, CDCl$_3$) δ ppm 7.57-7.51 (m, 2H), 7.44-7.39 (m, 2H), 7.29 (s, 1H); ES-LCMS m/z 214.0, 216.0 [M+H]$^+$.

Step 3: 2-[2-Hydroxyethyl(methyl)amino]ethyl 2-(1H-indole-3-carbonyl)thiazole-4-carboxylate To a stirred solution of 2-chloro-5-(4-chlorophenyl)oxazole (300 mg, 1.39 mmol, 1 eq) in DMF (5 mL) was added NaH (139.17 mg, 3.48 mmol, 60% purity, 2.5 eq) at 20° C. Then the mixture was stirred at 20° C. for 30 min under N$_2$ atmosphere. 4-(Trifluoromethyl)aniline (448.49 mg, 2.78 mmol, 344.99 μL, 2 eq) was added to the above mixture. The reaction mixture was stirred at 60° C. for 1 h. TLC (PE/EtOAc=3/1, R$_f$=0.50) showed the starting material was consumed completely and one new spot was detected. The reaction mixture was filtered and the filtered cake was added to MeOH (5 mL). The slurry was stirred at 20° C. for 15 min then filtered. The filtered cake was concentrated to yield 5-(4-chlorophenyl)-N-[4-(trifluoromethyl)phenyl]oxazol-2-amine (268.87 mg, 793.80 μmol, 57.0% yield, 100.0% purity) as a white solid which was lyophilized for delivery without further purification. $^1$H NMR (500 MHz, DMSO-d$_6$) δ ppm 10.86 (s, 1H), 7.82 (d, J=8.5 Hz, 2H), 7.68 (d, J=8.5 Hz, 2H), 7.66-7.58 (m, 3H), 7.52 (d, J=8.5 Hz, 2H); ES-LCMS m/z 339.0, 341.0 [M+H]$^+$.

I-67

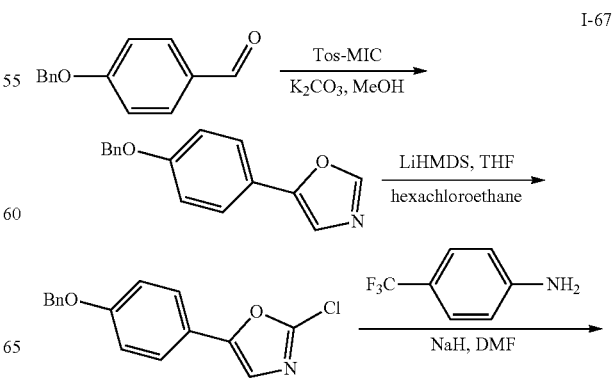

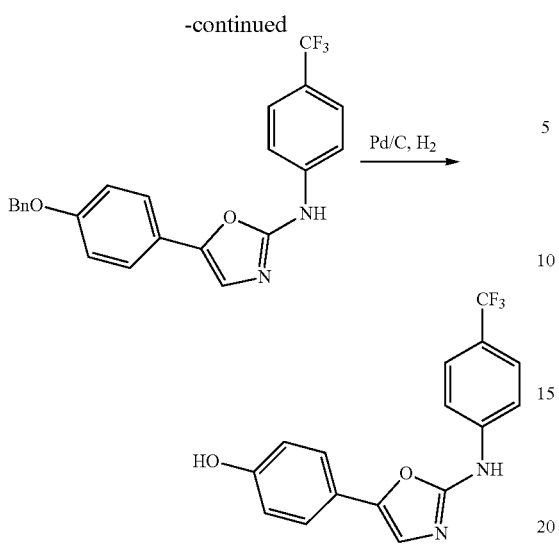

Step 1: 5-(4-Benzyloxyphenyl)oxazole

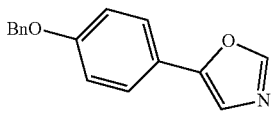 [SMILES: c1ccc(COc2ccc(-c3cnco3)cc2)cc1]

To a solution of 4-benzyloxybenzaldehyde (0.5 g, 2.36 mmol, 1 eq) in MeOH (20 mL) was added Tos-MIC (505.94 mg, 2.59 mmol, 1.1 eq) and $K_2CO_3$ (390.71 mg, 2.83 mmol, 1.2 eq). The mixture was stirred at 80° C. for 3 h. The reaction mixture was concentrated. The residue was added water (50 mL), extracted with EtOAc (50 mL×3). The combined organic layers were washed with brine (20 mL), dried over $Na_2SO_4$, filtered and concentrated under reduced pressure to yield a residue which was purified by flash silica gel chromatography (from PE/EtOAc=1/0 to 5/1, TLC: PE/EtOAc=5/1, $R_f$=0.14) to yield 5-(4-benzyloxyphenyl)oxazole (510 mg, 2.03 mmol, 86.1% yield, 100% purity) as a white solid. $^1$H NMR (500 MHz, $CDCl_3$) δ ppm 7.88 (s, 1H), 7.62-7.58 (m, 2H), 7.47-7.33 (m, 5H), 7.24 (s, 1H), 7.04 (d, J=8.9 Hz, 2H), 5.12 (s, 2H); ES-LCMS m/z 252.1 $[M+H]^+$.

Step 2: 5-(4-Benzyloxyphenyl)-2-chloro-oxazole

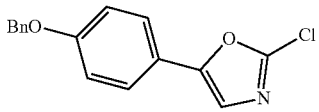 [SMILES: Clc1ncc(-c2ccc(OCc3ccccc3)cc2)o1]

To a solution of 5-(4-benzyloxyphenyl)oxazole (510 mg, 2.03 mmol, 1 eq) in THF (10 mL) was added LiHMDS (1 M, 2.44 mL, 1.2 eq) at −70° C. under $N_2$. After being stirred for 30 min, a solution of hexachloroethane (528.54 mg, 2.23 mmol, 252.89 μL, 1.1 eq) in THF (3 mL). After addition, the mixture was stirred at 15° C. for 3 h. TLC (PE/EtOAc=3/1, $R_f$=0.68) indicated the starting material was consumed completely and one new spot formed. The reaction mixture was quenched by addition of water (50 mL), extracted with EtOAc (30 mL×3). The combined organic layers were washed with brine (10 mL), dried over $Na_2SO_4$, filtered and concentrated under reduced pressure to yield a residue which was purified by flash silica gel chromatography (from PE/EtOAc=1/0 to 5/1, TLC: PE/EtOAc=5/1, $R_f$=0.68) to yield 5-(4-benzyloxyphenyl)-2-chloro-oxazole (500 mg, 1.75 mmol, 86.2% yield, 100% purity) as a white solid. $^1$H NMR (500 MHz, $CDCl_3$) δ ppm 7.53 (d, J=8.9 Hz, 2H), 7.48-7.33 (m, 5H), 7.18-7.15 (m, 1H), 7.03 (d, J=8.9 Hz, 2H), 5.14-5.09 (m, 2H); ES-LCMS m/z 327.0 $[M+H+MeCN]^+$.

Step 3: 5-(4-Benzyloxyphenyl)-N-[4-(trifluoromethyl)phenyl]oxazol-2-amine

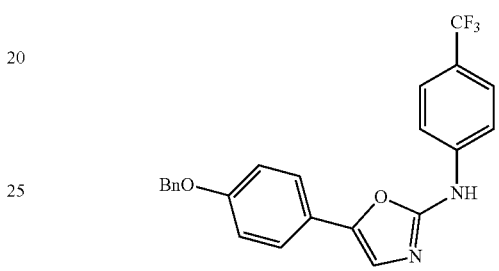

To a solution of 4-(trifluoromethyl)aniline (310.15 mg, 1.92 mmol, 238.58 μL 1.1 eq) in DMF (10 mL) was added NaH (139.98 mg, 3.50 mmol, 60% purity, 2 eq). After being stirred for 5 min, 5-(4-benzyloxyphenyl)-2-chloro-oxazole (500 mg, 1.75 mmol, 1 eq) was added. The mixture was stirred at 60° C. for 12 h. The reaction mixture was quenched by addition of water (50 mL), extracted with EtOAc (30 mL×3). The combined organic layers were washed with brine (10 mL), dried over $Na_2SO_4$, filtered and concentrated under reduced pressure to yield 5-(4-benzyloxyphenyl)-N-[4-(trifluoromethyl)phenyl]oxazol-2-amine (600 mg, 1.33 mmol, 76.0% yield, 91.0% purity) as a white solid which was used in the next step without further purification. $^1$H NMR (400 MHz, DMSO-$d_6$) δ ppm 10.79 (br s, 1H), 7.82 (d, J=8.6 Hz, 2H), 7.70-7.64 (m, 2H), 7.55 (d, J=8.6 Hz, 2H), 7.47-7.33 (m, 6H), 7.10 (d, J=9.0 Hz, 2H), 5.14 (s, 2H); ES-LCMS m/z 411.1 $[M+H]^+$.

Step 4: 4-[2-[4-(Trifluoromethyl)anilino]oxazol-5-yl]phenol

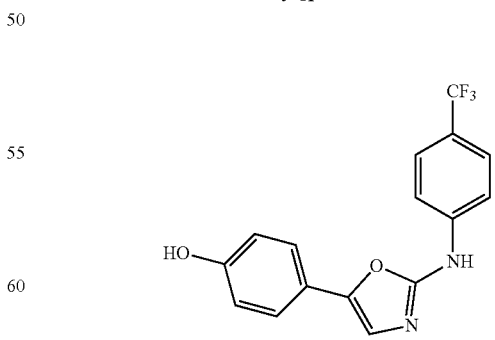

To a solution of 5-(4-benzyloxyphenyl)-N-[4-(trifluoromethyl)phenyl]oxazol-2-amine (300 mg, 665.22 μmol, 1 eq) in EtOAc (30 mL) was added Pd/C (300 mg, 10% purity) under $N_2$. The suspension was degassed under vacuum and purged with H₂ several times. The mixture was stirred under H₂ (30 psi) at 15° C. for 1 h. The reaction mixture was filtered through celite and the filtrate was concentrated to yield 4-[2-[4-(trifluoromethyl)anilino]oxazol-5-yl]phenol (150 mg, 444.94 μmol, 66.8% yield, 95.0% purity) as a white solid which was used in the next step without further purification. ¹H NMR (500 MHz, CD₃OD) δ ppm 7.70 (d, J=8.5 Hz, 2H), 7.62-7.56 (m, 2H), 7.45 (d, J=8.4 Hz, 2H), 7.08 (s, 1H), 6.83 (d, J=8.5 Hz, 2H); ES-LCMS m/z 321.0 [M+H]⁺.

Step 5: 4-[2-[4-(Trifluoromethyl)anilino]oxazol-5-yl]phenol

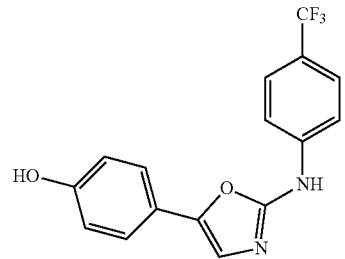 [SMILES: Oc1ccc(-c2cnc(Nc3ccc(C(F)(F)F)cc3)o2)cc1]

120 mg of 4-[2-[4-(trifluoromethyl)anilino]oxazol-5-yl]phenol (120 mg, 355.95 μmol, 1 eq) was purified by preparative HPLC (column: Welch Xtimate C18 150*30 mm*5 μm; mobile phase: [water(10 mM NH₄HCO₃)-ACN]; B %: 43%-73%, 10 min), followed by lyophilization to yield 4-[2-[4-(trifluoromethyl)anilino]oxazol-5-yl]phenol (18.92 mg, 59.08 μmol, 16.6% yield, 100% purity) as a white solid. ¹H NMR (500 MHz, CD₃OD) δ ppm 7.70 (d, J=8.7 Hz, 2H), 7.60 (d, J=8.7 Hz, 2H), 7.50-7.41 (m, 2H), 7.08 (s, 1H), 6.87-6.78 (m, 2H); ES-LCMS m/z 321.0 [M+H]⁺.

I-68

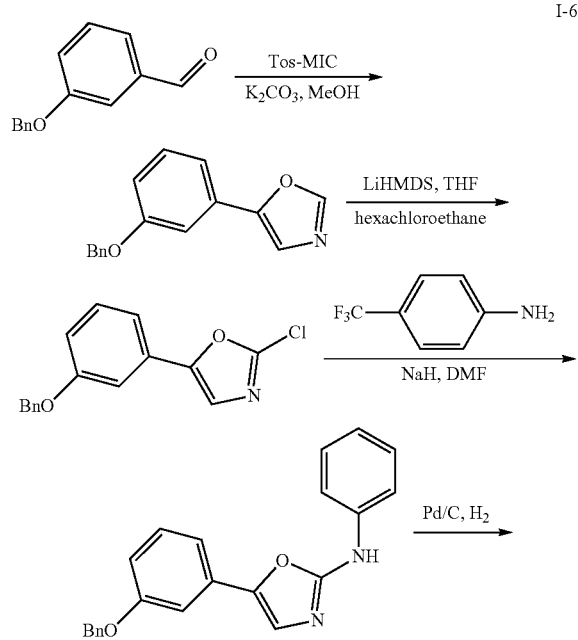

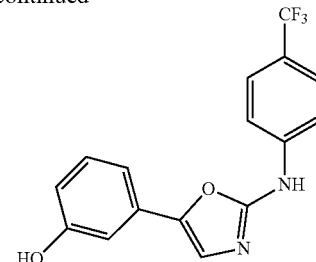

Step 1: 5-(3-Benzyloxyphenyl)oxazole

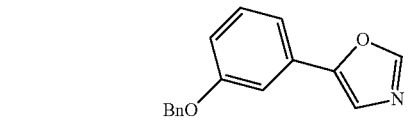 [SMILES: c1ccc(COc2cccc(-c3cnco3)c2)cc1]

A mixture of 3-benzyloxybenzaldehyde (5 g, 23.56 mmol, 1 eq), Tos-MIC (5.06 g, 25.91 mmol, 1.1 eq) and K₂CO₃ (3.91 g, 28.27 mmol, 1.2 eq) in MeOH (50 mL) was stirred at 90° C. for 3 h. TLC (PE/EtOAc=5/1, R_f=0.25) showed the starting material was consumed completely. The reaction mixture was diluted with H₂O (150 mL) and extracted with EtOAc (100 mL×3). The organic layer was dried over Na₂SO₄, filtered and concentrated under reduced pressure to yield a residue which was purified by flash silica gel chromatography (from PE/EtOAc=100/1 to 5/1, TLC: PE/EtOAc=5/1, R_f=0.25) to yield 5-(3-benzyloxyphenyl)oxazole (5 g, 19.90 mmol, 84.5% yield, 100.0% purity) as a white solid. ¹H NMR (400 MHz, CDCl₃) δ ppm 7.92 (s, 1H), 7.50-7.45 (m, 2H), 7.44-7.40 (m, 2H), 7.39-7.33 (m, 3H), 7.31-7.27 (m, 2H), 6.98 (dd, J=1.2, 7.1 Hz, 1H), 5.13 (s, 2H); ES-LCMS m/z 252.1 [M+H]⁺.

Step 2: 5-(3-Benzyloxyphenyl)-2-chloro-oxazole

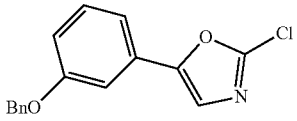 [SMILES: Clc1ncc(-c2cccc(OCc3ccccc3)c2)o1]

To a solution of 5-(3-benzyloxyphenyl)oxazole (2 g, 7.96 mmol, 1 eq) in THF (30 mL) was added LiHMDS (1 M, 10 mL, 1.26 eq) dropwise under N₂ atmosphere at −70° C. The mixture was stirred under N₂ atmosphere at −70° C. for 0.5 h. A solution of hexachloroethane (2.1 g, 8.87 mmol, 1.11 eq) in THF (10 mL) was added dropwise under N₂ atmosphere at −70° C. The mixture was stirred under N₂ atmosphere at −70° C. for 0.5 h and then at 20° C. for 1 h. TLC (PE/EtOAc=5/1, R_f=0.5) showed the starting material was consumed completely. The reaction mixture was quenched with H₂O (100 mL) and extracted with EtOAc (100 mL×3). The organic layer was dried over Na₂SO₄, filtered and concentrated under reduced pressure to yield a residue which was purified by flash silica gel chromatography (from PE/EtOAc=100/1 to 10/1, TLC: PE/EtOAc=5/1, R_f=0.50) to yield 5-(3-benzyloxyphenyl)-2-chloro-oxazole (2 g, 7.00 mmol, 87.9% yield, 100.0% purity) as a white solid. ¹H NMR (400 MHz, CDCl$_3$) δ ppm 7.49-7.43 (m, 2H), 7.43-7.38 (m, 2H), 7.37-7.31 (m, 2H), 7.27-7.26 (m, 1H), 7.23-7.17 (m, 2H), 7.01-6.94 (m, 1H), 5.11 (s, 2H); ES-LCMS m/z 286.0, 288.0 [M+H]$^+$.

Step 3: 5-(3-Benzyloxyphenyl)-N-[4-(trifluoromethyl)phenyl]oxazol-2-amine

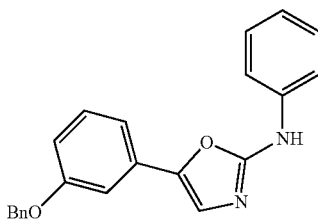 [SMILES: c1ccc(COc2cccc(-c3cnc(Nc4ccccc4)o3)c2)cc1]

To a solution of 4-(trifluoromethyl)aniline (565 mg, 3.51 mmol, 434.62 μL, 1 eq) in DMF (10 mL) was added NaH (210 mg, 5.25 mmol, 60% purity, 1.5 eq) partwise at 20° C. The mixture was stirred at 20° C. for 0.5 h. 5-(3-benzyloxyphenyl)-2-chloro-oxazole (1 g, 3.50 mmol, 1 eq) was added. The mixture was stirred at 60° C. for 12 h. TLC (PE/EtOAc=3/1, R$_f$=0.30) showed the starting material was consumed completely. The mixture was quenched with water (50 mL), stirred at 20° C. for 10 minutes and filtered. To the solid was added MeOH (50 mL). The mixture was stirred at 20° C. for 0.5 h and filtered. The solid was washed with MeOH (30 mL) and dried under reduced pressure to yield 5-(3-benzyloxyphenyl)-N-[4-(trifluoromethyl)phenyl]oxazol-2-amine (960 mg, 2.34 mmol, 66.8% yield, 100.0% purity) as a white solid. $^1$H NMR (400 MHz, CDCl$_3$) δ ppm 7.62 (d, J=4.2 Hz, 4H), 7.55 (s, 1H), 7.49-7.39 (m, 4H), 7.38-7.30 (m, 2H), 7.26 (d, J=4.4 Hz, 1H), 7.18 (d, J=3.9 Hz, 3H), 6.96-6.88 (m, 1H), 5.12 (d, J=3.7 Hz, 1H), 5.09-5.08 (m, 1H).

Step 4: 3-[2-[4-(Trifluoromethyl)anilino]oxazol-5-yl]phenol

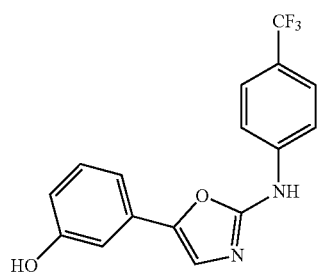 [SMILES: Oc1cccc(-c2cnc(Nc3ccc(C(F)(F)F)cc3)o2)c1]

A mixture of 5-(3-benzyloxyphenyl)-N-[4-(trifluoromethyl)phenyl]oxazol-2-amine (680 mg, 1.66 mmol, 1 eq) and Pd/C (500 mg, 10% purity) in EtOAc (50 mL) was stirred under H$_2$ (15 Psi) at 20° C. for 3 h. TLC (PE/EtOAc=2/1, R$_f$=0.21) showed the starting material was consumed completely. The reaction mixture was filtered. The filtrate was concentrated under reduced pressure to yield 3-[2-[4-(trifluoromethyl)anilino]oxazol-5-yl]phenol (400 mg, 1.17 mmol, 70.7% yield, 93.8% purity) as a white solid, which was used in the next step without further purification. $^1$H NMR (400 MHz, CD$_3$OD) δ ppm 7.72 (d, J=8.6 Hz, 2H), 7.60 (d, J=8.6 Hz, 2H), 7.24-7.18 (m, 2H), 7.09 (d, J=8.2 Hz, 1H), 7.03 (s, 1H), 6.73-6.68 (m, 1H); ES-LCMS m/z 321.0 [M+H]$^+$. 150 mg of above product was purified by preparative HPLC (column: Welch Xtimate C18 150*30 mm*5 um; mobile phase: [water(10 mM NH$_4$HCO$_3$)-ACN]; B %: 43%-73%, 10 min). The desired fraction was lyophilized to yield 3-[2-[4-(trifluoromethyl)anilino]oxazol-5-yl]phenol (120 mg, 374.69 μmol, 85.3% yield, 100.0% purity) as a white solid. $^1$H NMR (500 MHz, DMSO-d$_6$) δ ppm 10.80 (s, 1H), 9.63 (s, 1H), 7.83 (d, J=8.5 Hz, 2H), 7.68 (d, J=8.7 Hz, 2H), 7.45 (s, 1H), 7.23 (t, J=7.9 Hz, 1H), 7.06 (d, J=7.8 Hz, 1H), 6.99 (s, 1H), 6.70 (dd, J=1.8, 8.1 Hz, 1H); ES-LCMS m/z 321.0 [M+H]$^+$.

I-69

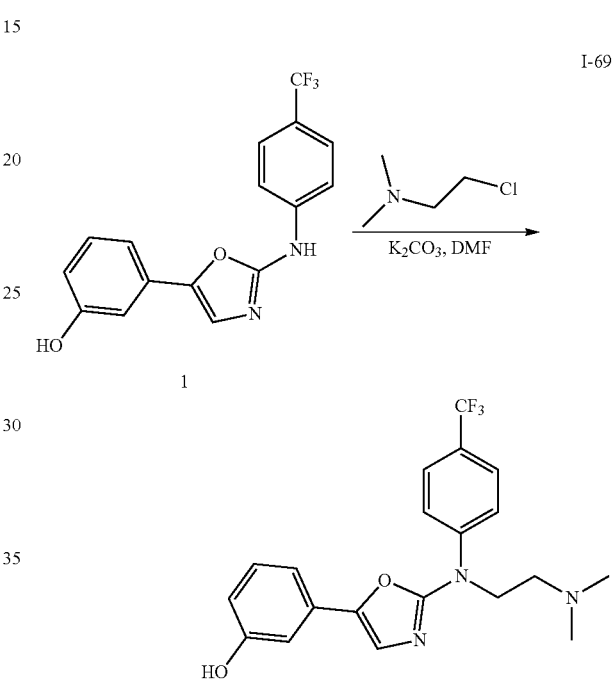

Step 1: 3-[2-[N-[2-(Dimethylamino)ethyl]-4-(trifluoromethyl)anilino]oxazol-5-yl]phenol

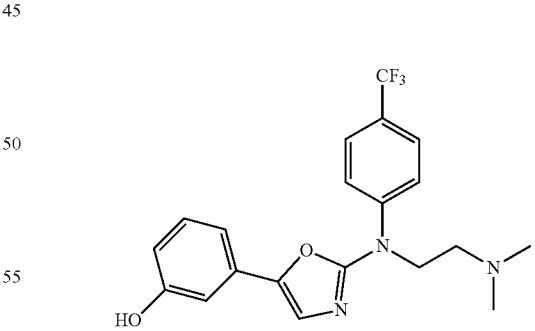

A mixture of 3-[2-[4-(trifluoromethyl)anilino]oxazol-5-yl]phenol (150 mg, 439.32 μmol, eq), 2-chloro-N,N-dimethyl-ethanamine (60 mg, 416.54 μmol, 9.48e-1 eq, HCl), K$_2$CO$_3$ (182.15 mg, 1.32 mmol, 3 eq) and NaI (18.76 mg, 125.16 μmol, 2.85e-1 eq) in DMF (3 mL) was stirred at 80° C. for 3 h. The reaction mixture was filtered. The filtrate was purified by preparative HPLC (column: Phenomenex Synergi C18 150*30 mm*4 μm; mobile phase: [water (0.05% HCl)-ACN]; B %: 31%-51%, 10 min). The desired fraction was basified with aqueous NaHCO₃ until pH=8 and extracted with EtOAc (50 mL×4). The organic layer was dried over Na₂SO₄, filtered and concentrated under reduced pressure. The residue was purified by preparative HPLC (column: Agela DuraShell C18 150*25 mm*5 μm; mobile phase: [water (0.04% NH₃.H₂O+10 mM NH₄HCO₃)-ACN]; B %: 36%-66%, 10 min) and lyophilized to yield 3-[2-[N-[2-(dimethylamino)ethyl]-4-(trifluoromethyl)anilino]oxazol-5-yl]phenol (17.04 mg, 43.54 μmol, 9.9% yield, 100.0% purity) as an off-white solid. ¹H NMR (500 MHz, CD₃OD) δ ppm 7.77-7.72 (m, 2H), 7.70-7.64 (m, 2H), 7.20-7.16 (m, 2H), 7.00 (td, J=1.1, 7.9 Hz, 1H), 6.94-6.90 (m, 1H), 6.68 (ddd, J=0.8, 2.4, 8.2 Hz, 1H), 4.17 (t, J=7.2 Hz, 2H), 2.67 (t, J=7.2 Hz, 2H), 2.32 (s, 6H); ES-LCMS m/z 392.2 [M+H]⁺.

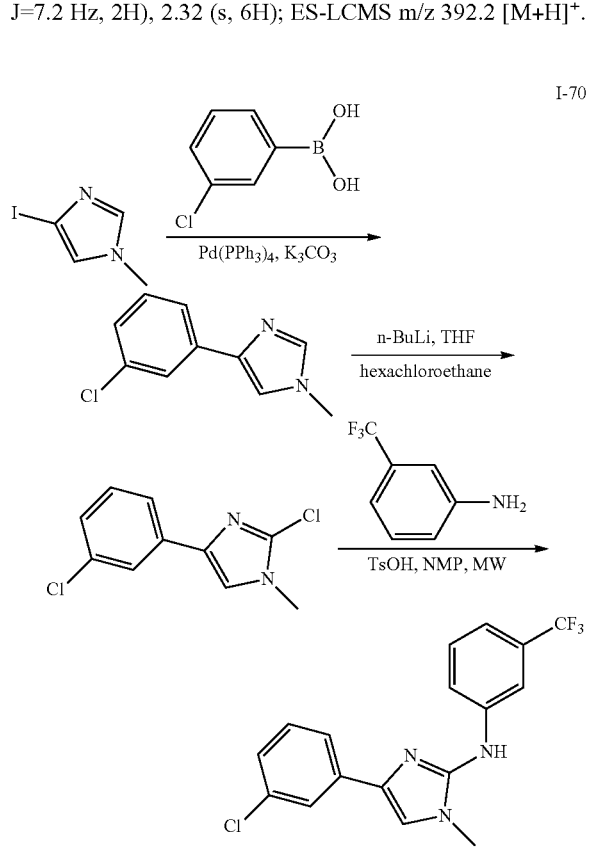

I-70

Step 1: 4-(3-Chlorophenyl)-1-methyl-imidazole

A mixture of 4-iodo-1-methyl-imidazole (750 mg, 3.61 mmol, 1 eq), (3-chlorophenyl)boronic acid (600 mg, 3.84 mmol, 1.06 eq), Cs₂CO₃ (3.52 g, 10.82 mmol, 3 eq) and Pd(dppf)Cl₂ (250 mg, 341.67 μmol, 9.48e-2 eq) in 1,4-dioxane (30 mL) and H₂O (10 mL) was stirred under N₂ atmosphere at 80° C. for 3 h. TLC (PE/EtOAc=1/1, R_f=0.14) showed the starting material was consumed completely. The reaction mixture was diluted with H₂O (50 mL) and extracted with EtOAc (50 mL×3). The organic layer was dried over Na₂SO₄, filtered and concentrated under reduced pressure to yield a residue which was purified by flash silica gel chromatography (from PE/EtOAc=10/1 to 1/1, TLC: PE/EtOAc=1/1, R_f=0.14) to yield 4-(3-chlorophenyl)-1-methyl-imidazole (500 mg, 2.28 mmol, 63.1% yield, 87.7% purity) as colorless oil. ¹H NMR (400 MHz, CDCl₃) δ ppm 7.76 (s, 1H), 7.63 (d, J=7.6 Hz, 1H), 7.49 (s, 1H), 7.32-7.28 (m, 1H), 7.23-7.17 (m, 2H), 3.75 (s, 3H); ES-LCMS m/z 193.1 [M+H]⁺.

Step 2: 2-Chloro-4-(3-chlorophenyl)-1-methyl-imidazole

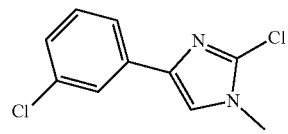

To a solution of 4-(3-chlorophenyl)-1-methyl-imidazole (400 mg, 1.82 mmol, 1 eq) in THF (20 mL) was added n-BuLi (2.5 M, 728.39 μL, 1 eq) under N₂ atmosphere at −78° C. The mixture was stirred under N₂ atmosphere at −78° C. for 0.5 h. A solution of hexachloroethane (431.09 mg, 1.82 mmol, 1 eq) in THF (5 mL) was added. The mixture was stirred under N₂ atmosphere at −78° C. for 0.5 h. TLC (PE/EtOAc=3/1, R_f=0.40) showed about 80% of the starting material was consumed. The reaction mixture was diluted with H₂O (50 mL) and extracted with EtOAc (50 mL×3). The organic layer was dried over Na₂SO₄, filtered and concentrated under reduced pressure to yield a residue which was purified by flash silica gel chromatography (from PE/EtOAc=100/1 to 8/1, TLC: PE/EtOAc=3/1, R_f=0.40) to yield 2-chloro-4-(3-chlorophenyl)-1-methyl-imidazole (168 mg, 739.80 μmol, 40.6% yield, 100.0% purity) as a yellow solid. ¹H NMR (400 MHz, CDCl₃) δ ppm 7.72 (s, 1H), 7.58 (d, J=7.6 Hz, 1H), 7.32-7.27 (m, 1H), 7.24-7.20 (m, 1H), 7.19 (s, 1H), 3.67 (s, 3H); ES-LCMS m/z 227.0, 229.0 [M+H]⁺.

Step 3: 4-(3-Chlorophenyl)-1-methyl-N-[3-(trifluoromethyl)phenyl]imidazol-2-amine

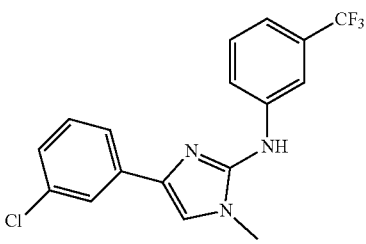 [SMILES: Cn1cc(-c2cccc(Cl)c2)nc1Nc1cccc(C(F)(F)F)c1]

A mixture of 2-chloro-4-(3-chlorophenyl)-1-methyl-imidazole (168 mg, 739.79, 1 eq), 3-(trifluoromethyl)aniline (500 mg, 3.10 mmol, 387.60 μL, 4.19 eq) and TsOH.H₂O (400 mg, 2.10 mmol, 2.84 eq) in NMP (4 mL) was sealed and irradiated under microwave (2 bar) at 200° C. for 30 minutes. The reaction mixture was diluted with H₂O (15 mL), basified with saturated aqueous NaHCO₃ until pH=8 and extracted with EtOAc (20 mL×3). The organic layer was dried over Na₂SO₄, filtered and concentrated under reduced pressure to yield a residue which was purified by preparative HPLC (column: Agela DuraShell C18 150*25 mm*5 um; mobile phase: [water (0.04% NH₃.H₂O+10 mM NH₄HCO₃)-ACN]; B %: 55%–70%, 14 min) and lyophilized to yield 4-(3-chlorophenyl)-1-methyl-N-[3-(trifluoromethyl)phenyl]imidazol-2-amine (25.65 mg, 69.52 μmol, 9.4% yield, 95.3% purity) as a yellow solid. $^1$H NMR (500 MHz, CD₃OD) δ ppm 7.72 (s, 1H), 7.62 (d, J=7.9 Hz, 1H), 7.52 (s, 1H), 7.44-7.38 (m, 2H), 7.35 (s, 1H), 7.31 (t, J=7.9 Hz, 1H), 7.19 (dd, J=1.1, 7.9 Hz, 1H), 7.12 (d, J=6.6 Hz, 1H), 3.60 (s, 3H); ES-LCMS m/z 352.0 [M+H]⁺.

I-71

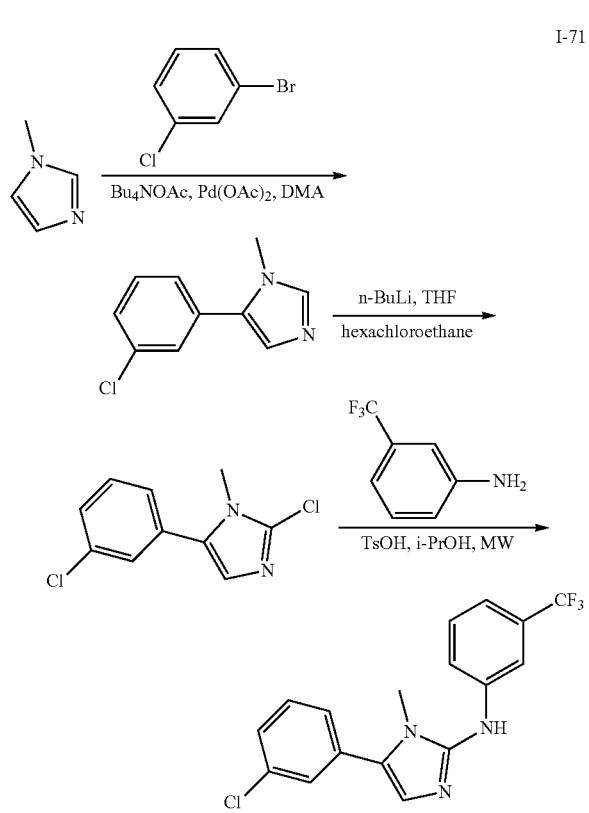

Step 1: 5-(3-Chlorophenyl)-1-methyl-imidazole

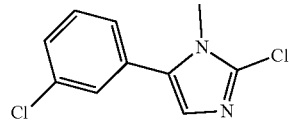

A mixture of 1-bromo-3-chloro-benzene (2.62 g, 13.70 mmol, 1.61 mL, 1.5 eq), 1-methylimidazole (750 mg, 9.13 mmol, 728.16 μL, 1 eq), Pd(OAc)₂ (100.00 mg, 445.42 μmol, 4.88e-2 eq) and tetrabutylammonium acetate (5.51 g, 18.27 mmol, 5.56 mL, 2 eq) in DMA (50 mL) was stirred under N₂ atmosphere at 115° C. for 12 h. The reaction mixture was diluted with H₂O (100 mL) and extracted with EtOAc (100 mL×3). The organic layer was dried over Na₂SO₄, filtered and concentrated under reduced pressure to yield a residue which was purified by flash silica gel chromatography (from PE/EtOAc=10/1 to 2/3, TLC: PE/EtOAc=0/1, R$_f$=0.50) to yield 5-(3-chlorophenyl)-1-methyl-imidazole (600 mg, 3.07 mmol, 33.6% yield, 98.5% purity) as colorless oil. $^1$H NMR (400 MHz, CDCl₃) δ ppm 7.54 (s, 1H), 7.42-7.33 (m, 3H), 7.31-7.27 (m, 1H), 7.13 (s, 1H), 3.69 (s, 3H); ES-LCMS m/z 193.0 [M+H]⁺.

Step 2: 2-Chloro-5-(3-chlorophenyl)-1-methyl-imidazole

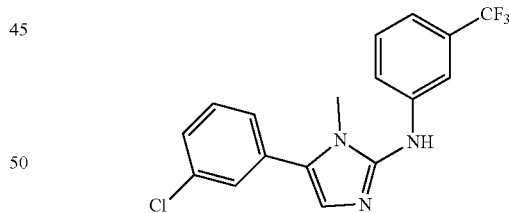

To a solution of 5-(3-chlorophenyl)-1-methyl-imidazole (550 mg, 2.81 mmol, 1 eq) in THF (20 mL) was added n-BuLi (2.5 M, 1.12 mL, 1 eq) under N₂ atmosphere at −78° C. The mixture was stirred under N₂ atmosphere at −78° C. for 0.5 h. A solution of hexachloroethane (665.75 mg, 2.81 mmol, 1 eq) in THF (5 mL) was added. The mixture was stirred under N₂ atmosphere at −78° C. for 0.5 h. TLC (PE/EtOAc=3/1, R$_f$=0.37) showed about 80% of the starting material was consumed. The reaction mixture was diluted with H₂O (50 mL) and extracted with EtOAc (50 mL×3). The organic layer was dried over Na₂SO₄, filtered and concentrated under reduced pressure to yield a residue which was purified by flash silica gel chromatography (from PE/EtOAc=100/1 to 8/1, TLC: PE/EtOAc=3/1, R$_f$=0.37) to yield 2-chloro-5-(3-chlorophenyl)-1-methyl-imidazole (600 mg, 2.64 mmol, 94.0% yield, 100.0% purity) as colorless oil. $^1$H NMR (400 MHz, CDCl₃) δ ppm 7.41-7.38 (m, 2H), 7.37-7.36 (m, 1H), 7.25 (ddd, J=1.7, 2.9, 5.9 Hz, 1H), 7.01 (s, 1H), 3.60 (s, 3H); ES-LCMS m/z 227.0 [M+H]⁺.

Step 3: 5-(3-Chlorophenyl)-1-methyl-N-[3-(trifluoromethyl)phenyl]imidazol-2-amine A mixture of 2-chloro-5-(3-chlorophenyl)-1-methyl-imidazole (100 mg, 440.35 μmol, 1 eq), 3-(trifluoromethyl)aniline (300 mg, 1.86 mmol, 232.56 μL, 4.23 eq) and TsOH.H₂O (250 mg, 1.31 mmol, 2.98 eq) in NMP (3 mL) was sealed and irradiated under microwave (2 bar) at 200° C. for 30 minutes. The reaction mixture was diluted with EtOAc (50 mL) and washed with saturated aqueous NaHCO₃ (10 mL) and brine (10 mL). The organic layer was dried over Na₂SO₄, filtered and concentrated under reduced pressure to yield a residue which was purified by preparative HPLC (column: Agela DuraShell C18 150*25 mm*5 μm; mobile phase: [water (0.04% NH₃.H₂O+10 mM NH₄HCO₃)-ACN]; B %: 50%-80%, 10 min). The desired fraction was lyophilized to yield a residue which was purified by preparative TLC (PE/EtOAc=1/1, $R_f$=0.66) to yield 5-(3-chlorophenyl)-1-methyl-N-[3-(trifluoromethyl) phenyl]imidazol-2-amine (17.11 mg, 48.64 μmol, 11.1% yield, 100.0% purity) as a yellow solid. $^1$H NMR (500 MHz, CD$_3$OD) δ ppm 7.53 (t, J=1.8 Hz, 1H), 7.48-7.40 (m, 5H), 7.38-7.34 (m, 1H), 7.16 (d, J=7.6 Hz, 1H), 6.98 (s, 1H), 3.58 (s, 3H); ES-LCMS m/z 352.0 [M+H]$^+$.

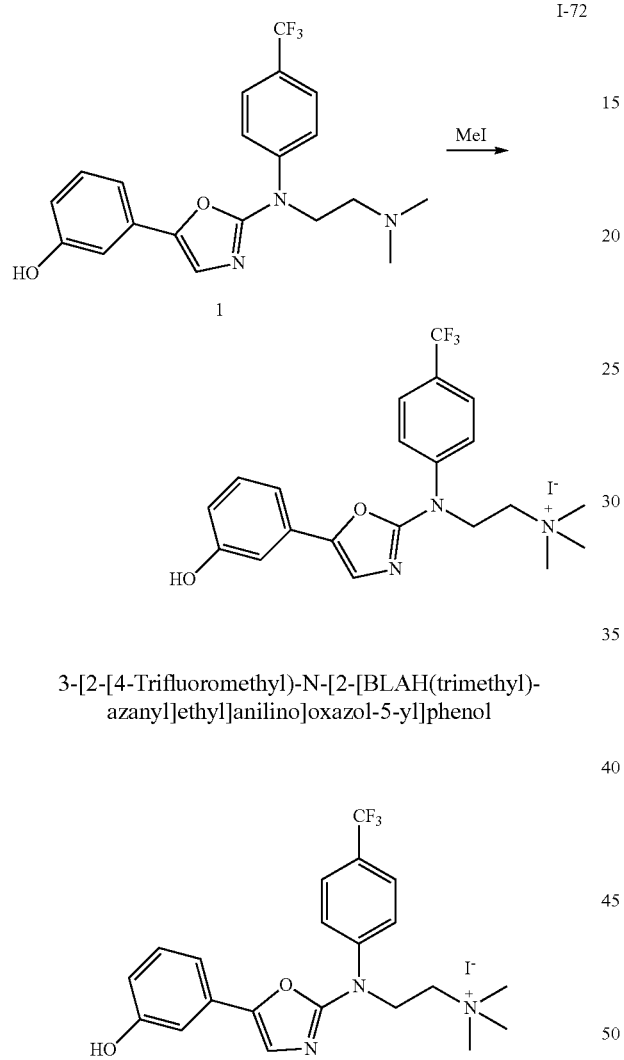

I-72

3-[2-[4-Trifluoromethyl)-N-[2-[BLAH(trimethyl)-azanyl]ethyl]anilino]oxazol-5-yl]phenol To a solution of 3-[2-[N-[2-(dimethylamino)ethyl]-4-(trifluoromethyl)anilino]oxazol-5-yl]phenol (18 mg, 45.99 μmol, 1 eq) in MeCN (5 mL) was added MeI (34.20 mg, 240.95 μmol, 15 μL, 5.24 eq) at 20° C. The mixture was stirred at 20° C. for 0.5 h. The mixture was diluted with water (10 mL) and lyophilized to yield 3-[2-[4-(trifluoromethyl)-N-[2-[BLAH(trimethyl)-azanyl]ethyl]anilino]oxazol-5-yl]phenol (18.70 mg, 35.06 μmol, 76.2% yield, 100.0% purity) as a white solid. $^1$H NMR (500 MHz, DMSO-d$_6$) δ ppm 9.61 (s, 1H), 7.85 (d, J=8.5 Hz, 2H), 7.76 (d, J=8.5 Hz, 2H), 7.51 (s, 1H), 7.22 (t, J=7.9 Hz, 1H), 7.01 (d, J=7.8 Hz, 1H), 6.91 (s, 1H), 6.69 (dd, J=1.7, 8.1 Hz, 1H), 4.53 (t, J=7.3 Hz, 2H), 3.71 (t, J=7.3 Hz, 2H), 3.19 (s, 9H); ES-LCMS m/z 406.1 [M−I]$^+$.

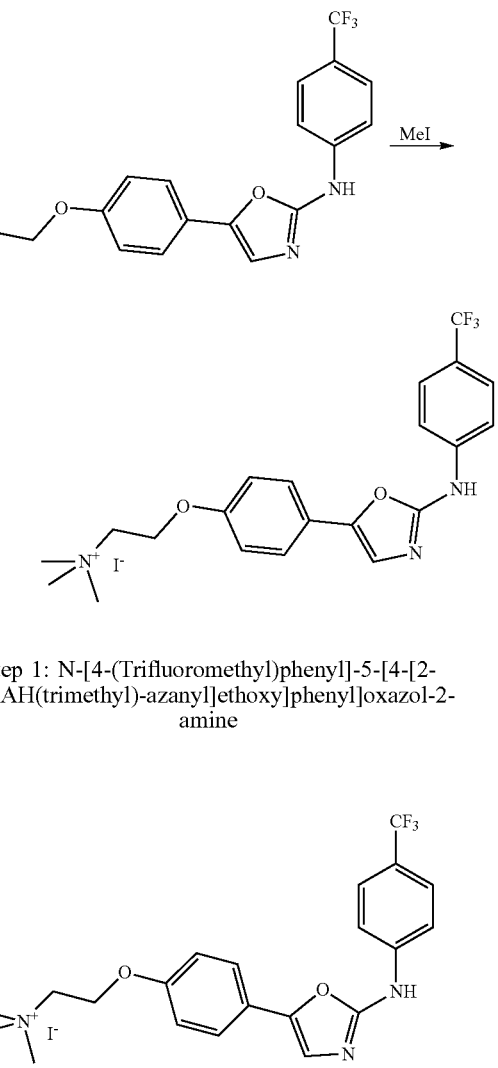

I-73

Step 1: N-[4-(Trifluoromethyl)phenyl]-5-[4-[2-[BLAH(trimethyl)-azanyl]ethoxy]phenyl]oxazol-2-amine To a solution of 5-[4-[2-(dimethylamino)ethoxy]phenyl]-N-[4-(trifluoromethyl)phenyl]oxazol-2-amine (30 mg, 73.97 μmol, 1 eq) in MeCN (5 mL) was added MeI (209.98 mg, 1.48 mmol, 92.10 μL, 20 eq). The mixture was stirred at 15° C. for 1 h under N$_2$ atmosphere. TLC (DCM/MeOH=10/1, $R_f$=0.13) indicated the starting material was consumed completely and one new spot formed. The solution was added water (5 mL), followed by lyophilization to yield N-[4-(trifluoromethyl)phenyl]-5-[4-[2-[BLAH(trimethyl)-azanyl]ethoxy]phenyl]oxazol-2-amine (30.03 mg, 55.35 μmol, 74.8% yield, 98.3% purity) as a white solid. $^1$H NMR (500 MHz, DMSO-d$_6$) δ ppm 10.76 (s, 1H), 7.82 (d, J=8.5 Hz, 2H), 7.68 (d, J=8.9 Hz, 2H), 7.59 (d, J=8.7 Hz, 2H), 7.40 (s, 1H), 7.11 (d, J=8.9 Hz, 2H), 4.50 (br s, 2H), 3.83-3.77 (m, 2H), 3.18 (s, 9H); ES-LCMS m/z 406.5 [M−I]$^+$.

I-74

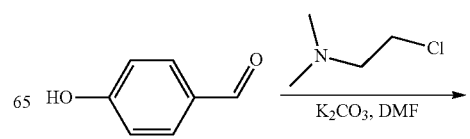

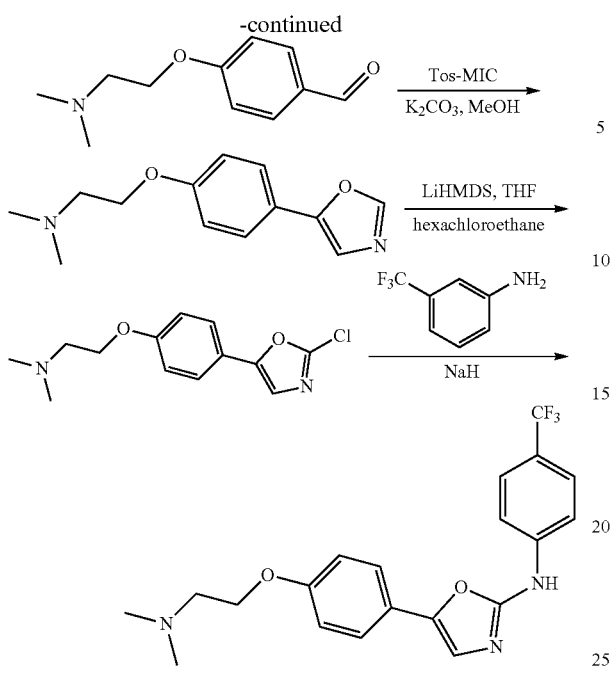

Step 1: 4-[2-(Dimethylamino)ethoxy]benzaldehyde

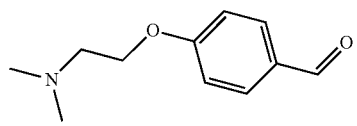

To a solution of 4-hydroxybenzaldehyde (190.00 mg, 1.56 mmol, 1 eq) in DMF (3 mL) was added Cs$_2$CO$_3$ (2.53 g, 7.78 mmol, 5 eq) and 2-chloro-N,N-dimethyl-ethanamine (1.12 g, 7.78 mmol, 5 eq, HCl). The mixture was stirred at 15° C. for 12 h. The reaction mixture was quenched by addition of water (50 mL), extracted with EtOAc (30 mL×3). The combined organic layers were washed with brine (10 mL), dried over Na$_2$SO$_4$, filtered and concentrated under reduced pressure to yield a residue which was purified by flash silica gel chromatography (from PE/EtOAc=1/0 to 0/1, TLC: EtOAc, R$_f$=0.10) to yield 4-[2-(dimethylamino)ethoxy]benzaldehyde (240 mg, 1.18 mmol, 75.8% yield, 95.0% purity) as a white solid. $^1$H NMR (400 MHz, CDCl$_3$) δ ppm 9.93-9.85 (m, 1H), 7.88-7.79 (m, 2H), 7.03 (d, J=8.6 Hz, 2H), 4.15 (t, J=5.7 Hz, 2H), 2.77 (t, J=5.7 Hz, 2H), 2.36 (s, 6H); ES-LCMS m/z 181.9 [M+H]$^+$.

Step 2:
N,N-Dimethyl-2-(4-oxazol-5-ylphenoxy)ethanamine

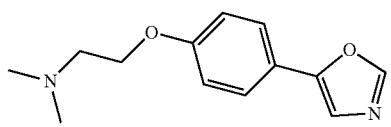 [SMILES: CN(C)CCOc1ccc(-c2cnco2)cc1]

To a solution of 4-[2-(dimethylamino)ethoxy]benzaldehyde (240 mg, 1.18 mmol, 1 eq) in MeOH (5 mL) was added Tos-Mic (276.43 mg, 1.42 mmol, 1.2 eq) and K$_2$CO$_3$ (228.30 mg, 1.65 mmol, 1.4 eq). The mixture was stirred at 80° C. for 3 h. The reaction mixture was concentrated under reduced pressure to yield a residue which was added water (50 mL), extracted with EtOAc (50 mL×3). The combined organic layers were washed with brine (20 mL), dried over Na$_2$SO$_4$, filtered and concentrated under reduced pressure. The residue was purified by flash silica gel chromatography (from PE/EtOAc=1/0 to 5/1, TLC: PE/EtOAc=5/1, R$_f$=0.14) to yield N,N-dimethyl-2-(4-oxazol-5-ylphenoxy) ethanamine (250 mg, 1.08 mmol, 91.2% yield, 100% purity) as a white solid. $^1$H NMR (500 MHz, CDCl$_3$) δ ppm 7.88 (s, 1H), 7.59 (d, J=8.2 Hz, 2H), 7.24 (s, 1H), 6.98 (d, J=8.4 Hz, 2H), 4.17-4.11 (m, 2H), 2.81 (br s, 2H), 2.40 (s, 6H); ES-LCMS m/z 233.1 [M+H]$^+$.

Step 3: 2-[4-(2-Chlorooxazol-5-yl)phenoxy]-N,N-dimethyl-ethanamine

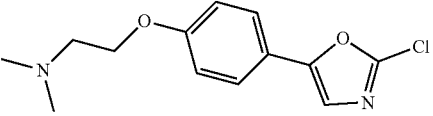 [SMILES: CN(C)CCOc1ccc(-c2cnc(Cl)o2)cc1]

To a solution of N,N-dimethyl-2-(4-oxazol-5-ylphenoxy) ethanamine (250 mg, 1.08 mmol, 1 eq) in THF (7 mL) was added LiHMDS (1 M, 1.40 mL, 1.3 eq) at −70° C. After being stirred for 0.5 h, a solution of 1,1,1,2,2,2-hexachloroethane (305.76 mg, 1.29 mmol, 146.30 μL, 1.2 eq) in THF (3 mL) was added. The mixture was stirred at 80° C. for 3 h. The reaction mixture was concentrated under reduced pressure to yield a residue which was added water (50 mL), extracted with EtOAc (50 mL×3). The combined organic layers were washed with brine (20 mL), dried over Na$_2$SO$_4$, filtered and concentrated under reduced pressure to yield 2-[4-(2-chlorooxazol-5-yl)phenoxy]-N,N-dimethyl-ethanamine (200 mg, 487.40 μmol, 45.2% yield, 65.0% purity) as yellow oil which was used in the next step without further purification.
ES-LCMS m/z 266.9, 268.9 [M+H]$^+$.

Step 4: 5-[4-[2-(Dimethylamino)ethoxy]phenyl]-N-[4-(trifluoromethyl)phenyl]oxazol-2-amine

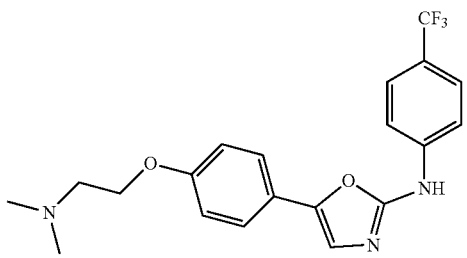 [SMILES: CN(C)CCOc1ccc(-c2cnc(Nc3ccc(C(F)(F)F)cc3)o2)cc1]

To a solution of 4-(trifluoromethyl)aniline (86.38 mg, 536.14 μmol, 66.45 μL, 1.1 eq) in DMF (8 mL) was added NaH (38.99 mg, 974.79 μmol, 60%, 2 eq). After being stirred for 30 min, 2-[4-(2-chlorooxazol-5-yl)phenoxy]-N,N-dimethyl-ethanamine (200 mg, 487.40 μmol, 1 eq) in DMF (2 mL) was added. The mixture was stirred at 60° C. for 12.5 h. The reaction mixture was quenched by addition of water (50 mL), extracted with EtOAc (30 mL×3). The combined organic layers were washed with brine (10 mL), dried over Na₂SO₄, filtered and concentrated under reduced pressure to yield a residue which was purified by preparative HPLC (column: Welch Xtimate C18 150*30 mm*5 μm; mobile phase: [water (10 mM NH₄HCO₃)-ACN]; B %: 55%-85%, 10 min), followed by lyophilization to yield 5-[4-[2-(dimethylamino)ethoxy]phenyl]-N-[4-(trifluoromethyl)phenyl]oxazol-2-amine (60 mg, 147.94 μmol, 30.3% yield, 96.5% purity) as a white solid. ¹H NMR (400 MHz, CD₃OD) δ ppm 7.72 (d, J=9.0 Hz, 2H), 7.64-7.54 (m, 4H), 7.15 (s, 1H), 7.02 (d, J=8.6 Hz, 2H), 4.15 (t, J=5.5 Hz, 2H), 2.81 (t, J=5.3 Hz, 2H), 2.37 (s, 6H); ES-LCMS m/z 392.0 [M+H]⁺.

I-75

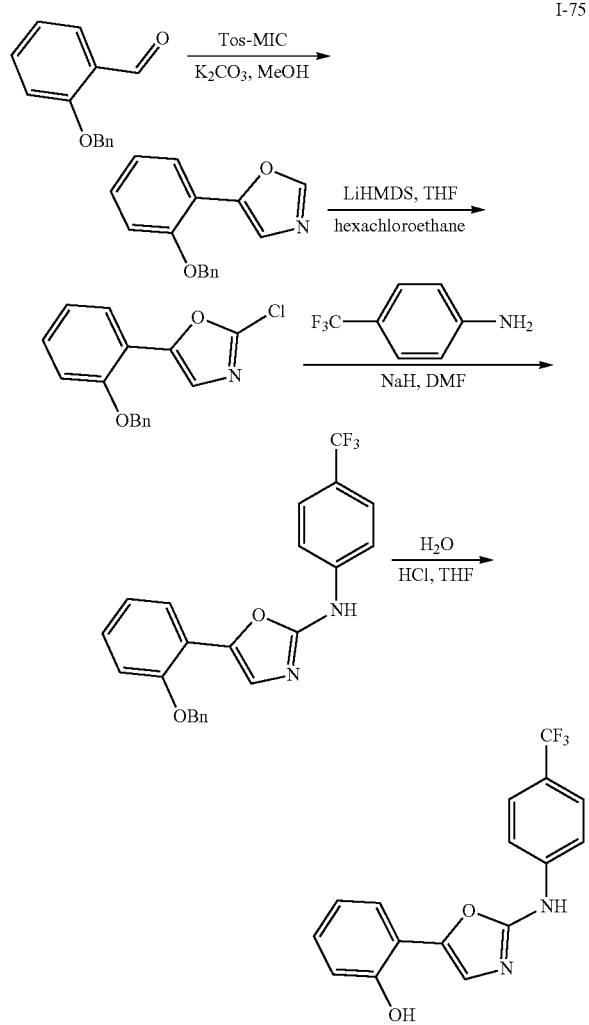

Step 1: 5-(2-Benzyloxyphenyl)oxazole

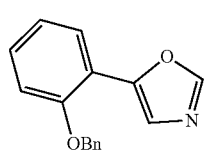 [SMILES: c1ccc(COc2ccccc2-c2cnco2)cc1]

To a solution of 2-benzyloxybenzaldehyde (5 g, 23.56 mmol, 1 eq) in MeOH (200 mL) was added Tos-MIC (5.06 g, 25.91 mmol, 1.1 eq) and K₂CO₃ (3.91 g, 28.27 mmol, 1.2 eq). The mixture was stirred at 80° C. for 3 h. TLC (PE/EtOAc=5/1, R_f=0.14) indicated the starting material was consumed completely and one new spot formed. The reaction mixture was concentrated under reduced pressure to yield a residue which was added water (100 mL), extracted with EtOAc (80 mL×3). The combined organic layers were washed with brine (50 mL), dried over Na₂SO₄, filtered and concentrated under reduced pressure to give a residue which was purified by flash silica gel chromatography (from PE/EtOAc=1/0 to 5/1, TLC: PE/EtOAc=5/1, R_f=0.14) to yield 5-(2-benzyloxyphenyl)oxazole (4.9 g, 19.36 mmol, 82.2% yield, 99.3% purity) as a white solid. ¹H NMR (400 MHz, CDCl₃) δ ppm 7.87 (d, J=2.4 Hz, 1H), 7.81 (d, J=7.6 Hz, 1H), 7.58-7.21 (m, 7H), 7.11-7.00 (m, 2H), 5.18 (d, J=2.0 Hz, 2H).

Step 2: 5-(2-Benzyloxyphenyl)-2-chloro-oxazole

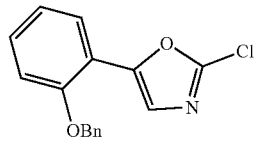 [SMILES: Clc1ncc(-c2ccccc2OCc2ccccc2)o1]

To a solution of 5-(2-benzyloxyphenyl)oxazole (2 g, 7.96 mmol, 1 eq) in THF (30 mL) was added LiHMDS (1 M, 10.35 mL, 1.3 eq) at −70° C. under N₂ atmosphere. After being stirred for 30 min, a solution of hexachloroethane (2.64 g, 11.14 mmol, 1.26 mL, 1.4 eq) in THF (10 mL) was added. After addition, the mixture was stirred at 15° C. for 3 h. TLC (PE/EtOAc=3/1, R_f=0.68) indicated starting material was consumed completely and one new spot formed. The reaction mixture was quenched by addition of water (50 mL), extracted with EtOAc (50 mL×3). The combined organic layers were washed with brine (30 mL), dried over Na₂SO₄, filtered and concentrated under reduced pressure to give a residue which was purified by flash silica gel chromatography (from PE/EtOAc=1/0 to 5/1, TLC: PE/EtOAc=3/1, R_f=0.68) to yield 5-(2-benzyloxyphenyl)-2-chloro-oxazole (2.1 g, 7.32 mmol, 91.9% yield, 99.6% purity) as a white solid. ¹H NMR (400 MHz, CD₃OD) δ ppm 7.68 (dd, J=1.6, 7.8 Hz, 1H), 7.50-7.46 (m, 2H), 7.45-7.29 (m, 5H), 7.19 (d, J=7.8 Hz, 1H), 7.06 (dt, J=1.0, 7.5 Hz, 1H), 5.23 (s, 2H); ES-LCMS m/z 286.0, 288.0 [M+H]⁺.

Step 3: 5-(2-Benzyloxyphenyl)-N-[4-(trifluoromethyl)phenyl]oxazol-2-amine

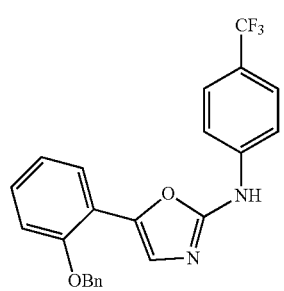 [SMILES: FC(F)(F)c1ccc(Nc2ncc(-c3ccccc3OCc3ccccc3)o2)cc1]

A mixture of 5-(2-benzyloxyphenyl)-2-chloro-oxazole (400 mg, 1.39 mmol, 1 eq), 4-(trifluoromethyl)aniline (247.13 mg, 1.53 mmol, 190.10 μL, 1.1 eq), NaH (111.54 mg, 2.79 mmol, 60%, 2 eq) in DMF (5 mL) was degassed and purged with N₂ for 3 times and the mixture was stirred at 70° C. for 12 h under N₂ atmosphere. The reaction mixture was quenched by addition of water (50 mL), extracted with EtOAc (50 mL×3). The combined organic layers were washed with brine (40 mL), dried over Na₂SO₄, concentrated under reduced pressure to give a residue which was treated with PE/EtOAc (4/1, 50 mL) and stirred at 25° C. for 1 h. The slurry was filtered, rinsed with PE (2×10 mL) to yield 5-(2-benzyloxyphenyl)-N-[4-(trifluoromethyl)phenyl]oxazol-2-amine (150 mg, 365.51 μmol, 26.2% yield, 100% purity) as a white solid. ¹H NMR (400 MHz, DMSO-d₆) δ ppm 10.79 (s, 1H), 7.80 (d, J=8.6 Hz, 2H), 7.65 (d, J=8.2 Hz, 2H), 7.58 (d, J=8.2 Hz, 1H), 7.53 (d, J=7.0 Hz, 2H), 7.44 (t, J=7.4 Hz, 2H), 7.38 (d, J=7.0 Hz, 1H), 7.30-7.21 (m, 3H), 7.09-7.04 (m, 1H), 5.27 (s, 2H); ES-LCMS m/z 411.0 [M+H]⁺

Step 4: 2-[2-[4-(trifluoromethyl)anilino]oxazol-5-yl]phenol

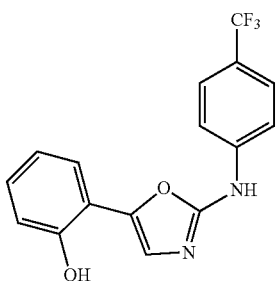 [SMILES: Oc1ccccc1-c1cnc(Nc2ccc(C(F)(F)F)cc2)o1]

To a solution of 5-(2-benzyloxyphenyl)-N-[4-(trifluoromethyl)phenyl]oxazol-2-amine (140 mg, 341.14 μmol, 1 eq) in THF (5 mL) was added con HCl (12 M, 10 mL, 351.76 eq) and H₂O (5 mL). The mixture was stirred at 100° C. for 4 h. TLC (PE/EtOAc=0/1, R𝑓=0.41) indicated the starting material was consumed completely and one new spot formed. The reaction mixture was concentrated under reduced pressure to give a residue which was purified by flash silica gel chromatography (from PE/EtOAc=1/0 to 3/1, TLC: PE/EtOAc=0/1, R𝑓=0.41) to yield 2-[2-[4-(trifluoromethyl)anilino]oxazol-5-yl]phenol (17.32 mg, 54.08 μmol, 15.8% yield, 100% purity) was obtained as a white solid. ¹H NMR (400 MHz, CD₃OD) δ ppm 7.72 (d, J=8.2 Hz, 2H), 7.64-7.54 (m, 3H), 7.36 (s, 1H), 7.13-7.07 (m, 1H), 6.95-6.80 (m, 2H); ES-LCMS m/z 320.9 [M+H]⁺.

I-52

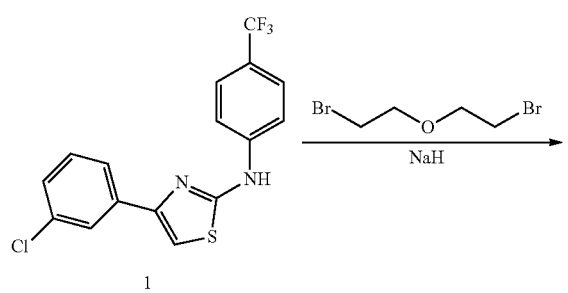

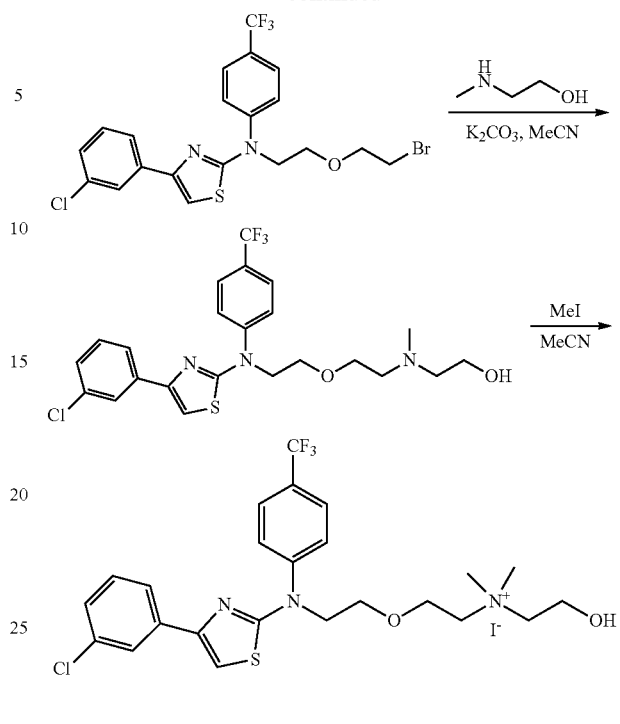

Step 1: N-[2-(2-Bromoethoxy)ethyl]-4-(3-chlorophenyl)-N-[4-(trifluoromethyl)phenyl]thiazol-2-amine

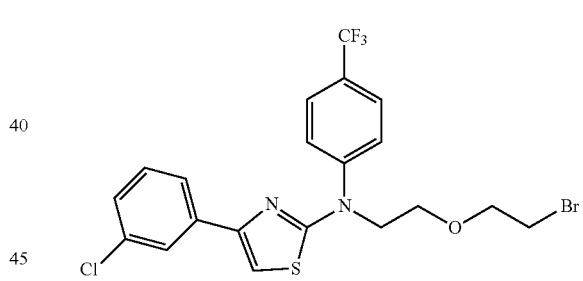

To a solution of 4-(3-chlorophenyl)-N-[4-(trifluoromethyl)phenyl]thiazol-2-amine (100 mg, 281.87 μmol, 1 eq) in DMF (3 mL) was added NaH (13.53 mg, 338.24 μmol, 60%, 1.2 eq) and 1-bromo-2-(2-bromoethoxy)ethane (130.74 mg, 563.73 μmol, 70.67 μL, 2 eq). The mixture was stirred at 20° C. for 12 h. The reaction mixture was quenched by addition of water (50 mL), extracted with EtOAc (30 mL×3). The combined organic layers were washed with brine (10 mL), dried over Na₂SO₄, filtered and concentrated under reduced pressure to yield a residue which was purified by flash silica gel chromatography (from PE/EtOAc=1/0 to 10/1, TLC: PE/EtOAc=5/1, R𝑓=0.66) to yield N-[2-(2-bromoethoxy)ethyl]-4-(3-chlorophenyl)-N-[4-(trifluoromethyl)phenyl]thiazol-2-amine (80 mg, 158.17 μmol, 56.1% yield, 100% purity) as colorless oil. ¹H NMR (400 MHz, CDCl₃) δ ppm 7.85 (s, 1H), 7.69 (s, 5H), 7.36-7.28 (m, 2H), 6.80 (s, 1H), 4.26 (t, J=5.3 Hz, 2H), 3.93 (t, J=5.4 Hz, 2H), 3.80 (t, J=6.0 Hz, 2H), 3.43 (t, J=6.0 Hz, 2H); ES-LCMS m/z 506.8 [M]⁺.

Step 2: 2-[2-[2-[N-[4-(3-chlorophenyl)thiazol-2-yl]-4-(trifluoromethyl)anilino]ethoxy]ethyl-methyl-amino]ethanol

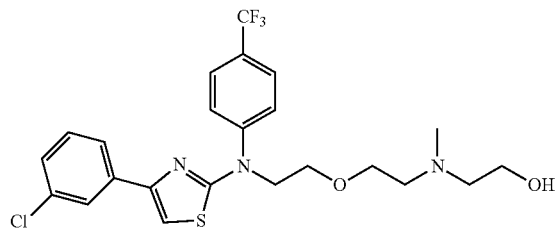 [SMILES: CN(CCO)CCOCCN(c1ccc(C(F)(F)F)cc1)c1nc(-c2cccc(Cl)c2)cs1]

A mixture of N-[2-(2-bromoethoxy)ethyl]-4-(3-chlorophenyl)-N-[4-(trifluoromethyl)phenyl]thiazol-2-amine (80 mg, 158.17 µmol, 1 eq), 2-(methylamino)ethanol (59.40 mg, 790.86 µmol, 63.53 µL, 5 eq), K$_2$CO$_3$ (109.30 mg, 790.86 µmol, 5 eq) in MeCN (5 mL) was degassed and purged with N$_2$ for 3 times, and then the mixture was stirred at 80° C. for 12 h under N$_2$ atmosphere. The reaction mixture was concentrated to yield a residue which was purified by preparative HPLC (column: Agela DuraShell C18 150*25 mm*5 µm; mobile phase: [water (0.04% NH$_3$H$_2$O+10 mM NH$_4$HCO$_3$)-ACN]; B %: 60%-90%, 10 min), followed by lyophilization to yield 2-[2-[2-[N-[4-(3-chlorophenyl)thiazol-2-yl]-4-(trifluoromethyl)anilino]ethoxy]ethyl-methyl-amino]ethanol (70 mg, 140.01 µmol, 88.5% yield, 100% purity) as colorless oil. $^1$H NMR (400 MHz, CD$_3$OD) δ ppm 7.90-7.87 (m, 1H), 7.80-7.73 (m, 5H), 7.39-7.33 (m, 1H), 7.31-7.26 (m, 1H), 7.10 (s, 1H), 4.29 (t, J=5.3 Hz, 2H), 3.85 (t, J=5.3 Hz, 2H), 3.59 (dt, J=3.5, 5.7 Hz, 4H), 2.64-2.50 (m, 4H), 2.25 (s, 3H); ES-LCMS m/z 500.1 [M]$^+$.

Step 3: 2-[BLAH-[2-[2-[N-[4-(3-chlorophenyl)thiazol-2-yl]-4-(trifluoromethyl)anilino]ethoxy]ethyl]-dimethyl-azanyl]ethanol

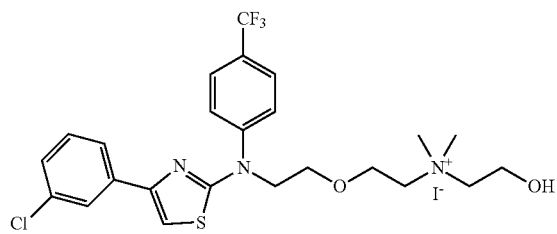 [SMILES: C[N+](C)(CCO)CCOCCN(c1ccc(C(F)(F)F)cc1)c1nc(-c2cccc(Cl)c2)cs1 ; [I-]]

To a solution of 2-[2[2-[N-[4-(3-chlorophenyl)thiazol-2-yl]-4-(trifluoromethyl)anilino]ethoxy]ethyl-methyl-amino]ethanol (70 mg, 140.01 µmol, 1 eq) in MeCN (5 mL) was added MeI (99.36 mg, 700.03 µmol, 43.58 µL, 5 eq) in one portion at 20° C. under N$_2$. The mixture was stirred at 20° C. for 1 h. TLC (PE/EtOAc=0/1, R$_f$=0.00) indicated the starting material was consumed completely and one new spot formed. The solution was added water (10 mL), then lypholization to yield 2-[BLAH-[2-[2-[N-[4-(3-chlorophenyl)thiazol-2-yl]-4-(trifluoromethyl)anilino]ethoxy]ethyl]-dimethyl-azanyl]ethanol (21.13 mg, 32.32 µmol, 23.0% yield, 98.2% purity) as a yellow solid. $^1$H NMR (400 MHz, DMSO-d$_6$) δ ppm 7.91 (s, 1H), 7.81 (q, J=9.0 Hz, 5H), 7.49 (s, 1H), 7.48-7.42 (m, 1H), 7.40-7.34 (m, 1H), 5.23 (t, J=4.7 Hz, 1H), 4.28 (t, J=5.1 Hz, 2H), 3.87-3.71 (m, 6H), 3.54 (br d, J=4.3 Hz, 2H), 3.37 (br s, 1H), 3.38-3.34 (m, 1H), 2.99 (s, 6H); ES-LCMS m/z 514.2 [M–I]$^+$.

I-76

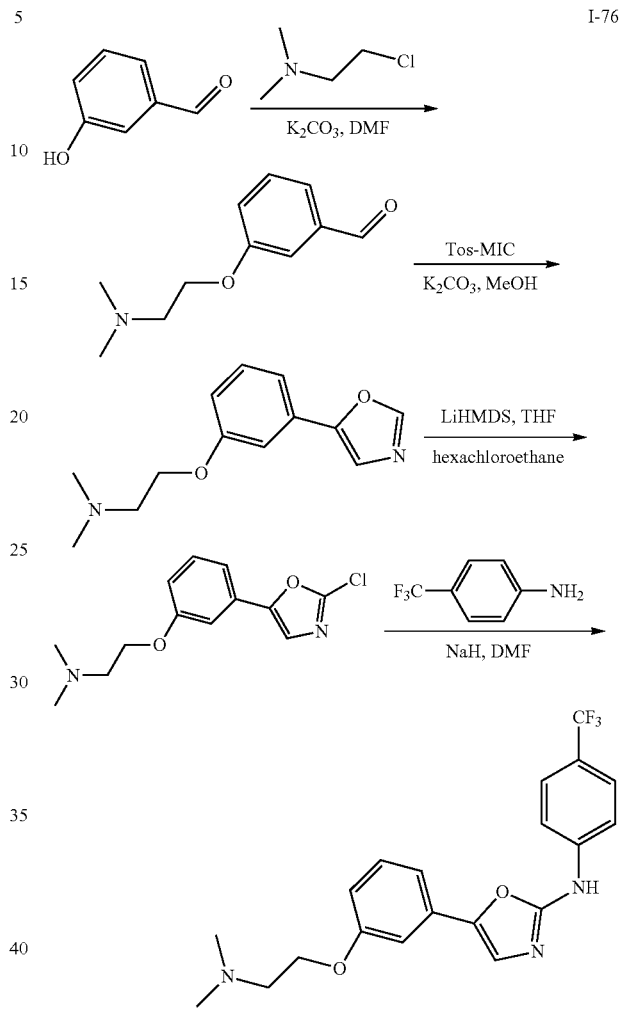

Step 1: 3-[2-(Dimethylamino)ethoxy]benzaldehyde

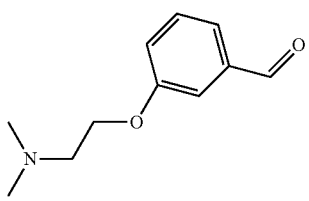

A mixture of 3-hydroxybenzaldehyde (2 g, 16.38 mmol, 1 eq), 2-chloro-N,N-dimethyl-ethanamine (2.80 g, 19.44 mmol, 1.19 eq, HCl) and K$_2$CO$_3$ (12 g, 86.83 mmol, 5.30 eq) in DMF (50 mL) was stirred at 25° C. for 12 h. TLC (PE/EtOAc=1/1, R$_f$=0.05) showed 80% of the starting material was consumed. The reaction mixture was filtered. The filtrate was concentrated under reduced pressure to yield a residue which was purified by flash silica gel chromatography (from PE/EtOAc=10/1 to 0/1, TLC: PE/EtOAc=1/1, R$_f$=0.05) to yield 3-[2-(dimethylamino)ethoxy]benzaldehyde (2 g, 6.21 mmol, 37.92% yield, 60.0% purity) as a colorless gum. ¹H NMR (400 MHz, CDCl₃) δ ppm 9.96 (s, 1H), 7.46-7.44 (m, 1H), 7.43-7.41 (m, 1H), 7.38 (s, 1H), 7.19-7.15 (m, 1H), 4.16 (t, J=5.5 Hz, 2H), 2.82 (t, J=5.6 Hz, 2H), 2.39 (s, 6H).

Step 2: N,N-Dimethyl-2-(3-oxazol-5-ylphenoxy)ethanamine

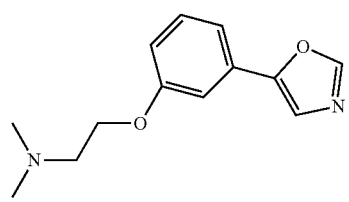 [SMILES: CN(C)CCOc1cccc(-c2cnco2)c1]

A mixture of 3-[2-(dimethylamino)ethoxy]benzaldehyde (2 g, 6.21 mmol, 1 eq), TOS-MIC (1.33 g, 6.83 mmol, 1.1 eq) and K₂CO₃ (1.29 g, 9.31 mmol, 1.5 eq) in MeOH (20 mL) was stirred at 90° C. for 3 h. The reaction mixture was concentrated under reduced pressure. The residue was diluted with H₂O (50 mL) and extracted with EtOAc (50 mL×4). The organic layer was dried over Na₂SO₄, filtered and concentrated under reduced pressure to yield a residue which was purified by flash silica gel chromatography (from PE/EtOAc=10/1 to 0/1, TLC: PE/EtOAc=1/1, R$_f$=0.05) to yield N,N-dimethyl-2-(3-oxazol-5-ylphenoxy)ethanamine (1.1 g, 4.50 mmol, 72.5% yield, 95.0% purity) as a colorless gum. ¹H NMR (400 MHz, CD₃OD) δ ppm 8.24 (s, 1H), 7.53 (s, 1H), 7.40-7.35 (m, 1H), 7.34-7.29 (m, 2H), 6.97 (ddd, J=1.2, 2.5, 8.0 Hz, 1H), 4.17 (t, J=5.4 Hz, 2H), 2.81 (t, J=5.5 Hz, 2H), 2.37 (s, 6H); ES-LCMS m/z 233.0 [M+H]⁺.

Step 3: 2-[3-(2-Chlorooxazol-5-yl)phenoxy]-N,N-dimethyl-ethanamine

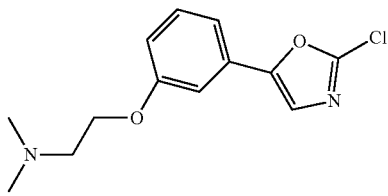 [SMILES: CN(C)CCOc1cccc(-c2cnc(Cl)o2)c1]

To a solution of N,N-dimethyl-2-(3-oxazol-5-ylphenoxy)ethanamine (500 mg, 2.04 mmol, 1 eq) in THF (10 mL) was added LiHMDS (1 M, 2.47 mL, 1.21 eq) dropwise under N₂ atmosphere at −78° C. The mixture was stirred under N₂ atmosphere at −78° C. for 0.5 h. A solution of perchloroethane (731.50 mg, 3.09 mmol, 1.51 eq) in THF (5 mL) was added under N₂ atmosphere at −78° C. The mixture was stirred under N₂ atmosphere at −78° C. for 0.5 h and then warmed to 25° C. slowly and stirred under N₂ atmosphere for 1 h. The reaction mixture was diluted with H₂O (50 mL) and extracted with EtOAc (50 mL×3). The organic layer was dried over Na₂SO₄, filtered and concentrated under reduced pressure to yield a residue which was purified by flash silica gel chromatography (from PE/EtOAc=10/1 to 0/1, TLC: PE/EtOAc=1/1, R$_f$=0.20) to yield 2-[3-(2-chlorooxazol-5-yl)phenoxy]-N,N-dimethyl-ethanamine (330 mg, 1.19 mmol, 58.4% yield, 96.5% purity) as a colorless gum. ¹H NMR (400 MHz, CD₃OD) δ ppm 7.51 (s, 1H), 7.39-7.33 (m, 1H), 7.27-7.21 (m, 2H), 6.97 (ddd, J=1.0, 2.4, 8.3 Hz, 1H), 4.15 (t, J=5.4 Hz, 2H), 2.81 (t, J=5.4 Hz, 2H), 2.36 (s, 6H); ES-LCMS m/z 267.0, 269.0 [M+H]⁺.

Step 4: 5-[3-[2-(Dimethylamino)ethoxy]phenyl]-N-[4-(trifluoromethyl)phenyl]oxazol-2-amine

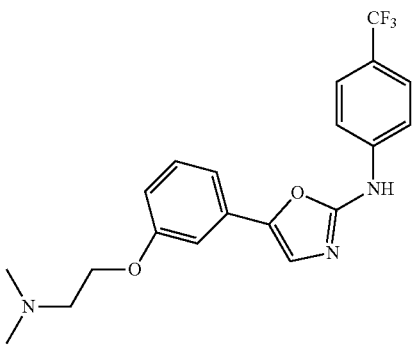 [SMILES: CN(C)CCOc1cccc(-c2cnc(Nc3ccc(C(F)(F)F)cc3)o2)c1]

To a solution of 4-(trifluoromethyl)aniline (100 mg, 620.64 μmol, 76.92 μL, 1.14 eq) in DMF (2 mL) was added NaH (35 mg, 875.08 μmol, 60% purity, 1.61 eq) at 25° C. The mixture was stirred at 25° C. for 0.5 h. 2-[3-(2-Chlorooxazol-5-yl)phenoxy]-N,N-dimethyl-ethanamine (150 mg, 542.70 μmol, 1 eq) was added. The mixture was stirred at 60° C. for 12 h. The reaction mixture was diluted with H₂O (50 mL) and extracted with EtOAc (50 mL×3). The organic layer was dried over Na₂SO₄, filtered and concentrated under reduced pressure to yield a residue which was purified by preparative HPLC (column: Welch Xtimate C18 150*30 mm*5 um; mobile phase: [water (10 mM NH₄HCO₃)-ACN]; B %: 50%-80%, 10 min) and lyophilized to yield 5-[3-[2-(dimethylamino)ethoxy]phenyl]-N-[4-(trifluoromethyl)phenyl]oxazol-2-amine (45 mg, 114.09 μmol, 21.0% yield, 99.2% purity) as a white solid. ¹H NMR (500 MHz, CD₃OD) δ ppm 7.76 (d, J=8.5 Hz, 2H), 7.63 (d, J=8.5 Hz, 2H), 7.39-7.32 (m, 2H), 7.24 (d, J=7.8 Hz, 1H), 7.22 (d, J=2.1 Hz, 1H), 6.91 (dd, J=1.9, 8.2 Hz, 1H), 4.18 (t, J=5.4 Hz, 2H), 2.83 (t, J=5.4 Hz, 2H), 2.40 (s, 6H); ES-LCMS m/z 392.2 [M+H]⁺.

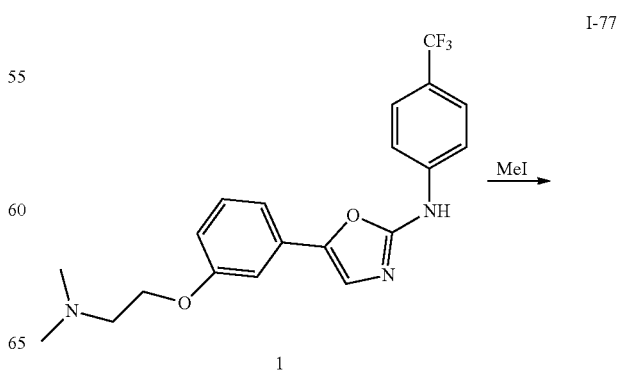

I-77

179

-continued

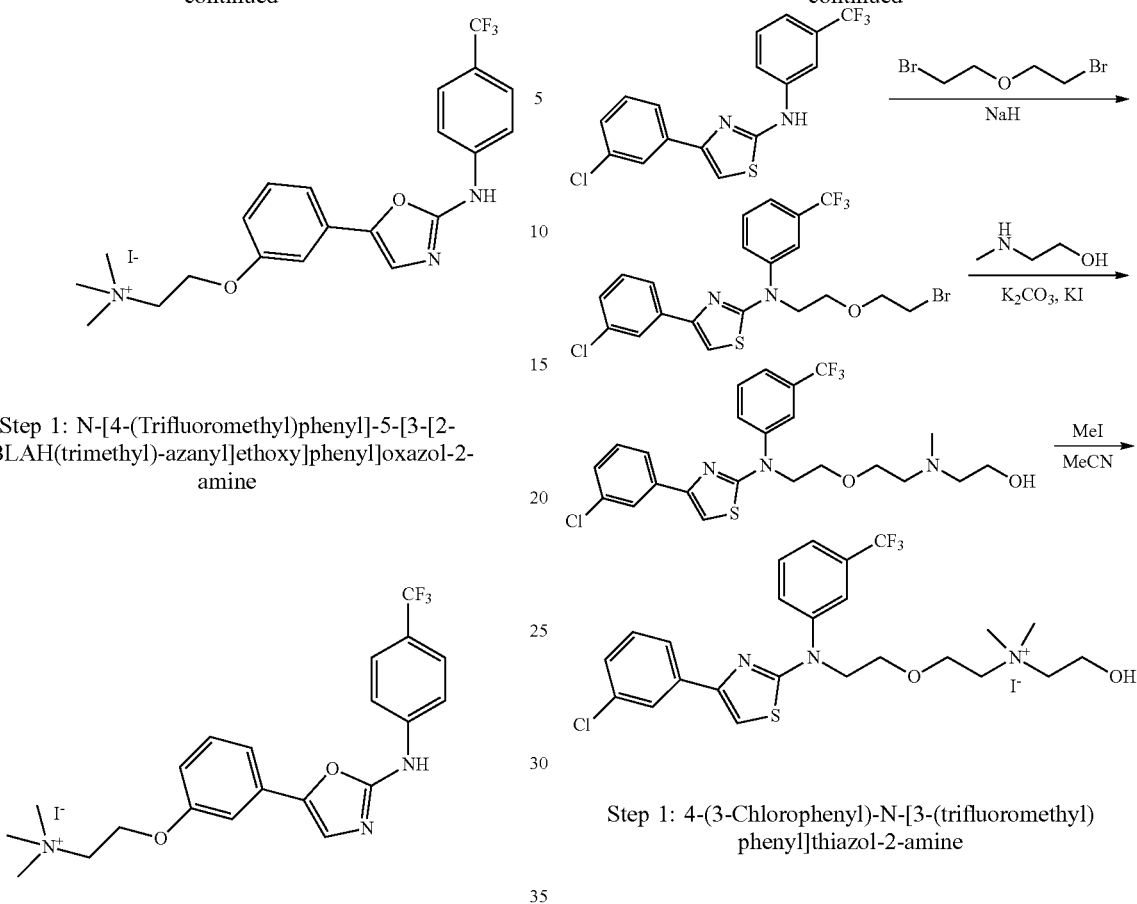

Step 1: N-[4-(Trifluoromethyl)phenyl]-5-[3-[2-[BLAH(trimethyl)-azanyl]ethoxy]phenyl]oxazol-2-amine To a solution of 5-[3-[2-(dimethylamino)ethoxy]phenyl]-N-[4-(trifluoromethyl)phenyl]oxazol-2-amine (25 mg, 63.38 μmol, 1 eq) in MeCN (10 mL) was added MeI (45.70 mg, 322.00 μmol, 20.05 μL, 5.08 eq) at 25° C. The mixture was stirred at 25° C. for 2 h. The mixture was diluted with water (10 mL) and lyophilized to yield N-[4-(trifluoromethyl) phenyl]-5-[3-[2[BLAH(trimethyl)-azanyl]ethoxy]phenyl] oxazol-2-amine (26.41 mg, 47.54 μmol, 75.0% yield, 96.0% purity) as a white solid. $^1$H NMR (500 MHz, DMSO-d$_6$) δ ppm 10.83 (s, 1H), 7.83 (d, J=8.5 Hz, 2H), 7.69 (d, J=8.5 Hz, 2H), 7.57 (s, 1H), 7.45-7.39 (m, 1H), 7.26 (d, J=7.8 Hz, 1H), 7.23 (s, 1H), 6.95 (dd, J=2.0, 8.2 Hz, 1H), 4.52 (s, 2H), 3.85-3.77 (m, 2H), 3.20 (s, 9H); ES-LCMS m/z 406.5 [M–I]$^+$.

I-45

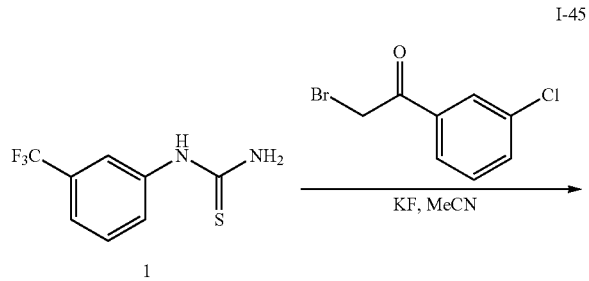

180

-continued

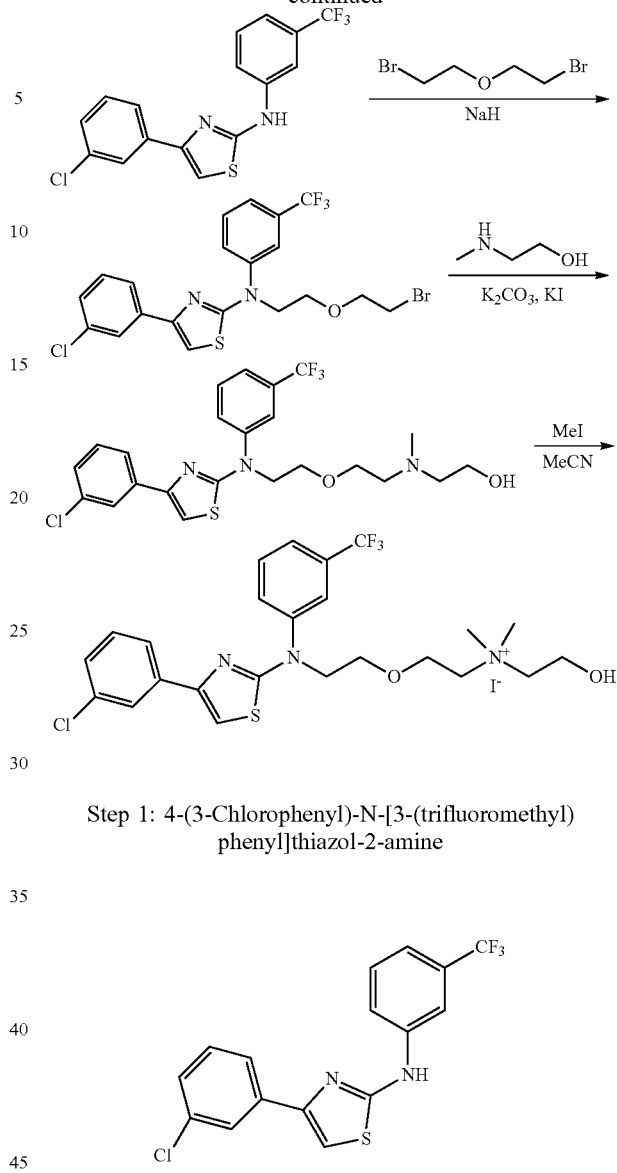

Step 1: 4-(3-Chlorophenyl)-N-[3-(trifluoromethyl) phenyl]thiazol-2-amine

A mixture of [3-(trifluoromethyl)phenyl]thiourea (705.05 mg, 3.17 mmol, 1 eq), 2-bromo-1-(3-chlorophenyl)ethanone (740.08 mg, 3.17 mmol, 1 eq), KF (184.15 mg, 3.17 mmol, 74.25 μL, 1 eq) in MeCN (15 mL) and H$_2$O (15 mL) was degassed and purged with N$_2$ for 3 times and the mixture was stirred at 25° C. for 2 h under N$_2$ atmosphere. The reaction mixture was concentrated to yield a residue which was treated with EtOAc (30 mL) and H$_2$O (30 mL). The combined organic layers was dried over Na$_2$SO$_4$, filtered and the filtrate was concentrated to yield a residue which was purified by flash silica gel chromatography (from PE/EtOAc=100/1 to 2/1, TLC: PE/EtOAc=1/1, R$_f$=0.5) to yield 4-(3-chlorophenyl)-N-[3-(trifluoromethyl)phenyl]thiazol-2-amine (0.851 g, 2.36 mmol, 74.5% yield, 98.5% purity) was obtained as a yellow solid. $^1$H NMR (400 MHz, DMSO-d$_6$) δ ppm 10.72 (s, 1H), 8.43 (s, 1H), 7.97 (t, J=1.8 Hz, 1H), 7.89 (td, J=1.2, 7.8 Hz, 1H), 7.79 (dd, J=1.6, 8.2 Hz, 1H), 7.61 (s, 2H), 7.51-7.44 (m, 1H), 7.41-7.36 (m, 1H), 7.31 (d, J=7.6 Hz, 1H); ES-LCMS m/z 354.9, 356.9 [M+H]$^+$.

Step 2: N-[2-(2-Bromoethoxy)ethyl]-4-(3-chlorophenyl)-N-[3-(trifluoromethyl)phenyl]thiazol-2-amine

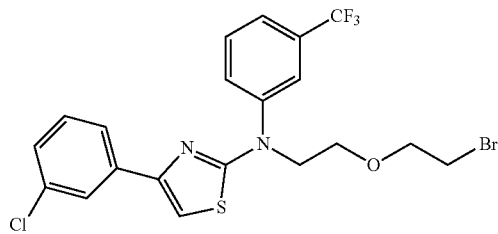 [SMILES: FC(F)(F)c1cccc(N(CCOCCBr)c2nc(-c3cccc(Cl)c3)cs2)c1]

To a solution of 4-(3-chlorophenyl)-N-[3-(trifluoromethyl)phenyl]thiazol-2-amine (100 mg, 277.64 µmol, 1 eq) in DMF (4 mL) was added NaH (33.31 mg, 832.92 µmol, 60% purity, 3 eq). The mixture was stirred at 0° C. for 30 min under $N_2$ atmosphere. 1-bromo-2-(2-bromoethoxy)ethane (193.16 mg, 832.92 µmol, 104.41 µL, 3 eq) was added and stirred at 0° C. for 30 min under $N_2$ atmosphere. The reaction mixture was diluted with water (50 mL), extracted with EtOAc (30 mL×3). The combined organic layers were dried over $Na_2SO_4$, filtered and the filtrate was concentrated to yield a residue which was purified by flash silica gel chromatography (from PE/EtOAc=100/1 to 2/1, TLC: PE/EtOAc=3/1, $R_f$=0.8) to yield N-[2-(2-bromoethoxy)ethyl]-4-(3-chlorophenyl)-N-[3-(trifluoromethyl)phenyl]thiazol-2-amine (115 mg, 222.37 µmol, 80.0% yield, 97.8% purity) as colorless oil. $^1$H NMR (400 MHz, DMSO-$d_6$) δ ppm 8.00 (s, 1H), 7.92-7.87 (m, 2H), 7.82 (d, J=7.6 Hz, 1H), 7.75-7.66 (m, 2H), 7.47-7.33 (m, 3H), 4.20 (t, J=5.3 Hz, 2H), 3.79 (t, J=5.4 Hz, 2H), 3.71 (t, J=5.5 Hz, 2H), 3.54-3.49 (m, 2H); ES-LCMS: m/z 503.9, 506.9 [M+H]$^+$.

Step 3: 2-[2-[2-[N-[4-(3-Chlorophenyl)thiazol-2-yl]-3-(trifluoromethyl)anilino]ethoxy]ethyl-methyl-amino]ethanol

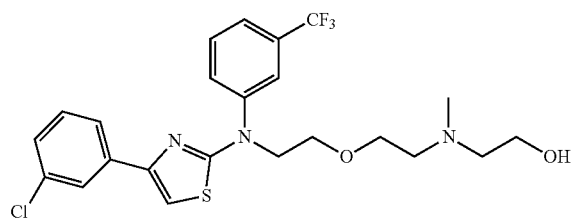 [SMILES: CN(CCO)CCOCCN(c1cccc(C(F)(F)F)c1)c1nc(-c2cccc(Cl)c2)cs1]

To a solution of N-[2-(2-bromoethoxy)ethyl]-4-(3-chlorophenyl)-N-[3-(trifluoromethyl)phenyl]thiazol-2-amine (114 mg, 220.44 µmol, 1 eq) in MeCN (3 mL) was added $Cs_2CO_3$ (215.47 mg, 661.31 µmol, 3 eq), 2-(methylamino)ethanol (82.78 mg, 1.10 mmol, 88.54 µL, 5 eq) and NaI (6.61 mg, 44.09 µmol, 0.2 eq). The mixture was stirred at 75° C. for 12 h. TLC (DCM/MeOH=10/1, $R_f$=0.60) indicated starting material was consumed completely and one new spot formed. The reaction mixture was quenched by addition of water (20 mL), extracted with EtOAc (20 mL×3). The combined organic layers were washed with brine (20 mL), dried over $Na_2SO_4$, filtered and concentrated under reduced pressure to yield a residue which was purified by preparative HPLC (column: Welch Xtimate C18 150*25 mm*5 µm; mobile phase: [water (10 mM $NH_4HCO_3$)-ACN]; B %: 57%-87%, 10 min), followed by lyophilization to yield 2-[2-[2-[N-[4-(3-chlorophenyl)thiazol-2-yl]-3-(trifluoromethyl)anilino]ethoxy]ethyl-methyl-amino]ethanol (80 mg, 160.01 µmol, 72.5% yield, 100% purity) a Colorless oil. $^1$H NMR (400 MHz, DMSO-$d_6$) δ ppm 7.97 (s, 1H), 7.90-7.84 (m, 2H), 7.80 (d, J=7.8 Hz, 1H), 7.72-7.62 (m, 2H), 7.46-7.38 (m, 2H), 7.37-7.31 (m, 1H), 4.24 (t, J=5.5 Hz, 1H), 4.16 (t, J=5.3 Hz, 2H), 3.71 (t, J=5.3 Hz, 2H), 3.42 (t, J=6.1 Hz, 4H), 2.40 (t, J=6.1 Hz, 2H), 2.33 (t, J=6.5 Hz, 2H), 2.09 (s, 3H); ES-LCMS m/z 500.1, 503.1 [M+H]$^+$

Step 4: 2-[2-[N-[4-(3-chlorophenyl)thiazol-2-yl]-3-(trifluoromethyl)anilino]ethoxy]ethyl-(2-hydroxyethyl)-dimethyl-ammonium

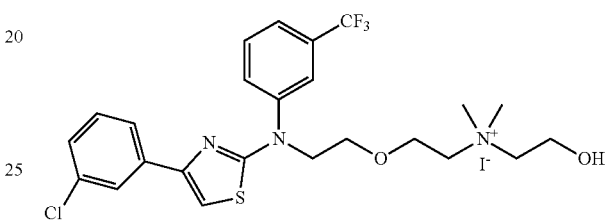

To a solution of 2-[2-[2-[N-[4-(3-chlorophenyl)thiazol-2-yl]-3-(trifluoromethyl)anilino]ethoxy]ethyl-methyl-amino]ethanol (80 mg, 160.01 µmol, 1 eq) in MeCN (5 mL) was added MeI (100 mg, 704.52 µmol, 43.86 L, 4.40 eq). The mixture was stirred at 25° C. for 2 h. TLC (DCM/MeOH=10/1, $R_f$=0.32) indicated starting material was consumed completely and one new spot formed. The reaction mixture was concentrated to yield a residue which was treated with ACN (20 mL), $H_2O$ (30 mL) and lyophilizated to yield 2-[2-[N-[4-(3-chlorophenyl)thiazol-2-yl]-3-(trifluoromethyl)anilino]ethoxy]ethyl-(2-hydroxyethyl)-dimethyl-ammonium (43.19 mg, 67.28 µmol, 42.0% yield, 100% purity, I*) as a brown solid. $^1$H NMR (500 MHz, $CD_3OD$) δ ppm 7.91 (d, J=1.5 Hz, 2H), 7.84 (d, J=8.1 Hz, 1H), 7.80 (d, J=7.8 Hz, 1H), 7.74 (t, J=7.9 Hz, 1H), 7.71-7.66 (m, 1H), 7.43-7.37 (m, 1H), 7.34-7.30 (m, 1H), 7.12 (s, 1H), 4.40 (t, J=5.1 Hz, 2H), 3.97 (s, 2H), 3.94-3.87 (m, 4H), 3.66-3.62 (m, 2H), 3.48-3.42 (m, 2H), 3.11 (s, 6H); ES-LCMS m/z 514.0, 516.0 [M–I]$^+$.

I-39

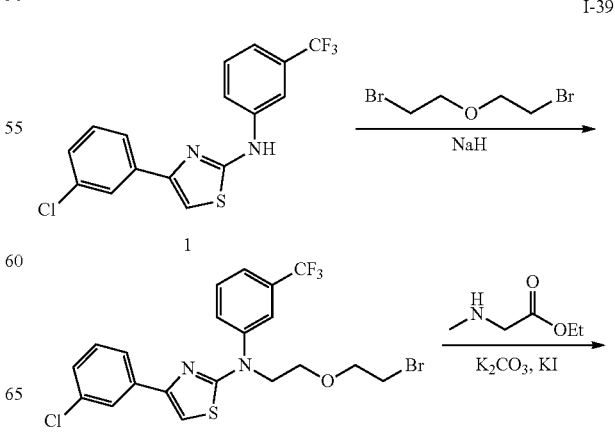

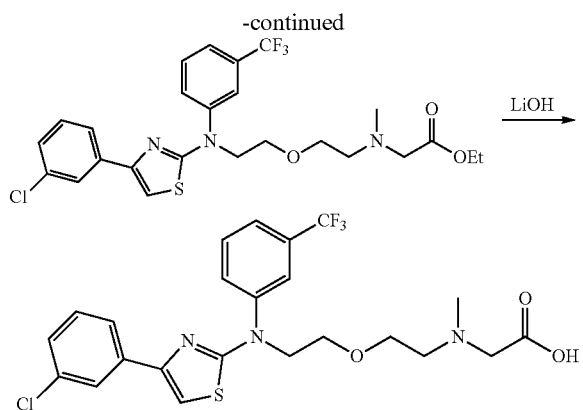

Step 1: N-[2-(2-Bromoethoxy)ethyl]-4-(3-chlorophenyl)-N-[3-(trifluoromethyl)phenyl]thiazol-2-amine

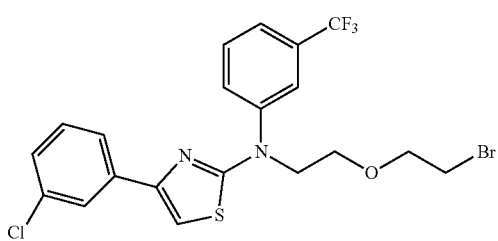 [SMILES: FC(F)(F)c1cccc(N(CCOCCBr)c2nc(-c3cccc(Cl)c3)cs2)c1]

To a solution of 4-(3-chlorophenyl)-N-[3-(trifluoromethyl)phenyl]thiazol-2-amine (507.61 mg, 1.41 mmol, 1 eq) in DMF (10 mL) was added NaH (169.10 mg, 4.23 mmol, 60%, 3 eq) at 25° C. After addition, the mixture was stirred at this temperature for 0.5 h and 1-bromo-2-(2-bromoethoxy)ethane (980.53 mg, 4.23 mmol, 530.02 μL, 3 eq) was added dropwise at 25° C. The resulting mixture was stirred at 25° C. for 12 h. TLC (PE/EtOAc=5/1, $R_f$=0.61) indicated starting material was consumed completely and one new spot formed. The reaction mixture was quenched by addition of water (100 mL), extracted with EtOAc (100 mL×3). The combined organic layers were washed with brine (50 mL), dried over $Na_2SO_4$, filtered and concentrated under reduced pressure to give a residue which was purified by flash silica gel chromatography (from PE/EtOAc=1/0 to 5/1, TLC: PE/EtOAc=5/1, $R_f$=0.61) to yield N-[2-(2-bromoethoxy)ethyl]-4-(3-chlorophenyl)-N-[3-(trifluoromethyl)phenyl]thiazol-2-amine (482 mg, 941.55 μmol, 66.81% yield, 98.8% purity) as a yellow oil. $^1$H NMR (500 MHz, $CD_3OD$) δ ppm 7.97 (s, 1H), 7.91-7.84 (m, 2H), 7.79 (d, J=7.8 Hz, 1H), 7.71-7.62 (m, 2H), 7.40-7.35 (m, 1H), 7.32-7.27 (m, 1H), 7.07 (s, 1H), 4.28 (t, J=5.2 Hz, 2H), 3.93 (t, J=5.2 Hz, 2H), 3.80 (t, J=5.8 Hz, 2H), 3.47 (t, J=5.8 Hz, 2H); ES-LCMS m/z 504.9, 506.9 [M+H]$^+$.

Step 2: Ethyl 2-[2-[2-[N-[4-(3-chlorophenyl)thiazol-2-yl]-3-(trifluoromethyl)anilino]ethoxy]ethyl-methyl-amino]acetate

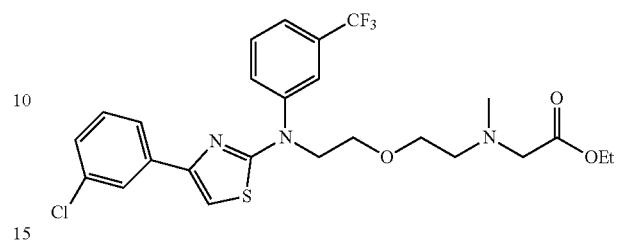

A mixture of N-[2-(2-bromoethoxy)ethyl]-4-(3-chlorophenyl)-N-[3-(trifluoromethyl)phenyl]thiazol-2-amine (250 mg, 488.36 μmol, 1 eq), ethyl 2-(methylamino)acetate (228.84 mg, 1.95 mmol, 4 eq), $Cs_2CO_3$ (477.35 mg, 1.47 mmol, 3 eq), NaI (2.20 mg, 14.65 μmol, 0.03 eq) in MeCN (4 mL) was degassed and purged with $N_2$ for 3 times and the mixture was stirred at 80° C. for 12 h under $N_2$ atmosphere. TLC (PE/EtOAc=5/1, $R_f$=0.45) indicated starting material was consumed completely and one new spot formed. The reaction mixture was quenched by addition of water (50 mL), extracted with EtOAc (50 mL×3). The combined organic layers were washed with brine (40 mL), dried over $Na_2SO_4$, filtered and concentrated under reduced pressure to give a residue which was purified by flash silica gel chromatography (from PE/EtOAc=1/0 to 5/1, TLC:PE/EtOAc=5/1, $R_f$=0.45) to yield Ethyl 2-[2-[2-[N-[4-(3-chlorophenyl)thiazol-2-yl]-3-(trifluoromethyl)anilino]ethoxy]ethyl-methyl-amino]acetate (220 mg, 401.43 μmol, 82.2% yield, 98.9% purity) was obtained as colorless oil. $^1$H NMR (400 MHz, DMSO-$d_6$) δ ppm 7.97 (s, 1H), 7.90-7.84 (m, 2H), 7.81 (dd, J=1.2, 7.8 Hz, 1H), 7.71-7.62 (m, 2H), 7.45-7.37 (m, 2H), 7.36-7.31 (m, 1H), 4.16 (t, J=5.1 Hz, 2H), 3.99 (q, J=7.0 Hz, 2H), 3.70 (t, J=5.1 Hz, 2H), 3.43 (t, J=5.7 Hz, 2H), 3.18 (s, 2H), 2.56 (t, J=5.7 Hz, 2H), 2.20 (s, 3H), 1.11 (t, J=7.2 Hz, 3H); ES-LCMS m/z 542.1, 544.1 [M+H]$^+$.

Step 3: 2-[2-[2-[N-[4-(3-Chlorophenyl)thiazol-2-yl]-3-(trifluoromethyl)anilino]ethoxy]ethyl-methyl-amino]acetic acid

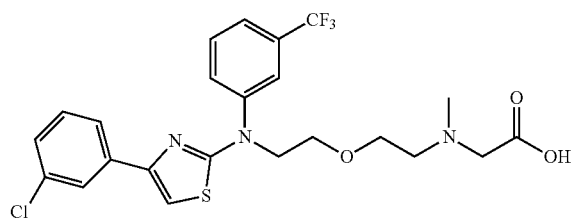 [SMILES: CN(CCOCCN(c1cccc(C(F)(F)F)c1)c1nc(-c2cccc(Cl)c2)cs1)CC(=O)O]

A mixture of ethyl 2-[2-[2-[N-[4-(3-chlorophenyl)thiazol-2-yl]-3-(trifluoromethyl)anilino]ethoxy]ethyl-methyl-amino]acetate (140 mg, 255.46 μmol, 1 eq), LiOH (18.35 mg, 766.37 μmol, 3 eq) in MeOH (2 mL) and $H_2O$ (2 mL) was degassed and purged with $N_2$ for 3 times and the mixture was stirred at 25° C. for 2 h under $N_2$ atmosphere. The reaction mixture was quenched by addition of water (20 mL), extracted with EtOAc (20 mL×3). The combined organic layers were washed with brine (20 mL), dried over Na$_2$SO$_4$, filtered and concentrated under reduced pressure to give a residue which was purified by preparative HPLC (column: Welch Xtimate C18 150*25 mm*5 μm; mobile phase: [water (10 mM NH$_4$HCO$_3$)-ACN]; B %: 35%-65%, 10 min), followed by lyophilization to yield 2-[2-[2-[N-[4-(3-chlorophenyl)thiazol-2-yl]-3-(trifluoromethyl)anilino]ethoxy]ethyl-methyl-amino]acetic acid (80 mg, 155.65 μmol, 60.9% yield, 100% purity) as a white solid. $^1$H NMR (400 MHz, DMSO-d$_6$) δ ppm 7.97 (s, 1H), 7.90-7.85 (m, 2H), 7.81 (d, J=7.8 Hz, 1H), 7.73-7.62 (m, 2H), 7.44-7.38 (m, 2H), 7.37-7.29 (m, 1H), 4.17 (br t, J=5.3 Hz, 2H), 3.72 (br t, J=5.3 Hz, 2H), 3.51 (t, J=5.7 Hz, 2H), 3.15 (s, 2H), 2.73 (t, J=5.7 Hz, 2H), 2.32 (s, 3H); ES-LCMS m/z 514.0, 516.0 [M+H]$^+$.

I-60

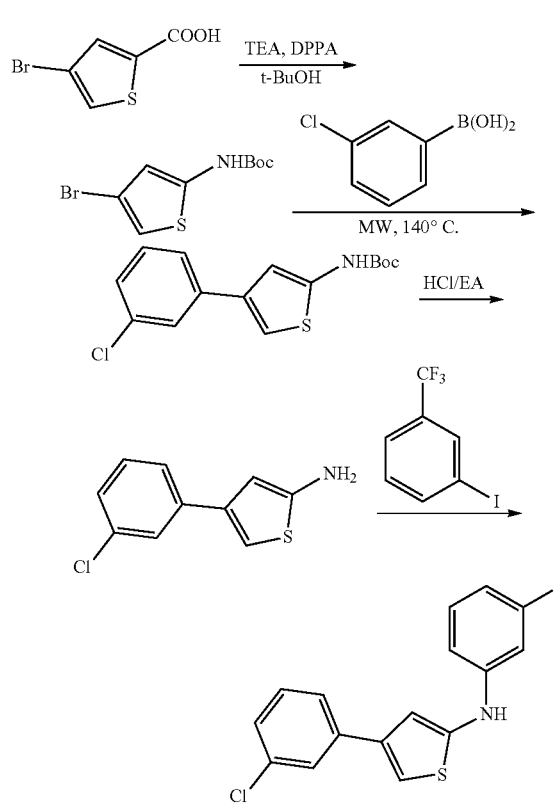

Step 1: Tert-Butyl N-(4-bromo-2-thienyl)carbamate

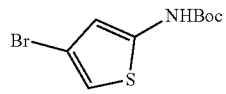

To a solution of 4-bromothiophene-2-carboxylic acid (820 mg, 3.96 mmol, 1 eq) in t-BuOH (10 mL) was added TEA (801.52 mg, 7.92 mmol, 1.10 mL, 2 eq) and DPPA (1.42 g, 5.15 mmol, 1.12 mL, 1.3 eq). The mixture was stirred at 100° C. for 5 h. The reaction mixture was concentrated under reduced pressure to yield a residue which was purified by flash silica gel chromatography (from PE/EtOAc=200/1 to 5/1, TLC: PE/EtOAc=5/1, R$_f$=0.55) to yield tert-butyl N-(4-bromo-2-thienyl)carbamate (720 mg, 2.48 mmol, 62.7% yield, 96.0% purity) as a yellow solid. $^1$H NMR (400 MHz, CD$_3$OD) δ ppm 6.77 (d, J=1.6 Hz, 1H), 6.42 (d, J=1.6 Hz, 1H), 1.51 (s, 9H); ES-LCMS m/z 279.9, 281.9 [M+H]$^+$.

Step 2: Tert-Butyl N-[4-(3-chlorophenyl)-2-thienyl]carbamate

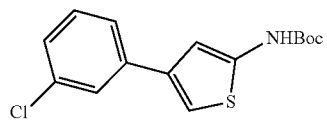 [SMILES: CC(C)(C)OC(=O)Nc1cc(-c2cccc(Cl)c2)cs1]

To a solution of tert-butyl N-(4-bromo-2-thienyl)carbamate (620 mg, 2.14 mmol, 1 eq) and (3-chlorophenyl)boronic acid (334.60 mg, 2.14 mmol, 1 eq) in 1,4-dioxane (3 mL) and H$_2$O (1 mL) was added Pd(dppf)Cl$_2$ (156.57 mg, 213.97 μmol, 0.1 eq) and Cs$_2$CO$_3$ (2.09 g, 6.42 mmol, 3 eq) under N$_2$ atmosphere. The mixture was stirred at 80° C. for 1 h under microwave (1 bar). To the mixture was added water (30 mL), extracted with ethyl acetate (30 mL×3). The combined organic phases were washed with brine (20 mL), dried with anhydrous Na$_2$SO$_4$, filtered and concentrated in vacuum to yield a residue which was purified by flash silica gel chromatography (from PE/EtOAc=200/1 to 5/1, TLC: PE/EtOAc=5/1, R$_f$=0.41) to yield tert-butyl N-[4-(3-chlorophenyl)-2-thienyl]carbamate (500 mg, 1.45 mmol, 67.8% yield, 90.0% purity) as a white solid. $^1$H NMR (500 MHz, CD$_3$OD) δ ppm 7.59 (s, 1H), 7.51 (d, J=7.8 Hz, 1H), 7.34 (t, J=7.9 Hz, 1H), 7.24 (d, J=7.3 Hz, 1H), 7.11 (s, 1H), 6.85 (d, J=1.4 Hz, 1H), 1.53 (s, 9H); ES-LCMS m/z 310.0, 312.0 [M+H]$^+$.

Step 3: 4-(3-Chlorophenyl)thiophen-2-amine

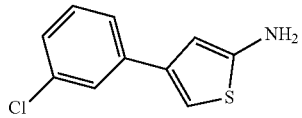 [SMILES: Nc1cc(-c2cccc(Cl)c2)cs1]

A solution of tert-butyl N-[4-(3-chlorophenyl)-2-thienyl]carbamate (500 mg, 1.45 mmol, 1 eq) in HCl/MeOH (10 mL, 4M) was stirred at 25° C. for 1 h. The reaction mixture was concentrated under reduced pressure to yield a residue which was neutralized by addition of sat. aq. NaHCO$_3$ (5 mL), and to the mixture was added water (30 mL), extracted with ethyl acetate (30 mL×3). The combined organic phase was washed with brine (20 mL), dried over anhydrous Na$_2$SO$_4$, filtered, concentrated in vacuum to yield 4-(3-chlorophenyl)thiophen-2-amine (250 mg, 1.13 mmol, 77.9% yield, 95.0% purity) as a yellow solid, which was used in the next step without further purification. $^1$H NMR (500 MHz, CD$_3$OD) δ ppm 7.54 (t, J=1.8 Hz, 1H), 7.47 (d, J=7.8 Hz, 1H), 7.31 (t, J=7.9 Hz, 1H), 7.21 (dd, J=1.1, 7.9 Hz, 1H), 6.75 (d, J=1.7 Hz, 1H), 6.46 (d, J=1.7 Hz, 1H); ES-LCMS m/z 209.9, 211.9 [M+H]$^+$.

187

Step 4: 4-(3-Chlorophenyl)-N-[3-(trifluoromethyl)phenyl]thiophen-2-amine

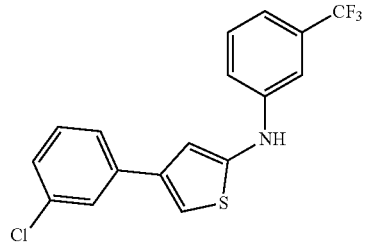 [SMILES: FC(F)(F)c1cccc(Nc2cc(-c3cccc(Cl)c3)cs2)c1]

To a solution of 4-(3-chlorophenyl)thiophen-2-amine (250 mg, 1.13 mmol, 1 eq) and 1-iodo-3-(trifluoromethyl)benzene (616.15 mg, 2.27 mmol, 326.00 μL, 2 eq) in 1,4-dioxane (10 mL) was added $Cs_2CO_3$ (1.11 g, 3.40 mmol, 3 eq), XantPhos (131.07 mg, 226.52 μmol, 0.2 eq) and $Pd_2(dba)_3$ (103.71 mg, 113.26 μmol, 0.1 eq). The mixture was stirred at 120° C. for 12 h under $N_2$. To the mixture was added water (50 mL) and extracted with ethyl acetate (50 mL×3). The combined organic phase was washed with brine (20 mL), dried over anhydrous $Na_2SO_4$, filtered, concentrated in vacuum to yield a residue which was purified by flash silica gel chromatography (from PE/EtOAc=200/1 to 5/1, TLC: PE/EtOAc=5/1, $R_f$=0.30) to yield a crude product. This crude product was purified by preparative HPLC (column: Phenomenex Synergi C18 150*30 mm*4 μm; mobile phase: [water (0.05% HCl)-ACN]; B %: 75%-95%, 10 min), followed by concentration in vacuum to yield a residue. To the residue was added sat. aq. $NaHCO_3$ (2 mL), water (30 mL) and extracted with ethyl acetate (50 mL×3). The combined organic phase was washed with brine (20 mL), dried over anhydrous $Na_2SO_4$, filtered and concentrated in vacuum to yield a residue, followed by lyophilization to yield 4-(3-chlorophenyl)-N-[3-(trifluoromethyl)phenyl]thiophen-2-amine (9.53 mg, 25.11 μmol, 2.2% yield, 93.2% purity) as a yellow solid. $^1$H NMR (500 MHz, $CD_3OD$) δ ppm 7.64 (t, J=1.7 Hz, 1H), 7.56 (d, J=7.8 Hz, 1H), 7.37 (t, J=7.8 Hz, 2H), 7.29-7.25 (m, 2H), 7.22-7.18 (m, 2H), 7.08-7.02 (m, 2H); ES-LCMS m/z 353.9, 355.9 [M+H]$^+$.

I-10

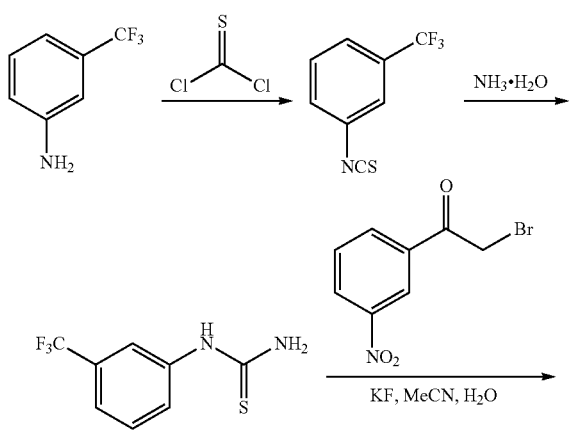

188

-continued

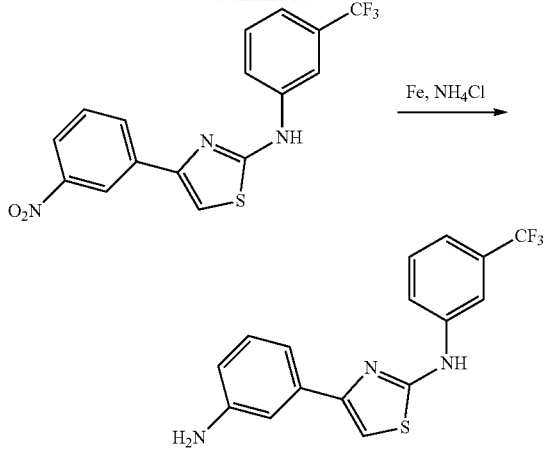

Step 1: 1-Isothiocyanato-3-(trifluoromethyl)benzene

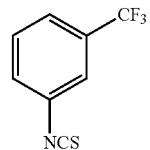

To a solution of 3-(trifluoromethyl)aniline (5 g, 31.03 mmol, 3.88 mL, 1 eq) in DCM (40 mL) and $H_2O$ (40 mL) was added $NaHCO_3$ (5.21 g, 62.06 mmol, 2 eq) and thiocarbonyl dichloride (5.35 g, 46.55 mmol, 3.57 mL, 1.5 eq) at 0° C. under $N_2$ atmosphere. The mixture was stirred at 0° C. for 1 h under $N_2$ atmosphere. TLC (PE/EtOAc=1/1, $R_f$=0.7) showed that new point was formed and start material was consumed completely. The reaction mixture was quenched with $H_2O$ (40 mL) and extracted with EtOAc (60 mL×3). The combined organic layer was washed with brine (60 mL), dried over $Na_2SO_4$, filtered and concentrated under reduced pressure to yield 1-isothiocyanato-3-(trifluoromethyl)benzene (6.35 g, 29.69 mmol, 95.7% yield, 95.0% purity) as a white solid, which was used in the next step without further purification. $^1$H NMR (400 MHz, DMSO-$d_6$) δ ppm 7.84-7.76 (m, 1H), 7.74-7.62 (m, 3H).

Step 2: [3-(Trifluoromethyl)phenyl]thiourea

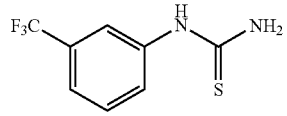 [SMILES: NC(=S)Nc1cccc(C(F)(F)F)c1]

To a solution of 1-isothiocyanato-3-(trifluoromethyl)benzene (6.35 g, 29.69 mmol, 4.74 mL, 1 eq) in ACN (30 mL) was added $NH_3 \cdot H_2O$ (30.87 g, 246.65 mmol, 33.93 mL, 28% purity, 8.31 eq). The mixture was stirred at 25° C. for 15 h. The reaction mixture was concentrated, diluted with $H_2O$ (30 mL) and extracted with EtOAc (30 mL×3). The combined organic layer was washed with brine (30 mL), dried over $Na_2SO_4$, filtered and concentrated under reduced pressure to yield [3-(trifluoromethyl)phenyl]thiourea (6.5 g, 28.04 mmol, 94.5% yield, 95.0% purity) as a white solid, which was used in the next step without further purification. ¹H NMR (400 MHz, DMSO-d₆) δ ppm 9.91 (s, 1H), 7.97 (s, 1H), 7.65 (d, J=8.0 Hz, 1H), 7.50 (t, J=8.0 Hz, 1H), 7.39 (d, J=8.0 Hz, 1H); ES-LCMS m/z 220.9 [M+H]⁺.

Step 3: 4-(3-Nitrophenyl)-N-[3-(trifluoromethyl) phenyl]thiazol-2-amine

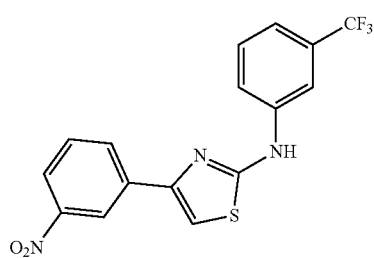 [SMILES: O=[N+]([O-])c1cccc(-c2csc(Nc3cccc(C(F)(F)F)c3)n2)c1]

To a solution of [3-(trifluoromethyl)phenyl]thiourea (500 mg, 2.16 mmol, 1.0 eq) and 2-bromo-1-(3-nitrophenyl) ethanone (526.40 mg, 2.16 mmol, 1.0 eq) in ACN (10 mL) and H₂O (10 mL) was added KF (125.32 mg, 2.16 mmol, 50.53 μL, 1 eq). The mixture was stirred at 25° C. for 15 h. The reaction mixture was quenched with H₂O (20 mL) and extracted with EtOAc (30 mL×3). The combined organic layer was washed with brine (30 mL), dried over Na₂SO₄, filtered and concentrated under reduced pressure to yield 4-(3-nitrophenyl)-N-[3-(trifluoromethyl)phenyl]thiazol-2-amine (520 mg, 1.21 mmol, 56.1% yield, 85.0% purity) as a yellow solid, which was used directly in the next step without further purification. ¹H NMR (400 MHz, DMSO-d₆) δ ppm 10.75 (s, 1H), 8.74 (s, 1H), 8.48 (s, 1H), 8.35 (d, J=8.0 Hz, 1H), 8.17 (dd, J=1.2, 8.0 Hz, 1H), 7.78-7.75 (m, 3H), 7.58 (t, J=8.0 Hz, 1H), 7.32 (d, J=8.4 Hz, 1H); ES-LCMS m/z 366.2 [M+H]⁺.

Step 4: 4-(3-Aminophenyl)-N-[3-(trifluoromethyl) phenyl]thiazol-2-amine

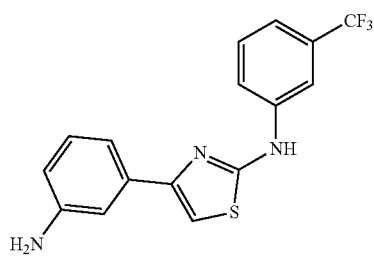

To a solution of 4-(3-nitrophenyl)-N-[3-(trifluoromethyl) phenyl]thiazol-2-amine (200 mg, 465.33 μmol, 1 eq) in THF (6 mL) and H₂O (6 mL) was added Fe (25.99 mg, 465.33 μmol, 1 eq) and NH₄Cl (24.89 mg, 465.33 μmol, 1.0 eq). The mixture was stirred at 25° C. for 25 min. TLC (PE/EtOAc=3/1, R_f=0.2) showed that new point was formed and start material was consumed completely. The mixture was filtrated and quenched with H₂O (20 mL) and extracted with EtOAc (30 mL×3). The combined organic layers were washed with brine (30 mL), dried over Na₂SO₄, filtered and concentrated under reduced pressure to yield a residue which was purified by preparative HPLC (column: Welch Xtimate C18 150*25 mm*5 um; mobile phase: [water (10 mM NH₄HCO₃)-ACN]; B %: 45%) to yield 4-(3-aminophenyl)-N-[3-(trifluoromethyl)phenyl]thiazol-2-amine (44.07 mg, 125.77 μmol, 27.0% yield, 95.7% purity) as a white solid. ¹H NMR (500 MHz, DMSO-d₆) δ ppm 10.58 (s, 1H), 8.20 (s, 1H), 7.96 (d, J=8.5 Hz, 1H), 7.56 (t, J=8.0 Hz, 1H), 7.28 (d, J=7.5 Hz, 1H), 7.18 (s, 1H), 7.13-7.04 (m, 3H), 6.55-6.20 (m, 1H), 5.09 (s, 2H); ES-LCMS m/z 335.9 [M+H]⁺.

I-35

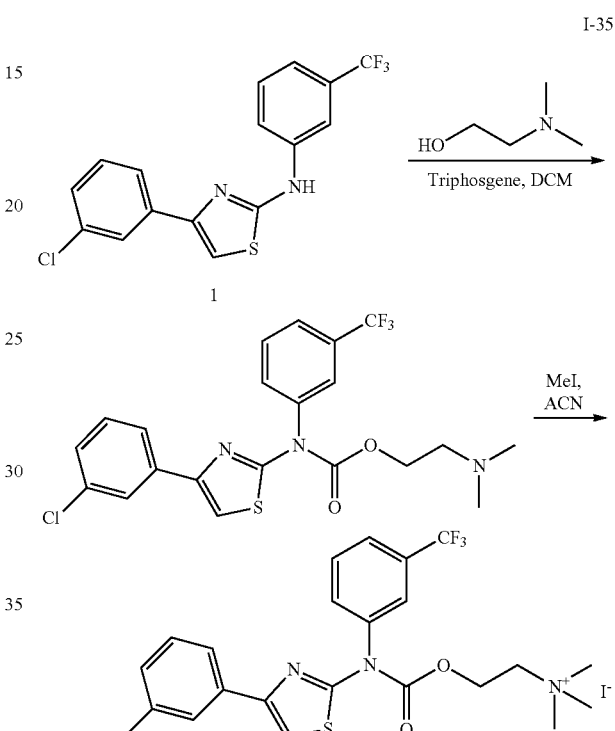

Step 1: 2-(Dimethylamino)ethyl N-[4-(3-chlorophenyl)thiazol-2-yl]-N-[3-(trifluoromethyl)phenyl]carbamate

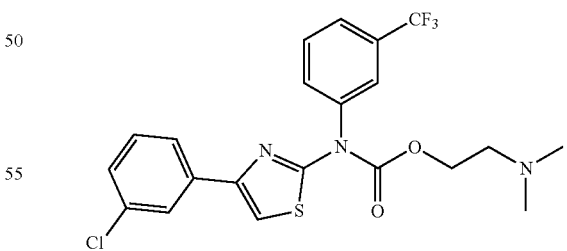

To a solution of 4-(3-chlorophenyl)-N-[3-(trifluoromethyl)phenyl]thiazol-2-amine (150 mg, 380.52 μmol, 1 eq) in THF (4 mL) was added bis(trichloromethyl) carbonate (369.00 mg, 1.24 mmol, 3.27 eq), DIEA (147.54 mg, 1.14 mmol, 198.84 μL, 3 eq) and stirred at 80° C. for 2 h. The reaction mixture was concentrated to yield (4-(3-chlorophenyl)thiazol-2-yl)(3-(trifluoromethyl)phenyl)carbamic chloride (crude). Then to a solution of 2-(dimethylamino)ethanol (169.59 mg, 1.90 mmol, 190.98 µL, 5 eq) in DCM (1 mL) was added DIEA (49.18 mg, 380.52 µmol, 66.28 µL, 1 eq), DMAP (4.65 mg, 38.05 µmol, 0.1 eq), (4-(3-chlorophenyl)thiazol-2-yl)(3-(trifluoromethyl)phenyl)carbamic chloride (crude) in DCM (3 mL) and stirred at 40° C. for 2 h. The reaction mixture was quenched by addition of water (20 mL), extracted with EtOAc (20 mL×3). The combined organic layers were washed with brine (20 mL), dried over Na$_2$SO$_4$, filtered and concentrated under reduced pressure to give a residue which was purified by preparative HPLC (column: Agela DuraShell C18 150*25 mm*5 µm; mobile phase: [water (0.04% NH$_3$H$_2$O+10 mM NH$_4$HCO$_3$)-ACN]; B %: 59%-89%, 10 min). The desired fraction was lyophilized to yield 2-(dimethylamino)ethyl N-[4-(3-chlorophenyl)thiazol-2-yl]-N-[3-(trifluoromethyl)phenyl]carbamate (100 mg, 211.53 µmol, 55.5% yield, 99.4% purity) as a brown solid. $^1$H NMR (400 MHz, DMSO-d$_6$) δ ppm 7.94 (s, 1H), 7.90 (s, 1H), 7.86-7.71 (m, 3H), 7.64 (s, 1H), 7.56 (d, J=7.8 Hz, 1H), 7.38-7.32 (m, 1H), 7.32-7.27 (m, 1H), 4.26 (t, J=5.3 Hz, 2H), 2.41 (t, J=5.3 Hz, 2H), 2.01 (s, 6H); ES-LCMS m/z 470.0, 472.0 [M+H]$^+$.

Step 2: 2-(((4-(3-Chlorophenyl)thiazol-2-yl)(3-(trifluoromethyl)phenyl)carbamoyl)oxy)-N,N,N-trimethylethanaminium iodide

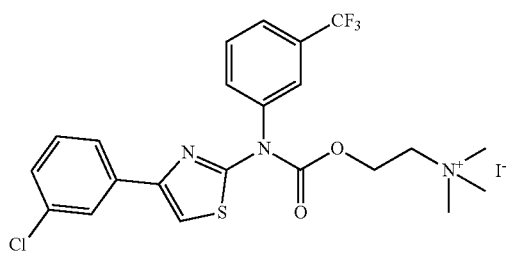 [SMILES: C[N+](C)(C)CCOC(=O)N(c1cccc(C(F)(F)F)c1)c1nc(-c2cccc(Cl)c2)cs1 ; [I-]]

To a solution of 2-(dimethylamino)ethyl N-[4-(3-chlorophenyl)thiazol-2-yl]-N-[3-(trifluoromethyl)phenyl]carbamate (80 mg, 170.25 µmol, 1 eq) in MeCN (10 mL) was added MeI (120.82 mg, 851.23 µmol, 52.99 µL, 5 eq). The mixture was stirred at 25° C. for 2 h. TLC (PE/EtOAc=0/1, R$_f$=0.03) indicated starting material was consumed completely and one new spot formed. The reaction mixture was concentrated to yield a residue which was treated with MeCN (15 mL) and H$_2$O (30 mL) then lyophilizated to yield 2-(((4-(3-chlorophenyl)thiazol-2-yl)(3-(trifluoromethyl)phenyl)carbamoyl)oxy)-N,N,N-trimethylethanaminium iodide (48.42 mg, 79.14 µmol, 46.4% yield, 100% purity) as a white solid. $^1$H NMR (400 MHz, DMSO-d$_6$) δ ppm 8.00 (s, 1H), 7.95 (s, 1H), 7.90-7.83 (m, 2H), 7.81-7.76 (m, 1H), 7.64 (s, 1H), 7.56 (d, J=7.8 Hz, 1H), 7.40-7.27 (m, 2H), 4.61 (s, 2H), 3.62 (s, 2H), 2.90 (s, 9H); ES-LCMS m/z 484.0, 486.0 [M−I]$^+$.

I-31

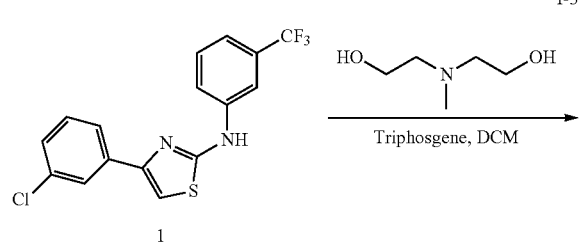

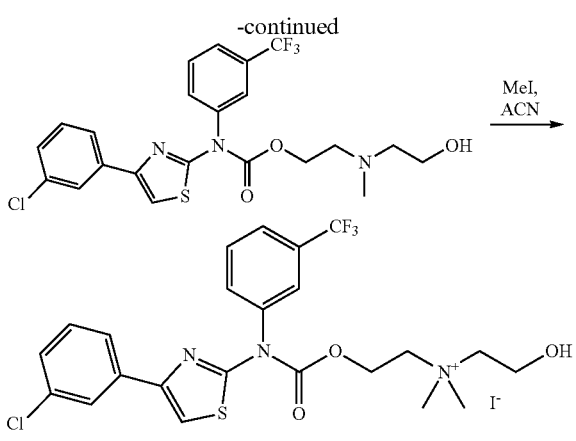

Step 1: 2-[2-Hydroxyethylmethyl)amino]ethyl N-[4-(3-chlorophenyl)thiazol-2-yl]-N-[3-(trifluoromethyl)phenyl]carbamate

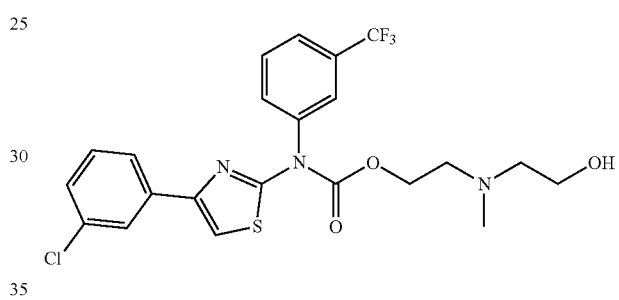

To a solution of 4-(3-chlorophenyl)-N-[3-(trifluoromethyl)phenyl]thiazol-2-amine (150 mg, 380.52 µmol, 1 eq) in THF (4 mL) was added bis(trichloromethyl) carbonate (63.00 mg, 212.30 µmol, 0.557 eq), DIEA (147.54 mg, 1.14 mmol, 198.84 µL, 3 eq) and stirred at 80° C. for 2 h. The reaction mixture was concentrated to yield (4-(3-chlorophenyl)thiazol-2-yl)(3-(trifluoromethyl)phenyl)carbamic chloride (crude). Then to a solution of 2-[2-hydroxyethyl(methyl)amino]ethanol (226.72 mg, 1.90 mmol, 218.00 µL, 5 eq) in DCM (1 mL) was added DIEA (147.54 mg, 1.14 mmol, 198.84 µL, 3 eq), DMAP (4.65 mg, 38.05 µmol, 0.1 eq), (4-(3-chlorophenyl)thiazol-2-yl)(3-(trifluoromethyl)phenyl)carbamic chloride (crude) in DCM (3 mL) and stirred at 40° C. for 2 h. The reaction mixture was quenched by addition of water (20 mL), extracted with EtOAc (20 mL×3). The combined organic layers were washed with brine (20 mL), dried over Na$_2$SO$_4$, filtered and concentrated under reduced pressure to give a residue which was purified by preparative HPLC (column: Agela DuraShell C18 150*25 mm*5 µm; mobile phase: [water (0.04% NH$_3$H$_2$O+10 mM NH$_4$HCO$_3$)-ACN]; B %: 52%-82%, 10 min), followed by lyophilization to yield 2-[2-hydroxyethyl(methyl)amino]ethyl N-[4-(3-chlorophenyl)thiazol-2-yl]-N-[3-(trifluoromethyl)phenyl]carbamate (120 mg, 236.91 µmol, 62.2% yield, 98.7% purity) as brown oil. $^1$H NMR (400 MHz, DMSO-d$_6$) δ ppm 7.94 (s, 1H), 7.89 (s, 1H), 7.85-7.78 (m, 2H), 7.77-7.71 (m, 1H), 7.63 (t, J=1.6 Hz, 1H), 7.58-7.53 (m, 1H), 7.38-7.32 (m, 1H), 7.31-7.27 (m, 1H), 4.25 (t, J=5.5 Hz, 3H), 3.37-3.32 (m, 2H), 2.54 (t, J=5.3 Hz, 2H), 2.32 (t, J=6.3 Hz, 2H), 2.05 (s, 3H); ES-LCMS m/z 500.0, 502.0 [M+H]$^+$

193

Step 2: 2-[[4-(3-chlorophenyl)thiazol-2-yl]-[3-(trifluoromethyl)phenyl]carbamoyl]oxyethyl-(2-hydroxyethyl)-dimethyl-ammonium iodide

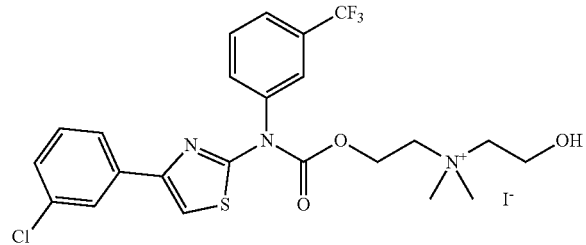 [SMILES: C[N+](C)(CCO)CCOC(=O)N(c1cccc(C(F)(F)F)c1)c1nc(-c2cccc(Cl)c2)cs1 ; [I-]]

To a solution of 2-[2-hydroxyethyl(methyl)amino]ethyl N-[4-(3-chlorophenyl)thiazol-2-yl]-N-[3-(trifluoromethyl)phenyl]carbamate (120 mg, 236.91 μmol, 1 eq) in MeCN (10 mL) was added MeI (386.90 mg, 2.73 mmol, 169.69 μL, 11.51 eq). The mixture was stirred at 25° C. for 2 h. TLC (PE/EtOAc=0/1, $R_f$=0.04) indicated starting material was consumed completely and one new spot formed. The reaction mixture was concentrated to yield a residue which was treated with MeCN (20 mL) and H2O (30 mL) then lyophilizated to yield 2-[[4-(3-chlorophenyl)thiazol-2-yl]-[3-(trifluoromethyl)phenyl]carbamoyl]oxyethyl-(2-hydroxyethyl)-dimethyl-ammonium iodide (101.77 mg, 196.24 μmol, 82.8% yield, 99.3% purity) was obtained as a white solid. $^1$H NMR (400 MHz, CD$_3$OD) δ ppm 7.88-7.82 (m, 2H), 7.81-7.73 (m, 2H), 7.60 (s, 2H), 7.58-7.53 (m, 1H), 7.30-7.19 (m, 2H), 4.74 (br s, 2H), 3.85 (br s, 2H), 3.82-3.77 (m, 2H), 3.38 (td, J=2.6, 4.6 Hz, 2H), 3.01 (s, 6H); ES-LCMS m/z 514.0, 516.0 [M−I]$^+$.

194

Step 1: N-(2-(2-((4-(3-chlorophenyl)thiazol-2-yl)(3-(trifluoromethyl)phenyl)amino)ethoxy)ethyl)-2-ethoxy-N,N-dimethyl-2-oxoethanaminium iodide

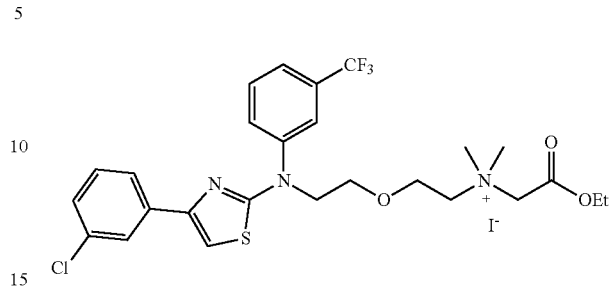

To a solution of ethyl 2-[2-[2-[N-[4-(3-chlorophenyl)thiazol-2-yl]-3-(trifluoromethyl)anilino]ethoxy]ethyl-methyl-amino]acetate (50 mg, 91.23 μmol, 1 eq) in MeCN (10 mL) was added MeI (129.50 mg, 912.34 μmol, 56.80 μL, 10 eq). The mixture was stirred at 25° C. for 2 h. The reaction mixture was concentrated to yield a residue which was added ACN (20 mL) and H$_2$O (30 mL), followed by lyophilization to yield N-(2-(2-((4-(3-chlorophenyl)thiazol-2-yl)(3-(trifluoromethyl)phenyl)amino)ethoxy)ethyl)-2-ethoxy-N,N-dimethyl-2-oxoethanaminium iodide (55 mg, 77.58 μmol, 85.0% yield, 96.4% purity) as brown oil. $^1$H NMR (400 MHz, CD$_3$OD) δ ppm 7.90-7.85 (m, 2H), 7.81-7.76 (m, 2H), 7.72 (t, J=7.8 Hz, 1H), 7.68-7.65 (m, 1H), 7.36 (d, J=7.8 Hz, 1H), 7.31-7.27 (m, 1H), 7.08 (s, 1H), 4.33 (t, J=5.3 Hz, 2H), 4.29 (s, 2H), 4.18 (d, J=7.0 Hz, 2H), 3.94 (d, J=5.5 Hz, 2H), 3.87 (t, J=5.3 Hz, 2H), 3.83-3.78 (m, 2H), 3.24 (s, 6H), 1.24-1.20 (m, 3H); ES-LCMS m/z 556.2, 558.2 [M]$^+$.

Step 2: Carboxymethyl-[2-[2-[N-[4-(3-chlorophenyl)thiazol-2-yl]-3-(trifluoromethyl)anilino]ethoxy]ethyl]-dimethyl-ammonium chloride

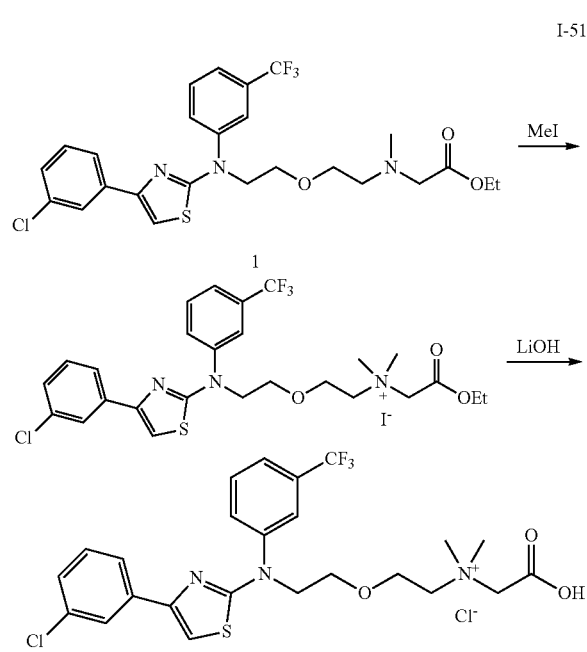

A mixture of N-(2-(2-((4-(3-chlorophenyl)thiazol-2-yl)(3-(trifluoromethyl)phenyl)amino)ethoxy)ethyl)-2-ethoxy-N,N-dimethyl-2-oxoethanaminium iodide (50 mg, 71.05 μmol, 1 eq), LiOH (5.11 mg, 213.16 μmol, 3 eq) in MeOH (2 mL) and H$_2$O (2 mL) was degassed and purged with N$_2$ for 3 times and the mixture was stirred at 25° C. for 2 h under N$_2$ atmosphere. The reaction mixture was quenched by addition of water (20 mL), extracted with EtOAc (20 mL×3). The combined organic layers were washed with brine (20 mL), dried over Na$_2$SO$_4$, filtered and concentrated under reduced pressure to yield a residue which was purified by preparative HPLC (Column: Welch Xtimate C18 150*25 mm*5 μm; mobile phase: [water (10 mM NH$_4$HCO$_3$)-ACN]; B %: 35%-65%, 10 min), followed by lyophilization to yield carboxymethyl-[2-[2-[N-[4-(3-chlorophenyl)thiazol-2-yl]-3-(trifluoromethyl)anilino]ethoxy]ethyl]-dimethyl-ammonium chloride (34.92 mg, 61.76 μmol, 86.9% yield, 100% purity) as a brown solid. $^1$H NMR (400 MHz, DMSO-d$_6$) δ ppm 7.97 (s, 1H), 7.89 (s, 1H), 7.86 (d, J=7.8 Hz, 1H), 7.82 (d, J=7.8 Hz, 1H), 7.74-7.70 (m, 1H), 7.70-7.66 (m, 1H), 7.45-7.40 (m, 2H), 7.38-7.33 (m, 1H), 4.26 (s, 2H), 4.23 (t, J=5.1 Hz, 2H), 3.82 (s, 2H), 3.78-3.75 (m, 4H), 3.11 (s, 6H); ES-LCMS m/z 528.0, 530.0 [M−Cl]$^+$.

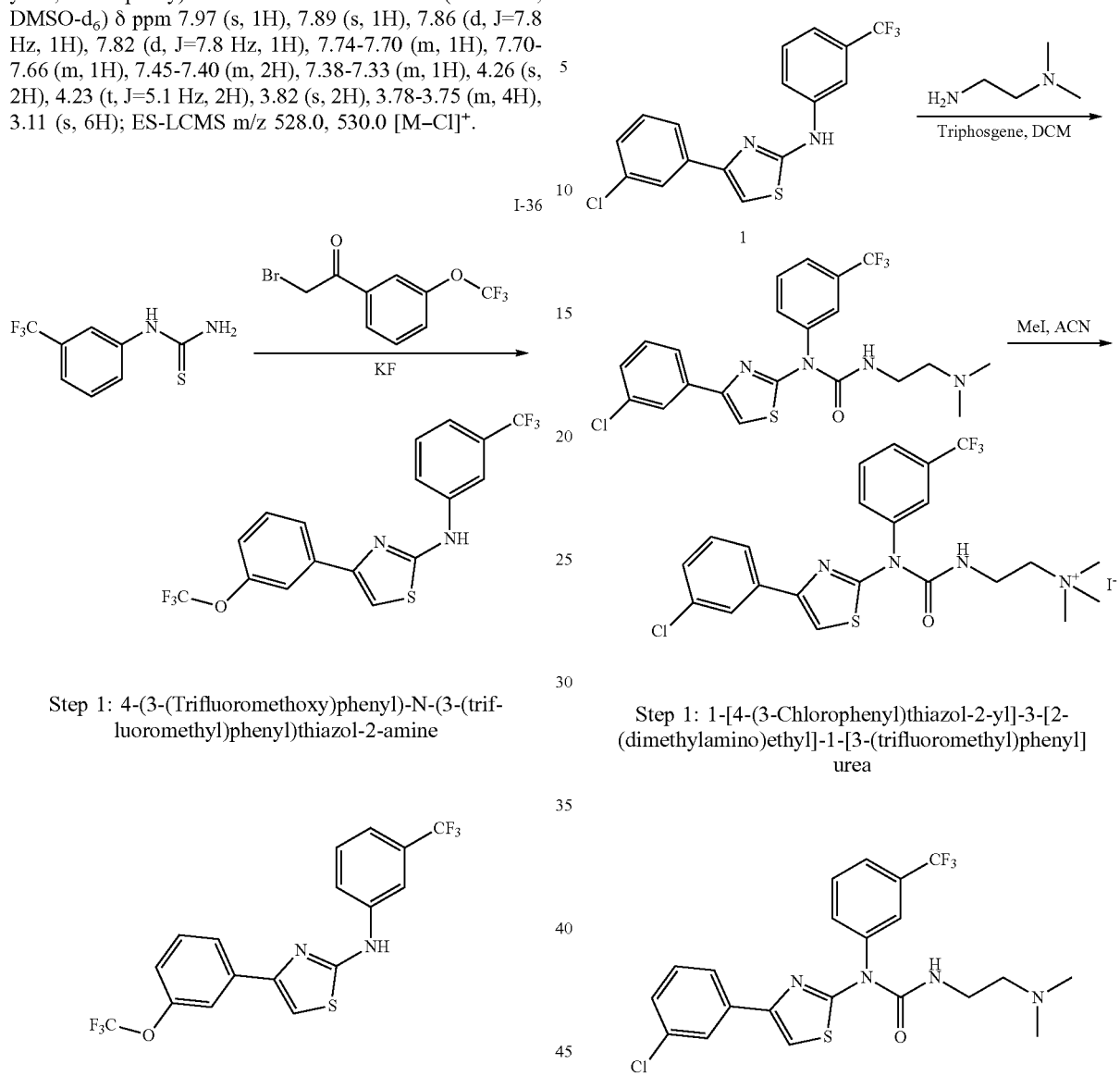

Step 1: 4-(3-(Trifluoromethoxy)phenyl)-N-(3-(trifluoromethyl)phenyl)thiazol-2-amine To a solution of 2-bromo-1-[3-(trifluoromethoxy)phenyl]ethanone (100 mg, 353.30 μmol, 1 eq) in CH$_3$CN (3 mL), H$_2$O (3 mL) was added [3-(trifluoromethyl)phenyl]thiourea (90 mg, 367.82 μmol, 1.04 eq), KF (20.53 mg, 353.30 μmol, 1 eq). The mixture was stirred under N$_2$ atmosphere at 30° C. for 1 h. The mixture was concentrated, diluted with water (10 mL) and extracted with EtOAc (10 mL×3). The combined organic layers were washed with brine (10 mL), dried over Na$_2$SO$_4$, filtered and concentrated to yield a residue which was purified by preparative HPLC (column: Agela DuraShell C18 150*25 mm*5 um; mobile phase: [water (0.04% NH$_3$H$_2$O+10 mM NH$_4$HCO$_3$)-ACN]; B %: 70%-100%, 10 min), followed by lyophilization to yield 4-[3-(trifluoromethoxy)phenyl]-N-[3-(trifluoromethyl)phenyl]thiazol-2-amine (123.72 mg, 305.99 μmol, 86.6% yield, 100.0% purity) as a white solid. $^1$H NMR (400 MHz, DMSO-d$_6$) δ ppm 10.73 (s, 1H), 8.54 (s, 1H), 7.95 (d, J=7.8 Hz, 1H), 7.88 (s, 1H), 7.68 (dd, J=7.8 Hz, 1H), 7.63 (s, 1H), 7.60-7.53 (m, 2H), 7.31 (dd, J=7.4 Hz, 2H); ES-LCMS m/z 404.8 [M+H]$^+$.

Step 1: 1-[4-(3-Chlorophenyl)thiazol-2-yl]-3-[2-(dimethylamino)ethyl]-1-[3-(trifluoromethyl)phenyl]urea To a solution of 4-(3-chlorophenyl)-N-[3-(trifluoromethyl)phenyl]thiazol-2-amine (150 mg, 419.84 μmol, 1 eq) in THF (4 mL) was added bis(trichloromethyl) carbonate (149.50 mg, 503.81 μmol, 1.2 eq), DIEA (162.78 mg, 1.26 mmol, 219.39 μL, 3 eq) and stirred at 80° C. for 2 h. The reaction mixture was concentrated to yield (4-(3-chlorophenyl)thiazol-2-yl)(3-(trifluoromethyl)phenyl)carbamic chloride (crude). To a solution of N',N'-dimethylethane-1,2-diamine (111.03 mg, 1.26 mmol, 137.58 μL, 3 eq) in DCM (1 mL) was added DMAP (5.13 mg, 41.98 μmol, 0.1 eq), DIEA (162.78 mg, 1.26 mmol, 219.39 μL, 3 eq), (4-(3-chlorophenyl)thiazol-2-yl)(3-(trifluoromethyl)phenyl)carbamic chloride (crude) in DCM (3 mL) and stirred at 25° C. for 2 h. The reaction mixture was concentrated and treated with water (50 mL), extracted with EtOAc (50 mL×3). The combined organic layers were washed with brine (20 mL), dried over Na$_2$SO$_4$, filtered and concentrated under reduced pressure to give a residue which was purified by preparative HPLC (Agela DuraShell C18 150*25 mm*5 um; mobile phase: [water(0.04% NH$_3$H$_2$O+10 mM NH$_4$HCO$_3$)-ACN];

B %: 60%-90%, 10 min), followed by lyophilization to yield 1-[4-(3-chlorophenyl)thiazol-2-yl]-3-[2-(dimethylamino)ethyl]-1-[3-(trifluoromethyl)phenyl]urea (150 mg, 316.04 µmol, 75.3% yield, 98.8% purity) as a white solid. $^1$H NMR (400 MHz, DMSO-d$_6$) δ ppm 8.03 (s, 1H), 7.94-7.86 (m, 2H), 7.83-7.71 (m, 5H), 7.44-7.37 (m, 1H), 7.36-7.30 (m, 1H), 3.31-3.26 (m, 2H), 2.37 (t, J=6.3 Hz, 2H), 2.19 (s, 6H); ES-LCMS m/z 469.2, 471.2 [M+H]$^+$.

Step 2: 2-(3-(4-(3-chlorophenyl)thiazol-2-yl)-3-(3-(trifluoromethyl)phenyl)ureido)-N,N,N-trimethylethanaminium iodide

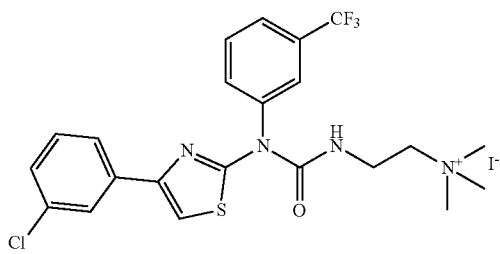 [SMILES: C[N+](C)(C)CCNC(=O)N(c1cccc(C(F)(F)F)c1)c1nc(-c2cccc(Cl)c2)cs1 ; [I-]]

To a solution of 1-[4-(3-chlorophenyl)thiazol-2-yl]-3-[2-(dimethylamino)ethyl]-1-[3-(trifluoromethyl)phenyl]urea (100 mg, 213.26 µmol, 1 eq) in MeCN (10 mL) was added MeI (242.16 mg, 1.71 mmol, 106.21 µl, 8 eq). The mixture was stirred at 25° C. for 2 h. TLC (PE/EtOAc=0/1, R$_f$=0) indicated starting material was consumed completely and one new spot formed. The reaction mixture was added H$_2$O (20 mL) and lyophilizated to yield 2-(3-(4-(3-chlorophenyl)thiazol-2-yl)-3-(3-(trifluoromethyl)phenyl)ureido)-N,N,N-trimethylethanaminium iodide (84.88 mg, 131.78 umol, 62.1% yield, 95.3% purity) as a white solid. $^1$H NMR (400 MHz, CD$_3$OD) δ ppm 7.93-7.88 (m, 1H), 7.86-7.80 (m, 2H), 7.73 (d, J=8.2 Hz, 1H), 7.68 (t, J=1.6 Hz, 1H), 7.65-7.61 (m, 1H), 7.47 (s, 1H), 7.35-7.28 (m, 1H), 7.28-7.22 (m, 1H), 3.80-3.72 (m, 2H), 3.58-3.53 (m, 2H), 3.21 (s, 9H); ES-LCMS m/z 483.1, 485.1 [M–I]$^+$.

I-13

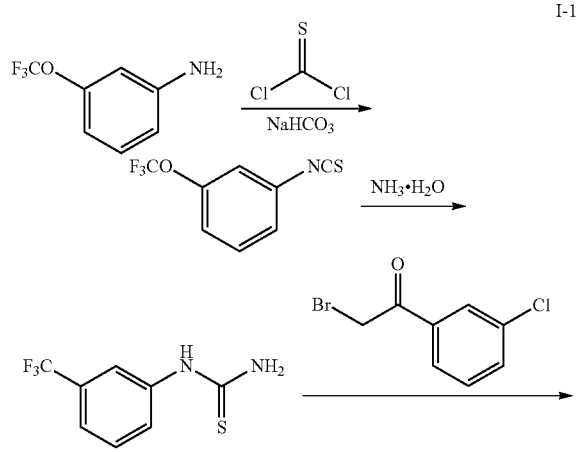

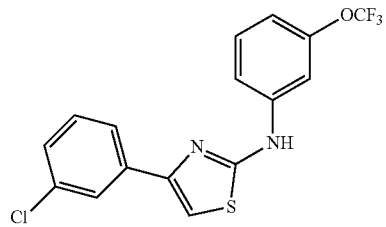

Step 1: 1-Isothiocyanato-3-(trifluoromethoxy)benzene

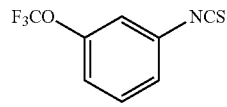

To a solution of 3-(trifluoromethoxy)aniline (300 mg, 1.69 mmol, 225.56 µL, 1 eq) and NaHCO$_3$ (569.16 mg, 6.77 mmol, 263.50 µL, 4 eq) in DCM (10 mL) and H$_2$O (10 mL) was added thiocarbonyl dichloride (389.50 mg, 3.39 mmol, 259.66 µL, 2 eq) at 0° C. The mixture was stirred at 25° C. for 12 h. TLC (PE/EtOAc=10/1, R$_f$=0.47) indicated the starting material was consumed completely and one new spot formed. The reaction mixture was quenched by addition of sat. aq. NaHCO$_3$ (30 mL), extracted with DCM (30 mL×3). The combined organic layers were washed with brine (10 mL), dried over Na$_2$SO$_4$, filtered and concentrated under reduced pressure below 30° C. to yield 1-isothiocyanato-3-(trifluoromethoxy)benzene (371 mg, crude) as yellow oil, which was used in the next step without further purification. ES-LCMS no desired m/z was detected.

Step 2: [3-(Trifluoromethoxy)phenyl]thiourea

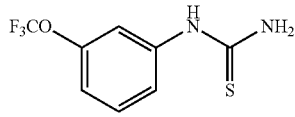 [SMILES: NC(=S)Nc1cccc(OC(F)(F)F)c1]

To a solution of MeCN (10 mL) and NH$_3$.H$_2$O (4.55 g, 36.35 mmol, 5 mL, 28%, 21.48 eq) was added a solution of 1-isothiocyanato-3-(trifluoromethoxy)benzene (371 mg, 1.69 mmol, 1 eq) in DCM (5 mL). The mixture was stirred at 30° C. for 1 h. The reaction mixture was concentrated, added water (30 mL), extracted with EtOAc (30 mL×3). The combined organic layers were washed with brine (10 mL), dried over Na$_2$SO$_4$, filtered and concentrated under reduced pressure to yield a residue which was purified by flash silica gel chromatography (from PE/EtOAc=1/0 to 1/2, TLC: PE/EtOAc=1/1, R$_f$=0.10) to yield [3-(trifluoromethoxy)phenyl]thiourea (170 mg, 719.69 µmol, 42.5% yield, 100% purity) as yellow oil. $^1$H NMR (400 MHz, CDCl$_3$) δ ppm 8.55 (br s, 1H), 7.54-7.43 (m, 1H), 7.25-7.11 (m, 3H), 6.30 (br s, 2H); ES-LCMS m/z 236.9 [M+H]$^+$.

Step 3: 4-(3-Chlorophenyl)-N-[3-(trifluoromethoxy)phenyl]thiazol-2-amine

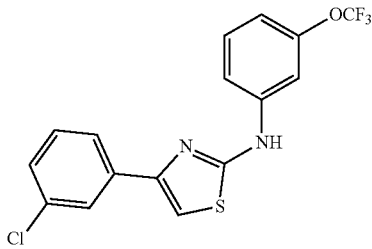 [SMILES: FC(F)(F)Oc1cccc(Nc2nc(-c3cccc(Cl)c3)cs2)c1]

To a solution of [3-(trifluoromethoxy)phenyl]thiourea (170 mg, 719.69 µmol, 1 eq) and 2-bromo-1-(3-chlorophenyl)ethanone (168.04 mg, 719.69 µmol, 1 eq) in MeCN (5 mL) and H$_2$O (5 mL) was added KF (83.62 mg, 1.44 mmol, 33.72 µL, 2 eq). The mixture was stirred at 30° C. for 12 h. The reaction mixture was quenched by addition of water (50 mL), extracted with EtOAc (30 mL×3). The combined organic layers were washed with brine (10 mL), dried over Na$_2$SO$_4$, filtered and concentrated under reduced pressure to yield a residue which was purified by preparative HPLC (column: Agela DuraShell C18 150*25 mm*5 µm; mobile phase: [water (0.04% NH$_3$H$_2$O+10 mM NH$_4$HCO$_3$)-ACN]; B %: 70%-100%, 10 min), followed by lyophilization to yield 4-(3-chlorophenyl)-N-[3-(trifluoromethoxy)phenyl]thiazol-2-amine (19.08 mg, 48.58 µmol, 6.7% yield, 94.4% purity) as yellow oil. $^1$H NMR (500 MHz, CD$_3$OD) δ ppm 8.12 (d, J=0.9 Hz, 1H), 7.94 (t, J=1.8 Hz, 1H), 7.83 (td, J=1.2, 7.9 Hz, 1H), 7.46-7.41 (m, 1H), 7.40-7.35 (m, 2H), 7.30 (ddd, J=1.0, 2.1, 7.9 Hz, 1H), 7.21 (s, 1H), 6.85 (td, J=1.1, 8.0 Hz, 1H); ES-LCMS m/z 370.9, 372.9 [M+H]$^+$.

I-25

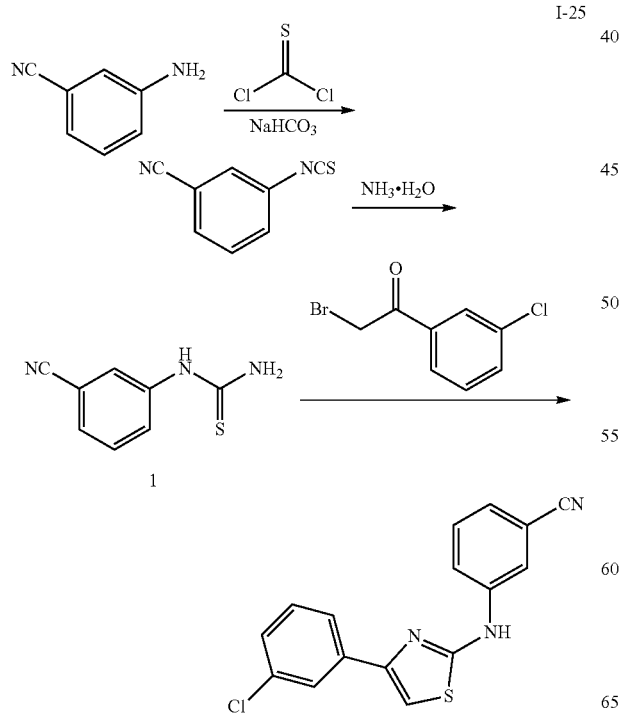

Step 1: 3-Isothiocyanatobenzonitrile

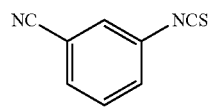

To a mixture of 3-aminobenzonitrile (200 mg, 1.69 mmol, 1 eq) and NaHCO$_3$ (284.45 mg, 3.39 mmol, 2 eq) in DCM (10 mL) and H$_2$O (10 mL) was added thiocarbonyl dichloride (389.32 mg, 3.39 mmol, 259.55 µL, 2 eq) at 0° C. The mixture was stirred at 25° C. for 1 h. TLC (PE/EtOAc=5/1, R$_f$=0.61) indicated the starting material was consumed and a new spot formed. The reaction mixture was quenched by addition of water (100 mL), then extracted with DCM (100 mL×3). The organic layer was washed with brine (20 mL), dried over Na$_2$SO$_4$, filtered, concentrated to yield 3-isothiocyanatobenzonitrile (230 mg, crude) as yellow oil which was used in the next step without further purification. ES-LCMS: no desired mass was found.

Step 2: 3-Cyanophenyl)thiourea

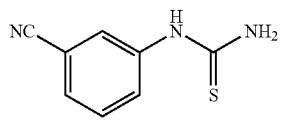 [SMILES: N#Cc1cccc(NC(N)=S)c1]

To a solution of MeCN (20 mL) and NH$_3$.H$_2$O (9.10 g, 72.70 mmol, 10 mL, 28%, 50.64 eq) was added 3-isothiocyanatobenzonitrile (230 mg, 1.44 mmol, 1 eq) slowly at 0° C. The mixture was stirred at 25° C. for 3 h. The reaction mixture was concentrated to remove MeCN, added water (100 mL), then extracted with EtOAc (100 mL×3). The organic layer was washed with brine (20 mL), dried over Na$_2$SO$_4$, filtered and concentrated to yield (3-cyanophenyl)thiourea (200 mg, 923.1 µmol, 64.3% yield, 81.8% purity) as a yellow solid, which was used in the next step without further purification. $^1$H NMR (400 MHz, DMSO-d$_6$) δ ppm 9.97 (s, 1H), 8.02 (s, 1H), 7.72-7.68 (m, 1H), 7.56-7.50 (m, 1H); ES-LCMS m/z 177.9 [M+H]$^+$.

Step 3: 3-[[4-(3-Chlorophenyl)thiazol-2-yl]amino]benzonitrile

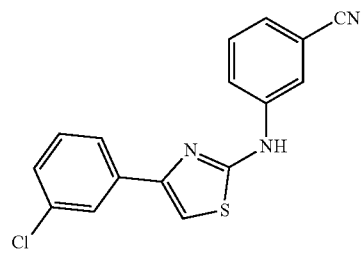 [SMILES: N#Cc1cccc(Nc2nc(-c3cccc(Cl)c3)cs2)c1]

To a solution of (3-cyanophenyl)thiourea (200 mg, 923.12 µmol, 1 eq), 2-bromo-1-(3-chlorophenyl)ethanone (215.54 mg, 923.12 µmol, 1 eq) in CH$_3$CN (10 mL) and H$_2$O (10 mL) was added KF (107.26 mg, 1.85 mmol, 43.25 µ2 eq).

The mixture was stirred at 30° C. for 12 h. The reaction mixture was quenched by addition of water (50 mL), extracted with EtOAc (30 mL×3). The combined organic layers were washed with brine (10 mL), dried over Na$_2$SO$_4$, filtered and concentrated to yield a residue which was purified by preparative HPLC (column: Agela DuraShell C18 150*25 mm*5 µm; mobile phase: [water (0.04% NH$_3$.H$_2$O+10 mM NH$_4$HCO$_3$)-ACN]; B %: 60%-90%, 10 min), followed by lyophilization to yield 3-[[4-(3-chlorophenyl)thiazol-2-yl]amino]benzonitrile (150 mg, 481.1 µmol, 52.1% yield, 100% purity) as a white solid. $^1$H NMR (400 MHz, CDCl$_3$) δ ppm 7.90-7.83 (m, 2H), 7.79-7.70 (m, 2H), 7.48 (t, J=8.0 Hz, 1H), 7.41-7.28 (m, 3H), 7.23 (s, 1H), 6.96 (s, 1H); ES-LCMS m/z 311.9, 313.9 [M+H]$^+$.

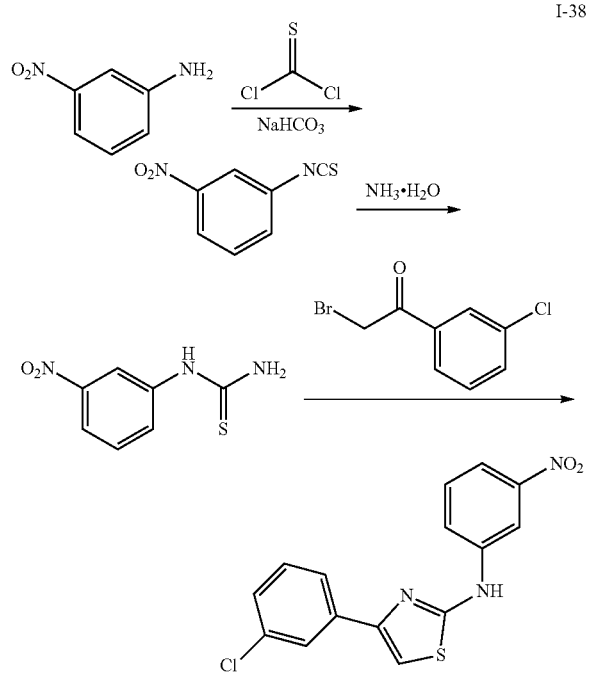

I-38

Step 1: 1-Isothiocyanato-3-nitro-benzene

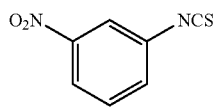

To a solution of 3-nitroaniline (300 mg, 2.17 mmol, 545.45 µL, 1 eq), NaHCO$_3$ (364.93 mg, 4.34 mmol, 2 eq) in DCM (5 mL) and H$_2$O (5 mL) was added dropwise thiocarbonyl dichloride (449.52 mg, 3.91 mmol, 299.68 µL, 1.8 eq) at 0° C. The mixture was stirred at 25° C. for 1 h. To the mixture was added water (30 mL) and extracted with DCM (30 mL×3). The combined organic phase was washed with brine (20 mL), dried over anhydrous Na$_2$SO$_4$, filtered and concentrated in vacuum to yield 1-isothiocyanato-3-nitrobenzene (350 mg, 1.75 mmol, 80.5% yield, 90% purity) as a yellow solid which was used in the next step without further purification. $^1$H NMR (400 MHz, DMSO-d$_6$) δ ppm 8.28 (t, J=2.2 Hz, 1H), 8.22-8.18 (m, 1H), 7.91-7.88 (m, 1H), 7.75-7.71 (m, 1H).

Step 2: (3-Nitrophenyl)thiourea

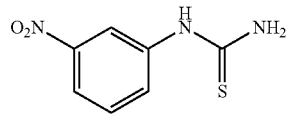 [SMILES: NC(=S)Nc1cccc([N+](=O)[O-])c1]

To a solution of 1-isothiocyanato-3-nitro-benzene (350 mg, 1.75 mmol, 1 eq) in MeCN (10 mL) was added NH$_3$.H$_2$O (328.22 mg, 2.62 mmol, 360.68 µL, 28%, 1.5 eq). The mixture was stirred at 25° C. for 3 h. The reaction mixture was concentrated under reduced pressure to yield a residue which was purified by flash silica gel chromatography (from PE/EtOAc=200/1 to 3/1, TLC: PE/EtOAc=3/1, R$_f$=0.30) to yield (3-nitrophenyl)thiourea (300 mg, 1.37 mmol, 78.3% yield, 90% purity) as a yellow solid. $^1$H NMR (500 MHz, DMSO-d$_6$) δ ppm 10.09 (s, 1H), 8.60 (t, J=2.1 Hz, 1H), 7.93 (dd, J=1.5, 8.1 Hz, 1H), 7.83 (dd, J=1.3, 8.0 Hz, 1H), 7.59 (t, J=8.2 Hz, 1H); ES-LCMS m/z 197.9 [M+H]$^+$.

Step 3: 4-(3-Chlorophenyl)-N-(3-nitrophenyl)thiazol-2-amine

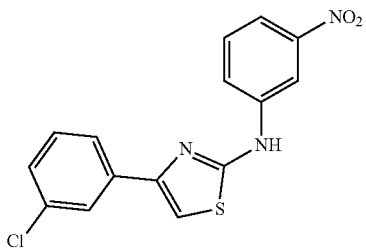 [SMILES: O=[N+]([O-])c1cccc(Nc2nc(-c3cccc(Cl)c3)cs2)c1]

To a solution of (3-nitrophenyl)thiourea (100 mg, 456.36 µmol, 1 eq) and 2-bromo-1-(3-chlorophenyl)ethanone (106.55 mg, 456.36 µmol, 1 eq) in MeCN (3 mL) and H$_2$O (3 mL) was added KF (26.51 mg, 456.36 µmol, 1 eq). The mixture was stirred at 25° C. for 1 h under N$_2$ atmosphere. To the mixture was added water (30 mL) and extracted with ethyl acetate (30 mL×3). The combined organic phase was washed with brine (20 mL), dried over anhydrous Na$_2$SO$_4$, filtered and concentrated in vacuum to yield a residue which was purified by flash silica gel chromatography (from PE/EtOAc=200/1 to 1/1, TLC: PE/EtOAc=1/1, R$_f$=0.40) to yield a product, and the product was triturated with PE (10 mL) at 25° C. for 12 h to yield 4-(3-chlorophenyl)-N-(3-nitrophenyl)thiazol-2-amine (78.31 mg, 236.03 µmol, 51.7% yield, 100% purity) as a red solid. $^1$H NMR (400 MHz, CD$_3$OD) δ ppm 9.09 (t, J=2.1 Hz, 1H), 8.00 (s, 1H), 7.92-7.86 (m, 2H), 7.84 (dd, J=1.5, 8.1 Hz, 1H), 7.59-7.52 (m, 1H), 7.45-7.37 (m, 1H), 7.31 (d, J=8.1 Hz, 1H), 7.28 (s, 1H); ES-LCMS m/z 331.9, 333.9 [M+H]$^+$.

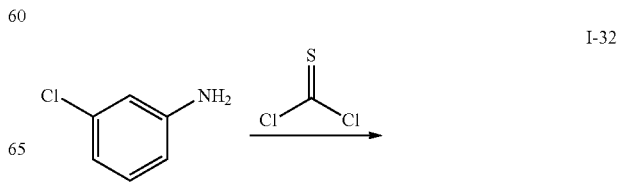

I-32

Step 1: 1-Chloro-3-isothiocyanato-benzene

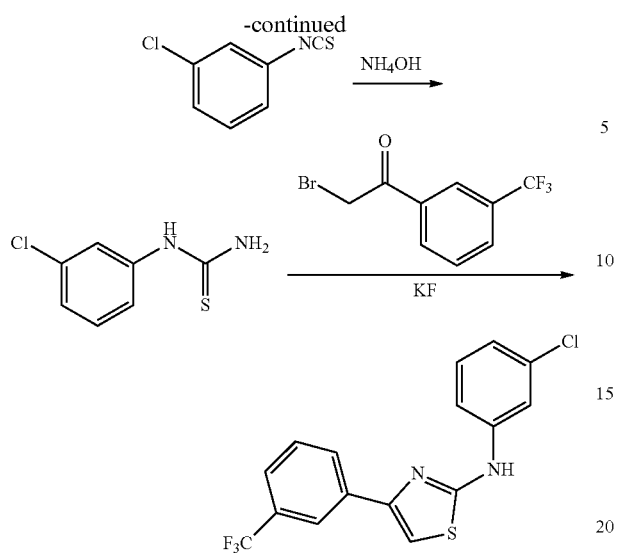

A mixture of 3-chloroaniline (1 g, 7.84 mmol, 833.33 μL, 1 eq), thiocarbonyl dichloride (1.35 g, 11.76 mmol, 901.31 μL, 1.5 eq), NaHCO₃ (1.32 g, 15.68 mmol, 609.75 μL, 2 eq) in DCM (10 mL) and H₂O (10 mL) was degassed and purged with N₂ for 3 times and the mixture was stirred at 25° C. for 1 h under N₂ atmosphere. TLC (PE/EtOAc=5/1, R$_f$=0.62) indicated starting material was consumed completely and one new spot formed. The reaction mixture was quenched by addition of water (20 mL), extracted with DCM (20 mL×3). The combined organic layers were washed with brine (20 mL), dried over Na₂SO₄, filtered and concentrated under reduced pressure to yield 1-chloro-3-isothiocyanato-benzene (1.5 g, 7.07 mmol, 90.3% yield, 80.0% purity) as yellow oil. ¹H NMR (400 MHz, DMSO-d₆) δ ppm 7.58-7.50 (m, 1H), 7.43-7.36 (m, 3H).

Step 2: (3-Chlorophenyl)thiourea

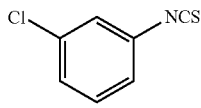

To a solution of 1-chloro-3-isothiocyanato-benzene (1.5 g, 7.07 mmol, 1.16 mL, 1 eq) in MeCN (20 mL) was added NH₃·H₂O (9.20 mmol, 1.3 mL, 28% purity, 1.3 eq). The mixture was stirred at 25° C. for 3 h. The reaction mixture was concentrated to yield (3-chlorophenyl)thiourea (1.6 g, 6.86 mmol, 96.9% yield, 80.0% purity) as a brown solid. ¹H NMR (400 MHz, DMSO-d₆) δ ppm 9.82 (s, 1H), 7.68 (s, 1H), 7.31-7.26 (m, 2H), 7.14-7.08 (m, 1H); ES-LCMS: m/z 186.8 [M+H]⁺.

Step 3: N-(3-Chlorophenyl)-4-[3-(trifluoromethyl)phenyl]thiazol-2-amine

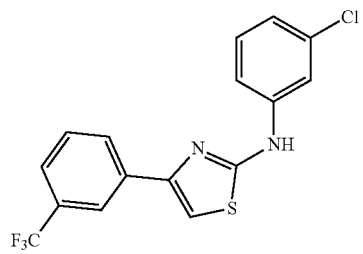 [SMILES: FC(F)(F)c1cccc(-c2csc(Nc3cccc(Cl)c3)n2)c1]

To a stirred solution of (3-chlorophenyl)thiourea (200 mg, 857.17 μmol, 1 eq) and 2-bromo-1-[3-(trifluoromethyl)phenyl]ethanone (228.90 mg, 857.17 μmol, 1 eq) in MeCN (5 mL) and H₂O (5 mL) was added KF (49.80 mg, 857.17 μmol, 1 eq). The reaction mixture was stirred at 25° C. for 3 h under N₂ atmosphere. The reaction mixture was concentrated under reduced pressure to remove MeCN. The residue was diluted with H₂O (10 mL) and extracted with EtOAc (20 mL×3). The combined organic layers were washed with brine (20 mL), dried over Na₂SO₄, filtered and concentrated under reduced pressure to yield a residue which was purified by preparative HPLC (column: Agela DuraShell C18 150*25 mm*5 μm; mobile phase: [water (0.05% NH₃·H₂O+10 mM NH₄HCO₃)-ACN]; B %: 68%-98%, 10 min) to yield N-(3-chlorophenyl)-4-[3-(trifluoromethyl)phenyl]thiazol-2-amine (76.37 mg, 213.39 μmol, 24.9% yield, 99.1% purity) as red oil. ¹H NMR (400 MHz, DMSO-d₆) δ ppm 10.60 (s, 1H), 8.24 (s, 1H), 8.23-8.18 (m, 1H), 8.05 (t, J=2.0 Hz, 1H), 7.71-7.66 (m, 3H), 7.50 (dd, J=1.2, 8.2 Hz, 1H), 7.37 (t, J=8.2 Hz, 1H), 7.03 (dd, J=1.4, 8.0 Hz, 1H); ES-LCMS m/z 354.9, 356.9 [M+H]⁺.

I-6

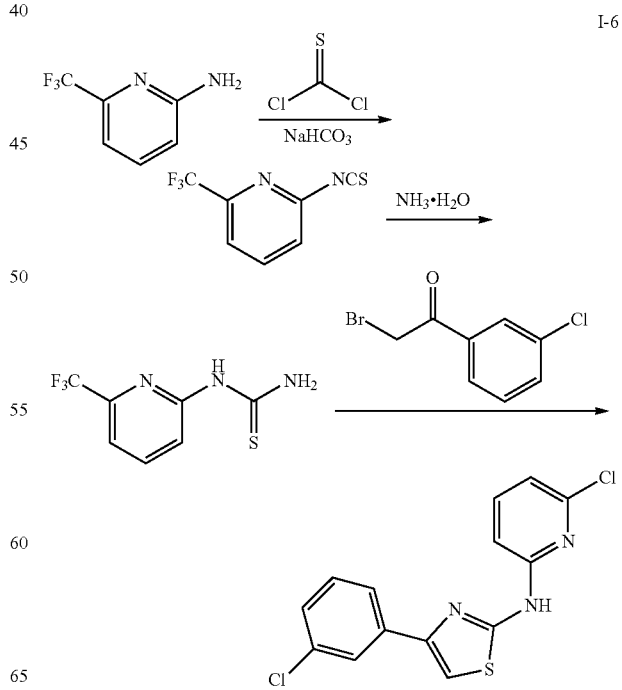

Step 1: 2-Isothiocyanato-6-(trifluoromethyl)pyridine

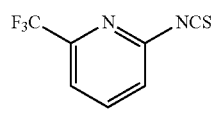

To a stirred solution of 6-(trifluoromethyl)pyridin-2-amine (0.8 g, 4.93 mmol, 1 eq) in DCM (15 mL) and H$_2$O (15 mL) was added NaHCO$_3$ (829.15 mg, 9.87 mmol, 2 eq) and thiocarbonyl dichloride (1.70 g, 14.80 mmol, 1.13 mL, 3 eq). The reaction mixture was stirred at 25° C. for 3 h under N$_2$ atmosphere. The reaction mixture was diluted with H$_2$O (5 mL) and extracted with DCM (20 mL×3). The combined organic layers were washed with brine (20 mL), dried over Na$_2$SO$_4$, filtered and concentrated under reduced pressure to yield a residue which was purified by flash silica gel chromatography (from PE/EtOAc=100/1 to 5/1, TLC: PE/EtOAc=5/1, R$_f$=0.61) to yield 2-isothiocyanato-6-(trifluoromethyl)pyridine (0.77 g, 3.58 mmol, 72.6% yield, 95.0% purity) as light yellow oil. $^1$H NMR (500 MHz, CDCl$_3$) δ ppm 7.91 (t, J=8.0 Hz, 1H), 7.58 (d, J=7.6 Hz, 1H), 7.30 (d, J=8.1 Hz, 1H); ES-LCMS no desired m/z was detected.

Step 2: [6-(Trifluoromethyl)-2-pyridyl]thiourea

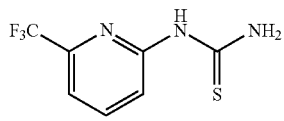 [SMILES: NC(=S)Nc1cccc(C(F)(F)F)n1]

To a stirred solution of 2-isothiocyanato-6-(trifluoromethyl)pyridine (760 mg, 3.54 mmol, 1 eq) in MeCN (15 mL) was added NH$_3$·H$_2$O (663.91 mg, 5.30 mmol, 729.57 μL, 28%, 1.5 eq). The reaction mixture was stirred at 25° C. for 1 h under N$_2$ atmosphere. The reaction mixture was concentrated under reduced pressure to remove MeCN. The residue was diluted with H$_2$O (10 mL) and extracted with EtOAc (20 mL×3). The combined organic layers were washed with brine (20 mL), dried over Na$_2$SO$_4$, filtered and concentrated under reduced pressure to yield the crude product which was used in the next step without further purification to yield [6-(trifluoromethyl)-2-pyridyl]thiourea (550 mg, 2.49 mmol, 70.3% yield, 100% purity) as a white solid. $^1$H NMR (500 MHz, DMSO-d$_6$) δ ppm 10.93 (s, 1H), 9.92 (s, 1H), 9.15 (s, 1H), 8.04 (t, J=7.9 Hz, 1H), 7.55 (d, J=7.3 Hz, 1H), 7.49 (d, J=8.4 Hz, 1H); ES-LCMS m/z 222.0 [M+H]$^+$.

Step 3: 4-(3-Chlorophenyl)-N-[6-(trifluoromethyl)-2-pyridyl]thiazol-2-amine

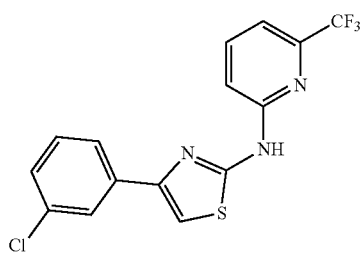 [SMILES: FC(F)(F)c1cccc(Nc2nc(-c3cccc(Cl)c3)cs2)n1]

To a stirred solution of [6-(trifluoromethyl)-2-pyridyl]thiourea (200 mg, 904.15 μmol, 1 eq) and 2-bromo-1-(3-chlorophenyl)ethanone (211.11 mg, 904.15 μmol, 1 eq) in MeCN (5 mL) and H$_2$O (5 mL) was added KF (52.53 mg, 904.15 μmol, 1 eq). The reaction mixture was stirred at 25° C. for 3 h under N$_2$ atmosphere. The reaction mixture was concentrated under reduced pressure to remove MeCN. The residue was diluted with H$_2$O (5 mL) and extracted with DCM (20 mL×3). The combined organic layers were washed with brine (20 mL), dried over Na$_2$SO$_4$, filtered and concentrated under reduced pressure to yield a residue which was purified by preparative HPLC (column: Boston Prime C18 150*30 mm*5 μm; mobile phase: [water (0.05% ammonia hydroxide v/v)-ACN]; B %: 65%-90%, 10 min) to yield 4-(3-chlorophenyl)-N-[6-(trifluoromethyl)-2-pyridyl]thiazol-2-amine (152.15 mg, 427.67 μmol, 47.3% yield, 100% purity) as a white solid. $^1$H NMR (500 MHz, DMSO-d$_6$) δ ppm 11.89 (br s, 1H), 8.00-7.94 (m, 2H), 7.88 (d, J=7.9 Hz, 1H), 7.70 (s, 1H), 7.50-7.44 (m, 1H), 7.42 (d, J=7.3 Hz, 1H), 7.39-7.34 (m, 2H); ES-LCMS m/z 356.1, 358.1 [M+H]$^+$.

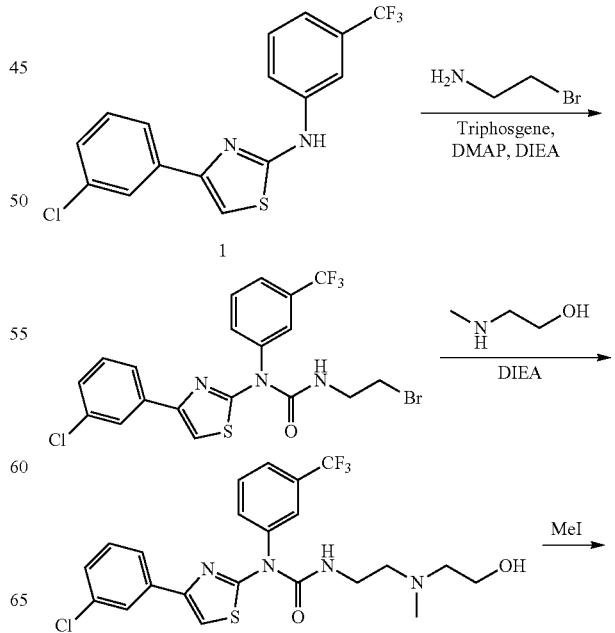

-continued

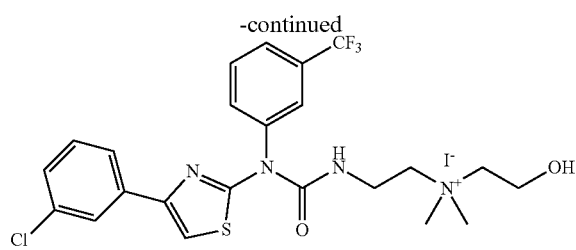

Step 1: 3-(2-Bromoethyl)-1-[4-(3-chlorophenyl)thiazol-2-yl]-1-[3-(trifluoromethyl)phenyl]urea

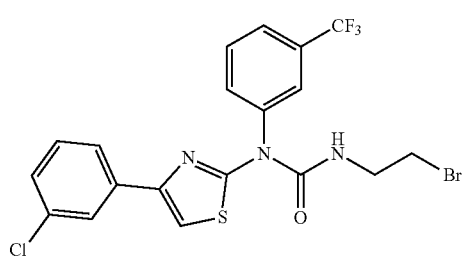 [SMILES: O=C(NCCBr)N(c1cccc(C(F)(F)F)c1)c1nc(-c2cccc(Cl)c2)cs1]

To a solution of 4-(3-chlorophenyl)-N-[3-(trifluoromethyl)phenyl]thiazol-2-amine (300 mg, 845.60 μmol, 1 eq) in THF (5 mL) was added bis(trichloromethyl) carbonate (301.12 mg, 1.01 mmol, 1.2 eq), DIEA (327.86 mg, 2.54 mmol, 441.86 μL, 3 eq) and stirred at 80° C. for 2 h. The reaction mixture was concentrated to yield (4-(3-chlorophenyl)thiazol-2-yl)(3-(trifluoromethyl)phenyl)carbamic chloride (crude). Then to a solution of 2-bromoethanamine (866.28 mg, 4.23 mmol, 5 eq, HBr), DIEA (327.86 mg, 2.54 mmol, 441.86 μL, 3 eq) and DMAP (10.33 mg, 84.56 μmol, 0.1 eq) in DCM (2 mL) was added (4-(3-chlorophenyl)thiazol-2-yl)(3-(trifluoromethyl)phenyl)carbamic chloride (crude) in DCM (3 mL) and stirred at 25° C. for 1 h. The solution was quenched by addition of sat. aq. NaHCO₃ (3 mL) and diluted with water (30 mL), and extracted with ethyl acetate (30 mL×3). The combined organic phase was washed with brine (20 mL), dried over anhydrous Na₂SO₄, filtered and concentrated in vacuum to yield a residue which was purified by flash silica gel chromatography (from PE/EtOAc=200/1 to 3/1, TLC: PE/EtOAc=3/1, $R_f$=0.40) to yield 3-(2-bromoethyl)-1-[4-(3-chlorophenyl)thiazol-2-yl]-1-[3-(trifluoromethyl)phenyl]urea (400 mg, 784.55 μmol, 92.8% yield, 99% purity) as a yellow solid. ¹H NMR (400 MHz, CD₃OD) δ ppm 7.90-7.86 (m, 1H), 7.82 (dd, J=2.5, 4.5 Hz, 3H), 7.74-7.68 (m, 2H), 7.45 (s, 1H), 7.36-7.31 (m, 1H), 7.30-7.26 (m, 1H), 3.76-3.73 (m, 2H), 3.62-3.56 (m, 2H); ES-LCMS m/z 505.8, 507.8 [M+H]⁺.

Step 2: 1-[4-(3-Chlorophenyl)thiazol-2-yl]-3-[2-[2-hydroxyethyl(methyl)amino]ethyl]-1-[3-(trifluoromethyl)phenyl]urea

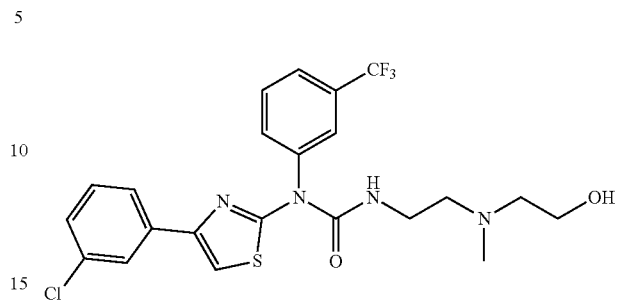

A mixture of 3-(2-bromoethyl)-1[4-(3-chlorophenyl)thiazol-2-yl]-1-[3-(trifluoromethyl)phenyl]urea (150 mg, 294.20 μmol, 1 eq) and 2-(methylamino)ethanol (110.49 mg, 1.47 mmol, 118.17 μL, 5 eq) in THF (10 mL) was added DIEA (76.05 mg, 588.41 μmol, 102.49 μL, 2 eq). The mixture was stirred at 25° C. for 48 h. The reaction mixture was concentrated under reduced pressure to yield a residue. To the residue was added water (30 mL) and extracted with ethyl acetate (30 mL×3). The combined organic phase was washed with brine (20 mL), dried over anhydrous Na₂SO₄, filtered and concentrated in vacuum to yield a residue which was purified by preparative HPLC (column: Agela DuraShell C18 150*25 mm*5 μm; mobile phase: [water (0.05% NH₃.H₂O+10 mM NH₄HCO₃)-ACN]; B %: 50%-80%, 10 min), followed by lyophilization to yield 1-[4-(3-chlorophenyl)thiazol-2-yl]-3-[2-[2-hydroxyethyl(methyl)amino]ethyl]-1-[3-(trifluoromethyl)phenyl]urea (80 mg, 158.73 μmol, 53.9% yield, 99% purity) as yellow oil. ¹H NMR (500 MHz, CD₃OD) δ ppm 7.86 (d, J=7.9 Hz, 1H), 7.81-7.76 (m, 2H), 7.74 (t, J=1.7 Hz, 1H), 7.70 (dd, J=1.0, 7.7 Hz, 2H), 7.40 (s, 1H), 7.36-7.31 (m, 1H), 7.29-7.25 (m, 1H), 3.59 (t, J=6.2 Hz, 2H), 3.45 (t, J=6.3 Hz, 2H), 2.64 (t, J=6.3 Hz, 2H), 2.59 (t, J=6.2 Hz, 2H), 2.39-2.33 (m, 3H); ES-LCMS m/z 499.2, 501.2 [M+H]⁺.

Step 3: 1-[4-(3-Chlorophenyl)thiazol-2-yl]-3-[2-[BLAH-(2-hydroxyethyl)-dimethyl-azanyl]ethyl]-1-[3-(trifluoromethyl)phenyl]urea

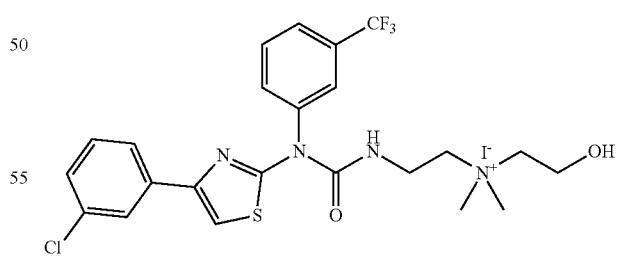

To a solution of 1-[4-(3-chlorophenyl)thiazol-2-yl]-3-[2-[2-hydroxyethyl(methyl)amino]ethyl]-1-[3-(trifluoromethyl)phenyl]urea (80 mg, 158.73 μmol, 1 eq) in MeCN (5 mL) was added MeI (225.31 mg, 1.59 mmol, 98.82 μL, 10 eq) in one portion at 25° C. under N₂ atmosphere. The mixture was stirred at 25° C. for 1 h. The solution was quenched by addition of sat. aq. NaHCO₃ (1 mL), diluted with water (10 mL), then lyophilization to yield 1-[4-(3- chlorophenyl)thiazol-2-yl]-3-[2-[BLAH-(2-hydroxy ethyl)-dimethyl-azanyl]ethyl]-1-[3-(trifluoromethyl)phenyl]urea (93.52 mg, 145.92 µmol, 91.9% yield, 100% purity) as a yellow solid. $^1$H NMR (500 MHz, DMSO-$d_6$) δ ppm 7.99-7.93 (m, 2H), 7.88-7.80 (m, 2H), 7.78 (s, 1H), 7.63 (d, J=1.7 Hz, 1H), 7.57 (d, J=7.8 Hz, 1H), 7.38-7.33 (m, 1H), 7.31-7.28 (m, 1H), 6.98 (t, J=5.1 Hz, 1H), 5.31 (t, J=4.8 Hz, 1H), 3.83 (s, 2H), 3.54 (d, J=5.6 Hz, 2H), 3.48 (d, J=5.6 Hz, 2H), 3.43-3.40 (m, 2H), 3.10 (s, 6H); ES-LCMS m/z 513.2, 515.2 [M−I]$^+$.

1H), 7.45-7.40 (m, 1H), 7.39 (s, 1H), 7.38-7.32 (m, 1H), 7.24 (d, J=7.8 Hz, 1H); ES-LCMS m/z 355.0 [M+H]$^+$.

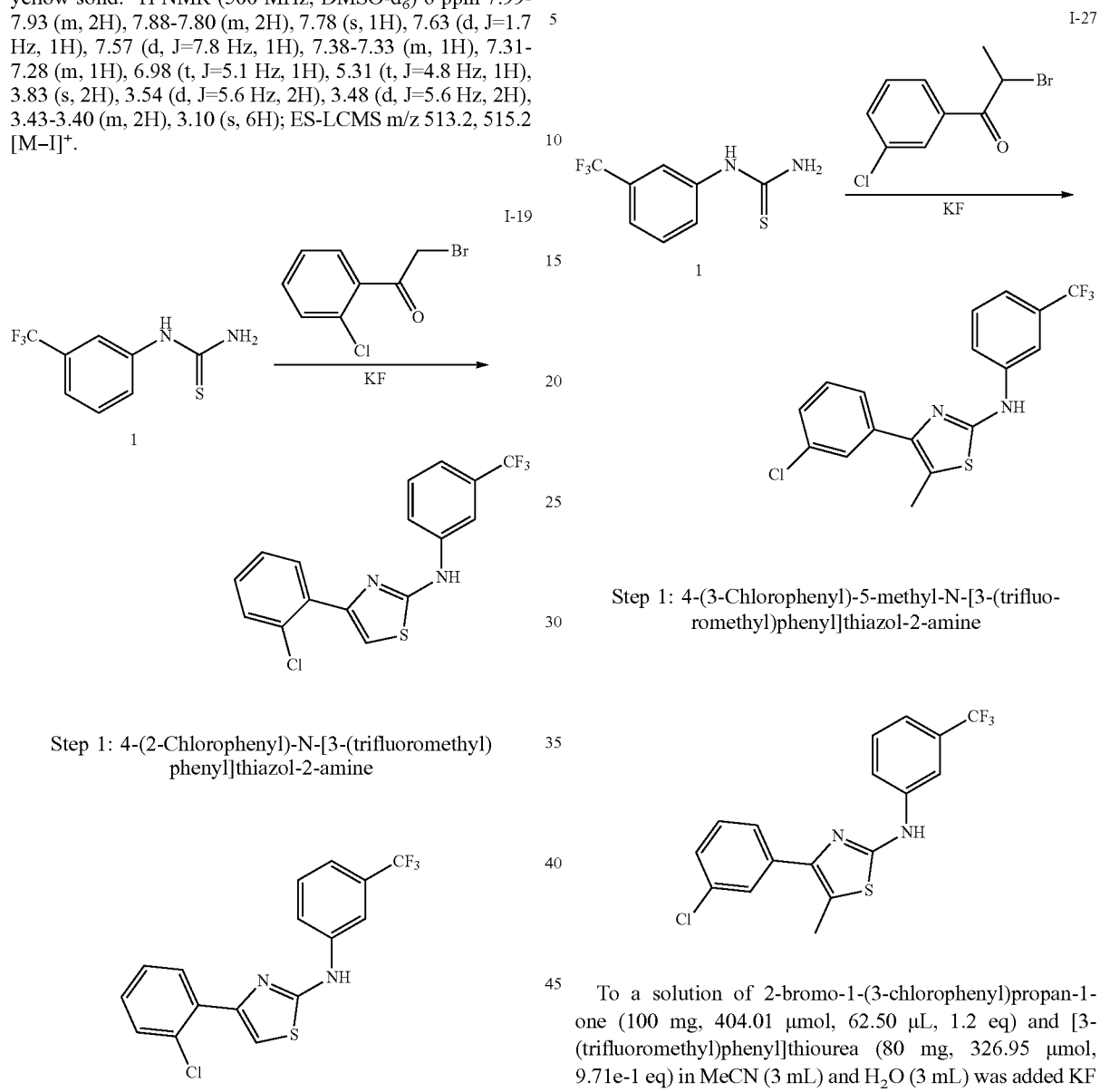

I-19

Step 1: 4-(2-Chlorophenyl)-N-[3-(trifluoromethyl)phenyl]thiazol-2-amine

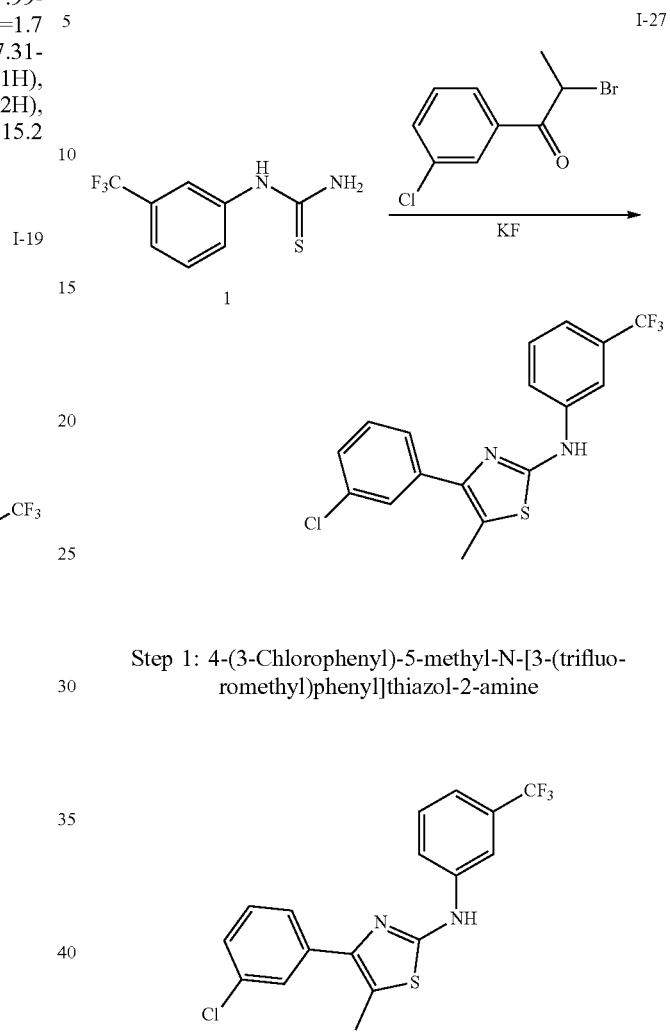

I-27

Step 1: 4-(3-Chlorophenyl)-5-methyl-N-[3-(trifluoromethyl)phenyl]thiazol-2-amine To a solution of 2-bromo-1-(2-chlorophenyl)ethanone (100 mg, 428.28 µmol, 62.50 µL, 1.2 eq) and [3-(trifluoromethyl)phenyl]thiourea (90 mg, 367.82 µmol, 1.03 eq) in ACN (3 mL) and H$_2$O (3 mL) was added KF (40 mg, 688.47 µmol, 1.93 eq). The mixture was stirred at 28° C. for 12 h. The mixture was diluted with water (10 mL) and extracted with EtOAc (10 mL×3). The combined organic layers were dried over Na$_2$SO$_4$, filtered and concentrated under reduced pressure to yield a residue which was purified by preparative HPLC (column: Welch Xtimate C18 150*25 mm*5 um; mobile phase: [water(10 mM NH$_4$HCO$_3$)-ACN]; B %: 62%-92%, 10 min), followed by lyophilization to yield 4-(2-chlorophenyl)-N-[3-(trifluoromethyl)phenyl]thiazol-2-amine (18.26 mg, 51.47 µmol, 14.4% yield, 100.0% purity) as a white solid. $^1$H NMR (400 MHz, DMSO-$d_6$) δ ppm 10.63 (br s, 1H), 8.31 (s, 1H), 7.87 (dd, J=1.6, 7.7 Hz, 1H), 7.76 (d, J=8.3 Hz, 1H), 7.56-7.52 (m, 1H), 7.52-7.48 (m, To a solution of 2-bromo-1-(3-chlorophenyl)propan-1-one (100 mg, 404.01 µmol, 62.50 µL, 1.2 eq) and [3-(trifluoromethyl)phenyl]thiourea (80 mg, 326.95 µmol, 9.71e-1 eq) in MeCN (3 mL) and H$_2$O (3 mL) was added KF (40 mg, 688.46 µmol, 2.04 eq). The mixture was stirred at 28° C. for 12 h. The mixture was diluted with water (10 mL) and extracted with EtOAc (10 mL×3). The combined organic layers were dried over Na$_2$SO$_4$, filtered and concentrated under reduced pressure to yield a residue which was purified by preparative HPLC (column: Agela DuraShell C18 150*25 mm*5 um; mobile phase: [water (0.05% NH$_3$.H$_2$O+10 mM NH$_4$HCO$_3$)-ACN]; B %: 70%-100%, 10 min), followed by lyophilization to yield 4-(3-chlorophenyl)-5-methyl-N-[3-(trifluoromethyl)phenyl]thiazol-2-amine (16.57 mg, 44.93 µmol, 13.3% yield, 100.0% purity) as a white solid. $^1$H NMR (400 MHz, DMSO-$d_6$) δ ppm 10.46 (s, 1H), 8.28 (s, 1H), 7.74-7.67 (m, 2H), 7.62 (d, J=7.8 Hz, 1H), 7.49 (td, J=7.9, 16.0 Hz, 2H), 7.42-7.35 (m, 1H), 7.23 (d, J=7.6 Hz, 1H), 2.44 (s, 3H); ES-LCMS m/z 369.0 [M+H]$^+$.

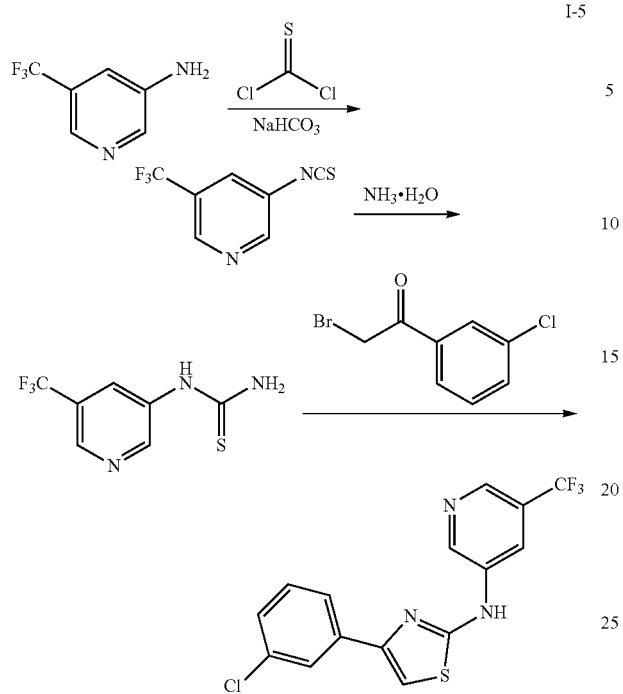

Step 1: 3-Isothiocyanato-5-(trifluoromethyl)pyridine

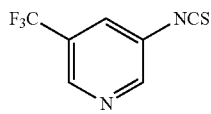

To a solution of 5-(trifluoromethyl)pyridin-3-amine (400 mg, 2.47 mmol, 1 eq) in DCM (5 mL) and H$_2$O (5 mL) was added NaHCO$_3$ (414.58 mg, 4.93 mmol, 2 eq) and thiocarbonyl dichloride (851.13 mg, 7.40 mmol, 567.42 μL, 3 eq) under N$_2$. The mixture was stirred at 0-25° C. for 12 h. TLC (PE/EtOAc=5/1, R$_f$=0.45) showed the reaction was completed. The mixture was concentrated. The residue was treated with water (30 mL), extracted with EtOAC (50 mL×3). The combined organic layers were washed with brine (50 mL), dried over Na$_2$SO$_4$, filtered and concentrated to yield 3-isothiocyanato-5-(trifluoromethyl)pyridine (500 mg, 2.20 mmol, 89.3% yield, 90.0% purity) as a red oil which was used in next step directly without further purification. $^1$H NMR (400 MHz, DMSO-d$_6$) δ ppm 9.01-8.89 (m, 2H), 8.41 (s, 1H);

Step 2: [5-(Trifluoromethyl)-3-pyridyl]thiourea

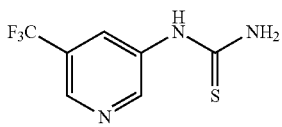

To a solution of 3-isothiocyanato-5-(trifluoromethyl)pyridine (500 mg, 2.20 mmol, 1 eq) in MeCN (10 mL) was added NH$_3$.H$_2$O (413.79 mg, 3.31 mmol, 454.72 μL, 28% purity, 1.5 eq) under N$_2$. The mixture was stirred at 25° C. for 1 h. TLC (PE/EtOAc=3:1, R$_f$=0.08) showed the reaction was completed. The mixture was concentrated and the residue was diluted with water (80 mL), extracted with EtOAc (50 mL×3). The combined organic layers were washed with brine (50 mL), dried over Na$_2$SO$_4$, filtered and concentrated to yield [5-(trifluoromethyl)-3-pyridyl]thiourea (540 mg, 2.20 mmol, 99.7% yield, 90.0% purity) as a red oil which was used in next step directly without further purification. $^1$H NMR (400 MHz, DMSO-d$_6$) δ ppm 10.13 (s, 1H), 8.81 (d, J=2.0 Hz, 1H), 8.65 (s, 1H), 8.57 (s, 1H); ES-LCMS m/z 222.1 [M+H]$^+$.

Step 3: 4-(3-Chlorophenyl)-N-[5-(trifluoromethyl)-3-pyridyl]-2H-thiazol-2-amine

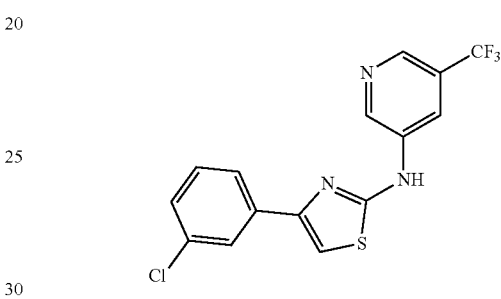

To a solution of [5-(trifluoromethyl)-3-pyridyl]thiourea (540 mg, 2.20 mmol, 1 eq) in MeCN (6 mL) and H$_2$O (6 mL) was added KF (127.82 mg, 2.20 mmol, 1 eq) and 2-bromo-1-(3-chlorophenyl)ethanone (513.68 mg, 2.20 mmol, 1 eq) under N$_2$. The mixture was stirred at 25° C. for 2 h. TLC (PE/EtOAc=3/1, R$_f$=0.67) showed the reaction was completed. The mixture was concentrated and diluted with water (80 mL), extracted with EtOAc (50 mL×3). The combined organic layers were washed with brine (50 mL), dried over Na$_2$SO$_4$, filtered and concentrated to yield a residue which was purified by flash silica gel chromatography (From PE/EtOAc=1/0 to 3/1, R$_f$=0.67) to yield 4-(3-chlorophenyl)-N-[5-(trifluoromethyl)-3-pyridyl]-2H-thiazol-2-amine (33.8 mg, 93.34 μmol, 4.2% yield, 98.8% purity) as a brown solid. $^1$H NMR (400 MHz, DMSO-d$_6$) δ ppm 10.99 (s, 1H), 8.91 (d, J=2.0 Hz, 1H), 8.85 (s, 1H), 8.53 (s, 1H), 7.93 (t, J=1.6 Hz, 1H), 7.84 (d, J=7.8 Hz, 1H), 7.65 (s, 1H), 7.49-7.43 (m, 1H), 7.36 (dd, J=1.0, 8.0 Hz, 1H); ES-LCMS m/z 356.1, 358.1 [M+H]$^+$.

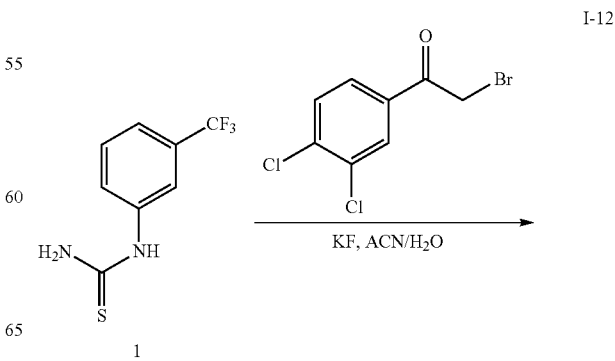

-continued

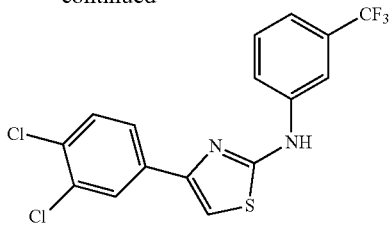

Step 1: 4-(3,4-Dichlorophenyl)-N-[3-(trifluoromethyl)phenyl]thiazol-2-amine

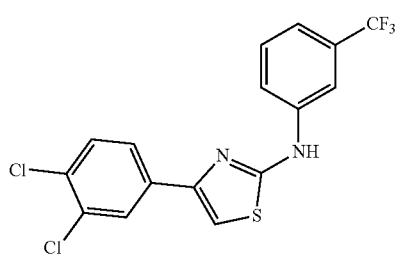 [SMILES: FC(F)(F)c1cccc(Nc2nc(-c3ccc(Cl)c(Cl)c3)cs2)c1]

To a solution of 2-bromo-1-(3,4-dichlorophenyl)ethanone (100 mg, 373.22 μmol, 1 eq) in ACN (3 mL) and H$_2$O (3 mL) was added KF (22 mg, 378.66 μmol, 1.01 eq) and [3-(trifluoromethyl)phenyl]thiourea (92 mg, 376.00 μmol, 1.01 eq). The mixture was stirred at 25 C for 15 h. TLC (PE/EtOAc=3/1, R$_f$=0.43) showed one main spot formed. The reaction mixture was diluted with H$_2$O (10 mL) and extracted with EtOAc (10 mL×3). The organic layer was dried over Na$_2$SO$_4$, filtered and concentrated under reduced pressure to yield a residue which was purified by flash silica gel chromatography (from PE/EtOAc=100/1 to 3/1, TLC: PE/EtOAc=3/1, R$_f$=0.43) to yield 4-(3,4-dichlorophenyl)-N-[3-(trifluoromethyl)phenyl]thiazol-2-amine (17.76 mg, 44.93 μmol, 12.0% yield, 98.5% purity) as a yellow solid. $^1$H NMR (400 MHz, CD$_3$OD) δ ppm 8.30 (s, 1H), 8.04 (d, J=1.96 Hz, 1H), 7.77 (dd, J=1.96, 8.31 Hz, 2H), 7.44-7.52 (m, 2H), 7.24 (d, J=7.58 Hz, 1H), 7.20 (s, 1H); ES-LCMS m/z 388.9 [M+H]$^+$.

Step 1: 4-(4-Methoxyphenyl)-N-[3-(trifluoromethyl)phenyl]thiazol-2-amine

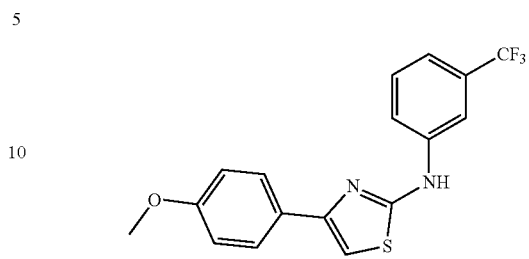

To a solution of 2-chloro-1-(4-methoxyphenyl)ethanone (100 mg, 541.65 μmol, 1 eq) and [3-(trifluoromethyl)phenyl]thiourea (132.22 mg, 540.38 μmol, 9.98e$^{-1}$ eq) in ACN (3 mL) and H$_2$O (3 mL) was added KF (38 mg, 654.04 μmol, 1.21 eq). The mixture was stirred at 25° C. for 12 h. TLC (PE/EtOAc=3/1, R$_f$=0.52) showed one main spot formed. The reaction mixture was diluted with H$_2$O (10 mL) and extracted with EtOAc (10 mL×3). The organic layer was dried over Na$_2$SO$_4$, filtered and concentrated under reduced pressure to yield a residue which was purified by flash silica gel chromatography (from PE/EtOAc=100/1 to 3/1, TLC: PE/EtOAc=3/1, R$_f$=0.52) to yield 4-(4-methoxyphenyl)-N-[3-(trifluoromethyl)phenyl]thiazol-2-amine (16.34 mg, 46.64 μmol, 8.6% yield, 100.0% purity) as a yellow solid. $^1$H NMR (400 MHz, CD$_3$OD) δ ppm 8.31 (s, 1H), 7.88-7.79 (m, 3H), 7.49 (t, J=8.07 Hz, 1H), 7.23 (d, J=7.58 Hz, 1H), 6.99-6.93 (m, 3H), 3.84 (s, 3H). ES-LCMS m/z 351.1 [M+H]$^+$.

I-47

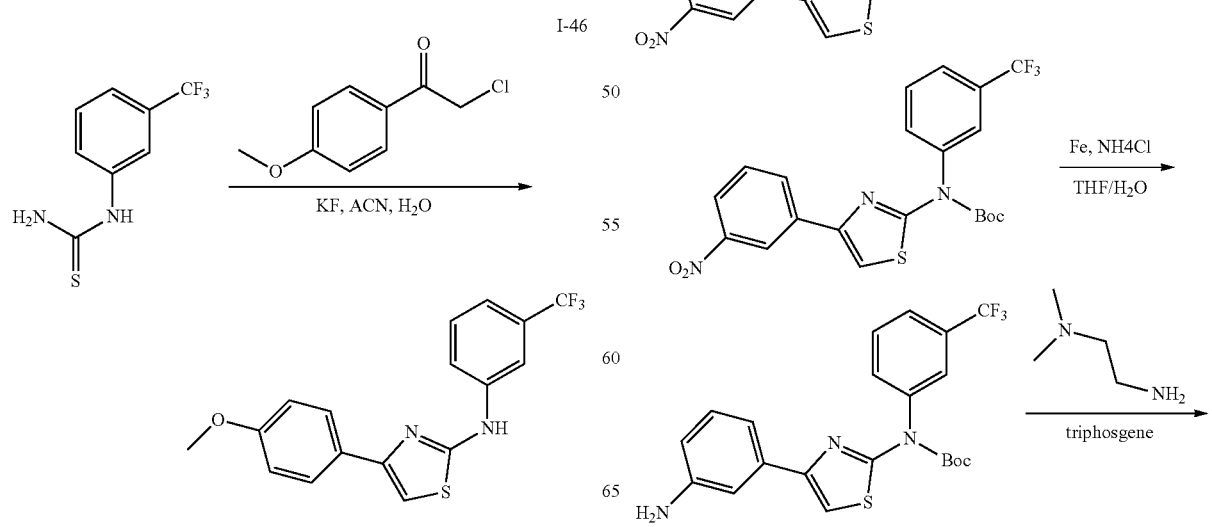

-continued

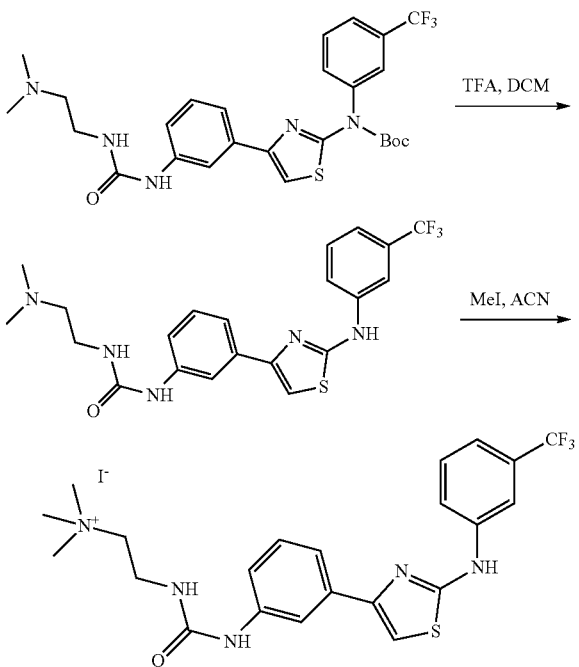

Step 1: tert-Butyl N-[4-(3-nitrophenyl)thiazol-2-yl]-N-[3-(trifluoromethyl)phenyl]carbamate

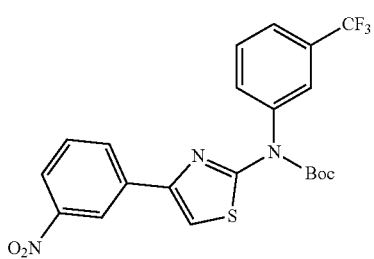 [SMILES: CC(C)(C)OC(=O)N(c1cccc(C(F)(F)F)c1)c1nc(-c2cccc([N+](=O)[O-])c2)cs1]

To a solution of 4-(3-nitrophenyl)-N-[3-(trifluoromethyl)phenyl]thiazol-2-amine (3.3 g, 8.58 mmol, 1 eq) in THF (15 mL) was added DMAP (838.70 mg, 6.87 mmol, 0.8 eq) and tert-butoxycarbonyl tert-butyl carbonate (2.81 g, 12.87 mmol, 2.96 mL, 1.5 eq). The mixture was stirred at 80° C. for 1 h. TLC (PE/EtOAc=3/1, $R_f$=0.5) showed that one new point was formed and start material was consumed completely. The reaction mixture was quenched by addition of $H_2O$ (20 mL) and extracted with EtOAc (30 mL×3). The combined organic layers were washed with brine (30 mL×1), dried over $Na_2SO_4$, filtered and concentrated under reduced pressure to yield a residue which was purified by flash silica gel chromatography (from PE/EtOAc=100/1 to 8/1, TLC: PE/EtOAc=3/1, $R_f$=0.50) to yield tert-butyl N-[4-(3-nitrophenyl)thiazol-2-yl]-N-[3-(trifluoromethyl)phenyl]carbamate (3.2 g, 6.88 mmol, 80.1% yield, 100.0% purity) as a light yellow solid. $^1$H NMR (400 MHz, DMSO-$d_6$) δ ppm 8.38 (t, J=1.7 Hz, 1H), 8.11-8.04 (m, 3H), 7.94 (s, 1H), 7.86-7.72 (m, 3H), 7.63 (t, J=7.9 Hz, 1H), 1.41 (s, 9H); ES-LCMS m/z 365.9 [M-Boc+H]$^+$.

Step 2: tert-Butyl N-[4-(3-aminophenyl)thiazol-2-yl]-N-[3-(trifluoromethyl)phenyl]carbamate

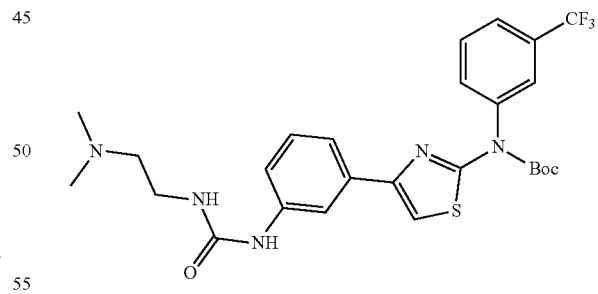

To a solution of tert-butyl N-[4-(3-nitrophenyl)thiazol-2-yl]-N-[3-(trifluoromethyl)phenyl]carbamate (3.2 g, 6.88 mmol, 1 eq) in THF (90 mL) and $H_2O$ (90 mL) was added Fe (383.98 mg, 6.88 mmol, 1 eq) and $NH_4Cl$ (367.75 mg, 6.88 mmol, 1 eq). The mixture was stirred at 35° C. for 2 h. TLC (PE/EtOAc=3/1, $R_f$=0.4) showed that new point was formed and start material was consumed completely. The reaction mixture was quenched by addition of $H_2O$ (100 mL) and extracted with EtOAc (200 mL×3). The combined organic layers were washed with brine (30 mL×1), dried over $Na_2SO_4$, filtered and concentrated under reduced pressure to yield a residue which was purified by flash silica gel chromatography (from PE/EtOAc=100/1 to 3/1, TLC: PE/EtOAc=3/1, $R_f$=0.4) to yield tert-butyl N-[4-(3-aminophenyl)thiazol-2-yl]-N-[3-(trifluoromethyl)phenyl]carbamate (1.8 g, 4.13 mmol, 60.1% yield, 100.0% purity) as a white solid. $^1$H NMR (400 MHz, DMSO-$d_6$) δ ppm 7.84 (s, 1H), 7.79-7.74 (m, 1H), 7.74-7.66 (m, 2H), 7.46 (s, 1H), 6.97-6.87 (m, 1H), 6.80-6.69 (m, 2H), 6.42 (dd, J=1.2, 7.8 Hz, 1H), 4.99 (s, 2H), 1.36 (s, 9H); ES-LCMS m/z 334.9 [M-t-Bu+H]$^+$.

Step 3: tert-Butyl N-[4-[3-[2-(dimethylamino)ethoxycarbonylamino]phenyl]thiazol-2-yl]-N-[3-(trifluoromethyl)phenyl]carbamate To a solution of tert-butyl N-[4-(3-aminophenyl)thiazol-2-yl]-N-[3-(trifluoromethyl)phenyl]carbamate (110 mg, 252.61 μmol, 1 eq) in THF (3 mL) was added bis(trichloromethyl) carbonate (80 mg, 269.59 μmol, 1.07 eq), DIEA (97.94 mg, 757.82 μmol, 131.99 μL, 3 eq) and stirred at 80° C. for 1 h. The reaction mixture was concentrated to yield tert-butyl (4-(3-((chlorocarbonyl)amino)phenyl)thiazol-2-yl)(3-(trifluoromethyl)phenyl)carbamate (crude). To a solution of N',N'-dimethylethane-1,2-diamine (66.80 mg, 757.82 μmol, 82.78 μL, 3 eq) in DCM (1 mL) was added DIEA (97.94 mg, 757.82 μmol, 131.99 μL, 3 eq), tert-butyl (4-(3-

((chlorocarbonyl)amino)phenyl)thiazol-2-yl)(3-(trifluoromethyl)phenyl)carbamate (crude) in DCM (2 mL) and stirred at 40° C. for 11 h. The reaction mixture was concentrated, diluted with H₂O (20 mL) and extracted with DCM (20 mL×3). The combine organic layers were dried over anhydrous Na₂SO₄, filtered and concentrated to yield tert-butyl N-[4-[3-[2-(dimethylamino)ethylcarbamoylamino]phenyl]thiazol-2-yl]-N-[3-(trifluoromethyl)phenyl]carbamate (250 mg, 204.69 μmol, 81.0% yield, 45.0% purity) as colorless oil. ¹H NMR (500 MHz, DMSO-d₆) δ ppm 8.62 (br s, 1H), 7.89 (s, 1H), 7.80 (s, 1H), 7.75 (s, 1H), 7.58 (s, 1H), 7.51 (s, 1H), 7.36 (d, J=7.9 Hz, 1H), 7.22 (s, 1H), 7.18-7.11 (m, 2H), 6.10-6.05 (m, 1H), 3.06 (d, J=7.0 Hz, 2H), 2.36-2.36 (m, 2H), 2.17 (s, 6H), 1.40 (s, 9H); ES-LCMS m/z 550.2 [M+H]⁺.

Step 4: 1-[2-(Dimethylamino)ethyl]-3-[3-[2-[3-(trifluoromethyl)anilino]thiazol-4-yl]phenyl]urea

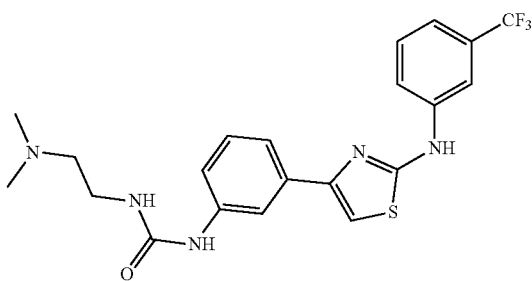 [SMILES: CN(C)CCNC(=O)Nc1cccc(-c2csc(Nc3cccc(C(F)(F)F)c3)n2)c1]

To a solution of tert-butyl N-[4-[3-[2-(dimethylamino)ethylcarbamoylamino]phenyl]thiazol-2-yl]-N-[3-(trifluoromethyl)phenyl]carbamate (250 mg, 204.69 μmol, 1 eq) in DCM (5 mL) was added TFA (1 mL). The mixture was stirred at 25° C. for 0.5 h. The mixture was diluted with H₂O (20 mL) and extracted with DCM (20 mL×3). The combine organic layers were dried over anhydrous Na₂SO₄, filtered and concentrated to yield a residue which was purified by preparative HPLC (column: Agela DuraShell C18 150*25 mm*5 μm; mobile phase: [water (0.05% ammonia hydroxide v/v)-ACN]; B %: 40%-80%, 10 min) and lyophilized to yield 1-[2-(dimethylamino)ethyl]-3-[3-[2-[3-(trifluoromethyl)anilino]thiazol-4-yl]phenyl]urea (40 mg, 88.99 μmol, 43.5% yield, 100.0% purity) as a white solid. ¹H NMR (500 MHz, DMSO-d₆) δ ppm 10.63 (s, 1H), 8.70 (s, 1H), 8.19 (s, 1H), 7.97 (d, J=8.7 Hz, 1H), 7.92 (s, 1H), 7.57 (t, J=8.0 Hz, 1H), 7.44 (d, J=7.6 Hz, 1H), 7.36-7.32 (m, 1H), 7.32-7.25 (m, 3H), 6.12 (t, J=5.2 Hz, 1H), 3.19 (q, J=6.1 Hz, 2H), 2.36-2.31 (m, 2H), 2.18 (s, 6H); ES-LCMS m/z 450.2 [M+H]⁺.

Step 5: 1-[3-[2-[3-(Trifluoromethyl)anilino]thiazol-4-yl]phenyl]-3-[2-[BLAH(trimethyl)-azanyl]ethyl]urea

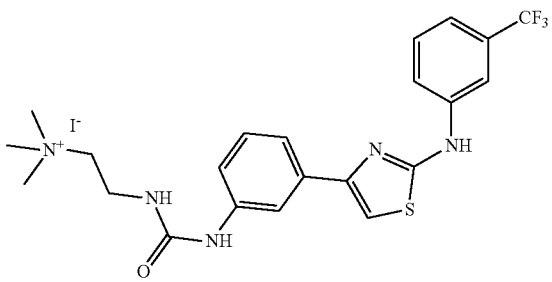 [SMILES: C[N+](C)(C)CCNC(=O)Nc1cccc(-c2csc(Nc3cccc(C(F)(F)F)c3)n2)c1 ; [I-]]

To a solution of 1-[2-(dimethylamino)ethyl]-3-[3-[2-[3-(trifluoromethyl)anilino]thiazol-4-yl]phenyl]urea (20 mg, 44.49 μmol, 1 eq) in ACN (2 mL) was added MeI (31.58 mg, 222.47 μmol, 13.85 μL, 5 eq) under N₂ atmosphere. The mixture was stirred at 25° C. for 1 h. The reaction mixture was concentrated to yield a residue which was added ACN (15 mL) and H₂O (30 mL) and lyophilized to yield 1-[3-[2-[3-(trifluoromethyl)anilino]thiazol-4-yl]phenyl]-3-[2-[BLAH(trimethyl)-azanyl]ethyl]urea (17.90 mg, 30.27 μmol, 68.0% yield, 100.0% purity) as a yellow solid. ¹H NMR (500 MHz, DMSO-d₆) δ ppm 10.63 (s, 1H), 8.84 (s, 1H), 8.23 (s, 1H), 7.97 (s, 1H), 7.94 (d, J=8.4 Hz, 1H), 7.57 (t, J=7.9 Hz, 1H), 7.48 (d, J=7.6 Hz, 1H), 7.40-7.36 (m, 1H), 7.33-7.28 (m, 2H), 7.27 (s, 1H), 6.43 (t, J=5.7 Hz, 1H), 3.56 (d, J=6.0 Hz, 2H), 3.44-3.40 (m, 2H), 3.13 (s, 9H); ES-LCMS m/z 464.1 [M−I]⁺.

I-58

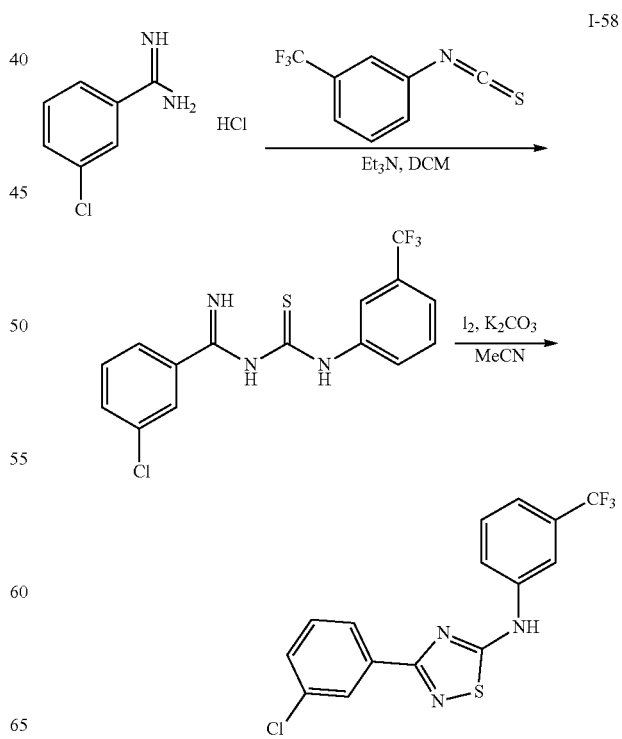

Step 1: 1-(3-Chlorobenzenecarboximidoyl)-3-[3-(trifluoromethyl)phenyl]thiourea

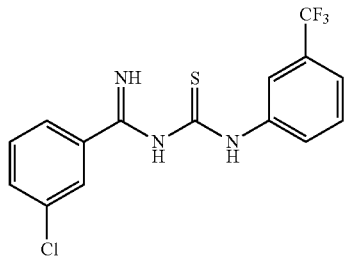 [SMILES: N=C(NC(=S)Nc1cccc(C(F)(F)F)c1)c1cccc(Cl)c1]

To a solution of 3-chlorobenzamidine (300 mg, 1.57 mmol, 1 eq, HCl) in DCM (10 mL) was added Et$_3$N (349.55 mg, 3.45 mmol, 480.82 µL, 2.2 eq) and stirred at 25° C. for 10 min. 1-isothiocyanato-3-(trifluoromethyl)benzene (319.04 mg, 1.57 mmol, 238.09 µL, 1 eq) was added and the mixture was stirred at 25° C. for 16 h. TLC (PE/EtOAc=3/1, R$_f$=0.69) indicated the starting material was consumed completely and one new spot formed. The mixture was concentrated. The residue was purified by flash silica gel chromatography (PE/EtOAc=1/0 to 3/1) to yield 1-(3-chlorobenzenecarboximidoyl)-3-[3-(trifluoromethyl)phenyl]thiourea (280 mg, 626.08 µmol, 39.9% yield, 80% purity) as a yellow solid. $^1$H NMR (500 MHz, CDCl$_3$) δ ppm 11.44 (br s, 2H), 8.41 (s, 1H), 8.03-8.01 (m, 2H), 7.92-7.90 (m, 1H), 7.80-7.78 (m, 1H), 7.70 (d, J=7.5 Hz, 2H), 7.53 (dd, J=1.0 Hz, 7.5 Hz, 2H); ES-LCMS m/z 358.1, 360.1 [M+H]$^+$.

Step 2: 3-(3-Chlorophenyl)-N-[3-(trifluoromethyl)phenyl]-1,2,4-thiadiazol-5-amine

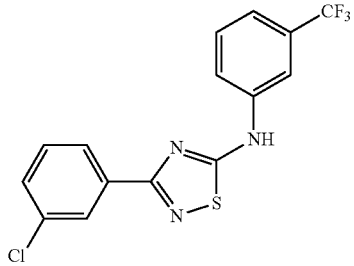 [SMILES: FC(F)(F)c1cccc(Nc2nc(-c3cccc(Cl)c3)ns2)c1]

To a solution of 1-(3-chlorobenzenecarboximidoyl)-3-[3-(trifluoromethyl)phenyl]thiourea (150 mg, 335.40 µmol, 1 eq) in MeCN (5 mL) were added I$_2$ (102.15 mg, 402.48 µmol, 1.2 eq) and K$_2$CO$_3$ (69.53 mg, 503.10 µmol, 1.5 eq). The mixture was stirred at 25° C. for 30 min. The reaction mixture was treated with sat.aq. Na$_2$S$_2$O$_3$ (10 mL) and water (20 mL), extracted with EtOAc (20×2 mL). The combined organic phases were washed with brine (15 mL), dried over anhydrous Na$_2$SO$_4$, filtered and concentrated to give a residue which was purified by preparative HPLC (column: Welch Xtimate C18 150*25 mm*5 um; mobile phase: [water (10 mM NH$_4$HCO$_3$)-ACN]; B %: 75%-100%, 10 min), followed by lyophilization to yield 3-(3-chlorophenyl)-N-[3-(trifluoromethyl)phenyl]-1,2,4-thiadiazol-5-amine (41 mg, 115.24 µmol, 34.36% yield, 100% purity) as colorless gum. $^1$H NMR (500 MHz, CDCl$_3$) δ ppm 8.27 (s, 1H), 8.21 (t, J=1.6 Hz, 1H), 8.09 (td, J=1.4, 7.5 Hz, 1H), 7.60 (s, 1H), 7.54 (td, J=8.2, 16.0 Hz, 2H), 7.45-7.35 (m, 3H); ES-LCMS m/z 355.9, 357.9 [M+H]$^+$.

I-14

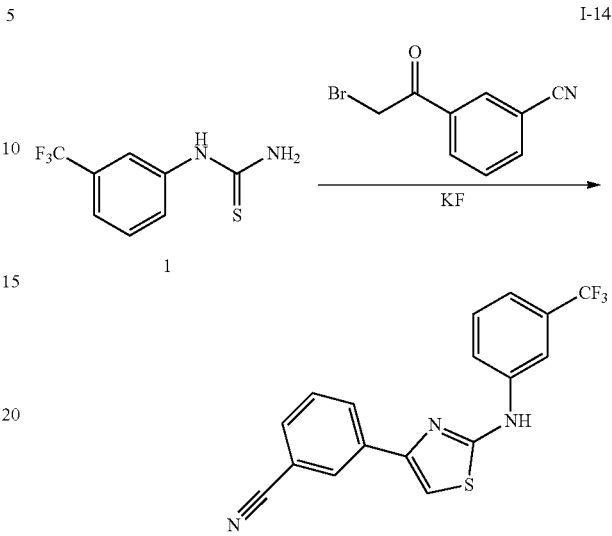

Step 1: 3-[2-[3-(Trifluoromethyl)anilino]thiazol-4-yl]benzonitrile

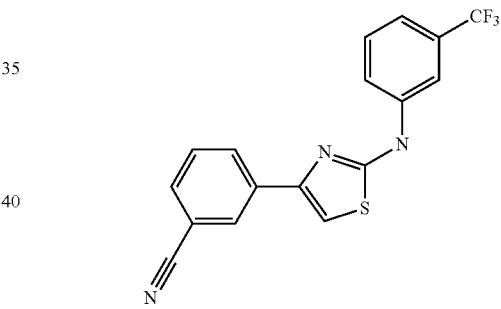

To a solution of [3-(trifluoromethyl)phenyl]thiourea (300 mg, 1.23 mmol, 1 eq) and 3-(2-bromoacetyl)benzonitrile (302.18 mg, 1.35 mmol, 1.1 eq) in MeCN (3 mL) and H$_2$O (3 mL) was added KF (71.24 mg, 1.23 mmol, 1 eq). The mixture was stirred at 25° C. for 2 h under N$_2$ atmosphere. To the mixture was added water (30 mL) and extracted with ethyl acetate (30 mL×3). The combined organic phase was washed with brine (20 mL), dried over anhydrous Na$_2$SO$_4$, filtered and concentrated in vacuum to yield a residue which was purified by flash silica gel chromatography (from PE/EtOAc=200/1 to 1/1, TLC: PE/EtOAc=1/1, R$_f$=0.40) to yield a product which was triturated with PE (10 mL) at 25° C. for 1 h to yield 3-[2-[3-(trifluoromethyl)anilino]thiazol-4-yl]benzonitrile (400 mg, 1.16 mmol, 94.5% yield, 100% purity) as a yellow solid. $^1$H NMR (500 MHz, DMSO-d$_6$) δ ppm 10.71 (s, 1H), 8.34 (d, J=7.6 Hz, 2H), 8.24 (d, J=8.1 Hz, 1H), 7.86 (d, J=8.1 Hz, 1H), 7.78 (d, J=7.6 Hz, 1H), 7.69-7.64 (m, 2H), 7.59 (t, J=7.9 Hz, 1H), 7.31 (d, J=7.8 Hz, 1H); ES-LCMS m/z 346.1 [M+H]$^+$.

Step 1: 3-[2-(Dimethylamino)ethyl]-1-[4-(3-nitrophenyl)thiazol-2-yl]-1-[3-(trifluoromethyl)phenyl]urea

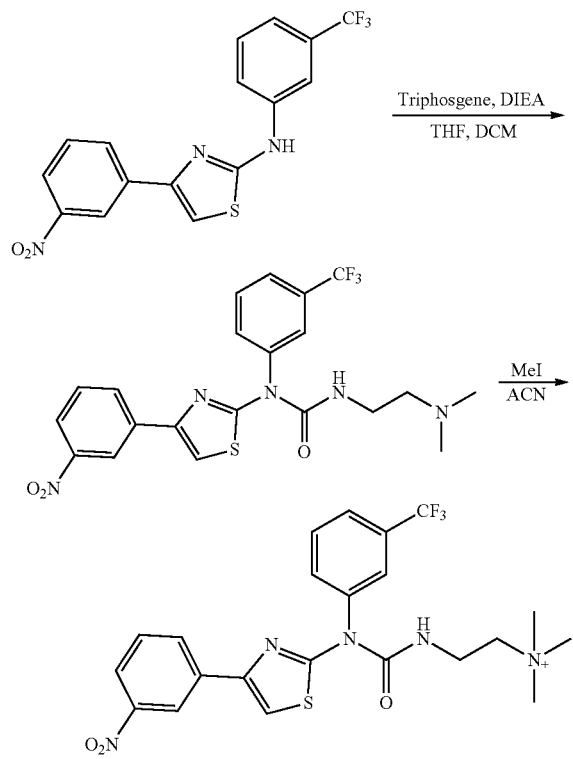

To a solution of 4-(3-nitrophenyl)-N-[3-(trifluoromethyl)phenyl]thiazol-2-amine (100 mg, 273.73 μmol, 1 eq) in THF (4 mL) was added DIEA (106.13 mg, 821.18 μmol, 143.03 μL, 3 eq) and Triphosgene (97.47 mg, 328.47 μmol, 1.2 eq). The mixture was stirred at 80° C. for 1 h. The reaction mixture was concentrated to yield trichloromethyl (4-(3-nitrophenyl)thiazol-2-yl)(3-(trifluoromethyl)phenyl)carbamate (crude). To a solution of N',N'-dimethylethane-1,2-diamine (72.39 mg, 821.18 μmol, 89.70 μL, 3 eq) in DCM (6 mL) was added DIEA (106.13 mg, 821.18 μmol, 143.03 μL, 3 eq) and trichloromethyl (4-(3-nitrophenyl)thiazol-2-yl)(3-(trifluoromethyl)phenyl)carbamate (crude). The mixture was stirred at 40° C. for 11 h. The mixture was quenched with saturated aqueous NaHCO₃ (30 mL) and extracted with EtOAc (30 mL×3). The combined organic layers were washed with brine (30 mL), dried over Na₂SO₄, filtered and concentrated under reduced pressure to yield a residue which was purified by preparative HPLC (column: Welch Xtimate C18 150*25 mm*5 μm; mobile phase: [water (10 mM NH₄HCO₃)-ACN]; B %: 51%-81%, 10 min) to yield 3-[2-(dimethylamino)ethyl]-1-[4-(3-nitrophenyl)thiazol-2-yl]-1-[3-(trifluoromethyl)phenyl]urea (20 mg, 41.71 μmol, 15.2% yield, 100.0% purity) as a white solid. $^1$H NMR (500 MHz, CDCl₃) δ ppm 8.61 (br s, 1H), 8.55 (s, 1H), 8.27 (d, J=8.0 Hz, 1H), 8.19-8.14 (m, 1H), 7.80 (d, J=8.0 Hz, 1H), 7.74-7.69 (m, 2H), 7.64 (d, J=8.0 Hz, 1H), 7.58 (t, J=8.0 Hz, 1H), 7.20 (s, 1H), 3.53-3.49 (m, 2H), 2.55 (t, J=5.5 Hz, 2H), 2.29 (s, 6H); ES-LCMS m/z 480.2 [M+H]⁺.

Step 2: 1-[4-(3-Nitrophenyl)thiazol-2-yl]-1-[3-(trifluoromethyl)phenyl]-3-[2-[BLAH(trimethyl)-azanyl]ethyl]urea

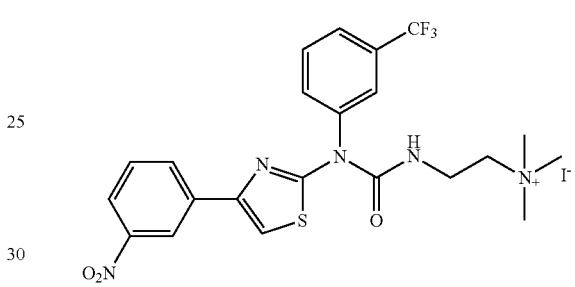

To a solution of 3-[2-(dimethylamino)ethyl]-1-[4-(3-nitrophenyl)thiazol-2-yl]-1-[3-(trifluoromethyl)phenyl]urea (20 mg, 41.71 μmol, 1 eq) in ACN (5 mL) was added MeI (5.92 mg, 41.71 μmol, 2.60 μL, 1 eq). The mixture was stirred at 28° C. for 2 h. The solution was quenched with water (10 mL) and lyophilized to yield 1-[4-(3-nitrophenyl)thiazol-2-yl]-1-[3-(trifluoromethyl)phenyl]-3-2-[BLAH(trimethyl)-azanyl]ethyl]urea (21.17 mg, 31.85 μmol, 76.4% yield, 93.5% purity) as a white solid. $^1$H NMR (500 MHz, CD₃OD) δ ppm 8.51 (s, 1H), 8.10 (dd, J=8.0, 18.0 Hz, 2H), 7.93 (d, J=8.0 Hz, 1H), 7.88-7.82 (m, 2H), 7.75 (d, J=8.0 Hz, 1H), 7.65 (s, 1H), 7.58 (t, J=8.0 Hz, 1H), 3.77 (t, J=6.0 Hz, 2H), 3.60-3.55 (m, 2H), 3.23 (s, 9H); ES-LCMS m/z 494.6 [M−I]⁺.

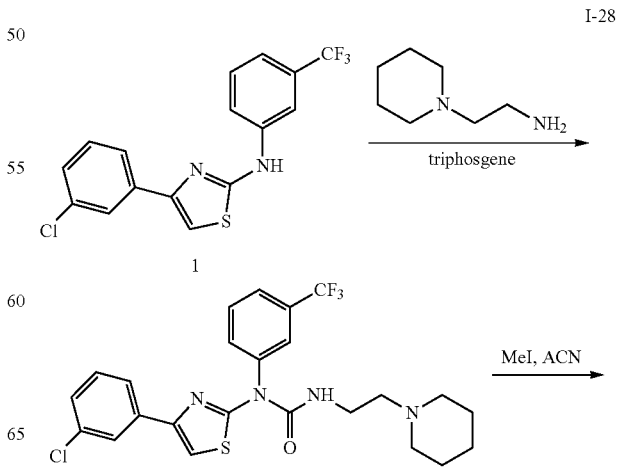

-continued

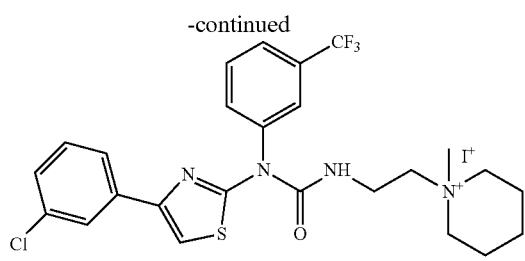

Step 1: 1-[4-(3-Chlorophenyl)thiazol-2-yl]-3-[2-(1-piperidyl)ethyl]-1-[3-(trifluoromethyl)phenyl]urea

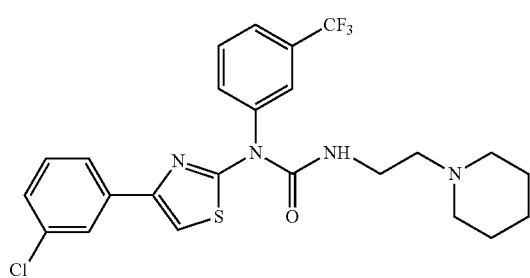 [SMILES: O=C(NCCN1CCCCC1)N(c1cccc(C(F)(F)F)c1)c1nc(-c2cccc(Cl)c2)cs1]

To a solution of 4-(3-chlorophenyl)-N-[3-(trifluoromethyl)phenyl]thiazol-2-amine (200 mg, 563.73 μmol, 1 eq) in THF (3 mL) was added bis(trichloromethyl) carbonate (200.74 mg, 676.48 μmol, 1.2 eq), DIEA (218.58 mg, 1.69 mmol, 294.58 μL, 3 eq) and stirred at 80° C. for 1 h. The reaction mixture was concentrated to yield (4-(3-chlorophenyl)thiazol-2-yl)(3-(trifluoromethyl)phenyl)carbamic chloride (crude). To a solution of 2-(1-piperidyl)ethanamine (361.40 mg, 2.82 mmol, 402.00 μL, 5 eq) in DCM (1 mL) was added DIEA (218.58 mg, 1.69 mmol, 294.58 μL, 3 eq), (4-(3-chlorophenyl)thiazol-2-yl)(3-(trifluoromethyl)phenyl) carbamic chloride (crude) in DCM (2 mL). The mixture was stirred at 40° C. for 4 h. The mixture was diluted with H$_2$O (20 mL) and extracted with DCM (20 mL×3). The combine organic layers were dried over anhydrous Na$_2$SO$_4$, filtered and concentrated to yield a residue which was purified by preparative HPLC (column: Phenomenex Gemini-NX 80*40 mm*3 μm; mobile phase: [water (0.05% NH$_3$H$_2$O+ 10 mM NH$_4$HCO$_3$)-ACN]; B %: 69%-93%, 8 min) and lyophilized to yield 1-[4-(3-chlorophenyl)thiazol-2-yl]-3-[2-(1-piperidyl)ethyl]-1-[3-(trifluoromethyl)phenyl]urea (80 mg, 157.18 μmol, 27.9% yield, 100.0% purity) as a white solid. $^1$H NMR (500 MHz, DMSO-d$_6$) δ ppm 7.96-7.90 (m, 2H), 7.86-7.77 (m, 2H), 7.73 (s, 1H), 7.67 (s, 1H), 7.62 (d, J=7.8 Hz, 1H), 7.40-7.33 (m, 1H), 7.33-7.28 (m, 1H), 6.91 (t, J=4.7 Hz, 1H), 3.27-3.20 (m, 2H), 2.37-2.26 (m, 6H), 1.41-1.30 (m, 6H); ES-LCMS m/z 509.2, 511.2, [M+H]$^+$.

Step 2: 1-[4-(3-Chlorophenyl)thiazol-2-yl]-3-[2-(1-BLAH-1-methyl-1azinan-1-yl)ethyl]-1-[3-(trifluoromethyl)phenyl]urea

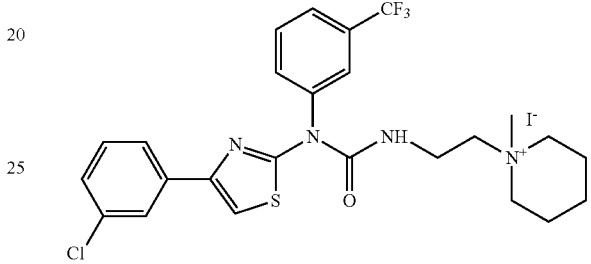

To a solution of 1-[4-(3-chlorophenyl)thiazol-2-yl]-3-[2-(1-piperidyl)ethyl]-1-[3-(trifluoromethyl)phenyl]urea (40 mg, 78.59 μmol, 1 eq) in ACN (5 mL) was added MeI (223.09 mg, 1.57 mmol, 97.85 μL, 20 eq) in one portion at 25° C. under N$_2$ atmosphere. The mixture was stirred at 25° C. for 1 h. The reaction mixture was concentrated to yield a residue which was dissolved in MeCN (15 mL) and H$_2$O (30 mL) and lyophilized to yield 1-[4-(3-chlorophenyl)thiazol-2-yl]-3-[2-(1-BLAH-1-methyl-1azinan-1-yl)ethyl]-1-[3-(trifluoromethyl)phenyl]urea (34.33 mg, 52.74 μmol, 67.1% yield, 100.0% purity) as a white solid. $^1$H NMR (500 MHz, DMSO-d$_6$) δ ppm 7.99-7.93 (m, 2H), 7.88-7.83 (m, 1H), 7.83-7.79 (m, 1H), 7.78 (s, 1H), 7.63 (s, 1H), 7.57 (d, J=7.6 Hz, 1H), 7.39-7.33 (m, 1H), 7.32-7.27 (m, 1H), 6.97 (t, J=5.3 Hz, 1H), 3.55 (d, J=5.5 Hz, 2H), 3.46-3.42 (m, 2H), 3.40-3.35 (m, 4H), 3.04 (s, 3H), 1.80-1.70 (m, 4H), 1.58-1.48 (m, 2H); ES-LCMS m/z 523.2, 525.2 [M−I]$^+$.

I-41

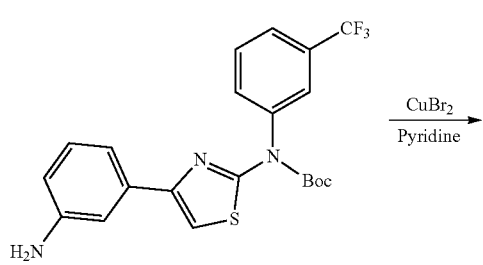

1

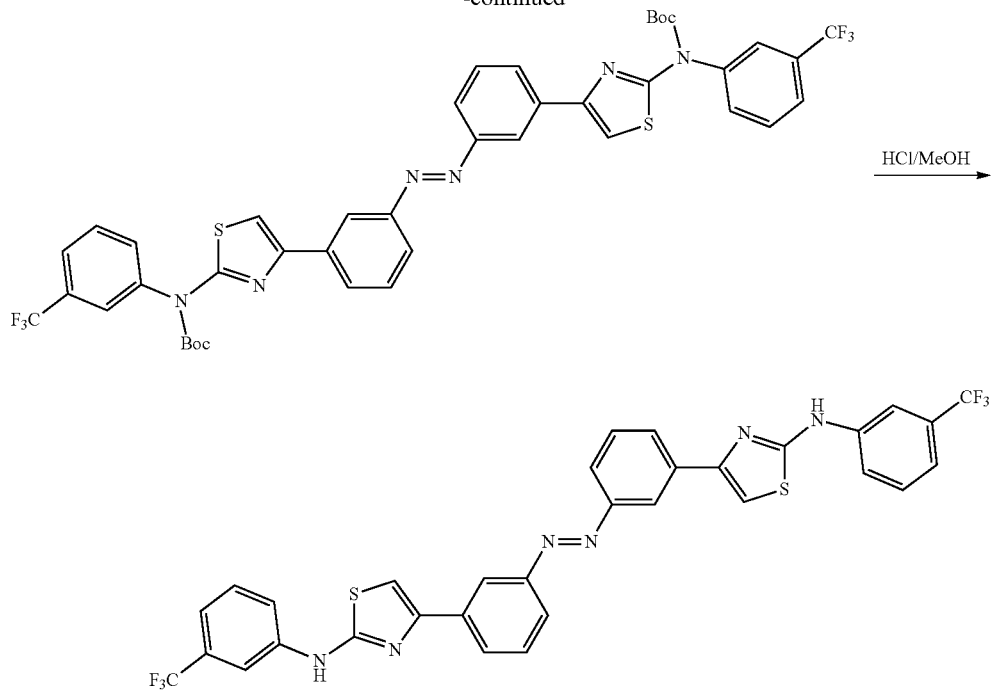

Step 1: tert-Butyl N-[4-[3-[(E)-[3-[2-[N-tert-butoxycarbonyl-3-(trifluoromethyl)anilino]thiazol-4-yl]phenyl]azo]phenyl]thiazol-2-yl]-N-[3-(trifluoromethyl)phenyl]carbamate

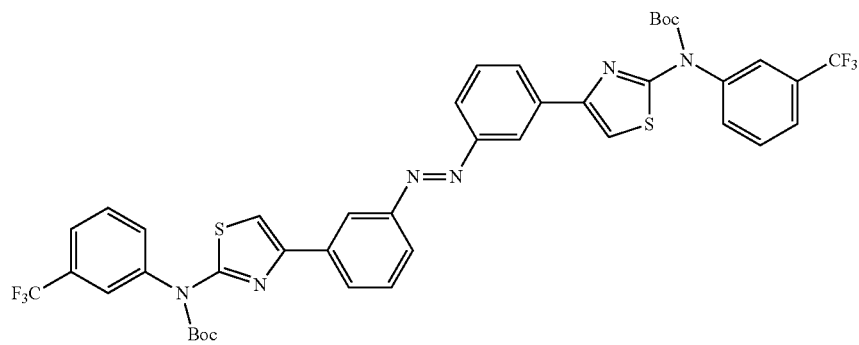 [SMILES: CC(C)(C)OC(=O)N(c1cccc(C(F)(F)F)c1)c1nc(-c2cccc(/N=N/c3cccc(-c4csc(N(C(=O)OC(C)(C)C)c5cccc(C(F)(F)F)c5)n4)c3)c2)cs1]

To a stirred solution of tert-butyl N-[4-(3-aminophenyl)thiazol-2-yl]-N-[3-(trifluoromethyl)phenyl]carbamate (150 mg, 344.46 μmol, 1 eq) in toluene (5 mL) was added CuBr (2.47 mg, 17.22 μmol, 0.05 eq) and pyridine (2.72 mg, 34.45 μmol, 2.78 μL, 0.1 eq). The reaction mixture was stirred at 80° C. for 48 h. The reaction mixture was concentrated to yield a residue which was purified by preparative TLC (PE/EtOAc=3/1, TLC: PE/EtOAc=3/1, $R_f$=0.60) to yield tert-butyl N-[4-[3-[(E)-[3-[2-[N-tert-butoxycarbonyl-3-(trifluoromethyl)anilino]thiazol-4-yl]phenyl]azo]phenyl]thiazol-2-yl]-N-[3-(trifluoromethyl)phenyl]carbamate (75 mg, 61.25 μmol, 17.8% yield, 70.8% purity) as yellow solid. $^1$H NMR (400 MHz, DMSO-$d_6$) δ ppm 8.11 (s, 2H), 7.95 (s, 2H), 7.92 (s, 2H), 7.84-7.78 (m, 6H), 7.75 (d, J=7.6 Hz, 2H), 7.71 (d, J=8.6 Hz, 2H), 7.61-7.54 (m, 2H), 1.42 (s, 18H); ES-LCMS m/z 867.2 [M+H]$^+$, 667.1 [M-2Boc+H]$^+$.

Step 2: N-[4-[4-(Trifluoromethyl)anilino]cyclo-hexyl]prop-2-enamide

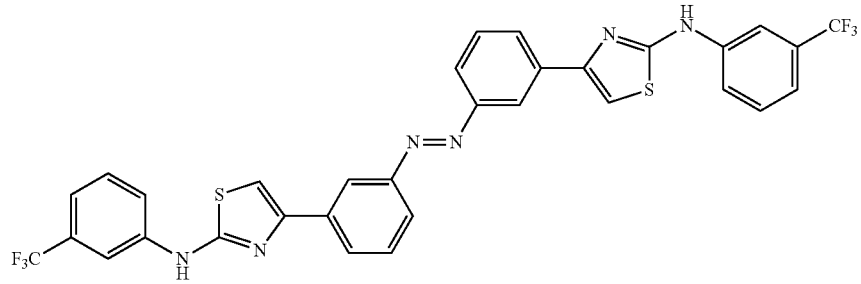 [SMILES: FC(F)(F)c1cccc(Nc2nc(-c3cccc(/N=N/c4cccc(-c5csc(Nc6cccc(C(F)(F)F)c6)n5)c4)c3)cs2)c1]

tert-Butyl N-[4-[3-[(E)-[3-[2-[N-tert-butoxycarbonyl-3-(trifluoromethyl)anilino]thiazol-4-yl]phenyl]azo]phenyl]thiazol-2-yl]-N-[3-(trifluoromethyl)phenyl]carbamate (75 mg, 61.25 µmol, 1 eq) was added HCl/MeOH (4 M, 5 mL, 326.51 eq). The reaction mixture was stirred at 28° C. for 1 h. The reaction mixture was concentrated to yield a residue which was purified by preparative HPLC (column: Phenomenex Synergi C18 150*30 mm*4 um; mobile phase: [water (0.05% HCl)-ACN]; B %: 80%-100%, 10 min). The desired fraction was lyophilized to yield 4-[3-[(E)[3-[2-[3-(trifluoromethyl)anilino]thiazol-4-yl]phenyl]azo]phenyl]-N-[3-(trifluoromethyl)phenyl]thiazol-2-amine (9.93 mg, 12.66 µmol, 20.7% yield, 94.3% purity, 2HCl) as yellow solid. $^1$H NMR (400 MHz, DMSO-$d_6$) δ ppm 10.75 (s, 1H), 8.49 (d, J=1.7 Hz, 2H), 8.15 (d, J=7.8 Hz, 1H), 7.91 (d, J=8.3 Hz, 1H), 7.81 (d, J=8.1 Hz, 1H), 7.71 (t, J=7.8 Hz, 1H), 7.64 (s, 1H), 7.57 (t, J=7.9 Hz, 1H), 7.29 (d, J=7.6 Hz, 1H); ES-LCMS m/z 667.1 [M+H]$^+$.

Step 1: N,N-Dimethyl-3-[2-[3-(trifluoromethyl)anilino]thiazol-4-yl]benzamide

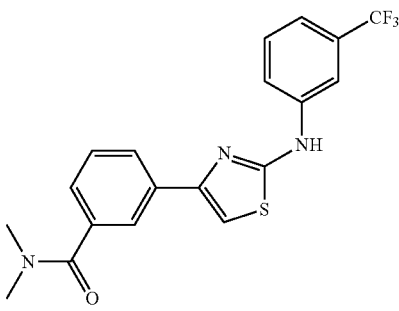 [SMILES: CN(C)C(=O)c1cccc(-c2csc(Nc3cccc(C(F)(F)F)c3)n2)c1]

To a solution of 3-[2-[3-(trifluoromethyl)anilino]thiazol-4-yl]benzoic acid (80 mg, 208.60 µmol, 1 eq) and N-methylmethanamine (51 mg, 625.43 µmol, 57.30 µL, 3 eq, HCl) in DCM (3 mL) was added HATU (95 mg, 249.85 µmol, 1.2 eq) and DIEA (80 mg, 618.99 µmol, 107.82 µL, 2.97 eq). The mixture was stirred at 28° C. for 3 h. The mixture was diluted with water (10 mL) and extracted with EtOAc (10 mL×3). The combined organic layers were dried over Na$_2$SO$_4$, filtered and concentrated under reduced pressure to yield a residue which was purified by preparative HPLC (column: Agela DuraShell C18 150*25 mm*5 um; mobile phase: [water (0.05% NH$_3$.H$_2$O+10 mM NH$_4$HCO$_3$)-ACN]; B %: 45%-75%, 10 min), followed by lyophilization to yield N,N-dimethyl-3-[2-[3-(trifluoromethyl)anilino]thiazol-4-yl]benzamide (43.44 mg, 110.08 µmol, 52.8% yield, 99.2% purity) as a white solid. $^1$H NMR (400 MHz, DMSO-$d_6$) δ ppm 10.65 (br s, 1H), 8.41 (s, 1H), 7.95 (d, J=7.8 Hz, 1H), 7.90 (s, 1H), 7.75 (d, J=8.6 Hz, 1H), 7.58-7.53 (m, 1H), 7.52 (s, 1H), 7.48 (t, J=7.7 Hz, 1H), 7.29 (dd, J=7.6, 14.9 Hz, 2H), 2.98 (s, 3H), 2.91 (s, 3H); ES-LCMS m/z 392.2 [M+H]$^+$.

I-50

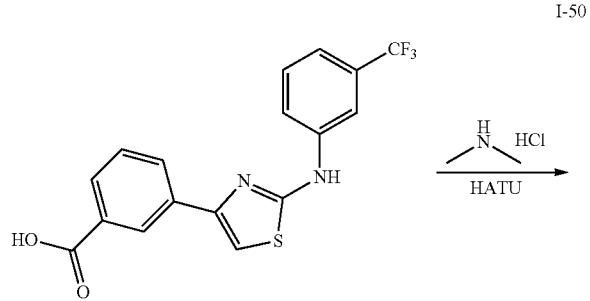

I-43

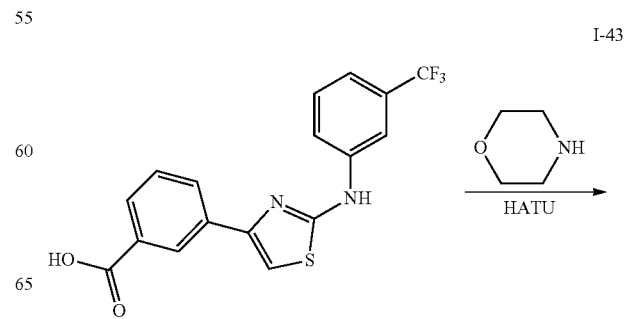

229
-continued

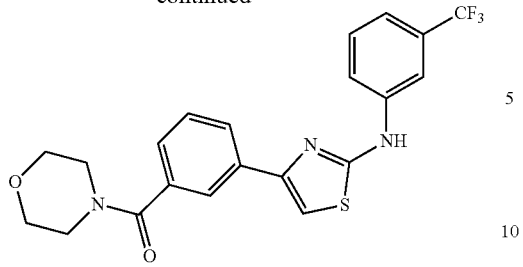

Step 1: Morpholino-[3-[2-[3-(trifluoromethyl)anilino]thiazol-4-yl]phenyl]methanone

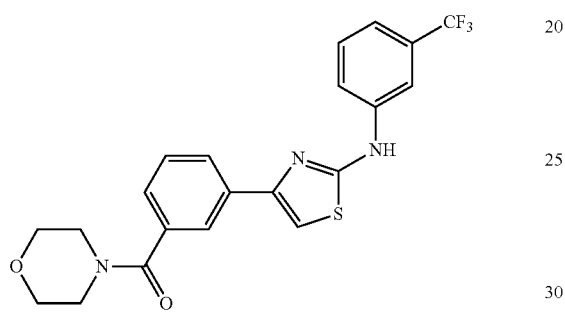

To a solution of 3-[2-[3-(trifluoromethyl)anilino]thiazol-4-yl]benzoic acid (55 mg, 143.41 μmol, 1 eq) and morpholine (65 mg, 746.09 μmol, 65.66 μL, 5.20 eq) in DCM (2 mL) was added HATU (65 mg, 170.95 μmol, 1.19 eq). The mixture was stirred at 25° C. for 2 h. TLC (PE/EtOAc=3/1, $R_f$=0.21) showed one main spot formed. The reaction mixture was diluted with $H_2O$ (20 mL) and extracted with EtOAc (20 mL×3). The organic layer was dried over $Na_2SO_4$, filtered and concentrated under reduced pressure to yield a residue which was purified by preparative HPLC (column: Welch Xtimate C18 150×25 mm×5 μm; mobile phase: [water (10 mM $NH_4HCO_3$)-ACN]; B %: 40%–70%, 10 min) to yield morpholino-[3-[2-[3-(trifluoromethyl)anilino]thiazol-4-yl]phenyl]methanone (46.94 mg, 107.15 μmol, 74.7% yield, 98.9% purity) as a white solid. $^1$H NMR (400 MHz, $CD_3OD$) δ ppm 8.38 (s, 1H), 8.06-7.99 (m, 2H), 7.80 (d, J=8.6 Hz, 1H), 7.56-7.46 (m, 2H), 7.37 (d, J=7.6 Hz, 1H), 7.29-7.23 (m, 2H), 3.86-3.76 (m, 4H), 3.70-3.60 (m, 2H), 3.58-3.50 (m, 2H); ES-LCMS m/z 434.0 $[M+H]^+$.

I-49

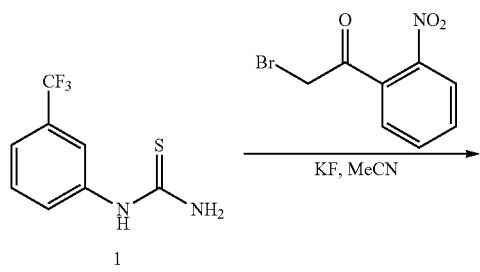

230
-continued

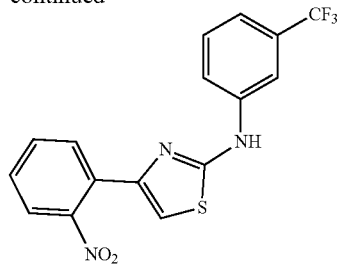

Step 1: 4-(2-Nitrophenyl)-N-[3-(Trifluoromethyl)phenyl]thiazol-2-amine

To a solution of 2-bromo-1-(2-nitrophenyl)ethanone (200 mg, 819.53 μmol, 1 eq), [3-(trifluoromethyl)phenyl]thiourea (200.53 mg, 819.53 μmol, 1 eq) in MeCN (5 mL) and $H_2O$ (5 mL) was added KF (95.22 mg, 1.64 mmol, 2 eq). The mixture was stirred at 25° C. for 12 h. The mixture was concentrated, diluted with water (50 mL) and extracted with EtOAc (20 mL×3). The combined organic layers were washed with brine (20 mL), dried over $Na_2SO_4$, filtered and concentrated to yield a residue which was purified by preparative HPLC (column: Welch Xtimate C18 150*25 mm*5 μm; mobile phase: [water (10 mM $NH_4HCO_3$)-ACN]; B %: 45%-75%, 10 min), followed by lyophilization to yield 4-(2-nitrophenyl)-N-[3-(trifluoromethyl)phenyl]thiazol-2-amine (90.19 mg, 237.47 μmol, 28.9% yield, 96.1% purity) as a yellow solid. $^1$H NMR (400 MHz, $CD_3OD$) δ ppm 7.86-7.82 (m, 2H), 7.80 (dd, J=1.2, 7.8 Hz, 1H), 7.75 (dd, J=1.2, 7.8 Hz, 1H), 7.66 (dt, J=1.6, 7.6 Hz, 1H), 7.57-7.51 (m, 1H), 7.46 (t, J=8.0 Hz, 1H), 7.22 (d, J=7.4 Hz, 1H), 7.11 (s, 1H); ES-LCMS m/z 366.2 $[M+H]^+$.

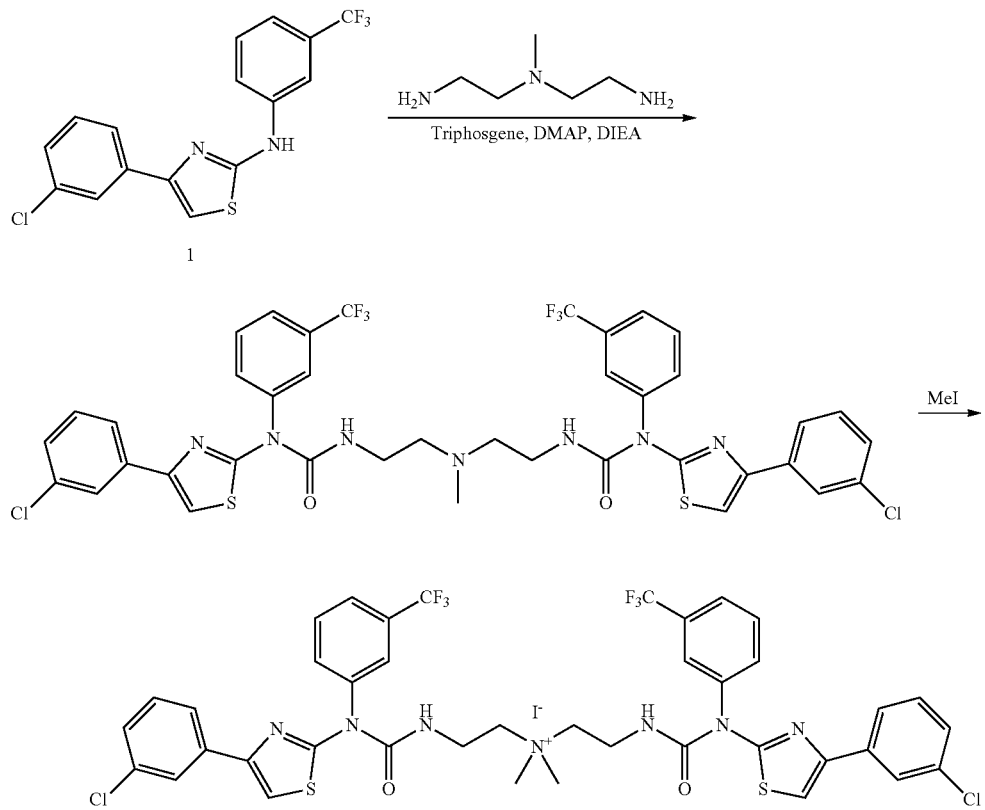

I-2

Step 1: 1-[4-(3-Chlorophenyl)thiazol-2-yl]-3-[2-[2-[[[4-(3-chlorophenyl)thiazol-2-yl]-[3-(trifluoromethyl)phenyl]carbamoyl]amino]ethyl-methyl-amino]ethyl]-1-[3-(trifluoromethyl)phenyl]urea

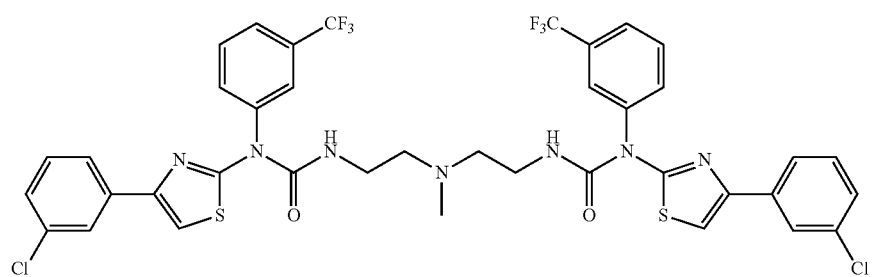 [SMILES: CN(CCNC(=O)N(c1cccc(C(F)(F)F)c1)c1nc(-c2cccc(Cl)c2)cs1)CCNC(=O)N(c1cccc(C(F)(F)F)c1)c1nc(-c2cccc(Cl)c2)cs1]

To a solution of 4-(3-chlorophenyl)-N-[3-(trifluoromethyl)phenyl]thiazol-2-amine (200 mg, 563.73 μmol, 1 eq) in THF (5 mL) was added bis(trichloromethyl) carbonate (250.93 mg, 845.60 μmol, 1.5 eq), DIEA (218.57 mg, 1.69 mmol, 294.57 μL, 3 eq) and stirred at 80° C. for 2 h. The reaction mixture was concentrated to yield (4-(3-chlorophenyl)thiazol-2-yl)(3-(trifluoromethyl)phenyl)carbamic chloride (crude). Then to a solution of N'-(2-aminoethyl)-N'-methyl-ethane-1,2-diamine (26.43 mg, 225.49 μmol, 0.4 eq), DIEA (218.57 mg, 1.69 mmol, 294.57 μl, 3 eq) and DMAP (6.89 mg, 56.37 μmol, 0.1 eq) in DCM (2 mL) was added (4-(3-chlorophenyl)thiazol-2-yl)(3-(trifluoromethyl)phenyl) carbamic chloride (crude) in DCM (3 mL) and stirred at 25° C. for 1 h. To the mixture was added water (30 mL) and extracted with ethyl acetate (30 mL×3). The combined organic phase was washed with brine (20 mL), dried over anhydrous $Na_2SO_4$, filtered and concentrated in vacuum to yield a residue which was purified by flash silica gel chromatography (from PE/EtOAc=100/1 to 0/1, TLC: PE/EtOAc=0/1, $R_f$=0.25) to yield the product which was purified by preparative HPLC (column: Agela DuraShell C18 150*25 mm*5 μm; mobile phase: [water (0.05% $NH_3H_2O$+10 mM $NH_4HCO_3$)-ACN]; B %: 78%-100%, 10 min), followed by lyophilization to yield 1-[4-(3-chlorophenyl)thiazol-2-yl]-3-[2-[2-[[[4-(3-chlorophenyl)thiazol-2-yl]-[3-(trifluoromethyl)phenyl]carbamoyl]amino]ethyl-methyl-amino]ethyl]-1-[3-(trifluoromethyl)phenyl]urea (80 mg, 86.49 μmol, 15.3% yield, 95% purity) as yellow oil. $^1H$ NMR (500 MHz, $CDCl_3$) δ ppm 8.76 (s, 2H), 7.75 (d, J=7.8 Hz, 2H), 7.69-7.62 (m, 8H), 7.53 (d, J=7.9 Hz, 2H), 7.33-7.26 (m, 4H), 7.04-6.92 (m, 2H), 3.51 (q, J=6.0 Hz, 4H), 2.75 (t, J=6.3 Hz, 4H), 2.45 (s, 3H); ES-LCMS m/z 878.0, 880.0 $[M+H]^+$.

Step 2: 1-[4-(3-Chlorophenyl)thiazol-2-yl]-3-(2-BLAHethyl)-1-[3-(trifluoromethyl)phenyl]urea

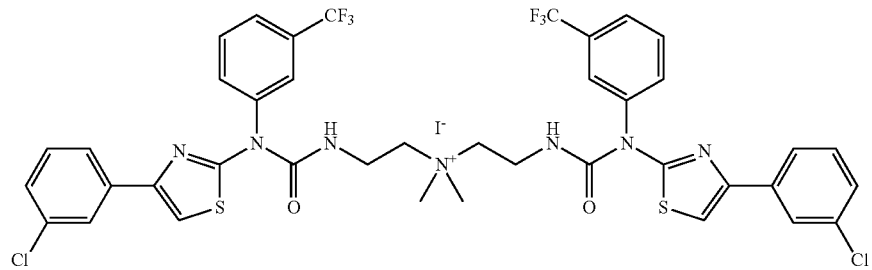 [SMILES: C[N+](C)(CCNC(=O)N(c1cccc(C(F)(F)F)c1)c1nc(-c2cccc(Cl)c2)cs1)CCNC(=O)N(c1cccc(C(F)(F)F)c1)c1nc(-c2cccc(Cl)c2)cs1 ; [I-]]

To a solution of 1-[4-(3-chlorophenyl)thiazol-2-yl]-3-[2-[2-[[[4-(3-chlorophenyl)thiazol-2-yl]-[3-(trifluoromethyl)phenyl]carbamoyl]amino]ethyl-methyl-amino]ethyl]-1-[3-(trifluoromethyl)phenyl]urea (80 mg, 81.94 µmol, 1 eq) in MeCN (5 mL) was added MeI (58.15 mg, 409.68 µmol, 25.50 µL, 5 eq). The mixture was stirred at 25° C. for 1 h. The residue was without further purification which was quenched by addition of sat. aq. NaHCO₃ (1 mL), diluted with water (10 mL), then lyophilization to yield 1-[4-(3-chlorophenyl)thiazol-2-yl]-3-(2-BLAHethyl)-1-[3-(trifluoromethyl)phenyl]urea (78.68 mg, 75.85 µmol, 92.6% yield, 98.4% purity) as a yellow solid. $^1$H NMR (500 MHz, DMSO-d₆) δ ppm 7.96 (s, 4H), 7.86 (t, J=7.9 Hz, 2H), 7.82-7.78 (m, 2H), 7.73 (s, 2H), 7.61 (s, 2H), 7.55 (d, J=7.8 Hz, 2H), 7.38-7.33 (m, 2H), 7.32-7.26 (m, 2H), 6.99 (t, J=5.3 Hz, 2H), 3.54 (d, J=5.8 Hz, 4H), 3.45 (d, J=5.8 Hz, 4H), 3.09 (s, 6H); ES-LCMS m/z 447.7 [M−I]⁺.

I-37

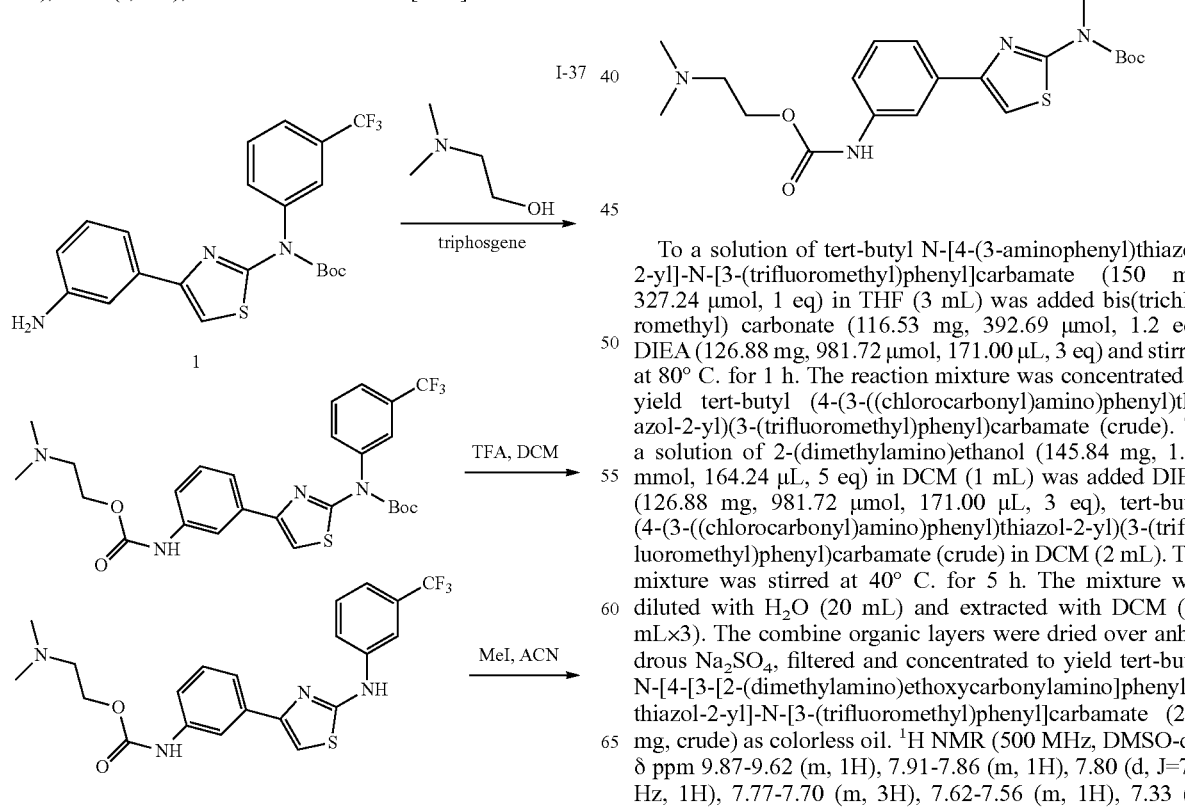

-continued

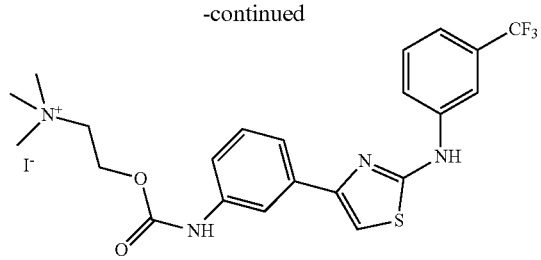

Step 1: tert-Butyl N-[4-[3-[2-(dimethylamino)ethoxycarbonylamino]phenyl]thiazol-2-yl]-N-[3-(trifluoromethyl)phenyl]carbamate To a solution of tert-butyl N-[4-(3-aminophenyl)thiazol-2-yl]-N-[3-(trifluoromethyl)phenyl]carbamate (150 mg, 327.24 µmol, 1 eq) in THF (3 mL) was added bis(trichloromethyl) carbonate (116.53 mg, 392.69 µmol, 1.2 eq), DIEA (126.88 mg, 981.72 µmol, 171.00 µL, 3 eq) and stirred at 80° C. for 1 h. The reaction mixture was concentrated to yield tert-butyl (4-(3-((chlorocarbonyl)amino)phenyl)thiazol-2-yl)(3-(trifluoromethyl)phenyl)carbamate (crude). To a solution of 2-(dimethylamino)ethanol (145.84 mg, 1.64 mmol, 164.24 µL, 5 eq) in DCM (1 mL) was added DIEA (126.88 mg, 981.72 µmol, 171.00 µL, 3 eq), tert-butyl (4-(3-((chlorocarbonyl)amino)phenyl)thiazol-2-yl)(3-(trifluoromethyl)phenyl)carbamate (crude) in DCM (2 mL). The mixture was stirred at 40° C. for 5 h. The mixture was diluted with H₂O (20 mL) and extracted with DCM (20 mL×3). The combine organic layers were dried over anhydrous Na₂SO₄, filtered and concentrated to yield tert-butyl N-[4-[3-[2-(dimethylamino)ethoxycarbonylamino]phenyl]thiazol-2-yl]-N-[3-(trifluoromethyl)phenyl]carbamate (280 mg, crude) as colorless oil. $^1$H NMR (500 MHz, DMSO-d₆) δ ppm 9.87-9.62 (m, 1H), 7.91-7.86 (m, 1H), 7.80 (d, J=7.0 Hz, 1H), 7.77-7.70 (m, 3H), 7.62-7.56 (m, 1H), 7.33 (d, J=6.7 Hz, 1H), 7.22 (s, 1H), 4.10 (t, J=6.1 Hz, 2H), 3.66 (t, J=6.3 Hz, 2H), 2.15 (s, 6H), 1.40 (s, 9H); ES-LCMS m/z 551.2 [M+H]⁺.

Step 2: 2-(Dimethylamino)ethyl N-[3-[2-[3-(trifluoromethyl)anilino]thiazol-4-yl]phenyl]carbamate

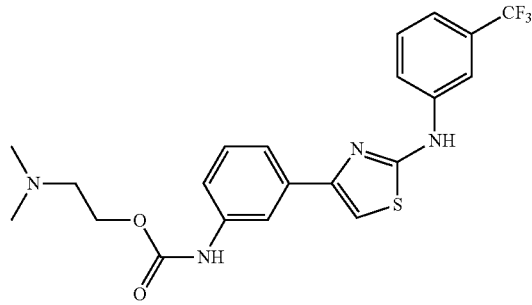 [SMILES: CN(C)CCOC(=O)Nc1cccc(-c2csc(Nc3cccc(C(F)(F)F)c3)n2)c1]

To a solution of tert-butyl N-[4-[3-[2-(dimethylamino)ethoxycarbonylamino]phenyl]thiazol-2-yl]-N-[3-(trifluoromethyl)phenyl]carbamate (280 mg, 508.54 µmol, 1 eq) in DCM (5 mL) was added TFA (1 mL). The mixture was stirred at 25° C. for 12 h. To the mixture was added sat. aq. NaHCO₃ (5 mL, adjust pH to 9) and H₂O (20 mL). The mixture was extracted with DCM (20 mL×3). The combine organic layers were dried over anhydrous Na₂SO₄, filtered and concentrated to yield a residue which was purified by preparative HPLC (column: Venusil ASB Phenyl 150*30 mm*5 µm; mobile phase: [water (0.05% HCl)-ACN]; B %: 40%–70%, 10 min) and lyophilized to yield a residue which was added H₂O (20 mL) and sat. aq. NaHCO₃ (20 mL, adjust pH to 8) and extracted with EtOAc (20 mL×3). The combine organic layers were dried over anhydrous Na₂SO₄, filtered and concentrated to yield a residue which was dissolved in MeCN (15 mL) and H₂O (30 mL) and lyophilized to yield 2-(dimethylamino)ethyl N-[3-[2-[3-(trifluoromethyl)anilino]thiazol-4-yl]phenyl]carbamate (40 mg, 84.36 µmol, 16.6% yield, 95.0% purity) as a yellow solid. ¹H NMR (400 MHz, CDCl₃) δ ppm 7.87 (s, 1H), 7.78 (s, 1H), 7.69 (d, J=8.1 Hz, 1H), 7.59-7.54 (m, 1H), 7.51-7.39 (m, 2H), 7.38-7.28 (m, 3H), 6.91 (s, 1H), 6.87 (s, 1H), 4.30 (t, J=5.5 Hz, 2H), 2.65 (t, J=5.5 Hz, 2H), 2.34 (s, 6H); ES-LCMS m/z 451.2 [M+H]⁺.

Step 3: 2-[BLAH(Trimethyl)-azanyl]ethyl N-[3-[2-[3-(trifluoromethyl)anilino]thiazol-4-yl]phenyl]carbamate

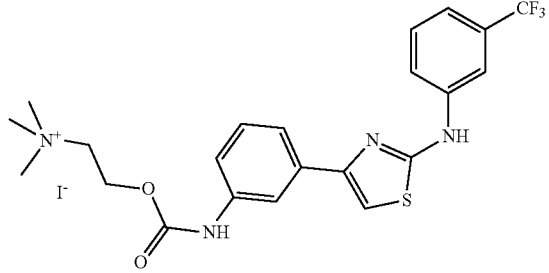 [SMILES: C[N+](C)(C)CCOC(=O)Nc1cccc(-c2csc(Nc3cccc(C(F)(F)F)c3)n2)c1 ; [I-]]

To a solution of 2-(dimethylamino)ethyl N-[3-[2-[3-(trifluoromethyl)anilino]thiazol-4-yl]phenyl]carbamate (20 mg, 42.18 µmol, 1 eq) in MeCN (5 mL) was added MeI (119.73 mg, 843.55 µmol, 52.51 µl, 20 eq) in one portion at 20° C. under N₂ atmosphere. The mixture was stirred at 20° C. for 1 h. The reaction mixture was concentrated to yield a residue which was dissolved in MeCN (15 mL) and H₂O (30 mL) and lyophilized to yield 2-[BLAH(trimethyl)-azanyl]ethyl N-[3-[2-[3-(trifluoromethyl)anilino]thiazol-4-yl]phenyl]carbamate (19.11 mg, 32.26 µmol, 76.5% yield, 100.0% purity) as a yellow solid. ¹H NMR (500 MHz, DMSO-d₆) δ ppm 10.65 (s, 1H), 9.84 (br s, 1H), 8.20 (s, 1H), 8.08 (br s, 1H), 7.98 (d, J=8.5 Hz, 1H), 7.60-7.55 (m, 2H), 7.45-7.35 (m, 2H), 7.33-7.28 (m, 2H), 4.60-4.50 (m, 2H), 3.74-3.67 (m, 2H), 3.17 (s, 9H); ES-LCMS m/z 465.2 [M-I]⁺.

I-22

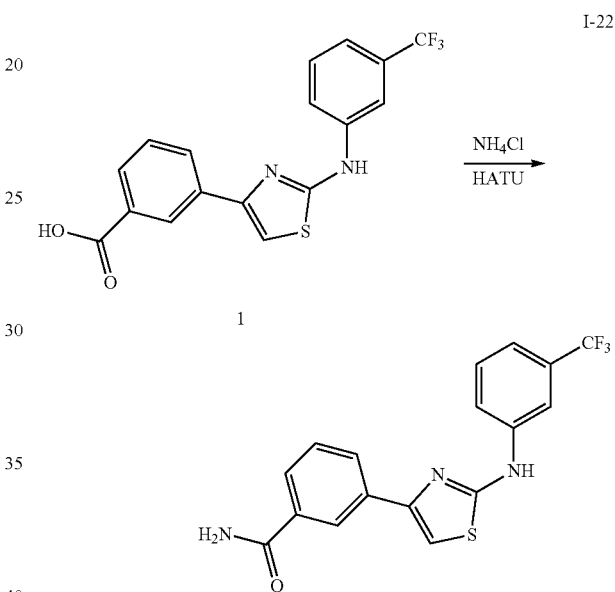

Step 1: 3-[2-[3-(Trifluoromethyl)anilino]thiazol-4-yl]benzamide

To a solution of 3-[2-[3-(trifluoromethyl)anilino]thiazol-4-yl]benzoic acid (80 mg, 208.60 µmol, 1 eq) in DCM (5 mL) was added HATU (95.18 mg, 250.31 µmol, 1.2 eq), NH₄Cl (55.79 mg, 1.04 mmol, 5 eq) and DIEA (80.88 mg, 625.79 µmol, 109.00 µL, 3 eq). The mixture was stirred at 25° C. for 2 h. The mixture was diluted with H₂O (20 mL) and extracted with DCM (20 mL×3). The combine organic layers were dried over anhydrous Na₂SO₄, filtered and concentrated to yield a residue which was purified by preparative HPLC (column: Agela DuraShell C18 150*25 mm*5 μm; mobile phase: [water (0.05% NH₃H₂O+10 mM NH₄HCO₃)-ACN]; B %: 37%-67%, 10 min) and lyophilized to yield 3-[2-[3-(trifluoromethyl)anilino]thiazol-4-yl]benzamide (22.13 mg, 60.90 μmol, 29.2% yield, 100.0% purity) as a white solid. ¹H NMR (500 MHz, DMSO-$d_6$) δ ppm 10.69 (s, 1H), 8.40 (s, 1H), 8.33 (s, 1H), 8.05 (d, J=8.1 Hz, 2H), 7.89 (d, J=8.2 Hz, 1H), 7.81 (d, J=7.6 Hz, 1H), 7.58 (t, J=8.0 Hz, 1H), 7.55-7.49 (m, 2H), 7.43 (br s, 1H), 7.30 (d, J=7.6 Hz, 1H); ES-LCMS m/z 364.1 [M+H]⁺.

I-48 and I-53

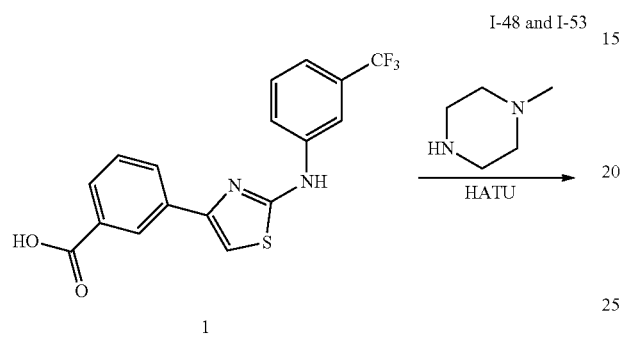

Step 1: (4-Methylpiperazin-1-yl)-[3-[2-[3-(trifluoromethyl)anilino]thiazol-4-yl]phenyl]methanone

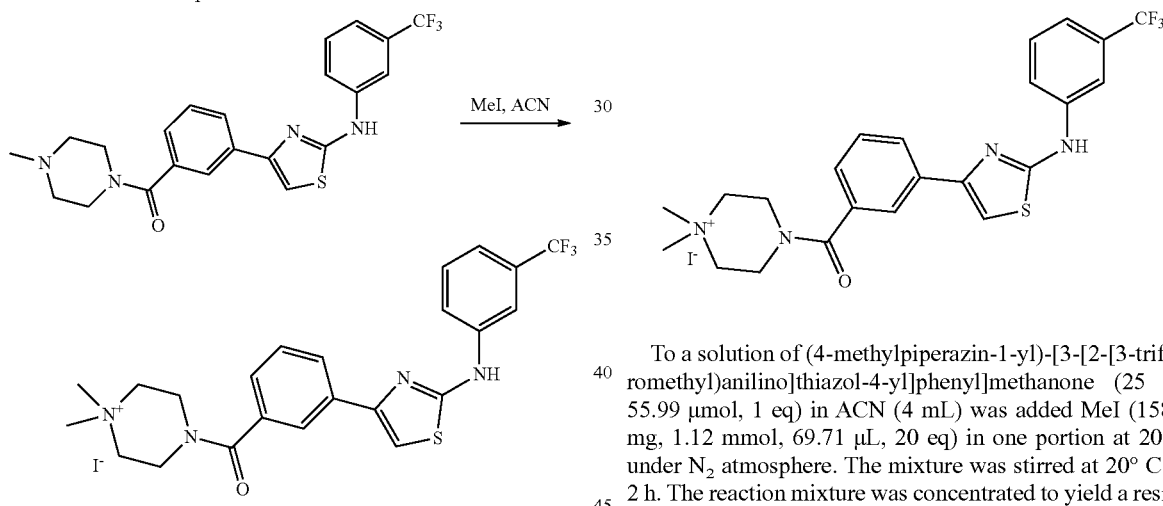

To a solution of 3-[2-[3-(trifluoromethyl)anilino]thiazol-4-yl]benzoic acid (150 mg, 391.12 μmol, 1 eq) in DCM (5 mL) was added HATU (178.46 mg, 469.34 μmol, 1.2 eq) and 1-methylpiperazine (117.52 mg, 1.17 mmol, 130.15 μL, 3 eq). The mixture was stirred at 25° C. for 2 h. The mixture was diluted with H₂O (20 mL) and extracted with DCM (20 mL×3). The combine organic layers were dried over anhydrous Na₂SO₄, filtered and concentrated to yield a residue which was purified by preparative HPLC (column: Agela DuraShell C18 150*25 mm*5 μm; mobile phase: [water (0.05% NH₃H₂O+10 mM NH₄HCO₃)-ACN]; B %: 38%-68%, 10 min) and lyophilized to yield (4-methylpiperazin-1-yl)-[3-[2-[3-(trifluoromethyl)anilino]thiazol-4-yl]phenyl]methanone (60 mg, 134.38 μmol, 34.4% yield, 100.0% purity) as a white solid. ¹H NMR (500 MHz, DMSO-$d_6$) δ ppm 10.70 (s, 1H), 8.45 (s, 1H), 7.99 (d, J=7.9 Hz, 1H), 7.91 (s, 1H), 7.79 (d, J=8.1 Hz, 1H), 7.61-7.55 (m, 2H), 7.52 (t, J=7.7 Hz, 1H), 7.34-7.28 (m, 2H), 3.70-3.60 (m, 2H), 3.40-3.30 (m, 2H), 2.37 (d, J=9.3 Hz, 2H), 2.30-2.20 (m, 2H), 2.19 (s, 3H); ES-LCMS m/z 447.0 [M+H]⁺.

Step 2: (4-BLAH-4,4-Dimethyl-1,4diazinan-1-yl)-[3-[2-[3-(trifluoromethyl)anilino]thiazol-4-yl]phenyl]methanone To a solution of (4-methylpiperazin-1-yl)-[3-[2-[3-trifluoromethyl)anilino]thiazol-4-yl]phenyl]methanone (25 mg, 55.99 μmol, 1 eq) in ACN (4 mL) was added MeI (158.95 mg, 1.12 mmol, 69.71 μL, 20 eq) in one portion at 20° C. under N₂ atmosphere. The mixture was stirred at 20° C. for 2 h. The reaction mixture was concentrated to yield a residue which was dissolved in MeCN (15 mL) and H₂O (30 mL) and lyophilized to yield (4-BLAH-4,4-dimethyl-1,4diazinan-1-yl)-[3-[2-[3-(trifluoromethyl)anilino]thiazol-4-yl]phenyl]methanone (28.06 mg, 46.26 μmol, 82.6% yield, 97.0% purity) as a yellow solid. ¹H NMR (500 MHz, DMSO-$d_6$) δ ppm 10.74 (d, J=4.9 Hz, 1H), 8.30 (s, 1H), 8.05 (d, J=7.8 Hz, 1H), 7.97 (s, 1H), 7.91 (d, J=8.1 Hz, 1H), 7.62-7.53 (m, 3H), 7.40 (d, J=7.6 Hz, 1H), 7.31 (d, J=7.9 Hz, 1H), 4.09-3.68 (m, 4H), 3.56-3.46 (m, 4H), 3.24 (s, 6H); ES-LCMS m/z 461.2 [M−I]⁺.

I-33

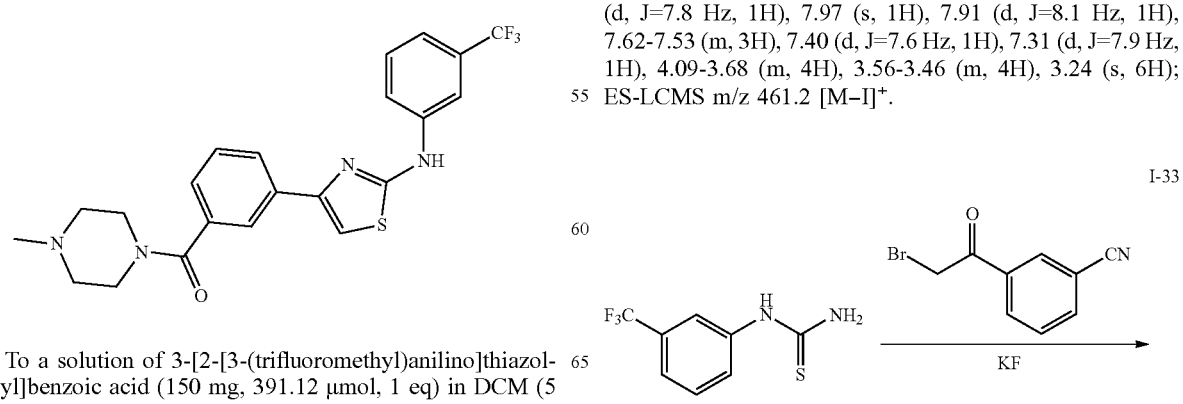

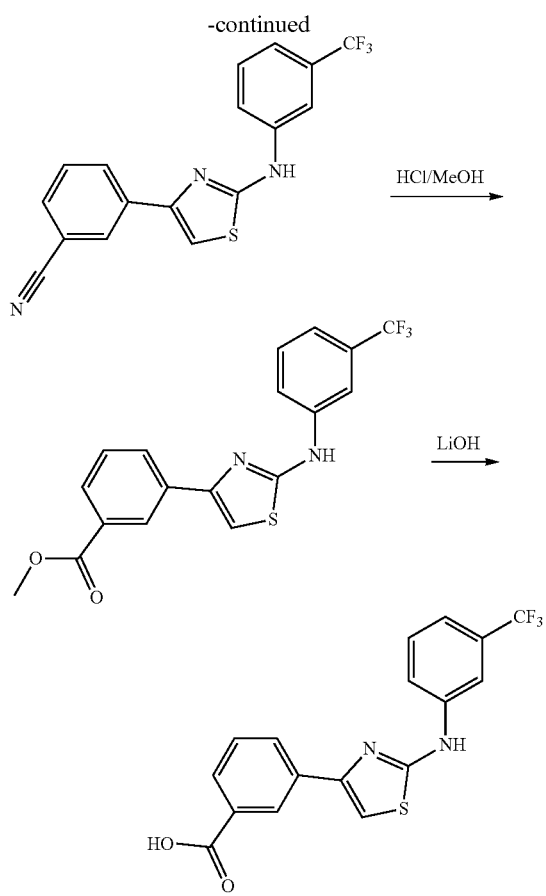

Step 1: 3-[2-[3-(Trifluoromethyl)anilino]thiazol-4-yl]benzonitrile

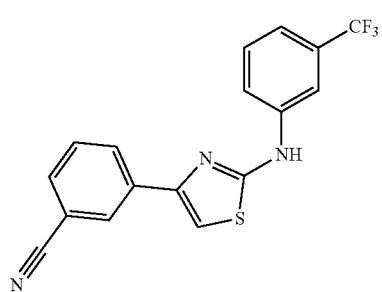 [SMILES: N#Cc1cccc(-c2csc(Nc3cccc(C(F)(F)F)c3)n2)c1]

To a solution of [3-(trifluoromethyl)phenyl]thiourea (550 mg, 2.25 mmol, 1 eq) and 3-(2-bromoacetyl)benzonitrile (553.99 mg, 2.47 mmol, 1.1 eq) in MeCN (5 mL) and H₂O (5 mL) was added KF (130.60 mg, 2.25 mmol, 1 eq). The mixture was stirred under N₂ atmosphere at 25° C. for 2 h. The mixture was diluted with water (30 mL) and extracted with ethyl acetate (30 mL×3). The combined organic phase was washed with brine (20 mL), dried over anhydrous Na₂SO₄, filtered and concentrated in vacuum to yield a residue which was purified by flash silica gel chromatography (from PE/EtOAc=200/1 to 1/1, TLC: PE/EtOAc=1/1, R$_f$=0.40) to yield 3-[2-[3-(trifluoromethyl)anilino]thiazol-4-yl]benzonitrile (750 mg, 1.74 mmol, 77.3% yield, 80.0% purity) as a yellow solid. ¹H NMR (500 MHz, DMSO-d₆) δ ppm 10.72 (s, 1H), 8.34 (d, J=7.2 Hz, 2H), 8.24 (d, J=7.9 Hz, 1H), 7.86 (d, J=8.2 Hz, 1H), 7.78 (d, J=7.8 Hz, 1H), 7.70-7.65 (m, 2H), 7.59 (t, J=7.9 Hz, 1H), 7.31 (d, J=7.6 Hz, 1H); ES-LCMS m/z 346.1 [M+H]⁺.

Step 2: Methyl 3-[2-[3-(trifluoromethyl)anilino]thiazol-4-yl]benzoate

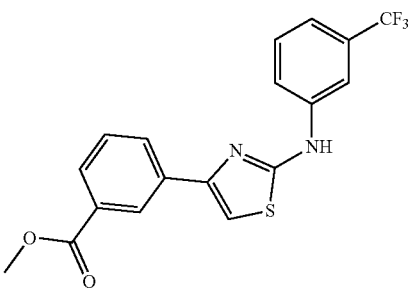 [SMILES: COC(=O)c1cccc(-c2csc(Nc3cccc(C(F)(F)F)c3)n2)c1]

A mixture of 3-[2-[3-(trifluoromethyl)anilino]thiazol-4-yl]benzonitrile (750 mg, 1.74 mmol, 1 eq) in HCl/MeOH (30 mL, 4 M) was stirred under N₂ atmosphere at 80° C. for 24 h. The reaction mixture was concentrated under reduced pressure, basified with saturated aqueous NaHCO₃ (30 mL) and extracted with ethyl acetate (30 mL×3). The combined organic phase was washed with brine (20 mL), dried over anhydrous Na₂SO₄, filtered and concentrated in vacuum to yield a residue which was purified by flash silica gel chromatography (from PE/EtOAc=100/1 to 3/1, TLC: PE/EtOAc=3/1, R$_f$=0.35) to yield methyl 3-[2-[3-(trifluoromethyl)anilino]thiazol-4-yl]benzoate (850 mg, 1.68 mmol, 96.9% yield, 75.0% purity) as a yellow solid. ¹H NMR (500 MHz, DMSO-d₆) δ ppm 10.73 (s, 1H), 8.56 (s, 2H), 8.19 (d, J=7.8 Hz, 1H), 7.92 (d, J=7.6 Hz, 1H), 7.71 (d, J=7.6 Hz, 1H), 7.62-7.59 (m, 2H), 7.59-7.56 (m, 1H), 7.32 (d, J=7.8 Hz, 1H), 3.90 (s, 3H); ES-LCMS m/z 379.1 [M+H]⁺.

Step 3: 3-[2-[3-(Trifluoromethyl)anilino]thiazol-4-yl]benzoic acid

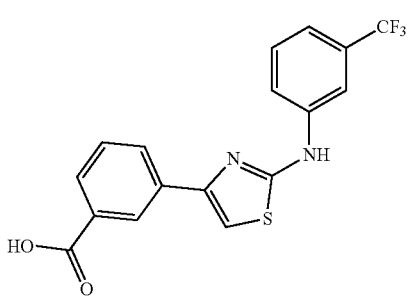 [SMILES: O=C(O)c1cccc(-c2csc(Nc3cccc(C(F)(F)F)c3)n2)c1]

To a solution of methyl 3-[2-[3-(trifluoromethyl)anilino]thiazol-4-yl]benzoate (850 mg, 1.68 mmol, 1 eq) in THF (10 mL), ACN (10 mL), H₂O (10 mL) was added LiOH.H₂O (424.22 mg, 10.11 mmol, 6 eq). The mixture was stirred at 25° C. for 12 h. TLC (PE/EtOAc=3/1, R$_f$=0.00) showed starting material was consumed completely and one major new spot was detected. The mixture was diluted with H₂O (20 mL) and PE (20 mL) and filtered. The filtered cake was dissolved in H₂O (20 mL) and acidified with aqueous HCl (1 M, 10 mL) until pH=6 and extracted with EtOAc (20 mL×3). The combine organic layers were dried over anhydrous Na₂SO₄, filtered and concentrated to yield 3-[2-[3-(trifluoromethyl)anilino]thiazol-4-yl]benzoic acid (600 mg, 1.56 mmol, 92.9% yield, 95.0% purity) as a yellow solid. ¹H NMR (500 MHz, DMSO-d₆) δ ppm 13.05 (br s, 1H), 10.71 (s, 1H), 8.51 (s, 1H), 8.44 (s, 1H), 8.15 (d, J=7.8 Hz, 1H), 7.89 (d, J=7.8 Hz, 1H), 7.78 (d, J=8.4 Hz, 1H), 7.61-7.53 (m, 3H), 7.31 (d, J=7.6 Hz, 1H); ES-LCMS m/z 365.2 [M+H]⁺.

I-24

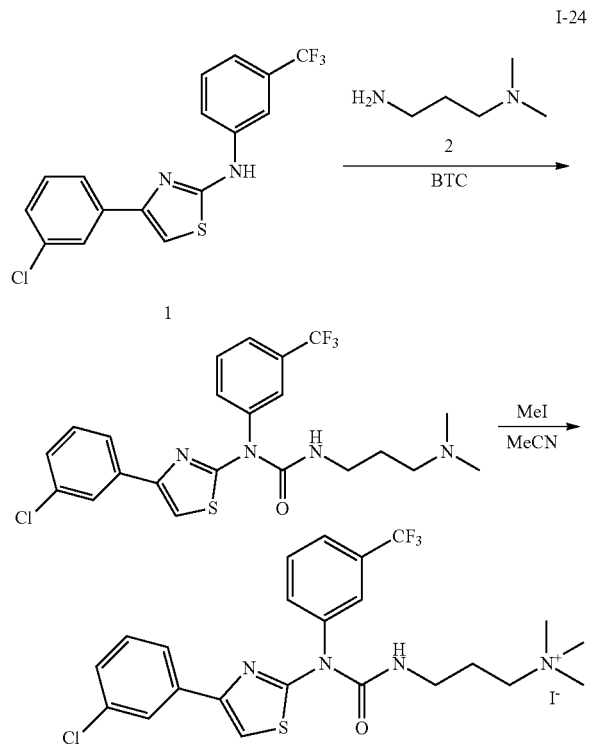

Step 1: 1-[4-(3-Chlorophenyl)thiazol-2-yl]-3-[3-(dimethylamino)propyl]-1-[3-(trifluoromethyl)phenyl]urea

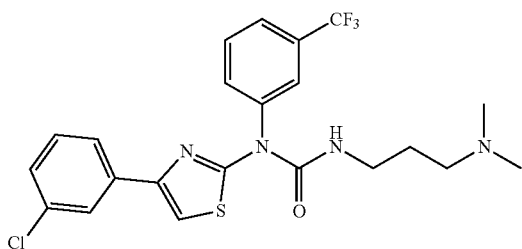 [SMILES: CN(C)CCCNC(=O)N(c1cccc(C(F)(F)F)c1)c1nc(-c2cccc(Cl)c2)cs1]

To a solution of 4-(3-chlorophenyl)-N-[3-(trifluoromethyl)phenyl]thiazol-2-amine (95.00 mg, 267.77 μmol, 1 eq) in THF (4 mL) was added bis(trichloromethyl) carbonate (95.35 mg, 321.33 μmol, 1.2 eq), DIEA (103.82 mg, 803.32 μmol, 139.92 μL, 3 eq) and stirred at 80° C. for 2 h under N₂ atmosphere. The reaction mixture was concentrated to yield (4-(3-chlorophenyl)thiazol-2-yl)(3-(trifluoromethyl)phenyl) carbamic chloride (crude). Then to a solution of N',N'-dimethylpropane-1,3-diamine (136.80 mg, 1.34 mmol, 167.45 μL, 5 eq), DIEA (103.82 mg, 803.32 μmol, 139.92 μL, 3 eq) and DMAP (3.27 mg, 26.78 μmol, 0.1 eq) in DCM (5 mL) was added (4-(3-chlorophenyl)thiazol-2-yl)(3-(trifluoromethyl)phenyl)carbamic chloride (crude) in DCM (3 mL) and stirred at 25° C. for 1 h. The solution was quenched by addition of sat. aq. NaHCO₃ (3 mL), then diluted with water (30 mL) and extracted with EtOAc (30 mL×3). The combined organic phase was washed with brine (20 mL), dried over anhydrous Na₂SO₄, filtered and concentrated in vacuum to yield a residue which was purified by preparative HPLC (column: Agela DuraShell C18 150*25 mm*5 μm; mobile phase: [water (0.05% NH₃H₂O+10 mM NH₄HCO₃)-ACN]; B %: 62%-92%, 10 min) to yield 1-[4-(3-chlorophenyl)thiazol-2-yl]-3-[3-(dimethylamino)propyl]-1-[3-(trifluoromethyl)phenyl]urea (90 mg, 182.63 μmol, 68.2% yield, 98.0% purity) as a white solid. ¹H NMR (500 MHz, CDCl₃) δ ppm 8.12 (s, 1H), 7.79 (d, J=8.1 Hz, 1H), 7.73-7.70 (m, 2H), 7.63-7.59 (m, 2H), 7.54-7.50 (m, 1H), 7.25 (d, J=7.6 Hz, 1H), 7.09 (s, 1H), 3.49-3.44 (m, 2H), 2.32 (t, J=6.0 Hz, 2H), 1.89 (s, 6H), 1.69-1.64 (m, 2H); ES-LCMS m/z 483.5, 485.5 [M+H]⁺.

Step 2: 1-[4-(3-Chlorophenyl)thiazol-2-yl]-3-(3-BLAHpropyl)-1-[3-(trifluoromethyl)phenyl]urea

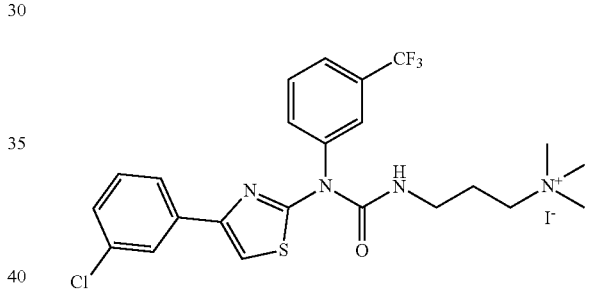

To a stirred solution of 1-[4-(3-chlorophenyl)thiazol-2-yl]-3-[3-(dimethylamino)propyl]-1-[3-(trifluoromethyl)phenyl]urea (55 mg, 111.61 μmol, 1 eq) in MeCN (3 mL) was added MeI (79.21 mg, 558.03 μmol, 34.74 μL, 5 eq). The reaction mixture was stirred at 25° C. for 1 h under N₂ atmosphere. The reaction mixture was by lyophilization to yield 1-[4-(3-chlorophenyl)thiazol-2-yl]-3-(3-BLAHpropyl)-1-[3-(trifluoromethyl)phenyl]urea (37.18 mg, 59.13 μmol, 53.0% yield, 99.4% purity) as a white solid. ¹H NMR (500 MHz, DMSO-d₆) δ ppm 7.98 (s, 1H), 7.93 (d, J=7.2 Hz, 1H), 7.86-7.79 (m, 2H), 7.75 (s, 1H), 7.63 (s, 1H), 7.57 (d, J=7.9 Hz, 1H), 7.38-7.33 (m, 1H), 7.31-7.28 (m, 1H), 6.96 (t, J=5.7 Hz, 1H), 3.29-3.24 (m, 2H), 3.20 (q, J=6.4 Hz, 2H), 3.04 (s, 9H), 1.92-1.80 (m, 2H); ES-LCMS m/z 497.2, 499.2 [M-I]⁺.

I-9

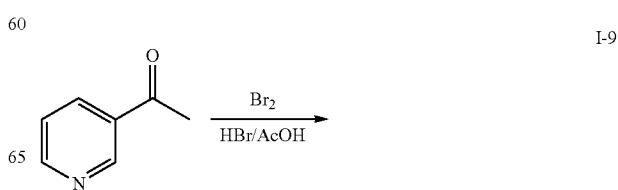

243
-continued

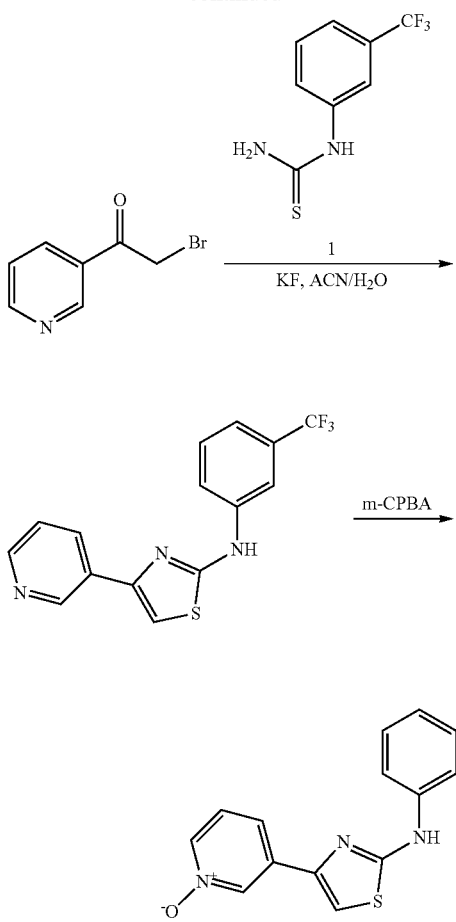

Step 1: 2-Bromo-1-(3-pyridyl)ethanone

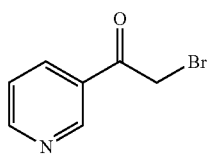

A mixture of 1-(3-pyridyl)ethanone (1 g, 8.26 mmol, 909.09 μL, 1 eq) in HBr/AcOH (10 mL) was stirred at 28° C. The mixture was cooled to 0° C., and then Br$_2$ (1.33 g, 8.29 mmol, 427.42 μL, 1 eq) was added dropwise at 0° C. The resulting mixture was stirred at 28° C. for 12 h. The reaction mixture was filtered to yield 2-bromo-1-(3-pyridyl) ethanone (2.2 g, 5.48 mmol, 66.4% yield, 70.0% purity, HBr) as a white solid, which was used in the next step without further purification. $^1$H NMR (400 MHz, DMSO-d$_6$) δ ppm 9.15 (d, J=1.7 Hz, 1H), 8.82 (dd, J=1.5, 4.9 Hz, 1H), 8.37 (d, J=8.1 Hz, 1H), 7.63 (dd, J=4.8, 7.9 Hz, 1H), 4.98 (s, 2H); ES-LCMS m/z 199.8, 201.8 [M+H]$^+$.

Step 2: 4-(3-Pyridyl)-N-[3-(trifluoromethyl)phenyl] thiazol-2-amine

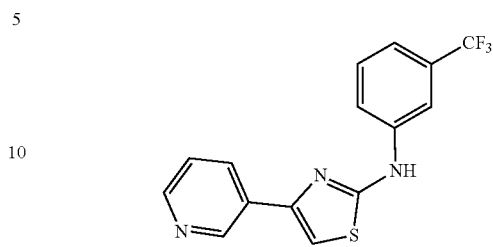

To a solution of 2-bromo-1-(3-pyridyl)ethanone (300 mg, 1.07 mmol, 1.2 eq, HBr) and [3-(trifluoromethyl)phenyl] thiourea (270 mg, 1.10 mmol, 1.24 eq) in ACN (4 mL) and H$_2$O (4 mL) was added KF (105 mg, 1.81 mmol, 2.03 eq). The mixture was stirred at 28° C. for 12 h. The mixture was diluted with water (10 mL) and extracted with EtOAc (10 mL×3). The combined organic layers were dried over Na$_2$SO$_4$, filtered and concentrated under reduced pressure to yield 4-(3-pyridyl)-N-[3-(trifluoromethyl)phenyl]thiazol-2-amine (300 mg, 840.28 μmol, 94.4% yield, 90.0% purity) as a yellow solid, which was used in the next step without further purification. $^1$H NMR (400 MHz, DMSO-d$_6$) δ ppm 10.72 (s, 1H), 9.12 (d, J=1.5 Hz, 1H), 8.51 (dd, J=1.5, 4.9 Hz, 1H), 8.30 (s, 1H), 8.24 (d, J=8.1 Hz, 1H), 7.85 (d, J=8.1 Hz, 1H), 7.61 (s, 1H), 7.56 (t, J=8.1 Hz, 1H), 7.51-7.44 (m, 1H), 7.28 (d, J=7.8 Hz, 1H); ES-LCMS m/z 322.2 [M+H]$^+$.

Step 3: 4-(1-Oxidopyridin-1-ium-3-yl)-N-[3-(trifluoromethyl)phenyl]thiazol-2-amine

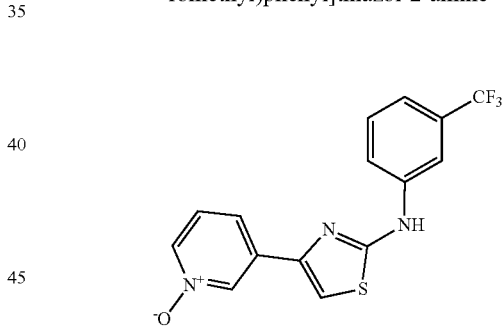

To a solution of 4-(3-pyridyl)-N-[3-(trifluoromethyl)phenyl]thiazol-2-amine (300 mg, 840.28 μmol, 1 eq) in DMF (10 mL) was added m-CPBA (1.00 g, 4.64 mmol, 80% purity, 5.52 eq). The mixture was stirred at 28° C. for 12 h. The mixture was quenched by Na$_2$S$_2$O$_3$, diluted with water (10 mL) and extracted with EtOAc (10 mL×3). The combined organic layers were dried over Na$_2$SO$_4$, filtered and concentrated under reduced pressure to yield a residue which was purified by preparative HPLC (column: Welch Xtimate C18 150*25 mm*5 um; mobile phase: [water (10 mM NH$_4$HCO$_3$)-ACN]; B %: 33%-63%, 10 min), followed by lyophilization to yield 4-(1-oxidopyridin-1-ium-3-yl)-N-[3-(trifluoromethyl)phenyl]thiazol-2-amine (24.30 mg, 71.68 μmol, 8.5% yield, 99.5% purity) as a white solid. $^1$H NMR (400 MHz, DMSO-d$_6$) δ ppm 10.75 (s, 1H), 8.69 (s, 1H), 8.21 (s, 1H), 8.15 (dd, J=0.7, 6.4 Hz, 1H), 7.85 (d, J=8.3 Hz, 1H), 7.80 (d, J=8.1 Hz, 1H), 7.75 (s, 1H), 7.56 (t, J=7.9 Hz, 1H), 7.47 (dd, J=6.6, 7.8 Hz, 1H), 7.29 (d, J=7.6 Hz, 1H); ES-LCMS m/z 338.1 [M+H]$^+$.

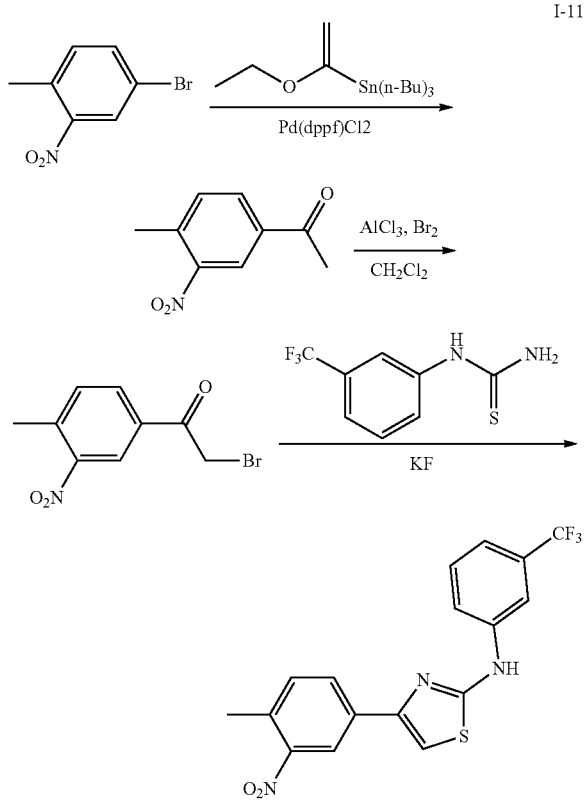

Step 1: 1-(4-Methyl-3-nitro-phenyl)ethanone

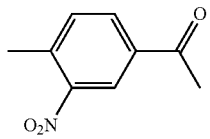

To a solution of 4-bromo-1-methyl-2-nitro-benzene (2.0 g, 9.26 mmol, 1 eq) in 1,4-dioxane (20 mL) was added tributyl(1-ethoxyvinyl)stannane (3.84 g, 10.63 mmol, 3.59 mL, 1.15 eq) and Pd(dppf)Cl$_2$ (338.70 mg, 462.89 μmol, 0.05 eq) under N$_2$. The mixture was stirred at 100° C. for 12 h. The reaction mixture was cooled to 0° C. and treated with 20 ml 2N hydrochloric acid and stirred for 1 h. Last the reaction mixture was adjusted pH to 8 with aq. NaOH (15%). TLC (PE/EtOAc=5/1, R$_f$=0.27) indicated the starting material was consumed completely and two new spots formed. The mixture was added aq. KF (80 mL) stirred for 1 h. The mixture was extracted with EtOAc (50 mL×3) and the combined organic layers were washed with brine (50 mL), dried over Na$_2$SO$_4$, filtered and concentrated to yield a residue which was purified by flash silica gel chromatography (From PE/EtOAc=1/0 to 5/1, R$_f$=0.30) to yield 1-(4-methyl-3-nitro-phenyl)ethanone (1.43 g, 7.66 mmol, 82.7% yield, 96.0% purity) as a yellow solid. $^1$H NMR (400 MHz, DMSO-d$_6$) δ ppm 8.42 (s, 1H), 8.15 (d, J=8.2 Hz, 1H), 7.66 (d, J=7.8 Hz, 1H), 2.62 (s, 3H), 2.57 (s, 3H);

Step 2: 2-Bromo-1-(4-methyl-3-nitro-phenyl)ethanone

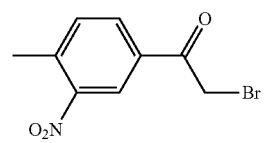

To a solution of 1-(4-methyl-3-nitro-phenyl)ethanone (500 mg, 2.68 mmol, 1 eq) in AcOH (15 mL) was added Br$_2$ (856.26 mg, 5.36 mmol, 276.21 μL, 2 eq) and HBr (65.69 mg, 267.90 umol, 8.46 μL, 33% purity, 0.1 eq) under N$_2$. The mixture was stirred at 25° C. for 12 h. TLC (PE/EtOAc=5/1, R$_f$=0.51) indicated the starting material was consumed completely and two new spots formed. The residue was partitioned between EtOAc (100 mL) and aqueous NaHCO$_3$ solution (50 mL). The organic layer was washed with brine (50 mL), dried over Na$_2$SO$_4$, filtered and concentrated to yield 2-bromo-1-(4-methyl-3-nitro-phenyl)ethanone (500 mg, crude) as a yellow solid which was used in next step directly without further purification $^1$H NMR (400 MHz, DMSO-d$_6$) δ ppm 8.49 (d, J=1.6 Hz, 1H), 8.19 (dd, J=2.0, 7.8 Hz, 1H), 7.69 (d, J=8.2 Hz, 1H), 4.98 (s, 2H), 2.58 (s, 3H);

Step 3: 4-(4-Methyl-3-nitro-phenyl)-N-[3-(trifluoromethyl)phenyl]thiazol-2-amine

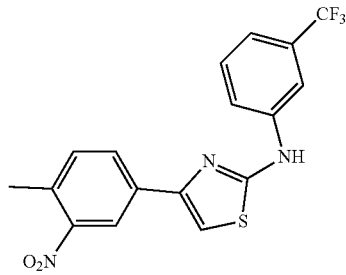 [SMILES: Cc1ccc(-c2csc(Nc3cccc(C(F)(F)F)c3)n2)cc1[N+](=O)[O-]]

To a solution of 2-bromo-1-(4-methyl-3-nitro-phenyl)ethanone (500 mg, 1.94 mmol, 1 eq) in MeCN (6 mL) and H$_2$O (6 mL) were added KF (135.08 mg, 2.32 mmol, 1.2 eq) and [3-(trifluoromethyl)phenyl]thiourea (426.66 mg, 1.94 mmol, 1 eq) under N$_2$. The mixture was stirred at 25° C. for 2 h. TLC (PE/EtOAc=5/1, R$_f$=0.33) indicated the starting material was consumed completely and many new spots formed. The mixture was concentrated and diluted with water (80 mL), extracted with EtOAc (50 mL×3). The combined organic layers were washed with brine (50 mL), dried over Na$_2$SO$_4$, filtered and concentrated to yield a residue which was purified by flash silica gel chromatography (From PE/EtOAc=1/0 to 5/1, R$_f$=0.33) to yield 4-(4-methyl-3-nitro-phenyl)-N-[3-(trifluoromethyl)phenyl]thiazol-2-amine (221.84 mg, 584.78 μmol, 30.2% yield, 100.0% purity) as a yellow solid. $^1$H NMR (400 MHz, CDCl$_3$) δ ppm 8.45 (d, J=2.0 Hz, 1H), 7.98 (dd, J=1.6, 7.8 Hz, 1H), 7.85 (s, 1H), 7.64 (d, J=8.2 Hz, 1H), 7.49 (t, J=8.0 Hz, 1H), 7.42-7.31 (m, 3H), 6.98 (s, 1H), 2.63 (s, 3H); ES-LCMS m/z 380.1 [M+H]$^+$.

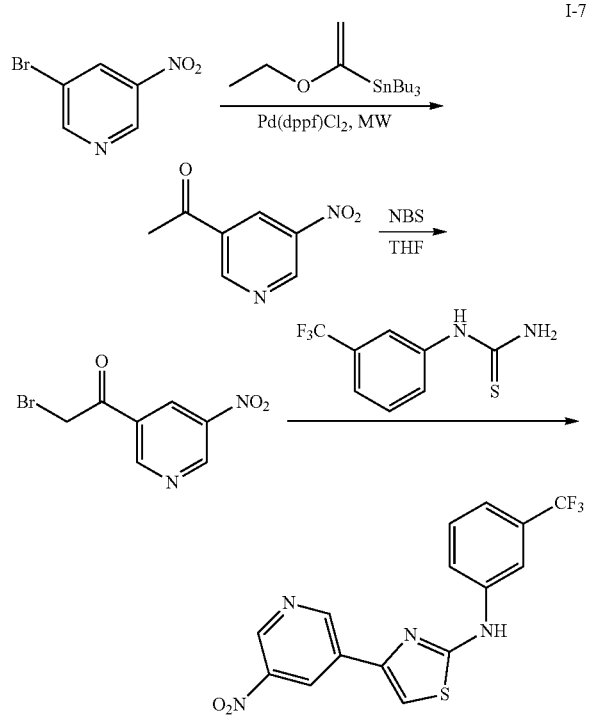

Step 1: 1-(5-Nitro-3-pyridyl)ethanone

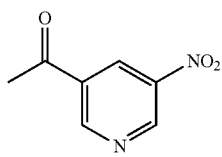

To a solution of 3-bromo-5-nitro-pyridine (500 mg, 2.46 mmol, 1 eq) in 1,4-dioxane (15 mL) was added Pd(PPh$_3$)$_2$Cl$_2$ (172.89 mg, 246.31 μmol, 0.1 eq), tributyl(1-ethoxyvinyl)stannane (1.10 g, 3.05 mmol, 1.03 mL, 1.24 eq). The mixture was degassed and purged with N$_2$ for three times and stirred at 100° C. for 12 h under N$_2$ atmosphere. The reaction mixture was diluted with 3 M HCl solution (6 mL) then stirred at 25° C. for 1 h. The reaction mixture was adjusted pH to 9-10 by 15% NaOH solution. The mixture was poured into saturated KF solution (50 mL, 2M), stirred for 1 h and extracted with EtOAc (50 mL×3). The organic layers were dried over Na$_2$SO$_4$, filtered and the filtrate was concentrated under reduced pressure to yield a residue which was purified by flash silica gel chromatography (from PE/EtOAc=100/1 to 2/1, TLC: PE/EtOAc=3/1, R$_f$=0.2) to yield 1-(5-nitro-3-pyridyl)ethanone (360 mg, 2.06 mmol, 83.6% yield, 95.0% purity) as yellow solid. $^1$H NMR (500 MHz, DMSO-d$_6$) δ ppm 9.57 (d, J=2.4 Hz, 1H), 9.47 (d, J=1.7 Hz, 1H), 8.86 (t, J=2.2 Hz, 1H), 2.81-2.66 (m, 3H); ES-LCMS m/z 167.1 [M+H]$^+$.

Step 2: 2-Bromo-1-(5-nitro-3-pyridyl)ethanone

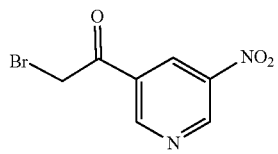 [SMILES: O=C(CBr)c1cncc([N+](=O)[O-])c1]

To a stirred solution of 1-(5-nitro-3-pyridyl)ethanone (200 mg, 1.14 mmol, 1 eq) in THF (10 mL) was added NBS (451.89 mg, 2.54 mmol, 2.22 eq). The reaction mixture was stirred at 50° C. for 12 h. The reaction mixture was concentrated to yield 2-bromo-1-(5-nitro-3-pyridyl)ethanone (250 mg, 1.02 mmol, 89.2% yield, N/A purity) as yellow oil which was used in the next step without further purification. ES-LCMS m/z 245.1, 247.1 [M+H]$^+$.

Step 3: 4-(5-Nitro-3-pyridyl)-N-[3-(trifluoromethyl)phenyl]thiazol-2-amine

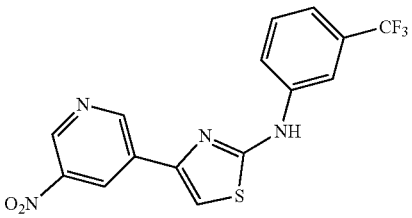 [SMILES: O=[N+]([O-])c1cncc(-c2csc(Nc3cccc(C(F)(F)F)c3)n2)c1]

To a stirred solution of 2-bromo-1-(5-nitro-3-pyridyl)ethanone (200 mg, 816.23 μmol, 1 eq) in ACN (5 mL) and water (5 mL) was added KF (56.99 mg, 980.86 μmol, 1.2 eq) and [3-(trifluoromethyl)phenyl]thiourea (200 mg, 817.38 μmol, 1 eq). The reaction mixture was stirred at 24° C. for 12 h. The reaction mixture was diluted with water (50 mL) and extracted with EtOAc (50 mL×3). The combined organic layers were dried over Na$_2$SO$_4$, filtered and the filtrate was concentrated to yield a residue which was purified by preparative HPLC (column: Agela DuraShell C18 150*25 mm*5 um; mobile phase: [water (0.05% NH$_3$H$_2$O+10 mM NH$_4$HCO$_3$)-ACN]; B %: 50%-80%, 10 min). The desired fraction was lyophilized to yield 4-(5-nitro-3-pyridyl)-N-[3-(trifluoromethyl)phenyl]thiazol-2-amine (150 mg, 393.92 μmol, 48.2% yield, 96.2% purity) as brown solid. $^1$H NMR (400 MHz, CDCl$_3$) δ ppm 9.39 (dd, J=2.1, 11.1 Hz, 2H), 8.91 (t, J=2.2 Hz, 1H), 7.87 (s, 1H), 7.70 (d, J=8.1 Hz, 1H), 7.54 (t, J=7.9 Hz, 1H), 7.43 (s, 1H), 7.38 (d, J=7.6 Hz, 1H), 7.18 (s, 1H); ES-LCMS m/z 367.1 [M+H]$^+$.

I-44

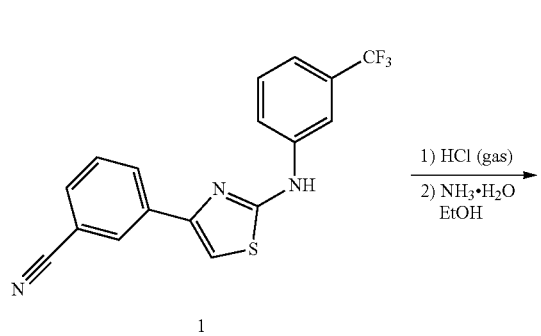

Step 1: 3-[2-[3-(Trifluoromethyl)anilino]thiazol-4-yl]benzamidine

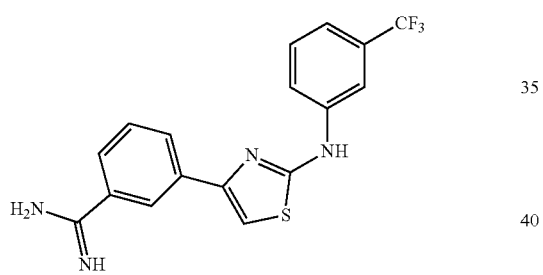

Hydrochloric acid (gas, 30 psi) was bubbled into a solution of 3-[2-[3-(trifluoromethyl)anilino]thiazol-4-yl]benzonitrile (250 mg, 723.92 μmol, 1 eq) in EtOH (30 mL) under dry ice bath (−60° C.) for 10 min. After excess HCl was purged by $N_2$, to the above mixture was dropwise added $NH_3 \cdot H_2O$ (13.65 g, 109.06 mmol, 15 mL, 28% purity, 150.65 eq) at 0° C. The mixture was stirred at 25° C. for 12 h. The reaction mixture was concentrated under reduced pressure to yield a residue. To the mixture was added water (30 mL) and extracted with ethyl acetate (30 mL×3). The combined organic phase was washed with brine (20 mL), dried over anhydrous $Na_2SO_4$, filtered and concentrated in vacuum to yield a residue which was purified by preparative HPLC (column: Phenomenex Synergi C18 150*30 mm*4 μm; mobile phase: [water (0.05% HCl)-ACN]; B %: 30%-50%, 10 min), followed by lyophilization to yield 3-[2-[3-(trifluoromethyl)anilino]thiazol-4-yl]benzamidine (28.63 mg, 64.79 μmol, 9.0% yield, 98.5% purity, 2HCl) as a white solid. $^1H$ NMR (400 MHz, DMSO-$d_6$) δ ppm 10.83 (s, 1H), 9.44 (s, 2H), 9.08 (s, 2H), 8.41 (s, 1H), 8.35 (s, 1H), 8.25 (d, J=7.0 Hz, 1H), 7.89 (d, J=7.8 Hz, 1H), 7.75-7.68 (m, 2H), 7.64 (s, 1H), 7.58 (t, J=8.0 Hz, 1H), 7.32 (d, J=7.8 Hz, 1H); ES-LCMS m/z 363.1 [M+H]$^+$.

I-4

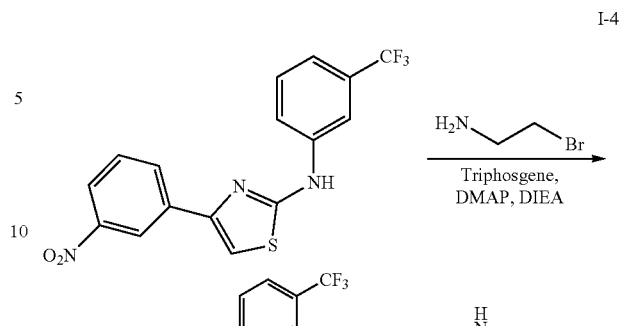

Step 1: 3-(2-bromoethyl)-1-[4-(3-nitrophenyl)thiazol-2-yl]-1-[3-(trifluoromethyl)phenyl]urea

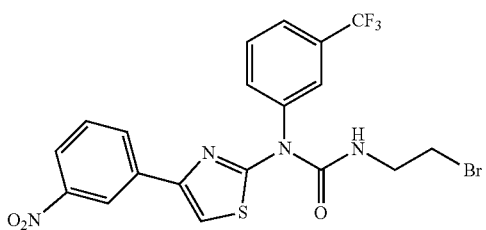 [SMILES: O=C(NCCBr)N(c1cccc(C(F)(F)F)c1)c1nc(-c2cccc([N+](=O)[O-])c2)cs1]

To a solution of 4-(3-nitrophenyl)-N-[3-(trifluoromethyl)phenyl]thiazol-2-amine (450 mg, 862.24 μmol, 1 eq) in THF (4 mL) was added bis(trichloromethyl) carbonate (332.63 mg, 1.12 mmol, 1.3 eq), DIEA (334.31 mg, 2.59 mmol, 450.55 μL, 3 eq) and stirred at 80° C. for 2 h. The reaction mixture was concentrated to yield (4-(3-chlorophenyl)thiazol-2-yl)(3-(trifluoromethyl)phenyl)carbamic chloride (crude). Then to a solution of 2-bromoethanamine (529.99 mg, 2.59 mmol, 190.98 μL, 3 eq, HBr) in DCM (1 mL) was added DIEA (557.18 mg, 4.31 mmol, 750.91 μL, 5 eq), DMAP (10.53 mg, 86.22 μmol, 0.1 eq), (4-(3-chlorophenyl)thiazol-2-yl)(3-(trifluoromethyl)phenyl)carbamic chloride (crude) in DCM (3 mL) and stirred at 25° C. for 1 h. The reaction mixture was quenched by addition of water (50 mL), extracted with EtOAc (50 mL×3). The combined organic layers were washed with brine (40 mL), dried over Na$_2$SO$_4$, filtered and concentrated under reduced pressure to give a residue which was purified by flash silica gel chromatography (from PE/EtOAc=1/0 to 3/1, TLC: PE/EtOAc=3/1, R$_f$=0.35) to yield 3-(2-bromoethyl)-1-[4-(3-nitrophenyl)thiazol-2-yl]-1-[3-(trifluoromethyl)phenyl]urea (180 mg, 296.91 μmol, 34.4% yield, 85% purity) as yellow oil. $^1$H NMR (500 MHz, DMSO-d$_6$) δ ppm 8.41 (s, 1H), 8.14-8.08 (m, 2H), 7.98-7.91 (m, 3H), 7.89-7.83 (m, 1H), 7.83-7.78 (m, 1H), 7.65 (t, J=7.9 Hz, 1H), 7.40-7.32 (m, 1H), 3.69 (t, J=6.3 Hz, 1H), 3.55 (s, 2H), 3.49-3.47 (m, 1H); ES-LCMS m/z 515.0, 517.0 [M+H]$^+$.

Step 2: 3-[2-[2-hydroxyethyl(methyl)amino]ethyl]-1-[4-(3-nitrophenyl)thiazol-2-yl]-1-[3-(trifluoromethyl)phenyl]urea

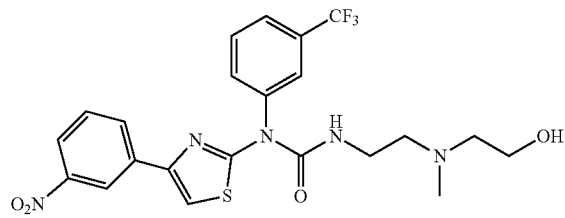 [SMILES: CN(CCO)CCNC(=O)N(c1cccc(C(F)(F)F)c1)c1nc(-c2cccc([N+](=O)[O-])c2)cs1]

To a solution of 3-(2-bromoethyl)-1-[4-(3-nitrophenyl)thiazol-2-yl]-1-[3-(trifluoromethyl)phenyl]urea (160 mg, 263.92 μmol, 1 eq) in THF (10 mL) were added DIEA (68.22 mg, 527.84 μmol, 91.94 μL, 2 eq) and 2-(methylamino)ethanol (99.12 mg, 1.32 mmol, 106.01 μL, 5 eq). The mixture was stirred at 25° C. for 12 h. After filtration, the filtrate was concentrated to give a residue which was purified by preparative HPLC (column: Welch Xtimate C18 150*25 mm*5 um; mobile phase: [water (10 mM NH$_4$HCO$_3$)-ACN]; B %: 42%-72%, 10 min), followed by lyophilization to yield 3-[2-[2-hydroxyethyl(methyl)amino]ethyl]-1-[4-(3-nitrophenyl)thiazol-2-yl]-1-[3-(trifluoromethyl)phenyl]urea (50 mg, 93.42 μmol, 35.4% yield, 95.2% purity) as a yellow solid. $^1$H NMR (500 MHz, CDCl$_3$) δ ppm 8.56 (s, 1H), 8.37 (s, 1H), 8.20-8.15 (m, 1H), 8.07 (d, J=7.8 Hz, 1H), 7.81 (d, J=8.1 Hz, 1H), 7.76-7.70 (m, 2H), 7.69-7.63 (m, 1H), 7.58 (t, J=8.0 Hz, 1H), 7.19 (s, 1H), 3.65-3.57 (m, 4H), 2.81 (t, J=5.5 Hz, 2H), 2.69 (s, 2H), 2.45 (s, 3H); ES-LCMS m/z 510.2 [M+H]$^+$.

Step 3: 2-hydroxy-N,N-dimethyl-N-(2-(3-(4-(3-nitrophenyl)thiazol-2-yl)-3-(3-(trifluoromethyl)phenyl)ureido)ethyl)ethanaminium iodide

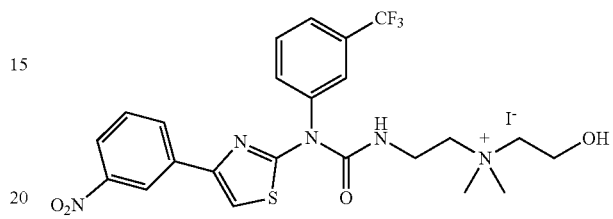

To a solution of 3-[2-[2-hydroxyethyl(methyl)amino]ethyl]-1-[4-(3-nitrophenyl)thiazol-2-yl]-1-[3-(trifluoromethyl)phenyl]urea (50 mg, 93.42 μmol, 1 eq) in MeCN (10 mL) was added MeI (125.26 mg, 882.51 μmol, 54.94 μL, 9.45 eq). The mixture was stirred at 20° C. for 2 h. TLC (PE/EtOAc=0/1, R$_f$=0) indicated starting material was consumed completely and one new spot formed. The reaction mixture was concentrated to yield a residue which was treated with ACN (20 mL) and H$_2$O (30 mL) then lyophilizated to yield 2-hydroxy-N,N-dimethyl-N-(2-(3-(4-(3-nitrophenyl)thiazol-2-yl)-3-(3-(trifluoromethyl)phenyl)ureido)ethyl)ethanaminium iodide (60.3 mg, 88.68 μmol, 94.9% yield, 95.8% purity) was obtained as a yellow solid. $^1$H NMR (500 MHz, CD$_3$OD) δ ppm 8.53 (t, J=1.8 Hz, 1H), 8.14 (dd, J=2.1, 8.6 Hz, 1H), 8.10 (d, J=7.8 Hz, 1H), 7.94 (d, J=7.8 Hz, 1H), 7.87 (d, J=3.1 Hz, 2H), 7.77 (d, J=8.2 Hz, 1H), 7.66 (s, 1H), 7.61 (d, J=7.9 Hz, 1H), 4.07-4.02 (m, 2H), 3.84-3.78 (m, 2H), 3.68-3.65 (m, 2H), 3.60-3.57 (m, 2H), 3.28 (s, 6H); ES-LCMS m/z 524.2 [M−I]$^+$.

I-29

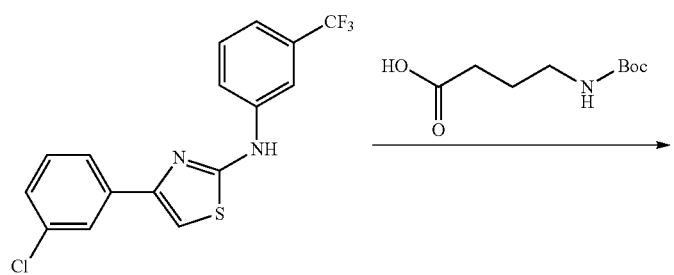

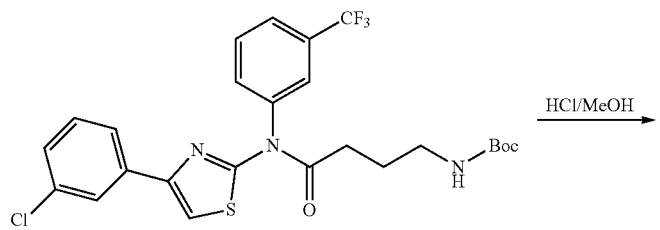

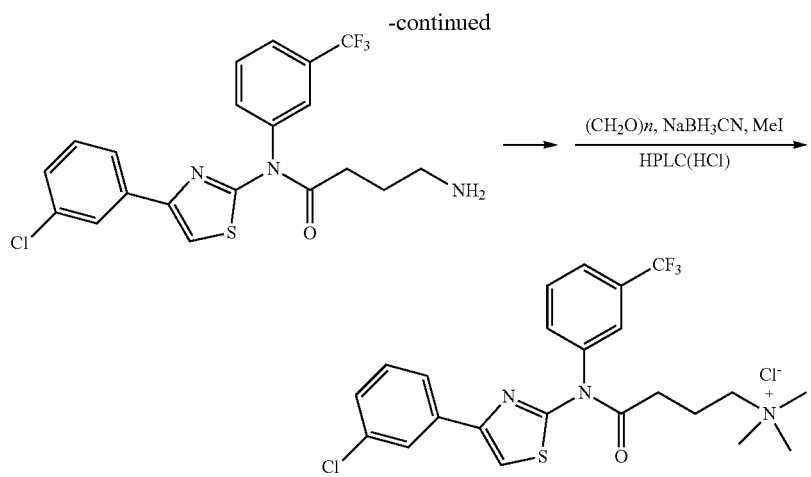

Step 1: tert-butyl N-[4-[N-[4-(3-chlorophenyl)thiazol-2-yl]-3-(trifluoromethyl)anilino]-4-oxo-butyl]carbamate

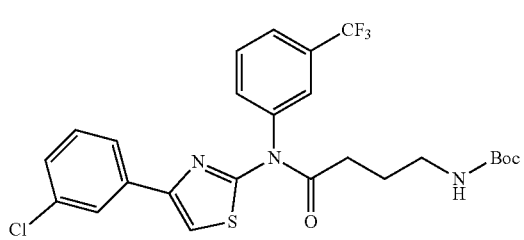 [SMILES: CC(C)(C)OC(=O)NCCCC(=O)N(c1cccc(C(F)(F)F)c1)c1nc(-c2cccc(Cl)c2)cs1]

A mixture of 4-(3-chlorophenyl)-N-[3-(trifluoromethyl)phenyl]thiazol-2-amine (1.3 g, 3.66 mmol, 1 eq), 4-(tert-butoxycarbonylamino)butanoic acid (893.65 mg, 4.40 mmol, 1.2 eq), HATU (1.67 g, 4.40 mmol, 1.2 eq), TEA (1.11 g, 10.99 mmol, 1.53 mL, 3 eq) in DMF (20 mL) was degassed and purged with $N_2$ for 3 times, and then the mixture was stirred at 25° C. for 2 h under $N_2$ atmosphere. TLC (PE/EtOAc=3/1, $R_f$=0.18) indicated starting material was consumed completely and one new spot formed. The reaction mixture was quenched by addition of water (100 mL), extracted with EtOAc (100 mL×3). The combined organic layers were washed with brine (40 mL), dried over $Na_2SO_4$, filtered and concentrated under reduced pressure to give a residue which was purified by flash silica gel chromatography (from PE/EtOAc=1/0 to 3/1, TLC:PE/EtOAc=3/1, $R_f$=0.18) to yield tert-butyl N-[4-[N-[4-(3-chlorophenyl)thiazol-2-yl]-3-(trifluoromethyl)anilino]-4-oxo-butyl]carbamate (500 mg, 879.64 μmol, 24.01% yield, 95% purity) as yellow oil. $^1$H NMR (400 MHz, DMSO-$d_6$) δ ppm 8.03 (s, 1H), 7.92 (d, J=7.4 Hz, 1H), 7.89-7.79 (m, 3H), 7.61 (s, 1H), 7.54 (d, J=7.8 Hz, 1H), 7.37-7.32 (m, 1H), 7.30-7.26 (m, 1H), 6.73 (s, 1H), 2.88 (q, J=6.0 Hz, 2H), 2.22 (t, J=7.0 Hz, 2H), 1.70-1.62 (m, 2H), 1.30 (s, 9H); ES-LCMS m/z 540.2, 542.2 [M+H]$^+$.

Step 2: 4-amino-N-[4-(3-chlorophenyl)thiazol-2-yl]-N-[3-(trifluoromethyl)phenyl]butanamide

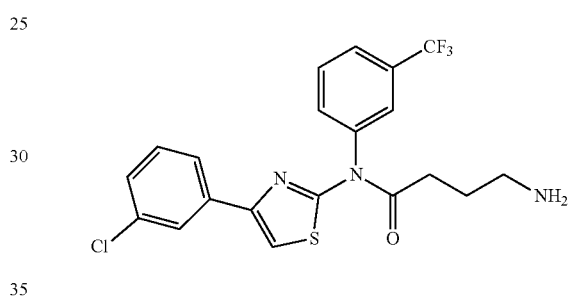

A mixture of tert-butyl N-[4-[N-[4-(3-chlorophenyl)thiazol-2-yl]-3-(trifluoromethyl)anilino]-4-oxo-butyl]carbamate (400 mg, 703.71 μmol, 1 eq) in HCl/MeOH (20 mL, 4 M) was degassed and purged with $N_2$ for 3 times and the mixture was stirred at 25° C. for 2 h under $N_2$ atmosphere. TLC (PE/EtOAc=1/1, $R_f$=0) indicated starting material was consumed completely and one new spot formed. The mixture was concentrated to yield 4-amino-N-[4-(3-chlorophenyl)thiazol-2-yl]-N-[3-(trifluoromethyl)phenyl]butanamide (300 mg, 593.34 μmol, 84.32% yield, 87% purity) as colorless oil which was used in the next step directly without further purification. $^1$H NMR (400 MHz, DMSO-$d_6$) δ ppm 8.06-7.93 (m, 2H), 7.89-7.85 (m, 2H), 7.83-7.81 (m, 1H), 7.63-7.58 (m, 1H), 7.54 (d, J=7.8 Hz, 1H), 7.38-7.31 (m, 1H), 7.31-7.26 (m, 1H), 2.78 (d, J=6.3 Hz, 2H), 2.40-2.29 (m, 2H), 1.89-1.77 (m, 2H); ES-LCMS m/z 440.1, 442.1 [M+H]$^+$.

Step 3: 4-((4-(3-chlorophenyl)thiazol-2-yl)(3-(trifluoromethyl)phenyl)amino)-N,N,N-trimethyl-4-oxobutan-1-aminium chloride

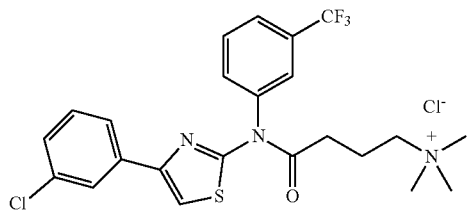

To a solution of 4-amino-N-[4-(3-chlorophenyl)thiazol-2-yl]-N-[3-(trifluoromethyl)phenyl]butanamide (300 mg, 593.34 μmol, 1 eq) in MeOH (10 mL) was added TEA (600.40 mg, 5.93 mmol, 825.86 μL, 10 eq), (CH₂O)ₙ (538.60 mg, 5.93 mmol, 10 eq) and sodium; cyanoboranuide (372.87 mg, 5.93 mmol, 10 eq). The mixture was stirred at 25° C. for 1 h. After filtration, the filtrate was concentrated to yield N-[4-(3-chlorophenyl)thiazol-2-yl]-4-(dimethylamino)-N-[3-(trifluoromethyl)phenyl]butanamide (crude), To a solution of N-[4-(3-chlorophenyl)thiazol-2-yl]-4-(dimethylamino)-N-[3-(trifluoromethyl)phenyl]butanamide (crude) in MeCN (20 mL) was added MeI (504.00 mg, 3.55 mmol, 221.05 μL, 6 eq). The mixture was stirred at 20° C. for 4 h. The mixture was concentrated to yield a residue which was purified by preparative HPLC (column: Phenomenex Synergi C18 150*30 mm*4 um; mobile phase: [water (0.05% HCl)-ACN]; B %: 35%-55%, 10 min), followed by lyophilization to yield 4-((4-(3-chlorophenyl)thiazol-2-yl)(3-(trifluoromethyl)phenyl)amino)-N,N,N-trim ethyl-4-oxobutan-1-aminium chloride (15.58 mg, 29.57 μmol, 5.0% yield, 98.4% purity) as a red solid. ¹H NMR (500 MHz, DMSO-d₆) δ ppm 8.10 (s, 1H), 8.00-7.96 (m, 1H), 7.93-7.91 (m, 2H), 7.87 (t, J=7.9 Hz, 1H), 7.64 (s, 1H), 7.57 (d, J=7.6 Hz, 1H), 7.39-7.35 (m, 1H), 7.32-7.30 (m, 1H), 3.32-3.24 (m, 2H), 3.06 (s, 9H), 2.34 (t, J=6.8 Hz, 2H), 2.01-1.96 (m, 2H); ES-LCMS m/z 482.2, 484.2 [M−Cl]⁺.

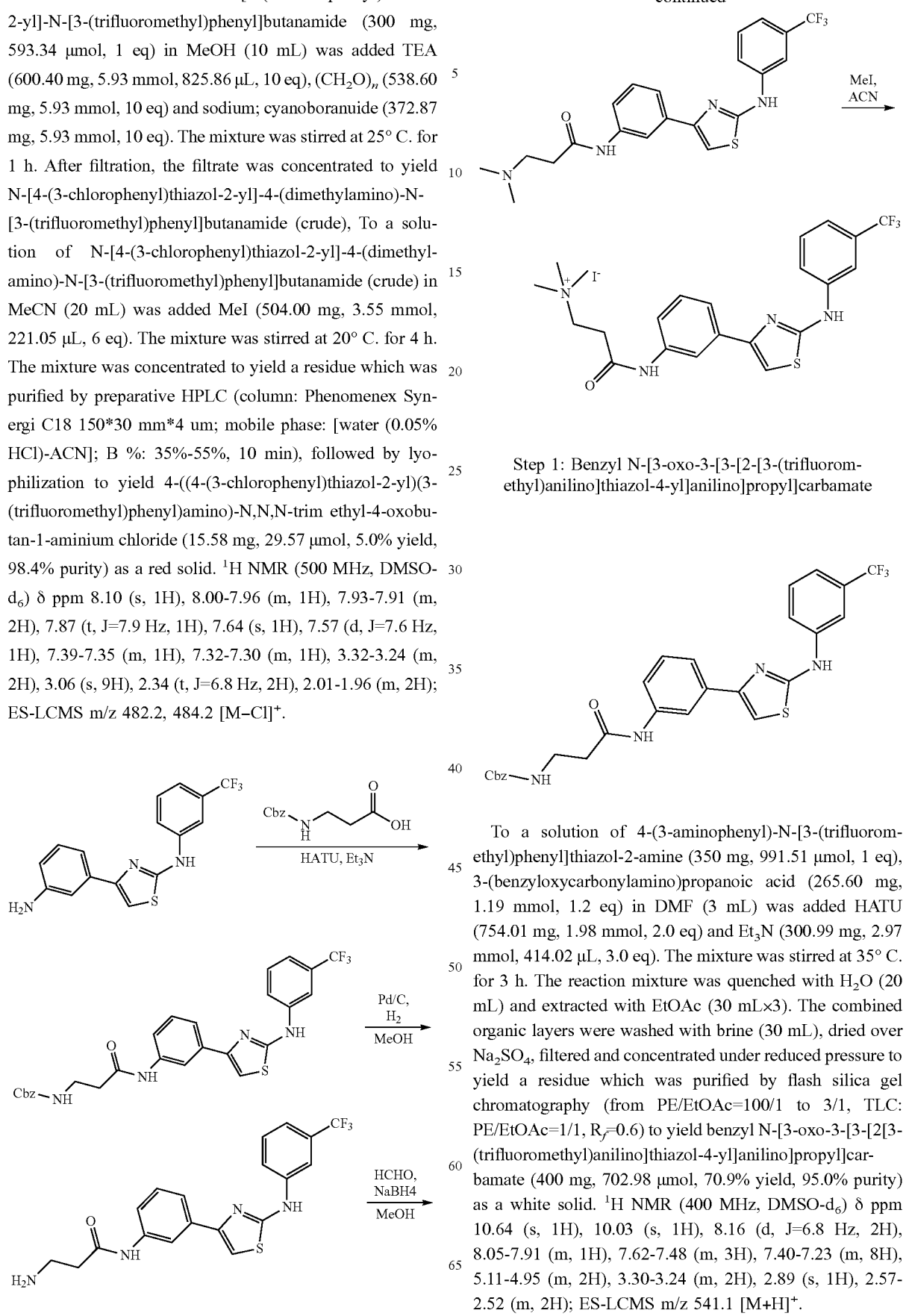

Step 1: Benzyl N-[3-oxo-3-[3-[2-[3-(trifluoromethyl)anilino]thiazol-4-yl]anilino]propyl]carbamate To a solution of 4-(3-aminophenyl)-N-[3-(trifluoromethyl)phenyl]thiazol-2-amine (350 mg, 991.51 μmol, 1 eq), 3-(benzyloxycarbonylamino)propanoic acid (265.60 mg, 1.19 mmol, 1.2 eq) in DMF (3 mL) was added HATU (754.01 mg, 1.98 mmol, 2.0 eq) and Et₃N (300.99 mg, 2.97 mmol, 414.02 μL, 3.0 eq). The mixture was stirred at 35° C. for 3 h. The reaction mixture was quenched with H₂O (20 mL) and extracted with EtOAc (30 mL×3). The combined organic layers were washed with brine (30 mL), dried over Na₂SO₄, filtered and concentrated under reduced pressure to yield a residue which was purified by flash silica gel chromatography (from PE/EtOAc=100/1 to 3/1, TLC: PE/EtOAc=1/1, R_f=0.6) to yield benzyl N-[3-oxo-3-[3-[2[3-(trifluoromethyl)anilino]thiazol-4-yl]anilino]propyl]carbamate (400 mg, 702.98 μmol, 70.9% yield, 95.0% purity) as a white solid. ¹H NMR (400 MHz, DMSO-d₆) δ ppm 10.64 (s, 1H), 10.03 (s, 1H), 8.16 (d, J=6.8 Hz, 2H), 8.05-7.91 (m, 1H), 7.62-7.48 (m, 3H), 7.40-7.23 (m, 8H), 5.11-4.95 (m, 2H), 3.30-3.24 (m, 2H), 2.89 (s, 1H), 2.57-2.52 (m, 2H); ES-LCMS m/z 541.1 [M+H]⁺.

Step 2: 3-Amino-N-[3-[2-[3-(trifluoromethyl)anilino]thiazol-4-yl]phenyl]propanamide

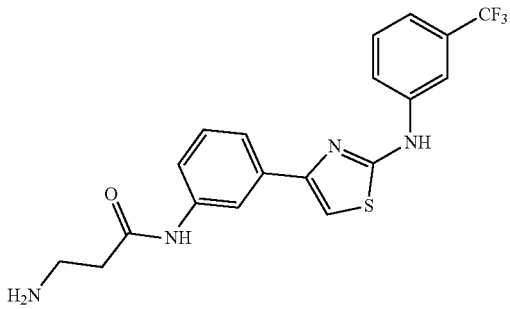 [SMILES: NCCC(=O)Nc1cccc(-c2csc(Nc3cccc(C(F)(F)F)c3)n2)c1]

To a solution of benzyl N-[3-oxo-3-[3-[2-[3-(trifluoromethyl)anilino]thiazol-4-yl]anilino]propyl]carbamate (400 mg, 702.98 μmol, 1 eq) in MeOH (50 mL) was added Pd/C (1.87 g, 10% purity) with stirred at 28° C. under H$_2$ (15 Psi). The mixture was stirred at 28° C. for 24 h. TLC (DCM/MeOH=8/1, R$_f$=0.2) showed that new point was formed and start material was remained. The mixture was filtrated and concentrated to yield a residue which was purified by preparative TLC (DCM/MeOH=8/1, TLC: DCM/MeOH=8/1, R$_f$=0.2) to yield 3-amino-N-[3-[2-[3-(trifluoromethyl)anilino]thiazol-4-yl]phenyl]propanamide (60 mg, 140.25 μmol, 20.0% yield, 95.0% purity) as yellow oil. $^1$H NMR (400 MHz, CD$_3$OD) δ ppm 8.12 (s, 2H), 7.94 (d, J=8.0 Hz, 1H), 7.64 (d, J=8.0 Hz, 1H), 7.52-7.44 (m, 2H), 7.35-7.29 (m, 1H), 7.19 (d, J=8.0 Hz, 1H), 7.07 (s, 1H), 3.23 (t, J=6.4 Hz, 2H), 2.83-2.76 (m, 2H); ES-LCMS m/z 407.0 [M+H]$^+$.

Step 3: 3-(Dimethylamino)-N-[3-[2-[3-(trifluoromethyl)anilino]thiazol-4-yl]phenyl]propanamide

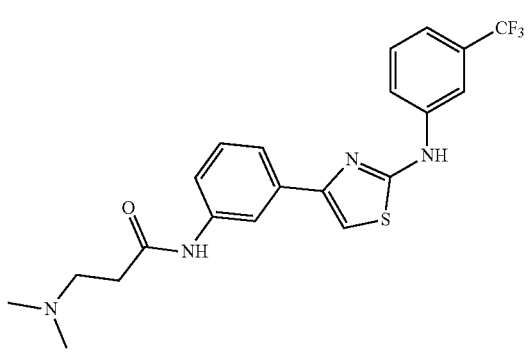 [SMILES: CN(C)CCC(=O)Nc1cccc(-c2csc(Nc3cccc(C(F)(F)F)c3)n2)c1]

To a solution of 3-amino-N-[3-[2-[3-(trifluoromethyl)anilino]thiazol-4-yl]phenyl]propanamide (60 mg, 140.25 μmol, 1 eq) in MeOH (5 mL) was added formaldehyde (4.21 mg, 140.25 μmol, 3.86 μL, 1 eq). The mixture was stirred at 25° C. for 5 h. NaBH$_4$ (5.31 mg, 140.25 μmol, 1 eq) was added into the mixture with stirred at 25° C. for 1 h. The reaction mixture was quenched with H$_2$O (20 mL) and extracted with EtOAc (30 mL×3). The combined organic layers were washed with brine (30 mL), dried over Na$_2$SO$_4$, filtered and concentrated under reduced pressure to yield a residue which was purified by preparative HPLC (column: Welch Xtimate C18 150*25 mm*5 um; mobile phase: [water (10 mM NH$_4$HCO$_3$)-ACN]; B %: 45%-75%, 10 min) to yield 3-(dimethylamino)-N-[3-[2-[3-(trifluoromethyl)anilino]thiazol-4-yl]phenyl]propanamide (18 mg, 39.36 μmol, 28.1% yield, 95.0% purity) as a white solid. $^1$H NMR (400 MHz, CDCl$_3$) δ ppm 10.96 (s, 1H), 7.96 (s, 1H), 7.81 (s, 1H), 7.65 (d, J=7.6 Hz, 1H), 7.57 (d, J=8.0 Hz, 1H), 7.52 (d, J=8.0 Hz, 1H), 7.45 (t, J=8.0 Hz, 1H), 7.37-7.31 (m, 1H), 7.28 (d, J=8.8 Hz, 2H), 6.91 (s, 1H), 2.68-2.62 (m, 2H), 2.54-2.48 (m, 2H), 2.38 (s, 6H); ES-LCMS m/z 435.1 [M+H]$^+$.

Step 4: N-[3-[2-[3-(Trifluoromethyl)anilino]thiazol-4-yl]phenyl]-3-[BLAH(trimethyl)-azanyl]propanamide

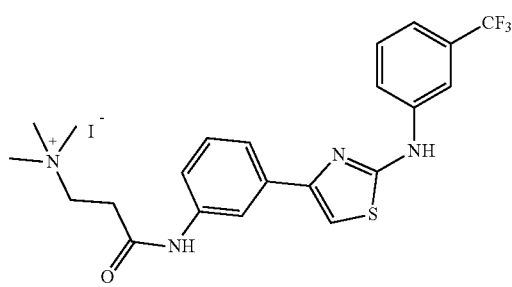

To a solution of 3-(dimethylamino)-N-[3-[2-[3-(trifluoromethyl)anilino]thiazol-4-yl]phenyl]propanamide (18 mg, 39.36 μmol, 1 eq) in ACN (10 mL) was added MeI (5.59 mg, 39.36 μmol, 2.45 μL, 1 eq). The mixture was stirred at 28° C. for 2 h. The solution was quenched with water (10 mL) and lyophilized to yield N-[3-[2-[3-(trifluoromethyl)anilino]thiazol-4-yl]phenyl]-3-[BLAH(trimethyl)-azanyl]propanamide (21.65 mg, 37.56 μmol, 95.4% yield, 100.0% purity) as a white solid. $^1$H NMR (400 MHz, DMSO-d$_6$) δ ppm 10.76 (s, 1H), 10.54 (s, 1H), 8.17 (s, 2H), 8.05 (d, J=9.2 Hz, 1H), 7.64-7.56 (m, 3H), 7.42-7.36 (m, 1H), 7.32-7.28 (m, 2H), 3.69 (t, J=7.6 Hz, 2H), 3.12 (s, 9H), 2.97 (t, J=7.2 Hz, 2H); ES-LCMS m/z 449.0 [M−I]$^+$.

I-40

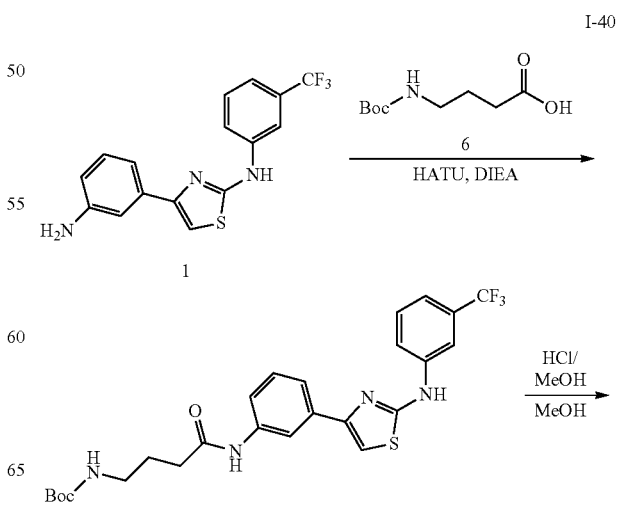

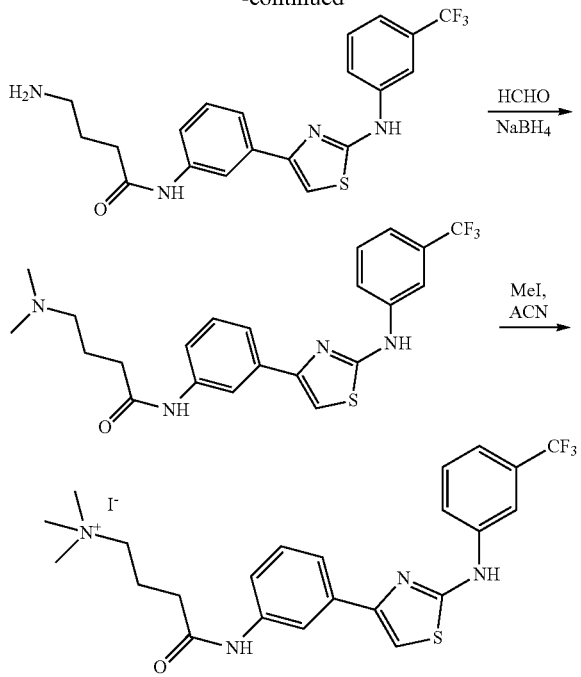

Step 1: tert-Butyl N-[4-oxo-4-[3-[2-[3-(trifluoromethyl)anilino]thiazol-4-yl]anilino]butyl]carbamate To a solution of 4-(3-aminophenyl)-N-[3-(trifluoromethyl)phenyl]thiazol-2-amine (300 mg, 849.87 μmol, 1 eq) and 4-(tert-butoxycarbonylamino)butanoic acid (190.00 mg, 934.85 μmol, 1.1 eq) in DMF (8 mL) was added HATU (646.29 mg, 1.70 mmol, 2.0 eq) and Et$_3$N (257.99 mg, 2.55 mmol, 354.88 μL, 3.0 eq). The mixture was stirred at 25° C. for 2 h. TLC (PE/EtOAc=1/1, R$_f$=0.6) showed that new point was formed and start material was consumed completely. The reaction mixture was quenched by addition H$_2$O (20 mL) and extracted with EtOAc (30 mL×3). The combined organic layers were washed with brine (30 mL), dried over Na$_2$SO$_4$, filtered and concentrated under reduced pressure to yield a residue which was purified by flash silica gel chromatography (from PE/EtOAc=100/1 to 3/1, TLC: PE/EtOAc=1/1, R$_f$=0.6) to yield tert-butyl N-[4-oxo-4-[3-[2-[3-(trifluoromethyl)anilino]thiazol-4-yl]anilino]butyl] carbamate (420 mg, 766.47 μmol, 90.2% yield, 95.0% purity) as a white solid. $^1$H NMR (400 MHz, CDCl$_3$) δ ppm 8.84 (s, 1H), 8.45 (s, 1H), 8.11 (s, 1H), 7.84 (s, 1H), 7.75-7.67 (m, 1H), 7.59 (d, J=7.6 Hz, 1H), 7.52 (d, J=7.6 Hz, 1H), 7.41 (t, J=8.0 Hz, 1H), 7.36-7.30 (m, 1H), 7.23 (d, J=8.0 Hz, 1H), 6.83 (s, 1H), 4.94 (s, 1H), 3.32-3.21 (m, 2H), 2.41 (t, J=6.8 Hz, 2H), 1.94-1.84 (m, 2H), 1.52-1.40 (m, 9H); ES-LCMS m/z 421.1 [M-Boc+H]$^+$.

Step 2: 4-Amino-N-[3-[2-[3-(trifluoromethyl)anilino]thiazol-4-yl]phenyl]butanamide

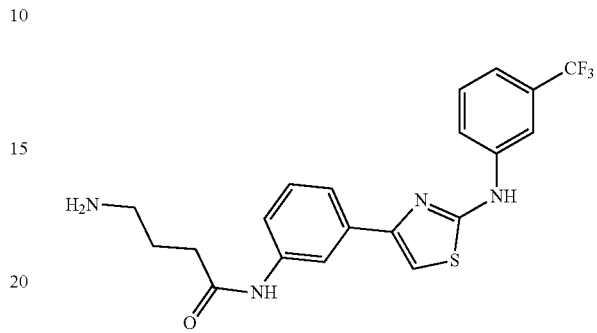

To a solution of tert-butyl N-[4-oxo-4-[3-[2-[3-(trifluoromethyl)anilino]thiazol-4-yl]anilino]butyl]carbamate (420 mg, 766.47 μmol, 1 eq) in MeOH (8 mL) was added HCl/MeOH (4 M, 8 mL). The mixture was stirred at 25° C. for 2 h. The mixture was concentrated to yield 4-amino-N-[3-[2-[3-(trifluoromethyl)anilino]thiazol-4-yl]phenyl]butanamide (380 mg, 748.50 μmol, 97.7% yield, 90.0% purity, HCl) as a white solid, which was used in the next step without further purification. $^1$H NMR (400 MHz, CDCl$_3$) δ ppm 8.83 (br s, 1H), 8.00 (s, 1H), 7.84 (d, J=7.2 Hz, 2H), 7.63 (d, J=8.0 Hz, 1H), 7.60-7.52 (m, 3H), 7.47-7.40 (m, 2H), 7.24-7.23 (m, 1H), 6.70-6.63 (m, 1H), 3.89-3.56 (m, 2H), 2.91-2.83 (m, 2H), 2.52 (t, J=6.8 Hz, 2H), 1.93-1.85 (m, 2H); ES-LCMS m/z 421.0 [M+H]$^+$.

Step 3: 4-(Dimethylamino)-N-[3-[2-[3-(trifluoromethyl)anilino]thiazol-4-yl]phenyl]butanamide

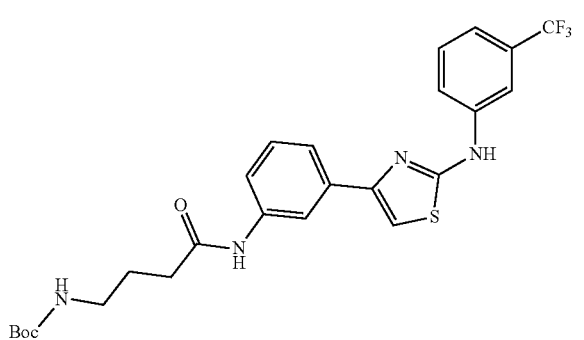 [SMILES: CC(C)(C)OC(=O)NCCCC(=O)Nc1cccc(-c2csc(Nc3cccc(C(F)(F)F)c3)n2)c1]

To a solution of 4-amino-N-[3-[2-[3-(trifluoromethyl)anilino]thiazol-4-yl]phenyl]butanamide (50 mg, 107.03 μmol, 1 eq) in MeOH (5 mL) was added formaldehyde (26.06 mg, 321.08 μmol, 23.91 μL, 37% purity, 3 eq) under N$_2$. The mixture was stirred at 25° C. for 2 h. NaBH$_4$ (12.15 mg, 321.08 μmol, 3 eq) was added into the mixture with stirred at 25° C. for 1 h under N$_2$ atmosphere. The mixture was filtrated and concentrated to yield a residue which was purified by preparative HPLC(column: Agela DuraShell C18 150*25 mm*5 um; mobile phase: [water (0.05% NH$_3$H$_2$O+10 mM NH$_4$HCO$_3$)-ACN]; B %: 49%-79%, 10 min) and concentrated to yield a residue which was purified by preparative HPLC (column: Welch Xtimate C18 150*25 mm*5 um; mobile phase: [water (0.225% FA)-ACN]; B %: 25%-55%, 8 min) to yield 4-(dimethylamino)-N-[3-[2-[3-(trifluoromethyl)anilino]thiazol-4-yl]phenyl]butanamide (15 mg, 28.82 μmol, 26.9% yield, 95.0% purity, FA) as a white solid. $^1$H NMR (400 MHz, DMSO-d$_6$) δ ppm 10.66 (s, 1H), 9.99 (s, 1H), 8.21 (d, J=9.6 Hz, 2H), 8.16 (s, 1H), 7.98 (d, J=8.8 Hz, 1H), 7.63-7.49 (m, 3H), 7.40-7.26 (m, 3H), 2.40-2.30 (m, 4H), 2.19 (s, 6H), 1.79-1.71 (m, 2H); ES-LCMS m/z 449.2 [M+H]$^+$.

Step 4: N-[3-[2-[3-(Trifluoromethyl)anilino]thiazol-4-yl]phenyl]-4-[BLAH(trimethyl)-azanyl]butanamide

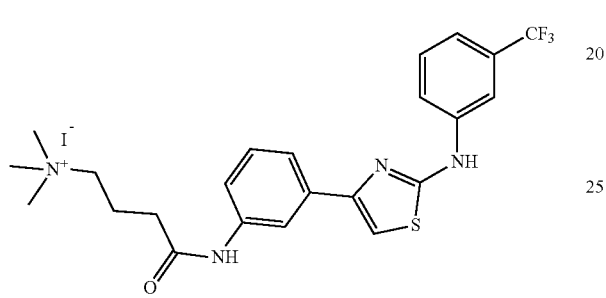

To a solution of 4-(dimethylamino)-N-[3-[2-[3-(trifluoromethyl)anilino]thiazol-4-yl]phenyl]butanamide (15 mg, 31.77 μmol, 1 eq) in ACN (5 mL) was added MeI (22.55 mg, 158.86 μmol, 9.89 μL, 5 eq). The mixture was stirred at 25° C. for 2 h. The mixture was lyophilized to yield N-[3-[2-[3-(trifluoromethyl)anilino]thiazol-4-yl]phenyl]-4-[BLAH(trimethyl)-azanyl]butanamide (17.73 mg, 29.76 μmol, 93.7% yield, 99.1% purity) as a white solid. $^1$H NMR (400 MHz, DMSO-d$_6$) δ ppm 10.71 (s, 1H), 10.17 (s, 1H), 8.19 (d, J=12.0 Hz, 2H), 8.00 (d, J=7.6 Hz, 1H), 7.62-7.53 (m, 3H), 7.41-7.34 (m, 1H), 7.32-7.26 (m, 2H), 3.46-3.40 (m, 2H), 3.08 (s, 9H), 2.47-2.41 (m, 2H), 2.10-1.96 (m, 2H); ES-LCMS m/z 463.0 [M−I]$^+$.

I-15

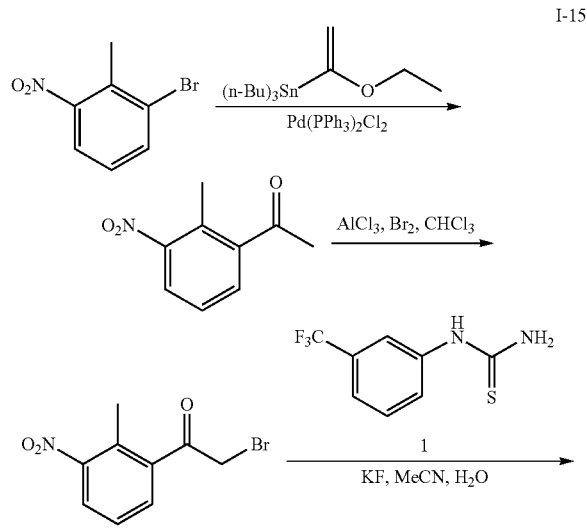

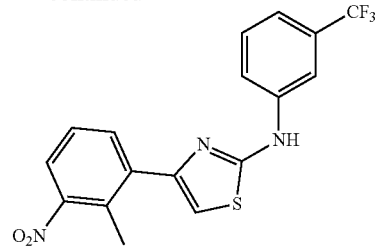

Step 1: 1-(2-Methyl-3-nitro-phenyl)ethanone

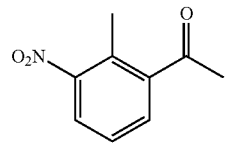

To a solution of 1-bromo-2-methyl-3-nitro-benzene (1 g, 4.63 mmol, 1 eq) in 1,4-dioxane (5 mL) was added tributyl (1-ethoxyvinyl)stannane (1.75 g, 4.85 mmol, 1.64 mL, 1.05 eq) and Pd(PPh$_3$)$_2$Cl$_2$ (324.90 mg, 462.89 μmol, 0.1 eq). The mixture was stirred at 100° C. for 12 h under N$_2$ atmosphere. Then the reaction mixture was cooled to 0° C. and treated with HCl (2 M, 2.44 mL, 1.05 eq) and stirred for 1 h. The pH was adjusted to around 9 by progressively adding NaOH solution. The reaction mixture was diluted with water (50 mL) then extracted with EtOAc (30 mL×3). The combined organic layers were dried over Na$_2$SO$_4$, filtered and the filtrate was concentrated to yield a residue which was purified by flash silica gel chromatography (from PE/EtOAc=100/1 to 2/1, TLC: PE/EtOAc=3/1, R$_f$=0.55) to yield 1-(2-methyl-3-nitro-phenyl)ethanone (750 mg, 3.77 mmol, 81.4% yield, 90.0% purity) as a light yellow solid. $^1$H NMR (400 MHz, DMSO-d$_6$) δ ppm 7.98 (dd, J=3.4, 7.8 Hz, 2H), 7.56 (t, J=7.9 Hz, 1H), 2.60 (s, 3H), 2.37 (s, 3H).

Step 2: 2-Bromo-1-(2-methyl-3-nitro-phenyl)ethanone

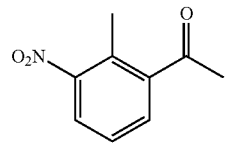

To a solution of 1-(2-methyl-3-nitro-phenyl)ethanone (350 mg, 1.95 mmol, 1 eq) in AcOH (2 mL) was added HBr (32.93 mg, 195.34 μmol, 22.10 μL, 48.0% purity, 0.1 eq) and Br$_2$ (624.35 mg, 3.91 mmol, 201.40 μL, 2 eq). The mixture was stirred at 25° C. for 12 h under N$_2$ atmosphere. The reaction mixture was diluted with water (50 mL) then extracted with EtOAc (30 mL×3). The combined organic layers were dried over Na$_2$SO$_4$, filtered and the filtrate was concentrated to yield 2-bromo-1-(2-methyl-3-nitro-phenyl) ethanone (350 mg, 1.36 mmol, 69.4% yield) as yellow oil. $^1$H NMR (400 MHz, DMSO-d$_6$) δ ppm 8.11 (dd, J=2.9, 8.1 Hz, 1H), 8.08 (d, J=8.1 Hz, 2H), 5.74 (s, 2H), 2.37 (s, 3H).

Step 3: 4-(2-Methyl-3-nitro-phenyl)-N-[3-(trifluoromethyl)phenyl]thiazol-2-amine

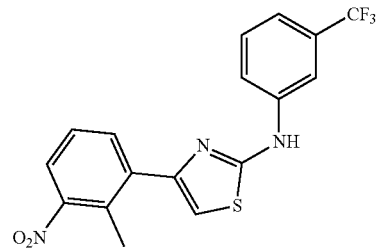 [SMILES: Cc1c(-c2csc(Nc3cccc(C(F)(F)F)c3)n2)cccc1[N+](=O)[O-]]

To a solution of 2-bromo-1-(2-methyl-3-nitro-phenyl)ethanone (300 mg, 1.16 mmol, 1 eq) and [3-(trifluoromethyl)phenyl]thiourea (256.00 mg, 1.16 mmol, 1 eq) in MeCN (2 mL) and H₂O (2 mL) was added KF (81.04 mg, 1.39 mmol, 1.2 eq). The mixture was stirred at 25° C. for 2 h under N₂ atmosphere. The reaction mixture was diluted with water (50 mL) then extracted with EtOAc (30 mL×3). The combined organic layers were dried over Na₂SO₄, filtered and the filtrate was concentrated to yield a residue which was purified by flash silica gel chromatography (from PE/EtOAc=100/1 to 2/1, TLC: PE/EtOAc=3/1, R$_f$=0.50) to yield 4-(2-methyl-3-nitro-phenyl)-N-[3-(trifluoromethyl)phenyl]thiazol-2-amine (240 mg, 632.65 μmol, 54.4% yield, 100.0% purity) as a yellow solid. ¹H NMR (500 MHz, CD₃OD) δ ppm 7.80 (d, J=7.9 Hz, 1H), 7.77-7.73 (m, 2H), 7.63 (d, J=7.9 Hz, 1H), 7.50-7.41 (m, 2H), 7.38 (t, J=7.9 Hz, 1H), 7.33 (d, J=7.9 Hz, 1H), 6.72 (s, 1H), 2.57 (s, 3H); ES-LCMS m/z 380.1 [M+H]⁺.

I-16

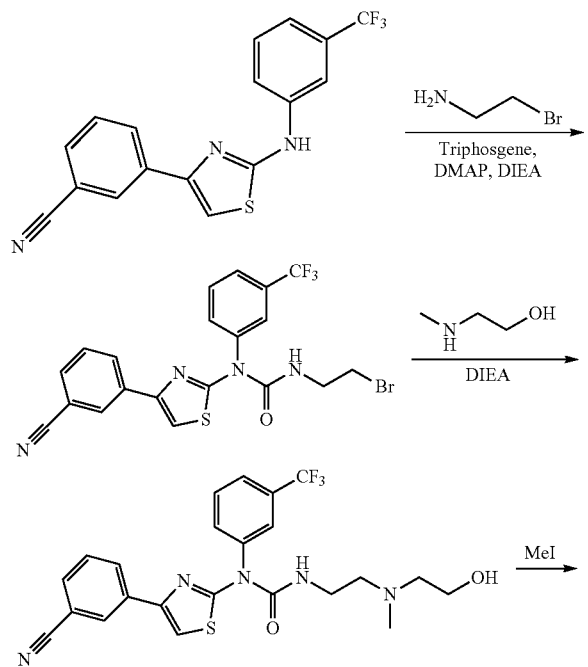

-continued

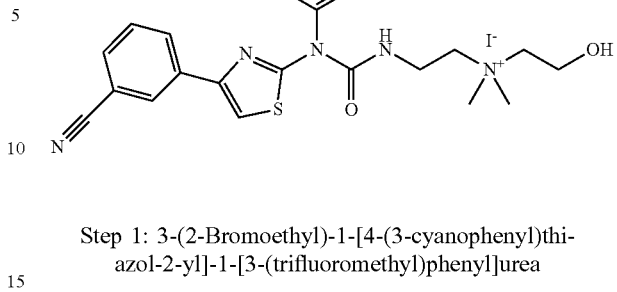

Step 1: 3-(2-Bromoethyl)-1-[4-(3-cyanophenyl)thiazol-2-yl]-1-[3-(trifluoromethyl)phenyl]urea

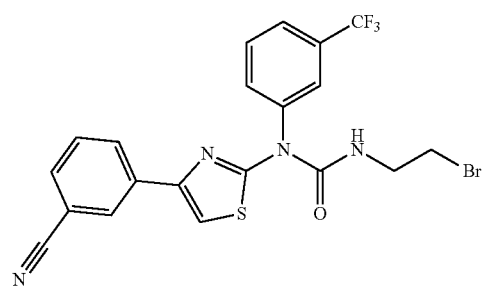 [SMILES: N#Cc1cccc(-c2csc(N(C(=O)NCCBr)c3cccc(C(F)(F)F)c3)n2)c1]

To a solution of 3-[2-[3-(trifluoromethyl)anilino]thiazol-4-yl]benzonitrile (200 mg, 486.48 μmol, 1 eq) and DIEA (188.62 mg, 1.46 mmol, 254.20 μL, 3 eq) in THF (5 mL) was added bis(trichloromethyl) carbonate (250 mg, 842.46 μmol, 1.73 eq) and stirred at 80° C. for 2 h. The reaction mixture was concentrated to yield (4-(3-chlorophenyl)thiazol-2-yl)(3-(trifluoromethyl)phenyl)carbamic chloride (crude). Then to a solution of 2-bromoethanamine (498.37 mg, 2.43 mmol, 5 eq, HBr), DIEA (188.62 mg, 1.46 mmol, 254.20 μL, 3 eq) and DMAP (5.94 mg, 48.65 μmol, 0.1 eq) in DCM (2 mL) was added (4-(3-chlorophenyl)thiazol-2-yl)(3-(trifluoromethyl)phenyl)carbamic chloride (crude) in DCM (3 mL) and stirred at 25° C. for 1 h. The solution was quenched by addition of sat. aq. NaHCO₃ (3 mL), diluted with water (30 mL) and extracted with ethyl acetate (30 mL×3). The combined organic phase was washed with brine (20 mL), dried over anhydrous Na₂SO₄, filtered and concentrated in vacuum to yield a residue which was purified by flash silica gel chromatography (from PE/EtOAc=200/1 to 3/1, TLC: PE/EtOAc=3/1, R$_f$=0.40) to yield 3-(2-bromoethyl)-1-[4-(3-cyanophenyl)thiazol-2-yl]-1-[3-(trifluoromethyl)phenyl]urea (140 mg, 245.90 μmol, 50.6% yield, 87% purity) as a yellow solid. ¹H NMR (400 MHz, CDCl₃) δ ppm 8.84 (s, 1H), 8.14 (s, 1H), 8.02 (d, J=7.8 Hz, 1H), 7.84-7.79 (m, 1H), 7.78-7.69 (m, 2H), 7.68-7.58 (m, 2H), 7.54-7.48 (m, 1H), 7.12 (s, 1H), 3.90 (q, J=5.7 Hz, 2H), 3.69-3.59 (m, 2H); ES-LCMS m/z 495.0, 497.0 [M+H]⁺.

Step 2: 1-[4-(3-Cyanophenyl)thiazol-2-yl]-3-[2-[2-hydroxyethyl(methyl)amino]ethyl]-1-[3-(trifluoromethyl)phenyl]urea

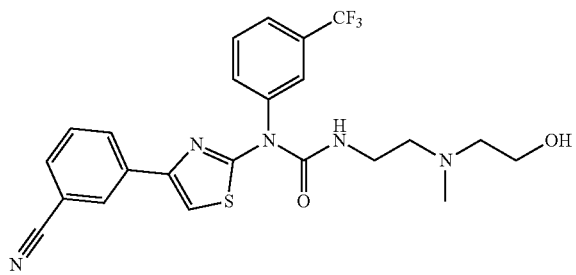 [SMILES: CN(CCO)CCNC(=O)N(c1cccc(C(F)(F)F)c1)c1nc(-c2cccc(C#N)c2)cs1]

To a solution of 3-(2-bromoethyl)-1-[4-(3-cyanophenyl)thiazol-2-yl]-1-[3-(trifluoromethyl)phenyl]urea (140 mg, 245.90 µmol, 1 eq) and 2-(methylamino)ethanol (184.70 mg, 2.46 mmol, 197.54 µL, 10 eq) in THF (5 mL) was added DIEA (63.56 mg, 491.81 µmol, 85.66 µL, 2 eq). The mixture was stirred at 25° C. for 48 h. To the mixture was added water (30 mL) and extracted with ethyl acetate (30 mL×3). The combined organic phase was washed with brine (20 mL), dried over anhydrous $Na_2SO_4$, filtered and concentrated in vacuum to yield a residue which was purified by preparative HPLC (column: Agela DuraShell C18 150*25 mm*5 µm; mobile phase: [water (0.05% $NH_3 \cdot H_2O$+10 mM $NH_4HCO_3$)-ACN]; B %: 40%–70%, 10 min), followed by lyophilization to yield 1-[4-(3-cyanophenyl)thiazol-2-yl]-3-[2-[2-hydroxyethyl(methyl)amino]ethyl]-1-[3-(trifluoromethyl)phenyl]urea (80 mg, 163.43 µmol, 66.5% yield, 100% purity) as colorless oil. $^1$H NMR (400 MHz, $CDCl_3$) δ ppm 8.38 (s, 1H), 8.04 (s, 1H), 7.96 (d, J=7.8 Hz, 1H), 7.84-7.77 (m, 1H), 7.75-7.69 (m, 2H), 7.67-7.57 (m, 2H), 7.54-7.48 (m, 1H), 7.10 (s, 1H), 3.61-3.50 (m, 4H), 2.67 (t, J=5.7 Hz, 2H), 2.60 (t, J=5.3 Hz, 2H), 2.41 (s, 3H), 2.24 (s, 1H); ES-LCMS m/z 490.1 [M+H]$^+$.

Step 3: 1-[4-(3-Cyanophenyl)thiazol-2-yl]-3-(2-BLAHethyl)-1-[3-(trifluoromethyl)phenyl]urea

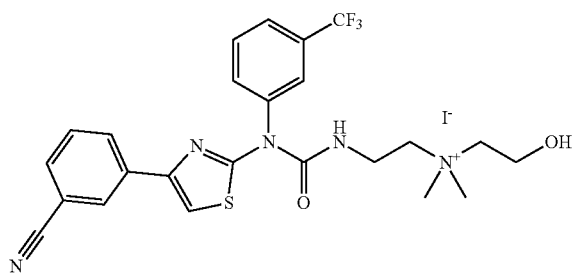 [SMILES: C[N+](C)(CCO)CCNC(=O)N(c1cccc(C(F)(F)F)c1)c1nc(-c2cccc(C#N)c2)cs1 ; [I-]]

To a solution of 1-[4-(3-cyanophenyl)thiazol-2-yl]-3-[2-[2-hydroxyethyl(methyl)amino]ethyl]-1-[3-(trifluoromethyl)phenyl]urea (80 mg, 163.43 µmol, 1 eq) in ACN (5 mL) was added MeI (231.97 mg, 1.63 mmol, 101.74 µL, 10 eq). The mixture was stirred at 25° C. for 1 h. The mixture was without further purification which was diluted with water (10 mL), then lyophilization to yield 1-[4-(3-cyanophenyl)thiazol-2-yl]-3-(2-BLAHethyl)-1-[3-(trifluoromethyl)phenyl]urea (86.8 mg, 137.46 µmol, 84.1% yield, 100% purity) as a white solid. $^1$H NMR (500 MHz, DMSO-d$_6$) δ ppm 8.03 (s, 1H), 7.98-7.95 (m, 2H), 7.91-7.80 (m, 4H), 7.71 (d, J=7.8 Hz, 1H), 7.55 (t, J=7.9 Hz, 1H), 7.00 (t, J=5.3 Hz, 1H), 5.31 (t, J=4.7 Hz, 1H), 3.83 (s, 2H), 3.55 (d, J=5.0 Hz, 2H), 3.50-3.46 (m, 2H), 3.43-3.40 (m, 2H), 3.10 (s, 6H); ES-LCMS m/z 504.2 [M−I]$^+$.

I-42

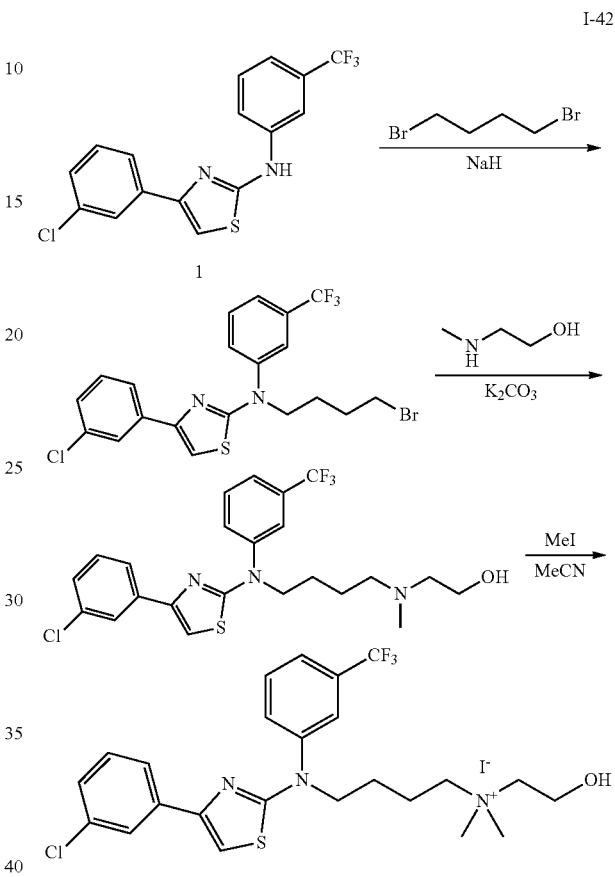

Step 1: N-(4-Bromobutyl)-4-(3-chlorophenyl)-N-[3-(trifluoromethyl)phenyl]thiazol-2-amine

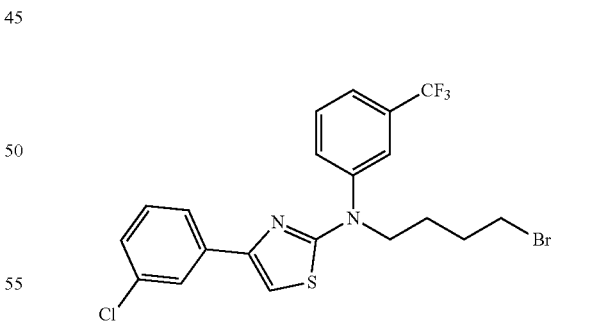

To a stirred solution of 4-(3-chlorophenyl)-N-[3-(trifluoromethyl)phenyl]thiazol-2-amine (100 mg, 281.87 µmol, 1 eq) in DMF (3 mL) was added NaH (13.53 mg, 338.24 µmol, 60%, 1.2 eq) at 0° C. for 0.5 h, then 1,4-dibromobutane (73.03 mg, 338.24 µmol, 40.80 µL, 1.2 eq) was added to the reaction mixture and stirred at 25° C. for 2.5 h under $N_2$ atmosphere. The reaction mixture was diluted with $H_2O$ (5 mL) and extracted with EtOAc (10 mL×3). The combined organic layers were washed with brine (10 mL), dried over Na$_2$SO$_4$, filtered and concentrated under reduced pressure to yield a residue which was purified by preparative TLC (PE/EtOAc=5/1, TLC: PE/EtOAc=5/1, R$_f$=0.68) to yield N-(4-bromobutyl)-4-(3-chlorophenyl)-N-[3-(trifluoromethyl)phenyl]thiazol-2-amine (60 mg, 116.38 μmol, 41.3% yield, 95.0% purity) as yellow oil. $^1$H NMR (400 MHz, CDCl$_3$) δ ppm 7.85 (t, J=1.7 Hz, 1H), 7.71 (dd, J=1.6, 6.0 Hz, 2H), 7.65-7.61 (m, 1H), 7.59 (d, J=6.4 Hz, 2H), 7.35-7.30 (m, 1H), 7.30-7.28 (m, 1H), 6.75 (s, 1H), 4.13 (t, J=7.1 Hz, 2H), 3.49 (t, J=6.4 Hz, 2H), 2.05-1.99 (m, 2H), 1.97-1.89 (m, 2H); ES-LCMS m/z 488.7, 490.7 [M+H]$^+$.

Step 2: 2-[4-[N-[4-(3-Chlorophenyl)thiazol-2-yl]-3-(trifluoromethyl)anilino]butyl-methyl-amino]ethanol

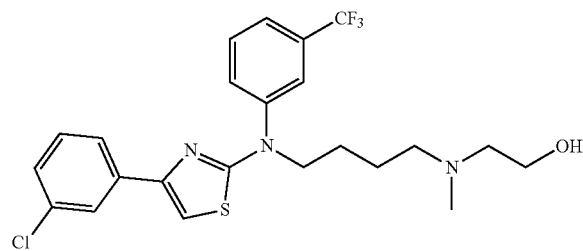 [SMILES: CN(CCO)CCCCN(c1cccc(C(F)(F)F)c1)c1nc(-c2cccc(Cl)c2)cs1]

To a stirred solution of N-(4-bromobutyl)-4-(3-chlorophenyl)-N-[3-(trifluoromethyl)phenyl]thiazol-2-amine (50 mg, 96.98 μmol, 1 eq) and 2-(methylamino)ethanol (36.42 mg, 484.91 μmol, 38.95 μL, 5 eq) in THF (5 mL) was added DIEA (37.60 mg, 290.95 μmol, 50.68 μL, 3 eq). The reaction mixture was stirred at 25° C. for 48 h under N$_2$ atmosphere. The reaction mixture was concentrated under reduced pressure to yield a residue which was purified by preparative HPLC (column: Agela DuraShell C18 150*25 mm*5 μm; mobile phase: [water (0.04% NH$_3$H$_2$O+10 mM NH$_4$HCO$_3$)-ACN]; B %: 70%-100%, 10 min) to yield 2-[4-[N-[4-(3-chlorophenyl)thiazol-2-yl]-3-(trifluoromethyl)anilino]butyl-methyl-amino]ethanol (45 mg, 91.12 μmol, 93.96% yield, 98% purity) as white gum. $^1$H NMR (500 MHz, CDCl$_3$) δ ppm 7.85 (s, 1H), 7.73-7.68 (m, 2H), 7.64-7.61 (m, 1H), 7.61-7.55 (m, 2H), 7.35-7.30 (m, 1H), 7.28 (d, J=1.4 Hz, 1H), 6.75 (s, 1H), 4.10 (t, J=7.3 Hz, 2H), 3.62 (t, J=5.1 Hz, 2H), 2.60 (d, J=5.3 Hz, 4H), 2.33 (s, 3H), 1.85-1.76 (m, 2H), 1.68 (d, J=7.2 Hz, 2H); ES-LCMS m/z 483.9, 485.9 [M+H]$^+$.

Step 3: 2-[BLAH-[4-[N-[4-(3-Chlorophenyl)thiazol-2-yl]-3-(trifluoromethyl)anilino]butyl]-dimethyl-azanyl]ethanol

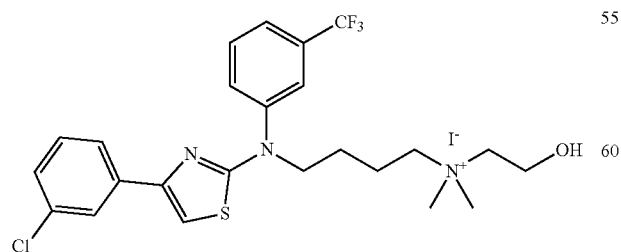

To a stirred solution of 2-[4-[N-[4-(3-chlorophenyl)thiazol-2-yl]-3-(trifluoromethyl)anilino]butyl-methyl-amino]ethanol (45 mg, 91.12 μmol, 1 eq) in MeCN (5 mL) was added MeI (129.33 mg, 911.20 μmol, 56.73 μL, 10 eq). The reaction mixture was stirred at 25° C. for 1 h under N$_2$ atmosphere. The reaction mixture was lyophilized to yield 2-[BLAH-[4-[N-[4-(3-chlorophenyl)thiazol-2-yl]-3-(trifluoromethyl)anilino]butyl]-dimethyl-azanyl]ethanol (28.95 mg, 45.02 μmol, 49.4% yield, 97.3% purity) as off-white gum. $^1$H NMR (500 MHz, DMSO-d$_6$) δ ppm 8.02-7.98 (m, 1H), 7.93-7.90 (m, 1H), 7.87-7.82 (m, 2H), 7.78-7.70 (m, 2H), 7.46-7.42 (m, 2H), 7.37 (d, J=7.2 Hz, 1H), 5.25 (t, J=5.0 Hz, 1H), 4.14-4.07 (m, 2H), 3.79 (s, 2H), 3.36 (d, J=2.7 Hz, 2H), 3.35-3.34 (m, 2H), 3.03 (s, 6H), 1.84-1.75 (m, 2H), 1.69-1.63 (m, 2H); ES-LCMS m/z 498.1, 500.1 [M–]$^+$.

I-26

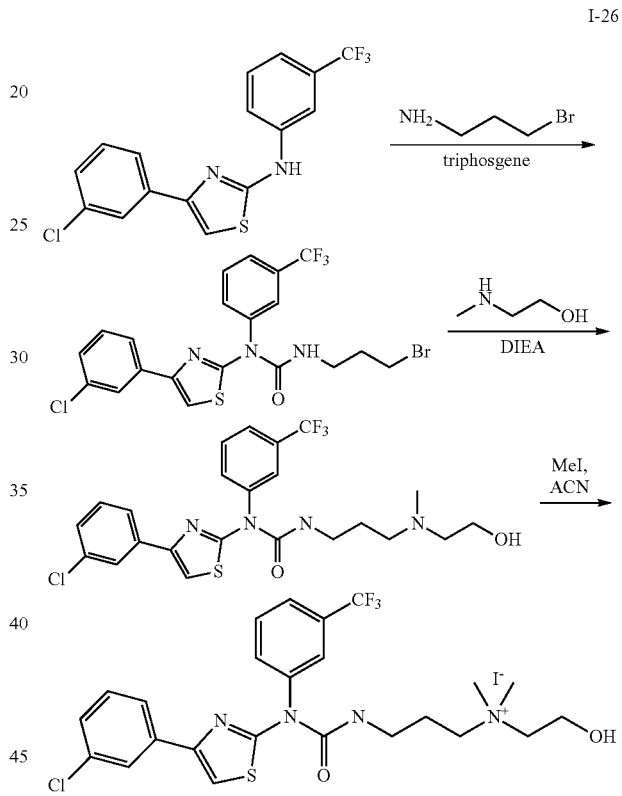

Step 1: 3-(3-Bromopropyl)-1-[4-(3-chlorophenyl)thiazol-2-yl]-1-[3-(trifluoromethyl)phenyl]urea

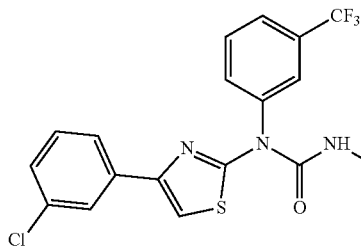

To a stirred solution of 4-(3-chlorophenyl)-N-[3-(trifluoromethyl)phenyl]thiazol-2-amine (200 mg, 535.55 μmol, 1 eq) and bis(trichloromethyl) carbonate (190.71 mg, 642.66

μmol, 1.2 eq) in THF (8 mL) was added DIEA (207.65 mg, 1.61 mmol, 279.85 μL, 3 eq.) The reaction mixture was stirred at 80° C. for 2 h. The reaction mixture was concentrated to yield (4-(3-chlorophenyl)thiazol-2-yl)(3-(trifluoromethyl)phenyl)carbamic chloride (crude). Then to a solution of 3-bromopropan-1-amine (369.54 mg, 2.68 mmol, 5 eq), DIEA (207.65 mg, 1.61 mmol, 279.85 μL, 3 eq) and DMAP (6.54 mg, 53.55 μmol, 0.1 eq) in DCM (9 mL) was added (4-(3-chlorophenyl)thiazol-2-yl)(3-(trifluoromethyl)phenyl)carbamic chloride (crude) in DCM (3 mL) and stirred at 25° C. for 1 h. The reaction mixture was quenched by addition of water (50 mL), extracted with EtOAc (30 mL×3). The combined organic layers were washed with brine (10 mL), dried over Na₂SO₄, filtered and concentrated under reduced pressure to yield a residue which was purified by flash silica gel chromatography (from PE/EtOAc=1/0 to 3/1, TLC: PE/EtOAc=3/1, R_f=0.60) to yield 3-(3-bromopropyl)-1-[4-(3-chlorophenyl)thiazol-2-yl]-1-[3-(trifluoromethyl)phenyl]urea (275 mg, 522.67 μmol, 97.6% yield, 98.6% purity) as yellow oil. ¹H NMR (400 MHz, CDCl₃) δ ppm 9.07 (s, 1H), 7.79 (d, J=7.6 Hz, 1H), 7.74 (t, J=1.6 Hz, 1H), 7.73-7.68 (m, 2H), 7.67-7.60 (m, 2H), 7.40-7.31 (m, 2H), 7.03 (s, 1H), 3.63 (q, J=6.4 Hz, 2H), 3.57 (t, J=6.5 Hz, 2H), 2.26-2.17 (m, 2H); ES-LCMS m/z 517.0, 519.0 [M+H]⁺.

Step 2: 1-[4-(3-Chlorophenyl)thiazol-2-yl]-3-[3-[2-hydroxyethyl(methyl)amino]propyl]-1-[3-(trifluoromethyl)phenyl]urea

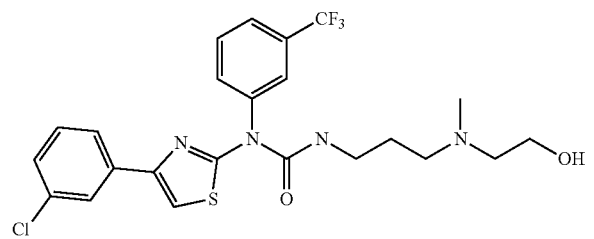 [SMILES: CN(CCO)CCCNC(=O)N(c1cccc(C(F)(F)F)c1)c1nc(-c2cccc(Cl)c2)cs1]

To a stirred solution of 3-(3-bromopropyl)-1-[4-(3-chlorophenyl)thiazol-2-yl]-1-[3-(trifluoromethyl)phenyl]urea (275 mg, 522.67 μmol, 1 eq) and 2-(methylamino)ethanol (274.80 mg, 3.66 mmol, 293.91 μL, 7 eq) in THF (4 mL) was added DIEA (202.65 mg, 1.57 mmol, 273.12 μL, 3 eq). The reaction mixture was stirred at 25° C. for 24 h. The solvent was removed to yield a residue which was purified by preparative HPLC(column: Agela DuraShell C18 150*25 mm*5 μm; mobile phase: [water (0.05% NH₃H₂O+10 mM NH₄HCO₃)-ACN]; B %: 55%-85%, 10 min) followed by lyophilized to yield 1-[4-(3-chlorophenyl)thiazol-2-yl]-3-[3-[2-hydroxyethyl(methyl)amino]propyl]-1-[3-(trifluoromethyl)phenyl]urea (100 mg, 193.58 μmol, 37.0% yield, 99.3% purity) as a yellow solid. ¹H NMR (400 MHz, DMSO-d₆) δ ppm 7.94-7.88 (m, 2H), 7.85-7.80 (m, 1H), 7.79-7.75 (m, 1H), 7.72 (s, 1H), 7.63 (s, 1H), 7.57 (d, J=7.6 Hz, 1H), 7.39-7.32 (m, 1H), 7.31-7.26 (m, 1H), 7.17 (t, J=5.0 Hz, 1H), 4.32 (t, J=5.1 Hz, 1H), 3.39-3.34 (m, 2H), 3.19 (q, J=6.4 Hz, 2H), 2.33 (t, J=6.5 Hz, 2H), 2.26 (t, J=6.4 Hz, 2H), 2.01 (s, 3H), 1.57 (q, J=6.5 Hz, 2H); ES-LCMS m/z 513.2, 515.1 [M+H]⁺.

Step 3: 1-[4-(3-Chlorophenyl)thiazol-2-yl]-3-[3-[BLAH-(2-hydroxyethyl)-dimethyl-azanyl]propyl]-1-[3-(trifluoromethyl)phenyl]urea

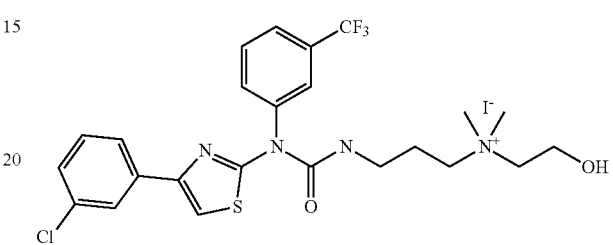

To a stirred solution of 1-[4-(3-chlorophenyl)thiazol-2-yl]-3-[3-[2-hydroxyethyl(methyl)amino]propyl]-1-[3-(trifluoromethyl)phenyl]urea (50 mg, 97.47 μmol, 1 eq) in MeCN (8 mL) was added MeI (69.17 mg, 487.35 μmol, 30.34 μL, 5 eq) slowly. The reaction mixture was stirred at 30° C. for 1 h. The solvent was removed to yield 1-[4-(3-chlorophenyl)thiazol-2-yl]-3-[3-[BLAH-(2-hydroxyethyl)-dimethyl-azanyl]propyl]-1-[3-(trifluoromethyl)phenyl]urea (37 mg, 56.50 μmol, 58.0% yield, 100% purity) as a white solid. ¹H NMR (400 MHz, DMSO-d₆) δ ppm 7.97 (s, 1H), 7.95-7.92 (m, 1H), 7.86-7.82 (m, 1H), 7.81-7.77 (m, 1H), 7.75 (s, 1H), 7.63 (s, 1H), 7.57 (d, J=7.8 Hz, 1H), 7.38-7.33 (m, 1H), 7.31-7.27 (m, 1H), 6.94 (t, J=5.7 Hz, 1H), 5.28 (t, J=4.9 Hz, 1H), 3.81 (s, 2H), 3.39-3.35 (m, 3H), 3.30 (s, 1H), 3.30-3.28 (m, 1H), 3.19 (d, J=5.9 Hz, 2H), 3.06 (s, 6H), 1.88 (s, 2H); ES-LCMS m/z 527.2 [M–I]⁺.

I-30

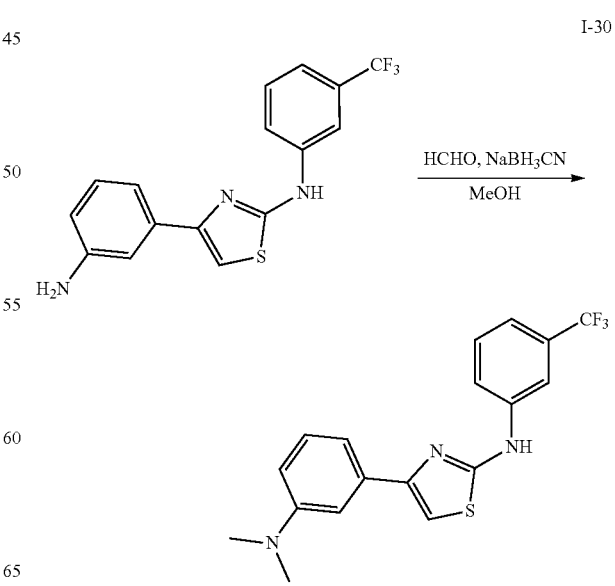

Step 1: 4-[3-(Dimethylamino)phenyl]-N-[3-(trifluoromethyl)phenyl]thiazol-2-amine

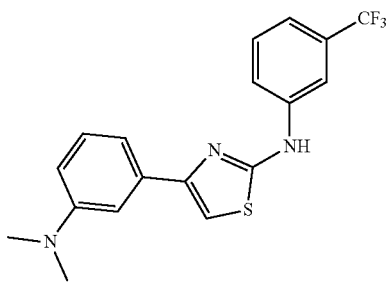 [SMILES: CN(C)c1cccc(-c2csc(Nc3cccc(C(F)(F)F)c3)n2)c1]

To a solution of 4-(3-aminophenyl)-N-[3-(trifluoromethyl)phenyl]thiazol-2-amine (240 mg, 679.89 μmol, 1 eq) in MeOH (6 mL) was added HCHO (133 mg, 4.43 mmol, 6.51 eq). The mixture was stirred at 28° C. for 12 h. NaBH$_3$CN (128 mg, 2.04 mmol, 3.00 eq) was added. The mixture was stirred at 28° C. for 3 h. The mixture was diluted with water (10 mL) and extracted with EtOAc (10 mL×3). The combined organic layers were dried over Na$_2$SO$_4$, filtered and concentrated under reduced pressure to yield a residue which was purified by preparative HPLC (column: Boston Prime C18 150*30 mm*5 um; mobile phase: [water (0.05% ammonia hydroxide v/v)-ACN]; B %: 52%-85%, 10 min), followed by lyophilization to yield 4-[3-(dimethylamino)phenyl]-N-[3-(trifluoromethyl)phenyl]thiazol-2-amine (21.04 mg, 57.90 μmol, 8.5% yield, 100.0% purity) as a brown gum. $^1$H NMR (400 MHz, DMSO-d$_6$) δ ppm 10.62 (s, 1H), 8.64 (s, 1H), 7.62-7.56 (m, 1H), 7.55-7.49 (m, 1H), 7.35 (s, 1H), 7.31 (s, 1H), 7.26 (d, J=7.8 Hz, 1H), 7.22-7.15 (m, 2H), 6.67 (d, J=7.3 Hz, 1H), 2.93 (s, 6H); ES-LCMS m/z 364.2 [M+H]$^+$.

I-23

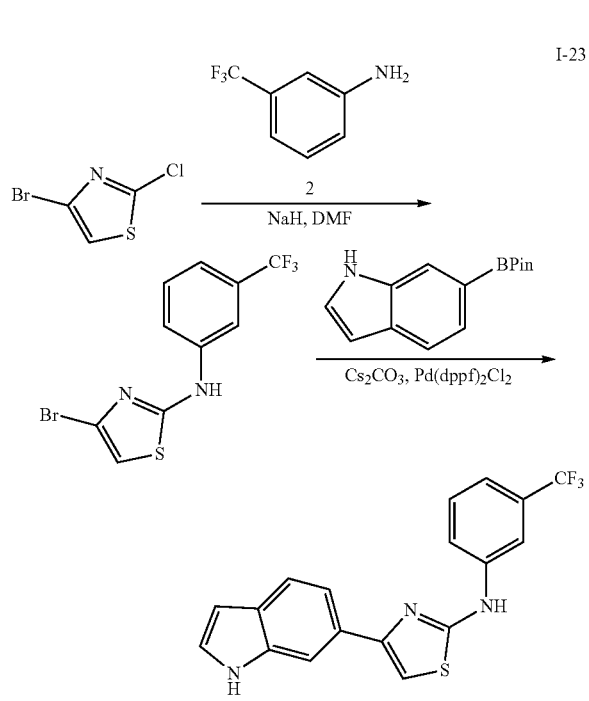

Step 1: 6-(4,4,5,5-Tetramethyl-1,3,2-dioxaborolan-2-yl)-1H-indole

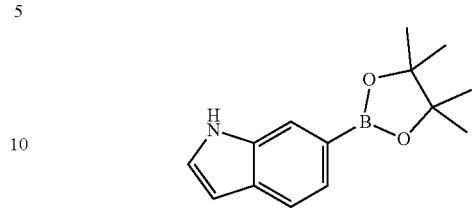

To a solution of 6-bromo-1H-indole (500 mg, 2.55 mmol, 1 eq) in 1,4-dioxane (6 mL) was added KOAc (750.92 mg, 7.65 mmol, 3 eq), Pd(dppf)Cl$_2$ (186.62 mg, 255.04 μmol, 0.1 eq) and 4,4,5,5-tetramethyl-2-(4,4,5,5-tetramethyl-1,3,2-dioxaborolan-2-yl)-1,3,2-dioxaborolane (777.19 mg, 3.06 mmol, 1.2 eq). The mixture was bubbled with N$_2$ for 3 min and stirred at 100° C. for 30 min under microwave. The reaction mixture was concentrated to yield a residue which was purified by flash silica gel chromatography (from PE/EtOAc=100/1 to 3/1, TLC: PE/EtOAc=3/1, R$_f$=0.35) to yield 6-(4,4,5,5-tetramethyl-1,3,2-dioxaborolan-2-yl)-1H-indole (500 mg, 1.95 mmol, 76.6% yield, 95% purity) as white solid. $^1$H NMR (400 MHz, CDCl$_3$) δ ppm 8.23 (s, 1H), 7.92 (s, 1H), 7.70-7.63 (m, 1H), 7.62-7.54 (m, 1H), 6.57 (t, J=2.1 Hz, 1H), 1.39 (s, 12H); ES-LCMS m/z 244.3 [M+H]$^+$.

Step 2: 4-Bromo-N-[3-(trifluoromethyl)phenyl]thiazol-2-amine

To a stirred solution of 3-(trifluoromethyl)aniline (150 mg, 930.96 μmol, 116.28 μL, 1 eq) in DMF (3 mL) was added NaH (75.00 mg, 1.88 mmol, 60% in mineral oil, 2.01 eq) at 20° C. The reaction mixture was stirred at 20° C. for 1 h. 4-Bromo-2-chloro-thiazole (225.00 mg, 1.13 mmol, 1.22 eq) was added to the above reaction mixture then stirred at 80° C. for 12 h. The reaction mixture was diluted with water (30 mL) then extracted with EtOAc (30 mL×3). The combined organic layers were dried over Na$_2$SO$_4$, filtered and the filtrate was concentrated to yield a residue which was purified by preparative TLC (PE/EtOAc=3/1, TLC: PE/EtOAc=3/1, R$_f$=0.50) to yield 4-bromo-N-[3-(trifluoromethyl)phenyl]thiazol-2-amine (100 mg, 160.31 μmol, 17.2% yield, 51.8% purity) as brown oil. ES-LCMS m/z 323.1, 325.1 [M+H]$^+$.

Step 3: 4-(1H-Indol-6-yl)-N-[3-(trifluoromethyl)phenyl]thiazol-2-amine

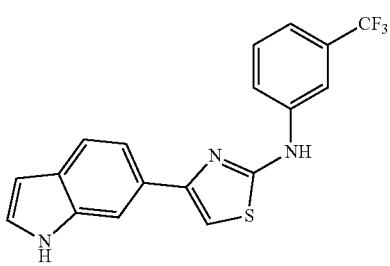 [SMILES: FC(F)(F)c1cccc(Nc2nc(-c3ccc4cc[nH]c4c3)cs2)c1]

To a solution of 6-(4,4,5,5-tetramethyl-1,3,2-dioxaborolan-2-yl)-1H-indole (36.10 mg, 141.07 μmol, 1.1 eq) in 1,4-dioxane (3 mL) and water (1 mL) was added Pd(dppf)Cl₂ (9.38 mg, 12.82 μmol, 0.1 eq), Cs₂CO₃ (83.57 mg, 256.49 μmol, 2 eq) and 4-bromo-N-[3-(trifluoromethyl)phenyl]thiazol-2-amine (80.00 mg, 128.24 μmol, 1 eq). The mixture was bubbled with N₂ for 3 min and stirred at 100° C. for 30 min under microwave. The reaction mixture was concentrated to yield a residue which was purified by preparative HPLC (column: Agela DuraShell C18 150*25 mm*5 um; mobile phase: [water (0.04% NH₃H₂O+10 mM NH₄HCO₃)-ACN]; B %: 50%-80%, 10 min). The desired fraction was lyophilized to yield 4-(1H-indol-6-yl)-N-[3-(trifluoromethyl)phenyl]thiazol-2-amine (19.11 mg, 51.58 μmol, 40.2% yield, 97.0% purity) as white solid. ¹H NMR (500 MHz, DMSO-d₆) δ ppm 11.21 (s, 1H), 10.60 (s, 1H), 8.33 (s, 1H), 7.97-7.91 (m, 2H), 7.60-7.55 (m, 3H), 7.38 (t, J=2.7 Hz, 1H), 7.33-7.26 (m, 2H), 6.44 (s, 1H); ES-LCMS m/z 360.0 [M+H]⁺.

I-17

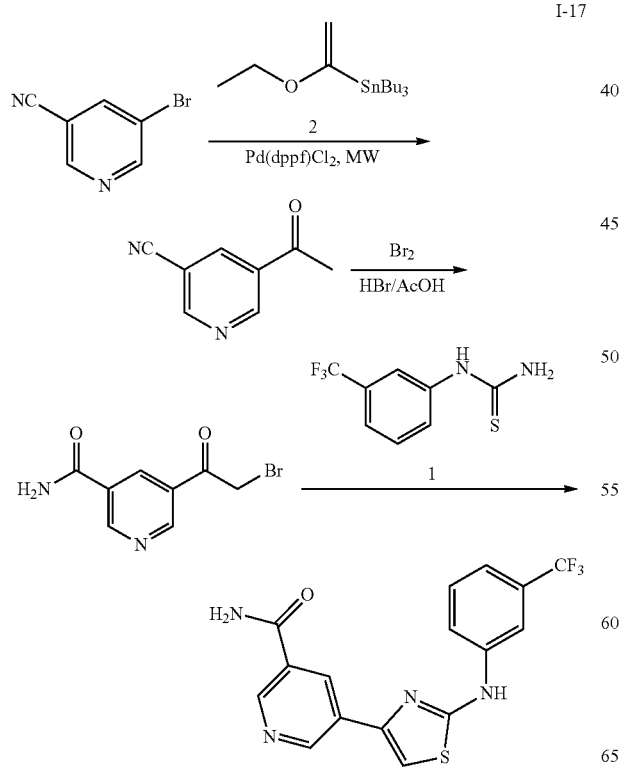

274

Step 1: 5-Acetylpyridine-3-carbonitrile

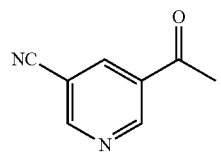

To a solution of 5-bromopyridine-3-carbonitrile (1.5 g, 8.20 mmol, 1 eq) in 1,4-dioxane (30 mL) was added Pd(PPh₃)₂Cl₂ (575.31 mg, 819.65 μmol, 0.1 eq), tributyl(1-ethoxyvinyl)stannane (4.6 g, 12.74 mmol, 4.30 mL, 1.55 eq). The mixture was degassed and purged with N₂ for three times and stirred at 100° C. for 12 h under N₂ atmosphere. The reaction mixture was diluted with 3 M HCl solution (12 mL) then stirred at 25° C. for 1 h. The reaction mixture was adjusted pH to 9-10 by 15% NaOH solution. The mixture was poured into KF (50 mL, 2M), stirred for 1 h and extracted with EtOAc (50 mL×3). The organic layer was dried over Na₂SO₄, filtered and concentrated under reduced pressure to yield a residue which was purified by flash silica gel chromatography (from PE/EtOAc=100/1 to 2/1, TLC: PE/EtOAc=3/1, R_f=0.2) to yield 5-acetylpyridine-3-carbonitrile (750 mg, 5.13 mmol, 62.6% yield, 100% purity) as white solid. ¹H NMR (400 MHz, DMSO-d₆) δ ppm 9.31 (d, J=2.0 Hz, 1H), 9.24 (d, J=2.0 Hz, 1H), 8.81 (t, J=2.1 Hz, 1H), 2.67 (s, 3H); ES-LCMS m/z 147.1 [M+H]⁺.

Step 2: 5-(2-Bromoacetyl)pyridine-3-carboxamide

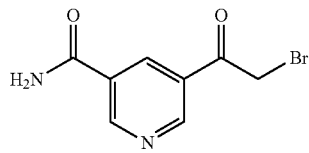 [SMILES: NC(=O)c1cncc(C(=O)CBr)c1]

To a stirred solution of 5-acetylpyridine-3-carbonitrile (50 mg, 342.12 μmol, 1 eq) in HBr/AcOH (2 mL) was added Br₂ (109.35 mg, 684.25 μmol, 35.27 μL, 2 eq). The reaction mixture was stirred at 20° C. for 12 h. The reaction mixture was concentrated to yield 5-(2-bromoacetyl)pyridine-3-carboxamide (80 mg, 246.94 μmol, 72.2% yield, N/A purity, HBr) as yellow solid which was used in the next step without further purification. ES-LCMS m/z 242.8, 244.9 [M+H]⁺.

Step 3: 5-[2-[3-(Trifluoromethyl)anilino]thiazol-4-yl]pyridine-3-carboxamide

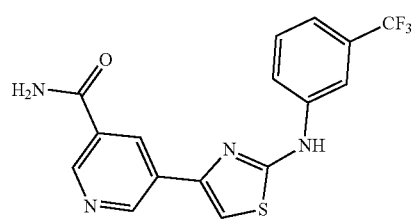 [SMILES: NC(=O)c1cncc(-c2csc(Nc3cccc(C(F)(F)F)c3)n2)c1]

To a stirred solution of 5-(2-bromoacetyl)pyridine-3-carboxamide (80 mg, 246.94 μmol, 1 eq, HBr) in ACN (1.5 mL)

and water (1.5 mL) was added KF (17.22 mg, 296.32 µmol, 1.2 eq) and [3-(trifluoromethyl)phenyl]thiourea (75 mg, 306.52 µmol, 1.24 eq). The reaction mixture was stirred at 20° C. for 12 h. 3 N HCl solution (15 mL) was added to the above reaction mixture then stirred at 20° C. for 1 h. The reaction mixture was concentrated to yield a residue which was purified by preparative HPLC (column: Phenomenex Gemini C18 250*50 mm*10 um; mobile phase: [water (0.05% ammonia hydroxide v/v)-ACN]; B %: 40%-60%, 10 min). The desired fraction was lyophilized to yield 5-[2-[3-(trifluoromethyl)anilino]thiazol-4-yl]pyridine-3-carboxamide (60 mg, 164.68 µmol, 66.7% yield, 100% purity) as white solid. $^1$H NMR (500 MHz, DMSO-$d_6$) δ ppm 10.76 (s, 1H), 9.24 (d, J=2.1 Hz, 1H), 8.95 (d, J=2.1 Hz, 1H), 8.66 (t, J=2.1 Hz, 1H), 8.34 (s, 1H), 8.23 (s, 1H), 7.88 (d, J=7.9 Hz, 1H), 7.70 (s, 1H), 7.66 (s, 1H), 7.59 (t, J=7.9 Hz, 1H), 7.32 (d, J=7.6 Hz, 1H); ES-LCMS m/z 364.9 [M+H]$^+$.

(208.94 mg, 1.62 mmol, 281.59 µL, 3 eq) and piperidin-4-ol (1.09 g, 10.78 mmol, 20 eq). The mixture was stirred at 80° C. for 12 h. The mixture was diluted with water (20 mL) and extracted with DCM (20 mL×3). The combined organic layers were dried over Na$_2$SO$_4$, filtered and concentrated under reduced pressure to yield a residue which was purified by preparative HPLC (column: Welch Xtimate C18 150*25 mm*5 um; mobile phase: [water(10 mM NH$_4$HCO$_3$)-ACN]; B %: 49%-79%, 10 min), followed by lyophilization to yield 1-[4-(3-chlorophenyl)thiazol-2-yl]-3-[2-(4-hydroxy-1-piperidyl)ethyl]-1-[3-(trifluoromethyl)phenyl]urea (50 mg, 95.24 µmol, 17.7% yield, 100.0% purity) as a white solid. $^1$H NMR (400 MHz, DMSO-$d_6$) δ ppm 7.93 (br s, 1H), 7.91 (s, 1H), 7.86-7.81 (m, 1H), 7.80-7.76 (m, 1H), 7.74 (s, 1H), 7.68 (s, 1H), 7.63 (d, J=7.8 Hz, 1H), 7.42-7.35 (m, 1H), 7.34-7.27 (m, 1H), 7.00 (t, J=4.9 Hz, 1H), 4.52 (d, J=3.9 Hz, 1H), 3.39 (dd, J=4.5, 8.9 Hz, 1H), 3.23 (q, J=6.1 Hz, 2H), 2.65 (d, J=11.7 Hz, 2H), 2.37 (t, J=6.2 Hz, 2H), 2.09-1.94 (m, 2H), 1.62 (d, J=9.8 Hz, 2H), 1.26 (q, J=9.1 Hz, 2H); ES-LCMS m/z 525.2 [M+H]$^+$.

Step 2: 1-[4-(3-Chlorophenyl)thiazol-2-yl]-3-[2-(4-hydroxy-1-methyl-piperidin-1-ium-1-yl)ethyl]-1-[3-(trifluoromethyl)phenyl]urea

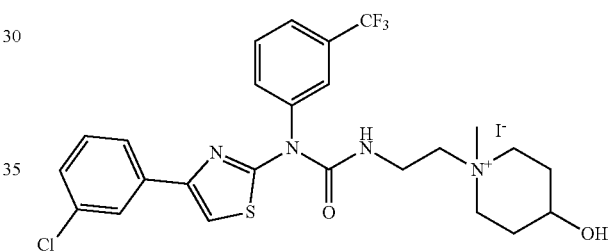

To a solution of 1-[4-(3-chlorophenyl)thiazol-2-yl]-3-[2-(4-hydroxy-1-piperidyl)ethyl]-1-[3-(trifluoromethyl)phenyl]urea (25 mg, 47.62 µmol, 1 eq) in ACN (5 mL) was added MeI (34.00 mg, 239.54 µmol, 14.91 µL, 5.03 eq). The mixture was stirred at 25° C. for 1 h. The solution was quenched by addition of water (10 mL) and then lyophilized to yield 1-[4-(3-chlorophenyl)thiazol-2-yl]-3-[2-(4-hydroxy-1-methyl-piperidin-1-ium-1-yl)ethyl]-1-[3-(trifluoromethyl)phenyl]urea (21.22 mg, 38.66 µmol, 81.2% yield, 98.4% purity) as a white solid. $^1$H NMR (400 MHz, DMSO-$d_6$) δ ppm 7.99-7.92 (m, 2H), 7.87-7.79 (m, 2H), 7.77 (s, 1H), 7.63 (s, 1H), 7.60-7.53 (m, 1H), 7.38-7.32 (m, 1H), 7.31-7.25 (m, 1H), 6.97 (br s, 1H), 5.16-5.06 (m, 1H), 3.73-3.83 (m, 1H), 3.53 (d, J=5.6 Hz, 2H), 3.50-3.35 (m, 6H), 3.05 (d, J=8.1 Hz, 3H), 1.90-2.01 (m, 2H), 1.64-1.76 (m, 2H); ES-LCMS m/z 539.2 [M−I]$^+$.

I-20

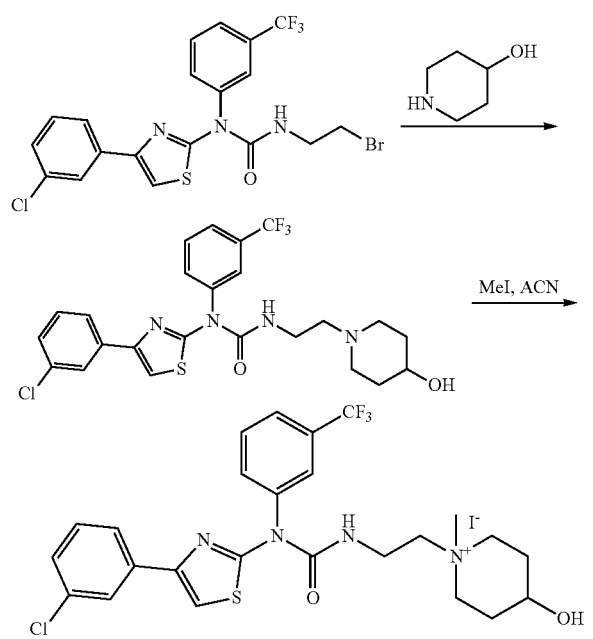

Step 1: 1-[4-(3-Chlorophenyl)thiazol-2-yl]-3-[2-(4-hydroxy-1-piperidyl)ethyl]-1-[3-(trifluoromethyl)phenyl]urea

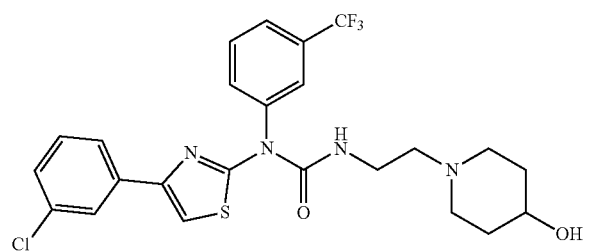 [SMILES: O=C(NCCN1CCC(O)CC1)N(c1cccc(C(F)(F)F)c1)c1nc(-c2cccc(Cl)c2)cs1]

To a solution of 3-(2-bromoethyl)-1-[4-(3-chlorophenyl)thiazol-2-yl]-1-[3-(trifluoromethyl)phenyl]urea (340 mg, 538.88 µmol, 1 eq) in DCM (20 mL) was added DIEA

I-54

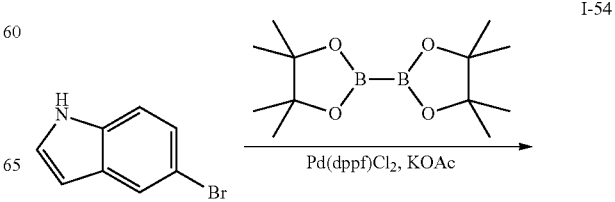

277
-continued

Step 2: 4-(1H-Indol-5-yl)-N-[3-(trifluoromethyl)phenyl]thiazol-2-amine

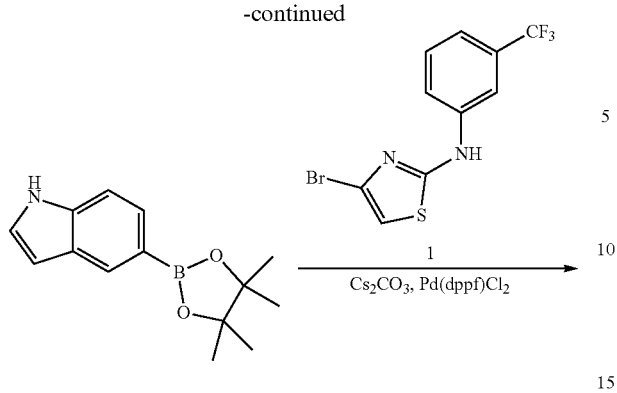

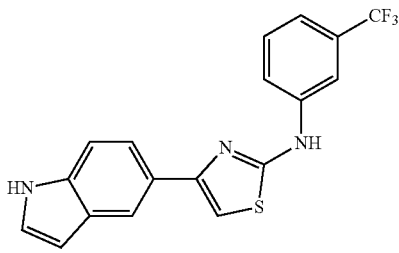

To a solution of 4-bromo-N-[3-(trifluoromethyl)phenyl]thiazol-2-amine (90 mg, 278.52 μmol, 1 eq) and 5-(4,4,5,5-tetramethyl-1,3,2-dioxaborolan-2-yl)-1H-indole (81.25 mg, 334.23 μmol, 1.2 eq) in 1,4-dioxane (5 mL) and H$_2$O (1 mL) were added Pd(dppf)Cl$_2$ (20.38 mg, 27.85 μmol, 0.1 eq) and Cs$_2$CO$_3$ (181.50 mg, 557.05 μmol, 2 eq). The mixture was stirred at 90° C. for 5 h under N$_2$ atmosphere. The solvent was removed and the residue was treated with EtOAc (20 mL). The mixture was filtered and the filtrate was concentrated to give a residue which was purified by preparative HPLC (column: Agela DuraShell C18 150*25 mm*5 um; mobile phase: [water (0.05% NH$_3$H$_2$O+10 mM NH$_4$HCO$_3$)-ACN]; B %: 50%-80%, 10 min), followed by lyophilization to yield 4-(1H-indol-5-yl)-N-[3-(trifluoromethyl)phenyl]thiazol-2-amine (48.46 mg, 133.50 μmol, 47.9% yield, 99.0% purity) as a brown solid. $^1$H NMR (400 MHz, CDCl$_3$) δ ppm 8.19 (s, 2H) 7.84 (s, 1H), 7.72 (dd, J=8.56, 1.47 Hz, 1H), 7.67 (d, J=8.31 Hz, 1H), 7.35-7.51 (m, 3H), 7.29 (d, J=7.83 Hz, 1H), 7.24 (t, J=2.69 Hz, 1H), 6.83 (s, 1H), 6.61 (br s, 1H); ES-LCMS m/z 360.0 [M+H]$^+$.

Step 1: 5-(4,4,5,5-Tetramethyl-1,3,2-dioxaborolan-2-yl)-1H-indole

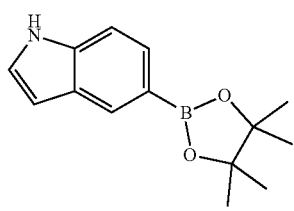 [SMILES: CC1(C)OB(c2ccc3[nH]ccc3c2)OC1(C)C]

To a mixture of 5-bromo-1H-indole (1 g, 5.10 mmol, 1 eq) in 1,4-Dioxane (15 mL) was added 4,4,5,5-tetramethyl-2-(4,4,5,5-tetramethyl-1,3,2-dioxaborolan-2-yl)-1,3,2-dioxaborolane (1.42 g, 5.61 mmol, 1.1 eq), Pd(dppf)Cl$_2$ (373.24 mg, 510.09 μmol, 0.1 eq) and AcOK (1.00 g, 10.20 mmol, 2 eq). The mixture was degassed and purged with N$_2$ for 3 times and the mixture was stirred at 90° C. for 16 h under N$_2$ atmosphere. The reaction mixture was concentrated to yield a residue which was purified by flash silica gel chromatography (from PE/EtOAc=1/0 to 3/1, TLC: PE/EtOAc=5/1, R$_f$=0.7) to yield 5-(4,4,5,5-tetramethyl-1,3,2-dioxaborolan-2-yl)-1H-indole (783 mg, 3.22 mmol, 63.1% yield, 100% purity) as a white solid. $^1$H NMR (400 MHz, CDCl$_3$) δ 8.19 (s, 1H), 7.66 (d, J=8.2 Hz, 1H), 7.40 (d, J=8.2 Hz, 1H), 7.21 (t, J=2.7 Hz, 1H), 6.58 (s, 1H), 1.38 (s, 12H); ES-LCMS m/z 244.0 [M+H]$^+$.

I-55

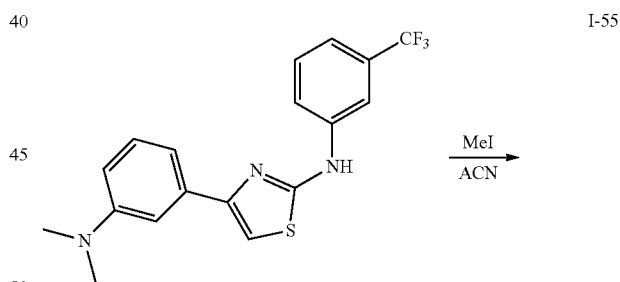

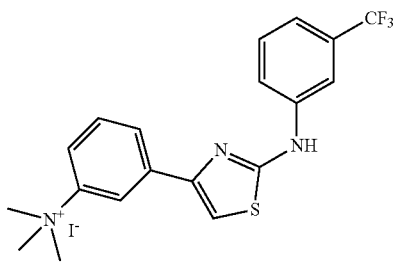

279

Step 1: Trimethyl-[3-[2-[3-(trifluoromethyl)anilino]thiazol-4-yl]phenyl]ammonium

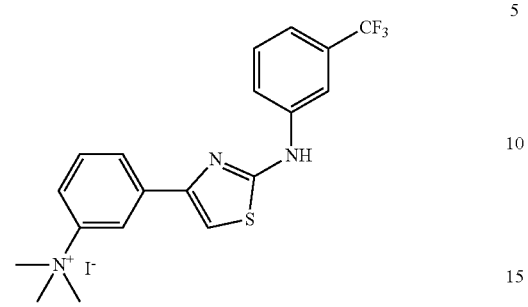

To a solution of 4-[3-(dimethylamino)phenyl]-N-[3-(trifluoromethyl)phenyl]thiazol-2-amine (40 mg, 108.97 μmol, 1 eq) in ACN (6 mL) was added MeI (495.00 mg, 3.49 mmol, 217.11 μL, 32.00 eq). The mixture was stirred at 50° C. for 1 h. The solution was quenched by addition of water (10 mL) and lyophilized to yield trimethyl-[3-[2-[3-(trifluoromethyl)anilino]thiazol-4-yl]phenyl]ammonium (36.07 mg, 91.29 μmol, 83.8% yield, 95.8% purity) as a yellow solid, which was delivered without further purification. $^1$H NMR (400 MHz, DMSO-$d_6$) δ ppm 10.80 (s, 1H), 8.51 (s, 1H), 8.39 (s, 1H), 8.10 (d, J=7.4 Hz, 1H), 7.95 (dd, J=2.3, 8.6 Hz, 1H), 7.79-7.70 (m, 3H), 7.59 (t, J=8.0 Hz, 1H), 7.33 (d, J=7.8 Hz, 1H), 3.68 (s, 9H); ES-LCMS m/z 378.2 [M−I]$^+$.

I-56

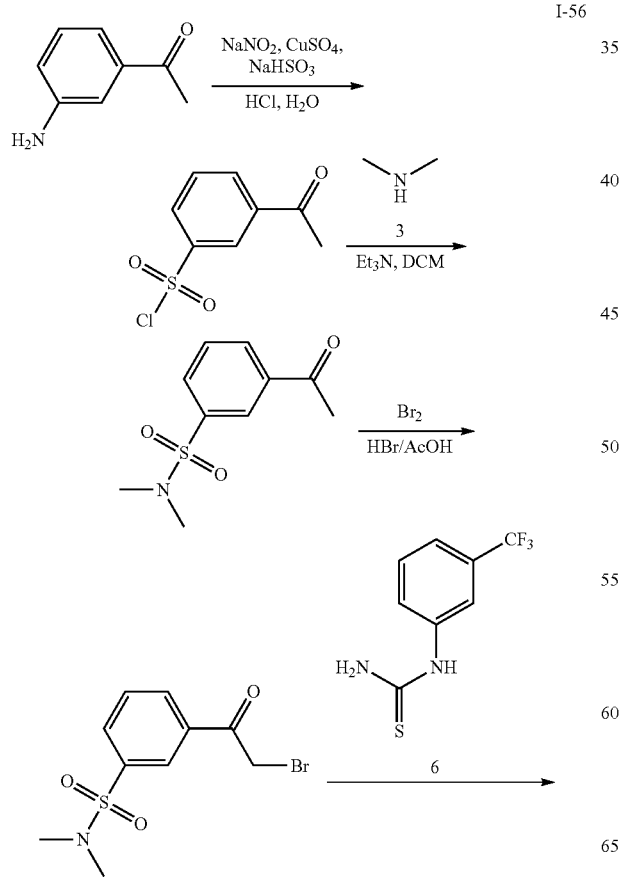

280

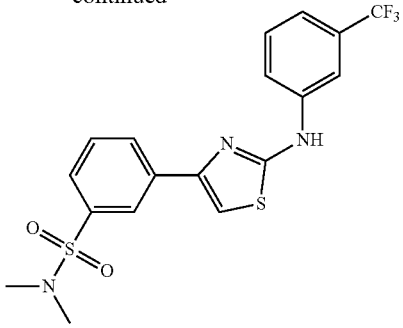

Step 1: 3-Acetylbenzenesulfonyl Chloride

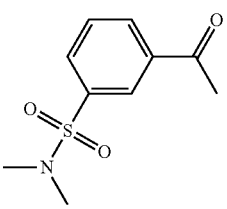

To a solution of 1-(3-aminophenyl)ethanone (4 g, 29.59 mmol, 1 eq) in HCl (12 M, 60.00 mL, 24.33 eq) was added a mixture of NaNO$_2$ (4.08 g, 59.19 mmol, 2 eq) in H$_2$O (20 mL) with stirred at 0° C. for 30 min under N$_2$ atmosphere. CuSO$_4$ (472.35 mg, 2.96 mmol, 0.1 eq) and NaHSO$_3$ (30.80 g, 295.94 mmol, 10 eq) were added into the mixture with stirred at 0° C. for 1 h under N$_2$ atmosphere. TLC (PE/EtOAc=3/1, R$_f$=0.6) showed that new point was formed and the start material was consumed completely. The reaction mixture was quenched by addition of H$_2$O (50 mL) and extracted with EtOAc (50 mL×3). The combined organic layers were dried over Na$_2$SO$_4$, filtered and concentrated under reduced pressure to yield 3-acetylbenzenesulfonyl chloride (2.2 g, 9.56 mmol, 32.3% yield, 95.0% purity) as a white solid, which was used in the next step without further purification. $^1$H NMR (400 MHz, DMSO-$d_6$) δ ppm 8.13 (s, 1H), 7.91 (d, J=8.0 Hz, 1H), 7.84 (d, J=7.6 Hz, 1H), 7.49 (t, J=8.0 Hz, 1H), 2.57 (s, 3H).

Step 2: 3-Acetyl-N,N-dimethyl-benzenesulfonamide

To a solution of 3-acetylbenzenesulfonyl chloride (1 g, 4.34 mmol, 1 eq) in THF (2 mL) was added DIEA (1.68 g, 13.03 mmol, 2.27 mL, 3 eq) and N-methylmethanamine (425.14 mg, 5.21 mmol, 1.2 eq, HCl). The mixture was stirred at 20° C. for 2 h. TLC (PE/EtOAc=3/1, R$_f$=0.4) showed that a new point was formed and the start material was consumed completely. The reaction mixture was quenched by addition of H$_2$O (20 mL) and extracted with EtOAc (30 mL×3). The combined organic layers were washed with brine (30 mL), dried over Na₂SO₄, filtered and concentrated under reduced pressure to yield 3-acetyl-N,N-dimethyl-benzenesulfonamide (854 mg, 3.38 mmol, 77.8% yield, 90.0% purity) as a white solid, which was used in the next step without further purification. ¹H NMR (400 MHz, DMSO-d₆) δ ppm 8.29 (d, J=6.4 Hz, 1H), 8.19-8.13 (m, 1H), 8.00 (d, J=6.4 Hz, 1H), 7.85-7.80 (m, 1H), 2.66 (s, 3H), 2.64 (s, 6H); ES-LCMS m/z 227.9 [M+H]⁺.

Step 3:
3-(2-Bromoacetyl)-N,N-dimethyl-benzenesulfonamide

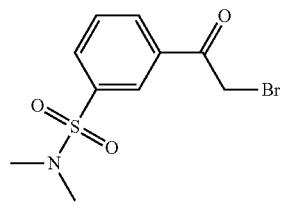 [SMILES: CN(C)S(=O)(=O)c1cccc(C(=O)CBr)c1]

To a solution of 3-acetyl-N,N-dimethyl-benzenesulfonamide (854 mg, 3.38 mmol, 1 eq) in AcOH (5 mL) was added HBr (3 mL, 33% purity) and Br₂ (594.48 mg, 3.72 mmol, 191.77 µL, 1.1 eq) at 0° C. under N₂ atmosphere. The mixture was stirred at 0° C. for 2 h under N₂ atmosphere. TLC (PE/EtOAc=3/1, R_f=0.45) showed that new point was formed and start material was consumed completely. The reaction mixture was quenched by addition of H₂O (20 mL) and extracted with EtOAc (30 mL×3). The combined organic layers were washed with brine (30 mL), dried over Na₂SO₄, filtered and concentrated under reduced pressure to give a residue which was purified by flash silica gel chromatography (from PE/EtOAc=100/1 to 6/1, TLC: PE/EtOAc=3/1, R_f=0.45) to yield 3-(2-bromoacetyl)-N,N-dimethyl-benzenesulfonamide (360 mg, 1.12 mmol, 33.0% yield, 95.0% purity) as a white solid. ¹H NMR (400 MHz, DMSO-d₆) δ ppm 8.31 (d, J=8.0 Hz, 1H), 8.23 (s, 1H), 8.01 (d, J=8.4 Hz, 1H), 7.88-7.81 (m, 1H), 5.06 (s, 2H), 2.67-2.62 (m, 6H); ES-LCMS m/z 307.8 [M+H]⁺.

Step 4: N,N-Dimethyl-3-[2-[3-(trifluoromethyl)anilino]thiazol-4-yl]benzenesulfonamide

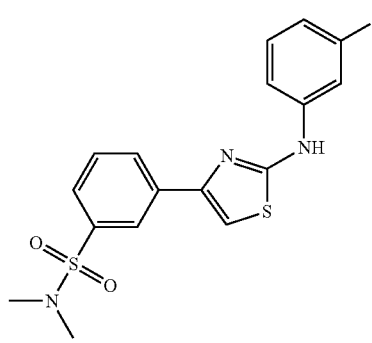

To a solution of 3-(2-bromoacetyl)-N,N-dimethyl-benzenesulfonamide (30 mg, 93.08 µmol, 1 eq) in ACN (3 mL) and H₂O (3 mL) was added [3-(trifluoromethyl)phenyl]thiourea (25.05 mg, 102.39 µmol, 1.1 eq). The mixture was stirred at 20° C. for 2 h. The reaction mixture was filtered and the filter cake was washed with ACN/H₂O (1:1) to yield N,N-dimethyl-3-[2-[3-(trifluoromethyl)anilino]thiazol-4-yl]benzenesulfonamide (33.3 mg, 76.24 µmol, 81.9% yield, 97.9% purity) as a white solid. ¹H NMR (400 MHz, CD₃OD) δ ppm 8.41 (s, 1H), 8.35 (s, 1H), 8.20 (d, J=8.0 Hz, 1H), 7.77-7.70 (m, 2H), 7.69-7.63 (m, 1H), 7.49 (t, J=8.0 Hz, 1H), 7.35 (s, 1H), 7.26 (d, J=7.6 Hz, 1H), 2.74 (s, 6H); ES-LCMS m/z 428.0 [M+H]⁺.

I-57

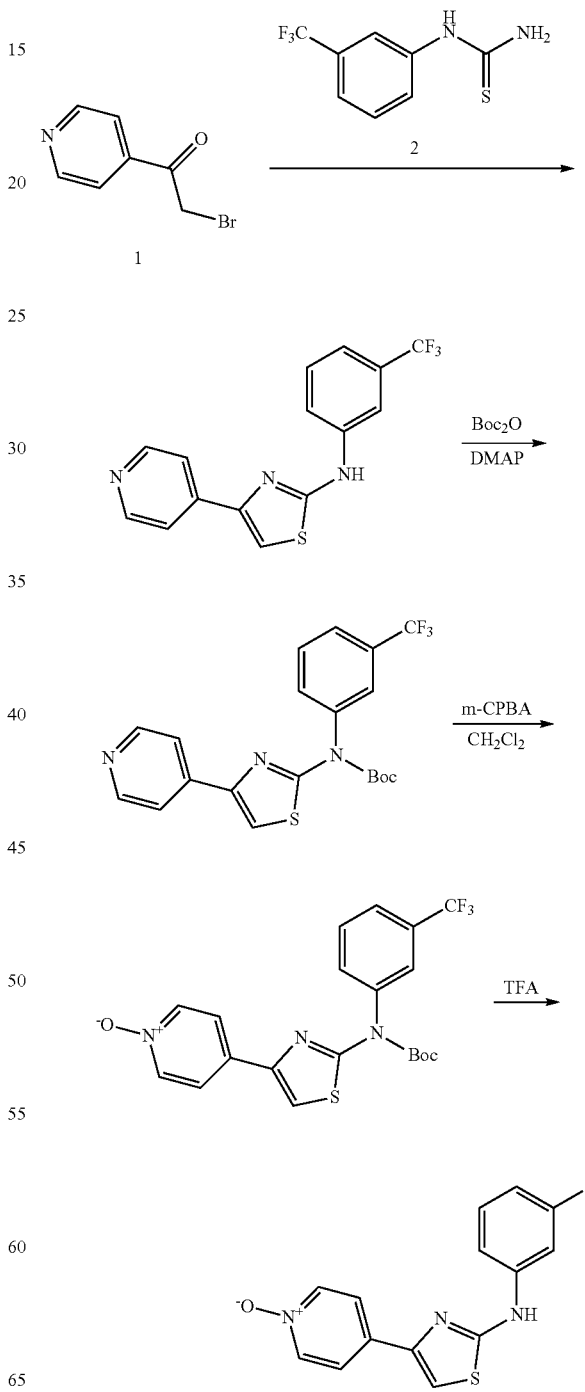

Step 1: 4-(4-Pyridyl)-N-[3-(trifluoromethyl)phenyl]thiazol-2-amine

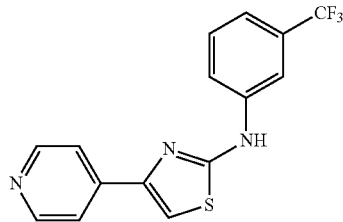 [SMILES: FC(F)(F)c1cccc(Nc2nc(-c3ccncc3)cs2)c1]

A mixture of 2-bromo-1-(4-pyridyl)ethanone (400 mg, 1.14 mmol, 1 eq, HBr), [3-(trifluoromethyl)phenyl]thiourea (278.70 mg, 1.14 mmol, 1 eq) in MeCN (5 mL) and H₂O (5 mL) was degassed and purged with N₂ for 3 times, stirred at 25° C. for 12 h under N₂ atmosphere. The reaction mixture was quenched by addition of water (50 mL), extracted with EtOAc (30 mL×3). The combined organic layers were washed with brine (10 mL), dried over Na₂SO₄, filtered and concentrated to yield a residue which was purified by flash silica gel chromatography (from PE/EtOAc=1/0 to 3/1, TLC: PE/EtOAc=3/1, R$_f$=0.54) to yield 4-(4-pyridyl)-N-[3-(trifluoromethyl)phenyl]thiazol-2-amine (170 mg, 529.07 μmol, 46.4% yield, 100% purity) as a white solid. ¹H NMR (400 MHz, CDCl₃) δ ppm 8.70-8.65 (m, 2H), 7.91 (s, 1H), 7.77-7.73 (m, 2H), 7.68 (d, J=7.8 Hz, 1H), 7.51 (t, J=7.9 Hz, 1H), 7.39-7.30 (m, 2H), 7.16 (s, 1H); ES-LCMS m/z 322.2 [M+H]⁺.

Step 2: tert-Butyl N-[4-(4-pyridyl)thiazol-2-yl]-N-[3-(trifluoromethyl)phenyl]carbamate

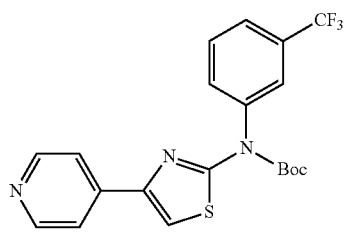 [SMILES: CC(C)(C)OC(=O)N(c1cccc(C(F)(F)F)c1)c1nc(-c2ccncc2)cs1]

To a solution of 4-(4-pyridyl)-N-[3-(trifluoromethyl)phenyl]thiazol-2-amine (150 mg, 466.82 μmol, 1 eq), Boc₂O (305.65 mg, 1.40 mmol, 321.73 μL, 3 eq) in THF (5 mL) was added DMAP (57.03 mg, 466.82 μmol, 1 eq). The mixture was stirred at 70° C. for 2 h. The reaction mixture was quenched by addition of water (50 mL), extracted with EtOAc (30 mL×3). The combined organic layers were washed with brine (10 mL), dried over Na₂SO₄, filtered and concentrated to yield tert-butyl N-[4-(4-pyridyl)thiazol-2-yl]-N-[3-(trifluoromethyl)phenyl]carbamate (190 mg, 450.84 μmol, 96.5% yield, 100% purity) as a white solid which was used in the next step without further purification. ¹H NMR (500 MHz, CDCl₃) δ ppm 8.40-8.36 (m, 2H), 7.55 (d, J=7.9 Hz, 1H), 7.50-7.44 (m, 2H), 7.38 (d, J=7.9 Hz, 1H), 7.34-7.31 (m, 2H), 7.27 (s, 1H); ES-LCMS m/z 422.2 [M+H]⁺.

Step 3: tert-Butyl N-[4-(1-oxidopyridin-1-ium-4-yl)thiazol-2-yl]-N-[3-(trifluoromethyl)phenyl]carbamate

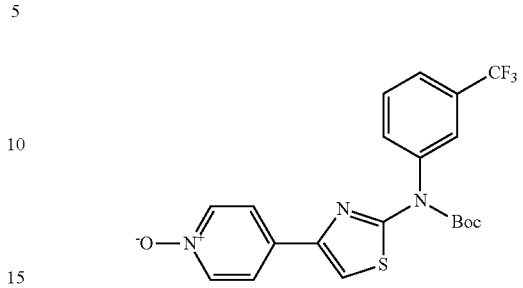

A mixture of tert-butyl N-[4-(4-pyridyl)thiazol-2-yl]-N-[3-(trifluoromethyl)phenyl]carbamate (170 mg, 403.38 μmol, 1 eq), m-CPBA (409.47 mg, 2.02 mmol, 85%, 5 eq) in DCM (5 mL) was degassed and purged with N₂ for 3 times, stirred at 25° C. for 2 h under N₂ atmosphere. The reaction mixture was concentrated to yield a residue which was purified by preparative HPLC (column: Phenomenex Synergi C18 150*30 mm*4 μm; mobile phase: [water (0.05% HCl)-ACN]; B %: 56%-76%, 9 min), followed by lyophilization to yield tert-butyl N-[4-(1-oxidopyridin-1-ium-4-yl)thiazol-2-yl]-N-[3-(trifluoromethyl)phenyl]carbamate (50 mg, 114.30 μmol, 28.3% yield, 100% purity) as a white solid. ¹H NMR (500 MHz, CDCl₃) δ ppm 8.67 (s, 2H), 7.96-7.84 (m, 2H), 7.75 (d, J=7.2 Hz, 2H), 7.66 (t, J=7.7 Hz, 1H), 7.58 (s, 1H), 7.51 (d, J=8.9 Hz, 1H), 1.48 (s, 9H); ES-LCMS m/z 438.2 [M+H]⁺.

Step 4: 4-(1-Oxidopyridin-1-ium-4-yl)-N-[3-(trifluoromethyl)phenyl]thiazol-2-amine

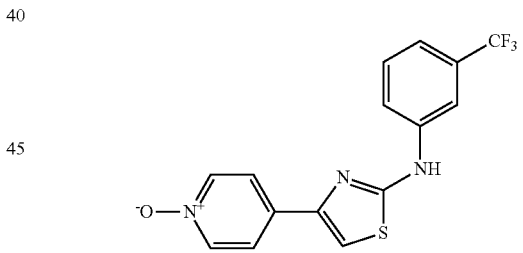

A mixture of tert-butyl N-[4-(1-oxidopyridin-1-ium-4-yl)thiazol-2-yl]-N-[3-(trifluoromethyl)phenyl]carbamate (50 mg, 114.30 μmol, 1 eq), TFA (13.03 mg, 114.30 μmol, 8.46 μL, 1 eq) in DCM (3 mL) was degassed and purged with N₂ for 3 times, stirred at 25° C. for 1 h under N₂ atmosphere. The reaction mixture was concentrated to yield a residue which was purified by preparative HPLC (column: Phenomenex Synergi C18 150*30 mm*4 μm; mobile phase: [water (0.05% HCl)-ACN]; B %: 41%-61%, 9 min), followed by lyophilization to yield 4-(1-oxidopyridin-1-ium-4-yl)-N-[3-(trifluoromethyl)phenyl]thiazol-2-amine (20 mg, 57.75 μmol, 50.5% yield, 97.4% purity) as a yellow solid. ¹H NMR (500 MHz, DMSO-d₆) δ ppm 9.64 (s, 1H), 7.21 (d, J=6.6 Hz, 2H), 6.90 (s, 1H), 6.73 (d, J=6.6 Hz, 2H), 6.70 (d, J=8.4 Hz, 1H), 6.59 (s, 1H), 6.31 (t, J=7.9 Hz, 1H), 6.04 (d, J=7.8 Hz, 1H); ES-LCMS m/z 338.1 [M+H]⁺.

I-18

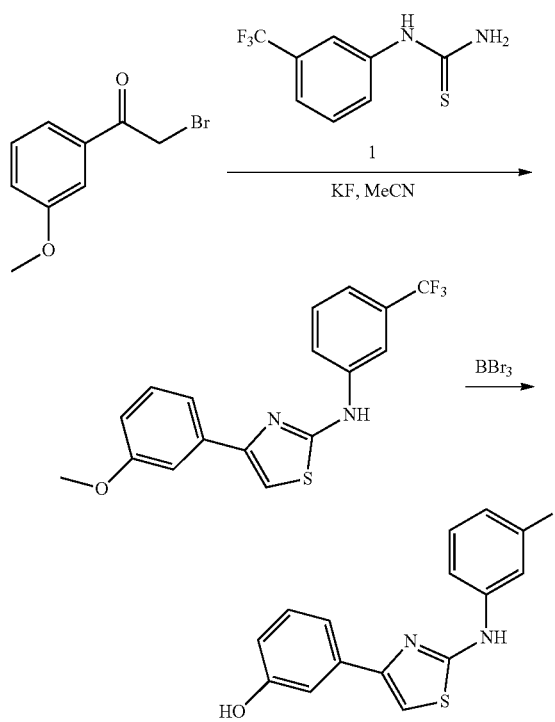

Step 1: 4-(3-Methoxyphenyl)-N-[3-(trifluoromethyl)phenyl]thiazol-2-amine

A mixture of 2-bromo-1-(3-methoxyphenyl)ethanone (500 mg, 2.18 mmol, 1 eq), [3-(trifluoromethyl)phenyl]thiourea (657.76 mg, 2.84 mmol, 330.97 μL, 1.3 eq), KF (126.82 mg, 2.18 mmol, 51.14 μL, 1 eq) in MeCN (15 mL) and H$_2$O (15 mL) was degassed and purged with N$_2$ for three times then the mixture was stirred at 25° C. for 2 h under N$_2$ atmosphere. TLC (PE/EtOAc=5/1, R$_f$=0.40) showed starting material was remained and one new spot was detected. The reaction mixture was concentrated, diluted with water (50 mL) and extracted with EtOAc (50 mL×3). The combined organic layers were dried over Na$_2$SO$_4$, filtered and the filtrate was concentrated to yield a residue which was purified by flash silica gel chromatography (from PE/EtOAc=100/1 to 2/1, TLC: PE/EtOAc=3/1, R$_f$=0.4) to yield 4-(3-methoxyphenyl)-N-[3-(trifluoromethyl)phenyl]thiazol-2-amine (672 mg, 1.92 mmol, 87.9% yield, 100.0% purity) as a white solid. $^1$H NMR (500 MHz, DMSO-d$_6$) δ ppm 10.67 (s, 1H), 8.52 (s, 1H), 7.74 (d, J=7.9 Hz, 1H), 7.57 (t, J=7.9 Hz, 1H), 7.52-7.49 (m, 2H), 7.48 (s, 1H), 7.35 (t, J=8.2 Hz, 1H), 7.30 (d, J=7.6 Hz, 1H), 6.92-6.87 (m, 1H), 3.82 (s, 3H); ES-LCMS m/z 351.0 [M+H]$^+$.

Step 2: 3-[2-[3-(Trifluoromethyl)anilino]thiazol-4-yl]phenol

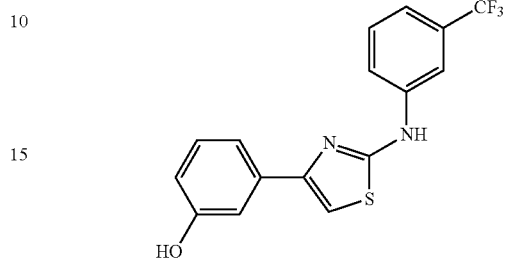

To a solution of 4-(3-methoxyphenyl)-N-[3-(trifluoromethyl)phenyl]thiazol-2-amine (200 mg, 570.84 μmol, 1 eq) in DCM (10 mL) was added BBr$_3$ (520.00 mg, 2.08 mmol, 0.2 mL, 3.64 eq) under ice-water bath. The mixture was stirred at 25° C. for 1 h. The reaction mixture was diluted with water (150 mL), extracted with EtOAc (50 mL×3). The combined organic layers were dried over Na$_2$SO$_4$, filtered and the filtrate was concentrated to yield a residue which was purified by flash silica gel chromatography (from PE/EtOAc=100/1 to 2/1, TLC: PE/EtOAc=5/1, R$_f$=0.65) and by preparative HPLC (column: Agela DuraShell C18 150*25 mm*5 um; mobile phase: [water (0.04% NH$_3$H$_2$O+10 mM NH$_4$HCO$_3$)-ACN]; B %: 45%-75%, 10 min) and lyophilized to yield 3-[2-[3-(trifluoromethyl)anilino]thiazol-4-yl]phenol (134 mg, 395.23 μmol, 69.2% yield, 99.2% purity) as a white solid. $^1$H NMR (500 MHz, DMSO-d$_6$) δ ppm 10.62 (s, 1H), 9.48 (s, 1H), 8.29 (s, 1H), 7.90 (d, J=8.5 Hz, 1H), 7.57 (t, J=7.9 Hz, 1H), 7.36-7.32 (m, 2H), 7.32-7.28 (m, 2H), 7.22 (t, J=7.9 Hz, 1H), 6.73 (dd, J=1.6, 8.0 Hz, 1H); ES-LCMS m/z 336.9 [M+H]$^+$.

I-80

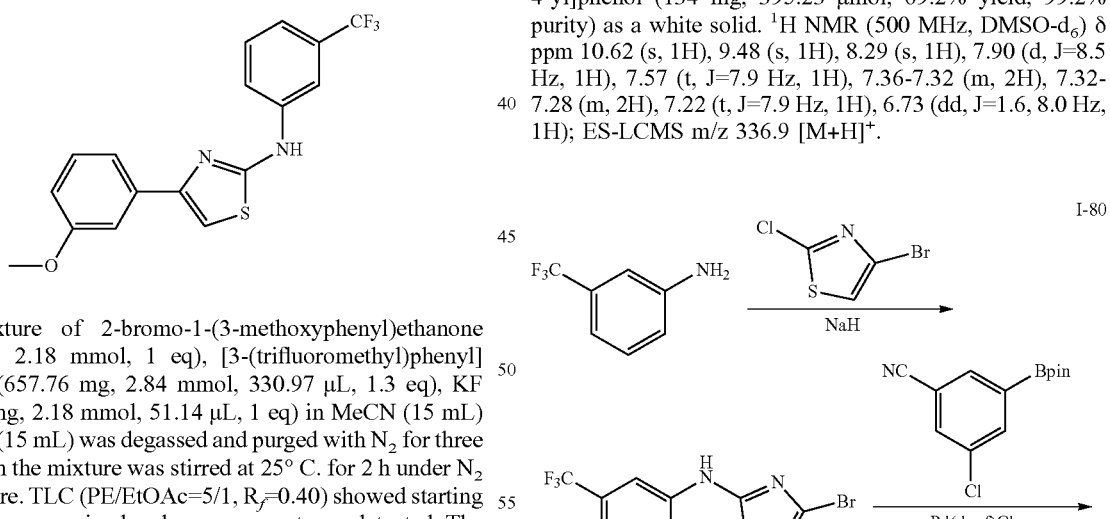

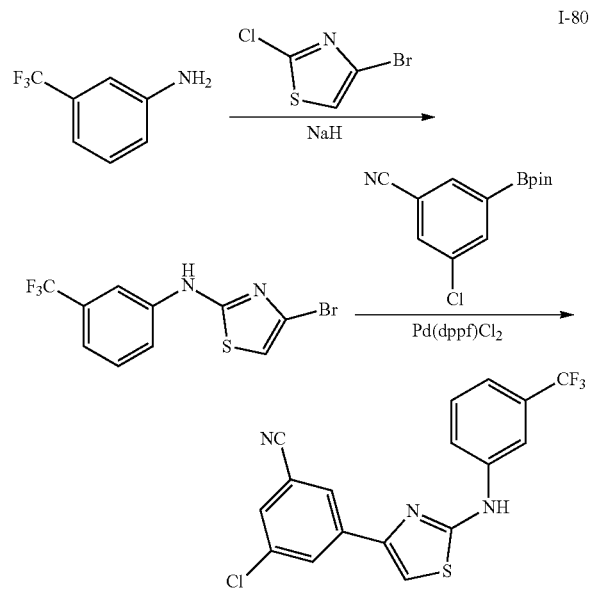

Step 1: 4-Bromo-N-[3-(trifluoromethyl)phenyl]thiazol-2-amine

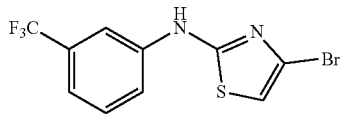 [SMILES: FC(F)(F)c1cccc(Nc2nc(Br)cs2)c1]

To a solution of 3-(trifluoromethyl)aniline (243.55 mg, 1.51 mmol, 188.80 µL, 1 eq) in THF (10 mL) was cooled to 0° C. then added NaH (211.60 mg, 5.29 mmol, 60%, 3.5 eq) slowly. The reaction mixture was warmed to 20° C. then stirred for 1 h. 4-Bromo-2-chloro-thiazole (300 mg, 1.51 mmol, 1 eq) was added to the above reaction mixture then stirred at 70° C. for 12 h. The reaction mixture was diluted with water (50 mL) and extracted with EtOAc (30 mL×3). The combined organic layers were dried over Na$_2$SO$_4$, filtered and the filtrate was concentrated to yield a residue which was purified by flash silica gel chromatography (from PE/EtOAc=100/1 to 2/1, TLC: PE/EtOAc=1/1, R$_f$=0.55) to yield 4-bromo-N-[3-(trifluoromethyl)phenyl]thiazol-2-amine (120 mg, 371.37 µmol, 24.6% yield, 100.0% purity) as a yellow solid. $^1$H NMR (400 MHz, DMSO-d$_6$) δ ppm 10.82 (s, 1H), 8.02 (s, 1H), 7.77 (d, J=8.1 Hz, 1H), 7.56 (t, J=8.1 Hz, 1H), 7.31 (d, J=7.8 Hz, 1H), 7.07 (s, 1H); ES-LCMS m/z 323.0, 325.0 [M+H]$^+$.

Step 2: 3-Chloro-5-[2-[3-(trifluoromethyl)anilino]thiazol-4-yl]benzonitrile

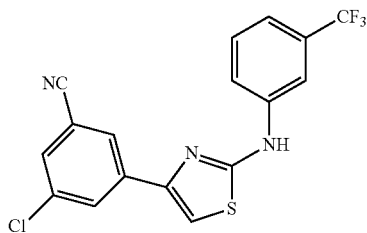 [SMILES: N#Cc1cc(Cl)cc(-c2csc(Nc3cccc(C(F)(F)F)c3)n2)c1]

To a solution of 3-chloro-5-(4,4,5,5-tetramethyl-1,3,2-dioxaborolan-2-yl)benzonitrile (44.85 mg, 170.21 µmol, 1.1 eq) in 1,4-dioxane (2 mL) and H$_2$O (0.4 mL) was added 4-bromo-N-[3-(trifluoromethyl)phenyl]thiazol-2-amine (50 mg, 154.74 µmol, 100.0%, 1 eq), Cs$_2$CO$_3$ (151.25 mg, 464.21 µmol, 3 eq) and Pd(dppf)Cl$_2$ (11.32 mg, 15.47 µmol, 0.1 eq). The mixture was bubbled with N$_2$ for 3 min and stirred at 100° C. for 0.5 h under microwave. To the mixture was added water (30 mL) and extracted with ethyl acetate (30 mL×3). The combined organic phase was washed with brine (20 mL), dried over anhydrous Na$_2$SO$_4$, filtered and concentrated in vacuum to yield a residue which was purified by preparative HPLC (column: Agela DuraShell C18 150*25 mm*5 µm; mobile phase: [water (0.05% NH$_3$.H$_2$O+ 10 mM NH$_4$HCO$_3$)-ACN]; B %: 63%-93%, 10 min), followed by lyophilization to yield 3-chloro-5-[2-[3-(trifluoromethyl)anilino]thiazol-4-yl]benzonitrile (29.21 mg, 75.62 µmol, 48.9% yield, 98.3% purity) as a yellow solid. $^1$H NMR (500 MHz, CDCl$_3$) δ ppm 8.11-8.06 (m, 1H), 8.04 (s, 1H), 7.82 (s, 1H), 7.69 (d, J=8.1 Hz, 1H), 7.58 (s, 1H), 7.53 (t, J=7.9 Hz, 1H), 7.37 (d, J=7.6 Hz, 1H), 7.29 (s, 1H), 7.02 (s, 1H); ES-LCMS m/z 380.1, 382.1 [M+H]$^+$.

I-83

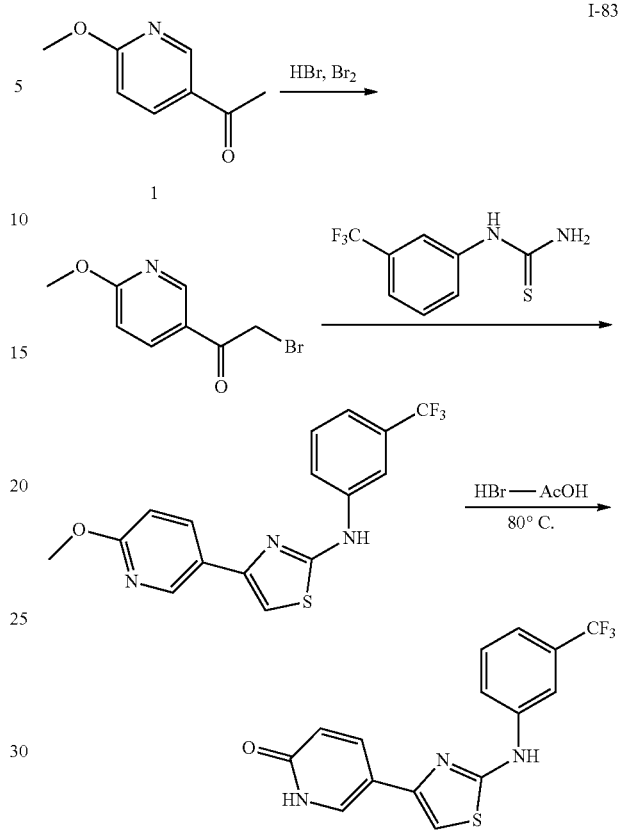

Step 1: 2-Bromo-1-(6-methoxy-3-pyridyl)ethanone

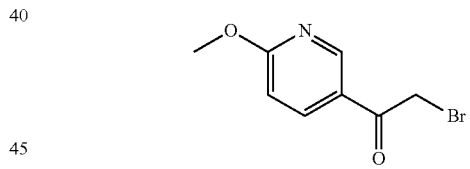

To a solution of 1-(6-methoxy-3-pyridyl)ethanone (2 g, 13.23 mmol, 1 eq) in AcOH (20) was added HBr (29.80 g, 121.54 mmol, 20 mL, 33%, 9.19 eq) and Br$_2$ (2.11 g, 13.23 mmol, 682.06 µL, 1 eq). The mixture was stirred at 25° C. for 12 h. The reaction mixture was quenched by addition of water (50 mL) and extracted with EtOAc (30 mL×3). The combined organic layers were washed with brine (10 mL), dried over Na$_2$SO$_4$, filtered and concentrated under reduced pressure to yield 2-bromo-1-(6-methoxy-3-pyridyl)ethanone (2.2 g, 5.58 mmol, 42.1% yield, 58.3% purity) as colorless oil, which was used in the next step without further purification. $^1$H NMR (500 MHz, CDCl$_3$) δ ppm 8.77-8.89 (m, 1H), 8.08-8.21 (m, 1H), 6.76-6.84 (m, 1H), 3.96-4.02 (m, 3H), 2.57 (s, 2H); ES-LCMS m/z 230.1, 232.1 [M+H]$^+$.

Step 2: 4-(6-Methoxy-3-pyridyl)-N-[3-(trifluoromethyl)phenyl]thiazol-2-amine

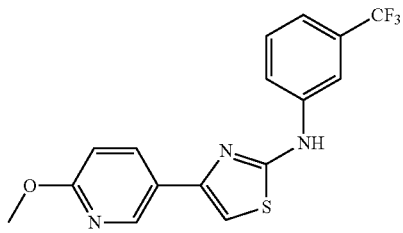 [SMILES: COc1ccc(-c2csc(Nc3cccc(C(F)(F)F)c3)n2)cn1]

To mixture of 2-bromo-1-(6-methoxy-3-pyridyl)ethanone (2.2 g, 5.58 mmol, 1 eq), [3-(trifluoromethyl)phenyl]thiourea (1.64 g, 6.69 mmol, 1.2 eq), in MeCN (20 mL) and H$_2$O (20 mL) was degassed and purged with N$_2$ for 3 times and the mixture was stirred under N$_2$ atmosphere at 25° C. for 12 h. The reaction mixture was quenched by addition of water (50 mL) and extracted with EtOAc (30 mL×3). The combined organic layers were washed with brine (10 mL), dried over Na$_2$SO$_4$, filtered and concentrated under reduced pressure to yield a residue which was purified by flash silica gel chromatography (from PE/EtOAc=1/0 to 1/1, TLC: PE/EtOAc=1/1, R$_f$=0.34) to yield 4-(6-methoxy-3-pyridyl)-N-[3-(trifluoromethyl)phenyl]thiazol-2-amine (1.1 g, 3.13 mmol, 56.1% yield, 100.0% purity) as a white solid. $^1$H NMR (500 MHz, CDCl$_3$) δ ppm 8.70 (d, J=1.98 Hz, 1H), 8.03 (dd, J=8.70, 2.44 Hz, 1H), 7.78 (s, 1H), 7.70 (d, J=8.24 Hz, 1H), 7.47 (t, J=7.93 Hz, 1H), 7.31 (d, J=7.78 Hz, 1H), 6.79-6.82 (m, 2H), 3.99 (s, 3H); ES-LCMS m/z 352.2 [M+H]$^+$.

Step 3: 5-[2-[3-(Trifluoromethyl)anilino]thiazol-4-yl]-1H-pyridin-2-one

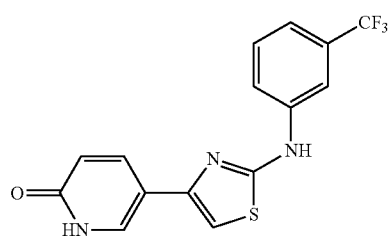 [SMILES: O=c1ccc(-c2csc(Nc3cccc(C(F)(F)F)c3)n2)c[nH]1]

A mixture of 4-(6-methoxy-3-pyridyl)-N-[3-(trifluoromethyl)phenyl]thiazol-2-amine (200 mg, 569.24 μmol, 1 eq) in HBr (25 mL) was degassed and purged with N$_2$ for 3 times and the mixture was stirred under N$_2$ atmosphere at 80° C. for 12 h. The reaction mixture was quenched by addition of water (50 mL) and extracted with EtOAc (30 mL×3). The combined organic layers were washed with brine (10 mL), dried over Na$_2$SO$_4$, filtered and concentrated under reduced pressure to yield a residue which was purified by preparative HPLC (column: Phenomenex Synergi C18 150*30 mm*4 μm; mobile phase: [water (0.05% HCl)-ACN]; B %: 39%-59%, 9 min), followed by lyophilization to yield 5-[2-[3-(trifluoromethyl)anilino]thiazol-4-yl]-1H-pyridin-2-one (120 mg, 355.75 μmol, 62.4% yield, 100.0% purity) as a white solid. $^1$H NMR (500 MHz, DMSO-d$_6$) δ ppm 10.77 (s, 1H), 8.26 (s, 1H), 8.01 (dd, J=9.39, 2.35 Hz, 1H), 7.88 (d, J=2.35 Hz, 1H), 7.84 (d, J=8.61 Hz, 1H), 7.55 (t, J=8.02 Hz, 1H), 7.29 (d, J=7.83 Hz, 1H), 7.21 (s, 1H), 6.48 (d, J=9.39 Hz, 1H); ES-LCMS m/z 338.1 [M+H]$^+$.

I-84

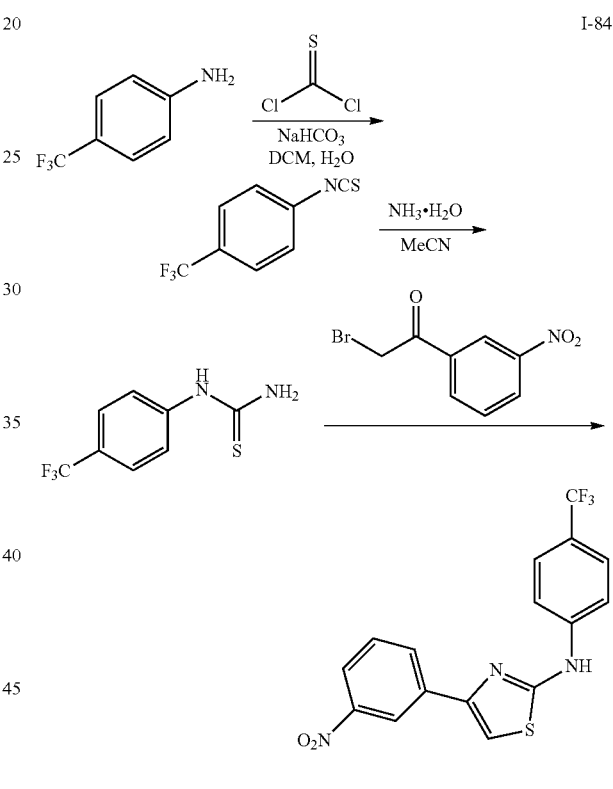

Step 1: 1-Isothiocyanato-4-(trifluoromethyl)benzene

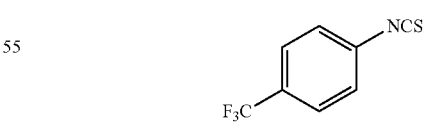

To a solution of 4-(trifluoromethyl)aniline (5 g, 31.03 mmol, 3.85 mL, 1 eq) and NaHCO$_3$ (5.21 g, 62.06 mmol, 2 eq) in DCM (30 mL) and H$_2$O (30 mL) was added thiocarbonyl dichloride (5.35 g, 46.55 mmol, 3.57 mL, 1.5 eq) at 0° C. The mixture was stirred at 25° C. for 3 h. The reaction mixture was diluted with H$_2$O (50 mL) and extracted with DCM (150 mL×3). The combined organic layers were washed with brine (50 mL×2), dried over Na₂SO₄, filtered and concentrated under reduced pressure to yield 1-isothiocyanato-4-(trifluoromethyl)benzene (6.24 g, crude) as yellow oil.

Step 2: [4-(Trifluoromethyl)phenyl]thiourea

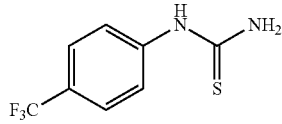 [SMILES: NC(=S)Nc1ccc(C(F)(F)F)cc1]

To a solution of 1-isothiocyanato-4-(trifluoromethyl)benzene (6.24 g, 21.50 mmol, 1 eq) in MeCN (200 mL) was added NH₃H₂O (4.04 g, 32.25 mmol, 4.44 mL, 28% purity, 1.5 eq) and the mixture was stirred at 25° C. for 2 h. The solvent was removed and the residue was treated with H₂O (50 mL) and extracted with EtOAc (100 mL×2). The combined organic phases were washed with brine (100 mL), dried over Na₂SO₄, filtered and concentrated to yield [4-(trifluoromethyl)phenyl]thiourea (6.67 g, 15.14 mmol, 70.5% yield, 50.0% purity) as a yellow gum. 1H NMR (500 MHz, DMSO-d₆) δ 10.04 (s, 1H), 7.76-7.70 (m, 2H), 7.66 (d, J=8.5 Hz, 2H), 4.03 (q, J=7.0 Hz, 2H).

Step 3: 4-(3-Nitrophenyl)-N-[4-(trifluoromethyl)phenyl]thiazol-2-amine

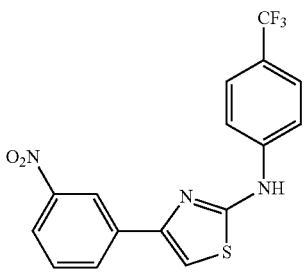 [SMILES: O=[N+]([O-])c1cccc(-c2csc(Nc3ccc(C(F)(F)F)cc3)n2)c1]

To a solution of 2-bromo-1-(3-nitrophenyl) ethanone (50 mg, 204.88 µmol, 1 eq) in ACN (3 mL) and H₂O (3 mL) was added [4-(trifluoromethyl)phenyl]thiourea (90.24 mg, 204.88 µmol, 1 eq). The mixture was stirred at 25° C. for 5 h. The reaction mixture was concentrated to yield a residue which was purified by preparative HPLC (column: Agela DuraShell C18 150*25 mm*5 µm; mobile phase: [water (0.05% NH₃H₂O+10 mM NH₄HCO₃)-ACN]; B %: 60%-90%, 10 min) and lyophilized to yield 4-(3-nitrophenyl)-N-[4-(trifluoromethyl)phenyl]thiazol-2-amine (22.49 mg, 60.94 µmol, 29.7% yield, 99.0% purity) as a yellow solid. ¹H NMR (400 MHz, CDCl₃) δ 8.71 (d, J=1.7 Hz, 1H), 8.23-8.17 (m, 2H), 7.68-7.59 (m, 5H), 7.35-7.31 (m, 1H), 7.10 (s, 1H); ES-LCMS m/z 366.1 [M+H]⁺.

I-86

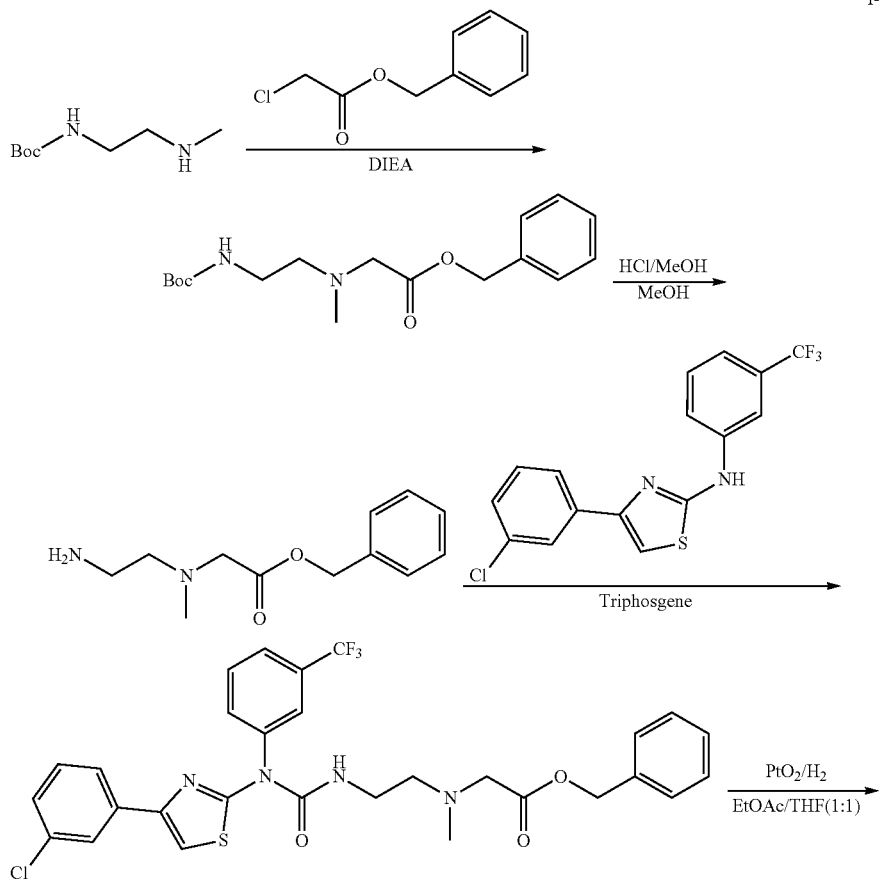

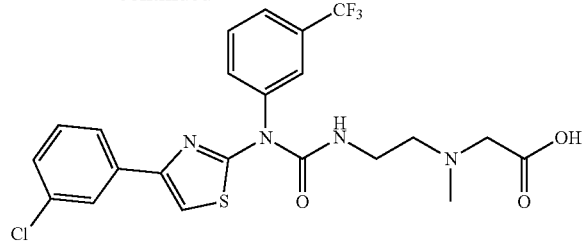

Step 1: Benzyl 2-[2-(tert-butoxycarbonylamino) ethyl-methyl-amino]acetate

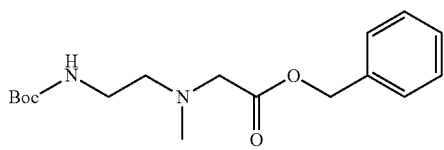 [SMILES: CN(CCNC(=O)OC(C)(C)C)CC(=O)OCc1ccccc1]

To a solution of tert-butyl N-[2-(methylamino)ethyl]carbamate (2.5 g, 14.35 mmol, 1 eq) in THF (50 mL) was added DIEA (5.56 g, 43.04 mmol, 7.50 mL, 3 eq) and benzyl 2-chloroacetate (2.65 g, 14.35 mmol, 1 eq). The mixture was stirred at 20° C. for 10 h. The mixture was concentrated to yield benzyl 2-[2-(tert-butoxycarbonylamino)ethyl-methyl-amino]acetate (3.5 g, 8.68 mmol, 60.5% yield, 80.0% purity) as a white solid, which was used in the next step without further purification. $^1$H NMR (400 MHz, DMSO-$d_6$) δ ppm 7.38-7.35 (m, 5H), 5.10 (s, 2H), 3.34 (s, 2H), 2.99 (q, J=6.2 Hz, 2H), 2.55-2.51 (m, 2H), 2.28 (s, 3H), 1.36 (s, 9H); ES-LCMS m/z 323.1 [M+H]$^+$.

Step 2: Benzyl 2-[2-aminoethyl(methyl)amino]acetate

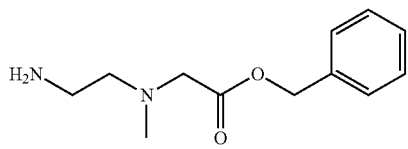 [SMILES: CN(CCN)CC(=O)OCc1ccccc1]

To a solution of benzyl 2-[2-(tert-butoxycarbonylamino) ethyl-methyl-amino]acetate (1.25 g, 3.10 mmol, 1 eq) in DCM (15 mL) was added TFA (1 mL). The mixture was stirred at 20° C. for 1 h. The mixture was concentrated to yield benzyl 2-[2-aminoethyl(methyl)amino]acetate (1 g, 2.38 mmol, 76.7% yield, 80.0% purity, TFA) as a white solid, which was used in the next step without further purification. ES-LCMS no MS found.

Step 3: Benzyl 2-[2-[[[4-(3-chlorophenyl)thiazol-2-yl]-[3-(trifluoromethyl)phenyl]carbamoyl]amino] ethyl-methyl-amino]acetate To a solution of 4-(3-chlorophenyl)-N-[3-(trifluoromethyl)phenyl]thiazol-2-amine (400 mg, 1.07 mmol, 1 eq) in THF (5 mL) was added DIEA (553.71 mg, 4.28 mmol, 746.24 μL, 4 eq) and bis(trichloromethyl) carbonate (381.42 mg, 1.29 mmol, 1.2 eq). The mixture was stirred at 80° C. for 1 h. The reaction mixture was concentrated to yield trichloromethyl (4-(3-chlorophenyl)thiazol-2-yl)(3-(trifluoromethyl)phenyl)carbamate (crude). To a solution of bis (trichloromethyl) carbonate (381.42 mg, 1.29 mmol, 1.2 eq) in DCM (5 mL) was added DIEA (553.71 mg, 4.28 mmol, 746.24 μL, 4 eq) and benzyl 2-[2-aminoethyl(methyl)amino] acetate (1 g, 2.38 mmol, 2.22 eq, TFA). The mixture was stirred at 40° C. for 11 h. The mixture was quenched with H$_2$O (30 mL) and extracted with EtOAc (30 mL×3). The combined organic layers were washed with brine (30 mL), dried over Na$_2$SO$_4$, filtered and concentrated under reduced pressure to yield a residue which was purified by preparative HPLC (column: Welch Xtimate C18 150*25 mm*5 μm; mobile phase: [water (10 mM NH$_4$HCO$_3$)-ACN]; B %: 63%-93%, 10 min) to yield benzyl 2-[2-[[[4-(3-chlorophenyl)thiazol-2-yl]-[3-(trifluoromethyl)phenyl]carbamoyl] amino]ethyl-methyl-amino]acetate (250 mg, 393.83 μmol, 36.8% yield, 95.0% purity) as a white solid. $^1$H NMR (400 MHz, CDCl$_3$) δ ppm 8.61 (s, 1H), 7.76-7.70 (m, 2H), 7.70-7.62 (m, 3H), 7.61-7.57 (m, 1H), 7.37-7.25 (m, 7H), 7.01 (s, 1H), 5.03 (s, 2H), 3.51-3.44 (m, 2H), 3.38 (s, 2H), 2.77 (t, J=5.7 Hz, 2H), 2.47 (s, 3H); ES-LCMS m/z 603.1 [M+H]$^+$.

295

Step 4: 2-[2-[[[4-(3-Chlorophenyl)thiazol-2-yl]-[3-(trifluoromethyl)phenyl]carbamoyl]amino]ethyl-methyl-amino]acetic acid

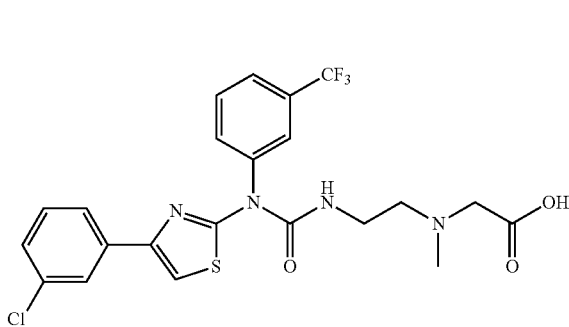 [SMILES: CN(CCNC(=O)N(c1cccc(C(F)(F)F)c1)c1nc(-c2cccc(Cl)c2)cs1)CC(=O)O]

To a solution of benzyl 2-[2-[[[4-(3-chlorophenyl)thiazol-2-yl]-[3-(trifluoromethyl)phenyl]carbamoyl]amino]ethyl-methyl-amino]acetate (100 mg, 157.53 μmol, 1 eq) in MeOH (20 mL) was added Pd/C (300 mg, 10% purity, 50% wet) with stirred at 20° C. under H$_2$ (15 Psi). The mixture was stirred at 20° C. for 25 min. The reaction mixture was filtered and washed with MeOH. The filtrate was concentrated to yield a residue which was purified by preparative HPLC (column: Welch Xtimate C18 150*25 mm*5 μm; mobile phase: [water (10 mM NH$_4$HCO$_3$)-ACN]; B %: 32%-62%, 10 min) to yield 2-[2-[[[4-(3-chlorophenyl)thiazol-2-yl]-[3-(trifluoromethyl)phenyl]carbamoyl]amino]ethyl-methyl-amino]acetic acid (23.16 mg, 45.15 μmol, 28.7% yield, 100.0% purity) as a white solid. $^1$H NMR (400 MHz, CD$_3$OD) δ ppm 7.91-7.85 (m, 2H), 7.85-7.76 (m, 2H), 7.69 (s, 1H), 7.64 (d, J=7.8 Hz, 1H), 7.45 (s, 1H), 7.34-7.28 (m, 1H), 7.27-7.23 (m, 1H), 3.70-3.63 (m, 4H), 3.34-3.32 (m, 2H), 2.97 (s, 3H); ES-LCMS m/z 513.1 [M+H]$^+$.

296

Step 1: 5-[2-[3-(Trifluoromethyl)anilino]thiazol-4-yl]pyridine-3-carbonitrile

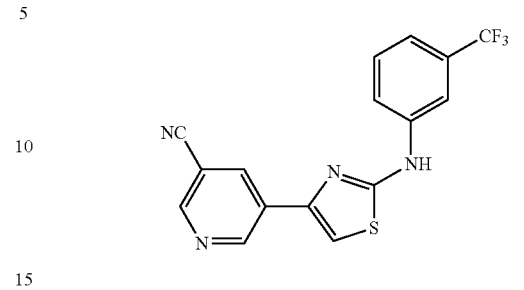

To a stirred solution of 5-[2-[3-(trifluoromethyl)anilino]thiazol-4-yl]pyridine-3-carboxamide (500 mg, 1.37 mmol, 1 eq) in DMF (5 mL) was cooled to 0° C. under ice-water bath then added Et$_3$N (277.73 mg, 2.74 mmol, 382.02 μL, 2 eq) and TFAA (576.46 mg, 2.74 mmol, 381.76 μL, 2 eq) slowly. The reaction mixture was stirred at 110° C. for 12 h. The reaction mixture was quenched by addition of water (50 mL), extracted with EtOAc (30 mL×3). The combined organic layers were washed with brine (10 mL), dried over Na$_2$SO$_4$, filtered and concentrated under reduced pressure to yield a residue which was purified by preparative HPLC (column: Agela DuraShell C18 150*25 mm*5 μm; mobile phase: [water (0.05% NH$_3$H$_2$O+10 mM NH$_4$HCO$_3$)-ACN]; B %: 50%-80%, 10 min). The desired fraction was lyophilized to yield 5-[2-[3-(trifluoromethyl)anilino]thiazol-4-yl]pyridine-3-carbonitrile (140 mg, 400.20 μmol, 29.2% yield, 99.0% purity) as a white solid. $^1$H NMR (400 MHz, CDCl$_3$) δ ppm 9.29 (d, J=2.2 Hz, 1H), 8.82 (d, J=2.0 Hz, 1H), 8.42 (t, J=2.1 Hz, 1H), 7.79 (s, 1H), 7.74 (d, J=8.1 Hz, 1H), 7.54 (t, J=7.9 Hz, 1H), 7.38 (d, J=7.6 Hz, 1H), 7.31 (s, 1H), 7.11 (s, 1H); ES-LCMS m/z 347.1 [M+H]$^+$.

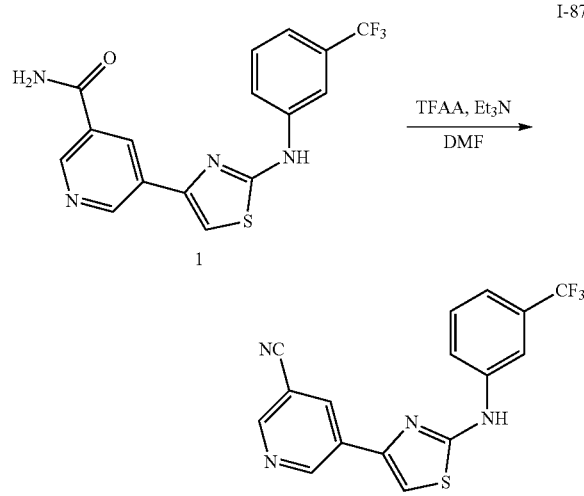

1

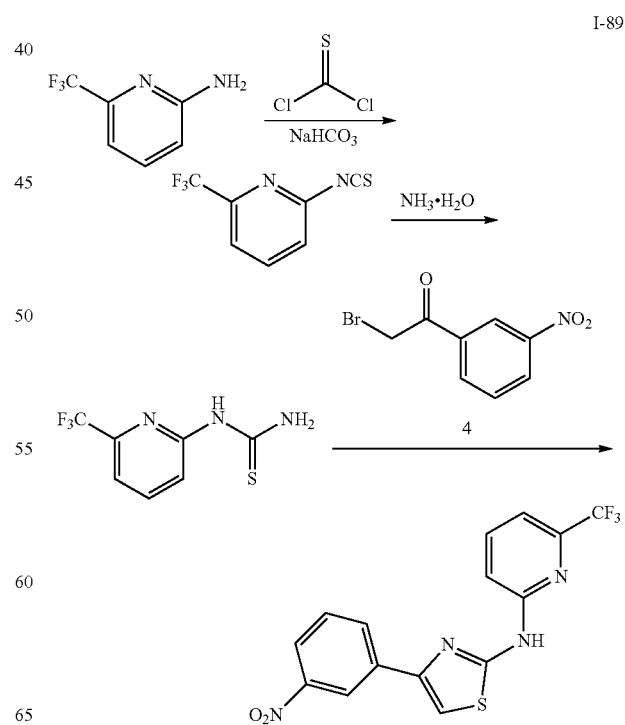

I-89

Step 1: 2-Isothiocyanato-6-(trifluoromethyl)pyridine

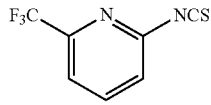

To a solution of 6-(trifluoromethyl)pyridin-2-amine (1 g, 6.17 mmol, 1 eq) in DCM (15 mL) and H$_2$O (15 mL) was added NaHCO$_3$ (1.04 g, 12.34 mmol, 2 eq) and thiocarbonyl dichloride (2.13 g, 18.51 mmol, 1.42 mL, 3 eq). The mixture was stirred at 20° C. for 3 h. TLC (PE/EtOAc=5/1, R$_f$=0.51) indicated the starting material was consumed and one major new spot with lower polarity was detected. The organic phase was concentrated to yield 2-isothiocyanato-6-(trifluoromethyl)pyridine (1.72 g, crude) as yellow oil.

Step 2: [6-(Trifluoromethyl)-2-pyridyl]thiourea

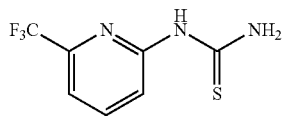 [SMILES: NC(=S)Nc1cccc(C(F)(F)F)n1]

To a solution of 2-isothiocyanato-6-(trifluoromethyl)pyridine (1.72 g, 5.05 mmol, 1 eq) in MeCN (15 mL) was added NH$_3$·H$_2$O (948.97 mg, 7.58 mmol, 1.04 mL, 1.5 eq) and the mixture was stirred at 20° C. for 2 h. TLC (PE/EtOAc=3/1, R$_f$=0.24) indicated the starting material was consumed and one major new spot with lower polarity was detected. The solvent was removed and the residue was treated with water (30 mL), extracted with EtOAc (50 mL×2). The combined organic phases were washed with brine (50 mL), dried over anhydrous Na$_2$SO$_4$, filtered and concentrated to yield [6-(trifluoromethyl)-2-pyridyl]thiourea (1.36 g, 4.92 mmol, 97.3% yield, 80.0% purity) as a red solid. $^1$H NMR (400 MHz, DMSO-d$_6$) δ ppm 10.90 (s, 1H) 9.89 (s, 1H) 9.12 (s, 1H) 8.00 (t, J=7.95 Hz, 1H) 7.54-7.40 (m, 2H).

Step 3: 4-(3-Chlorophenyl)-N-[4-(trifluoromethyl)phenyl]thiazol-2-amine

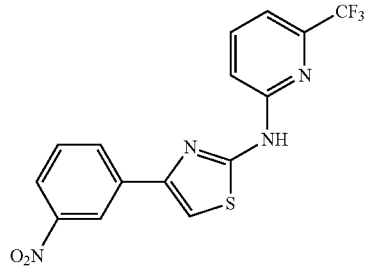 [SMILES: O=[N+]([O-])c1cccc(-c2csc(Nc3cccc(C(F)(F)F)n3)n2)c1]

To a solution of [6-(trifluoromethyl)-2-pyridyl]thiourea (200 mg, 723.32 μmol, 1 eq) in MeCN (5 mL) and H$_2$O (5 mL) was added 2-bromo-1-(3-nitrophenyl)ethanone (176.52 mg, 723.32 μmol, 1 eq). The mixture was stirred at 20° C. for 2 h. The solvent was removed and the residue was treated with water (30 mL), extracted with EtOAc (50 mL×2). The combined organic phases were washed with brine (50 mL), dried over anhydrous Na$_2$SO$_4$, filtered and concentrated to give a residue which was purified by flash silica gel chromatography (from PE/EtOAc=1/0 to 2/1, TLC: PE/EtOAc=2/1, R$_f$=0.48) to yield a product which was dissolved in MeCN (40 mL) and H$_2$O (40 mL), followed by lyophilization to yield 4-(3-nitrophenyl)-N-[6-(trifluoromethyl)-2-pyridyl]thiazol-2-amine (215 mg, 562.86 μmol, 77.8% yield, 95.9% purity) as a yellow solid. $^1$H NMR (400 MHz, DMSO-d$_6$) δ ppm 12.01 (s, 1H) 8.76 (s, 1H) 8.36 (d, J=7.83 Hz, 1H) 8.21-8.13 (m, 1H) 7.98 (t, J=7.83 Hz, 1H) 7.87 (s, 1H) 7.74 (t, J=8.02 Hz, 1H) 7.43 (d, J=7.43 Hz, 1H) 7.35 (d, J=8.61 Hz, 1H); ES-LCMS m/z 367.0 [M+H]$^+$.

I-90

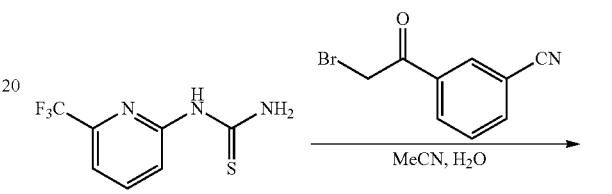

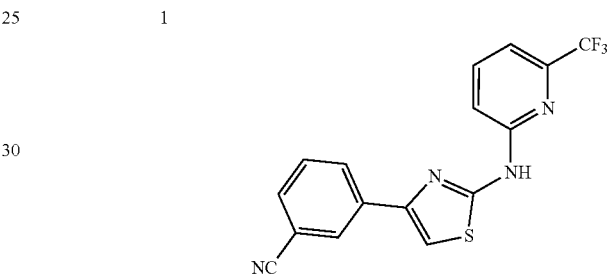

Step 1: 3-[2-[[6-(Trifluoromethyl)-2-pyridyl]amino]thiazol-4-yl]benzonitrile

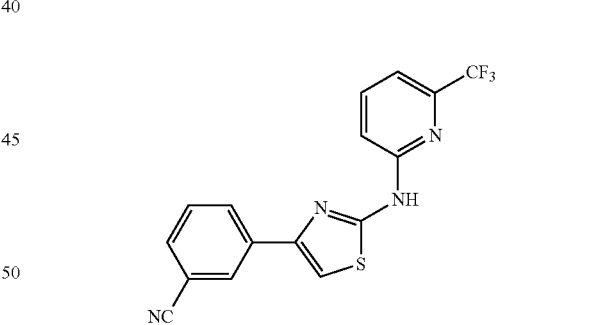

To a solution of [6-(trifluoromethyl)-2-pyridyl]thiourea (300 mg, 1.08 mmol, 1 eq) in MeCN (5 mL) and H$_2$O (5 mL) was added 3-(2-bromoacetyl)benzonitrile (243.09 mg, 1.08 mmol, 1 eq). The mixture was stirred at 20° C. for 2 h. The reaction mixture was diluted with water (30 mL) and extracted with EtOAc (50 mL×2). The combined organic phases were washed with brine (50 mL), dried over anhydrous Na$_2$SO$_4$, filtered and concentrated under reduced pressure to give a residue which was purified by silica gel chromatography (from PE/EtOAc=1/0 to 2/1, TLC: PE/EA=2/1, R$_f$=0.43) to yield a product which was added H$_2$O (20 ml) and MeCN (20 mL), followed by lyophilization to yield 3-[2-[[6-(trifluoromethyl)-2-pyridyl]amino]thiazol-4-yl]benzonitrile (360 mg, 1.02 mmol, 94.3% yield, 98.4% purity) as a pink solid. ¹H NMR (400 MHz, DMSO-d₆) δ ppm 11.93 (s, 1H) 8.34 (s, 1H) 8.24 (d, J=8.22 Hz, 1H) 7.98 (t, J=8.02 Hz, 1H) 7.84-7.75 (m, 2H) 7.69-7.60 (m, 1H) 7.43 (d, J=7.43 Hz, 1H) 7.37 (d, J=8.22 Hz, 1H); ES-LCMS m/z 347.0 [M+H]⁺.

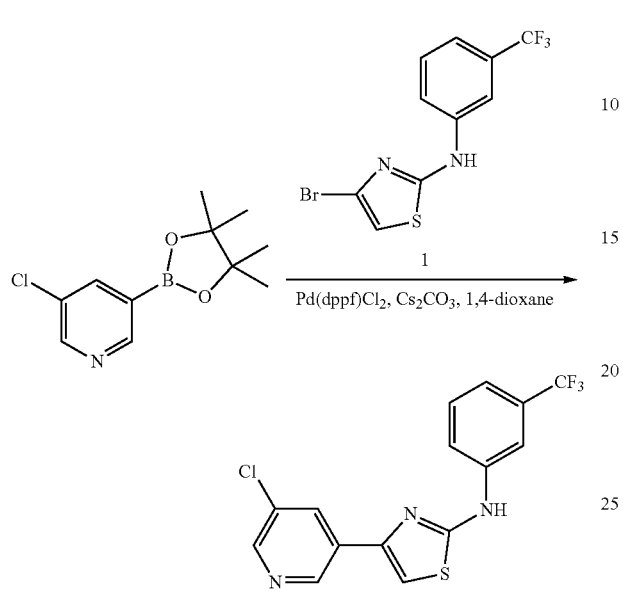

Step 1: 4-(5-Chloro-3-pyridyl)-N-[3-(trifluoromethyl)phenyl]thiazol-2-amine

To a solution of 3-chloro-5-(4,4,5,5-tetramethyl-1,3,2-dioxaborolan-2-yl)pyridine (700 mg, 2.92 mmol, 1 eq) and 4-bromo-N-[3-(trifluoromethyl)phenyl]thiazol-2-amine (930 mg, 2.30 mmol, 7.89e-1 eq) in 1,4-dioxane (12 mL) and H₂O (4 mL) was added Cs₂CO₃ (2.86 g, 8.76 mmol, 3 eq) and Pd(dppf)Cl₂ (106.93 mg, 146.00 μmol, 0.05 eq). The reaction mixture was bubbled with N₂ for 3 min then stirred at 100° C. for 30 min under microwave. TLC (PE/EtOAc=3/1, R_f=0.20) indicated starting material was consumed completely and three new spots formed. The mixture was diluted with water (20 mL) and extracted with EtOAc (20 mL×3). The combined organic layers were dried over Na₂SO₄, filtered and concentrated under reduced pressure to yield a residue which was purified by flash silica gel chromatography (from PE/EtOAc=100/1 to 4/1, TLC: PE/EtOAc=5/1, R_f=0.20) to yield 4-(5-chloro-3-pyridyl)-N-[3-(trifluoromethyl)phenyl]thiazol-2-amine (17.68 mg, 49.70 μmol, 1.7% yield, 100.0% purity) as a white solid. ¹H NMR (400 MHz, CD₃OD) δ ppm 9.04 (d, J=1.7 Hz, 1H), 8.48 (d, J=2.3 Hz, 1H), 8.38-8.32 (m, 2H), 7.79 (d, J=7.8 Hz, 1H), 7.52 (t, J=8.0 Hz, 1H), 7.47 (s, 1H), 7.27 (d, J=7.6 Hz, 1H); ES-LCMS m/z 356.1 [M+H]⁺.

I-92

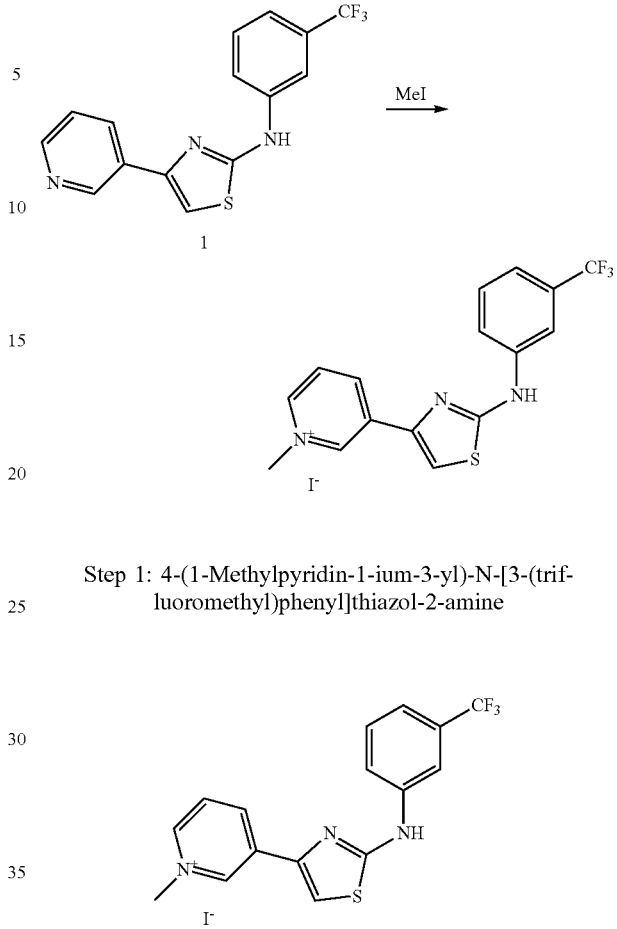

Step 1: 4-(1-Methylpyridin-1-ium-3-yl)-N-[3-(trifluoromethyl)phenyl]thiazol-2-amine To a solution of 4-(3-pyridyl)-N-[3-(trifluoromethyl)phenyl]thiazol-2-amine (100 mg, 295.66 μmol, 1 eq) in ACN (2 mL) was added MeI (83.93 mg, 591.31 μmol, 36.81 μL, 2 eq). The mixture was stirred at 30° C. for 12 h. The solution was quenched by addition water (10 mL), followed by lyophilization to yield 4-(1-methylpyridin-1-ium-3-yl)-N-[3-(trifluoromethyl)phenyl]thiazol-2-amine (64.9 mg, 184.58 μmol, 62.4% yield, 95.7% purity) as a yellow solid, which was delivered without further purification. ¹H NMR (400 MHz, DMSO-d₆) δ ppm 10.89 (s, 1H), 9.48-9.39 (m, 1H), 8.96-8.89 (m, 2H), 8.21 (dd, J=6.4, 8.1 Hz, 1H), 8.10 (d, J=1.7 Hz, 2H), 7.94 (s, 1H), 7.61 (t, J=8.2 Hz, 1H), 7.36 (d, J=7.8 Hz, 1H), 4.42 (s, 3H); ES-LCMS m/z 336.2 [M−I]⁺.

I-93

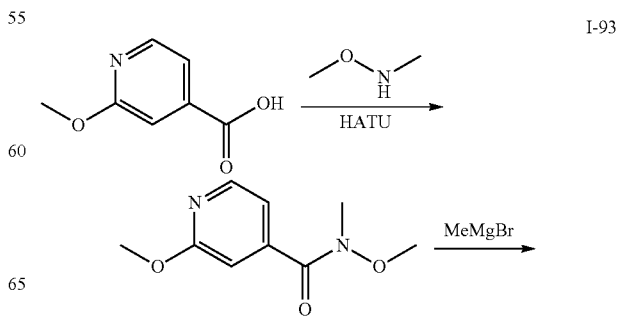

301
-continued

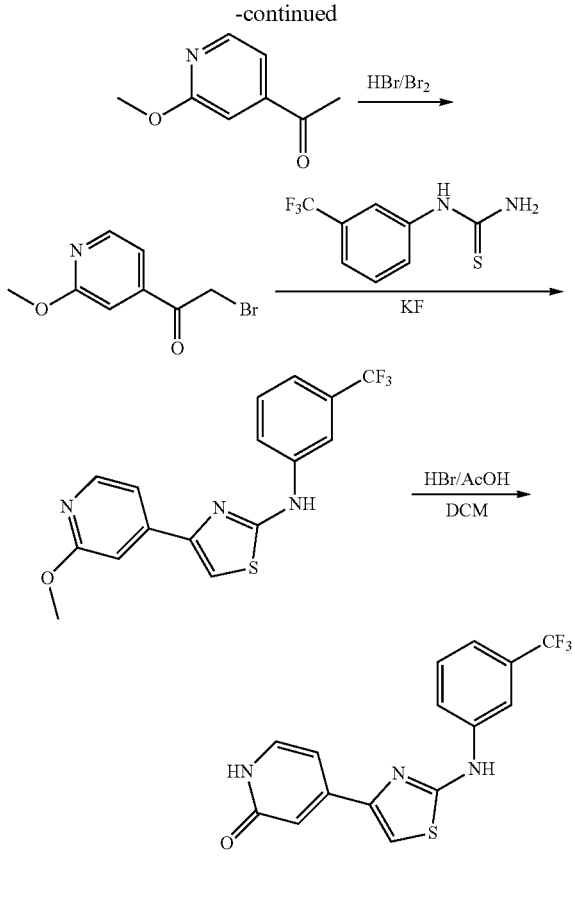

Step 1: N,2-Dimethoxy-N-methyl-pyridine-4-carboxamide

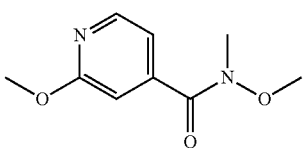

To a solution of 2-methoxypyridine-4-carboxylic acid (2 g, 13.06 mmol, 1 eq) in DMF (40 mL) was added HATU (7.45 g, 19.59 mmol, 1.5 eq), N-methoxymethanamine (3.18 g, 32.65 mmol, 2.5 eq, HCl) and DIEA (5.06 g, 39.18 mmol, 6.82 mL, 3 eq). The mixture was stirred at 60° C. for 12 h. The reaction mixture was quenched by addition of water (50 mL), extracted with EtOAc (30 mL×3). The combined organic layers were washed with brine (10 mL), dried over $Na_2SO_4$, filtered and concentrated under reduced pressure to yield a residue which was purified by flash silica gel chromatography (from PE/EtOAc=1/0 to 1/1, TLC: PE/EtOAc=1/1, $R_f$=0.45) to yield N,2-dimethoxy-N-methyl-pyridine-4-carboxamide (2 g, 8.66 mmol, 66.3% yield, 85.0% purity) as yellow oil. $^1$H NMR (400 MHz, DMSO-$d_6$) δ ppm 8.10-8.01 (m, 1H), 6.89 (dd, J=1.3, 5.3 Hz, 1H), 6.73 (d, J=1.2 Hz, 1H), 3.69 (s, 3H), 3.06 (s, 3H), 2.34-2.29 (m, 3H); ES-LCMS m/z 197.3 [M+H]$^+$.

302
Step 2: 1-(2-Methoxy-4-pyridyl)ethanone

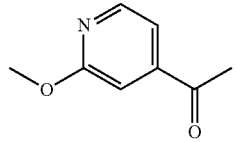

To a solution of N,2-dimethoxy-N-methyl-pyridine-4-carboxamide (2 g, 8.66 mmol, 1 eq) in THF (20 mL) was added MeMgBr (3 M, 23.11 mL, 8 eq). The mixture was stirred at 0° C. for 2 h. The reaction mixture was quenched by addition of water (50 mL), extracted with EtOAc (30 mL×3). The combined organic layers were washed with brine (10 mL), dried over $Na_2SO_4$, filtered and concentrated under reduced pressure to yield 1-(2-methoxy-4-pyridyl)ethanone (1 g, 5.62 mmol, 64.9% yield, 85.0% purity) as yellow oil, which was used in the next step without further purification. $^1$H NMR (400 MHz, DMSO-$d_6$) δ ppm 8.16 (d, J=5.1 Hz, 1H), 7.19 (dd, J=1.2, 5.1 Hz, 1H), 7.06 (s, 1H), 3.72 (s, 3H), 2.41 (s, 3H); ES-LCMS m/z 152.3 [M+H]$^+$.

Step 3: 2-Bromo-1-(2-methoxy-4-pyridyl)ethanone

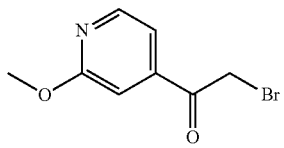

To a solution of 1-(2-methoxy-4-pyridyl)ethanone (800.00 mg, 4.50 mmol, 1 eq) in HBr (32 mL) was added $Br_2$ (718.89 mg, 4.50 mmol, 231.90 μL, 1 eq). The mixture was stirred at 25° C. for 12 h. The reaction mixture was adjusted pH to 9-10 by 15% $Na_2CO_3$ solution. The mixture extracted with EtOAc (50 mL×3). The organic layer was dried over $Na_2SO_4$, filtered and concentrated under reduced pressure to yield 2-bromo-1-(2-methoxy-4-pyridyl)ethanone (1.22 g, crude) as a yellow solid, which was used in the next step without further purification. $^1$H NMR (400 MHz, DMSO-$d_6$) δ ppm 8.40-8.37 (m, 1H), 7.41-7.36 (m, 1H), 7.32 (s, 1H), 4.98 (s, 2H), 3.91 (s, 3H); ES-LCMS m/z 230.1 [M+H]$^+$.

Step 4: 4-(2-Methoxy-4-pyridyl)-N-[3-(trifluoromethyl)phenyl]thiazol-2-amine

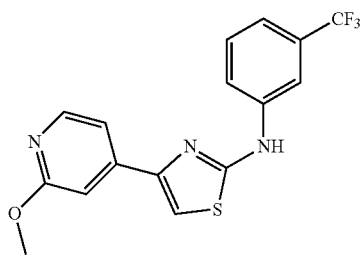 [SMILES: COc1cc(-c2csc(Nc3cccc(C(F)(F)F)c3)n2)ccn1]

To a solution of 2-bromo-1-(2-methoxy-4-pyridyl)ethanone (1.22 g, 5.30 mmol, 1 eq) in MeCN (6 mL) and $H_2O$ (6 mL) was added [3-(trifluoromethyl)phenyl]thiourea (1.43 g, 5.83 mmol, 1.1 eq). The mixture was stirred at 15° C. for 12 h. The reaction mixture was quenched by addition of water (50 mL), extracted with EtOAc (30 mL×3). The combined organic layers were washed with brine (10 mL), dried over $Na_2SO_4$, filtered and concentrated under reduced pressure to yield a residue which was purified by flash silica gel chromatography (from PE/EtOAc=1/0 to 1/1, TLC: PE/EtOAc=1/1, $R_f$=0.75) to yield 4-(2-methoxy-4-pyridyl)-N-[3-(trifluoromethyl)phenyl]thiazol-2-amine (790 mg, 2.14 mmol, 40.3% yield, 95.0% purity) as a yellow solid. $^1$H NMR (400 MHz, DMSO-$d_6$) δ ppm 10.75 (s, 1H), 8.38 (s, 1H), 8.21 (d, J=5.4 Hz, 1H), 7.85-7.78 (m, 2H), 7.59 (t, J=7.9 Hz, 1H), 7.47 (dd, J=1.2, 5.4 Hz, 1H), 7.33-7.27 (m, 2H), 3.89 (s, 3H); ES-LCMS m/z 352.2 [M+H]$^+$.

Step 5: 4-[2-[3-(Trifluoromethyl)anilino]thiazol-4-yl]-1H-pyridin-2-one

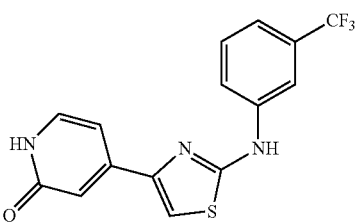 [SMILES: O=c1cc(-c2csc(Nc3cccc(C(F)(F)F)c3)n2)cc[nH]1]

To a solution of 4-(2-methoxy-4-pyridyl)-N-[3-(trifluoromethyl)phenyl]thiazol-2-amine (100 mg, 270.39 μmol, 1 eq) in AcOH (5 mL) was added HBr (21.45 g, 87.47 mmol, 14.39 mL, 33%, 323.50 eq). The mixture was stirred at 70° C. for 12 h. The reaction mixture was quenched by addition of water (50 mL), extracted with EtOAc (30 mL×3). The combined organic layers were washed with brine (10 mL), dried over $Na_2SO_4$, filtered and concentrated under reduced pressure to yield a residue which was purified by preparative HPLC (column: Agela DuraShell C18 150*25 mm*5 μm; mobile phase: [water (0.05% $NH_3H_2O$+10 mM $NH_4HCO_3$)-ACN]; B %: 32%-62%, 10 min), followed by lyophilization to yield 4-[2-[3-(trifluoromethyl)anilino]thiazol-4-yl]-1H-pyridin-2-one (59.45 mg, 176.24 μmol, 65.2% yield, 100.0% purity) as a white solid. $^1$H NMR (400 MHz, DMSO-$d_6$) δ ppm 11.48 (s, 1H), 10.75 (s, 1H), 8.32 (s, 1H), 7.83 (d, J=8.3 Hz, 1H), 7.74 (s, 1H), 7.59 (t, J=8.1 Hz, 1H), 7.41 (d, J=6.8 Hz, 1H), 7.32 (d, J=7.8 Hz, 1H), 6.84 (s, 1H), 6.67 (d, J=6.8 Hz, 1H); ES-LCMS m/z 338.2 [M+H]$^+$.

I-96

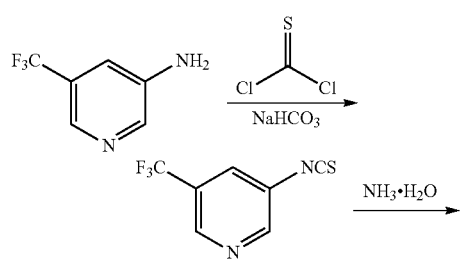

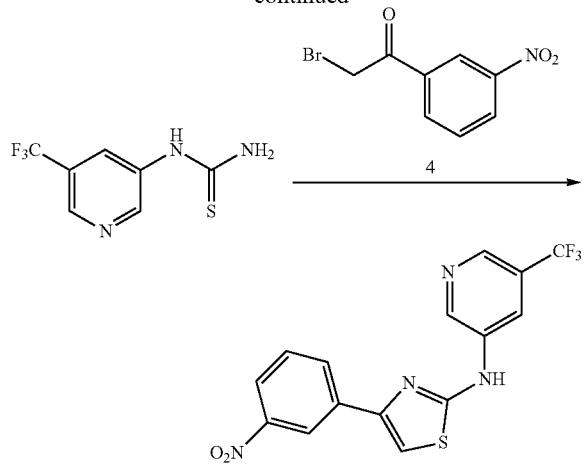

Step 1: 3-Isothiocyanato-5-(trifluoromethyl)pyridine

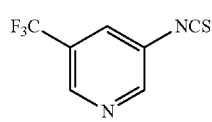

To a solution of 5-(trifluoromethyl)pyridin-3-amine (1 g, 6.17 mmol, 1 eq) in DCM (15 mL) and $H_2O$ (15 mL) was added $NaHCO_3$ (1.04 g, 12.34 mmol, 2 eq) and thiocarbonyl dichloride (1.06 g, 9.25 mmol, 709.27 μL, 1.5 eq). The mixture was stirred at 20° C. for 3 h. TLC (PE/EtOAc=1/1, $R_f$=0.69) indicated the starting material was consumed and one major new spot with lower polarity was detected. The organic phase was concentrated to yield 3-isothiocyanato-5-(trifluoromethyl)pyridine (1.83 g, crude) as black brown oil. $^1$H NMR (400 MHz, DMSO-$d_6$) δ ppm 8.75 (s, 1H) 8.50 (s, 1H) 8.42 (s, 1H).

Step 2: [5-(Trifluoromethyl)-3-pyridyl]thiourea

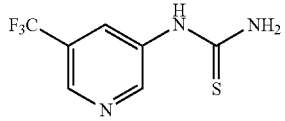 [SMILES: NC(=S)Nc1cncc(C(F)(F)F)c1]

To a solution of 3-isothiocyanato-5-(trifluoromethyl)pyridine (1.83 g, 6.27 mmol, 1 eq) in MeCN (15 mL) was added $NH_3.H_2O$ (1.18 g, 9.41 mmol, 1.29 mL, 28.0%, 1.5 eq). The mixture was stirred at 20° C. for 2 h. TLC (PE/EtOAc=1/1, $R_f$=0.24) indicated the starting material was consumed and one major new spot with lower polarity was detected. The solvent was removed and the residue was treated with water (30 mL) and extracted with EtOAc (50 mL×2). The combined organic phases were washed with brine (50 mL), dried over anhydrous $Na_2SO_4$, filtered and concentrated to yield [5-(trifluoromethyl)-3-pyridyl]thiourea (1.22 g, crude) as a black brown solid. $^1$H NMR (400 MHz, DMSO-$d_6$) δ ppm 10.15 (s, 1H) 8.82 (d, J=1.96 Hz, 1H) 8.73-8.60 (m, 2H) 8.58 (s, 1H) 8.51 (s, 1H).

305

Step 3: 4-(3-Nitrophenyl)-N-[5-(trifluoromethyl)-3-pyridyl]thiazol-2-amine

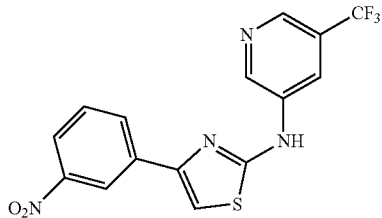 [SMILES: O=[N+]([O-])c1cccc(-c2csc(Nc3cncc(C(F)(F)F)c3)n2)c1]

To a solution of [5-(trifluoromethyl)-3-pyridyl]thiourea (100 mg, 316.45 μmol, 1 eq) in MeCN (5 mL) and H₂O (5 mL) was added 2-bromo-1-(3-nitrophenyl)ethanone (77.23 mg, 316.45 μmol, 1 eq). The mixture was stirred at 20° C. for 2 h. The reaction mixture was concentrated to yield a residue which was added MeCN/H₂O (1/5, 50 mL) and stirred at 20° C. for 0.5 h. The slurry was filtered and the cake was rinsed with H₂O (30 mL×2). The solid was dissolved in MeCN (20 mL) and H₂O (20 mL), followed by lyophilization to yield 4-(3-nitrophenyl)-N-[5-(trifluoromethyl)-3-pyridyl]thiazol-2-amine (63.75 mg, 172.12 μmol, 27.2% yield, 98.9% purity) as a yellow solid. ¹H NMR (500 MHz, CDCl₃) δ ppm 8.87 (d, J=2.59 Hz, 1H) 8.71 (t, J=1.91 Hz, 1H) 8.66 (s, 1H) 8.60 (s, 1H) 8.25-8.18 (m, 2H) 7.63 (t, J=8.01 Hz, 1H) 7.36-7.29 (m, 1H) 7.15 (s, 1H); ES-LCMS m/z 367.0 [M+H]⁺.

306

Step 1: 3-[2-[[5-(Trifluoromethyl)-3-pyridyl]amino]thiazol-4-yl]benzonitrile

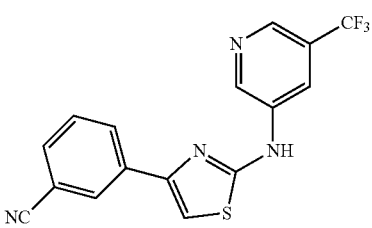 [SMILES: N#Cc1cccc(-c2csc(Nc3cncc(C(F)(F)F)c3)n2)c1]

To a solution of [5-(trifluoromethyl)-3-pyridyl]thiourea (300 mg, 949.36 μmol, 1 eq) in MeCN (5 mL) and H₂O (5 mL) was added 3-(2-bromoacetyl)benzonitrile (212.71 mg, 949.36 μmol, 1 eq). The mixture was stirred at 20° C. for 2 h. The reaction mixture was concentrated to yield a residue which was purified by preparative HPLC (column: Agela DuraShell C18 150*25 mm*5 μm; mobile phase: [water (0.05% NH₃H₂O+10 mM NH₄HCO₃)-ACN]; B %: 50%-80%, 10 min), followed by lyophilization to yield 3-[2-[[5-(trifluoromethyl)-3-pyridyl]amino]thiazol-4-yl]benzonitrile (110 mg, 317.62 μmol, 33.5% yield, 100.0% purity) as a yellow solid. ¹H NMR (400 MHz, CDCl₃) δ ppm 8.87 (d, J=2.45 Hz, 1H) 8.55 (d, J=11.25 Hz, 2H) 8.15-8.04 (m, 2H) 7.63-7.57 (m, 1H) 7.56-7.48 (m, 1H) 7.04 (s, 1H); ES-LCMS m/z 347.1 [M+H]⁺.

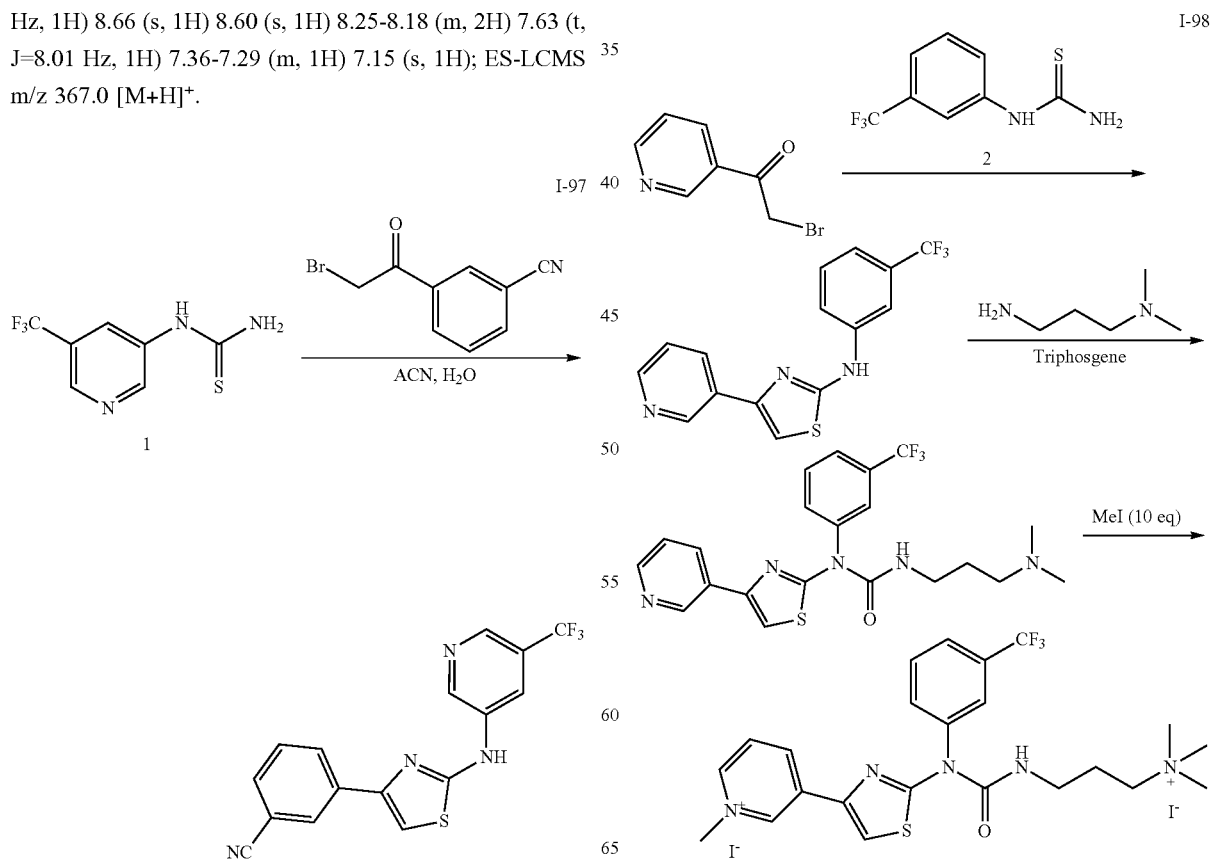

Step 1: 4-(3-Pyridyl)-N-[3-(trifluoromethyl)phenyl]thiazol-2-amine

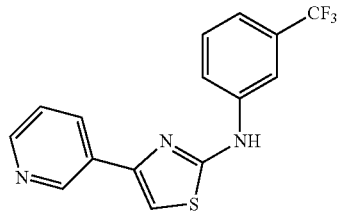 [SMILES: FC(F)(F)c1cccc(Nc2nc(-c3cccnc3)cs2)c1]

To a solution of 2-bromo-1-(3-pyridyl)ethanone (1 g, 4.50 mmol, 1 eq) in ACN (20 mL) and H$_2$O (20 mL) was added [3-(trifluoromethyl)phenyl]thiourea (1.10 g, 4.50 mmol, 1 eq). The mixture was stirred at 15° C. for 12 h. TLC (PE/EtOAc=1/1, R$_f$=0.50) showed starting material was consumed and one major new spot was detected. The mixture was filtered and the filtered cake was concentrated to yield 4-(3-pyridyl)-N-[3-(trifluoromethyl)phenyl]thiazol-2-amine (1.2 g, 3.36 mmol, 74.7% yield, 90.0% purity) as a yellow solid. $^1$H NMR (500 MHz, DMSO-d$_6$) δ ppm 10.74 (s, 1H), 9.15 (d, J=2.0 Hz, 1H), 8.53 (dd, J=1.4, 4.7 Hz, 1H), 8.34 (s, 1H), 8.25 (td, J=1.8, 8.0 Hz, 1H), 7.88 (d, J=8.2 Hz, 1H), 7.63 (s, 1H), 7.59 (t, J=8.0 Hz, 1H), 7.48 (dd, J=4.7, 7.9 Hz, 1H), 7.31 (d, J=7.6 Hz, 1H).

Step 2: 3-[3-(Dimethylamino)propyl]-1-[4-(3-pyridyl)thiazol-2-yl]-1-[3-(trifluoromethyl)phenyl]urea

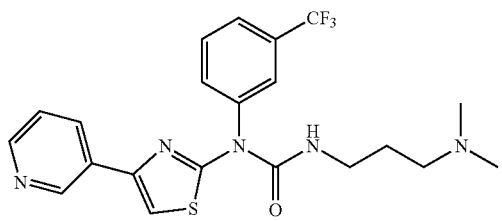 [SMILES: CN(C)CCCNC(=O)N(c1cccc(C(F)(F)F)c1)c1nc(-c2cccnc2)cs1]

To a solution of 4-(3-pyridyl)-N-[3-(trifluoromethyl)phenyl]thiazol-2-amine (1.1 g, 3.08 mmol, 1 eq) in THF (20 mL) was added triphosgene (1.4 g, 4.72 mmol, 1.53 eq), DIEA (1.19 g, 9.24 mmol, 1.61 mL, 3 eq) and stirred at 80° C. for 1 h. The reaction mixture was concentrated to yield (4-(pyridin-3-yl)thiazol-2-yl)(3-(trifluoromethyl)phenyl)carbamic chloride (crude). Then to a solution of N',N'-dimethylpropane-1,3-diamine (1.89 g, 18.49 mmol, 2.31 mL, 6 eq) in DCM (10 mL) was added DIEA (1.19 g, 9.24 mmol, 1.61 mL, 3 eq), (4-(pyridin-3-yl)thiazol-2-yl)(3-(trifluoromethyl)phenyl)carbamic chloride (crude) in DCM (10 mL). The mixture was stirred at 40° C. for 5 h. TLC (EtOAc/MeOH=5/1, R$_f$=0.50) showed starting material was consumed and one major new spot was detected. The mixture was diluted with H$_2$O (80 mL) and extracted with DCM (100 mL×3). The combine organic layers were dried over anhydrous Na$_2$SO$_4$, filtered and concentrated to yield a residue which was purified by flash silica gel chromatography (from pure EtOAc to EtOAc/MeOH=9/1, TLC: EtOAc/MeOH=5/1, R$_f$=0.50) to yield 3-[3-(dimethylamino)propyl]-1-[4-(3-pyridyl)thiazol-2-yl]-1-[3-(trifluoromethyl)phenyl]urea (1.2 g, 2.40 mmol, 77.9% yield, 90.0% purity) as a yellow solid. $^1$H NMR (500 MHz, DMSO-d$_6$) δ ppm 8.81 (d, J=1.7 Hz, 1H), 8.46-8.40 (m, 1H), 7.95-7.88 (m, 3H), 7.84 (t, J=7.8 Hz, 1H), 7.81-7.77 (m, 1H), 7.75 (s, 1H), 7.39 (t, J=4.7 Hz, 1H), 7.35 (dd, J=4.8, 7.9 Hz, 1H), 3.22 (q, J=6.1 Hz, 2H), 2.23 (t, J=6.2 Hz, 2H), 1.96-1.89 (s, 6H), 1.56 (q, J=6.3 Hz, 2H).

Step 3: 1-[4-(1-BLAH-1-Methyl-3-pyridyl)thiazol-2-yl]-1-[3-(trifluoromethyl)phenyl]-3-[3-[BLAH(trimethyl)-azanyl]propyl]urea

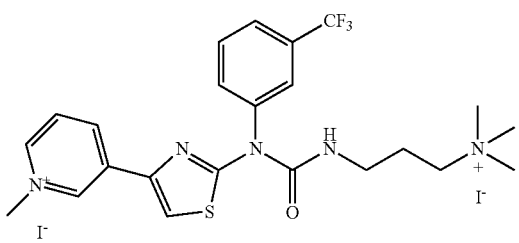

To a solution of 3-[3-(dimethylamino)propyl]-1-[4-(3-pyridyl)thiazol-2-yl]-1-[3-(trifluoromethyl)phenyl]urea (300 mg, 600.68 μmol, 1 eq) in ACN (5 mL) was added MeI (852.59 mg, 6.01 mmol, 373.94 μL, 10 eq) in one portion at 15° C. under N$_2$ atmosphere. The mixture was stirred at 15° C. for 3 h. The solution was added ACN (5 mL), diluted with water (10 mL) and lyophilized to yield 1-[4-(1-BLAH-1-methyl-3-pyridyl)thiazol-2-yl]-1-[3-(trifluoromethyl)phenyl]-3-[3-[BLAH(trimethyl)-azanyl]propyl]urea (272.91 mg, 372.13 μmol, 61.9% yield, 100.0% purity) as a yellow solid. $^1$H NMR (500 MHz, DMSO-d$_6$) δ ppm 9.19 (s, 1H), 8.83 (d, J=6.0 Hz, 1H), 8.47 (d, J=8.4 Hz, 1H), 8.10-8.05 (m, 2H), 7.99 (s, 1H), 7.95 (d, J=7.0 Hz, 1H), 7.88-7.82 (m, 2H), 6.93 (t, J=5.7 Hz, 1H), 4.31 (s, 3H), 3.29-3.24 (m, 2H), 3.19 (q, J=6.4 Hz, 2H), 3.05 (s, 9H), 1.91-1.82 (m, 2H); ES-LCMS m/z 239.6 [(M−2I)/2]$^+$.

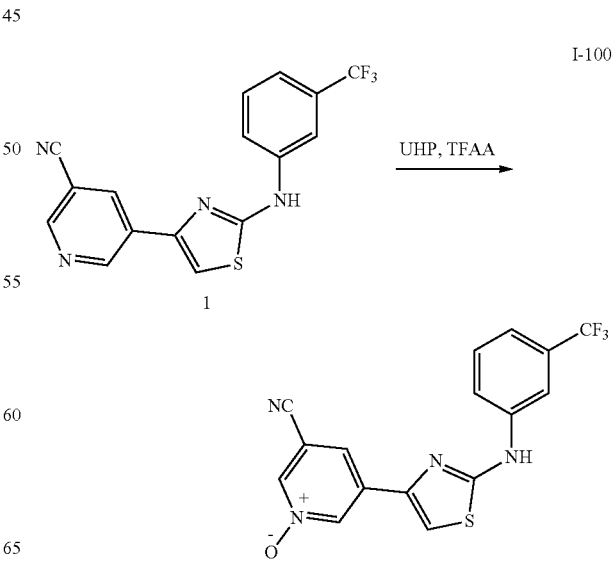

Step 1: 1-Oxido-5-[2-[3-(trifluoromethyl)anilino]thiazol-4-yl]pyridin-1-ium-3-carbonitrile

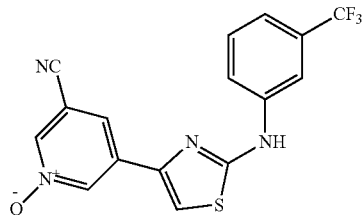 [SMILES: N#Cc1cc(-c2csc(Nc3cccc(C(F)(F)F)c3)n2)c[n+](O)c1]

To a stirred solution of 5-[2-[3-(trifluoromethyl)anilino]thiazol-4-yl]pyridine-3-carbonitrile (90 mg, 257.27 μmol, 1 eq) in ACN (3 mL) was added hydrogen peroxide; urea (48.40 mg, 514.54 μmol, 2 eq) and TFAA (108.07 mg, 514.54 μmol, 71.57 μL, 2 eq). The reaction mixture was stirred at 40° C. for 12 h. The reaction mixture was concentrated to yield a residue which was purified by preparative HPLC (column: Agela DuraShell C18 150*25 mm*5 um; mobile phase: [water (0.04% NH$_3$H$_2$O+10 mM NH$_4$HCO$_3$)-ACN]; B %: 34%-64%, 10 min). The desired fraction was lyophilized to yield 1-oxido-5-[2-[3-(trifluoromethyl)anilino]thiazol-4-yl]pyridin-1-ium-3-carbonitrile (19.48 mg, 52.80 μmol, 20.5% yield, 98.2% purity) as a white solid. $^1$H NMR (400 MHz, DMSO-d$_6$) δ ppm 8.90 (t, J=1.5 Hz, 1H), 8.83 (t, J=1.3 Hz, 1H), 8.29 (t, J=1.2 Hz, 1H), 8.23 (s, 1H), 7.95-7.86 (m, 2H), 7.61 (t, J=7.9 Hz, 1H), 7.34 (d, J=7.8 Hz, 1H); ES-LCMS m/z 363.1 [M+H]$^+$.

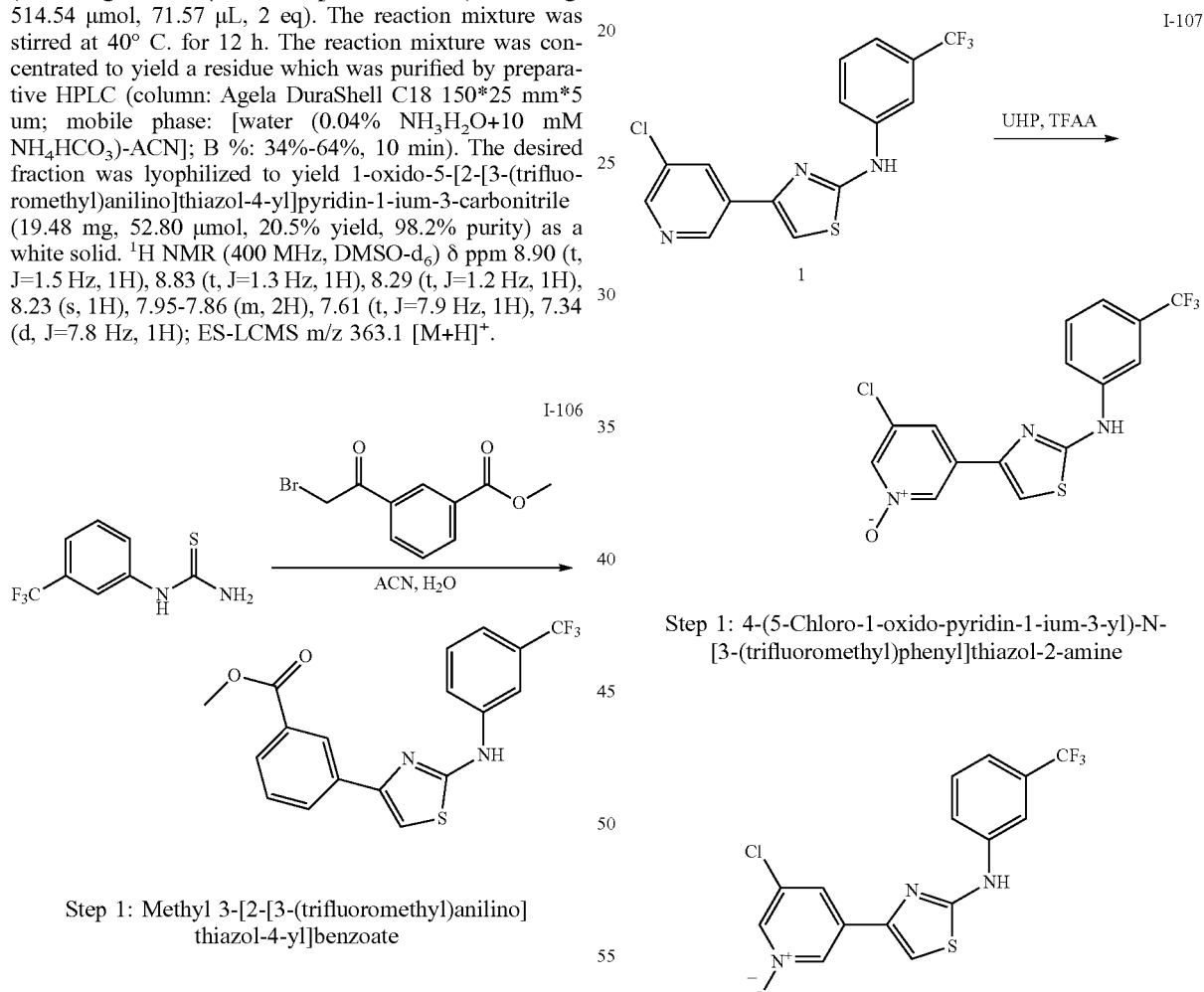

Step 1: Methyl 3-[2-[3-(trifluoromethyl)anilino]thiazol-4-yl]benzoate

To a solution of [3-(trifluoromethyl)phenyl]thiourea (70 mg, 317.87 μmol, 1 eq) in MeCN (5 mL) and H$_2$O (5 mL) was added methyl 3-(2-bromoacetyl)benzoate (81.72 mg, 317.87 μmol, 1 eq). The mixture was stirred at 20° C. for 2 h. The reaction mixture was filtered to yield a residue which was purified by preparative HPLC (column: Agela DuraShell C18 150*25 mm*5 um; mobile phase: [water (0.04% NH$_3$H$_2$O+10 mM NH$_4$HCO$_3$)-ACN]; B %: 60%-90%, 10 min), followed by lyophilization to yield methyl 3-[2-[3-(trifluoromethyl)anilino]thiazol-4-yl]benzoate (23.45 mg, 59.37 μmol, 18.7% yield, 95.8% purity) as a yellow solid. $^1$H NMR (400 MHz, CDCl$_3$) δ ppm 8.54 (t, J=1.37 Hz, 1H) 8.10-8.06 (m, 1H) 8.01 (t, J=7.83, 1.37 Hz, 1H) 7.96 (s, 1H) 7.59 (d, J=8.22 Hz, 1H) 7.54-7.46 (m, 3H) 7.32 (d, J=7.83 Hz, 1H) 7.00 (s, 1H) 3.97 (s, 3H); ES-LCMS m/z 379.0 [M+H]$^+$.

Step 1: 4-(5-Chloro-1-oxido-pyridin-1-ium-3-yl)-N-[3-(trifluoromethyl)phenyl]thiazol-2-amine

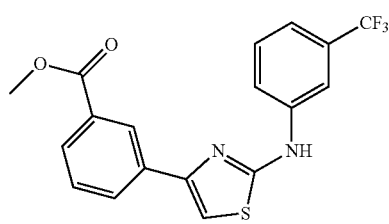 [SMILES: COC(=O)c1cccc(-c2csc(Nc3cccc(C(F)(F)F)c3)n2)c1]

To a solution of 4-(5-chloro-3-pyridyl)-N-[3-(trifluoromethyl)phenyl]thiazol-2-amine (230 mg, 581.84 μmol, 1 eq) in DMF (6 mL) was added urea hydrogen peroxide (218.94 mg, 2.33 mmol, 4 eq) and TFAA (488.82 mg, 2.33 mmol, 323.72 μL, 4 eq) at 0° C. The mixture was stirred at 10° C. for 12 h. The reaction mixture was quenched by Na$_2$S$_2$O$_3$, diluted with water (10 mL) and extracted with EtOAc (10 mL×3). The combined organic layers were dried over Na$_2$SO$_4$, filtered and concentrated under reduced pressure to yield a residue which was purified by preparative HPLC (column: Welch Xtimate C18 150*25 mm*5 um; mobile phase: [water (10 mM NH$_4$HCO$_3$)-ACN]; B %: 35%-65%, 10 min), followed by lyophilization to yield 4-(5-chloro-1-oxido-pyridin-1-ium-3-yl)-N-[3-(trifluoromethyl)phenyl] thiazol-2-amine (24.29 mg, 65.34 μmol, 11.2% yield, 100.0% purity) as a white solid. $^1$H NMR (400 MHz, DMSO-d$_6$) δ ppm 10.85 (br s, 1H), 8.70 (s, 1H), 8.48 (s, 1H), 8.31 (s, 1H), 7.97 (s, 1H), 7.90 (s, 1H), 7.82 (d, J=7.8 Hz, 1H), 7.60 (t, J=8.2 Hz, 1H), 7.33 (d, J=7.4 Hz, 1H); ES-LCMS m/z 372.1 [M+H]$^+$.

which was purified by preparative HPLC (column: Agela DuraShell C18 150*25 mm*5 μm; mobile phase: [water (0.04% NH$_3$H$_2$O+10 mM NH$_4$HCO$_3$)-ACN]; B %: 66%-81%, 14 min) to yield a crude product which was purified by silica gel column chromatography (from PE/EtOAc=5/1 to 2/1, R$_f$=0.50) to yield methyl 3-nitro-5-[2-[3-(trifluoromethyl)anilino]thiazol-4-yl]benzoate (42 mg, 99.21 μmol, 22.3% yield, 100.0% purity) as a yellow solid. $^1$H NMR (400 MHz, CDCl$_3$) δ ppm 8.89 (s, 1H), 8.84 (s, 1H), 8.80 (d, J=1.6 Hz, 1H), 8.01 (s, 1H), 7.62-7.57 (m, 1H), 7.54-7.48 (m, 1H), 7.36 (d, J=7.8 Hz, 1H), 7.30 (s, 1H), 7.16 (s, 1H), 4.03 (s, 3H); ES-LCMS m/z 424.1 [M+H]$^+$.

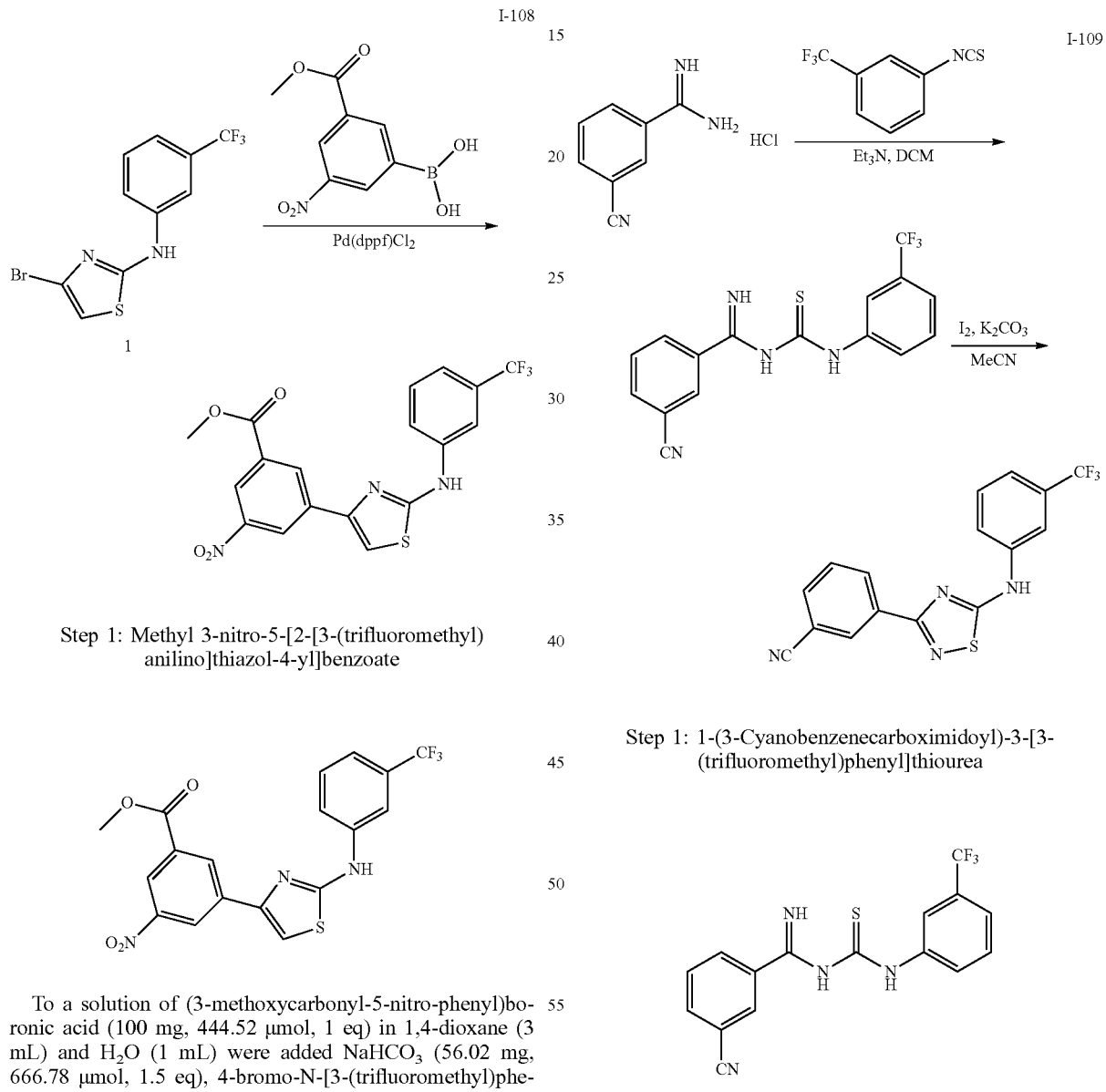

Step 1: Methyl 3-nitro-5-[2-[3-(trifluoromethyl)anilino]thiazol-4-yl]benzoate

To a solution of (3-methoxycarbonyl-5-nitro-phenyl)boronic acid (100 mg, 444.52 μmol, 1 eq) in 1,4-dioxane (3 mL) and H$_2$O (1 mL) were added NaHCO$_3$ (56.02 mg, 666.78 μmol, 1.5 eq), 4-bromo-N-[3-(trifluoromethyl)phenyl]thiazol-2-amine (161.57 mg, 444.52 μmol, 1 eq) and Pd(dppf)Cl$_2$ (32.53 mg, 44.45 μmol, 0.1 eq). The mixture was stirred under N$_2$ atmosphere at 90° C. for 2 h. TLC (PE/EtOAc=5/1, R$_f$=0.50) indicated starting material was consumed completely and one new spot formed. The mixture was concentrated and water (80 mL) was added. The mixture was extracted with EtOAc (50 mL×3). The combined organic layers were washed with brine (50 mL), dried over Na$_2$SO$_4$, filtered and concentrated to yield a residue Step 1: 1-(3-Cyanobenzenecarboximidoyl)-3-[3-(trifluoromethyl)phenyl]thiourea To a solution of 3-cyanobenzamidine (200 mg, 1.10 mmol, 1 eq, HCl) in DCM (10 mL) was added 1-isothiocyanato-3-(trifluoromethyl)benzene (246.12 mg, 1.21 mmol, 183.67 μL, 1.1 eq) and Et$_3$N (334.29 mg, 3.30 mmol, 459.82 μL, 3 eq). The mixture was stirred at 20° C. for 16 h. The reaction mixture was concentrated to yield a residue which was purified by flash silica gel chromatography (from PE/EtOAc=1/0 to 3/1, TLC: PE/EtOAc=3/1, R$_f$=0.6) to yield 1-(3-cyanobenzenecarboximidoyl)-3-[3-(trifluoromethyl)phenyl]thiourea (221 mg, 596.36 μmol, 54.2% yield, 94.0% purity) as a yellow solid. $^1$H NMR (400 MHz, CDCl$_3$) δ ppm 11.51 (s, 1H), 8.81-8.20 (m, 1H), 8.11-7.98 (m, 2H), 7.86 (d, J=7.6 Hz, 1H), 7.73-7.58 (m, 1H), 7.46 (s, 2H), 7.02-5.72 (m, 1H), 1.57 (s, 1H); ES-LCMS m/z 349.3 [M+H]$^+$.

Step 2: 3-[5-[3-(Trifluoromethyl)anilino]-1,2,4-thiadiazol-3-yl]benzonitrile

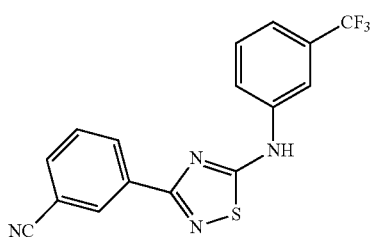 [SMILES: N#Cc1cccc(-c2nsc(Nc3cccc(C(F)(F)F)c3)n2)c1]

To a solution of 1-(3-cyanobenzenecarboximidoyl)-3-[3-(trifluoromethyl)phenyl]thiourea (80 mg, 215.88 μmol, 1 eq) in MeCN (10 mL) was added I$_2$ (65.75 mg, 259.05 μmol, 52.18 μL, 1.2 eq) and K$_2$CO$_3$ (44.75 mg, 323.82 μmol, 1.5 eq). The mixture was stirred at 20° C. for 0.5 h. The reaction mixture was quenched by sat.aq. Na$_2$S$_2$O$_3$ (10 mL) and treated with water (20 mL), extracted with EtOAc (20 mL×3). The combined organic phases were dried over anhydrous Na$_2$SO$_4$, filtered and concentrated to yield a residue which was purified by flash silica gel chromatography (from PE/EtOAc=1/0 to 1/1, TLC: PE/EtOAc=1/1, R$_f$=0.7). The desired fraction was lyophilization to yield 3-[5-[3-(trifluoromethyl)anilino]-1,2,4-thiadiazol-3-yl]benzonitrile (65 mg, 183.37 μmol, 84.9% yield, 97.7% purity) as a white solid. $^1$H NMR (400 MHz, CD$_3$OD) δ ppm 8.54-8.49 (m, 2H), 8.17 (s, 1H), 7.85 (dd, J=7.8, 18.4 Hz, 2H), 7.71-7.65 (m, 1H), 7.61 (t, J=8.0 Hz, 1H), 7.39 (d, J=7.4 Hz, 1H); ES-LCMS m/z 347.2 [M+H]$^+$.

I-112

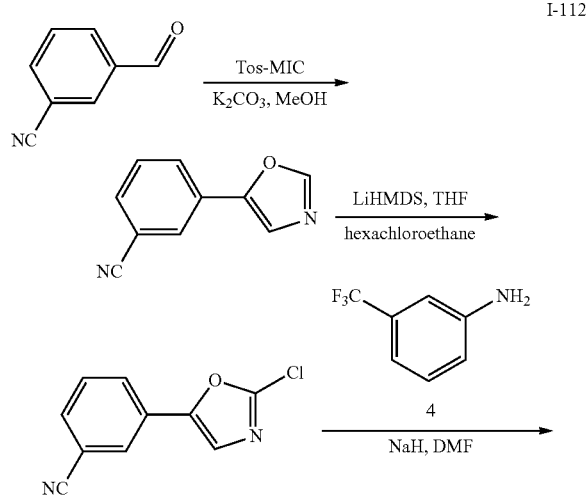

-continued

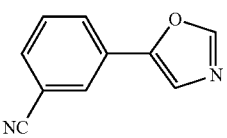

Step 1: 3-Oxazol-5-ylbenzonitrile

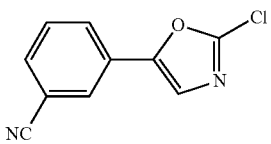

To a solution of 3-formylbenzonitrile (1 g, 7.63 mmol, 1 eq) in MeOH (10 mL) was added K$_2$CO$_3$ (1.27 g, 9.16 mmol, 1.2 eq) and Tos-MIC (1.64 g, 8.39 mmol, 1.1 eq). The mixture was stirred at 90° C. for 12 h. The mixture was concentrated, diluted with H$_2$O (10 mL) and extracted with EtOAc(30 mL×3). The combine organic layers were washed with brine (10 mL), dried over anhydrous Na$_2$SO$_4$, filtered and concentrated to yield a residue which was purified by silica gel column chromatography (from pure PE to PE/EtOAc=5/1, TLC: PE/EtOAc=3/1, R$_f$=0.30) to yield 3-oxazol-5-ylbenzonitrile (970 mg, 5.59 mmol, 73.2% yield, 98.0% purity) as a white solid. $^1$H NMR (400 MHz, CDCl$_3$) δ ppm 7.98 (s, 1H), 7.95 (d, J=1.2 Hz, 1H), 7.89 (td, J=1.3, 7.8 Hz, 1H), 7.66-7.62 (m, 1H), 7.60-7.54 (m, 1H), 7.47 (s, 1H); ES-LCMS m/z 171.0 [M+H]$^+$.

Step 2: 3-(2-Chlorooxazol-5-yl)benzonitrile

To a solution of 3-oxazol-5-ylbenzonitrile (600 mg, 3.49 mmol, 1 eq) in THF (10 mL) was added LiHMDS (1 M, 4.54 mL, 1.3 eq) dropwise under N$_2$ atmosphere at −70° C. The mixture was stirred under N$_2$ atmosphere at −70° C. for 0.5 h. A solution of 1,1,1,2,2,2-hexachloroethane (909.02 mg, 3.84 mmol, 1.1 eq) in THF (5 mL) was added dropwise under N$_2$ atmosphere at −70° C. The mixture was stirred under N$_2$ atmosphere at −70° C. for 0.5 h and at 20° C. for 12 h. TLC (PE/EtOAc=1/1, R$_f$=0.6) showed starting material was consumed and one major new spot was detected. The mixture was diluted with H$_2$O (20 mL) and extracted with EtOAc (20 mL×3). The combine organic layers were washed with brine (20 mL), dried over anhydrous Na$_2$SO$_4$, filtered and concentrated to yield a residue which was purified by silica gel column chromatography (from PE/EtOAc=6/1 to 3/1, TLC: PE/EtOAc=1/1, R$_f$=0.6) to yield 3-(2-chlorooxazol-5-yl)benzonitrile (380 mg, 1.76 mmol, 50.54% yield, 95.0% purity) as a white solid. $^1$H

315

NMR (400 MHz, CDCl$_3$) δ ppm 7.89 (d, J=1.2 Hz, 1H), 7.83 (td, J=1.4, 7.9 Hz, 1H), 7.67-7.63 (m, 1H), 7.60-7.55 (m, 1H), 7.40 (s, 1H); ES-LCMS m/z 205.0 [M+H]$^+$.

Step 3: 3-[2-[3-(Trifluoromethyl)anilino]oxazol-5-yl]benzonitrile

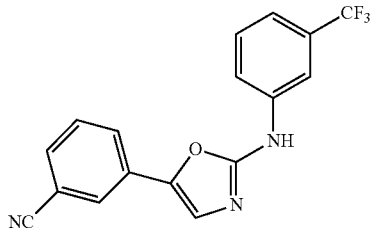 [SMILES: N#Cc1cccc(-c2cnc(Nc3cccc(C(F)(F)F)c3)o2)c1]

To a solution of 3-(trifluoromethyl)aniline (94.50 mg, 586.48 μmol, 73.25 μL, 0.8 eq) in DMF (2 mL) was added NaH (29.32 mg, 733.09 μmol, 60% purity, 1 eq) partwise at 20° C. The mixture was stirred at 20° C. for 0.5 h. 3-(2-Chlorooxazol-5-yl) benzonitrile (150 mg, 733.09 μmol, 1 eq) was added. The mixture was stirred at 60° C. for 12 h. The mixture was diluted with H$_2$O (20 mL) and extracted with EtOAc (20 mL×3). The combine organic layers were washed with brine (20 mL), dried over anhydrous Na$_2$SO$_4$, filtered and concentrated to yield a residue which was purified by preparative HPLC (column: Phenomenex Synergi C18 150*30 mm*4 μm; mobile phase: [water (0.05% HCl)-ACN]; B %: 56%-76%, 9 min), followed by lyophilization to yield 3-[2-[3-(trifluoromethyl) anilino]oxazol-5-yl]benzonitrile as a white solid. $^1$H NMR (400 MHz, DMSO-d$_6$) δ ppm 10.87 (br s, 1H), 8.14 (s, 1H), 8.05 (s, 1H), 7.86 (d, J=7.8 Hz, 1H), 7.81 (d, J=8.3 Hz, 1H), 7.74-7.70 (m, 2H), 7.68-7.63 (m, 1H), 7.55 (t, J=7.9 Hz, 1H), 7.29 (d, J=7.6 Hz, 1H); ES-LCMS m/z 330.2 [M+H]$^+$.

I-117

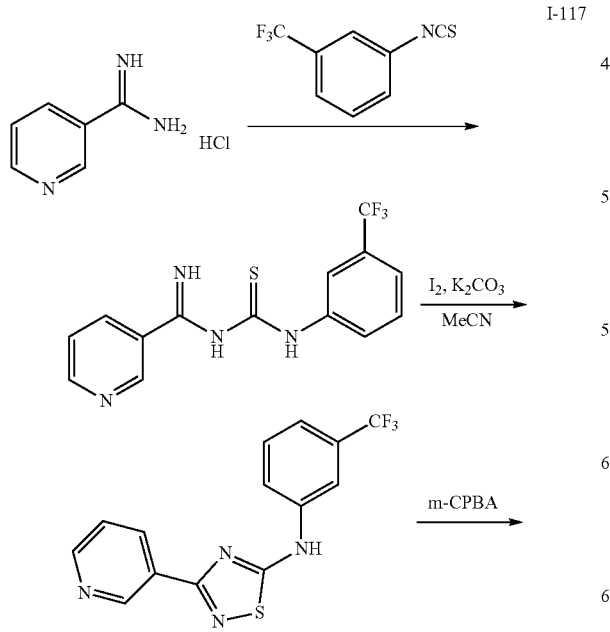

316

-continued

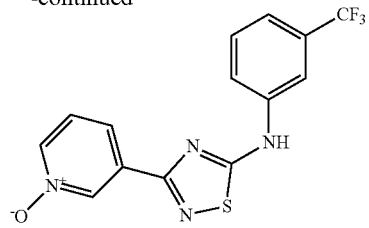

Step 1: 1-(Pyridine-3-carboximidoyl)-3-[3-(trifluoromethyl)phenyl]thiourea

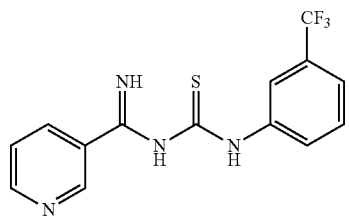 [SMILES: N=C(NC(=S)Nc1cccc(C(F)(F)F)c1)c1cccnc1]

To a solution of pyridine-3-carboxamidine (400 mg, 2.54 mmol, 1 eq, HCl) in ACN (12 mL) was added 1-isothiocyanato-3-(trifluoromethyl)benzene (489.91 mg, 2.41 mmol, 365.60 μL, 0.95 eq) and Et$_3$N (770.47 mg, 7.61 mmol, 1.06 mL, 3 eq). The mixture was stirred at 20° C. for 16 h. The reaction mixture was concentrated to yield a residue which was purified by flash silica gel chromatography (from PE/EtOAc=1/0 to 1/2, TLC: PE/EtOAc=1/2, R$_f$=0.5) to yield 1-(pyridine-3-carboximidoyl)-3-[3-(trifluoromethyl)phenyl]thiourea (558 mg, 1.38 mmol, 54.2% yield, 80.0% purity) as a yellow solid. $^1$H NMR (500 MHz, DMSO-d$_6$) δ ppm 11.33-10.08 (m, 2H), 9.80-9.02 (m, 2H), 8.74 (s, 1H), 8.01 (s, 2H), 7.71-7.41 (m, 4H); ES-LCMS m/z 325.2 [M+H]$^+$.

Step 2: 3-(3-Pyridyl)-N-[3-(trifluoromethyl)phenyl]-1,2,4-thiadiazol-5-amine

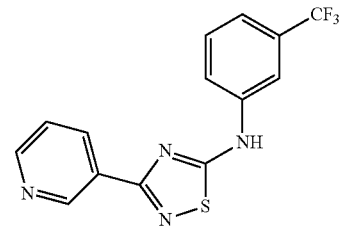 [SMILES: FC(F)(F)c1cccc(Nc2nc(-c3cccnc3)ns2)c1]

To a solution of 1-(pyridine-3-carboximidoyl)-3-[3-(trifluoromethyl)phenyl]thiourea (200 mg, 493.33 μmol, 1 eq) in MeCN (25 mL) was added I$_2$ (150.25 mg, 592.00 μmol, 119.25 μL, 1.2 eq) and K$_2$CO$_3$ (102.27 mg, 740.00 μmol, 1.5 eq). The mixture was stirred at 20° C. for 0.5 h. The reaction mixture was quenched by sat.aq. Na$_2$S$_2$O$_3$ (10 mL) and treated with water (20 mL), extracted with EtOAc (30 mL×3). The combined organic phases were dried over anhydrous Na$_2$SO$_4$, filtered and concentrated to yield 3-(3-pyridyl)-N-[3-(trifluoromethyl)phenyl]-1,2,4-thiadiazol-5-amine (150 mg, 418.85 μmol, 84.9% yield, 90.0% purity) as a yellow solid. ¹H NMR (400 MHz, DMSO-d₆) δ ppm 11.41 (s, 1H), 9.33 (d, J=1.5 Hz, 1H), 8.71 (dd, J=1.6, 4.8 Hz, 1H), 8.46 (td, J=1.9, 8.0 Hz, 1H), 8.21 (s, 1H), 7.91 (d, J=8.3 Hz, 1H), 7.67 (t, J=7.9 Hz, 1H), 7.61-7.55 (m, 1H), 7.45 (d, J=7.6 Hz, 1H).

Step 3: 3-(1-Oxidopyridin-1-ium-3-yl)-N-[3-(trifluoromethyl)phenyl]-1,2,4-thiadiazol-5-amine

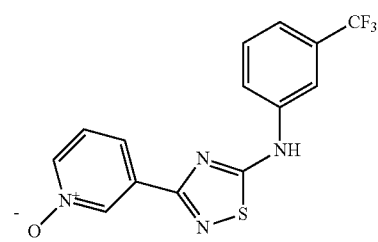 [SMILES: O[n+]1cccc(-c2nsc(Nc3cccc(C(F)(F)F)c3)n2)c1]

To a solution of 3-(3-pyridyl)-N-[3-(trifluoromethyl)phenyl]-1,2,4-thiadiazol-5-amine (150 mg, 418.85 μmol, 1 eq) in ACN (5 mL) was added TFAA (439.86 mg, 2.09 mmol, 291.30 μL, 5 eq) and hydrogen peroxide; urea (157.61 mg, 1.68 mmol, 4 eq). The mixture was stirred at 75° C. for 16 h. The reaction mixture was concentrated to yield a residue which was purified by preparative HPLC (column: Agela DuraShell C18 150*25 mm*5 μm; mobile phase: [water (0.04% NH₃H₂O+10 mM NH₄HCO₃)-ACN]; B %: 38%-58%, 10 min), followed by lyophilization to yield 3-(1-oxidopyridin-1-ium-3-yl)-N-[3-(trifluoromethyl)phenyl]-1,2,4-thiadiazol-5-amine (18.98 mg, 55.54 μmol, 13.2% yield, 99.0% purity) as a white solid. ¹H NMR (400 MHz, CD₃OD) δ ppm 9.05 (s, 1H), 8.45-8.33 (m, 2H), 8.04 (s, 1H), 7.92 (d, J=8.6 Hz, 1H), 7.71-7.58 (m, 2H), 7.41 (d, J=7.8 Hz, 1H); ES-LCMS m/z 339.1 [M+H]⁺.

I-118

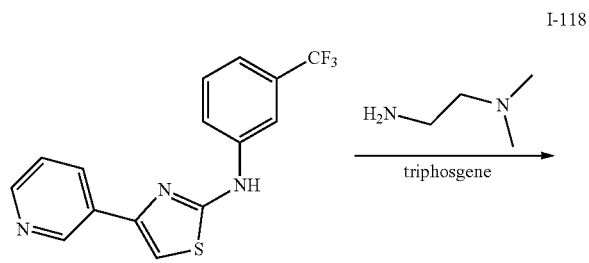

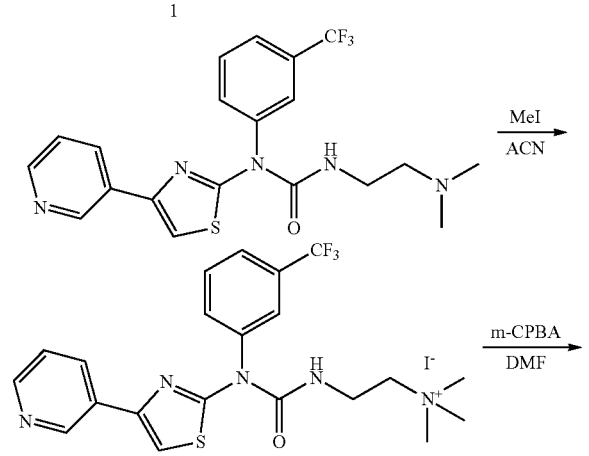

-continued

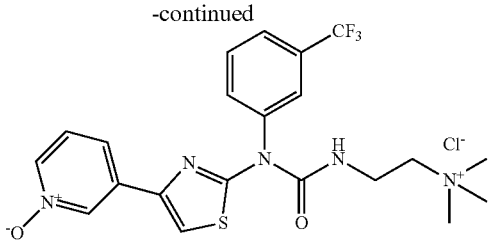

Step 1: 3-[2-(Dimethylamino)ethyl]-1-[4-(3-pyridyl)thiazol-2-yl]-1-[3-(trifluoromethyl)phenyl]urea

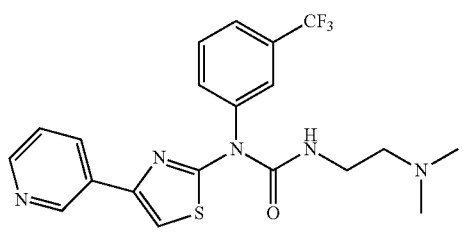 [SMILES: CN(C)CCNC(=O)N(c1cccc(C(F)(F)F)c1)c1nc(-c2cccnc2)cs1]

To a solution of 4-(3-pyridyl)-N-[3-(trifluoromethyl)phenyl]thiazol-2-amine (500 mg, 1.48 mmol, 1 eq) in THF (20 mL) was added bis(trichloromethyl) carbonate (874.00 mg, 2.95 mmol, 1.99 eq), DIEA (573.16 mg, 4.43 mmol, 772.45 μL, 3 eq) and stirred at 80° C. for 1 h. The reaction mixture was concentrated to yield 3-(2-(dimethylamino)ethyl)-1-(4-(pyridin-3-yl)thiazol-2-yl)-1-(3-(trifluoromethyl)phenyl) urea(crude). To a solution of 3-(2-(dimethylamino)ethyl)-1-(4-(pyridin-3-yl)thiazol-2-yl)-1-(3-(trifluoromethyl)phenyl) urea(crude) in DCM (10 mL) was added DIEA (191.05 mg, 1.48 mmol, 257.48 μL, 1 eq) and N′,N′-dimethylethane-1,2-diamine (650.75 mg, 7.38 mmol, 806.38 μL, 4.99 eq). The mixture was stirred at 40° C. for 1 h. The mixture was diluted with H₂O (10 mL) and extracted with DCM (10 mL×3). The combine organic layers were dried over anhydrous Na₂SO₄, filtered and concentrated to yield a residue which was purified by flash silica gel chromatography (from EtOAc/MeOH=100/1 to 5/1, R_f=0.60) to yield 3-[2-(dimethylamino)ethyl]-1-[4-(3-pyridyl)thiazol-2-yl]-1-[3-(trifluoromethyl)phenyl]urea (500 mg, 1.13 mmol, 76.1% yield, 98.0% purity) as a yellow solid. ¹H NMR (400 MHz, DMSO-d₆) δ ppm 9.08 (d, J=1.6 Hz, 1H), 8.49 (dd, J=1.6, 4.7 Hz, 1H), 8.42 (br s, 1H), 8.16 (d, J=8.2 Hz, 1H), 7.96-7.88 (m, 2H), 7.81 (d, J=4.3 Hz, 2H), 7.77 (s, 1H), 7.43 (dd, J=4.9, 8.0 Hz, 1H), 3.33-3.28 (m, 2H), 2.41 (t, J=6.1 Hz, 2H), 2.23 (s, 6H); ES-LCMS m/z 436.2 [M+H]⁺.

Step 2: Trimethyl-[2-[[[4-(3-pyridyl)thiazol-2-yl]-[3-(trifluoromethyl)phenyl]carbamoyl]amino]ethyl]ammonium

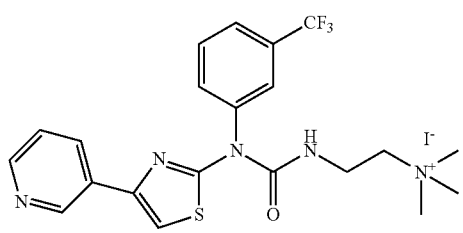 [SMILES: C[N+](C)(C)CCNC(=O)N(c1cccc(C(F)(F)F)c1)c1nc(-c2cccnc2)cs1 ; [I-]]

319

To a solution of 3-[2-(dimethylamino)ethyl]-1-[4-(3-pyridyl)thiazol-2-yl]-1-[3-(trifluoromethyl)phenyl]urea (250 mg, 562.62 μmol, 1 eq) in ACN (4 mL) was added MeI (81.67 mg, 575.36 μmol, 35.82 μL, 1.02 eq). The mixture was stirred at 10° C. for 12 h. The solution was quenched by addition water (10 mL), followed by lyophilization to yield trimethyl-[2-[[[4-(3-pyridyl)thiazol-2-yl]-[3-(trifluoromethyl)phenyl]carbamoyl]amino]ethyl]ammonium (250 mg, 554.94 μmol, 98.6% yield, 100.0% purity) as a yellow solid, which was used in the next step without further purification. $^1$H NMR (400 MHz, DMSO-d$_6$) δ ppm 8.82 (d, J=1.6 Hz, 1H), 8.44 (dd, J=1.6, 5.1 Hz, 1H), 7.95 (d, J=7.0 Hz, 2H), 7.93 (d, J=2.0 Hz, 1H), 7.89-7.85 (m, 1H), 7.84 (d, J=1.6 Hz, 1H), 7.81 (s, 1H), 7.36 (dd, J=4.9, 7.6 Hz, 1H), 7.04 (t, J=5.7 Hz, 1H), 3.55 (d, J=4.7 Hz, 2H), 3.46-3.42 (m, 2H), 3.08 (s, 9H); ES-LCMS m/z 450.2 [M−I]$^+$.

Step 3: Trimethyl-[2-[[[4-(1-oxidopyridin-1-ium-3-yl)thiazol-2-yl]-[3-(trifluoromethyl)phenyl]carbamoyl]amino]ethyl]ammonium

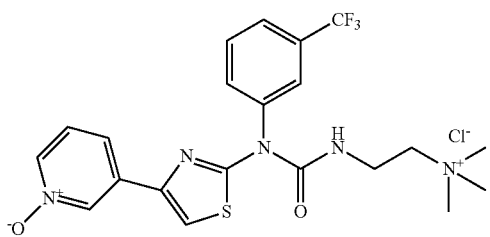

To a solution of trimethyl-[2-[[[4-(3-pyridyl)thiazol-2-yl]-[3-(trifluoromethyl)phenyl]carbamoyl]amino]ethyl]ammonium (200 mg, 443.95 μmol, 1 eq) in DMF (8 mL) was added m-CPBA (575.00 mg, 2.67 mmol, 80% purity, 6 eq). The mixture was stirred at 30° C. for 12 h. The reaction mixture was added Na$_2$S$_2$O$_3$, filtered and concentrated to yield a residue which was purified by preparative HPLC (column: Phenomenex Synergi C18 150*30 mm*4 um; mobile phase: [water(0.05% HCl)-ACN]; B %: 17%-37%, 9 min), followed by lyophilization to yield trimethyl-[2-[[[4-(1-oxidopyridin-1-ium-3-yl)thiazol-2-yl]-[3-(trifluoromethyl)phenyl]carbamoyl]amino]ethyl]ammonium (34.23 mg, 73.38 μmol, 16.5% yield, 100.0% purity) as a white gum. $^1$H NMR (400 MHz, DMSO-d$_6$) δ ppm 8.51 (s, 1H), 8.27 (d, J=6.3 Hz, 1H), 8.02 (s, 1H), 7.97-7.93 (m, 2H), 7.89-7.80 (m, 2H), 7.73 (d, J=8.1 Hz, 1H), 7.53 (dd, J=6.6, 7.9 Hz, 1H), 7.01 (t, J=5.4 Hz, 1H), 3.53 (d, J=5.3 Hz, 2H), 3.47-3.42 (m, 2H), 3.08 (s, 9H); ES-LCMS m/z 466.2 [M−Cl]$^+$.

I-119

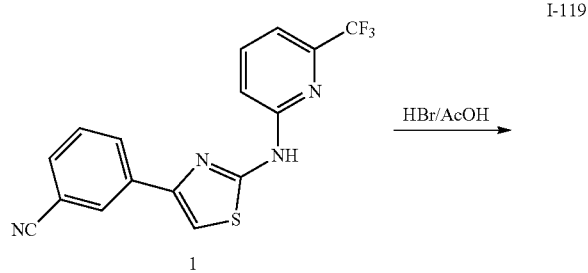

1

320

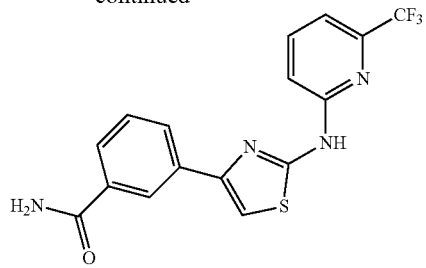

Step 1: 3-[2-[[6-(Trifluoromethyl)-2-pyridyl]amino]thiazol-4-yl]benzamide

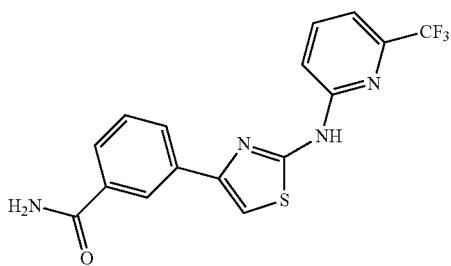 [SMILES: NC(=O)c1cccc(-c2csc(Nc3cccc(C(F)(F)F)n3)n2)c1]

A solution of 3-[2-4-[[6-(trifluoromethyl)-2-pyridyl]amino]thiazol-4-yl]benzonitrile (200 mg, 577.49 μmol, 1 eq) in HBr/AcOH (5 mL) was stirred at 20° C. for 16 h. The reaction mixture was filtered to yield a residue which was purified by preparative HPLC (column: Agela DuraShell C$_{18}$ 150*25 mm*5 um; mobile phase: [water(0.04% NH$_3$H$_2$O+ 10 mM NH$_4$HCO$_3$)-ACN]; B %: 35%-65%, 10 min), followed by lyophilization to yield 3-[2-[[6-(trifluoromethyl)-2-pyridyl]amino]thiazol-4-yl]benzamide (12.27 mg, 33.68 μmol, 5.8% yield, 100.0% purity) as a white solid. $^1$H NMR (400 MHz, DMSO-d$_6$) δ ppm 11.89 (s, 1H), 8.44 (s, 1H), 8.05 (d, J=7.1 Hz, 2H), 7.97 (t, J=7.9 Hz, 1H), 7.80 (d, J=7.6 Hz, 1H), 7.62 (s, 1H), 7.51 (t, J=7.7 Hz, 1H), 7.41 (d, J=7.3 Hz, 2H), 7.35 (d, J=8.3 Hz, 1H); ES-LCMS m/z 365.2 [M+H]$^+$.

I-120

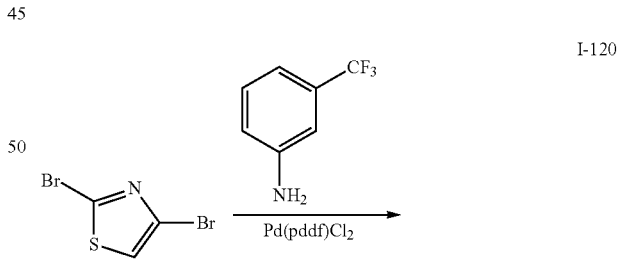

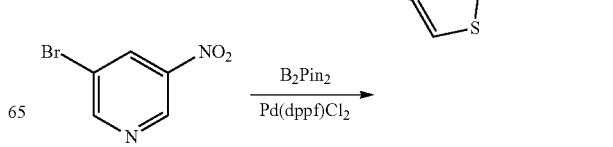

-continued

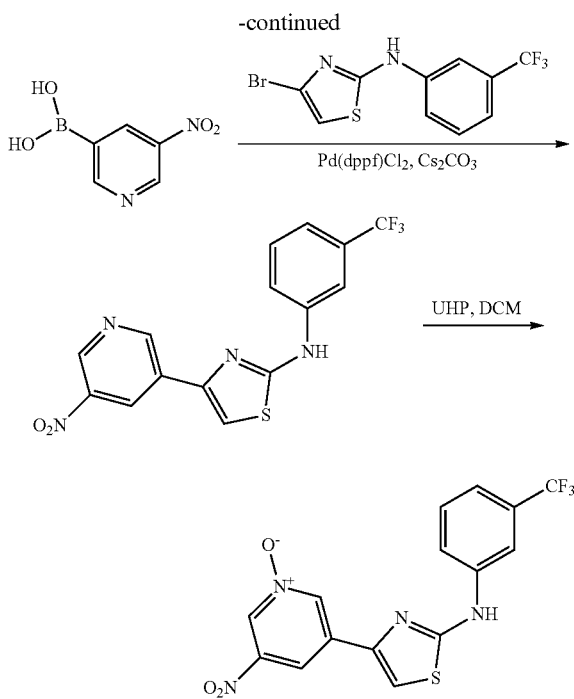

Step 1: 4-Bromo-N-[3-(trifluoromethyl)phenyl]thiazol-2-amine

To a solution of 2,4-dibromothiazole (1 g, 4.12 mmol, 1 eq), 3-(trifluoromethyl)aniline (795.94 mg, 4.94 mmol, 617.00 μL, 1.2 eq) in toluene (10 mL) was added K$_2$CO$_3$ (1.71 g, 12.35 mmol, 3 eq) and Xantphos (142.92 mg, 246.99 μmol, 0.06 eq), Pd$_2$(dba)$_3$ (113.09 mg, 123.50 μmol, 0.03 eq). The mixture was stirred under N$_2$ atmosphere at 100° C. for 12 h. The reaction mixture was quenched by addition of water (50 mL), extracted with EtOAc (30 mL×3). The combined organic layers were washed with brine (10 mL), dried over Na$_2$SO$_4$, filtered and concentrated. The residue was purified by flash silica gel chromatography (from PE/EtOAc=1/0 to 5/1, TLC: PE/EtOAc=5/1, R$_f$=0.47) to yield 4-bromo-N-[3-(trifluoromethyl)phenyl]thiazol-2-amine (240 mg, 695.94 μmol, 16.9% yield, 93.7% purity) as a yellow solid. $^1$H NMR (500 MHz, CDCl$_3$) δ ppm 7.86 (s, 1H), 7.63-7.60 (m, 2H), 7.53-7.47 (m, 1H), 7.38-7.35 (m, 1H), 6.59 (s, 1H); ES-LCMS m/z 323.0, 325.0 [M+H]$^+$.

Step 2: (5-Nitro-3-pyridyl)boronic acid

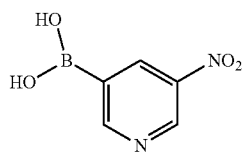

To a solution of 3-bromo-5-nitro-pyridine (1 g, 4.93 mmol, 1 eq), 4,4,5,5-tetramethyl-2-(4,4,5,5-tetramethyl-1,3,2-dioxaborolan-2-yl)-1,3,2-dioxaborolane (3.75 g, 14.78 mmol, 3 eq) in 1,4-dioxane (15 mL) was added KOAc (966.95 mg, 9.85 mmol, 2 eq), Pd(dppf)Cl$_2$ (360.46 mg, 492.63 μmol, 0.1 eq). The mixture was stirred under N$_2$ atmosphere at 80° C. for 4 h. The reaction mixture was quenched by addition of water (50 mL), extracted with EtOAc (30 mL×3). The combined organic layers were washed with brine (10 mL), dried over Na$_2$SO$_4$, filtered and concentrated to yield (5-nitro-3-pyridyl)boronic acid (800 mg, 4.05 mmol, 82.2% yield, 85.0% purity) as black brown oil, which was used in the next step without further purification. $^1$H NMR (400 MHz, CDCl$_3$) δ ppm 9.46 (s, 1H), 9.18 (s, 1H), 8.82 (s, 1H), 2.04 (s, 1H), 1.92-1.77 (m, 1H); ES-LCMS m/z 169.2 [M+H]$^+$.

Step 3: 4-(5-Nitro-3-pyridyl)-N-[3-(trifluoromethyl)phenyl]thiazol-2-amine

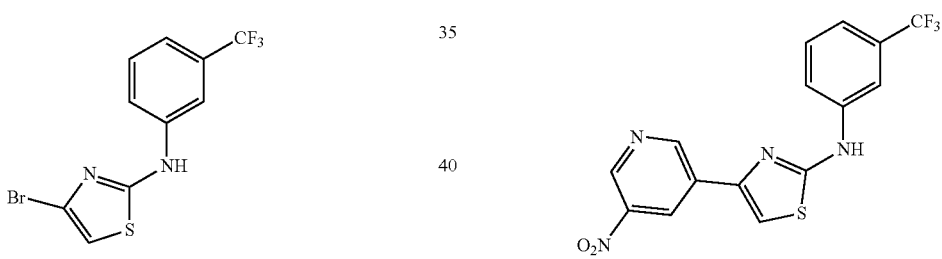

To a solution of 4-bromo-N-[3-(trifluoromethyl)phenyl]thiazol-2-amine (662.91 mg, 2.02 mmol, 1 eq), (5-nitro-3-pyridyl)boronic acid (600 mg, 3.04 mmol, 1.5 eq) in 1,4-dioxane (20 mL) was added Pd(dppf)Cl$_2$.CH$_2$Cl$_2$ (165.36 mg, 202.48 μmol, 0.1 eq) and Cs$_2$CO$_3$ (1.98 g, 6.07 mmol, 3 eq). The mixture was stirred under N$_2$ atmosphere at 110° C. for 12 h. The reaction mixture was quenched by addition of water (50 mL), extracted with EtOAc (30 mL×3). The combined organic layers were washed with brine (10 mL), dried over Na$_2$SO$_4$, filtered and concentrated. The residue was purified by flash silica gel chromatography (from PE/EtOAc=1/0 to 3/1, TLC: PE/EtOAc=3/1, R$_f$=0.45) to yield a product which was further purified by preparative HPLC (column: Phenomenex Synergi C18 150*30 mm*4 μm; mobile phase: [water (0.05% HCl)-ACN]; B %: 60%-80%, 9 min), followed by lyophilization to yield 4-(5-nitro-3-pyridyl)-N-[3-(trifluoromethyl)phenyl]thiazol-2-amine (50 mg, 118.30 μmol, 5.8% yield, 95.3% purity, HCl) as a yellow solid. $^1$H NMR (400 MHz, CDCl$_3$) δ ppm 9.42 (d, J=13.3 Hz, 2H), 8.93 (s, 1H), 7.80 (s, 1H), 7.69 (d, J=7.8 Hz, 1H), 7.60 (t, J=7.8 Hz, 1H), 7.49 (d, J=7.4 Hz, 1H), 7.14 (s, 1H); ES-LCMS m/z 367.0 [M+H]$^+$.

Step 4: 4-(5-Nitro-1-oxido-pyridin-1-ium-3-yl)-N-[3-(trifluoromethyl)phenyl]thiazol-2-amine

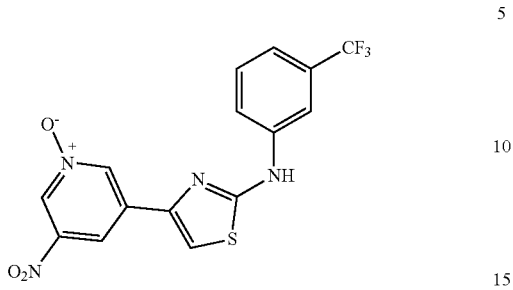

To a solution of 4-(5-nitro-3-pyridyl)-N-[3-(trifluoromethyl)phenyl]thiazol-2-amine (50 mg, 130.08 μmol, 95.3% purity, 1 eq, HCl), hydrogen peroxide; urea (73.42 mg, 780.47 μmol, 6 eq) in DCM (3 mL) was added TFAA (109.28 mg, 520.31 μmol, 72.37 μL, 4 eq). The mixture was stirred at 20° C. for 12 h. The residue was purified by preparative HPLC (column: Agela DuraShell C18 150*25 mm*5 μm; mobile phase: [water (0.04% NH$_3$.H$_2$O+10 μmM NH$_4$HCO$_3$)-ACN]; B %: 35%-65%, 10 min), followed by lyophilization to yield 4-(5-nitro-1-oxido-pyridin-1-ium-3-yl)-N-[3-(trifluoromethyl)phenyl]thiazol-2-amine (14.37 mg, 37.59 μmol, 28.9% yield, 100.0% purity) as a yellow solid. $^1$H NMR (400 MHz, DMSO-d$_6$) δ ppm 9.10 (s, 1H), 8.92 (t, J=1.6 Hz, 1H), 8.53 (s, 1H), 8.41 (s, 1H), 8.09 (s, 1H), 7.76 (d, J=9.3 Hz, 1H), 7.60 (t, J=8.1 Hz, 1H), 7.35 (d, J=8.6 Hz, 1H); ES-LCMS m/z 383.0 [M+H]$^+$.

I-121

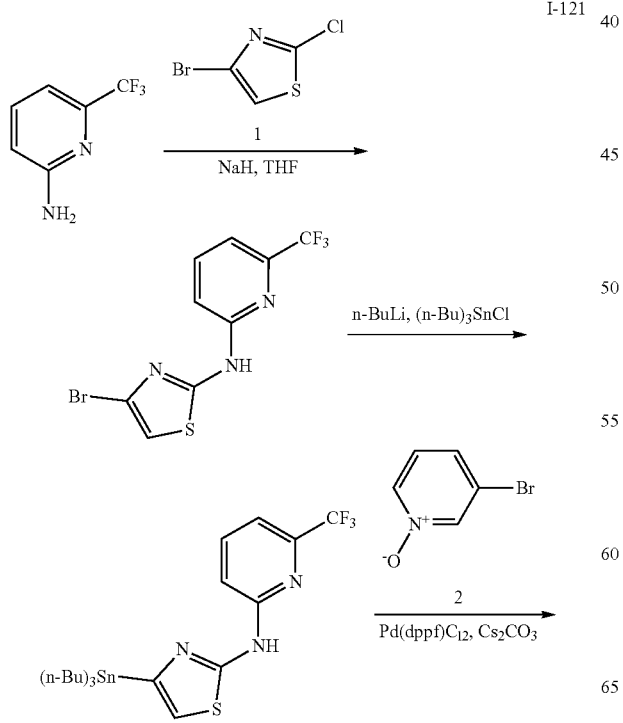

-continued

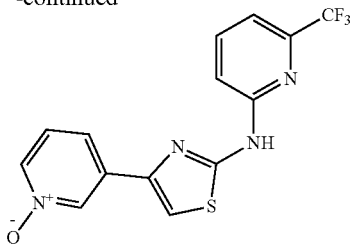

Step 1: 4-Bromo-N-[6-(trifluoromethyl)-2-pyridyl]thiazol-2-amine

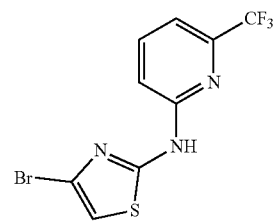

To a solution of NaH (616.00 mg, 15.40 mmol, 60% purity, 5 eq) in THF (25 mL) was added a mixture of 6-(trifluoromethyl)pyridin-2-amine (500 mg, 3.08 mmol, 1 eq) in THF (25 mL) under N$_2$ atmosphere. The mixture was stirred at 0° C. for 1 h under N$_2$ atmosphere. A mixture of 4-bromo-2-chloro-thiazole (643.46 mg, 3.08 mmol, 1 eq) in THF (25 mL) was added. The reaction mixture was stirred under N$_2$ atmosphere at 10° C. for 1 h. TLC (PE/EtOAc=3/1, R$_f$=0.6) showed that new point was formed and start material was consumed completely. The reaction mixture was quenched by addition of H$_2$O (20 mL) and extracted with EtOAc (30 mL×3). The combined organic layers were washed with brine (30 mL), dried over Na$_2$SO$_4$, filtered and concentrated under reduced pressure to give a residue which was purified by flash silica gel chromatography (from PE/EtOAc=100/1 to 3/1, TLC: PE/EtOAc=3/1, R$_f$=0.40) to yield 4-bromo-N-[6-(trifluoromethyl)-2-pyridyl]thiazol-2-amine (600 mg, 1.57 mmol, 51.1% yield, 85.0% purity) as a white solid. $^1$H NMR (400 MHz, DMSO-d$_6$) δ ppm 12.01 (s, 1H), 7.98 (t, J=6.4 Hz, 1H), 7.43 (d, J=6.0 Hz, 1H), 7.29 (d, J=6.8 Hz, 1H), 7.17 (s, 1H) ES-LCMS m/z 326.0 [M+H]$^+$.

Step 2: 4-Tributylstannyl-N-[6-(trifluoromethyl)-2-pyridyl]thiazol-2-amine

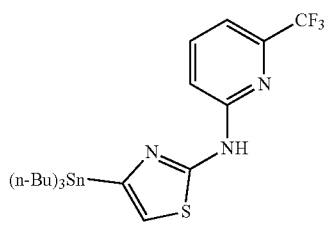

To a solution of 4-bromo-N-[6-(trifluoromethyl)-2-pyridyl]thiazol-2-amine (300 mg, 925.58 μmol, 1 eq) in THF (20 mL) was added n-BuLi (2.5 M, 1.11 mL, 3.0 eq) −78° C. under N₂ atmosphere. The mixture was stirred under N₂ atmosphere at −78° C. for 2 h and a solution of tributyl (chloro)stannane (602.56 mg, 1.85 mmol, 497.99 μL, 2.0 eq) in THF (2 mL) was added dropwise. The reaction mixture was stirred under N₂ atmosphere at −78° C. for another 1 h and allowed to warm to room temperature (20° C.) slowly. TLC (PE/EtOAc=3/1, R_f=0.75) showed that new point was formed and start material was consumed completely. The reaction mixture was quenched by addition of sat.aq KF (20 mL) and extracted with EtOAc (30 mL×3). The combined organic layers were washed with brine (30 mL), dried over Na₂SO₄, filtered and concentrated under reduced pressure to yield 4-tributylstannyl-N-[6-(trifluoromethyl)-2-pyridyl]thiazol-2-amine (600 mg, 898.43 μmol, 97.1% yield, 80.0% purity) as a white solid, which was used in the next step without further purification. ES-LCMS m/z 534.7 [M+H]⁺.

Step 3: 4-(1-Oxidopyridin-1-ium-3-yl)-N-[6-(trifluoromethyl)-2-pyridyl]thiazol-2-amine

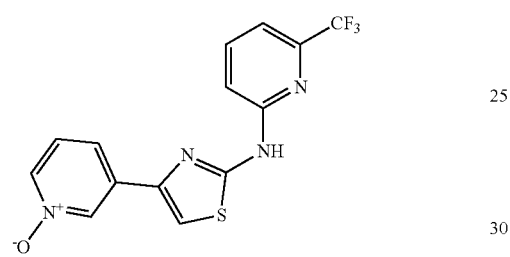

To a solution of 3-bromo-1-oxido-pyridin-1-ium (111.11 mg, 574.73 μmol, 90.0% purity, 1 eq) and 4-tributylstannyl-N-[6-(trifluoromethyl)-2-pyridyl]thiazol-2-amine (383.82 mg, 574.73 μmol, 80.0% purity, 1 eq) in DMF (5 mL) was added Pd(PPh₃)₄ (66.41 mg, 57.47 μmol, 0.1 eq) under N₂ atmosphere. The mixture was stirred under N₂ atmosphere at 100° C. for 10 h. TLC (EtOAc/MeOH=7/1, R_f=0.5) showed that new point was formed and start material was consumed completely. The reaction mixture was quenched by addition of H₂O (20 mL) and extracted with EtOAc (30 mL×3). The combined organic layers were washed with brine (30 mL), dried over Na₂SO₄, filtered and concentrated under reduced pressure to yield a residue which was purified by flash silica gel chromatography (from EtOAc/MeOH=100/1 to 3/1, TLC: EtOAc/MeOH=7/1, R_f=0.50) to yield 4-(1-oxidopyridin-1-ium-3-yl)-N-[6-(trifluoromethyl)-2-pyridyl]thiazol-2-amine (55.8 mg, 161.64 μmol, 28.1% yield, 98.0% purity) as a white solid. ¹H NMR (400 MHz, DMSO-d₆) δ ppm 11.95 (s, 1H), 8.72 (s, 1H), 8.18 (d, J=6.4 Hz, 1H), 7.99 (t, J=8.0 Hz, 1H), 7.88 (s, 1H), 7.82 (d, J=8.0 Hz, 1H), 7.49 (d, 7.6 Hz, 1H), 7.44 (d, J=7.6 Hz, 1H), 7.37 (d, J=8.8 Hz, 1H); ES-LCMS m/z 339.0 [M+H]⁺.

I-125

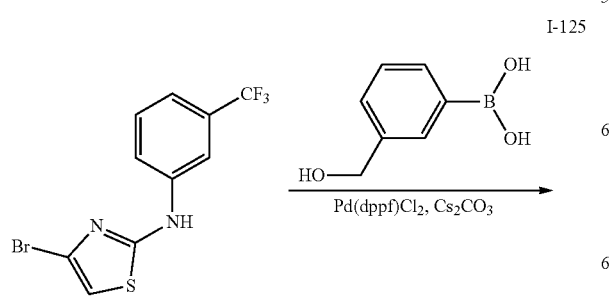

Step 1: [3-[2-[3-(Trifluoromethyl)anilino]thiazol-4-yl]phenyl]methanol

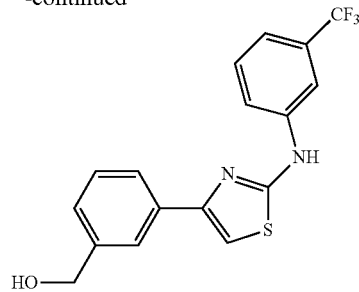

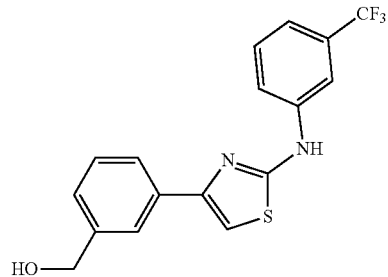 [SMILES: OCc1cccc(-c2csc(Nc3cccc(C(F)(F)F)c3)n2)c1]

To a solution of 4-bromo-N-[3-(trifluoromethyl)phenyl]thiazol-2-amine (157.89 mg, 464.21 μmol, 1 eq) in H₂O (0.6 mL) and 1,4-dioxane (3 mL) were added Cs₂CO₃ (302.49 mg, 928.41 μmol, 2 eq), Pd(dppf)Cl₂ (33.97 mg, 46.42 μmol, 0.1 eq) and [3-(hydroxymethyl)phenyl]boronic acid (70.54 mg, 464.21 μmol, 1 eq). The mixture was degassed and purged with N₂ for three times and stirred under N₂ atmosphere at 90° C. for 6 h. The reaction mixture was diluted with H₂O (20 mL) and extracted with EtOAc (50 mL×3). The combined organic phases were washed with brine (20 mL), dried over anhydrous Na₂SO₄, filtered and concentrated under reduced pressure to yield a residue which was purified by preparative HPLC (column: Agela DuraShell C₁₈ 150*25 mm*5 um; mobile phase: [water(0.04% NH₃H₂O+10 mM NH₄HCO₃)-ACN]; B %: 44%-74%, 10 min), followed by lyophilization to yield [3-[2-[3-(trifluoromethyl)anilino]thiazol-4-yl]phenyl]methanol (48.57 mg, 138.63 μmol, 29.9% yield, 100.0% purity) as a white solid. ¹H NMR (400 MHz, CDCl₃) δ ppm 7.89 (s, 2H), 7.80 (d, J=7.4 Hz, 1H), 7.62 (d, J=7.8 Hz, 1H), 7.48 (t, J=8.0 Hz, 1H), 7.45-7.41 (m, 1H), 7.38-7.30 (m, 3H), 6.93 (s, 1H), 4.77 (s, 2H), 1.75 (s, 1H); ES-LCMS m/z 351.1 [M+H]⁺.

I-127

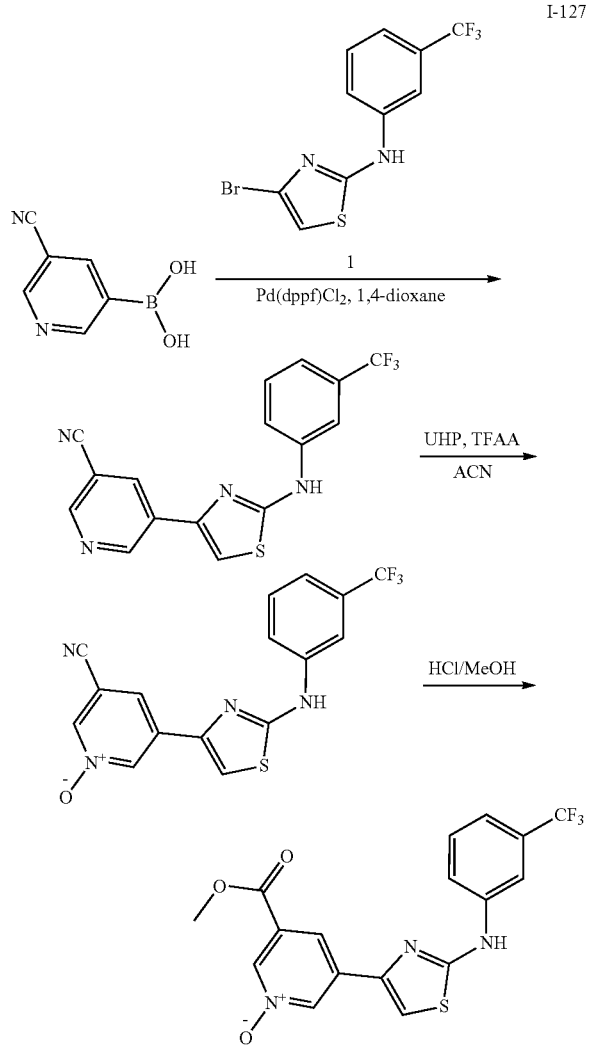

Step 1: 5-[2-[3-(Trifluoromethyl)anilino]thiazol-4-yl]pyridine-3-carbonitrile

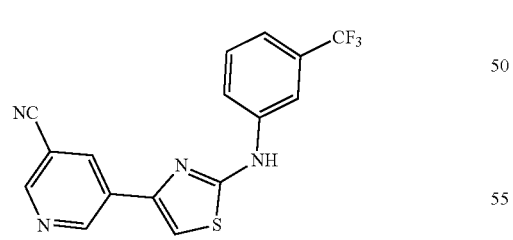

To a solution of (5-cyano-3-pyridyl)boronic acid (400 mg, 2.70 mmol, 1 eq) and 4-bromo-N-[3-(trifluoromethyl)phenyl]thiazol-2-amine (699.01 mg, 2.16 mmol, 100% purity, 0.8 eq) in 1,4-dioxane (12 mL) and H₂O (4 mL) was added Cs₂CO₃ (2.64 g, 8.11 mmol, 3 eq) and Pd(dppf)Cl₂ (98.93 mg, 135.20 µmol, 0.05 eq). The reaction mixture was bubbled with N₂ for 3 min and stirred under microwave at 100° C. for 30 min. The mixture was diluted with water (20 mL) and extracted with EtOAc (20 mL×3). The combined organic layers were dried over Na₂SO₄, filtered and concentrated under reduced pressure to yield a residue which was purified by flash silica gel chromatography (from PE/EtOAc=100/1 to 4/1, TLC: PE/EtOAc=1/1, R$_f$=0.60) to yield 5-[2-[3-(trifluoromethyl)anilino]thiazol-4-yl]pyridine-3-carbonitrile (560 mg, 1.54 mmol, 56.8% yield, 95.0% purity) as a light yellow solid. ¹H NMR (400 MHz, DMSO-d₆) δ ppm 10.81 (s, 1H), 9.38 (d, J=2.0 Hz, 1H), 8.96 (d, J=2.0 Hz, 1H), 8.74 (t, J=2.0 Hz, 1H), 8.28 (s, 1H), 7.92 (d, J=8.2 Hz, 1H), 7.82 (s, 1H), 7.60 (t, J=8.0 Hz, 1H), 7.32 (d, J=7.8 Hz, 1H); ES-LCMS m/z 347.1 [M+H]⁺.

Step 2: 1-Oxido-5-[2-[3-(trifluoromethyl)anilino]thiazol-4-yl]pyridin-1-ium-3-carbonitrile

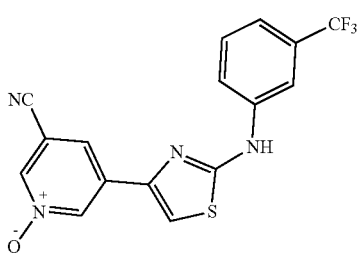

To a solution of 5-[2-[3-(trifluoromethyl)anilino]thiazol-4-yl]pyridine-3-carbonitrile (500 mg, 1.37 mmol, 95% purity, 1 eq) in ACN (11 mL) was added TFAA (1.15 g, 5.49 mmol, 763.08 µL, 4 eq) and urea hydrogen peroxide (516.08 mg, 5.49 mmol, 4 eq). The mixture was stirred at 40° C. for 12 h. The reaction mixture was quenched by Na₂S₂O₃, diluted with water (10 mL) and extracted with EtOAc (10 mL×3). The combined organic layers were dried over Na₂SO₄, filtered and concentrated under reduced pressure to yield a residue which was purified by flash silica gel chromatography (from PE/EtOAc=100/1 to 2/3, TLC: PE/EtOAc=1/1, R$_f$=0.10) to yield 1-oxido-5-[2-[3-(trifluoromethyl)anilino]thiazol-4-yl]pyridin-1-ium-3-carbonitrile (70 mg, 183.54 µmol, 13.4% yield, 95.0% purity) as a yellow solid. ¹H NMR (400 MHz, DMSO-d₆) δ ppm 10.85 (s, 1H), 8.93-8.88 (m, 1H), 8.86-8.81 (m, 1H), 8.32-8.28 (m, 1H), 8.23 (s, 1H), 7.93 (s, 1H), 7.89 (d, J=7.6 Hz, 1H), 7.61 (t, J=8.0 Hz, 1H), 7.34 (d, J=7.6 Hz, 1H); ES-LCMS m/z 363.1 [M+H]⁺.

Step 3: Methyl 1-oxido-5-[2-[3-(trifluoromethyl)anilino]thiazol-4-yl]pyridin-1-ium-3-carboxylate

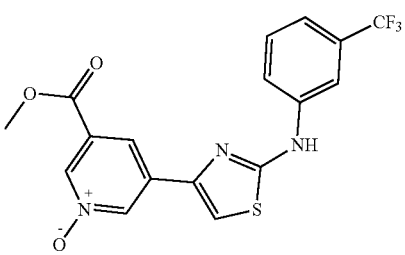

A solution of 1-oxido-5-[2-[3-(trifluoromethyl)anilino]thiazol-4-yl]pyridin-1-ium-3-carbonitrile (70 mg, 183.54 µmol, 95% purity, 1 eq) in HCl/MeOH (7 mL) was stirred at 80° C. for 6 h. The reaction mixture was basified with saturated aqueous NaHCO$_3$ until pH=8 and extracted with EtOAc (25 mL×3). The combined organic layers were dried over Na$_2$SO$_4$, filtered and concentrated under reduced pressure to yield a residue which was purified by preparative HPLC (column: Phenomenex Synergi C18 150*21.2 mm*4 um; mobile phase: [water (0.1% TFA)-ACN]; B %: 37%-67%, 11 min). The reaction mixture was basified with saturated aqueous NaHCO$_3$ until pH=8 and extracted with EtOAc (25 mL×3). The combined organic layers were dried over Na$_2$SO$_4$, filtered and concentrated under reduced pressure, followed by lyophilization to yield methyl 1-oxido-5-[2-[3-(trifluoromethyl)anilino]thiazol-4-yl]pyridin-1-ium-3-carboxylate (12.27 mg, 31.04 μmol, 16.9% yield, 100.0% purity) as a white solid. $^1$H NMR (400 MHz, DMSO-d$_6$) δ ppm 10.99 (br s, 1H), 9.01-8.98 (m, 1H), 8.49 (s, 1H), 8.47-8.46 (m, 1H), 8.31-8.28 (m, 1H), 7.95 (s, 1H), 7.72 (d, J=8.5 Hz, 1H), 7.58 (t, J=7.9 Hz, 1H), 7.33 (d, J=7.8 Hz, 1H), 3.93 (s, 3H); ES-LCMS m/z 396.1 [M+H]$^+$.

I-128

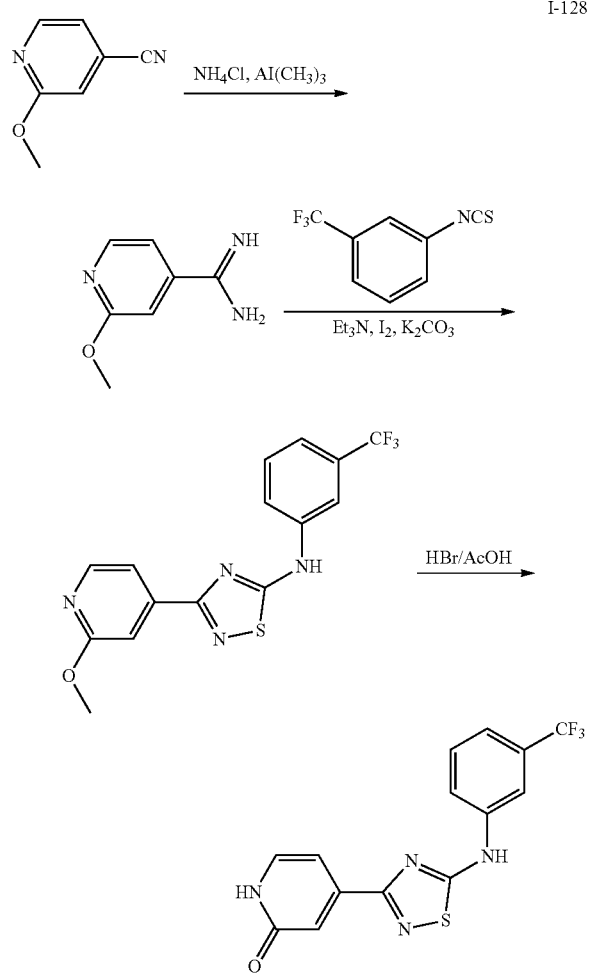

Step 1: 2-Methoxypyridine-4-carboxamidine

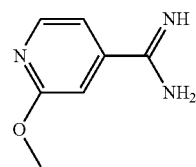

To a stirred solution of 2-methoxypyridine-4-carbonitrile (480 mg, 3.58 mmol, 1 eq) in toluene (20 mL) was added NH$_4$Cl (1.34 g, 25.05 mmol, 7 eq) at 0° C. followed by Al(CH$_3$)$_3$ (2 M, 12.52 mL, 7 eq) was added. The reaction was heated at 80° C. for 3 h. TLC (DCM/MeOH=5/1, R$_f$=0.30) indicated starting material was consumed completely and one new spot formed. The reaction mixture was concentrated under reduced pressure to give a residue which was purified by flash silica gel chromatography (from DCM/MeOH=1/0 to 3/1, TLC: DCM/MeOH=5/1, R$_f$=0.30) to yield 2-methoxypyridine-4-carboxamidine (300 mg, 1.89 mmol, 52.7% yield, 95.0% purity) as a white solid. $^1$H NMR (400 MHz, DMSO-d$_6$) δ ppm 9.66 (s, 3H), 8.40 (d, J=5.5 Hz, 1H), 7.37 (dd, J=1.4, 5.3 Hz, 1H), 7.28 (s, 1H), 3.90 (s, 3H); ES-LCMS m/z 152.2 [M+H]$^+$.

Step 2: 3-(2-Methoxy-4-pyridyl)-N-[3-(trifluoromethyl)phenyl]-1,2,4-thiadiazol-5-amine

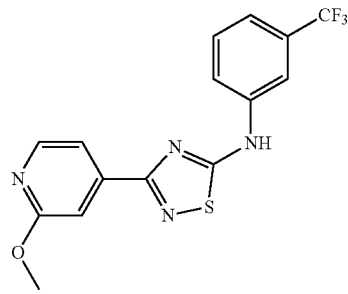 [SMILES: COc1cc(-c2nsc(Nc3cccc(C(F)(F)F)c3)n2)ccn1]

To a solution of 2-methoxypyridine-4-carboxamidine (200 mg, 1.26 mmol, 95% purity, 1 eq) in MeCN (10 mL) was added 1-isothiocyanato-3-(trifluoromethyl)benzene (306.46 mg, 1.51 mmol, 228.70 μL, 1.2 eq) and TEA (381.55 mg, 3.77 mmol, 524.83 μL, 3 eq). The mixture was stirred at 10° C. for 2 h. The mixture was added I$_2$ (186.95 mg, 736.56 μmol, 1.2 eq) and K$_2$CO$_3$ (127.25 mg, 920.70 μmol, 1.5 eq). The mixture was stirred at 10° C. for 2 h. TLC (PE/EtOAc=5/1, R$_f$=0.70) indicated starting material was consumed completely and one new spot formed. The reaction mixture was quenched by addition of water (50 mL) and extracted with EtOAc (50 mL×3). The combined organic layers were washed with brine (40 mL), dried over Na$_2$SO$_4$, filtered and concentrated under reduced pressure to yield a residue which was purified by flash silica gel chromatography (from PE/EtOAc=1/0 to 10/1, TLC:PE/EtOAc=5/1, R$_f$=0.70) to yield 3-(2-methoxy-4-pyridyl)-N-[3-(trifluoromethyl)phenyl]-1,2,4-thiadiazol-5-amine (200 mg, 551.75 μmol, 89.9% yield, 97.2% purity) as a white solid. $^1$H NMR (500 MHz, DMSO-d$_6$) δ ppm 11.40 (s, 1H), 8.33 (d, J=5.2

Hz, 1H), 8.23 (s, 1H), 7.88-7.80 (m, 1H), 7.70-7.63 (m, 2H), 7.45 (d, J=7.6 Hz, 1H), 7.42 (s, 1H), 3.92 (s, 3H); ES-LCMS m/z 353.6 [M+H]⁺.

Step 3: 4-[5-[3-(Trifluoromethyl)anilino]-1,2,4-thiadiazol-3-yl]-1H-pyridin-2-one

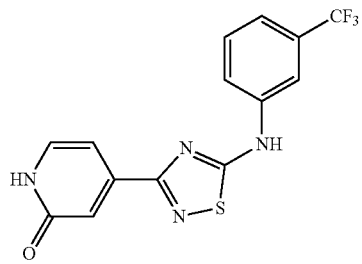 [SMILES: O=c1cc(-c2nsc(Nc3cccc(C(F)(F)F)c3)n2)cc[nH]1]

To a solution of 3-(2-methoxy-4-pyridyl)-N-[3-(trifluoromethyl)phenyl]-1,2,4-thiadiazol-5-amine (50 mg, 137.94 µmol, 97.2% purity, 1 eq) was added HBr (33.82 mg, 137.94 µmol, 22.70 µL, 33% purity, 1 eq). The mixture was stirred at 70° C. for 2 h under N₂ atmosphere. The reaction mixture was quenched by addition of water (50 mL) and extracted with EtOAc (50 mL×3). The combined organic layers were washed with brine (10 mL), dried over Na₂SO₄, filtered and concentrated under reduced pressure to yield a residue which was purified by preparative HPLC (column: Agela DuraShell C18 150*25 mm*5 um; mobile phase: [water (0.04% NH₃H₂O+10 mM NH₄HCO₃)-ACN]; B %: 29%-59%, 10 min) and lyophilized to yield 4-[5-[3-(trifluoromethyl)anilino]-1,2,4-thiadiazol-3-yl]-1H-pyridin-2-one (24.45 mg, 69.24 µmol, 50.2% yield, 95.8% purity) as a white solid. ¹H NMR (500 MHz, DMSO-d₆) δ ppm 11.65 (br s, 1H), 8.21 (s, 1H), 7.85 (d, J=7.9 Hz, 1H), 7.68 (t, J=7.9 Hz, 1H), 7.52 (d, J=6.7 Hz, 1H), 7.45 (d, J=7.6 Hz, 1H), 7.05 (s, 1H), 6.85 (d, J=6.4 Hz, 1H); ES-LCMS m/z 339.0 [M+H]⁺.

I-129

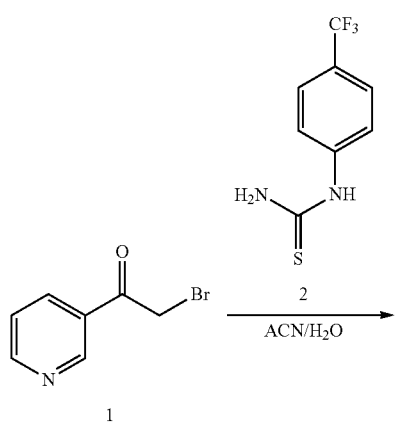

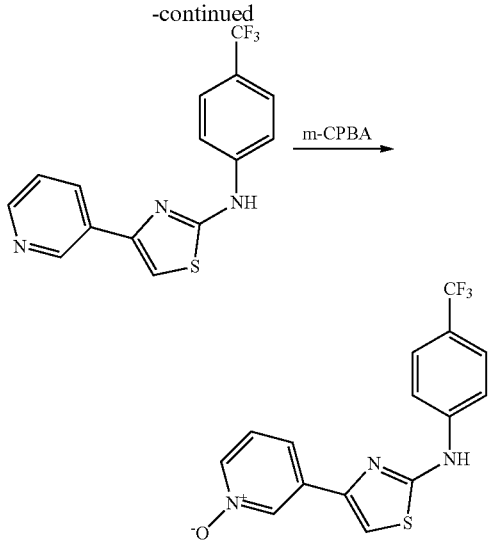

Step 1: 4-(3-Pyridyl)-N-[4-(trifluoromethyl)phenyl]thiazol-2-amine

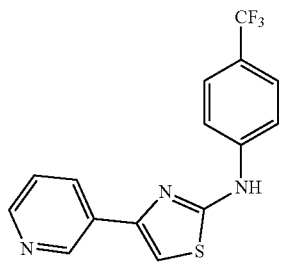 [SMILES: FC(F)(F)c1ccc(Nc2nc(-c3cccnc3)cs2)cc1]

To a solution of 2-bromo-1-(3-pyridyl)ethanone (1 g, 3.03 mmol, 85% purity, 1.2 eq, HBr) in ACN (5 mL) and H₂O (5 mL) was added [4-(trifluoromethyl)phenyl]thiourea (1.11 g, 2.52 mmol, 50% purity, 1 eq). The mixture was stirred at 30° C. for 3 h. TLC (PE/EtOAc=1/1, R_f=0.40) indicated starting material was consumed completely and two new spots formed. The reaction mixture was diluted with water (5 mL), basified with saturated aqueous NaHCO₃ until pH=8 and extracted with EtOAc (10 mL×3). The combined organic layers were dried over Na₂SO₄, filtered and concentrated under reduced pressure to yield a residue which was purified by flash silica gel chromatography (from PE/EtOAc=100/1 to 2/3, TLC: PE/EtOAc=1/1, R_f=0.40) to yield 4-(3-pyridyl)-N-[4-(trifluoromethyl)phenyl]thiazol-2-amine (500 mg, 1.40 mmol, 55.6% yield, 90.0% purity) as a yellow solid. ¹H NMR (400 MHz, DMSO-d₆) δ ppm 10.79 (br s, 1H), 9.18 (br s, 1H), 8.57-8.48 (m, 1H), 8.30 (d, J=7.8 Hz, 1H), 7.94 (d, J=7.8 Hz, 2H), 7.72 (d, J=7.8 Hz, 2H), 7.65 (s, 1H), 7.49-7.45 (m, 1H); ES-LCMS m/z 322.3 [M+H]⁺.

Step 2: 4-(1-Oxidopyridin-1-ium-3-yl)-N-[4-(trifluoromethyl)phenyl]thiazol-2-amine

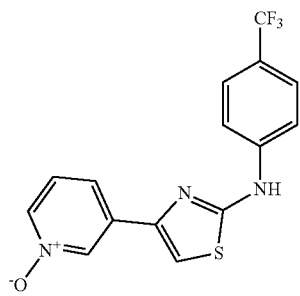

To a solution of 4-(3-pyridyl)-N-[4-(trifluoromethyl)phenyl]thiazol-2-amine (500 mg, 1.40 mmol, 90% purity, 1 eq) in DMF (10 mL) was added m-CPBA (1.66 g, 7.70 mmol, 80% purity, 5.5 eq). The mixture was stirred at 30° C. for 12 h. The mixture was diluted with water (40 mL), quenched with Na$_2$S$_2$O$_3$ (1.5 g) and extracted with EtOAc (40 mL×3). The combined organic layers were dried over Na$_2$SO$_4$, filtered and concentrated under reduced pressure to yield a residue which was purified by preparative HPLC (column: Welch Xtimate C18 150*25 mm*5 um; mobile phase: [water (10 mM NH$_4$HCO$_3$)-ACN]; B %: 30%-60%, 10 min), followed by lyophilization to yield 4-(1-oxidopyridin-1-ium-3-yl)-N-[4-(trifluoromethyl)phenyl]thiazol-2-amine (56.8 mg, 163.29 μmol, 11.7% yield, 97.0% purity) as a white solid. $^1$H NMR (400 MHz, DMSO-d$_6$) δ ppm 10.83 (s, 1H), 8.80-8.73 (m, 1H), 8.19 (d, J=6.3 Hz, 1H), 7.92-7.87 (m, 3H), 7.80 (s, 1H), 7.72 (d, J=8.2 Hz, 2H), 7.49 (dd, J=6.5, 8.0 Hz, 1H); ES-LCMS m/z 338.1 [M+H]$^+$.

I-130

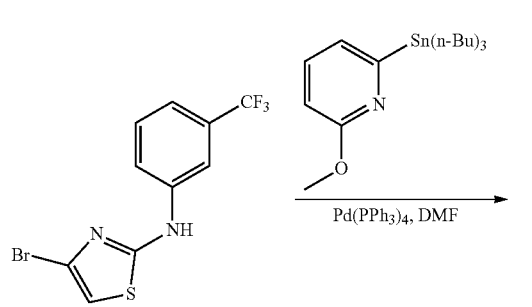

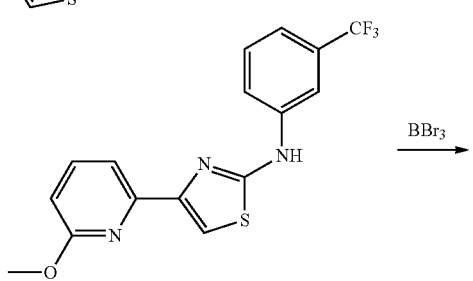

Step 1: 4-(6-Methoxy-2-pyridyl)-N-[3-(trifluoromethyl)phenyl]thiazol-2-amine

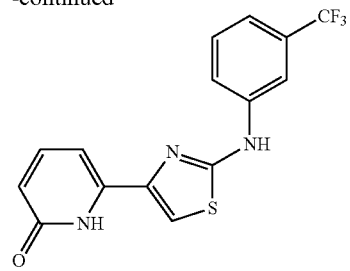

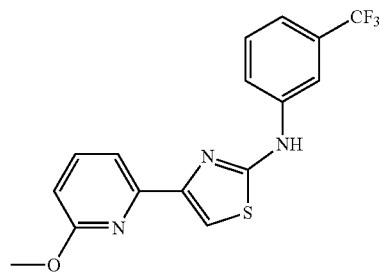 [SMILES: COc1cccc(-c2csc(Nc3cccc(C(F)(F)F)c3)n2)n1]

To a solution of 4-bromo-N-[3-(trifluoromethyl)phenyl]thiazol-2-amine (200 mg, 618.94 μmol, 100% purity, 1 eq) and tributyl-(6-methoxy-2-pyridyl)stannane (295.73 mg, 742.73 μmol, 1.2 eq) in DMF (3 mL) was added Pd(PPh$_3$)$_4$ (35.76 mg, 30.95 μmol, 0.05 eq) under N$_2$ atmosphere. The mixture was stirred under N$_2$ atmosphere at 120° C. for 2 h. TLC (PE/EtOAc=3/1, R$_f$=0.5) showed that new point was formed and the start material was consumed completely. The reaction mixture was quenched by addition of H$_2$O (20 mL) and extracted with EtOAc (30 mL×3). The combined organic layers were washed with brine (30 mL), dried over Na$_2$SO$_4$, filtered and concentrated under reduced pressure to give a residue which was purified by flash silica gel chromatography (from PE/EtOAc=100/1 to 3/1, TLC: PE/EtOAc=3/1, R$_f$=0.5) to yield 4-(6-methoxy-2-pyridyl)-N-[3-(trifluoromethyl)phenyl]thiazol-2-amine (200 mg, 426.93 μmol, 68.9% yield, 75.0% purity) as yellow oil. $^1$H NMR (400 MHz, DMSO-d$_6$) δ ppm 10.66 (s, 1H), 8.33 (s, 1H), 7.84 (d, J=8.4 Hz, 1H), 7.78 (dd, J=7.6, 8.4 Hz, 1H), 7.58 (s, 1H), 7.53 (t, J=6.4 Hz, 2H), 7.30-7.24 (m, 1H), 6.72 (d, J=8.0 Hz, 1H), 3.91 (s, 3H); ES-LCMS m/z 326.0 [M+H]$^+$.

Step 2: 6-[2-[3-(Trifluoromethyl)anilino]thiazol-4-yl]-1H-pyridin-2-one

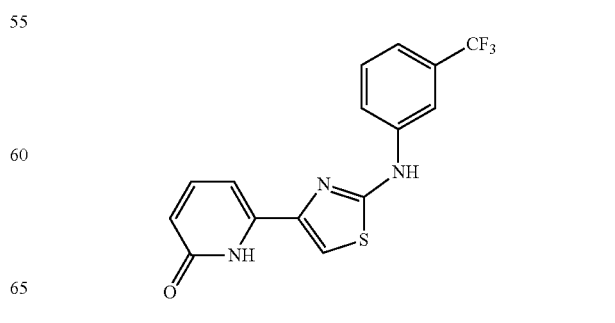

To a solution of 4-(6-methoxy-2-pyridyl)-N-[3-(trifluoromethyl)phenyl]thiazol-2-amine (133.33 mg, 284.62 μmol, 75% purity, 1 eq) in AcOH (2 mL) was added HBr (2 mL, 33% purity). The mixture was stirred at 80° C. for 2 h. The reaction mixture was quenched by the addition of H₂O (20 mL) and extracted with EtOAc (30 mL×3). The combined organic layers were washed with brine (30 mL), dried over Na₂SO₄, filtered and concentrated under reduced pressure to give a residue which was purified by preparative HPLC (column: Welch Xtimate C18 150*25 mm*5 um; mobile phase: [water (10 mM NH₄HCO₃)-ACN]; B %: 32%-62%, 10 min) to yield 6-[2-[3-(trifluoromethyl)anilino]thiazol-4-yl]-1H-pyridin-2-one (21.74 mg, 60.95 μmol, 21.4% yield, 94.6% purity) as a white solid. ¹H NMR (400 MHz, DMSO-d₆) δ ppm 11.49 (s, 1H), 10.74 (s, 1H), 8.21 (s, 1H), 7.90 (d, J=8.8 Hz, 1H), 7.82 (s, 1H), 7.61-7.54 (m, 2H), 7.31 (d, J=7.6 Hz, 1H), 6.89 (s, 1H), 6.35 (d, J=9.2 Hz, 1H); ES-LCMS m/z 338.0 [M+H]⁺.

I-133

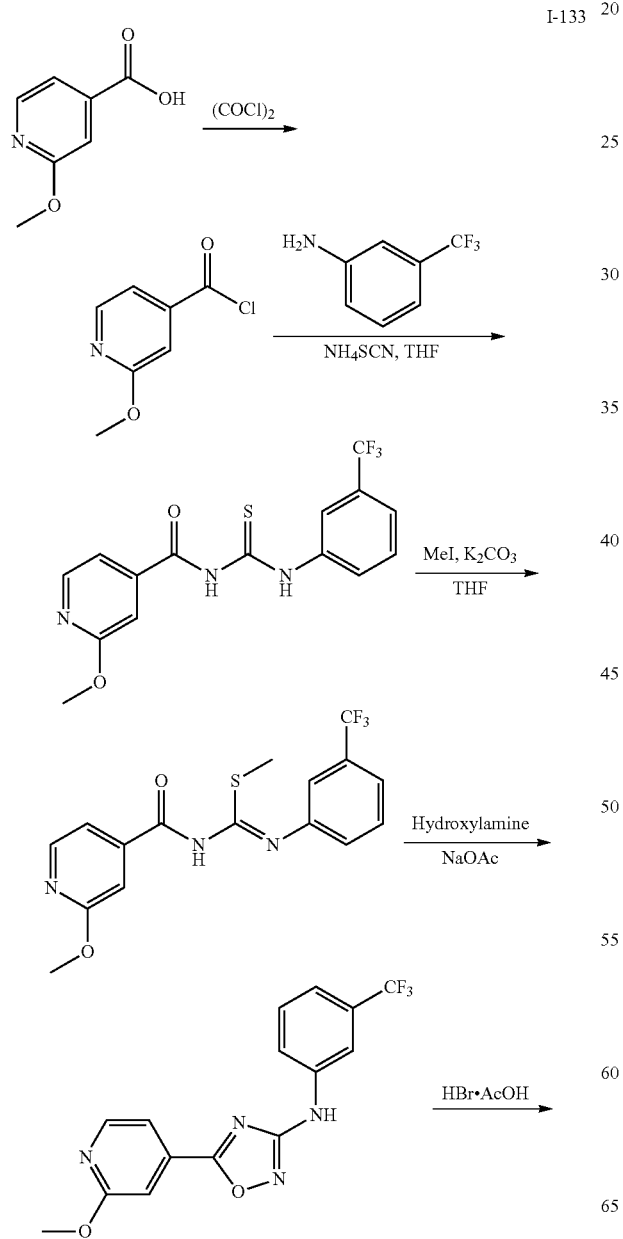

-continued

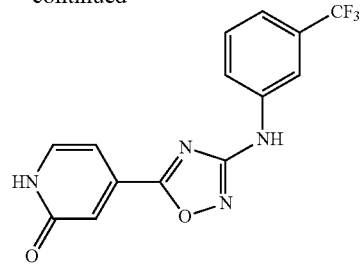

Step 1: 2-Methoxypyridine-4-carbonyl chloride

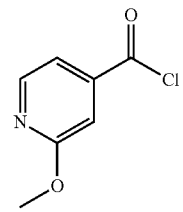

To a solution of 2-methoxypyridine-4-carboxylic acid (2 g, 13.06 mmol, 1 eq) in toluene (15 mL) was added oxalyl dichloride (4.97 g, 39.18 mmol, 3.43 mL, 3 eq) at 10° C. The mixture was stirred at 80° C. for 10 h. The mixture was concentrated to yield 2-methoxypyridine-4-carbonyl chloride (2.7 g, 12.98 mmol, 99.4% yield, 100.0% purity, HCl salt) as a white solid, which was used in the next step without further purification.

Step 2: 2-Methoxy-N-[[3-(trifluoromethyl)phenyl]carbamothioyl]pyridine-4-carboxamide

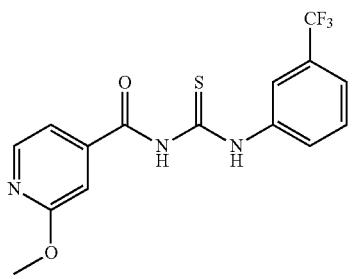 [SMILES: COc1cc(C(=O)NC(=S)Nc2cccc(C(F)(F)F)c2)ccn1]

To a solution of NH₄SCN (1.44 g, 18.88 mmol, 1.2 eq) in THF (20 mL) was added 2-methoxypyridine-4-carbonyl chloride (2.7 g, 15.74 mmol, 100% purity, 1 eq) with stirred at 0° C. for 1 h under N₂ atmosphere. 3-(Trifluoromethyl)aniline (3.04 g, 18.88 mmol, 2.36 mL, 1.2 eq) was added into the mixture at 0° C. The mixture was stirred under N₂ atmosphere at 10° C. for 2 h. TLC (PE/EtOAc=3/1, R_f=0.55) showed that new point was formed and the start material was consumed completely. The reaction mixture was quenched by the addition of H₂O (20 mL) and extracted with EtOAc (30 mL×3). The combined organic layers were washed with brine (30 mL), dried over Na₂SO₄, filtered and concentrated under reduced pressure to yield a residue which was purified by flash silica gel chromatography (from PE/EtOAc=100/1 to 3/1, TLC: PE/EtOAc=3/1, R_f=0.55) to yield 2-methoxy- N-[[3-(trifluoromethyl)phenyl]carbamothioyl]pyridine-4-carboxamide (1.66 g, 4.44 mmol, 28.2% yield, 95.0% purity) as a white solid. ¹H NMR (400 MHz, DMSO-d₆) δ ppm 12.40 (s, 1H), 11.91 (s, 1H), 8.36 (d, J=4.8 Hz, 1H), 8.17 (s, 1H), 7.90 (d, J=6.8 Hz, 1H), 7.72-7.60 (m, 2H), 7.42 (dd, J=1.2, 5.6 Hz, 1H), 7.31 (s, 1H), 3.92 (s, 3H); ES-LCMS m/z 356.0 [M+H]⁺.

Step 3: 2-Methoxy-N—[(Z)—C-methylsulfanyl-N-[3-(trifluoromethyl)phenyl]carbonimidoyl]pyridine-4-carboxamide

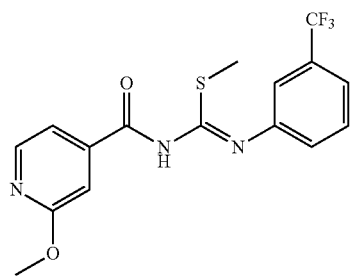 [SMILES: COc1cc(C(=O)N/C(=N/c2cccc(C(F)(F)F)c2)SC)ccn1]

To a solution of 2-methoxy-N-[[3-(trifluoromethyl)phenyl]carbamothioyl]pyridine-4-carboxamide (1.05 g, 2.81 mmol, 95.0% purity, 1 eq) and K₂CO₃ (777.92 mg, 5.63 mmol, 2 eq) in THF (8 mL) was added MeI (798.91 mg, 5.63 mmol, 350.40 μL, 2 eq) under N₂ atmosphere at 0° C. The mixture was stirred at 0° C. for 1.5 h. The reaction mixture was quenched by addition of saturated aqueous NaHCO₃ (20 mL) and extracted with EtOAc (30 mL×3). The combined organic layers were washed with brine (30 mL), dried over Na₂SO₄, filtered and concentrated under reduced pressure to yield 2-methoxy-N—[(Z)—C-methylsulfanyl-N-[3-(trifluoromethyl)phenyl]carbonimidoyl]pyridine-4-carboxamide (1 g, 2.57 mmol, 91.4% yield, 95.0% purity) as a white solid, which was used in the next step without further purification. ¹H NMR (400 MHz, DMSO-d₆) δ ppm 10.62 (s, 1H), 8.28 (d, J=5.2 Hz, 1H), 8.06-7.50 (m, 4H), 7.44-7.30 (m, 1H), 7.24-7.11 (m, 1H), 3.87 (s, 3H), 3.34 (s, 3H); ES-LCMS m/z 369.9 [M+H]⁺.

Step 4: 5-(2-Methoxy-4-pyridyl)-N-[3-(trifluoromethyl)phenyl]-1,2,4-oxadiazol-3-amine

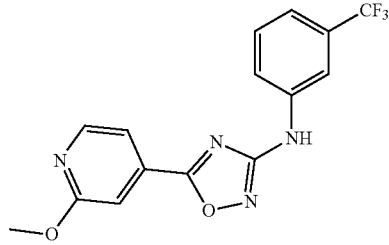 [SMILES: COc1cc(-c2nc(Nc3cccc(C(F)(F)F)c3)no2)ccn1]

To a solution of Hydroxylamine (268.27 mg, 8.12 mmol, 10 eq) and NaOAc (666.26 mg, 8.12 mmol, 10 eq) in MeOH (8 mL) was added 2-methoxy-N-[(Z)—C-methylsulfanyl-N-[3-(trifluoromethyl)phenyl]carbonimidoyl]pyridine-4-carboxamide (315.79 mg, 812.21 μmol, 95.0% purity, 1 eq) under N₂ atmosphere at 0° C. The mixture was stirred under N₂ atmosphere at 10° C. for 2 h. The reaction mixture was quenched by the addition of H₂O (20 mL) and extracted with EtOAc (30 mL×3). The combined organic layers were washed with brine (30 mL), dried over Na₂SO₄, filtered and concentrated under reduced pressure to yield 5-(2-methoxy-4-pyridyl)-N-[3-(trifluoromethyl)phenyl]-1,2,4-oxadiazol-3-amine (300 mg, 802.93 μmol, 98.9% yield, 90.0% purity) as a white solid, which was used in the next step without further purification. ES-LCMS m/z 370.5 [M+H]⁺.

Step 5: 4-[3-[3-(Trifluoromethyl)anilino]-1,2,4-oxadiazol-5-yl]-1H-pyridin-2-one

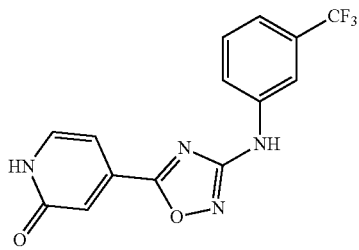 [SMILES: O=c1cc(-c2nc(Nc3cccc(C(F)(F)F)c3)no2)cc[nH]1]

To a solution of 5-(2-methoxy-4-pyridyl)-N-[3-(trifluoromethyl)phenyl]-1,2,4-oxadiazol-3-amine (50 mg, 133.82 μmol, 90.0% purity, 1 eq) in THF (2 mL) was added HBr (2.98 g, 2 mL, 33% purity). The mixture was stirred at 50° C. for 10 h. The reaction mixture was quenched by saturated aqueous NaHCO₃ (100 mL) and extracted with EtOAc (80 mL×3). The combined organic layers were washed with brine (80 mL), dried over Na₂SO₄, filtered and concentrated under reduced pressure to give a residue which was purified by preparative HPLC (column: YMC-Actus Triart C18 150*30 mm*5 μm; mobile phase: [water (0.225% FA)ACN]; B %: 45%-68%, 11 min) to yield 4-[3-[3-(trifluoromethyl)anilino]-1,2,4-oxadiazol-5-yl]-1H-pyridin-2-one (14.94 mg, 44.10 μmol, 32.9% yield, 95.1% purity) as a white solid. ¹H NMR (500 MHz, CD₃OD) δ ppm 7.87 (s, 1H), 7.71 (d, J=8.5 Hz, 1H), 7.65 (d, J=7.0 Hz, 1H), 7.52 (t, J=8.0 Hz, 1H), 7.31-7.23 (m, 2H), 6.97 (d, J=6.5 Hz, 1H); ES-LCMS m/z 323.0 [M+H]⁺.

I-136

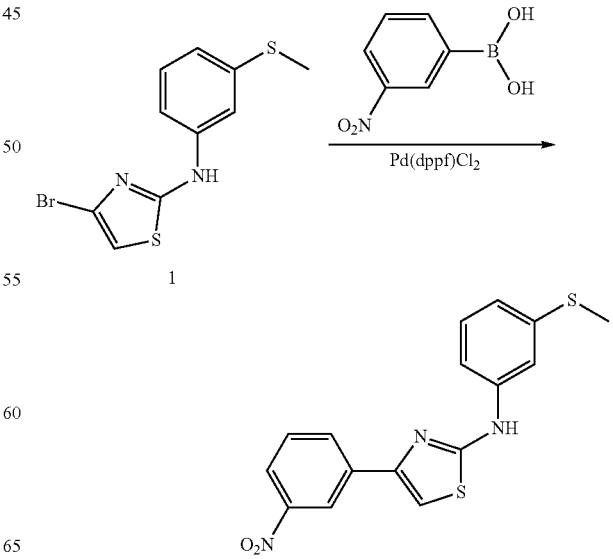

339

Step 1: N-(3-Methylsulfanylphenyl)-4-(3-nitrophenyl)thiazol-2-amine

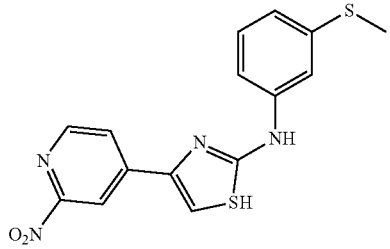 [SMILES: CSc1cccc(Nc2nc(-c3ccnc([N+](=O)[O-])c3)cs2)c1]

A mixture of 4-bromo-N-(3-methylsulfanylphenyl)thiazol-2-amine (220 mg, 657.31 μmol, 90%, 1 eq), (3-nitrophenyl)boronic acid (164.59 mg, 985.97 μmol, 1.5 eq), Pd(dppf)Cl$_2$ (4.81 mg, 6.57 μmol, 0.01 eq), Cs$_2$CO$_3$ (428.33 mg, 1.31 mmol, 2 eq) in 1,4-dioxane (10 mL) and H$_2$O (2 mL) was degassed and purged with N$_2$ for 3 times, and then the mixture was stirred at 80° C. for 12 h under N$_2$ atmosphere. The reaction mixture was quenched by addition of water (50 mL), extracted with EtOAc (30 mL×3). The combined organic layers were washed with brine (10 mL), dried over Na$_2$SO$_4$, filtered and concentrated under reduced pressure to yield a residue which was purified by preparative HPLC (column: Agela DuraShell C18 150*25 mm*5 μm; mobile phase: [water (0.04% NH$_3$H$_2$O+10 mM NH$_4$HCO$_3$)-ACN]; B %: 60%-90%, 10 min) and lyophilized to yield N-(3-methylsulfanylphenyl)-4-(3-nitrophenyl)thiazol-2-amine (45.27 mg, 126.81 μmol, 19.3% yield, 96.2% purity) as a yellow solid. $^1$H NMR (400 MHz, CDCl$_3$) δ ppm 8.72 (t, J=1.8 Hz, 1H), 8.21-8.15 (m, 2H), 7.59 (t, J=8.1 Hz, 1H), 7.49 (t, J=1.8 Hz, 1H), 7.32-7.28 (m, 1H), 7.21 (s, 1H), 7.12 (dd, J=1.3, 7.9 Hz, 1H), 7.04-6.98 (m, 2H), 2.57 (s, 3H); ES-LCMS m/z 344.1 [M+H]$^+$.

I-139

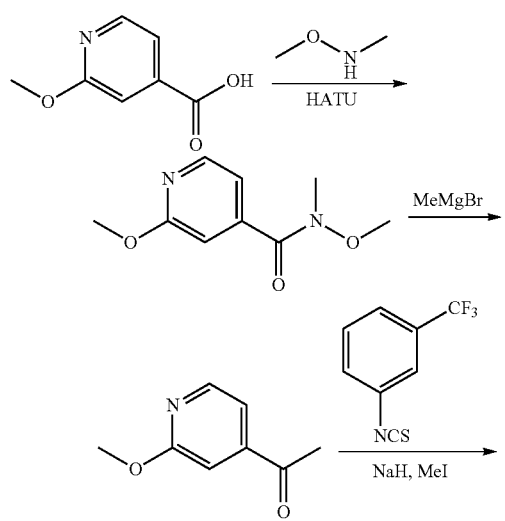

340

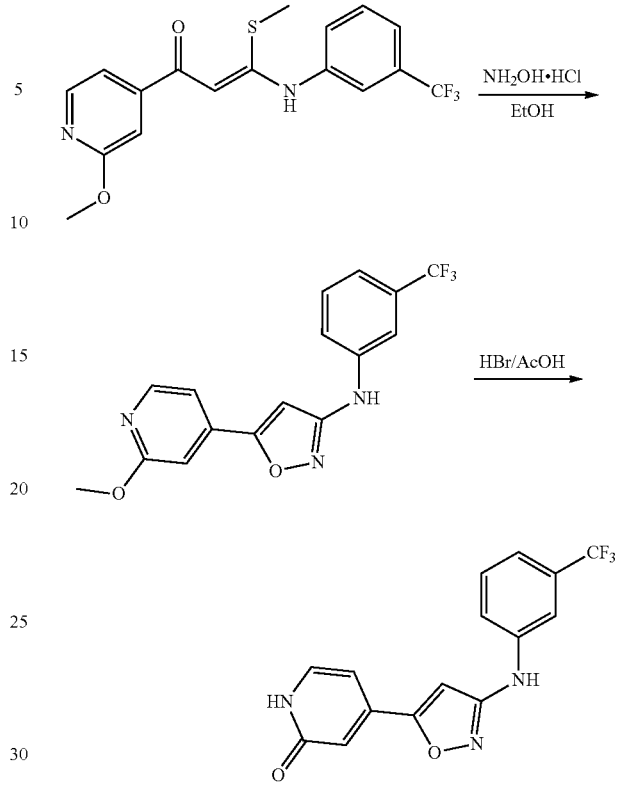

Step 1:
N,2-Dimethoxy-N-methyl-pyridine-4-carboxamide

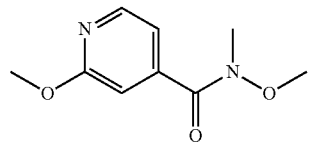

To a solution of 2-methoxypyridine-4-carboxylic acid (5 g, 32.65 mmol, 1 eq) in DMF (100 mL) was added N-methoxymethanamine (7.96 g, 81.63 mmol, 2.5 eq, HCl), HATU (18.62 g, 48.98 mmol, 1.5 eq) and DIEA (14.77 g, 114.28 mmol, 19.90 mL, 3.5 eq). The mixture was stirred at 60° C. for 12 h. The reaction mixture was quenched by the addition of water (50 mL) and extracted with EtOAc (50 mL×3). The combined organic layers were washed with brine (20 mL), dried over Na$_2$SO$_4$, filtered and concentrated under reduced pressure to yield a residue which was purified by flash silica gel chromatography (from PE/EtOAc=100/1 to 3/1, TLC: PE/EtOAc=1/1, R$_f$=0.40) to yield N,2-dimethoxy-N-methyl-pyridine-4-carboxamide (6.8 g, 31.19 mmol, 95.5% yield, 90.0% purity) as colorless oil. $^1$H NMR (400 MHz, DMSO-d$_6$) δ ppm 8.27-8.22 (m, 1H), 7.08 (dd, J=1.2, 5.1 Hz, 1H), 6.91 (d, J=0.8 Hz, 1H), 3.88 (s, 3H), 3.55 (s, 3H), 3.25 (s, 3H); ES-LCMS m/z 197.3 [M+H]$^+$.

341

Step 2: 1-(2-Methoxy-4-pyridyl)ethanone

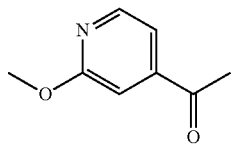

To a solution of N,2-dimethoxy-N-methyl-pyridine-4-carboxamide (5.0 g, 22.94 mmol, 90% purity, 1 eq) in THF (50 mL) was added MeMgBr (26.76 mL, 3.5 eq, 3 M in THF) dropwise under $N_2$ atmosphere at 0° C. The mixture was stirred under $N_2$ atmosphere at 0° C. for 2 h. TLC (PE/EtOAc=1/1, $R_f$=0.76) indicated the starting material was consumed completely and one new spot formed. The mixture was poured into sat.aq.$Na_2CO_3$ (100 mL) and extracted with EtOAc (50 mL×2). The combined organic layers were washed with brine (50 mL), dried over $Na_2SO_4$, filtered and concentrated under reduced pressure to yield 1-(2-methoxy-4-pyridyl)ethanone (3.5 g, 20.84 mmol, 90.9% yield, 90.0% purity) as light yellow oil, which was used in the next step without further purification. $^1$H NMR (400 MHz, $CDCl_3$) δ ppm 8.33-8.27 (m, 1H), 7.30 (dd, J=1.5, 5.4 Hz, 1H), 7.17 (s, 1H), 3.97 (s, 3H), 2.58 (s, 3H).

Step 3: (Z)-1-(2-Methoxy-4-pyridyl)-3-methylsulfanyl-3-[3-(trifluoromethyl)anilino]prop-2-en-1-one

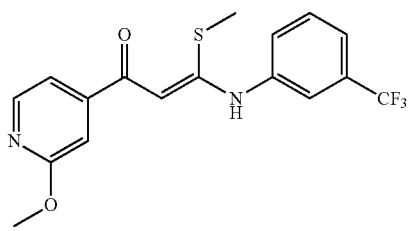 [SMILES: COc1cc(C(=O)/C=C(/Nc2cccc(C(F)(F)F)c2)SC)ccn1]

To a solution of 1-(2-methoxy-4-pyridyl)ethanone (455 mg, 2.71 mmol, 90% purity, 1 eq) in DMF (10 mL) was added NaH (129.92 mg, 3.25 mmol, 60% purity, 1.2 eq). The mixture was stirred at 0° C. for 5 min. 1-Isothiocyanato-3-(trifluoromethyl)benzene (550 mg, 2.71 mmol, 410.45 µL, 1 eq) was added and the mixture was stirred at 15° C. for 30 min. MeI (385.00 mg, 2.71 mmol, 168.86 µL, 1 eq) was added and the resulting mixture was stirred at 15° C. for 30 min. The mixture was quenched with water (10 mL) and extracted with EtOAc (10 mL×3). The combined organic layers were dried over $Na_2SO_4$, filtered and concentrated under reduced pressure to yield a residue which was purified by flash silica gel chromatography (from PE/EtOAc=100/1 to 10/1, TLC: PE/EtOAc=3/1, $R_f$=0.50) to yield (Z)-1-(2-methoxy-4-pyridyl)-3-methylsulfanyl-3-[3-(trifluoromethyl)anilino]prop-2-en-1-one (550 mg, 1.34 mmol, 49.6% yield, 90.0% purity) as a yellow solid. $^1$H NMR (400 MHz, DMSO-$d_6$) δ ppm 13.54 (s, 1H), 8.30 (d, J=4.7 Hz, 1H), 7.74 (s, 1H), 7.71-7.65 (m, 3H), 7.46 (dd, J=1.4, 5.3 Hz, 1H), 7.29 (s, 1H), 6.08 (s, 1H), 3.90 (s, 3H), 2.59 (s, 3H); ES-LCMS m/z 369.6 [M+H]$^+$.

342

Step 4: 5-(2-Methoxy-4-pyridyl)-N-[3-(trifluoromethyl)phenyl]isoxazol-3-amine

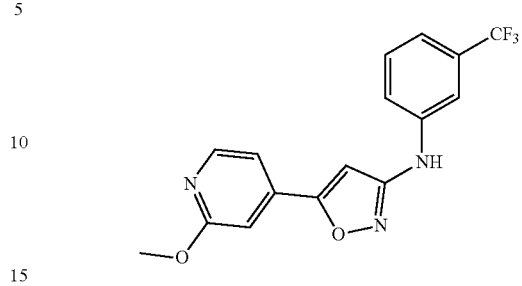

To a solution of (Z)-1-(2-methoxy-4-pyridyl)-3-methylsulfanyl-3-[3-(trifluoromethyl)anilino]prop-2-en-1-one (500 mg, 1.22 mmol, 90% purity, 1 eq) in EtOH (10 mL) was added $NH_2OH\cdot HCl$ (339.55 mg, 4.89 mmol, 4 eq) and KOH (205.63 mg, 3.66 mmol, 3 eq). The mixture was stirred at 100° C. for 12 h. The mixture was diluted with water (10 mL) and extracted with EtOAc (10 mL×3). The combined organic layers were dried over $Na_2SO_4$, filtered and concentrated under reduced pressure to yield a residue which was purified by preparative HPLC (column: Welch Xtimate C18 150*25 mm*5 um; mobile phase: [water (10 mM $NH_4HCO_3$)-ACN]; B %: 45%-75%, 10 min), followed by lyophilization to yield 5-(2-methoxy-4-pyridyl)-N-[3-(trifluoromethyl)phenyl]isoxazol-3-amine (60 mg, 170.01 µmol, 13.9% yield, 95.0% purity) as a white solid. $^1$H NMR (400 MHz, $CDCl_3$) δ ppm 8.28 (d, J=5.3 Hz, 1H), 7.64 (s, 1H), 7.58 (d, J=8.1 Hz, 1H), 7.46 (t, J=7.9 Hz, 1H), 7.29-7.27 (m, 1H), 7.20 (dd, J=1.4, 5.3 Hz, 1H), 7.09 (s, 1H), 6.41 (s, 1H), 6.38 (s, 1H), 3.99 (s, 3H).

Step 5: 4-[3-[3-(Trifluoromethyl)anilino]isoxazol-5-yl]-1H-pyridin-2-one

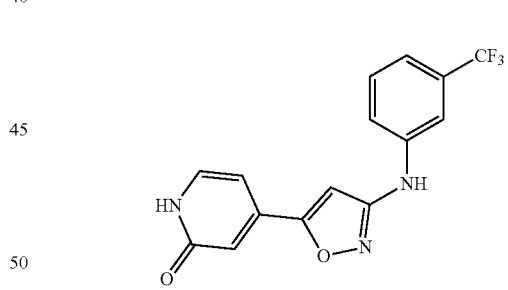

A solution of 5-(2-methoxy-4-pyridyl)-N-[3-(trifluoromethyl)phenyl]isoxazol-3-amine (50 mg, 134.22 µmol, 90% purity, 1 eq) in THF (1.5 mL) and HBr/AcOH (1.5 mL) was stirred at 70° C. for 12 h. The mixture was diluted with water (5 mL) and extracted with EtOAc (5 mL×3). The combined organic layers were dried over $Na_2SO_4$, filtered and concentrated under reduced pressure to yield a residue which was purified by preparative HPLC (column: Phenomenex Synergi C18 150*30 mm*4 um; mobile phase: [water (0.1% TFA)-ACN]; B %: 35%-55%, 9 min). The desired fraction was basified with saturated aqueous $NaHCO_3$ until pH=8 and extracted with EtOAc (25 mL×3). The combined organic layers were dried over $Na_2SO_4$, filtered and concentrated under reduced pressure, followed by lyophilization to yield 4-[3-[3-(trifluoromethyl)anilino]isoxazol-5-yl]-1H- pyridin-2-one (29.53 mg, 91.92 µmol, 68.5% yield, 100.0% purity) as a white solid. ¹H NMR (400 MHz, DMSO-d$_6$) δ ppm 11.85 (br s, 1H), 9.84 (s, 1H), 7.92 (s, 1H), 7.67 (d, J=7.6 Hz, 1H), 7.59-7.47 (m, 2H), 7.25 (d, J=7.5 Hz, 1H), 6.88-6.81 (m, 2H), 6.62 (d, J=6.7 Hz, 1H); ES-LCMS m/z 322.1 [M+H]$^+$.

I-143 and I-144

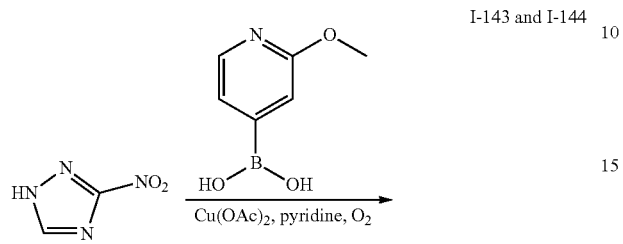

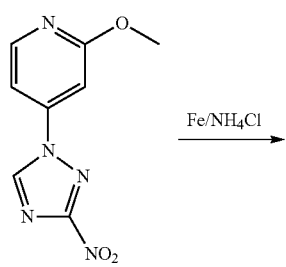

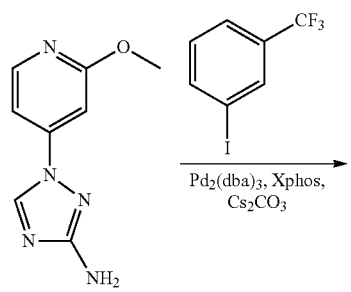

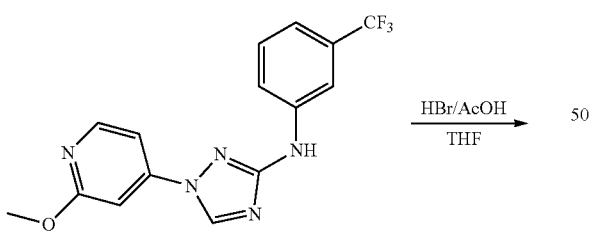

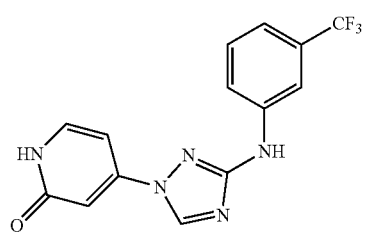

Step 1:
2-Methoxy-4-(3-nitro-1,2,4-triazol-1-yl)pyridine

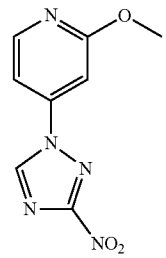 [SMILES: COc1cc(-n2cnc([N+](=O)[O-])n2)ccn1]

To a solution of (2-methoxy-4-pyridyl)boronic acid (4 g, 26.15 mmol, 1.2 eq) and 3-nitro-1H-1,2,4-triazole (2.49 g, 21.79 mmol, 1 eq) in DCM (50 mL) was added Cu(OAc)$_2$ (5.94 g, 32.69 mmol, 1.5 eq) and pyridine (3.45 g, 43.59 mmol, 3.52 mL, 2.0 eq) under O$_2$ (15 Psi). The mixture was stirred under O$_2$ (15 Psi) at 10° C. for 10 h. TLC (DCM/MeOH=10/1, R$_f$=0.55) showed that new point was formed and the start material was consumed completely. The reaction mixture was quenched by the addition of H$_2$O (200 mL) and extracted with EtOAc (300 mL×3). The combined organic layers were washed with brine (300 mL), dried over Na$_2$SO$_4$, filtered and concentrated under reduced pressure to yield a residue which was purified by preparative TLC (DCM/MeOH=5/1, TLC: DCM/MeOH=10/1, R$_f$=0.55) to yield 2-methoxy-4-(3-nitro-1,2,4-triazol-1-yl)pyridine (1.2 g, 5.43 mmol, 24.9% yield, 100.0% purity) as a white solid. ¹H NMR (400 MHz, DMSO-d$_6$) δ ppm 9.77 (s, 1H), 8.41 (d, J=5.6 Hz, 1H), 7.58 (dd, J=2.0, 6.0 Hz, 1H), 7.42 (d, J=1.2 Hz, 1H), 3.95 (s, 3H).

Step 2:
1-(2-Methoxy-4-pyridyl)-1,2,4-triazol-3-amine

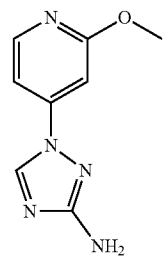

To a solution of 2-methoxy-4-(3-nitro-1,2,4-triazol-1-yl)pyridine (1 g, 4.52 mmol, 100% purity, 1 eq) in MeOH (25 mL) was added Pd/C (10% purity) under H$_2$ (15 Psi). The mixture was stirred under H$_2$ (15 Psi) at 10° C. for 2 h. TLC (DCM/MeOH=10/1, R$_f$=0.35) showed that new point was formed and the start material was consumed completely. The mixture was filtrated and concentrated to yield 1-(2-methoxy-4-pyridyl)-1,2,4-triazol-3-amine (850 mg, 4.22 mmol, 93.4% yield, 95.0% purity) as a white solid, which was used in the next step without further purification. ¹H NMR (400 MHz, DMSO-d$_6$) δ ppm 9.03 (s, 1H), 8.20 (d, J=5.6 Hz, 1H), 7.35 (dd, J=2.0, 6.0 Hz, 1H), 7.08 (d, J=2.0 Hz, 1H), 5.93 (s, 2H), 3.88 (s, 3H).

Step 3: 1-(2-Methoxy-4-pyridyl)-N-[3-(trifluoromethyl)phenyl]-1,2,4-triazol-3-amine

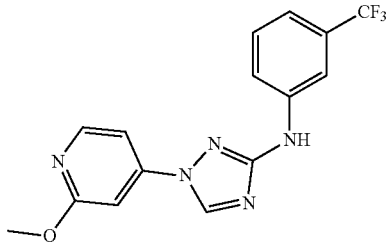 [SMILES: COc1cc(-n2cnc(Nc3cccc(C(F)(F)F)c3)n2)ccn1]

To a solution of 1-(2-methoxy-4-pyridyl)-1,2,4-triazol-3-amine (500 mg, 2.48 mmol, 95% purity, 1 eq) and 1-iodo-3-(trifluoromethyl)benzene (675.78 mg, 2.48 mmol, 357.56 μL, 1 eq) in 1,4-dioxane (8 mL) was added Cs$_2$CO$_3$ (1.21 g, 3.73 mmol, 1.5 eq), XPhos (59.22 mg, 124.22 μmol, 0.05 eq) and Pd$_2$(dba)$_3$ (113.75 mg, 124.22 μmol, 0.05 eq) under N$_2$ atmosphere. The mixture was stirred under N$_2$ atmosphere at 80° C. for 2 h. TLC (PE/EtOAc=2/1, R$_f$=0.4) showed that new point was formed and the start material was consumed completely. The reaction mixture was quenched by the addition of H$_2$O (20 mL) and extracted with EtOAc (30 mL×3). The combined organic layers were washed with brine (30 mL), dried over Na$_2$SO$_4$, filtered and concentrated under reduced pressure to give a residue which was purified by flash silica gel chromatography (from PE/EtOAc=100/1 to, TLC: PE/EtOAc=2/1, R$_f$=0.4) to yield a residue which was purified by preparative HPLC (column: Phenomenex Synergi C18 150*30 mm*4 μm; mobile phase: [water (0.05% HCl)-ACN]; B %: 53%-73%, 9 min) to yield 1-(2-methoxy-4-pyridyl)-N-[3-(trifluoromethyl)phenyl]-1,2,4-triazol-3-amine (520 mg, 1.51 mmol, 60.9% yield, 97.6% purity) as a white solid. $^1$H NMR (400 MHz, DMSO-d$_6$) δ ppm 10.07 (s, 1H), 9.36 (s, 1H), 8.31 (d, J=6.0 Hz, 1H), 8.04 (s, 1H), 7.88 (d, J=8.4 Hz, 1H), 7.58-7.46 (m, 2H), 7.25 (d, J=1.2 Hz, 1H), 7.21 (d, J=7.6 Hz, 1H), 3.92 (s, 3H); ES-LCMS m/z 335.9 [M+H]$^+$.

Step 4: 4-[3-[3-(Trifluoromethyl)anilino]-1,2,4-triazol-1-yl]-1H-pyridin-2-one

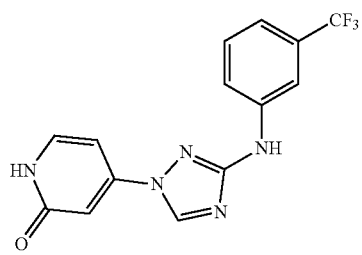 [SMILES: O=c1cc(-n2cnc(Nc3cccc(C(F)(F)F)c3)n2)cc[nH]1]

To a solution of 1-(2-methoxy-4-pyridyl)-N-[3-(trifluoromethyl)phenyl]-1,2,4-triazol-3-amine (200 mg, 581.90 μmol, 97.55% purity, 1 eq) in THF (8 mL) was added HBr (10.57 g, 43.11 mmol, 7.09 mL, 33% purity, 74.09 eq). The mixture was stirred at 60° C. for 5 h. The reaction mixture was quenched by the addition of H$_2$O (20 mL) and extracted with EtOAc (30 mL×3). The combined organic layers were washed with brine (30 mL), dried over Na$_2$SO$_4$, filtered and concentrated under reduced pressure to yield a residue which was purified by preparative HPLC (column: Phenomenex Synergi C18 150*30 mm*4 μm; mobile phase: [water (0.05% HCl)-ACN]; B %: 40%-60%, 9 min) to yield 4-[3-[3-(trifluoromethyl)anilino]-1,2,4-triazol-1-yl]-1H-pyridin-2-one (126.01 mg, 388.86 μmol, 66.8% yield, 99.1% purity) as a white solid. $^1$H NMR (400 MHz, DMSO-d$_6$) δ ppm 11.73 (s, 1H), 10.07 (s, 1H), 9.27 (s, 1H), 8.03 (s, 1H), 7.86 (d, J=8.4 Hz, 1H), 7.60 (d, J=7.2 Hz, 1H), 7.53 (t, J=8.0 Hz, 1H), 7.21 (d, J=7.6 Hz, 1H), 6.78 (dd, J=2.4, 7.2 Hz, 1H), 6.71 (d, J=1.6 Hz, 1H); ES-LCMS m/z 322.0 [M+H]$^+$.

I-145

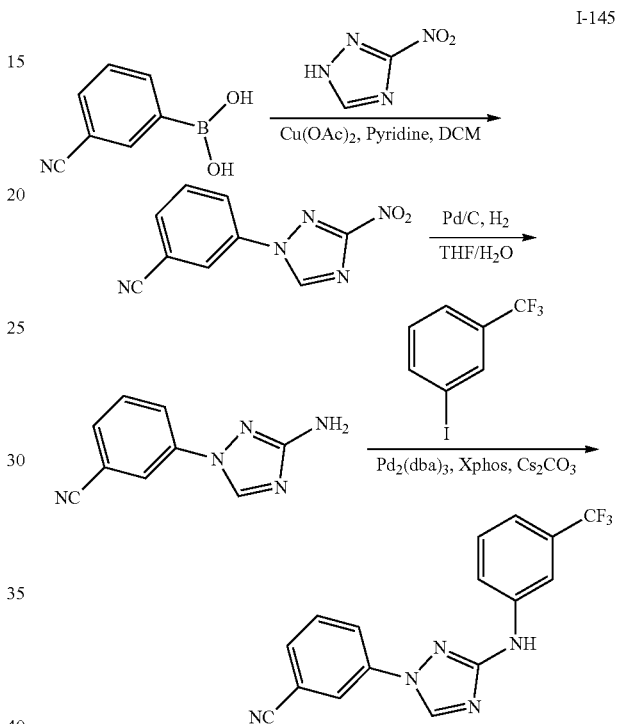

Step 1: 3-(3-Nitro-1,2,4-triazol-1-yl)benzonitrile

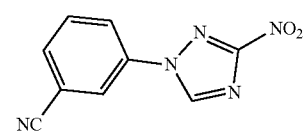

To a solution of (3-cyanophenyl)boronic acid (4 g, 27.22 mmol, 1.2 eq) and 3-nitro-1H-1,2,4-triazole (2.59 g, 22.69 mmol, 1 eq) in DCM (25 mL) was added pyridine (3.59 g, 45.37 mmol, 3.66 mL, 2.0 eq) and Cu(OAc)$_2$ (6.18 g, 34.03 mmol, 1.5 eq) with stirred under O$_2$ (15 Psi). The mixture was stirred at 15° C. for 12 h under O$_2$ (15 Psi) atmosphere. TLC (DCM/MeOH=10/1, R$_f$=0.5) showed that new point was formed and the start material was consumed completely. The reaction mixture was quenched by the addition of H$_2$O (200 mL) and extracted with EtOAc (200 mL×3). The combined organic layers were washed with brine (200 mL), dried over Na$_2$SO$_4$, filtered and concentrated under reduced pressure to yield a residue which was purified by flash silica gel chromatography (from PE/EtOAc=100/1 to 2/1, TLC: DCM/MeOH=10/1, R$_f$=0.5) to yield 3-(3-nitro-1,2,4-triazol- 1-yl)benzonitrile (700 mg, 3.25 mmol, 14.3% yield, 100.0% purity) as a white solid. ¹H NMR (400 MHz, DMSO-d₆) δ ppm 9.66 (s, 1H), 8.55-8.45 (m, 1H), 8.31-8.21 (m, 1H), 8.09-8.00 (m, 1H), 7.92-7.81 (m, 1H).

Step 2: 3-(3-Amino-1,2,4-triazol-1-yl)benzonitrile

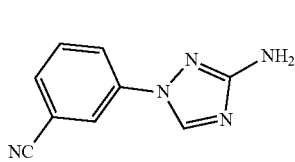 [SMILES: N#Cc1cccc(-n2cnc([N+](=O)[O-])n2)c1]

A mixture of 3-(3-nitro-1,2,4-triazol-1-yl)benzonitrile (300 mg, 1.39 mmol, 100% purity, 1 eq) and Pd/C (1.48 g, 1.39 mmol, 10% purity, 1.0 eq) in MeOH (25 mL) was degassed and purged with $H_2$ (15 Psi) for 3 times. The mixture was stirred under $H_2$ (15 Psi) atmosphere at 10° C. for 2 h. TLC (PDCM/MeOH=10/1, $R_f$=0.4) showed that new point was formed and the start material was consumed completely. The mixture was filtrated and the filtrate was concentrated to yield 3-(3-amino-1,2,4-triazol-1-yl)benzonitrile (250 mg, 1.28 mmol, 91.9% yield, 95.0% purity) as a white solid, which was used in the next step without further purification. ¹H NMR (400 MHz, DMSO-d₆) δ ppm 8.94 (s, 1H), 8.20 (s, 1H), 8.09-7.99 (m, 1H), 7.76-7.64 (m, 2H), 5.84 (s, 2H).

Step 3: 3-[3-[3-(Trifluoromethyl)anilino]-1,2,4-triazol-1-yl]benzonitrile

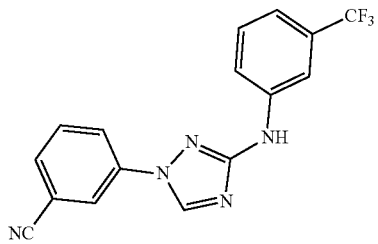 [SMILES: N#Cc1cccc(-n2cnc(Nc3cccc(C(F)(F)F)c3)n2)c1]

To a solution of 3-(3-amino-1,2,4-triazol-1-yl)benzonitrile (200 mg, 864.00 µmol, 80% purity, 1 eq) and 1-iodo-3-(trifluoromethyl)benzene (235.01 mg, 864.00 µmol, 124.35 µL, 1 eq) in 1,4-dioxane (2 mL) was added $Cs_2CO_3$ (422.26 mg, 1.30 mmol, 1.5 eq), XPhos (20.59 mg, 43.20 µmol, 0.05 eq) and $Pd_2(dba)_3$ (39.56 mg, 43.20 µmol, 0.05 eq) under $N_2$ atmosphere. The mixture was stirred under $N_2$ atmosphere at 80° C. for 2 h. The reaction mixture was quenched by the addition of $H_2O$ (20 mL) and extracted with EtOAc (30 mL×3). The combined organic layers were washed with brine (30 mL), dried over $Na_2SO_4$, filtered and concentrated under reduced pressure to yield a residue which was purified by preparative HPLC (column: Phenomenex Synergi C18 150*30 mm*4 µm; mobile phase: [water (0.05% HCl)-ACN]; B %: 55%-75%, 9 min) to yield 3-[3-[3-(trifluoromethyl)anilino]-1,2,4-triazol-1-yl]benzonitrile (33.56 mg, 99.85 µmol, 11.6% yield, 97.9% purity) as a white solid. ¹H NMR (400 MHz, DMSO-d₆) δ ppm 10.02 (s, 1H), 9.26 (s, 1H), 8.36 (s, 1H), 8.21-8.15 (m, 1H), 8.00 (s, 1H), 7.94 (d, J=8.4 Hz, 1H), 7.87-7.75 (m, 2H), 7.53 (t, J=8.0 Hz, 1H), 7.20 (d, J=7.6 Hz, 1H); ES-LCMS m/z 329.9 [M+H]⁺.

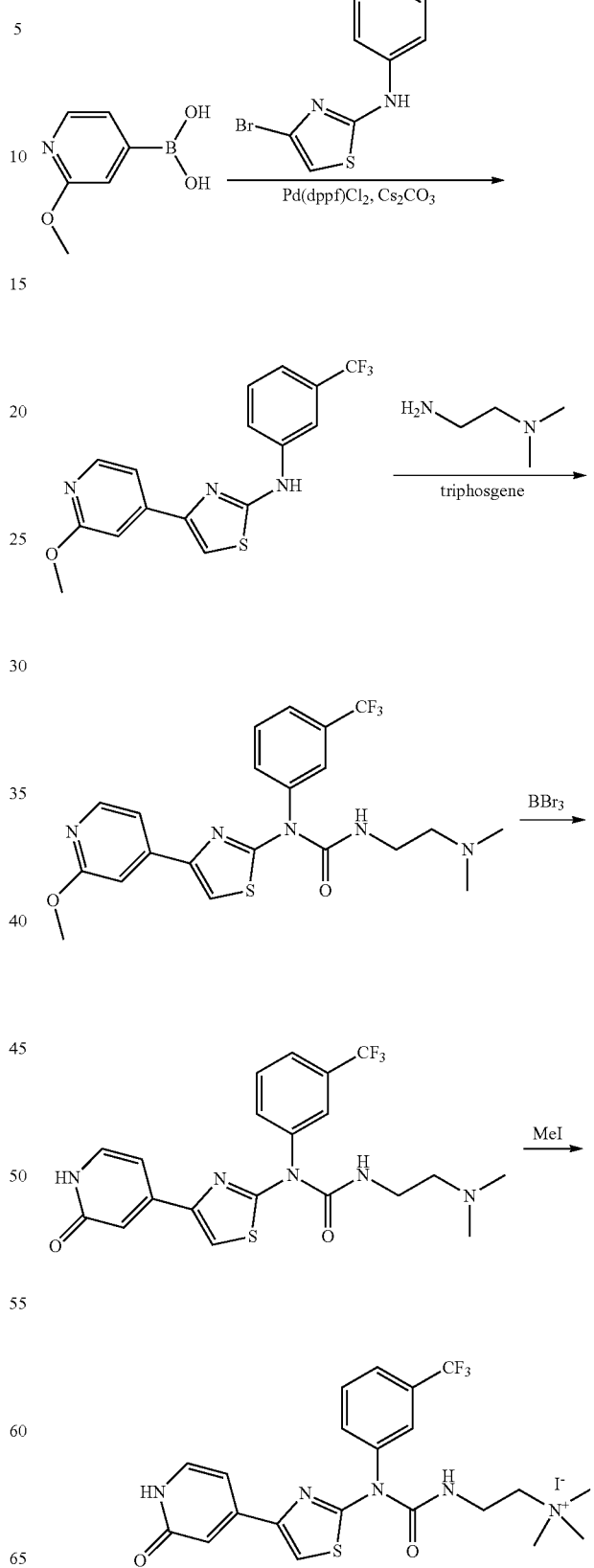

I-146

Step 1: 4-(2-Methoxy-4-pyridyl)-N-[3-(trifluoromethyl)phenyl]thiazol-2-amine

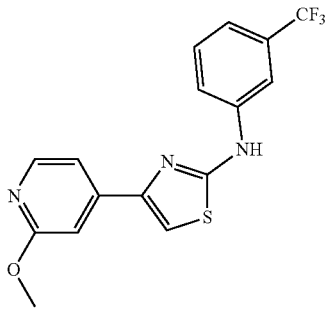 [SMILES: COc1cc(-c2csc(Nc3cccc(C(F)(F)F)c3)n2)ccn1]

To a solution of 4-bromo-N-[3-(trifluoromethyl)phenyl]thiazol-2-amine (600 mg, 1.67 mmol, 90% purity, 0.84 eq) in 1,4-dioxane (5 mL) and H$_2$O (1 mL) were added (2-methoxy-4-pyridyl)boronic acid (350 mg, 2.29 mmol, 1.15 eq) and Cs$_2$CO$_3$ (1.30 g, 3.98 mmol, 2 eq) and Pd(dppf)Cl$_2$ (72.80 mg, 99.50 µmol, 0.05 eq). The mixture was stirred under N$_2$ atmosphere at 110° C. for 16 h. The mixture was concentrated and water (80 mL) was added. The mixture was extracted with EtOAc (50 mL×3). The combined organic layers were washed with brine (50 mL), dried over Na$_2$SO$_4$, filtered and concentrated to yield a residue which was purified by flash silica gel chromatography (From PE/EtOAc=1/0 to 5/1, R$_f$=0.15) to yield 4-(2-methoxy-4-pyridyl)-N-[3-(trifluoromethyl)phenyl]thiazol-2-amine (390 mg, 1.01 mmol, 50.7% yield, 90.9% purity) as a yellow solid. $^1$H NMR (400 MHz, DMSO-d$_6$) δ ppm 10.76 (s, 1H), 8.39 (s, 1H), 8.22 (d, J=4.7 Hz, 1H), 7.85-7.80 (m, 2H), 7.60 (t, J=7.8 Hz, 1H), 7.48 (dd, J=1.4, 5.3 Hz, 1H), 7.32 (d, J=7.8 Hz, 1H), 7.28 (s, 1H), 3.90 (s, 3H); ES-LCMS m/z 352.6 [M+H]$^+$.

Step 2: 3-[2-(Dimethylamino)ethyl]-1-[4-(2-methoxy-4-pyridyl)thiazol-2-yl]-1-[3-(trifluoromethyl)phenyl]urea

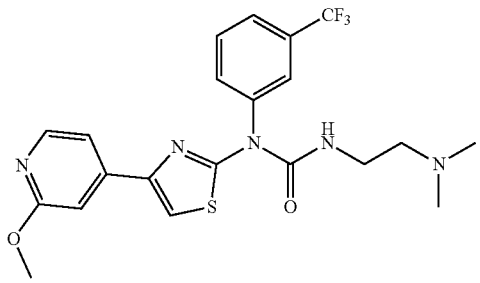 [SMILES: COc1cc(-c2csc(N(C(=O)NCCN(C)C)c3cccc(C(F)(F)F)c3)n2)ccn1]

To a solution of 4-(2-methoxy-4-pyridyl)-N-[3-(trifluoromethyl)phenyl]thiazol-2-amine (390 mg, 1.01 mmol, 90.9% purity, 1 eq) in THF (10 mL) was added bis(trichloromethyl) carbonate (449.13 mg, 1.51 mmol, 1.5 eq), DIEA (391.21 mg, 3.03 mmol, 527.24 µL, 3 eq) and stirred at 80° C. for 2 h. The reaction mixture was concentrated to yield (4-(2-methoxypyridin-4-yl)thiazol-2-yl)(3-(trifluoromethyl)phenyl)carbamic chloride (crude). To a solution of N',N'-dimethylethane-1,2-diamine (71.16 mg, 807.20 µmol, 88.17 µL, 0.8 eq), DIEA (391.21 mg, 3.03 mmol, 527.24 µL, 3 eq) and DMAP (12.33 mg, 100.90 µmol, 0.1 eq) in DCM (15 mL) was added (4-(2-methoxypyridin-4-yl)thiazol-2-yl)(3-(trifluoromethyl)phenyl)carbamic chloride (crude) in DCM (15 mL) and stirred at 25° C. for 1 h. To the mixture was added water (30 mL) and extracted with ethyl acetate (30 mL×3). The combined organic phase was washed with brine (20 mL), dried over anhydrous Na$_2$SO$_4$, filtered and concentrated in vacuum to yield a residue which was purified by flash silica gel chromatography (From EtOAc/MeOH=1/0 to 1/1, R$_f$=0.38) to yield 3-[2-(dimethylamino)ethyl]-1-[4-(2-methoxy-4-pyridyl)thiazol-2-yl]-1-[3-(trifluoromethyl)phenyl]urea (120 mg, 246.45 µmol, 24.4% yield, 95.6% purity) as a red solid. $^1$H NMR (400 MHz, CDCl$_3$) δ ppm 9.14 (s, 1H), 8.18 (d, J=5.1 Hz, 1H), 7.80-7.75 (m, 1H), 7.72-7.66 (m, 2H), 7.64-7.59 (m, 1H), 7.32-7.27 (m, 2H), 7.19 (s, 1H), 3.98 (s, 3H), 3.58-3.48 (m, 2H), 2.54 (t, J=5.9 Hz, 2H), 2.34 (s, 6H); ES-LCMS m/z 466.1 [M+H]$^+$.

Step 3: 3-[2-(Dimethylamino)ethyl]-1-[4-(2-oxo-1H-pyridin-4-yl)thiazol-2-yl]-1-[3-(trifluoromethyl)phenyl]urea

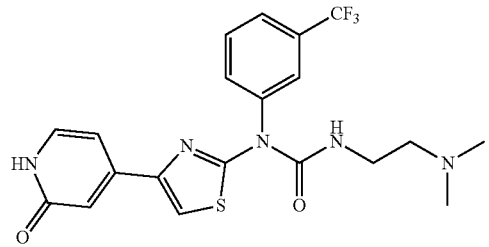 [SMILES: CN(C)CCNC(=O)N(c1cccc(C(F)(F)F)c1)c1nc(-c2cc[nH]c(=O)c2)cs1]

To a solution of 3-[2-(dimethylamino)ethyl]-1-[4-(2-methoxy-4-pyridyl)thiazol-2-yl]-1-[3-(trifluoromethyl)phenyl]urea (120 mg, 246.45 µmol, 95.6% purity, 1 eq) was added HBr$_3$ (5 mL, 33% purity). The mixture was stirred at 70° C. for 12 h under N$_2$. The mixture neutralized with 2 N NaOH to pH=8. The residue was partitioned between EtOAc (100 mL) and saturated aqueous NaHCO$_3$ solution (50 mL). The organic layer was washed with brine (50 mL), dried over Na$_2$SO$_4$, filtered and concentrated to yield a residue which was purified by preparative HPLC (column: Agela DuraShell C18 150*25 mm*5 um; mobile phase: [water (0.04% NH$_3$H$_2$O+10 mM NH$_4$HCO$_3$)-ACN]; B %: 28%-58%, 10 min) to yield 3-[2-(dimethylamino)ethyl]-1-[4-(2-oxo-1H-pyridin-4-yl)thiazol-2-yl]-1-[3-(trifluoromethyl)phenyl]urea (42 mg, 91.91 µmol, 37.3% yield, 98.8% purity) as a white solid. $^1$H NMR (400 MHz, CDCl$_3$) δ ppm 11.97 (s, 1H), 8.40 (s, 1H), 7.80-7.76 (m, 1H), 7.73-7.67 (m, 2H), 7.63 (s, 1H), 7.33 (d, J=6.3 Hz, 1H), 7.22 (s, 1H), 7.06 (s, 1H), 6.70 (s, 1H), 3.49 (s, 2H), 2.51 (s, 2H), 2.30 (s, 6H); ES-LCMS m/z 452.2 [M+H]$^+$.

Step 4: 3-(2-BLAHethyl)-1-[4-(2-oxo-1H-pyridin-4-yl)thiazol-2-yl]-1-[3-(trifluoromethyl)phenyl]urea

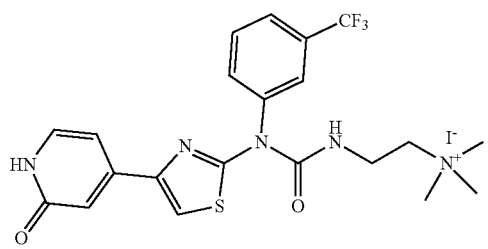 [SMILES: C[N+](C)(C)CCNC(=O)N(c1cccc(C(F)(F)F)c1)c1nc(-c2cc[nH]c(=O)c2)cs1 ; [I-]]

To a solution of 3-[2-(dimethylamino)ethyl]-1-[4-(2-oxo-1H-pyridin-4-yl)thiazol-2-yl]-1-[3-(trifluoromethyl)phenyl]urea (42 mg, 91.91 μmol, 98.8% purity, 1 eq) in MeCN (4 mL) was added MeI (65.23 mg, 459.57 μmol, 28.61 μL, 5 eq). The mixture was stirred under $N_2$ atmosphere at 25° C. for 2 h. The solution was diluted with water (10 mL) and lyophilization to yield 3-(2-BLAHethyl)-1-[4-(2-oxo-1H-pyridin-4-yl)thiazol-2-yl]-1-[3-(trifluoromethyl)phenyl]urea (25.59 mg, 43.12 μmol, 46.9% yield, 100.0% purity) as a brown solid. $^1$H NMR (400 MHz, DMSO-$d_6$) δ ppm 11.41 (s, 1H), 7.97-7.77 (m, 5H), 7.31 (d, J=6.7 Hz, 1H), 6.92 (s, 1H), 6.48-6.37 (m, 2H), 3.52 (s, 2H), 3.44 (d, J=5.5 Hz, 2H), 3.08 (s, 9H); ES-LCMS m/z 466.2 [M-I]$^+$.

I-147

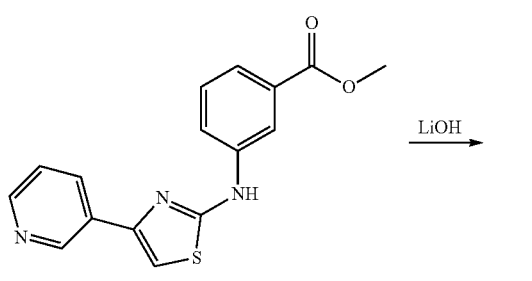

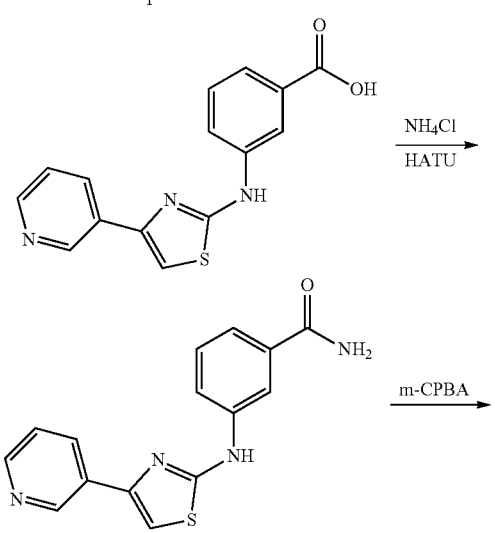

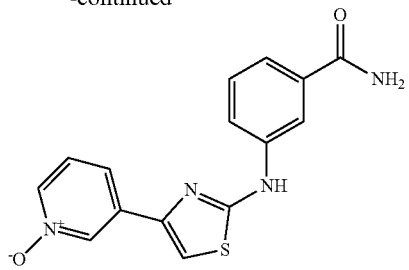

Step 1: 3-[[4-(3-Pyridyl)thiazol-2-yl]amino]benzoic acid

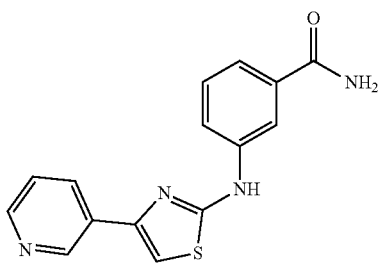 [SMILES: NC(=O)c1cccc(Nc2nc(-c3cccnc3)cs2)c1]

To a solution of methyl 3-[[4-(3-pyridyl)thiazol-2-yl]amino]benzoate (800 mg, 2.31 mmol, 90% purity, 1 eq) in THF (10 mL) and MeOH (2 mL) was added LiOH.H$_2$O (1 M, 11.56 mL, 5 eq). The mixture was stirred at 60° C. for 12 h. The reaction mixture was concentrated to yield a residue. To the residue was added H$_2$O (30 mL) and 1 N HCl (20 mL, adjusted pH to 6). The mixture was filtered and the solid was dried under reduced pressure to yield 3-[[4-(3-pyridyl)thiazol-2-yl]amino]benzoic acid (800 mg, crude) as a yellow solid, which was used in the next step without further purification. $^1$H NMR (500 MHz, DMSO-$d_6$) δ ppm 13.55-12.33 (m, 1H), 10.68 (s, 1H), 9.17 (s, 1H), 8.52 (d, J=4.3 Hz, 1H), 8.43 (s, 1H), 8.28 (d, J=7.9 Hz, 1H), 7.98 (d, J=7.8 Hz, 1H), 7.59-7.53 (m, 2H), 7.49-7.42 (m, 2H); ES-LCMS m/z 298.0 [M+H]$^+$.

Step 2: 3-[[4-(3-Pyridyl)thiazol-2-yl]amino]benzamide

To a solution of 3-[[4-(3-pyridyl)thiazol-2-yl]amino]benzoic acid (400 mg, 1.35 mmol, N/A purity, 1 eq) in DMF (5 mL) was added NH$_4$Cl (287.84 mg, 5.38 mmol, 4 eq), DIEA (173.87 mg, 1.35 mmol, 234.32 μL, 1 eq) and HATU (613.83 mg, 1.61 mmol, 1.2 eq). The mixture was stirred at 15° C. for 12 h. The reaction mixture was concentrated to yield a residue which was added H$_2$O (20 mL) and extracted with EtOAc (20 mL×3). The combine organic layers were washed with brine (20 mL), dried over anhydrous $Na_2SO_4$, filtered and concentrated to yield a residue which was purified by flash silica gel chromatography (from pure EtOAc to EtOAc/MeOH=7/1, TLC: EtOAc/MeOH=5/1, $R_f$=0.50) to yield 3-[[4-(3-pyridyl)thiazol-2-yl]amino]benzamide (200 mg, 539.91 μmol, 40.1% yield, 80.0% purity) as a yellow solid. $^1$H NMR (500 MHz, DMSO-$d_6$) δ ppm 10.52 (s, 1H), 9.16 (d, J=1.8 Hz, 1H), 8.52 (dd, J=1.4, 4.7 Hz, 1H), 8.30-8.26 (m, 1H), 8.19 (s, 1H), 7.97-7.93 (m, 1H), 7.97-7.93 (m, 1H), 7.56 (s, 1H), 7.48-7.41 (m, 3H), 7.34 (br s, 1H); ES-LCMS m/z 297.0 [M+H]$^+$.

Step 3: 3-[[4-(1-Oxidopyridin-1-ium-3-yl)thiazol-2-yl]amino]benzamide

To a solution of 3-[[4-(3-pyridyl)thiazol-2-yl]amino]benzamide (100 mg, 269.95 μmol, 80% purity, 1 eq) in DMF (3 mL) was added m-CPBA (174.69 mg, 809.86 μmol, 80% purity, 3 eq). The mixture was stirred at 60° C. for 12 h. The reaction mixture was concentrated to yield a residue which was purified by preparative HPLC (column: Phenomenex Synergi C18 150*30 mm*4 μm; mobile phase: [water (0.1% TFA)-ACN]; B %: 15%-35%, 9 min) and lyophilized to yield a residue which was added sat. aq. $NaHCO_3$ (10 mL, adjusted pH to 9) and extracted with EtOAc (20 mL×3). The combine organic layers were dried over anhydrous $Na_2SO_4$, filtered and concentrated to yield a residue which was dissolved in MeCN (10 mL) and $H_2O$ (20 mL) and lyophilized to yield 3-[[4-(1-oxidopyridin-1-ium-3-yl)thiazol-2-yl]amino]benzamide (21.77 mg, 69.70 μmol, 25.8% yield, 100.0% purity) as a white solid. $^1$H NMR (500 MHz, DMSO-$d_6$) δ ppm 10.54 (s, 1H), 8.74 (s, 1H), 8.17 (d, J=6.4 Hz, 1H), 8.10 (s, 1H), 8.00-7.92 (m, 2H), 7.86 (d, J=8.1 Hz, 1H), 7.72 (s, 1H), 7.50-7.41 (m, 3H), 7.35 (br s, 1H); ES-LCMS m/z 313.0 [M+H]$^+$.

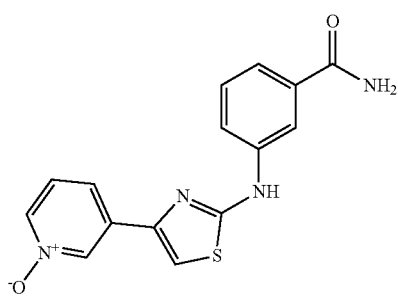

I-148

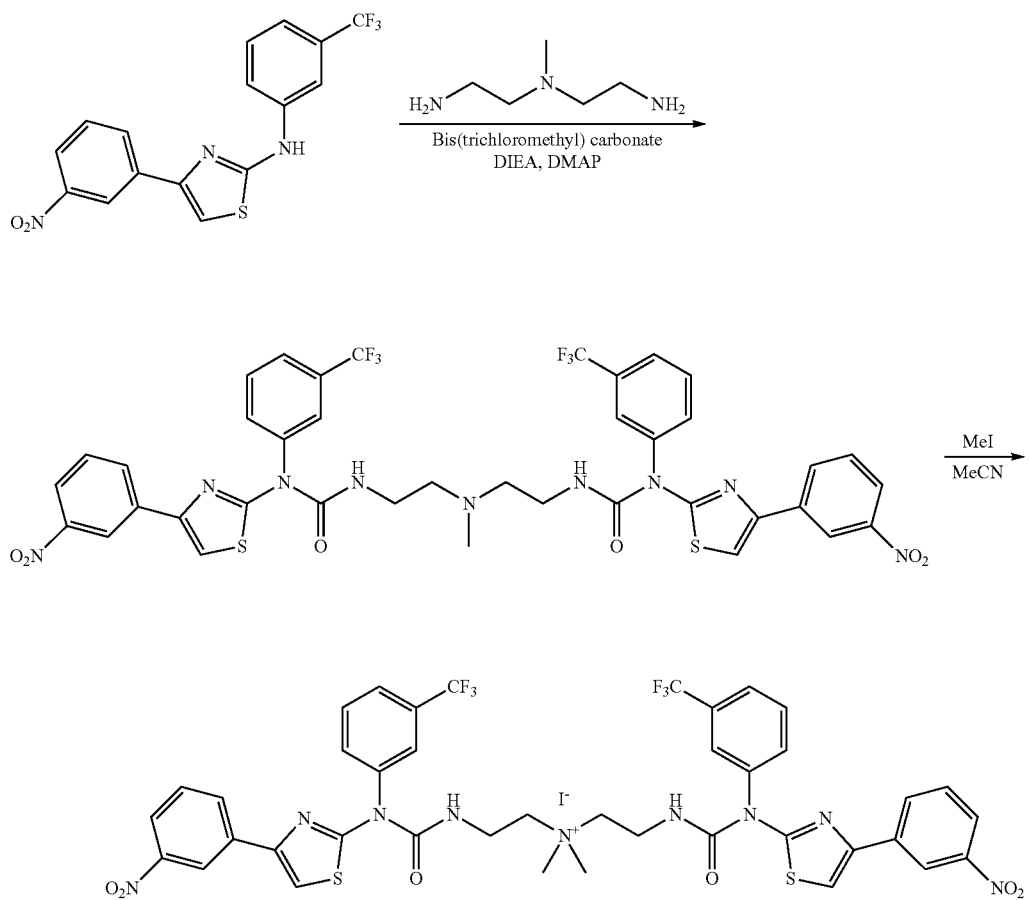

Step 1: 3-[2-[Methyl-[2-[[[4-(3-nitrophenyl)thiazol-2-yl]-[3-(trifluoromethyl)phenyl]carbamoyl]amino]ethyl]amino]ethyl]-1-[4-(3-nitrophenyl)thiazol-2-yl]-1-[3-(trifluoromethyl)phenyl]urea

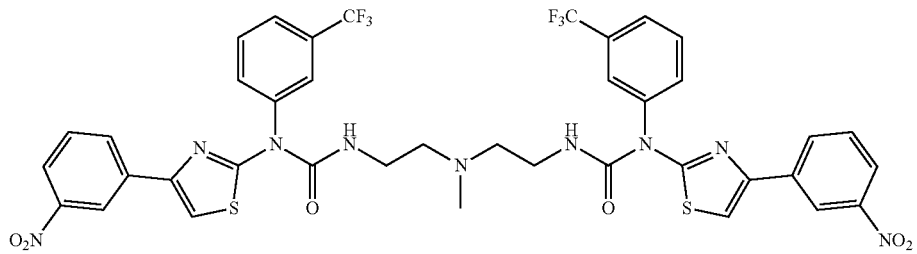 [SMILES: CN(CCNC(=O)N(c1cccc(C(F)(F)F)c1)c1nc(-c2cccc([N+](=O)[O-])c2)cs1)CCNC(=O)N(c1cccc(C(F)(F)F)c1)c1nc(-c2cccc([N+](=O)[O-])c2)cs1]

To a solution of 4-(3-nitrophenyl)-N-[3-(trifluoromethyl)phenyl]thiazol-2-amine (200 mg, 383.22 μmol, 70%, 1 eq) in THF (5 mL) was added bis(trichloromethyl) carbonate (159.21 mg, 536.50 μmol, 1.4 eq), DIEA (148.58 mg, 1.15 mmol, 200.24 μL, 3 eq) and stirred at 80° C. for 2 h. The reaction mixture was concentrated to yield (4-(3-nitrophenyl)thiazol-2-yl)(3-(trifluoromethyl)phenyl)carbamic chloride (crude). Then to a solution of N'-(2-aminoethyl)-N'-methyl-ethane-1,2-diamine (17.96 mg, 153.29 μmol, 0.4 eq), DIEA (148.58 mg, 1.15 mmol, 200.24 μL, 3 eq) and DMAP (4.68 mg, 38.32 μmol, 0.1 eq) in DCM (3 mL) was added (4-(3-nitrophenyl)thiazol-2-yl)(3-(trifluoromethyl)phenyl) carbamic chloride (crude) in DCM (2 mL) and stirred at 25° C. for 1 h. To the mixture was added water (30 mL) and extracted with DCM (30 mL×3). The combined organic phase was washed with brine (20 mL), dried over anhydrous Na$_2$SO$_4$, filtered and concentrated in vacuum at 25° C. to yield a residue which was purified by preparative HPLC (column:Phenomenex Synergi C18 150*30 mm*4 μm: [water (0.05% HCl)-ACN]; B %: 48%-68%, 9 min), followed by lyophilization to yield product. To the product was added sat. aq. NaHCO$_3$ (20 mL) and extracted with ethyl acetate (20 mL×3). The combined organic phase was washed with brine (20 mL), dried over anhydrous Na$_2$SO$_4$, filtered and concentrated in vacuum at 25° C. to yield 3-[2-[methyl-[2-[[[4-(3-nitrophenyl)thiazol-2-yl]-[3-(trifluoromethyl)phenyl]carbamoyl]amino]ethyl]amino]ethyl]-1-[4-(3-nitrophenyl)thiazol-2-yl]-1-[3-(trifluoromethyl)phenyl]urea (30 mg, 33.34 μmol, 8.7% yield, 100.0% purity) as a yellow solid. $^1$H NMR (500 MHz, CDCl$_3$) δ ppm 8.51-8.51 (m, 1H), 8.50 (s, 2H), 8.23 (s, 1H), 8.11 (dd, J=1.4, 8.1 Hz, 2H), 8.06 (d, J=7.9 Hz, 2H), 7.78 (d, J=7.9 Hz, 2H), 7.72-7.65 (m, 4H), 7.61-7.52 (m, 4H), 7.15 (s, 2H), 3.46 (q, J=6.1 Hz, 4H), 2.72 (t, J=6.4 Hz, 4H), 2.38 (s, 3H); ES-LCMS m/z 900.0 [M+H]$^+$.

Step 2: 3-(2-BLAHethyl)-1-[4-(3-nitrophenyl)thiazol-2-yl]-1-[3-(trifluoromethyl)phenyl]urea

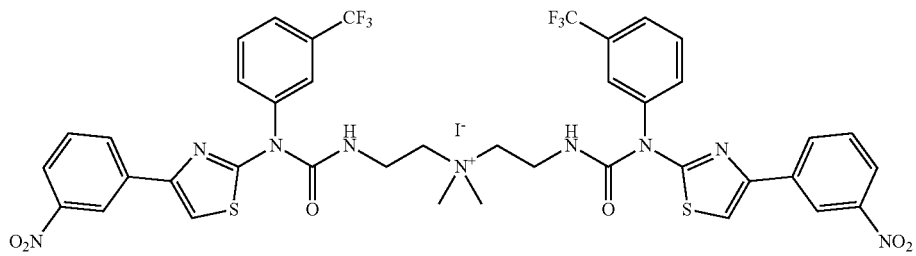 [SMILES: C[N+](C)(CCNC(=O)N(c1cccc(C(F)(F)F)c1)c1nc(-c2cccc([N+](=O)[O-])c2)cs1)CCNC(=O)N(c1cccc(C(F)(F)F)c1)c1nc(-c2cccc([N+](=O)[O-])c2)cs1 ; [I-]]

To a solution of 3-[2-[methyl-[2-[[[4-(3-nitrophenyl)thiazol-2-yl]-[3-(trifluoromethyl)phenyl]carbamoyl]amino]ethyl]amino]ethyl]-1-[4-(3-nitrophenyl)thiazol-2-yl]-1-[3-(trifluoromethyl)phenyl]urea (30 mg, 33.34 μmol, 100%, 1 eq) in MeCN (3 mL) was added MeI (47.32 mg, 333.39 μmol, 20.75 μL, 10 eq). The mixture was stirred at 25° C. for 4 h. The solution was diluted with water (10 mL), then lyophilization to yield 3-(2-BLAHethyl)-1-[4-(3-nitrophenyl)thiazol-2-yl]-1-[3-(trifluoromethyl)phenyl]urea (22.42 mg, 21.52 μmol, 64.6% yield, 100.0% purity) as a yellow solid. $^1$H NMR (400 MHz, DMSO-d$_6$) δ ppm 8.32 (s, 2H), 8.08 (dd, J=1.4, 8.0 Hz, 2H), 8.03 (d, J=8.2 Hz, 2H), 7.99 (s, 4H), 7.89-7.87 (m, 3H), 7.86-7.80 (m, 3H), 7.62 (t, J=8.2 Hz, 2H), 7.00-6.95 (m, 2H), 3.55 (d, J=5.1 Hz, 4H), 3.46 (d, J=5.9 Hz, 4H), 3.10 (s, 6H); ES-LCMS m/z 914.1 [M−I]$^+$.

I-149

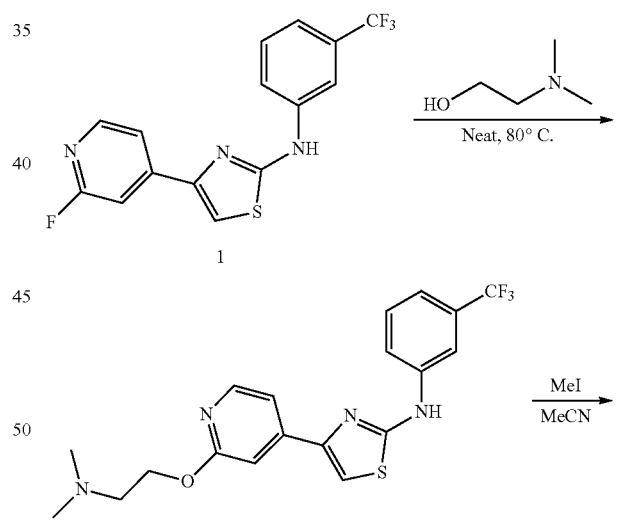

Step 1: 4-[2-[2-(Dimethylamino)ethoxy]-4-pyridyl]-N-[3-(trifluoromethyl)phenyl]thiazol-2-amine

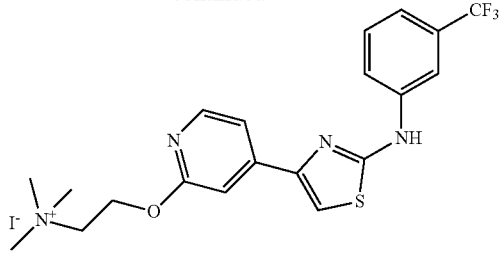

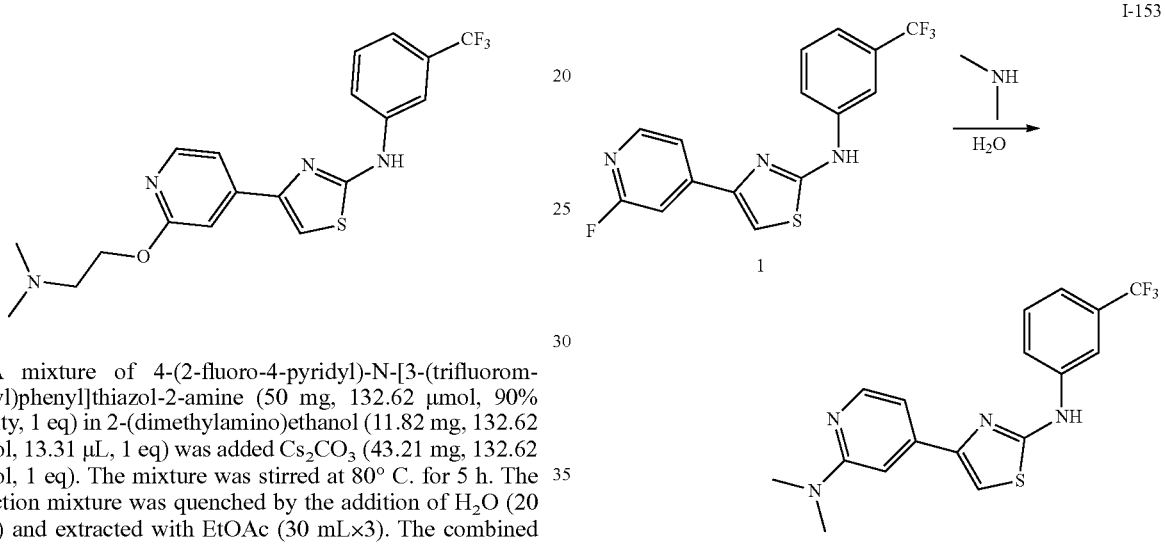

A mixture of 4-(2-fluoro-4-pyridyl)-N-[3-(trifluoromethyl)phenyl]thiazol-2-amine (50 mg, 132.62 µmol, 90% purity, 1 eq) in 2-(dimethylamino)ethanol (11.82 mg, 132.62 µmol, 13.31 µL, 1 eq) was added $Cs_2CO_3$ (43.21 mg, 132.62 µmol, 1 eq). The mixture was stirred at 80° C. for 5 h. The reaction mixture was quenched by the addition of $H_2O$ (20 mL) and extracted with EtOAc (30 mL×3). The combined organic layers were washed with brine (30 mL), dried over $Na_2SO_4$, filtered and concentrated under reduced pressure to yield a residue which was purified by preparative HPLC (column:Welch Xtimate C18 150*25 mm*5 um; mobile phase: water (10 mM $NH_4HCO_3$)-ACN; B %: 46%-76%, 10 min) to yield 4-[2-[2-(dimethylamino)ethoxy]-4-pyridyl]-N-[3-(trifluoromethyl)phenyl]thiazol-2-amine (15 mg, 34.89 µmol, 26.3% yield, 95.0% purity) as a white solid. ES-LCMS m/z 409.1 $[M+H]^+$.

Step 2: N-[3-(Trifluoromethyl)phenyl]-4-[2-[2-[BLAH(trimethyl)-λ5-azanyl]ethoxy]-4-pyridyl]thiazol-2-amine

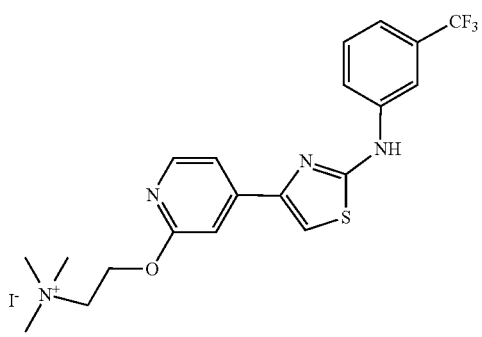 [SMILES: [I-] ; C[N+](C)(C)CCOc1cc(-c2csc(Nc3cccc(C(F)(F)F)c3)n2)ccn1]

To a solution of 4-[2-[2-(dimethylamino)ethoxy]-4-pyridyl]-N-[3-(trifluoromethyl)phenyl]thiazol-2-amine (15 mg, 34.89 µmol, 95% purity, 1 eq) in MeCN (5 mL) was added MeI (24.76 mg, 174.44 µmol, 10.86 µL, 5 eq). The mixture was stirred at 15° C. for 5 h. The solution was quenched by the addition of $H_2O$ (0.5 mL) and lyophilized to yield N-[3-(trifluoromethyl)phenyl]-4-[2-[2-[BLAH(trimethyl)-$\lambda^5$-azanyl]ethoxy]-4-pyridyl]thiazol-2-amine (17.44 mg, 29.56 µmol, 84.7% yield, 93.3% purity) as a white solid. $^1H$ NMR (400 MHz, DMSO-$d_6$) δ ppm 10.92 (s, 1H), 8.54 (s, 1H), 8.25 (d, J=5.2 Hz, 1H), 7.84 (s, 1H), 7.75 (d, J=7.6 Hz, 1H), 7.62-7.52 (m, 2H), 7.36-7.28 (m, 2H), 4.77 (s, 2H), 3.81 (s, 2H), 3.21 (s, 9H); ES-LCMS m/z 423.2 $[M-I]^+$.

I-153 by preparative HPLC (column: YMC-Actus Triart C18 100*30 mm*5 um; mobile phase: [water (0.1% TFA)-ACN]; B %: 35%-55%, 11 min), followed by lyophilization to yield 4-[2-(dimethylamino)-4-pyridyl]-N-[3-(trifluoromethyl)phenyl]thiazol-2-amine (25.18 mg, 67.88 μmol, 32.0% yield, 98.2% purity) as a white solid. $^1$H NMR (400 MHz, CDCl$_3$) δ ppm 8.26-8.16 (m, 2H), 7.47 (d, J=5.2 Hz, 2H), 7.32 (br s, 2H), 7.15 (s, 1H), 7.07 (s, 1H), 6.91 (dd, J=1.2, 5.2 Hz, 1H), 3.18 (s, 6H); ES-LCMS m/z 365.2 [M+H]$^+$.

I-154

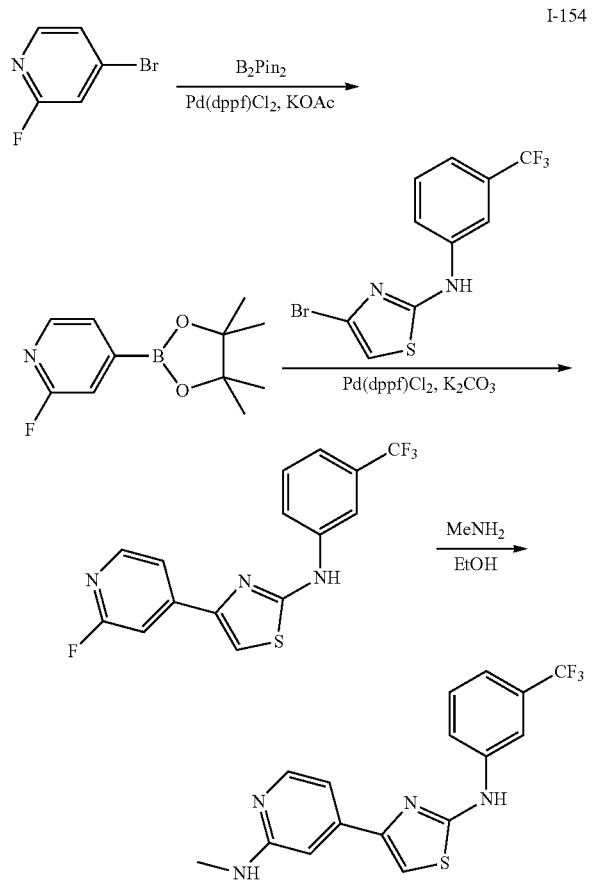

Step 1: 2-Fluoro-4-(4,4,5,5-tetramethyl-1,3,2-dioxaborolan-2-yl)pyridine

To a solution of 4-bromo-2-fluoro-pyridine (2.8 g, 15.91 mmol, 1 eq), 4,4,5,5-tetramethyl-2-(4,4,5,5-tetramethyl-1,3,2-dioxaborolan-2-yl)-1,3,2-dioxaborolane (4.85 g, 19.09 mmol, 1.2 eq) and KOAc (3.12 g, 31.82 mmol, 2 eq) in DMSO (30 mL) was added Pd(dppf)Cl$_2$ (582.08 mg, 795.52 μmol, 0.05 eq) under N$_2$. The mixture was stirred at 100° C. for 12 h. TLC (PE/EtOAc=5/1, R$_f$=0.66) showed that new point was formed and start material was consumed completely. The mixture was quenched with H$_2$O (150 mL) and extracted with EtOAc (80 mL×4). The combined organic layer was dried over Na$_2$SO$_4$, filtrated and concentrated to yield a residue which was purified by flash silica gel chromatography (from PE/EtOAc=100/1 to 5/1, TLC: PE/EtOAc=5/1, R$_f$=0.66) to yield 2-fluoro-4-(4,4,5,5-tetramethyl-1,3,2-dioxaborolan-2-yl)pyridine (3.7 g, 15.76 mmol, 99.1% yield, 95.0% purity) as a yellow solid. $^1$H NMR (400 MHz, CDCl$_3$) δ ppm 8.24 (d, J=4.8 Hz, 1H), 7.50 (m, 1H), 7.29 (d, J=2.4 Hz, 1H), 1.36 (s, 12H).

Step 2: 4-(2-Fluoropyridin-4-yl)-N-(3-(trifluoromethyl)phenyl)thiazol-2-amine

To a solution of 2-fluoro-4-(4,4,5,5-tetramethyl-1,3,2-dioxaborolan-2-yl)pyridine (784.74 mg, 3.34 mmol, 95% purity, 1.2 eq), 4-bromo-N-[3-(trifluoromethyl)phenyl]thiazol-2-amine (1 g, 2.79 mmol, 90% purity, 1 eq) and K$_2$CO$_3$ (577.42 mg, 4.18 mmol, 1.5 eq) in 1,4-dioxane (20 mL) and H$_2$O (4 mL) was added Pd(dppf)Cl$_2$ (101.90 mg, 139.26 μmol, 0.05 eq) under N$_2$ atmosphere. The mixture was stirred under N$_2$ atmosphere at 90° C. for 12 h. TLC (PE/EtOAc=3/1, R$_f$=0.32) showed that new point was formed and start material was consumed. The mixture was quenched with H$_2$O (20 mL) and extracted with EtOAc (50 mL×3). The combined organic layer was dried over Na$_2$SO$_4$, filtrated and concentrated to yield a residue which was purified by flash silica gel chromatography (from PE/EtOAc=100/1 to 3/1, TLC: PE/EtOAc=3/1, R$_f$=0.32) to yield 4-(2-fluoro-4-pyridyl)-N-[3-(trifluoromethyl)phenyl]thiazol-2-amine (310 mg, 822.26 μmol, 29.5% yield, 90.0% purity) as a yellow solid. $^1$H NMR (400 MHz, CDCl$_3$) δ ppm 8.26 (d, J=4.8 Hz, 1H), 7.88 (s, 1H), 7.70 (d, J=8.4 Hz, 1H), 7.62-7.59 (m, 1H), 7.52 (t, J=7.6 Hz, 1H), 7.40-7.35 (m, 2H), 7.18 (s, 1H).

Step 3: 4-(2-(Methylamino)pyridin-4-yl)-N-(3-(trifluoromethyl)phenyl)thiazol-2-amine

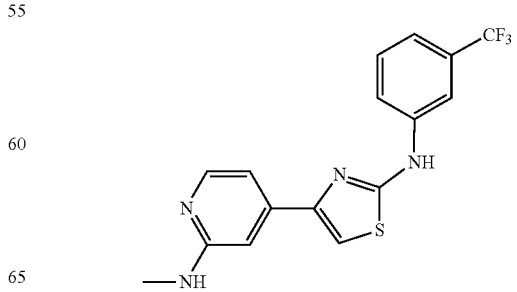

A mixture of 4-(2-fluoro-4-pyridyl)-N-[3-(trifluoromethyl)phenyl]thiazol-2-amine (50 mg, 132.62 μmol, 90.0% purity, 1 eq) and MeNH₂ (12.48 mg, 132.62 μmol, 2 mL, 33% purity, 1 eq) in EtOH (1 mL) was purged with N₂. The mixture was stirred under microwave irradiation (1 bar) at 90° C. for 5 h. The mixture was concentrated and MeOH (1 mL) was added. The mixture was filtered and the filtrate was purified by preparative HPLC (column: Abela DuraShell C18 150*25 mm*5 um; mobile phase: [water(0.05% NH₃H₂O+10 mM NH₄HCO₃)-ACN]; B %: 45%-75%, 10 min), followed by lyophilization to yield 4-[2-(methylamino)-4-pyridyl]-N-[3-(trifluoromethyl)phenyl]thiazol-2-amine (17.49 mg, 49.92 μmol, 37.6% yield, 100.0% purity) as a white solid. ¹H NMR (400 MHz, CDCl₃) δ ppm 8.12 (s, 1H), 8.07 (d, J=5.6 Hz, 1H), 7.56-7.45 (m, 2H), 7.39 (s, 1H), 7.34 (d, J=7.2 Hz, 1H), 7.10 (s, 1H), 7.03 (s, 1H), 6.98 (m, 1H), 5.13 (s, 1H), 3.01 (d, J=5.6 Hz, 3H); ES-LCMS m/z 351.2 [M+H]⁺.

I-155

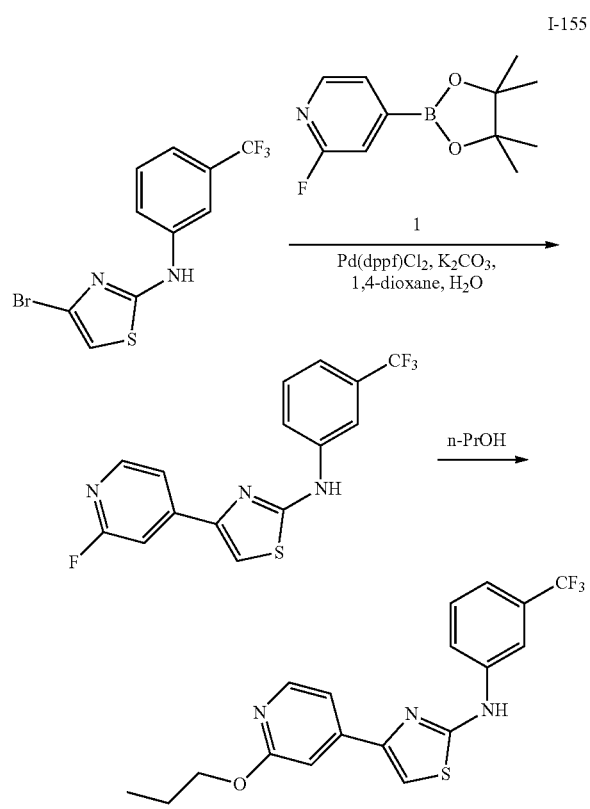

Step 1: 4-(2-Fluoro-4-pyridyl)-N-[3-(trifluoromethyl)phenyl]thiazol-2-amine

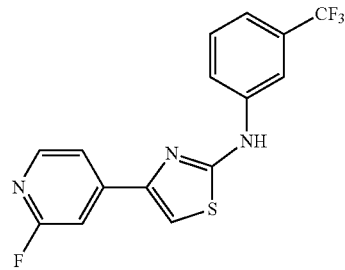 [SMILES: Fc1cc(-c2csc(Nc3cccc(C(F)(F)F)c3)n2)ccn1]

To a solution of 4-bromo-N-[3-(trifluoromethyl)phenyl]thiazol-2-amine (526.32 mg, 1.55 mmol, 95.0% purity, 1 eq) and 2-fluoro-4-(4,4,5,5-tetramethyl-1,3,2-dioxaborolan-2-yl)pyridine (435.97 mg, 1.86 mmol, 95.0% purity, 1.2 eq) in 1,4-dioxane (15 mL) and H₂O (3 mL) was added K₂CO₃ (320.79 mg, 2.32 mmol, 1.5 eq) and Pd(dppf)Cl₂ (56.61 mg, 77.37 μmol, 0.05 eq) under N₂ atmosphere. The mixture was stirred under N₂ atmosphere at 90° C. for 3 h. TLC (PE/EtOAc=3/1, R𝑓=0.25) showed that new point was formed and the start material was consumed completely. The reaction mixture was quenched by addition of H₂O (20 mL) and extracted with EtOAc (30 mL×3). The combined organic layers were washed with brine (30 mL), dried over Na₂SO₄, filtered and concentrated under reduced pressure to yield a residue which was purified by flash silica gel chromatography (from PE/EtOAc=100/1 to 3/1, TLC: PE/EtOAc=3/1, R𝑓=0.25) to yield 4-(2-fluoro-4-pyridyl)-N-[3-(trifluoromethyl)phenyl]thiazol-2-amine (100 mg, 235.77 μmol, 15.2% yield, 80.0% purity) as a white solid. ¹H NMR (400 MHz, CDCl₃) δ ppm 8.26 (d, J=4.8 Hz, 1H), 7.88 (s, 1H), 7.69 (s, 2H), 7.60 (d, J=5.2 Hz, 1H), 7.52 (s, 1H), 7.36 (d, J=8.0 Hz, 1H), 7.18 (s, 1H); ES-LCMS m/z 340.1 [M+H]⁺.

Step 2: 4-(2-Propoxy-4-pyridyl)-N-[3-(trifluoromethyl)phenyl]thiazol-2-amine

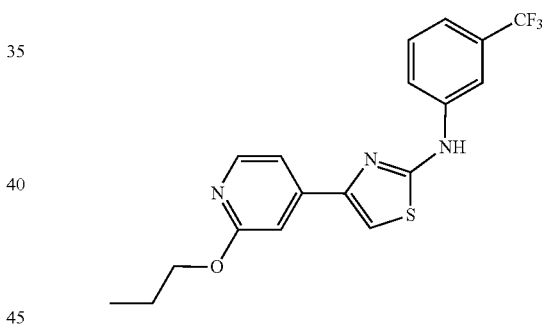

A mixture of 4-(2-fluoro-4-pyridyl)-N-[3-(trifluoromethyl)phenyl]thiazol-2-amine (80 mg, 212.20 μmol, 90% purity, 1 eq) and Cs₂CO₃ (103.71 mg, 318.29 μmol, 1.5 eq) in propan-1-ol (12.75 mg, 212.20 μmol, 15.94 μL, 1 eq) was degassed and purged with N₂ for 3 times. The mixture was stirred under N₂ atmosphere at 90° C. for 5 h. The mixture was concentrated to give residue which was purified by preparative HPLC (column: Welch Xtimate C18 150*25 mm*5 μm; mobile phase: [water (10 mM NH₄HCO₃)-ACN]; B %: 65%-95%, 10 min) to yield 4-(2-propoxy-4-pyridyl)-N-[3-(trifluoromethyl)phenyl]thiazol-2-amine (25.33 mg, 66.62 μmol, 31.4% yield, 99.8% purity) as a white solid. ¹H NMR (400 MHz, DMSO-d₆) δ ppm 10.75 (s, 1H), 8.38 (s, 1H), 8.19 (d, J=4.8 Hz, 1H), 7.85-7.78 (m, 2H), 7.59 (t, J=8.0 Hz, 1H), 7.45 (dd, J=1.2, 5.2 Hz, 1H), 7.32 (d, J=8.0 Hz, 1H), 7.27 (s, 1H), 4.24 (t, J=6.4 Hz, 2H), 1.75 (q, J=6.8 Hz, 2H), 0.99 (t, J=7.6 Hz, 3H); ES-LCMS m/z 380.0 [M+H]⁺.

I-156

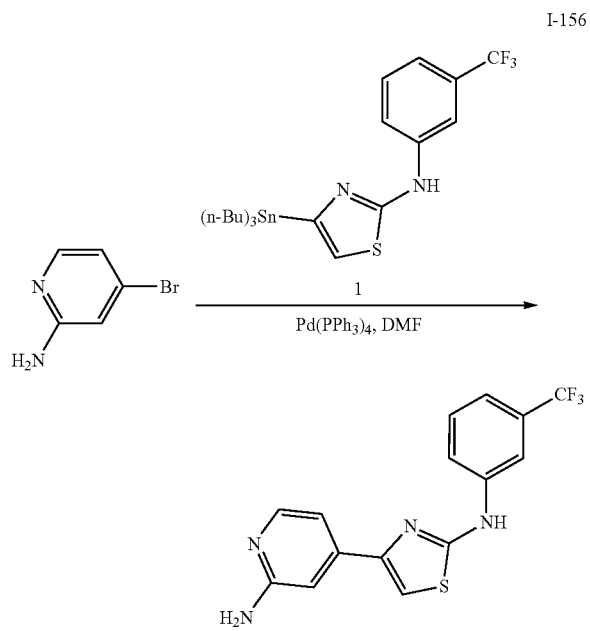

Step 1: 4-(2-Amino-4-pyridyl)-N-[3-(trifluoromethyl)phenyl]thiazol-2-amine

To a solution of 4-bromopyridin-2-amine (60 mg, 346.80 μmol, 1 eq) and 4-tributylstannyl-N-[3-(trifluoromethyl)phenyl]thiazol-2-amine (369.88 mg, 416.16 μmol, 60% purity, 1.2 eq) in DMF (2 mL) was added Pd(PPh$_3$)$_4$ (40.07 mg, 34.68 μmol, 0.1 eq) under N$_2$ atmosphere. The mixture was stirred under N$_2$ atmosphere at 120° C. for 12 h. The reaction mixture was quenched by addition of H$_2$O (20 mL) and extracted with EtOAc (20 mL×3). The combined organic layers were washed with H$_2$O (40 mL×3) and brine (10 mL), dried over Na$_2$SO$_4$, filtered and concentrated under reduced pressure to yield a residue which was purified by preparative HPLC (column: Agela DuraShell C18 150*25 mm*5 um; mobile phase: [water (0.05% NH$_3$H$_2$O+10 mM NH$_4$HCO$_3$)-ACN]; B %: 35%-65%, 10 min), followed by lyophilization to yield 4-(2-amino-4-pyridyl)-N-[3-(trifluoromethyl)phenyl]thiazol-2-amine (14.48 mg, 42.97 μmol, 12.4% yield, 99.8% purity) as a white solid. $^1$H NMR (400 MHz, CD$_3$OD) δ ppm 6.51 (s, 1H), 6.47 (d, J=8.3 Hz, 1H), 6.35 (d, J=5.6 Hz, 1H), 5.95 (t, J=7.9 Hz, 1H), 5.79 (s, 1H), 5.69 (d, J=7.8 Hz, 1H), 5.59-5.53 (m, 2H); ES-LCMS m/z 337.2 [M+H]$^+$.

I-157

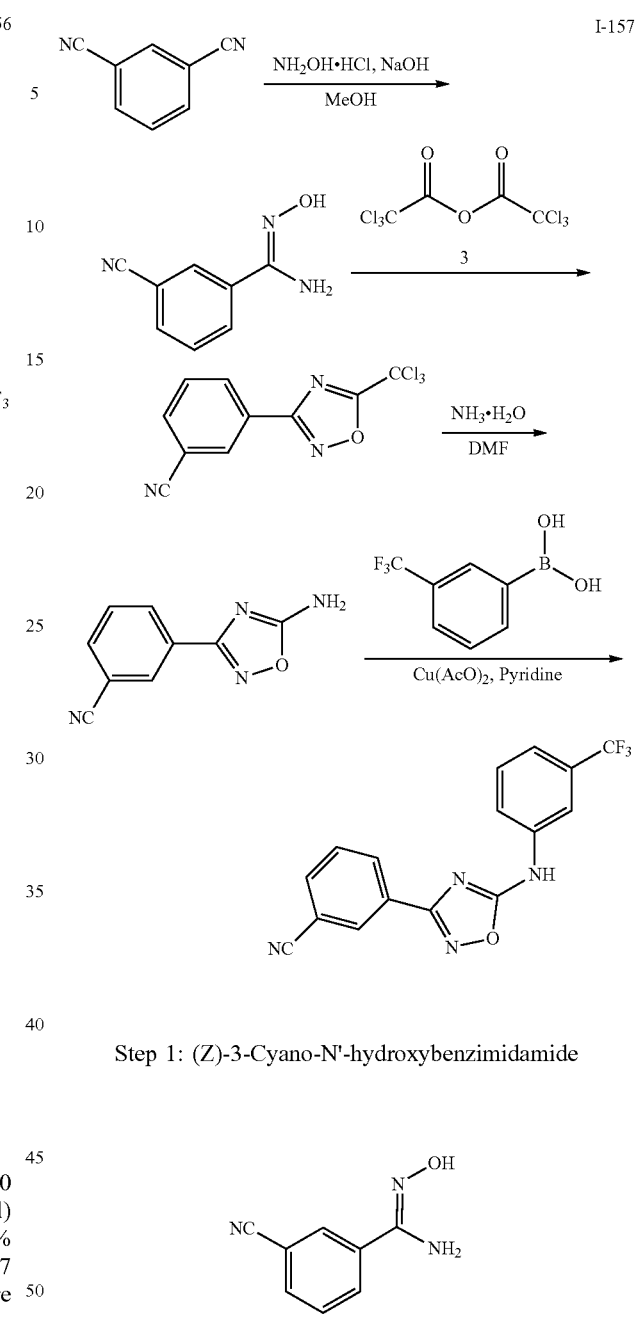

Step 1: (Z)-3-Cyano-N'-hydroxybenzimidamide

To a solution of benzene-1,3-dicarbonitrile (4 g, 31.22 mmol, 1 eq) and NH$_2$OH.HCl (2.60 g, 37.46 mmol, 1.2 eq) in EtOH (60 mL) was added NaOH (1.50 g, 37.46 mmol, 1.2 eq). The mixture was stirred at 80° C. for 12 h. TLC (DCM/MeOH=10/1, R$_f$=0.54) showed that one new point was formed and start material was consumed completely. The mixture was concentrated to give residue which was purified by flash silica gel chromatography (from DCM/MeOH=100/1 to 10/1, TLC: DCM/MeOH=10/1, R$_f$=0.54) to yield 3-cyano-N'-hydroxy-benzamidine (3.45 g, 19.27 mmol, 61.7% yield, 90.0% purity) as a yellow solid. $^1$H NMR (400 MHz, DMSO-d$_6$) δ ppm 9.90 (s, 1H), 8.06 (s, 1H), 8.01 (d, J=8.0 Hz, 1H), 7.84 (d, J=8.0 Hz, 1H), 7.59 (t, J=8.0 Hz, 1H), 6.00 (s, 2H).

Step 2: 3-(5-(Trichloromethyl)-1,2,4-oxadiazol-3-yl)benzonitrile

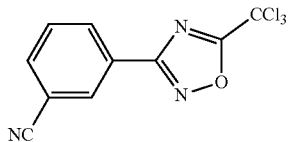

To a solution of 3-cyano-N'-hydroxy-benzamidine (1 g, 5.58 mmol, 90.0% purity, 1 eq), HOBt (754.59 mg, 5.58 mmol, 1 eq) and $K_2CO_3$ (1.16 g, 8.38 mmol, 1.5 eq) in toluene (40 mL) was added (2,2,2-trichloroacetyl) 2,2,2-trichloroacetate (2.07 g, 6.70 mmol, 1.22 mL, 1.2 eq) under $N_2$ atmosphere. The mixture was stirred at 120° C. for 5 h. TLC (PE/EtOAc=3/1, $R_f$=0.73) showed that new point was formed and start material was consumed completely. The reaction mixture was quenched by addition of $H_2O$ (30 mL) and extracted with EtOAc (30 mL×3). The combined organic layers were washed with brine (30 mL), dried over $Na_2SO_4$, filtered and concentrated under reduced pressure to give a residue which was purified by flash silica gel chromatography (from PE/EtOAc=100/1 to 3/1, TLC: PE/EtOAc=3/1, $R_f$=0.73) to yield 3-[5-(trichloromethyl)-1,2,4-oxadiazol-3-yl]benzonitrile (570 mg, 1.88 mmol, 33.6% yield, 95.0% purity) as a yellow solid. $^1$H NMR (400 MHz, DMSO-$d_6$) δ ppm 8.43 (t, J=1.2 Hz, 1H), 8.36 (d, J=9.2 Hz, 1H), 8.16 (d, J=8.0 Hz, 1H), 7.84 (t, J=8.4 Hz, 1H).

Step 3: 3-(5-Amino-1,2,4-oxadiazol-3-yl)benzonitrile

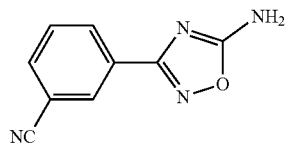 [SMILES: N#Cc1cccc(-c2noc(N)n2)c1]

To a solution of 3-[5-(trichloromethyl)-1,2,4-oxadiazol-3-yl]benzonitrile (570 mg, 1.88 mmol, 95.0% purity, 1 eq) in DMF (2 mL) was added $NH_3 \cdot H_2O$ (299.34 μmol, 4 mL, 28% purity). The mixture was stirred at 15° C. for 10 min. TLC (PE/EtOAc=4/1, $R_f$=0.2) showed that new point was formed and start material was consumed completely. The mixture was filtrated and washed with $H_2O$ and PE. The filter cake was dried under reduced pressure to yield 3-(5-amino-1,2,4-oxadiazol-3-yl)benzonitrile (250 mg, 1.28 mmol, 67.9% yield, 95.0% purity) as a white solid, which was used in the next step without further purification. $^1$H NMR (400 MHz, DMSO-$d_6$) δ ppm 8.22-8.14 (m, 2H), 8.09 (s, 2H), 8.01 (td, J=1.2, 7.6 Hz, 1H), 7.73 (t, J=8.0 Hz, 1H).

Step 4: 3-[5-[3-(Trifluoromethyl)anilino]-1,2,4-oxadiazol-3-yl]benzonitrile

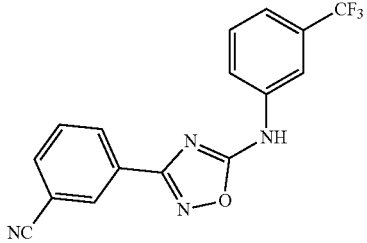 [SMILES: N#Cc1cccc(-c2noc(Nc3cccc(C(F)(F)F)c3)n2)c1]

To a solution of 3-(5-amino-1,2,4-oxadiazol-3-yl)benzonitrile (250 mg, 1.28 mmol, 95.0% purity, 1 eq) and [3-(trifluoromethyl)phenyl]boronic acid (363.44 mg, 1.91 mmol, 1.5 eq) in DMF (3 mL) was added pyridine (201.82 mg, 2.55 mmol, 205.94 μL, 2 eq) and Cu(OAc)$_2$ (347.56 mg, 1.91 mmol, 1.5 eq) under $O_2$ (15 Psi) atmosphere. The mixture was stirred at 15° C. for 24 h. The reaction mixture was quenched by addition of $H_2O$ (80 mL) and extracted with EtOAc (80 mL×3). The combined organic layers were washed with brine (50 mL), dried over $Na_2SO_4$, filtered and concentrated under reduced pressure to give a residue which was purified by preparative HPLC (column: Phenomenex Synergi C18 150*25*10 μm; mobile phase: [water (0.05% HCl)-ACN]; B %: 55%-85%, 9 min) to yield 3-[5-[3-(trifluoromethyl)anilino]-1,2,4-oxadiazol-3-yl]benzonitrile (49.67 mg, 150.39 μmol, 11.8% yield, 100.0% purity) as a white solid. $^1$H NMR (400 MHz, DMSO-$d_6$) δ ppm 11.60 (br s, 1H), 8.35 (s, 1H), 8.30 (d, J=8.0 Hz, 1H), 8.07 (d, J=7.6 Hz, 1H), 8.03-7.96 (m, 2H), 7.80 (t, J=7.6 Hz, 1H), 7.64 (t, J=7.6 Hz, 1H), 7.42 (d, J=7.6 Hz, 1H); ES-LCMS m/z 330.9 [M+H]$^+$.

I-158

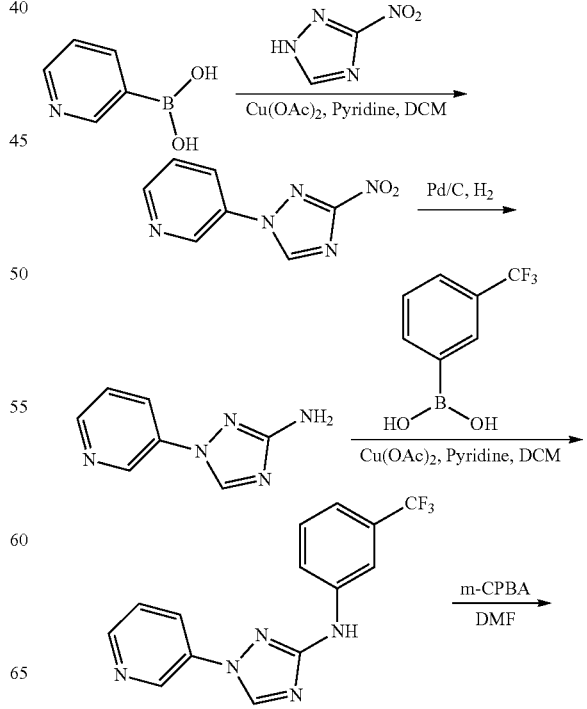

-continued

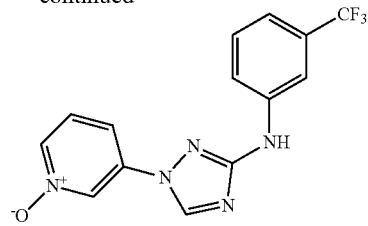

Step 1: 3-(3-Nitro-1,2,4-triazol-1-yl)pyridine

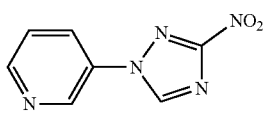

To a solution of 3-nitro-1H-1,2,4-triazole (2.5 g, 21.92 mmol, 1 eq) and 3-pyridylboronic acid (3.23 g, 26.30 mmol, 1.2 eq) in DCM (150 mL) was added pyridine (5.20 g, 65.75 mmol, 5.31 mL, 3 eq) and Cu(OAc)$_2$ (5.97 g, 32.88 mmol, 1.5 eq) under O$_2$ (15 Psi) atmosphere. The mixture was stirred under O$_2$ (15 Psi) atmosphere at 35° C. for 24 h. TLC (DCM/MeOH=10/1, R$_f$=0.5) showed that new point was formed and the start material was consumed completely. The mixture was filtered and the solid was washed with MeOH (50 mL). The filtrate was diluted with H$_2$O (150 mL) and extracted with EtOAc (150 mL×3). The combined organic layers were washed with brine (150 mL), dried over Na$_2$SO$_4$, filtered and concentrated under reduced pressure to give a residue which was purified by flash silica gel chromatography (from PE/EtOAc=100/1 to 0/1, TLC: DCM/MeOH=10/1, R$_f$=0.5) to yield 3-(3-nitro-1,2,4-triazol-1-yl)pyridine (1 g, 5.23 mmol, 23.9% yield, 100.0% purity) as a white solid. $^1$H NMR (500 MHz, CDCl$_3$) δ ppm 9.07 (d, J=2.5 Hz, 1H), 8.81 (dd, J=1.0, 4.5 Hz, 1H), 8.75-8.70 (m, 1H), 8.17-8.11 (m, 1H), 7.59 (dd, J=5.0, 8.5 Hz, 1H).

Step 2: 1-(3-Pyridyl)-1,2,4-triazol-3-amine

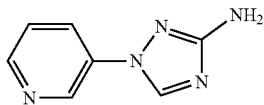 [SMILES: O=[N+]([O-])c1ncn(-c2cccnc2)n1]

To a solution of 3-(3-nitro-1,2,4-triazol-1-yl)pyridine (1 g, 5.23 mmol, 100% purity, 1 eq) in MeOH (40 mL) was added Pd/C (5.55 g, 5.23 mmol, 10% purity, 1 eq) with stirred under H$_2$ (15 Psi) atmosphere. The mixture was stirred under H$_2$ (15 Psi) atmosphere at 10° C. for 2 h. TLC (DCM/MeOH=10/1, R$_f$=0.2) showed that new point was formed and start material was consumed completely. The reaction mixture was filtered and the filtrate was concentrated under reduced pressure to yield 1-(3-pyridyl)-1,2,4-triazol-3-amine (800 mg, 4.72 mmol, 90.1% yield, 95.0% purity) as yellow oil, which was used in the next step without further purification. $^1$H NMR (400 MHz, CDCl$_3$) δ ppm 8.93 (d, J=2.4 Hz, 1H), 8.61-8.54 (m, 1H), 8.27 (s, 1H), 7.93 (dd, J=0.8, 8.4 Hz, 1H), 7.50-7.37 (m, 1H), 4.58-4.28 (m, 2H).

Step 3: 1-(3-Pyridyl)-N-[3-(trifluoromethyl)phenyl]-1,2,4-triazol-3-amine

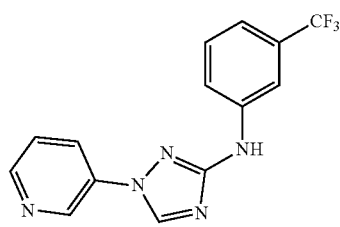 [SMILES: FC(F)(F)c1cccc(Nc2ncn(-c3cccnc3)n2)c1]

To a solution of 1-(3-pyridyl)-1,2,4-triazol-3-amine (800 mg, 4.72 mmol, 95% purity, 1 eq) and [3-(trifluoromethyl)phenyl]boronic acid (1.34 g, 7.07 mmol, 1.5 eq) in DMF (5 mL) was added pyridine (1.12 g, 14.15 mmol, 1.14 mL, 3 eq) and Cu(OAc)$_2$ (1.28 g, 7.07 mmol, 1.5 eq) under O$_2$ (15 Psi) atmosphere. The mixture was stirred at 35° C. for 10 h. TLC (DCM/MeOH=10/1, R$_f$=0.55) showed that new point was formed and start material was consumed completely. The reaction mixture was quenched by addition of H$_2$O (30 mL) and extracted with EtOAc (30 mL×3). The combined organic layers were washed with brine (30 mL), dried over Na$_2$SO$_4$, filtered and concentrated under reduced pressure to give a residue which was purified by flash silica gel chromatography (from PE/EtOAc=100/1 to 1/100, TLC: DCM/MeOH=10/1, R$_f$=0.55) and preparative HPLC (column: Phenomenex Synergi C18 150*30 mm*4 μm; mobile phase: [water (0.225% FA)-ACN]; B %: 40%-70%, 11 min) to yield 1-(3-pyridyl)-N-[3-(trifluoromethyl)phenyl]-1,2,4-triazol-3-amine (90 mg, 294.83 μmol, 6.3% yield, 100.0% purity) as a white solid. $^1$H NMR (500 MHz, CDCl$_3$) δ ppm 9.03 (s, 1H), 8.64 (d, J=4.0 Hz, 1H), 8.42 (s, 1H), 8.06 (d, J=8.5 Hz, 1H), 7.92 (s, 1H), 7.69 (d, J=8.0 Hz, 1H), 7.52-7.43 (m, 2H), 7.25 (d, J=7.5 Hz, 1H), 6.94 (s, 1H); ES-LCMS m/z 305.9 [M+H]$^+$.

Step 4: 1-(1-Oxidopyridin-1-ium-3-yl)-N-[3-(trifluoromethyl)phenyl]-1,2,4-triazol-3-amine

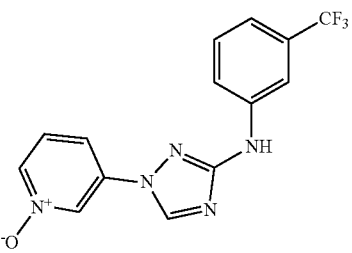

To a solution of 1-(3-pyridyl)-N-[3-(trifluoromethyl)phenyl]-1,2,4-triazol-3-amine (50 mg, 163.80 μmol, 100% purity, 1 eq) in DMF (2 mL) was added m-CPBA (133.02 mg, 655.18 μmol, 85% purity, 4 eq). The mixture was stirred at 35° C. for 10 h. The reaction mixture was quenched by addition of H$_2$O (20 mL) and extracted with EtOAc (30 mL×3). The combined organic layers were washed with brine (30 mL), dried over Na$_2$SO$_4$, filtered and concentrated under reduced pressure to yield a residue which was purified by preparative HPLC (column: Welch Xtimate C18 150*25 mm*5 μm; mobile phase: [water (10 mM NH$_4$HCO$_3$)-ACN]; B %: 25%-55%, 10 min) to yield 1-(1-oxidopyridin- 1-ium-3-yl)-N-[3-(trifluoromethyl)phenyl]-1,2,4-triazol-3-amine (14.87 mg, 43.17 μmol, 26.4% yield, 93.3% purity) as a white solid. $^1$H NMR (400 MHz, DMSO-$d_6$) δ ppm 10.07 (s, 1H), 9.24 (s, 1H), 8.84 (s, 1H), 8.22 (d, J=7.2 Hz, 1H), 7.99 (s, 1H), 7.91 (d, J=6.8 Hz, 1H), 7.81 (d, J=10.0 Hz, 1H), 7.64-7.58 (m, 1H), 7.53 (t, J=7.6 Hz, 1H), 7.21 (d, J=8.0 Hz, 1H); ES-LCMS m/z 322.1 [M+H]$^+$.

pressure to yield a residue which was purified by preparative HPLC (column: Agela DuraShell C18 150*25 mm*5 μm; mobile phase: [water (0.05% NH$_3$.H$_2$O+10 mM NH$_4$HCO$_3$)-ACN]; B %: 57%-72%, 14 min), followed by lyophilization to yield methyl 2-[[4-[2-[3-(trifluoromethyl)anilino]thiazol-4-yl]-2-pyridyl]oxy]acetate (30 mg, 72.37 μmol, 27.3% yield, 98.8% purity) as a white solid. $^1$H NMR (500 MHz, CDCl$_3$) δ ppm 8.13 (d, J=5.3 Hz, 1H), 7.79 (s, 1H), 7.75 (d, J=8.1 Hz, 1H), 7.51 (t, J=8.0 Hz, 2H), 7.36-7.33 (m, 2H), 7.31 (s, 1H), 7.08 (s, 1H), 4.97 (s, 2H), 3.81 (s, 3H); ES-LCMS m/z 410.1 [M+H]$^+$.

I-160

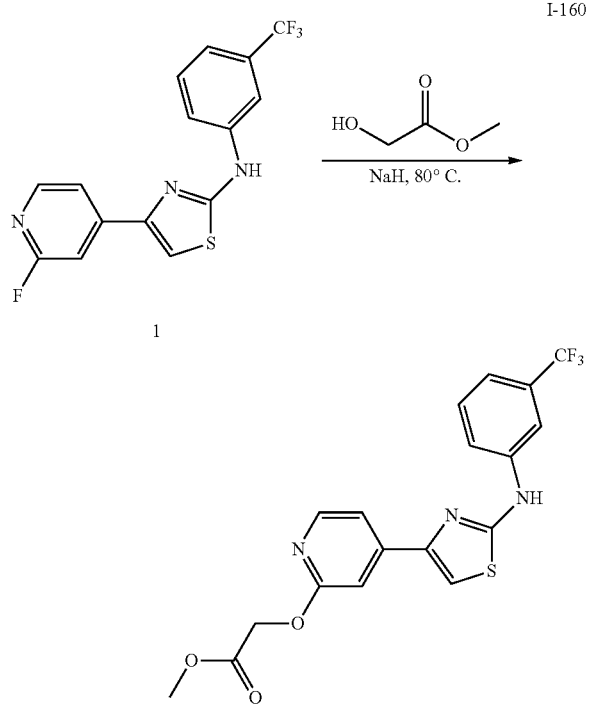

Step 1: Methyl 2-[[4-[2-[3-(trifluoromethyl)anilino]thiazol-4-yl]-2-pyridyl]oxy]acetate

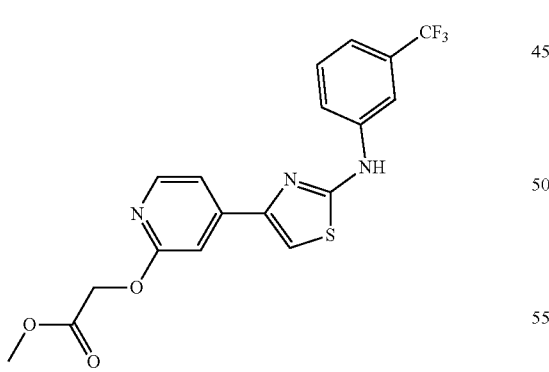

To a solution of 4-(2-fluoro-4-pyridyl)-N-[3-(trifluoromethyl)phenyl]thiazol-2-amine (100 mg, 265.24 μmol, 90%, 1 eq) in THF (5 mL) was added NaH (106.09 mg, 2.65 mmol, 60%, 10 eq) and methyl 2-hydroxyacetate (526.50 mg, 5.84 mmol, 450.00 μL, 22.04 eq). The mixture was stirred at 80° C. for 12 h. The reaction mixture was quenched by addition of water (50 mL), extracted with EtOAc (30 mL×3). The combined organic layers were washed with brine (10 mL), dried over Na$_2$SO$_4$, filtered and concentrated under reduced

I-161

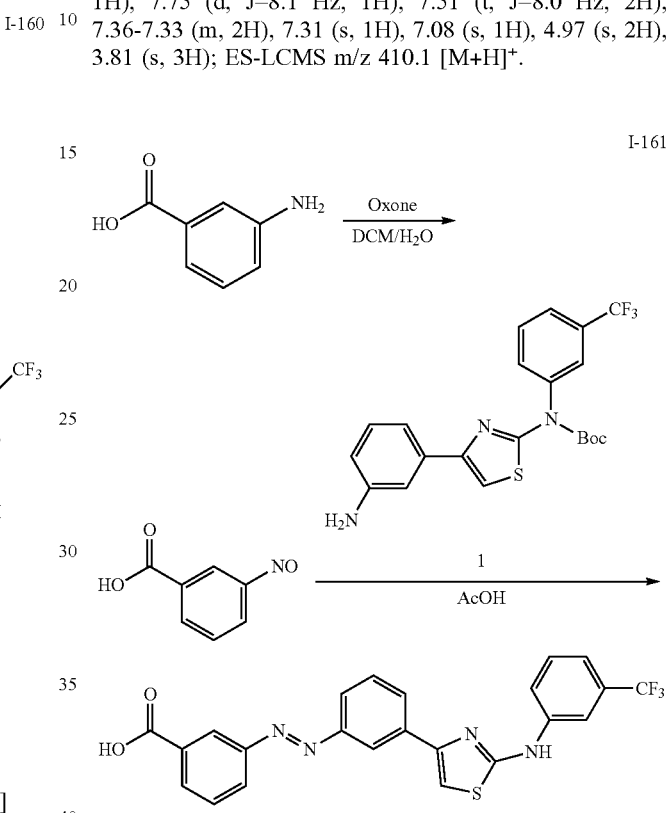

Step 1: 3-Nitrosobenzoic acid

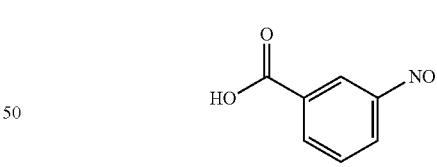

To a solution of 3-aminobenzoic acid (1 g, 7.29 mmol, 1 eq) in DCM (18 mL) and H$_2$O (80 mL) was added oxone (8.97 g, 14.58 mmol, 2.0 eq) under N$_2$ atmosphere. The mixture was stirred at 25° C. for 4 h under N$_2$ atmosphere. TLC (PE/EtOAc=1/1, R$_f$=0.6) showed that new point was formed and start material was consumed completely. The reaction mixture was filtered and the filtrate cake was dried under reduced pressure to yield 3-nitrosobenzoic acid (800 mg, 4.50 mmol, 61.7% yield, 85.0% purity) as a white solid, which was used in the next step without further purification. $^1$H NMR (400 MHz, DMSO-$d_6$) δ ppm 8.39 (d, J=7.6 Hz, 1H), 8.35 (s, 1H), 8.18 (d, J=7.6 Hz, 1H), 7.88 (t, J=8.0 Hz, 1H).

Step 2: 3-[(Z)-[3-[2-[3-(Trifluoromethyl)anilino]thiazol-4-yl]phenyl]azo]benzoic acid

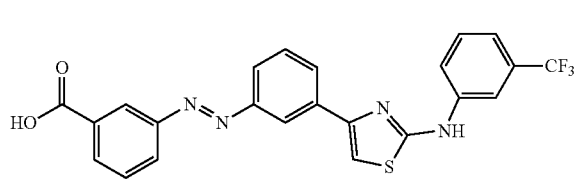 [SMILES: O=C(O)c1cccc(/N=N/c2cccc(-c3csc(Nc4cccc(C(F)(F)F)c4)n3)c2)c1]

To a solution of tert-butyl N-[4-(3-aminophenyl)thiazol-2-yl]-N-[3-(trifluoromethyl)phenyl]carbamate (150 mg, 327.24 mmol, 95.0% purity, 1 eq) in AcOH (3 mL) was added 3-nitrosobenzoic acid (116.36 mg, 654.48 mmol, 85% purity, 2 eq). The mixture was stirred at 80° C. for 4 h. The reaction mixture was concentrated to yield a residue which was purified by flash silica gel chromatography (from PE/EtOAc=100/1 to 3/1, TLC: PE/EtOAc=10/1, $R_f$=0.40) and preparative HPLC (column: Welch Xtimate C18 150*25 mm*5 um; mobile phase: [water (10 mM $NH_4HCO_3$)-ACN]; B %: 24%-54%, 10 min) to yield 3-[(Z)-[3-[2-[3-(trifluoromethyl)anilino]thiazol-4-yl]phenyl]azo]benzoic acid (20.91 mg, 41.63 mmol, 12.7% yield, 93.3% purity) as a yellow solid. $^1$H NMR (500 MHz, DMSO-$d_6$) δ ppm 10.76 (s, 1H), 8.50 (d, J=11.0 Hz, 2H), 8.44 (s, 1H), 8.25 (s, 1H), 8.17-8.05 (m, 3H), 7.91 (br d, J=8.5 Hz, 1H), 7.79 (d, J=8.5 Hz, 1H), 7.73-7.66 (m, 3H), 7.59 (t, J=8.0 Hz, 1H), 7.32 (d, J=8.0 Hz, 1H); ES-LCMS m/z 469.1 [M+H]$^+$.

I-163

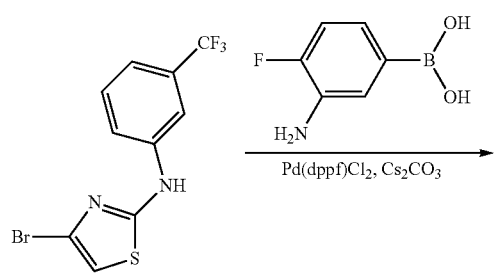

Step 1: 4-(3-Amino-4-fluoro-phenyl)-N-[3-(trifluoromethyl)phenyl]thiazol-2-amine

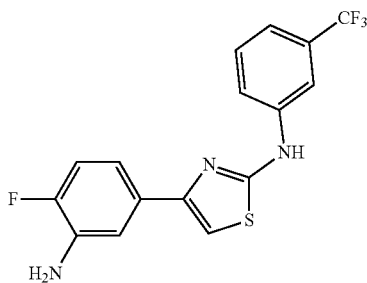 [SMILES: Nc1cc(-c2csc(Nc3cccc(C(F)(F)F)c3)n2)ccc1F]

A mixture of 4-bromo-N-[3-(trifluoromethyl)phenyl]thiazol-2-amine (150 mg, 417.79 μmol, 90% purity, 1 eq), (3-amino-4-fluoro-phenyl)boronic acid (80 mg, 516.35 μmol, 1.24 eq), $Cs_2CO_3$ (400 mg, 1.23 mmol, 2.94 eq) and Pd(dppf)$Cl_2$ (30 mg, 41.00 μmol, 9.81e-2 eq) in 1,4-dioxane (3 mL) and $H_2O$ (1 mL) was stirred under $N_2$ atmosphere at 100° C. for 12 h. The reaction mixture was diluted with EtOAc (50 mL), dried over $Na_2SO_4$, filtered and concentrated under reduced pressure to yield a residue which was purified by preparative HPLC (column: Agela DuraShell C18 150*25 mm*5 um; mobile phase: [water (0.05% $NH_3H_2O$+10 mM $NH_4HCO_3$)-ACN]; B %: 46%-76%, 10 min) and lyophilized to yield 4-(3-amino-4-fluoro-phenyl)-N-[3-(trifluoromethyl)phenyl]thiazol-2-amine (20.54 mg, 56.97 μmol, 13.6% yield, 98.0% purity) as a brown solid. $^1$H NMR (500 MHz, $CD_3OD$) δ ppm 8.16 (s, 1H), 7.97 (d, J=8.2 Hz, 1H), 7.52 (t, J=8.0 Hz, 1H), 7.42 (dd, J=2.1, 8.7 Hz, 1H), 7.27-7.22 (m, 2H), 7.04-6.98 (m, 2H); ES-LCMS m/z 354.6 [M+H]$^+$.

I-164

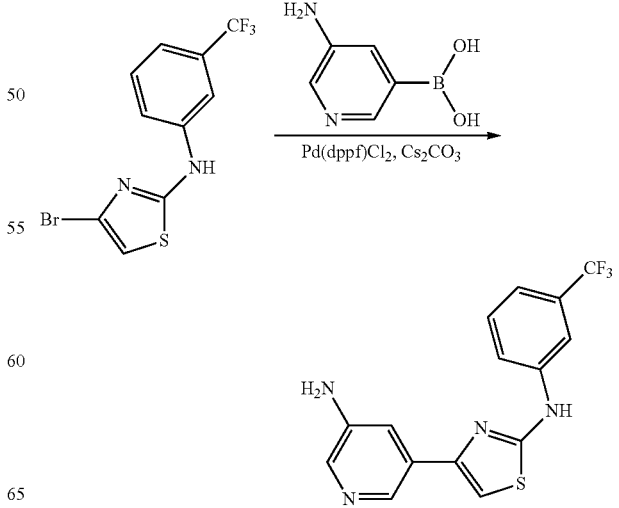

373

Step 1: 4-(5-Amino-3-pyridyl)-N-[3-(trifluoromethyl)phenyl]thiazol-2-amine

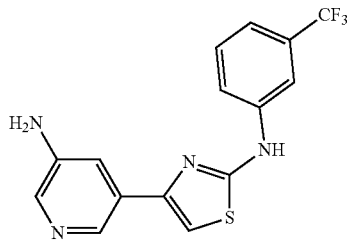 [SMILES: Nc1cncc(-c2csc(Nc3cccc(C(F)(F)F)c3)n2)c1]

A mixture of 4-bromo-N-[3-(trifluoromethyl)phenyl]thiazol-2-amine (150 mg, 441.00 µmol, 95% purity, 1 eq), 5-(4,4,5,5-tetramethyl-1,3,2-dioxaborolan-2-yl)pyridin-3-amine (110 mg, 499.83 µmol, 1.13 eq), $Cs_2CO_3$ (400 mg, 1.23 mmol, 2.78 eq) and $Pd(dppf)Cl_2$ (28.50 mg, 38.95 µmol, 8.83e-2 eq) in 1,4-dioxane (3 mL) and $H_2O$ (1 mL) was stirred under $N_2$ atmosphere at 100° C. for 12 h. The reaction mixture was diluted with EtOAc (50 mL), dried over $Na_2SO_4$, filtered and concentrated under reduced pressure to yield a residue which was purified by preparative HPLC (column: Agela DuraShell C18 150*25 mm*5 um; mobile phase: [water (0.05% $NH_3H_2O$+10 mM $NH_4HCO_3$)-ACN]; B %: 33%-63%, 10 min) and lyophilized to yield 4-(5-amino-3-pyridyl)-N-[3-(trifluoromethyl)phenyl]thiazol-2-amine (17.67 mg, 51.70 µmol, 11.7% yield, 98.4% purity) as a brown solid. $^1$H NMR (500 MHz, $CD_3OD$) δ ppm 8.40 (d, J=1.7 Hz, 1H), 8.20 (s, 1H), 7.97-7.91 (m, 2H), 7.60 (t, J=2.1 Hz, 1H), 7.52 (t, J=7.9 Hz, 1H), 7.27 (d, J=7.8 Hz, 1H), 7.23 (s, 1H); ES-LCMS m/z 337.2 [M+H]$^+$.

374

Step 1: 4-(5-Amino-2,4-difluoro-phenyl)-N-[3-(trifluoromethyl)phenyl]thiazol-2-amine

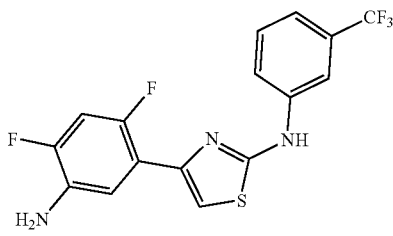 [SMILES: Nc1cc(-c2csc(Nc3cccc(C(F)(F)F)c3)n2)c(F)cc1F]

A mixture of 5-bromo-2,4-difluoro-aniline (50 mg, 240.38 µmol, 1 eq), 4-tributylstannyl-N-[3-(trifluoromethyl)phenyl]thiazol-2-amine (366.26 mg, 480.76 µmol, 70% purity, 2 eq) and $Pd(dppf)Cl_2$ (17.59 mg, 24.04 µmol, 0.1 eq) in DMF (2 mL) was degassed and purged with $N_2$ for 3 times and the mixture was stirred under $N_2$ atmosphere at 140° C. for 12 h. The mixture was diluted with water (10 mL) and extracted with EtOAc (10 mL×3). The combined organic layers were dried over $Na_2SO_4$, filtered and concentrated under reduced pressure to yield a residue which was purified by preparative HPLC (column: Agela DuraShell C18 150*25 mm*5 um; mobile phase: [water (0.05% $NH_3H_2O$+10 mM $NH_4HCO_3$)-ACN]; B %: 455%-85%, 10 min), followed by lyophilization to yield 4-(5-amino-2,4-difluoro-phenyl)-N-[3-(trifluoromethyl)phenyl]thiazol-2-amine (21.22 mg, 54.73 µmol, 22.8% yield, 95.8% purity) as a gray solid. $^1$H NMR (500 MHz, DMSO-$d_6$) δ ppm 10.62 (s, 1H), 8.15 (d, J=9.0 Hz, 1H), 7.94 (s, 1H), 7.59 (t, J=8.0 Hz, 1H), 7.46 (dd, J=8.1, 10.2 Hz, 1H), 7.30 (d, J=7.6 Hz, 1H), 7.20-7.11 (m, 2H), 5.10 (s, 2H); ES-LCMS m/z 372.1 [M+H]$^+$.

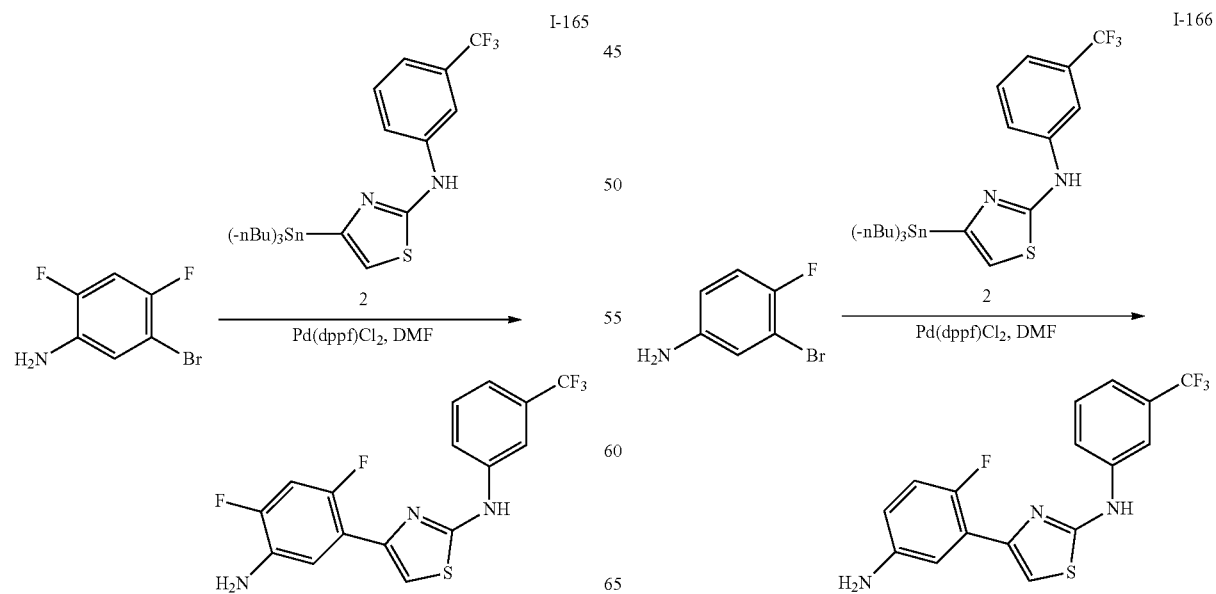

Step 1: 4-(5-Amino-2-fluoro-phenyl)-N-[3-(trifluoromethyl)phenyl]thiazol-2-amine

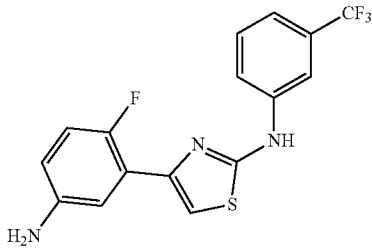 [SMILES: Nc1ccc(F)c(-c2csc(Nc3cccc(C(F)(F)F)c3)n2)c1]

A mixture of 3-bromo-4-fluoro-aniline (150 mg, 789.42 µmol, 1 eq), 4-tributylstannyl-N-[3-(trifluoromethyl)phenyl]thiazol-2-amine (467.76 mg, 789.42 µmol, 90% purity, 1 eq) and Pd(dppf)Cl$_2$ (57.76 mg, 78.94 µmol, 0.1 eq) in DMF (2 mL) was degassed and purged with N$_2$ for 3 times and the mixture was stirred under N$_2$ atmosphere at 140° C. for 12 h. The mixture was diluted with water (10 mL) and extracted with EtOAc (10 mL×3). The combined organic layers were dried over Na$_2$SO$_4$, filtered and concentrated under reduced pressure to yield a residue which was purified by preparative HPLC (column: Welch Xtimate C18 150*25 mm*5 um; mobile phase: [water (10 mM NH$_4$HCO$_3$)-ACN]; B %: 50%-80%, 10 min), followed by lyophilization to yield 4-(5-amino-2-fluoro-phenyl)-N-[3-(trifluoromethyl)phenyl]thiazol-2-amine (46.28 mg, 130.98 µmol, 16.6% yield, 100.0% purity) as a brown solid. $^1$H NMR (400 MHz, CDCl$_3$) δ ppm 7.98 (s, 1H), 7.59 (d, J=7.8 Hz, 1H), 7.51-7.46 (m, 2H), 7.32 (d, J=7.8 Hz, 1H), 7.24 (br s, 1H), 7.20 (d, J=2.0 Hz, 1H), 6.95 (dd, J=8.6, 11.3 Hz, 1H), 6.60 (td, J=3.5, 8.6 Hz, 1H), 3.63 (br s, 2H); ES-LCMS m/z 354.1 [M+H]$^+$.

I-167

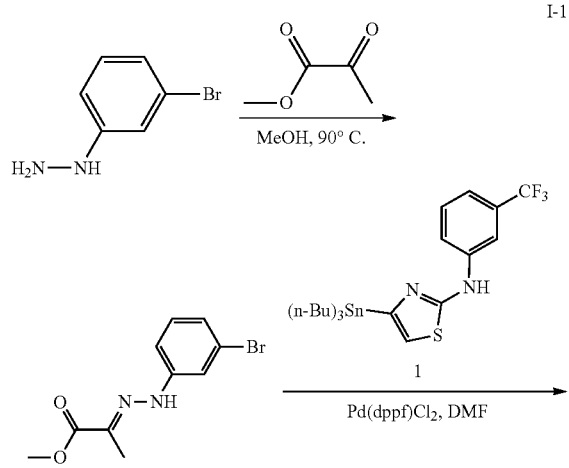

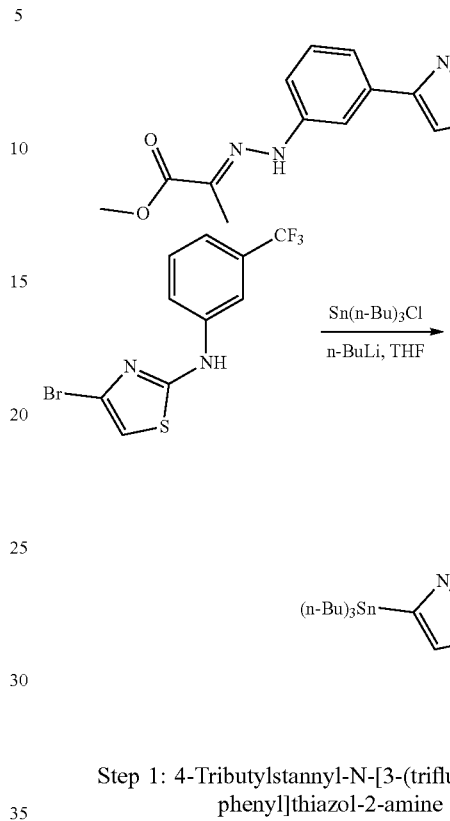

Step 1: 4-Tributylstannyl-N-[3-(trifluoromethyl)phenyl]thiazol-2-amine

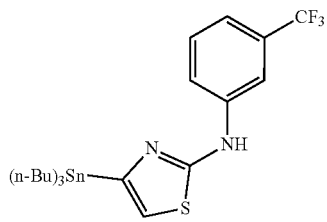

To a solution of 4-bromo-N-[3-(trifluoromethyl)phenyl]thiazol-2-amine (10 g, 29.40 mmol, 95% purity, 1 eq) in THF (100 mL) was added n-BuLi (2.5 M, 29.40 mL, 2.5 eq) −78° C. under N$_2$ atmosphere. The mixture was stirred under N$_2$ atmosphere at −78° C. for 2 h and tributyl(chloro)stannane (19.14 g, 58.80 mmol, 15.82 mL, 2 eq) was added dropwise. The reaction mixture was stirred under N$_2$ atmosphere for another 1 h and allowed to warm to room temperature (20° C.) slowly. The mixture was stirred under N$_2$ atmosphere at 20° C. for 1 h. TLC (PE/EtOAc=4/1, R$_f$=0.7) showed that new point was formed and start material was consumed completely. The reaction mixture was quenched by addition sat.aq KF (200 mL) and extracted with EtOAc (150 mL×3). The combined organic layers were washed with brine (100 mL), dried over Na$_2$SO$_4$, filtered and concentrated under reduced pressure to give a residue which was purified by flash silica gel chromatography (from PE/EtOAc=100/1 to 3/1, TLC: PE/EtOAc=4/1, R$_f$=0.7) to yield 4-tributylstannyl-N-[3-(trifluoromethyl)phenyl]thiazol-2-amine (14.5 g, 24.47 mmol, 83.2% yield, 90.0% purity) as colorless oil. ¹H NMR (400 MHz, CDCl₃) δ ppm 7.88 (s, 1H), 7.55 (d, J=6.4 Hz, 1H), 7.42 (t, J=8.0 Hz, 1H), 7.25 (d, J=7.2 Hz, 1H), 6.73-6.69 (m, 1H), 1.62-1.57 (m, 6H), 1.37 (s, 6H), 1.13-1.09 (m, 6H), 0.95-0.91 (m, 9H); ES-LCMS m/z 535.2 [M+H]⁺.

Step 2: Methyl (2E)-2-[(3-bromophenyl)hydrazono]propanoate

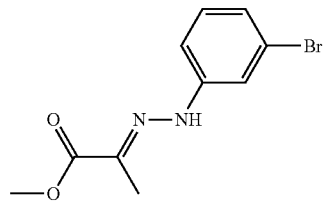

To a solution of (3-bromophenyl)hydrazine (1 g, 4.47 mmol, 1 eq, HCl) in MeOH (20 mL) was added methyl 2-oxopropanoate (456.78 mg, 4.47 mmol, 404.23 μL, 1 eq). The mixture was stirred at 90° C. for 3 h. TLC (PE/EtOAc=3/1, R_f=0.4) showed that new point was formed and start material was consumed completely. The reaction mixture was quenched by addition H₂O (80 mL) and extracted with EtOAc (80 mL×3). The combined organic layers were washed with brine (80 mL), dried over Na₂SO₄, filtered and concentrated under reduced pressure to give a residue. The residue was purified by flash silica gel chromatography (from PE/EtOAc=100/1 to 3/1, TLC: PE/EtOAc=3/1, R_f=0.40) to yield methyl (2E)-2-[(3-bromophenyl)hydrazono]propanoate (750 mg, 2.49 mmol, 55.7% yield, 90.0% purity). ¹H NMR (400 MHz, DMSO-d₆) δ ppm 9.97 (s, 1H), 7.49-7.38 (m, 1H), 7.28-7.18 (m, 2H), 7.10-7.01 (m, 1H), 3.74 (s, 3H), 2.06 (s, 3H); ES-LCMS m/z 273.1 [M+H]⁺.

Step 3: Methyl (2E)-2-[[3-[2-[3-(trifluoromethyl)anilino]thiazol-4-yl]phenyl]hydrazono]propanoate

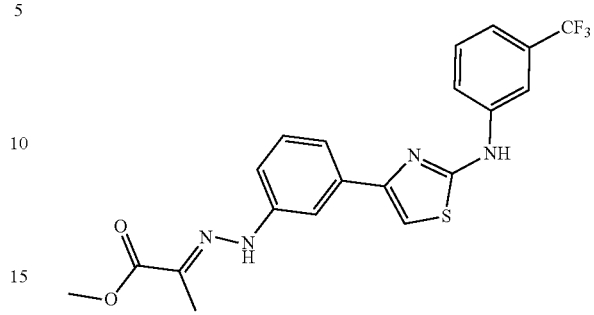

To a solution of methyl (2E)-2-[(3-bromophenyl)hydrazono]propanoate (222.22 mg, 737.71 μmol, 90.0% purity, 1 eq) and 4-tributylstannyl-N-[3-(trifluoromethyl)phenyl]thiazol-2-amine (524.54 mg, 885.25 μmol, 90% purity, 1.2 eq) in DMF (10 mL) was added Pd(dppf)Cl₂ (539.79 mg, 737.71 μmol, 1 eq) under N₂ atmosphere. The mixture was stirred under N₂ atmosphere at 100° C. for 2 h. The reaction mixture was quenched by addition sutural KF (20 mL) and extracted with EtOAc (30 mL×3). The combined organic layers were washed with brine (30 mL), dried over Na₂SO₄, filtered and concentrated under reduced pressure to give a residue which was purified by preparative HPLC(column: Welch Xtimate C18 150*25 mm*5 μm; mobile phase: [water (10 mM NH₄HCO₃)-ACN]; B %: 55%-85%, 10 min) to yield methyl (2E)-2-[[3-[2-[3-(trifluoromethyl)anilino]thiazol-4-yl]phenyl]hydrazono]propanoate (88.73 mg, 204.24 μmol, 27.7% yield, 100.0% purity) as a white solid. ¹H NMR (400 MHz, DMSO-d₆) δ ppm 10.64 (s, 1H), 9.93 (s, 1H), 8.13 (s, 1H), 8.04 (d, J=8.4 Hz, 1H), 7.81 (s, 1H), 7.59 (t, J=8.0 Hz, 1H), 7.45 (d, J=8.0 Hz, 1H), 7.37-7.28 (m, 3H), 7.24 (d, J=9.2 Hz, 1H), 3.73 (s, 3H), 2.10 (s, 3H); ES-LCMS m/z 435.2 [M+H]⁺.

I-169

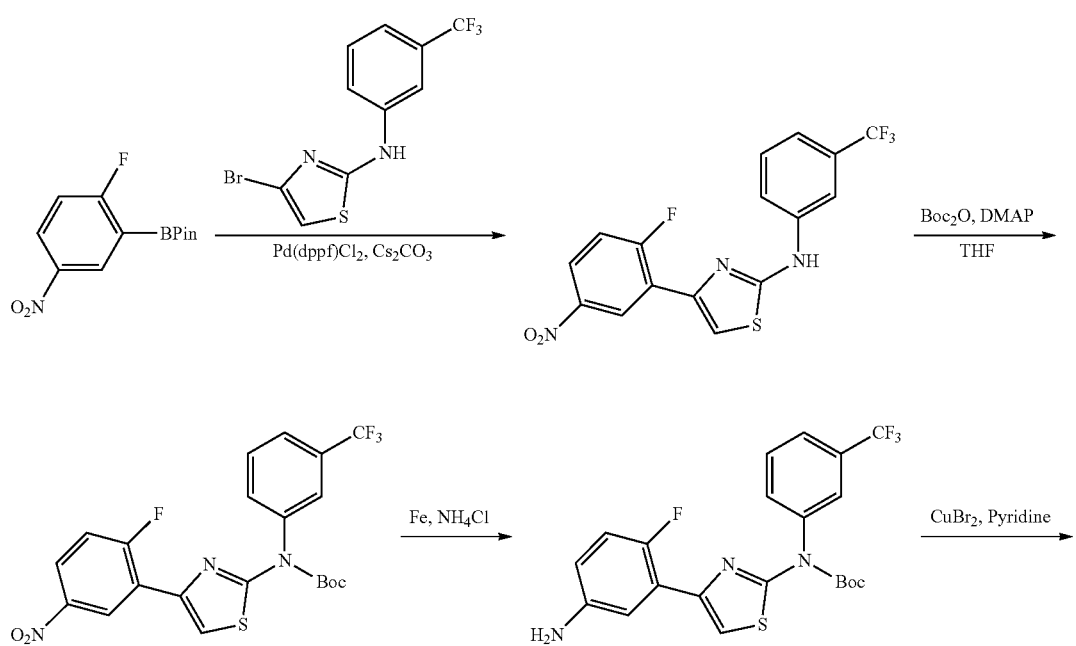

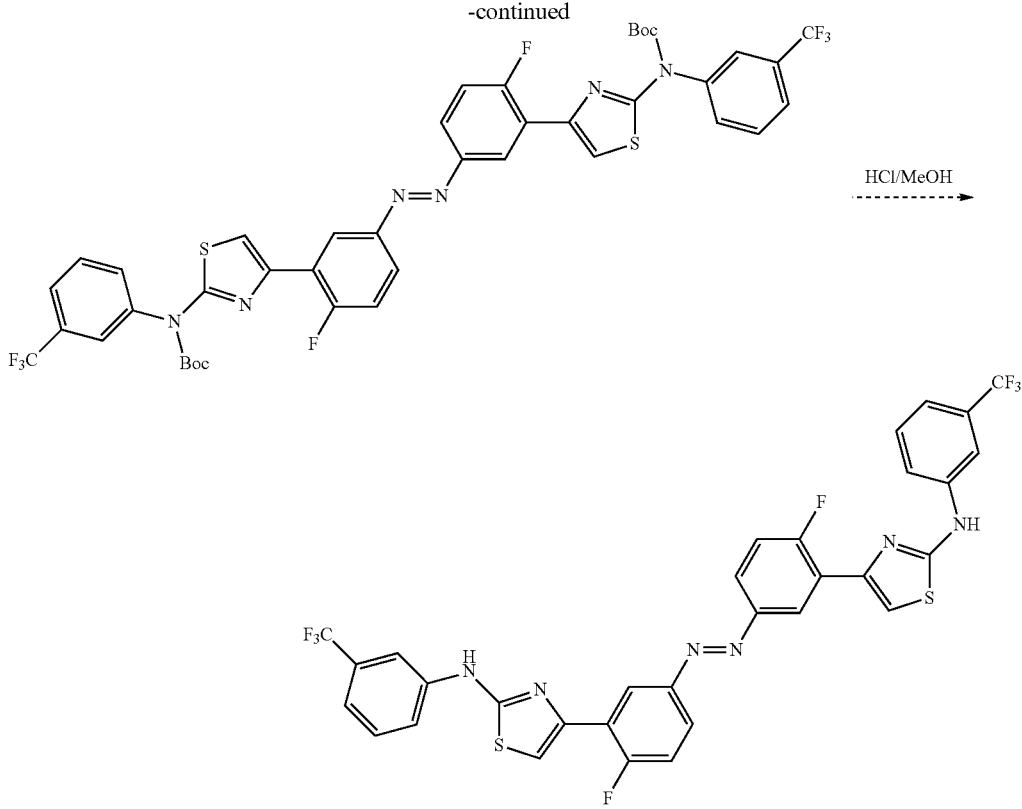

Step 1: 4-(2-Fluoro-5-nitrophenyl)-N-(3-(trifluoromethyl)phenyl)thiazol-2-amine

To a solution of 4-bromo-N-[3-(trifluoromethyl)phenyl]thiazol-2-amine (2.35 g, 6.62 mmol, 91.0% purity, 1 eq) in 1,4-dioxane (30 mL) and H$_2$O (10 mL) was added 2-(2-fluoro-5-nitro-phenyl)-4,4,5,5-tetramethyl-1,3,2-dioxaborolane (1.74 g, 6.51 mmol, 1 eq), Cs$_2$CO$_3$ (5.39 g, 16.55 mmol, 2.5 eq) and Pd(dppf)Cl$_2$ (242.12 mg, 330.90 μmol, 0.05 eq). The mixture was stirred at 100° C. for 12 h. The reaction mixture was quenched by addition of water (60 mL) and extracted with EtOAc (100 mL×3). The combined organic layers were washed with brine (50 mL), dried over Na$_2$SO$_4$, filtered and concentrated under reduced pressure to give a residue which was purified by flash silica gel chromatography (from pure PE to PE/EtOAc=5/1, TLC: PE/EtOAc=5/1, R$_f$=0.43) to yield 4-(2-fluoro-5-nitro-phenyl)-N-[3-(trifluoromethyl)phenyl]thiazol-2-amine (2.3 g, 5.22 mmol, 78.8% yield, 87.0% purity) as a white solid. $^1$H NMR (400 MHz, CDCl$_3$) δ ppm 9.10 (dd, J=2.9, 6.6 Hz, 1H), 8.19 (d, J=3.7, 8.7 Hz, 1H), 7.91 (s, 1H), 7.65 (d, J=8.1 Hz, 1H), 7.53 (t, J=7.9 Hz, 1H), 7.37 (d, J=7.1 Hz, 2H), 7.33-7.28 (m, 2H); ES-LCMS m/z 384.0 [M+H]$^+$.

Step 2: tert-Butyl N-[4-(2-fluoro-5-nitro-phenyl)thiazol-2-yl]-N-[3-(trifluoromethyl)phenyl]carbamate

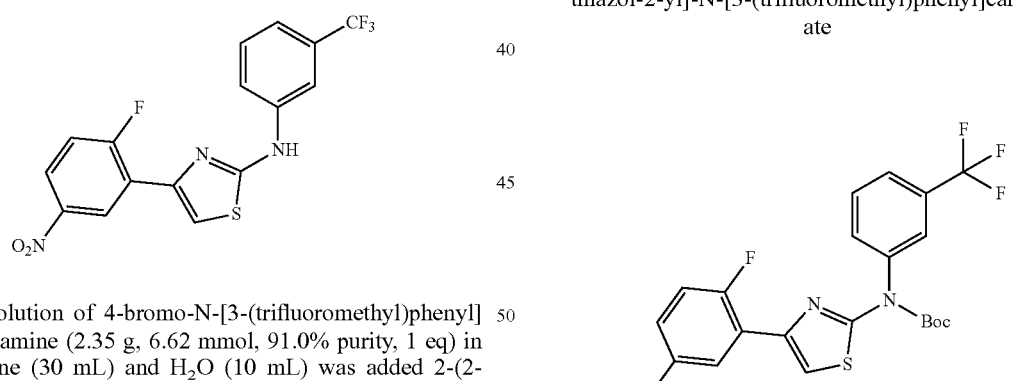

To a solution of 4-(2-fluoro-5-nitro-phenyl)-N-[3-(trifluoromethyl)phenyl]thiazol-2-amine (2.2 g, 4.99 mmol, 87.0% purity, 1 eq) in THF (40 mL) was added (Boc)$_2$O (3.27 g, 14.98 mmol, 3.44 mL, 3 eq) and DMAP (610.01 mg, 4.99 mmol, 1 eq). The mixture was stirred at 80° C. for 1 h. The reaction mixture was quenched by addition of water (50 mL) and extracted with EtOAc (50 mL×3). The combined organic layers were washed with brine (20 mL), dried over Na$_2$SO$_4$, filtered and concentrated under reduced pressure to give a residue which was purified by flash silica gel chromatography (from pure PE to PE/EtOAc=5/1, TLC: PE/EtOAc=5/1, R$_f$=0.58) to yield tert-butyl N-[4-(2-fluoro- 5-nitro-phenyl)thiazol-2-yl]-N-[3-(trifluoromethyl)phenyl]carbamate (2.15 g, 3.56 mmol, 71.2% yield, 80.0% purity) as a yellow solid. $^1$H NMR (400 MHz, DMSO-d$_6$) δ ppm 8.36 (dd, J=2.9, 6.5 Hz, 1H), 8.16 (d, J=3.6, 8.8 Hz, 1H), 7.96 (s, 1H), 7.85-7.82 (m, 1H), 7.84-7.81 (m, 1H), 7.85-7.81 (m, 1H), 7.88-7.74 (m, 1H), 7.79-7.74 (m, 1H), 7.79-7.74 (m, 1H), 7.78-7.74 (m, 1H), 7.88-7.71 (m, 1H), 7.60-7.51 (m, 1H), 1.42 (s, 9H); ES-LCMS m/z 428.0 [M-t-Bu+H]$^+$.

Step 3: tert-Butyl (4-(5-amino-2-fluorophenyl)thiazol-2-yl)(3-(trifluoromethyl)phenyl)carbamate

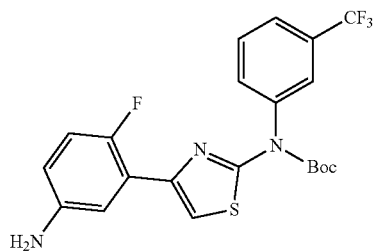 [SMILES: CC(C)(C)OC(=O)N(c1cccc(C(F)(F)F)c1)c1nc(-c2cc(N)ccc2F)cs1]

To a solution of tert-butyl N-[4-(2-fluoro-5-nitro-phenyl)thiazol-2-yl]-N-[3-(trifluoromethyl)phenyl]carbamate (1 g, 1.65 mmol, 80.0% purity, 1 eq) in THF (10 mL), EtOH (10 mL) and H$_2$O (10 mL) was added Fe (462.07 mg, 8.27 mmol, 5 eq) and NH$_4$Cl (885.19 mg, 16.55 mmol, 10 eq). The mixture was stirred at 25° C. for 5 h. The reaction mixture was quenched by addition of water (300 mL) and extracted with EtOAc (50 mL×3). The combined organic layers were washed with brine (20 mL), dried over Na$_2$SO$_4$, filtered and concentrated under reduced pressure to give a residue which was purified by flash silica gel chromatography (from pure PE to PE/EtOAc=3/1, TLC: PE/EtOAc=3/1, R$_f$=0.49) to yield tert-butyl N-[4-(5-amino-2-fluoro-phenyl)thiazol-2-yl]-N-[3-(trifluoromethyl)phenyl]carbamate (697 mg, 1.46 mmol, 88.2% yield, 95.0% purity) as a yellow oil. $^1$H NMR (400 MHz, CDCl$_3$) δ ppm 7.68-7.49 (m, 4H), 7.45 (d, J=2.0 Hz, 1H), 7.01 (dd, J=2.9, 6.5 Hz, 1H), 6.86 (dd, J=8.6, 11.0 Hz, 1H), 6.51-6.43 (m, 1H), 3.45 (s, 2H), 1.47 (s, 9H) ES-LCMS m/z 454.1 [M+H]$^+$.

Step 4: (E)-Di-tert-butyl (4,4'-(diazene-1,2-diylbis(2-fluoro-5,1-phenylene))bis(thiazole-4,2-diyl))bis((3-(trifluoromethyl)phenyl)carbamate)

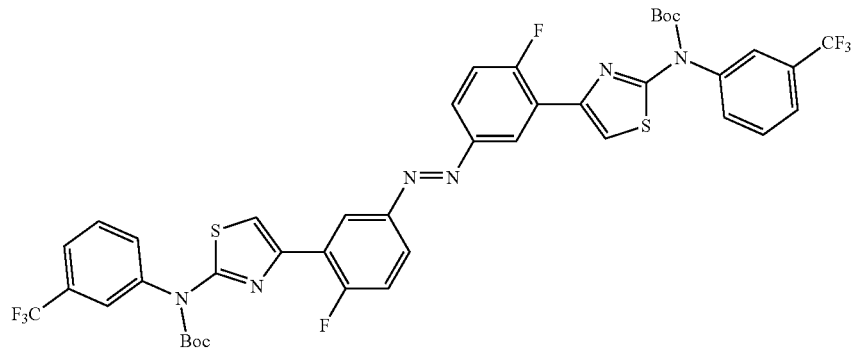 [SMILES: CC(C)(C)OC(=O)N(c1cccc(C(F)(F)F)c1)c1nc(-c2cc(/N=N/c3ccc(F)c(-c4csc(N(C(=O)OC(C)(C)C)c5cccc(C(F)(F)F)c5)n4)c3)ccc2F)cs1]

To a solution of tert-butyl N-[4-(5-amino-2-fluoro-phenyl)thiazol-2-yl]-N-[3-(trifluoromethyl)phenyl]carbamate (200 mg, 419.01 μmol, 95.0% purity, 1 eq) in toluene (4 mL) was added CuBr (601.07 μg, 4.19 μmol, 0.01 eq) and pyridine (331.43 μg, 4.19 μmol, 21.12 μmL, 0.01 eq). The mixture was stirred at 80° C. for 12 h. The reaction mixture was concentrated to yield tert-butyl N-[4-[5-[(E)-[3-[2-[N-tert-butoxycarbonyl-3-(trifluoromethyl)anilino]thiazol-4-yl]-4-fluoro-phenyl]azo]-2-fluoro-phenyl]thiazol-2-yl]-N-[3-(trifluoromethyl)phenyl]carbamate (285 mg, crude) as a black solid, which was used in the next step without further purification. ES-LCMS m/z 903.1 [M+H]$^+$.

Step 5: (E)-4,4'-(Diazene-1,2-diylbis(2-fluoro-5,1-phenylene))bis(N-(3-(trifluoromethyl)phenyl)thiazol-2-amine)

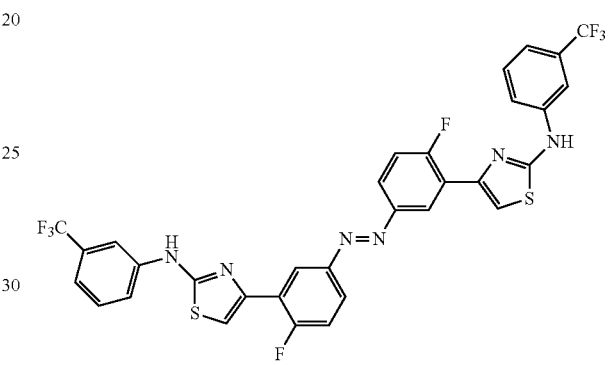

To a solution of tert-butyl N-[4-[5-[(E)-[3-[2-[N-tert-butoxycarbonyl-3-(trifluoromethyl)anilino]thiazol-4-yl]-4-fluoro-phenyl]azo]-2-fluoro-phenyl]thiazol-2-yl]-N-[3-(trifluoromethyl)phenyl]carbamate (260 mg, 287.97 μmol, N/A purity, 1 eq) in MeOH (5 mL) was added HCl/1,4-dioxane (4 M, 20 mL, 277.81 eq). The mixture was stirred at 25° C. for 1 h. The reaction mixture was concentrated to yield a residue which was purified by preparative HPLC (column: Phenomenex Synergi C18 150*30 mm*4 um; mobile phase: [water (0.05% HCl)-ACN]; B %: 90%-100%, 10 min), followed by lyophilization to yield. 4-[2-fluoro-5-[(E)-[4-fluoro-3-[2-[3-(trifluoromethyl)anilino]thiazol-4-yl]phenyl]azo]phenyl]-N-[3-(trifluoromethyl)phenyl]thiazol-2-amine (11.79 mg, 16.78 μmol, 5.8% yield, 100.0% purity) as a yellow solid. $^1$H NMR (400 MHz, DMSO-d$_6$) δ ppm 10.76-10.63 (m, 2H), 8.64 (dd, J=2.3, 7.2 Hz, 2H), 8.49 (s, 2H), 7.94 (dd, J=3.9, 7.8 Hz, 2H), 7.69 (d, J=8.1 Hz, 2H), 7.61-7.52 (m, 2H), 7.53-7.42 (m, 4H), 7.16 (d, J=7.6 Hz, 2H); ES-LCMS m/z 703.0 [M+H]⁺.

g, 1.48 mmol, 0.1 eq), 4-tributylstannyl-N-[3-(trifluoromethyl)phenyl]thiazol-2-amine (8.76 g, 14.78 mmol, 90% purity, 1.0 eq). The mixture was stirred under N₂ atmosphere at 140° C. for 16 h. TLC (PE/EtOAc=1/1, R$_f$=0.2) showed the reaction was completed. The mixture was added water (20 mL) and extracted with EtOAc (20 mL×3). The combined organic layers were washed with brine (20 mL×3), dried over Na₂SO₄, filtered and concentrated to yield a residue which was purified by silica gel column chromatography (from PE/EtOAc=5/1 to 1/1, TLC: PE/EtOAc=1/1, R$_f$=0.5 & 0.2) to yield two fraction. The fraction (R$_f$=0.5) was concentrated to yield 4-(5-nitro-3-pyridyl)-N-[3-(trifluoromethyl)phenyl]thiazol-2-amine (1.5 g, 3.69 mmol, 24.9% yield, 90.0% purity) as a red solid. ¹H NMR (400 MHz, CDCl₃) δ ppm 9.39 (dd, J=2.2, 10.4 Hz, 2H), 8.91 (t, J=2.2 Hz, 1H), 8.08-8.00 (m, 1H), 7.87 (s, 1H), 7.70 (d, J=10.2 Hz, 1H), 7.59-7.50 (m, 2H), 7.37 (d, J=7.8 Hz, 1H); ES-LCMS m/z 367.1 [M+H]⁺. The fraction (R$_f$=0.2) was concentrated to yield 4-(5-amino-3-pyridyl)-N-[3-(trifluoromethyl)phenyl]thiazol-2-amine (0.5 g, 1.34 mmol, 9.1% yield, 90.0% purity) as a red solid. ¹H NMR (400 MHz, CDCl₃) δ ppm 8.37 (s, 1H), 8.17 (s, 1H), 7.94-7.87 (m, 2H), 7.57 (s, 1H), 7.49 (t, J=7.9 Hz, 1H), 7.23 (d, J=7.6 Hz, 1H), 7.18 (s, 1H); ES-LCMS m/z 337.1 [M+H]⁺.

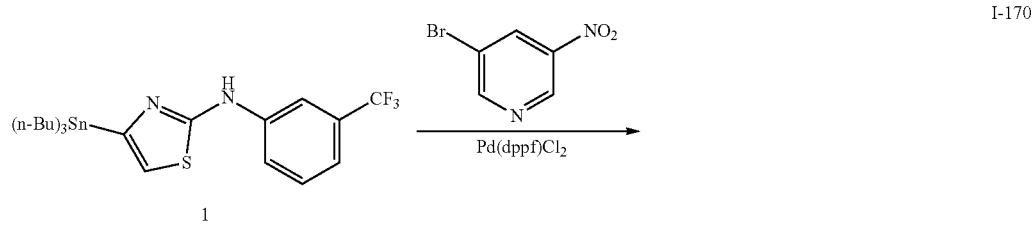

I-170

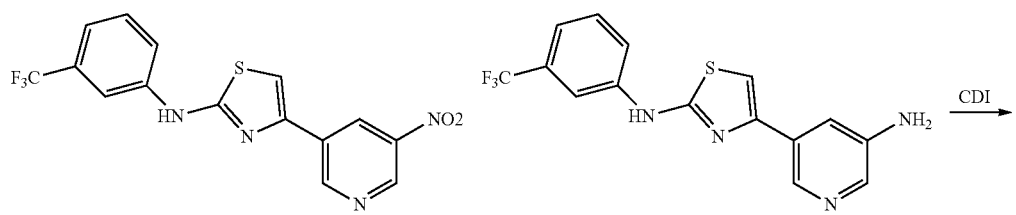

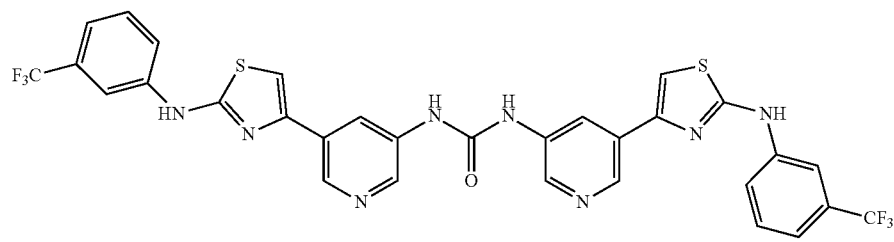

40

Step 1: 4-(5-Nitropyridin-3-yl)-N-(3-(trifluoromethyl)phenyl)thiazol-2-amine and 4-(5-aminopyridin-3-yl)-N-(3-(trifluoromethyl)phenyl)thiazol-2-amine

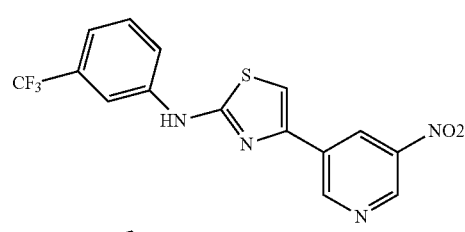

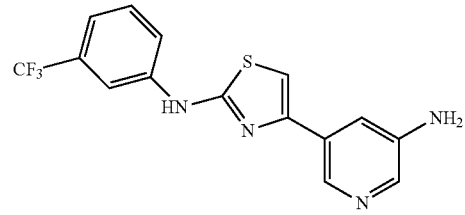

To a solution of 3-bromo-5-nitro-pyridine (3 g, 14.78 mmol, 1 eq) in DMF (20 mL) was added Pd(dppf)Cl₂ (1.08

Step 2: 1,3-Bis(5-(2-((3-(trifluoromethyl)phenyl)amino)thiazol-4-yl)pyridin-3-yl)urea

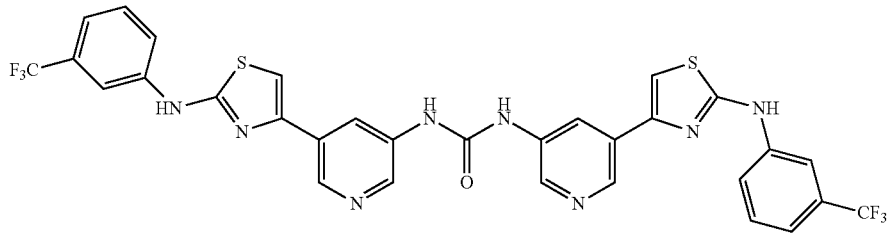 [SMILES: O=C(Nc1cncc(-c2csc(Nc3cccc(C(F)(F)F)c3)n2)c1)Nc1cncc(-c2csc(Nc3cccc(C(F)(F)F)c3)n2)c1]

To a solution of 4-(5-amino-3-pyridyl)-N-[3-(trifluoromethyl)phenyl]thiazol-2-amine (300 mg, 802.77 µmol, 90.0% purity, 1 eq) in THF (3 mL) was added CDI (260.34 mg, 1.61 mmol, 2 eq), DMAP (49.04 mg, 401.39 µmol, 0.5 eq). The mixture was stirred under $N_2$ atmosphere at 80° C. for 16 h. The mixture was concentrated to yield a residue which was purified by preparative HPLC: [water (0.05% HCl)-ACN]; B %: 40%-70%) to yield 1,3-bis[5-[2-[3-(trifluoromethyl)anilino]thiazol-4-yl]-3-pyridyl]urea (17 mg, 22.25 µmol, 2.8% yield, 96.2% purity, HCl) as a yellow solid. $^1$H NMR (400 MHz, DMSO-$d_6$) δ ppm 10.85 (s, 2H), 9.81 (s, 2H), 8.88 (s, 2H), 8.76 (s, 2H), 8.64 (s, 2H), 8.19 (s, 2H), 7.99 (s, 2H), 7.71-7.64 (m, 2H), 7.58 (t, J=8.1 Hz, 2H), 7.30 (d, J=7.8 Hz, 2H); ES-LCMS m/z 669.3 [M+H]$^+$.

I-172

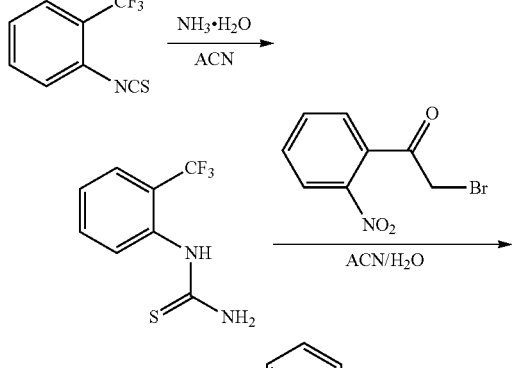

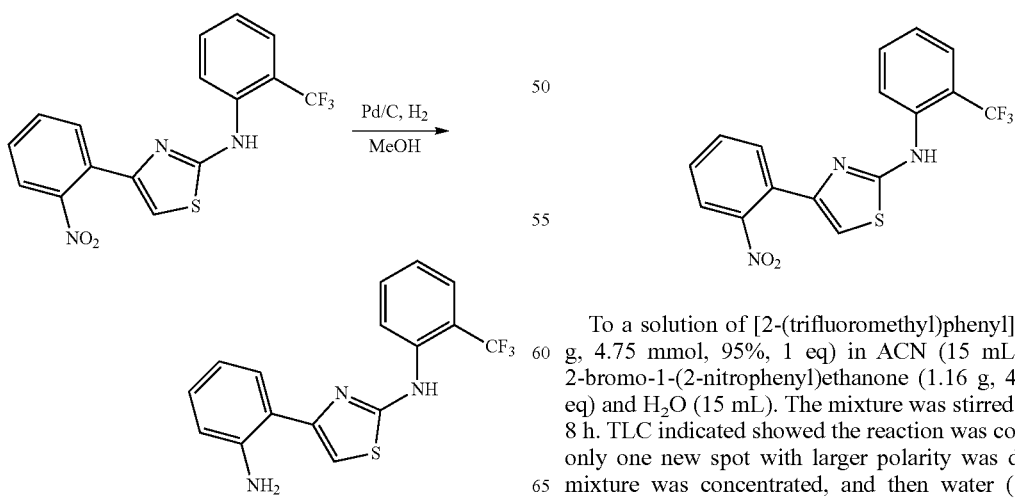

Step 1: [2-(Trifluoromethyl)phenyl]thiourea

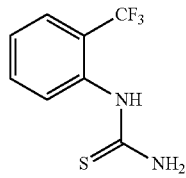

To a solution of 1-isothiocyanato-2-(trifluoromethyl)benzene (1 g, 4.92 mmol, 746.27 µL, 1 eq) in ACN (25 mL) was added $NH_3 \cdot H_2O$ (1.23 g, 9.84 mmol, 1.35 mL, 28%, 2 eq). The mixture was stirred at 25° C. for 2 h. The reaction mixture was quenched by addition $H_2O$ (80 mL) and extracted with EtOAc (80 mL×3). The combined organic layers were washed with brine (80 mL), dried over $Na_2SO_4$, filtered and concentrated under reduced pressure to yield [2-(trifluoromethyl)phenyl]thiourea (1.1 g, 4.75 mmol, 96.4% yield, 95.0% purity) as a white solid, which was used in the next step without further purification. $^1$H NMR (400 MHz, DMSO-$d_6$) δ ppm 9.24 (s, 1H), 7.74-7.62 (m, 2H), 7.54 (d, J=7.6 Hz, 1H), 7.45 (t, J=7.6 Hz, 1H); ES-LCMS m/z 221.2 [M+H]$^+$.

Step 2: 4-(2-Nitrophenyl)-N-[2-(trifluoromethyl)phenyl]thiazol-2-amine

To a solution of [2-(trifluoromethyl)phenyl]thiourea (1.1 g, 4.75 mmol, 95%, 1 eq) in ACN (15 mL) was added 2-bromo-1-(2-nitrophenyl)ethanone (1.16 g, 4.75 mmol, 1 eq) and $H_2O$ (15 mL). The mixture was stirred at 25° C. for 8 h. TLC indicated showed the reaction was completed, and only one new spot with larger polarity was detected. The mixture was concentrated, and then water (60 mL) was added. The mixture was extracted with EtOAc (70 mL×3). The combined organic layers were washed with brine (20 mL), dried over Na$_2$SO$_4$, filtered and concentrated to yield 4-(2-nitrophenyl)-N-[2-(trifluoromethyl)phenyl]thiazol-2-amine (1.7 g, 4.14 mmol, 87.2% yield, 89.0% purity) as a yellow solid, which was used in the next step directly without further purification.

Step 3: 4-(2-Aminophenyl)-N-[2-(trifluoromethyl)phenyl]thiazol-2-amine

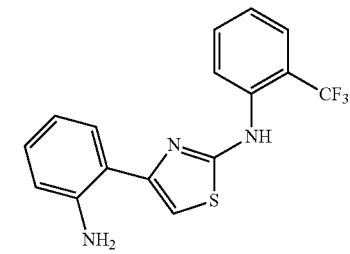 [SMILES: O=[N+]([O-])c1ccccc1-c1csc(Nc2ccccc2C(F)(F)F)n1]

To a solution of 4-(2-nitrophenyl)-N-[2-(trifluoromethyl)phenyl]thiazol-2-amine (200 mg, 487.23 μmol, 89%, 1 eq) in THF (10 mL) and H$_2$O (10 mL) was added Zn (318 mg, 4.86 mmol, 9.98 eq) and NH$_4$Cl (260 mg, 4.86 mmol, 9.98 eq). The mixture was stirred at 25° C. for 15 min. The mixture was concentrated, and then water (40 mL) was added. The mixture was extracted with EtOAc (50 mL×3). The combined organic layers were washed with brine (20 mL), dried over Na$_2$SO$_4$, filtered and concentrated to yield crude 4-(2-aminophenyl)-N-[2-(trifluoromethyl)phenyl]thiazol-2-amine. The residue was purified by preparative HPLC (column: Welch Xtimate C18 150*25 mm*5 μm; mobile phase: [water (10 mM NH$_4$HCO$_3$)-ACN]; B %: 47%-77%, 10 min) and lyophilized to yield 4-(2-aminophenyl)-N-[2-(trifluoromethyl)phenyl]thiazol-2-amine (118 mg, 334.28 μmol, 68.6% yield, 95.0% purity). $^1$H NMR (400 MHz, CDCl$_3$) δ ppm 8.06 (d, J=8.3 Hz, 1H), 7.64 (d, J=7.6 Hz, 1H), 7.56 (t, J=8.1 Hz, 1H), 7.45 (d, J=7.6 Hz, 1H), 7.19-7.11 (m, 2H), 6.81 (s, 1H), 6.77-6.72 (m, 2H), ES-LCMS m/z 336.0 [M+H]$^+$.

I-173

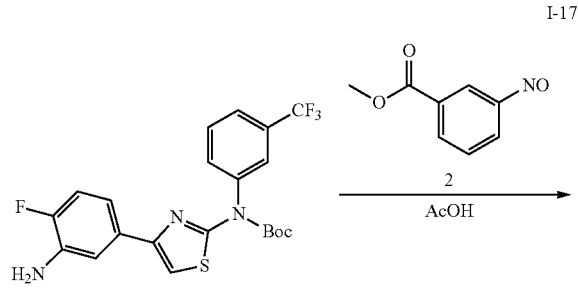

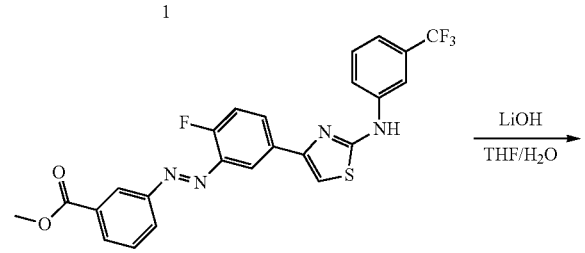

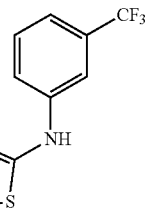

Step 1: Methyl 3-[(E)-[2-fluoro-5-[2-[3-(trifluoromethyl)anilino]thiazol-4-yl]phenyl]azo]benzoate

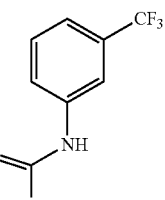

A solution of tert-butyl N-[4-(3-amino-4-fluoro-phenyl)thiazol-2-yl]-N-[3-(trifluoromethyl)phenyl]carbamate (200 mg, 419.01 μmol, 95% purity, 1 eq) and methyl 3-nitrosobenzoate (83.04 mg, 502.81 μmol, 100% purity, 1.2 eq) in AcOH (3 mL) was stirred at 100° C. for 12 h. The mixture was diluted with water (10 mL) and extracted with EtOAc (10 mL×3). The combined organic layers were dried over Na$_2$SO$_4$, filtered and concentrated under reduced pressure to yield a residue which was purified by preparative TLC (PE/EtOAc=3/1, R$_f$=0.50) to yield methyl 3-[(E)-[2-fluoro-5-[2-[3-(trifluoromethyl)anilino]thiazol-4-yl]phenyl]azo]benzoate (60 mg, 119.89 μmol, 28.6% yield, 100.0% purity) as a yellow solid. $^1$H NMR (400 MHz, DMSO-d$_6$) δ ppm 10.75 (s, 1H), 8.64 (s, 1H), 8.51 (s, 1H), 8.35 (dd, J=2.2, 7.3 Hz, 1H), 8.20 (dd, J=1.7, 7.8 Hz, 3H), 7.81 (t, J=7.8 Hz, 1H), 7.66-7.55 (m, 4H), 7.33 (d, J=7.6 Hz, 1H), 3.94 (s, 3H); ES-LCMS m/z 501.1 [M+H]$^+$.

Step 2: 3-[(E)-[2-Fluoro-5-[2-[3-(trifluoromethyl)anilino]thiazol-4-yl]phenyl]azo]benzoic acid To a solution of methyl 3-[(E)-[2-fluoro-5-[2-[3-(trifluoromethyl)anilino]thiazol-4-yl]phenyl]azo]benzoate (60 mg, 119.89 μmol, 100% purity, 1 eq) in THF (1 mL) was added LiOH·H$_2$O (41.9 mg, 998.48 μmol, 8.33 eq) in H$_2$O (1 mL). The mixture was stirred at 25° C. for 1 h. TLC (PE/EtOAc=3/1, R$_f$=0.05) indicated starting material was consumed completely and one new spot formed. The mixture was added 1 M HCl until pH=6 and extracted with EtOAc (5 mL×3). The combined organic layers were dried over Na$_2$SO$_4$, filtered and concentrated under reduced pressure. The crude product was triturated with MeOH at 25° C. for 12 h. The mixture was filtered. The crude product was triturated with water at 25° C. for 12 h. The mixture was lyophilized to yield 3-[(E)-[2-fluoro-5-[2-[3-(trifluoromethyl)anilino]thiazol-4-yl]phenyl]azo]benzoic acid (17.14 mg, 35.24 μmol, 29.4% yield, 100.0% purity) as a yellow solid. $^1$H NMR (400 MHz, DMSO-d$_6$) δ ppm 10.76 (s, 1H), 8.59 (s, 1H), 8.52-8.44 (m, 1H), 8.33 (dd, J=2.1, 7.2 Hz, 1H), 8.22-8.14 (m, 3H), 7.77 (t, J=7.7 Hz, 1H), 7.69-7.55 (m, 4H), 7.32 (d, J=7.9 Hz, 1H); ES-LCMS m/z 487.1 [M+H]$^+$.

I-174

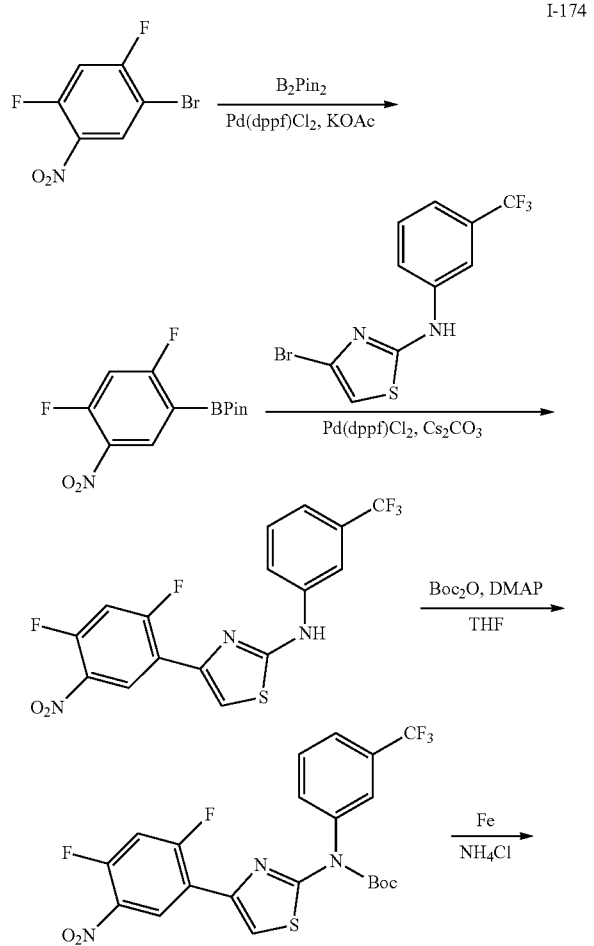

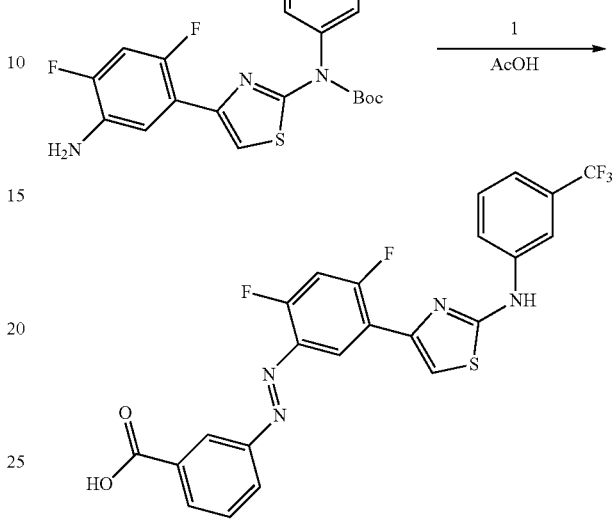

Step 1: 2-(2,4-Difluoro-5-nitrophenyl)-4,4,5,5-tetramethyl-1,3,2-dioxaborolane

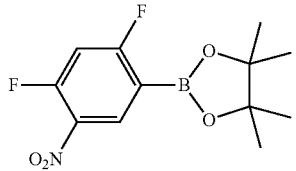 [SMILES: CC1(C)OB(c2cc([N+](=O)[O-])c(F)cc2F)OC1(C)C]

To a stirred solution of 1-bromo-2,4-difluoro-5-nitrobenzene (5 g, 21.01 mmol, 1 eq), 4,4,5,5-tetramethyl-2-(4,4,5,5-tetramethyl-1,3,2-dioxaborolan-2-yl)-1,3,2-dioxaborolane (7.47 g, 29.41 mmol, 1.4 eq), KOAc (6.19 g, 63.03 mmol, 3 eq) in 1,4-dioxane (70 mL) was added Pd(dppf)Cl$_2$ (768.65 mg, 1.05 mmol, 0.05 eq) under N$_2$ atmosphere. The mixture was stirred at 110° C. for 12 h. The reaction mixture was partitioned between water (200 mL) and EtOAc (400 mL×3). The organic phase was separated, washed with saturated brine (200 mL), dried over Na$_2$SO$_4$, filtered and concentrated under reduced pressure to yield a residue which was purified by silica gel column chromatography (using pure PE, TLC: PE/EtOAc=10/1, R$_f$=0.22) to yield 2-(2,4-difluoro-5-nitro-phenyl)-4,4,5,5-tetramethyl-1,3,2-dioxaborolane (2.5 g, 7.89 mmol, 37.6% yield, 90.0% purity) as a yellow solid. $^1$H NMR (400 MHz, CDCl$_3$) δ ppm 8.57 (d, J=6.1 Hz, 1H), 6.79 (d, J=9.5 Hz, 1H), 1.36 (d, J=1.5 Hz, 12H); ES-LCMS show no desired m/z.

Step 2: 4-(2,4-Difluoro-5-nitrophenyl)-N-(3-(trifluoromethyl)phenyl)thiazol-2-amine

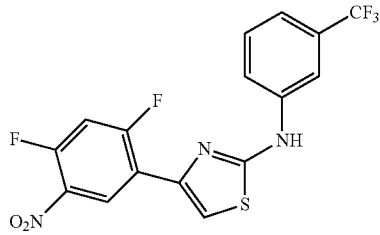 [SMILES: O=[N+]([O-])c1cc(-c2csc(Nc3cccc(C(F)(F)F)c3)n2)c(F)cc1F]

To a stirred solution of 2-(2,4-difluoro-5-nitro-phenyl)-4,4,5,5-tetramethyl-1,3,2-dioxaborolane (2.05 g, 6.47 mmol, 90.0%, 1.1 eq) and 4-bromo-N-[3-(trifluoromethyl)phenyl]thiazol-2-amine (2 g, 5.88 mmol, 95.0%, 1 eq) in 1,4-dioxane (50 mL) and water (10 mL) was added $Cs_2CO_3$ (5.75 g, 17.64 mmol, 3 eq) and $Pd(dppf)Cl_2$ (215.12 mg, 294.00 μmol, 0.05 eq) under $N_2$ atmosphere. The reaction mixture was stirred under $N_2$ atmosphere at 100° C. for 12 h. The reaction mixture was partitioned between water (50 mL) and EtOAc (100×3 mL). The organic phase was separated, washed with saturated brine (50 mL), dried over $Na_2SO_4$, filtered and concentrated under reduced pressure to yield a residue which was purified by preparative HPLC (column: 3_Phenomenex Luna C18 75*30 mm*3 μm; mobile phase: [water (0.1% TFA)-ACN]; B %: 65%-85%, 10 min) to yield 4-(2,4-difluoro-5-nitro-phenyl)-N-[3-(trifluoromethyl)phenyl]thiazol-2-amine (0.4 g, 996.73 μmol, 16.9% yield, 100.0% purity) as a yellow solid. $^1$H NMR (400 MHz, $CDCl_3$) δ ppm 8.98 (t, J=8.1 Hz, 1H), 7.89 (s, 1H), 7.64-7.60 (m, 1H), 7.52 (t, J=7.9 Hz, 1H), 7.37 (d, J=7.3 Hz, 1H), 7.30 (s, 1H), 7.25 (d, J=2.2 Hz, 1H), 7.12 (t, J=10.4 Hz, 1H); ES-LCMS m/z 402.1 $[M+H]^+$.

Step 3: tert-Butyl (4-(2,4-difluoro-5-nitrophenyl)thiazol-2-yl)(3-(trifluoromethyl)phenyl)carbamate

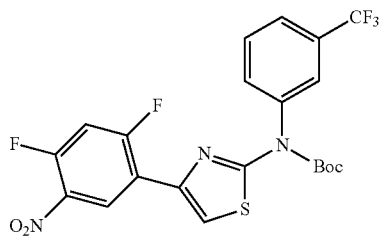 [SMILES: CC(C)(C)OC(=O)N(c1cccc(C(F)(F)F)c1)c1nc(-c2cc([N+](=O)[O-])c(F)cc2F)cs1]

To a stirred solution of 4-(2,4-difluoro-5-nitro-phenyl)-N-[3-(trifluoromethyl)phenyl]thiazol-2-amine (270 mg, 672.80 μmol, 100.0% purity, 1 eq) and DMAP (65.76 mg, 538.24 μmol, 0.8 eq) in THF (10 mL) was added $Boc_2O$ (220.26 mg, 1.01 mmol, 231.85 μL, 1.5 eq). The reaction mixture was stirred at 80° C. for 2 h. The reaction mixture was partitioned between water (50 mL) and EtOAc (100 mL×3). The organic phase was separated, washed with saturated brine (50 mL), dried over $Na_2SO_4$, filtered and concentrated under reduced pressure to yield a residue which was purified by silica gel column chromatography (from pure PE to PE/EtOAc=10/1, TLC: PE/EtOAc=10/1, $R_f$=0.57) to yield tert-butyl N-[4-(2,4-difluoro-5-nitro-phenyl)thiazol-2-yl]-N-[3-(trifluoromethyl)phenyl]carbamate (230 mg, 435.76 μmol, 64.8% yield, 95.0% purity) as a yellow solid. $^1$H NMR (400 MHz, $CDCl_3$) δ ppm 8.49-8.43 (m, 1H), 7.74-7.71 (m, 1H), 7.69-7.59 (m, 3H), 7.55-7.50 (m, 2H), 1.49 (s, 9H); ES-LCMS m/z 446.0 $[M-t-Bu+H]^+$.

Step 4: tert-Butyl (4-(5-amino-2,4-difluorophenyl)thiazol-2-yl)(3-(trifluoromethyl)phenyl)carbamate

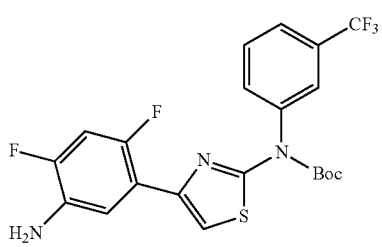

To a stirred solution of tert-butyl N-[4-(2,4-difluoro-5-nitro-phenyl)thiazol-2-yl]-N-[3-(trifluoromethyl)phenyl]carbamate (230 mg, 435.76 μmol, 95.0%, 1 eq) and $NH_4Cl$ (233.09 mg, 4.36 mmol, 10 eq) in EtOH (1 mL), THF (1 mL) and $H_2O$ (1 mL) was added Fe (24.34 mg, 435.76 μmol, 1 eq). The reaction mixture was stirred at 25° C. for 5 h. The reaction mixture was filtered using silicate to remove iron. The residue was diluted with water (30 mL) and extracted with EtOAc (50 mL×3). The combined organic layers were washed with brine (30 mL), dried over $Na_2SO_4$, filtered and concentrated under reduced pressure to yield a residue which was purified by silica gel column chromatography (from pure PE to PE/EtOAc=10/1, TLC: PE/EtOAc=10/1, $R_f$=0.46) to yield tert-butyl N-[4-(5-amino-2,4-difluoro-phenyl)thiazol-2-yl]-N-[3-(trifluoromethyl)phenyl]carbamate (70 mg, 139.57 μmol, 32.0% yield, 94.0% purity) as a yellow solid. $^1$H NMR (500 MHz, $CDCl_3$) δ ppm 7.71-7.64 (m, 2H), 7.60 (t, J=7.9 Hz, 1H), 7.52 (d, J=8.1 Hz, 1H), 7.39 (d, J=2.0 Hz, 1H), 7.12 (dd, J=7.6, 10.1 Hz, 1H), 6.79 (t, J=10.8 Hz, 1H), 3.49 (s, 2H), 1.48 (s, 9H); ES-LCMS m/z 472.6 $[M+H]^+$.

Step 5: (E)-3-((2,4-Difluoro-5-(2-((3-(trifluoromethyl)phenyl)amino)thiazol-4-yl)phenyl)diazenyl)benzoic acid

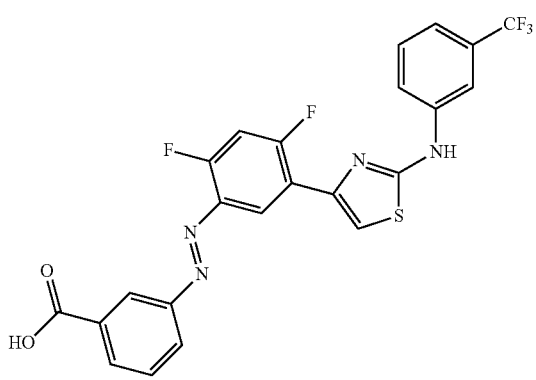 [SMILES: O=C(O)c1cccc(/N=N/c2cc(-c3csc(Nc4cccc(C(F)(F)F)c4)n3)c(F)cc2F)c1]

To a stirred solution of tert-butyl N-[4-(5-amino-2,4-difluoro-phenyl)thiazol-2-yl]-N-[3-(trifluoromethyl)phenyl]

carbamate (70 mg, 139.57 µmol, 94.0%, 1 eq) in AcOH (5 mL) was added 3-nitrosobenzoic acid (70.31 mg, 418.71 µmol, 90.0%, 3 eq). The reaction mixture was stirred at 100° C. for 12 h. The reaction mixture was partitioned between water (30 mL) and EtOAc (50 mL×3). The organic phase was separated, washed with saturated brine (30 mL), dried over $Na_2SO_4$, filtered and concentrated under reduced pressure to yield a residue which was purified by preparative HPLC (column: 3_henomenex Luna C18 75*30 mm*3 µm; mobile phase: [water (0.1% TFA)-ACN]; B %: 63%-93%, 10 min) to yield 3-[(E)-[2,4-difluoro-5-[2-[3-(trifluoromethyl)anilino]thiazol-4-yl]phenyl]azo]benzoic acid (6.87 mg, 11.42 µmol, 8.2% yield, 96.0% purity) as a yellow solid. $^1$H NMR (400 MHz, DMSO-$d_6$) δ ppm 10.79 (s, 1H), 8.62 (s, 1H), 8.55 (t, J=8.4 Hz, 1H), 8.47 (s, 1H), 8.16 (t, J=7.5 Hz, 2H), 7.86-7.73 (m, 3H), 7.62-7.56 (m, 2H), 7.47 (s, 1H), 7.33 (d, J=6.4 Hz, 1H); ES-LCMS m/z 505.1 [M+H]$^+$.

added $NH_4Cl$ (26.28 mg, 491.38 µmol, 2.0 eq), zinc (64.26 mg, 982.76 µmol, 4.0 eq). The mixture was stirred under microwave (1 bar) at 130° C. for 3 h. The mixture was filtered, washed with DMF (1 mL×2) which was purified by preparative HPLC: ([water (10 mM $NH_4HCO_3$)-ACN]; B %: 47%-77%), followed by lyophilization to yield 4-[5-[2-[5-[2-[3-(trifluoromethyl)anilino]thiazol-4-yl]-3-pyridyl]hydrazino]-3-pyridyl]-N-[3-(trifluoromethyl)phenyl]thiazol-2-amine (10 mg, 14.64 µmol, 6.0% yield, 98.2% purity) as a white solid. $^1$H NMR (400 MHz, $CD_3OD$) δ ppm 8.52 (d, J=1.5 Hz, 2H), 8.11 (d, J=2.7 Hz, 4H), 7.91 (d, J=7.8 Hz, 2H), 7.83 (s, 2H), 7.44 (t, J=8.1 Hz, 2H), 7.25 (s, 2H), 7.19 (d, J=7.6 Hz, 2H), 4.61 (s, 2H); ES-LCMS m/z 671.1 [M+H]$^+$.

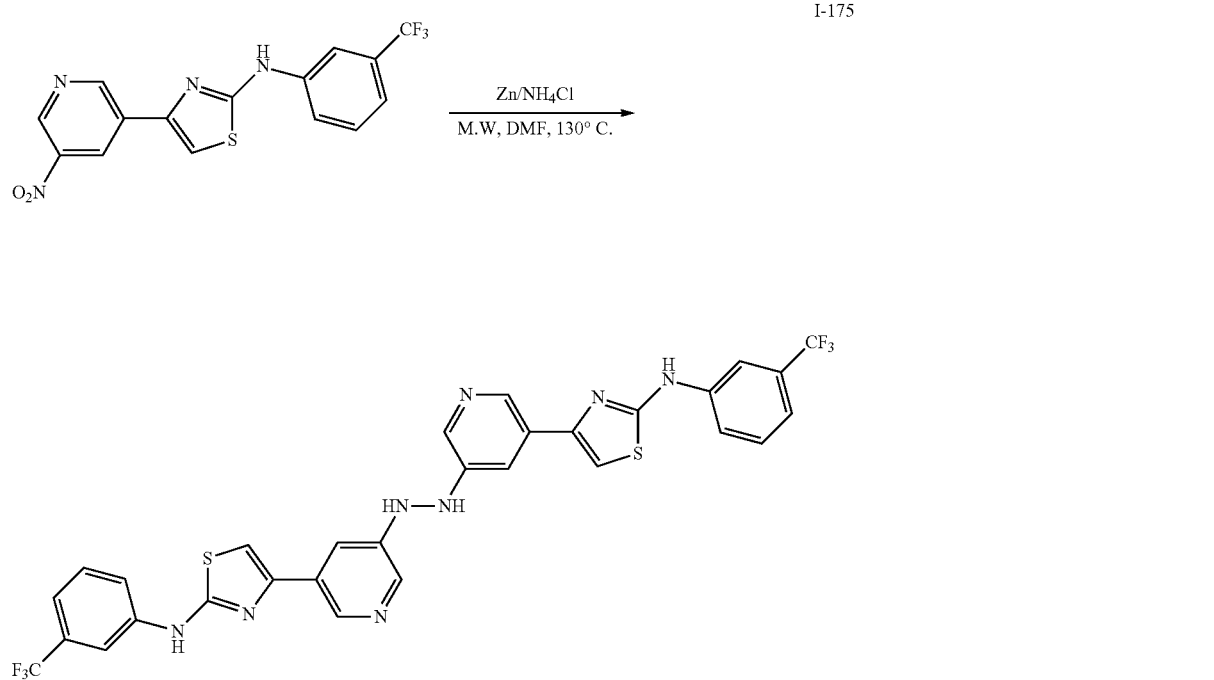

I-175

Step 1: 4,4'-(5,5'-(Hydrazine-1,2-diyl)bis(pyridine-5,3-diyl))bis(N-(3-(trifluoromethyl)phenyl)thiazol-2-amine)

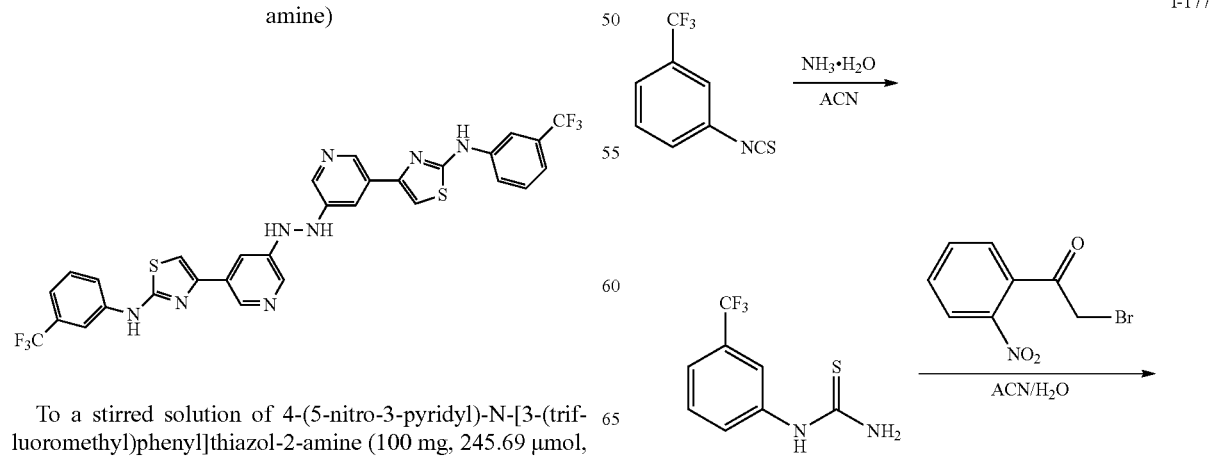

I-177

To a stirred solution of 4-(5-nitro-3-pyridyl)-N-[3-(trifluoromethyl)phenyl]thiazol-2-amine (100 mg, 245.69 µmol, 90% purity, 1 eq) in DMF (0.95 mL) and $H_2O$ (0.05 mL) was

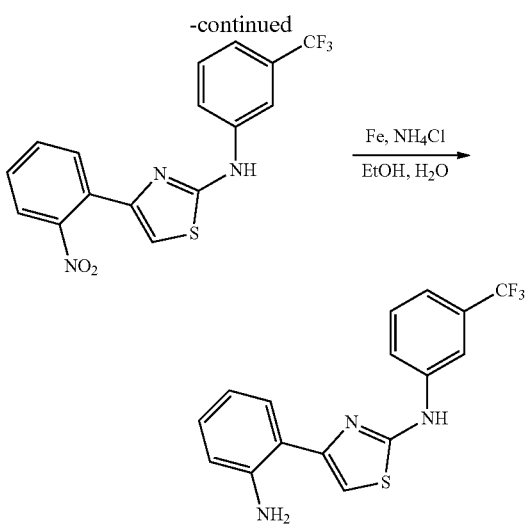

Step 1: [3-(Trifluoromethyl)phenyl]thiourea

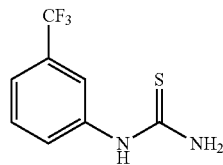 [SMILES: NC(=S)Nc1cccc(C(F)(F)F)c1]

To a solution of 1-isothiocyanato-3-(trifluoromethyl)benzene (2.5 g, 11.69 mmol, 1.87 mL, 95%, 1 eq) in ACN (25 mL) was added $NH_3 \cdot H_2O$ (7.32 g, 58.44 mmol, 8.04 mL, 28%, 5 eq). The mixture was stirred at 25° C. for 8 h. The mixture was concentrated and then water (120 mL) was added. The mixture was extracted with EtOAc (120 mL×3). The combined organic layers were washed with brine (30 mL), dried over $Na_2SO_4$, filtered and concentrated to yield crude [3-(trifluoromethyl)phenyl]thiourea (2.8 g, 11.44 mmol, 97.9% yield, 90.0% purity) as a yellow solid, which was used in the the next step directly without further purification. $^1$H NMR (400 MHz, DMSO-$d_6$) δ ppm 9.95 (s, 1H), 8.00 (s, 1H), 7.68 (d, J=8.3 Hz, 1H), 7.54 (t, J=7.9 Hz, 1H), 7.43 (d, J=7.6 Hz, 1H). LCMS m/z 221.2 [M+H]$^+$.

Step 2: 4-(2-Nitrophenyl)-N-[3-(trifluoromethyl)phenyl]thiazol-2-amine

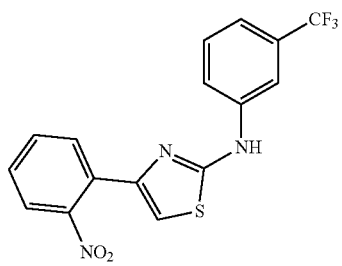

A mixture of [3-(trifluoromethyl)phenyl]thiourea (2.8 g, 11.44 mmol, 90%, 1 eq) and 2-bromo-1-(2-nitrophenyl)ethanone (2.79 g, 11.44 mmol, 1 eq) in ACN (25 mL) and $H_2O$ (25 mL) was stirred at 25° C. for 8 h. The mixture was concentrated and then water (150 mL) was added. The mixture was extracted with EtOAc (150 mL×3). The combined organic layers were washed with brine (40 mL), dried over $Na_2SO_4$, filtered and concentrated to yield the crude 4-(2-nitrophenyl)-N-[3-(trifluoromethyl)phenyl]thiazol-2-amine (4.8 g, 11.04 mmol, 96.4% yield, 84.0% purity) as a yellow solid, which was used in the the next step without further purification. $^1$H NMR (400 MHz, CDCl$_3$) δ ppm 8.76-8.28 (m, 1H), 8.19 (dd, J=0.9, 7.9 Hz, 1H), 8.13 (dd, J=1.1, 7.7 Hz, 1H), 8.07-7.99 (m, 3H), 7.96-7.89 (m, 1H), 7.85 (t, J=7.8 Hz, 1H), 7.74-7.68 (m, 1H); LCMS m/z 366.6 [M+H]$^+$.

Step 3: 4-(2-Aminophenyl)-N-[3-(trifluoromethyl)phenyl]thiazol-2-amine

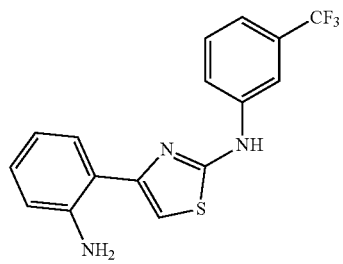 [SMILES: Nc1ccccc1-c1csc(Nc2cccc(C(F)(F)F)c2)n1]

To a solution of 4-(2-nitrophenyl)-N-[3-(trifluoromethyl)phenyl]thiazol-2-amine (200 mg, 459.86 μmol, 84%, 1 eq) in $H_2O$ (2 mL) was added EtOH (6 mL), $NH_4Cl$ (122.99 mg, 2.30 mmol, 5 eq) and Fe (256.83 mg, 4.60 mmol, 10 eq). The mixture was stirred at 100° C. for 1 h. The mixture was concentrated and then water (50 mL) was added. The mixture was extracted with EtOAc (50 mL×3). The combined organic layers were washed with brine (10 mL), dried over $Na_2SO_4$, filtered and concentrated. The crude was purified by preparative HPLC (column: Welch Xtimate C18 150*25 mm*5 μm; mobile phase: [water (10 mM $NH_4HCO_3$)-ACN]; B %: 52%-82%, 10 min) and lyophilized to yield 4-(2-aminophenyl)-N-[3-(trifluoromethyl)phenyl]thiazol-2-amine (65 mg, 193.83 μmol, 42.1% yield, 100.0% purity) as a yellow solid. $^1$H NMR (400 MHz, CDCl$_3$) δ ppm 7.75 (s, 1H), 7.55-7.51 (m, 1H), 7.49-7.43 (m, 2H), 7.31 (d, J=7.6 Hz, 1H), 7.16 (t, J=7.7 Hz, 1H), 6.85-6.70 (m, 3H), LCMS m/z 336.2 [M+H]$^+$.

I-179

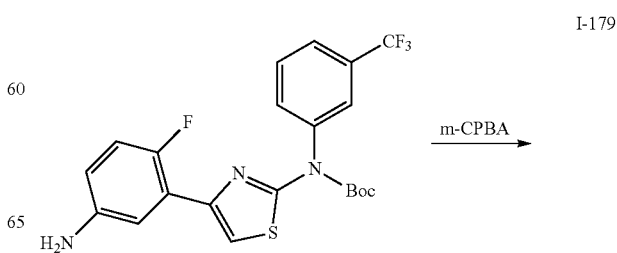

397

-continued

Step 1: Tert-butyl N-[4-(2-fluoro-5-nitroso-phenyl)thiazol-2-yl]-N-[3-(trifluoromethyl)phenyl]carbamate

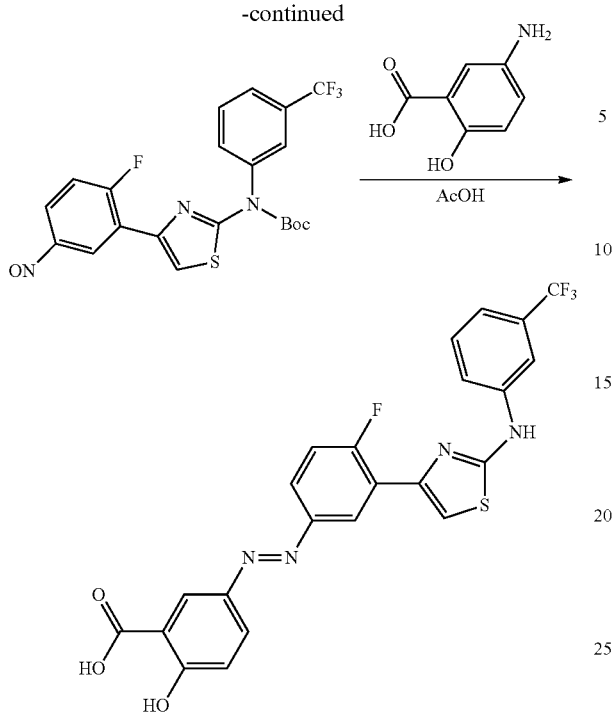

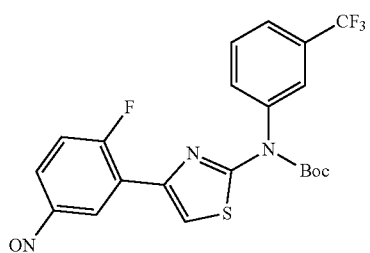

To a solution of tert-butyl N-[4-(5-amino-2-fluoro-phenyl)thiazol-2-yl]-N-[3-(trifluoromethyl)phenyl]carbamate (400 mg, 811.55 µmol, 92.0% purity, 1 eq) in DCM (10 mL) was added dropwise slowly a solution of m-CPBA (350.12 mg, 1.62 µmol, 80% purity, 2 eq) in DCM (10 mL) over 20 min under 0° C. The mixture was stirred at 25° C. for 2 h. The reaction mixture was quenched by addition of water (30 mL) and extracted with EtOAc (20 mL×3). The combined organic layers were washed with brine (10 mL), dried over Na₂SO₄, filtered and concentrated under reduced pressure to give a residue which was purified by flash silica gel chromatography (from pure PE to PE/EtOAc=5/1, TLC: PE/EtOAc=5/1, R$_f$=0.49) to yield tert-butyl N-[4-(2-fluoro-5-nitroso-phenyl)thiazol-2-yl]-N-[3-(trifluoromethyl)phenyl]carbamate (120 mg, 256.72 µmol, 31.6% yield, 100.0% purity) as a green solid. $^1$H NMR (400 MHz, DMSO-d$_6$) δ ppm 8.06 (dd, J=2.4, 7.1 Hz, 1H), 7.95 (s, 1H), 7.94-7.89 (m, 1H), 7.85 (d, J=7.3 Hz, 1H), 7.82 (d, J=2.7 Hz, 1H), 7.78 (d, J=4.9 Hz, 1H), 7.76-7.73 (m, 1H), 7.63 (dd, J=8.8, 10.8 Hz, 1H), 1.40 (s, 9H); ES-LCMS m/z 468.2 [M+H]⁺.

398

Step 2: (E)-5-((4-Fluoro-3-(2-((3-(trifluoromethyl)phenyl)amino)thiazol-4-yl)phenyl)diazenyl)-2-hydroxybenzoic acid

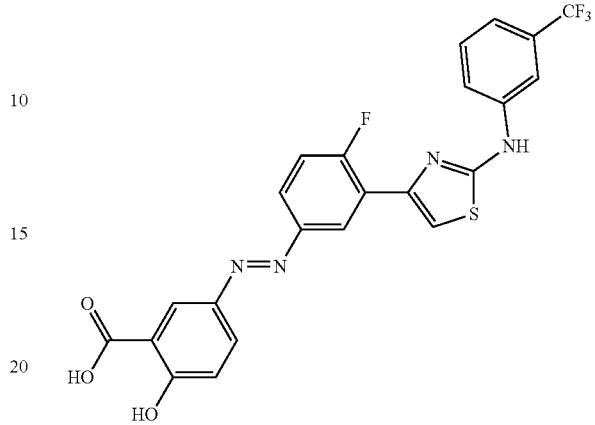

To a solution of tert-butyl N-[4-(2-fluoro-5-nitroso-phenyl)thiazol-2-yl]-N-[3-(trifluoromethyl)phenyl]carbamate (110 mg, 235.33 µmol, 100.0% purity, 1 eq) in AcOH (10 mL) was added 5-amino-2-hydroxy-benzoic acid (36.04 mg, 235.33 µmol, 1 eq). The mixture was stirred at 100° C. for 8 h. The reaction mixture was concentrated to yield a residue which was purified by preparative HPLC (column: Phenomenex Synergi C18 150*30 mm*4 um; mobile phase: [water (0.05% HCl)-ACN]; B %: 75%-95%, 10 min), followed by lyophilization to yield 5-[(E)[4-fluoro-3-[2-[3-(trifluoromethyl)anilino]thiazol-4-yl]phenyl]azo]-2-hydroxy-benzoic acid (22.25 mg, 42.33 µmol, 17.9% yield, 95.6% purity) as a yellow solid. $^1$H NMR (400 MHz, DMSO-d$_6$) δ ppm 10.81 (s, 1H), 8.51 (dd, J=2.3, 7.4 Hz, 1H), 8.44 (s, 1H), 8.30 (d, J=2.7 Hz, 1H), 7.84-7.75 (m, 3H), 7.58 (t, J=8.0 Hz, 1H), 7.52-7.43 (m, 2H), 7.31 (d, J=7.0 Hz, 1H), 6.76 (d, J=8.6 Hz, 1H); ES-LCMS m/z 503.1 [M+H]⁺.

I-181

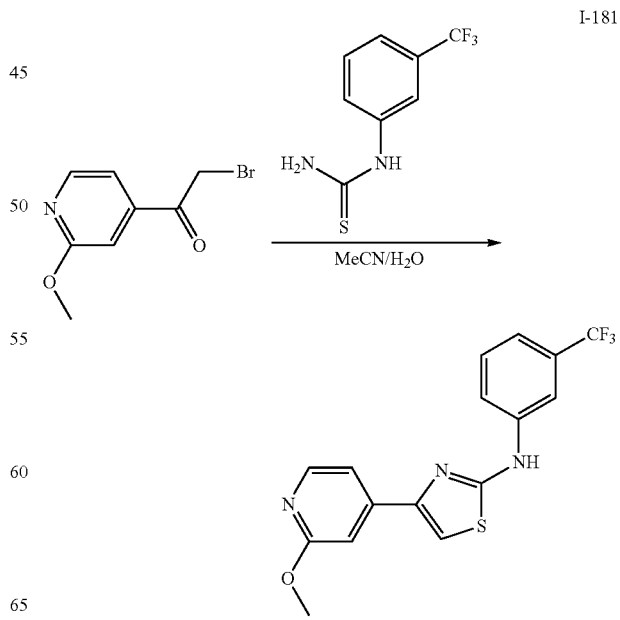

Step 1: 4-(2-Methoxy-4-pyridyl)-N-[3-(trifluoromethyl)phenyl]thiazol-2-amine

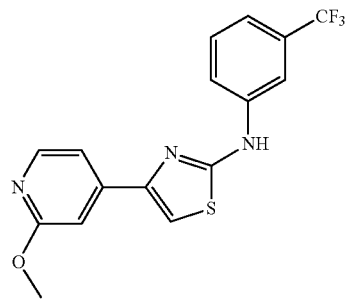 [SMILES: COc1cc(-c2csc(Nc3cccc(C(F)(F)F)c3)n2)ccn1]

To a solution of 2-bromo-1-(2-methoxy-4-pyridyl)ethanone (1.22 g, 5.30 mmol, 1 eq) in MeCN (6 mL) and water (6 mL) was added [3-(trifluoromethyl)phenyl]thiourea (1.43 g, 5.83 mmol, 90%, 1.1 eq). The mixture was stirred at 15° C. for 12 h. The reaction mixture was quenched by addition of water (50 mL), extracted with EtOAc (30 mL×3). The combined organic layers were washed with brine (10 mL), dried over $Na_2SO_4$, filtered and concentrated under reduced pressure to yield a residue which was purified by flash silica gel chromatography (from PE/EtOAc=1/0 to 1/1, TLC: PE/EtOAc=1/1, $R_f$=0.75) to yield 4-(2-methoxy-4-pyridyl)-N-[3-(trifluoromethyl)phenyl]thiazol-2-amine (790 mg, 1.87 mmol, 35.2% yield, 95% purity) as a yellow solid. 100 mg of 4-(2-methoxy-4-pyridyl)-N-[3-(trifluoromethyl)phenyl]thiazol-2-amine (790 mg, 1.87 mmol, 35.2% yield, 95.0% purity) was re-purified by preparative HPLC(column: Agela DuraShell C18 150*25 mm*5 μm; mobile phase: [water (0.04% $NH_3H_2O$+10 mM $NH_4HCO_3$)-ACN]; B %: 52%-82%, 10 min). The desired fraction was lyophilized to yield 4-(2-methoxy-4-pyridyl)-N-[3-(trifluoromethyl)phenyl]thiazol-2-amine (49.9 mg, 142.03 μmol, 2.7% yield, 100.0% purity) as a white solid. $^1$H NMR (400 MHz, DMSO-$d_6$) δ ppm 10.75 (s, 1H), 8.38 (s, 1H), 8.21 (d, J=5.4 Hz, 1H), 7.85-7.78 (m, 2H), 7.59 (t, J=7.9 Hz, 1H), 7.47 (dd, J=1.2, 5.4 Hz, 1H), 7.35-7.25 (m, 2H), 3.89 (s, 3H); ES-LCMS m/z 352.2 $[M+H]^+$.

Example 2: In Vitro Assay

DRE-Luciferase Reporter Assay

AHR binds to Dioxin Responsive Elements (DRE) upstream of genes that it activates. One measure of AHR activity is activation of a reporter gene, such as luciferase, downstream of one or multiple DRE elements. Luciferase activity reflects activation and inhibition of AHR in the cells expressing this reporter.

Murine Hepa1-6 or Hepa-1c1c7 or other murine cell line with a DRE-luciferase reporter either stably or transiently transfected are plated in media in plates (96-well, 384-well or other plates) and incubated overnight at 37 C in a CO2 incubator. Likewise, human HepG2 or other human cell line with a DRE-luciferase reporter either stably or transiently transfected are plated in media in plates (96-well, 384-well or other plates) and incubated overnight at 37 C in a CO2 incubator.

The next day, an AHR agonist compound is added. Cells are incubated for 6, 16 or 24 hours or another time point and then lysed for determination of luciferase activity as a read-out of the AHR activation. Luciferase can be measured with a commercial kit such as the Promega Luciferase kit or any kit or reagents that provide the luciferin substrate for measuring luciferase activity. The level of luciferase with only activating ligand (e.g. such as TCDD, kynurenine, ITE (2-(1H-indole-3-ylcarbonyl)-4-thiazolecarboxylic methyl ester), VAF347, BNF (beta-naphthoflavone), ICZ (6-formylindolo(3,2-b) carbazole or other AHR ligands) added is the maximum signal while the luciferase with no ligand is the minimum signal. EC50s can be determined as the concentration which activates half of the maximum luciferase activity.

In some embodiments, compounds have an EC50>1 μM. In some embodiments, compounds have an EC50<1 μM. In some embodiments, compounds have an EC50<0.1 μM. In some embodiments, compounds have an EC50<0.01 μM.

P450 CYP1A1 Luciferase Assay

AHR binds to Dioxin Responsive Elements (DRE) upstream of genes that it activates. One measure of AHR activity is P450 CYP1A1 protein levels determined by measuring CYP1A1 enzyme activity using a luminogenic CYP1A1 luciferin-based substrate. Luciferase activity will reflect CYP1A1 activity resulting from activation of AHR in the cells.

Murine Hepa1-6 or Hepa-1c1c7 or other murine cell line, human HepG2 or other human cell line are plated in media (96-well, 384-well or other plates) and incubated overnight at 37 C in a CO2 incubator.

The next day, an AHR agonist compound is added. Cells are incubated for 6, 16 or 24 hours or another time point and then lysed and incubated with a CYP1A1 luciferase-based substrate (e.g. Luciferin-CEE) for 3, 6, or 12 hours of another time point. Determination of luciferase activity as a read-out of CYP1A1 enzyme activity can be measured with a commercial kit such as the Promega P450 Glo CYP1A1 detection reagent or any kit or reagents that provide for measuring luciferase activity. The level of luciferase with only activating ligand (e.g. such as TCDD, kynurenine, ITE (2-(1H-indole-3-ylcarbonyl)-4-thiazolecarboxylic methyl ester), VAF347, BNF (beta-naphthoflavone), ICZ (6-formylindolo(3,2-b) carbazole or other AHR ligands) added is the maximum signal while the luciferase with no ligand is the minimum signal. EC50s can be determined as the concentration which activates half of the maximum luciferase activity.

Certain compounds were tested in the assays. The data are listed in Table 2 below. A: EC50≤0.010 μM; B: 0.010 μM<EC50≤0.1 μM; C: 0.1 μM<EC50≤1.0 μM; and D: EC50>1.0 μM.

TABLE 2

In vitro Data of Certain Exemplary Compounds.

| Compound # | DRE-Luc HepG2 - Agonist: Average EC50 (μM) | Cyp1a1 Hepa1.6 - Agonist: Average EC50 (μM) |
|---|---|---|
| I-1 | A | B |
| I-2 | A | C |
| I-3 | A | C |
| I-4 | A | B |
| I-5 | A | D |
| I-6 | A | D |
| I-7 | A | C |
| I-8 | A | D |
| I-9 | A | B |
| I-10 | A | C |
| I-11 | A | C |
| I-12 | A | D |
| I-13 | A | D |

TABLE 2-continued

In vitro Data of Certain Exemplary Compounds.

| Compound # | DRE-Luc HepG2 - Agonist: Average EC50 (µM) | Cyp1a1 Hepa1.6 - Agonist: Average EC50 (µM) |
|---|---|---|
| I-14 | A | B |
| I-15 | A | D |
| I-16 | A | C |
| I-17 | A | C |
| I-18 | A | D |
| I-19 | A | D |
| I-20 | A | D |
| I-21 | A | D |
| I-22 | A | C |
| I-23 | A | D |
| I-24 | B | D |
| I-25 | B | D |
| I-26 | B | D |
| I-27 | B | D |
| I-28 | B | D |
| I-29 | B | C |
| I-30 | B | C |
| I-31 | B | D |
| I-32 | B | D |
| I-33 | C | D |
| I-34 | C | D |
| I-35 | C | D |
| I-36 | C | D |
| I-37 | C | C |
| I-38 | C | D |
| I-39 | C | D |
| I-40 | C | D |
| I-41 | C | D |
| I-42 | C | D |
| I-43 | C | D |
| I-44 | C | D |
| I-45 | C | |
| I-46 | D | D |
| I-47 | D | D |
| I-48 | D | D |
| I-49 | D | D |
| I-50 | D | D |
| I-51 | D | |
| I-52 | D | |
| I-53 | D | D |
| I-54 | | |
| I-55 | | |
| I-56 | | |
| I-57 | | |
| I-58 | A | D |
| I-59 | A | D |
| I-60 | B | D |
| I-61 | C | D |
| I-62 | C | |
| I-63 | C | |
| I-64 | D | |
| I-65 | D | |
| I-66 | D | |
| I-67 | D | |
| I-68 | D | |
| I-69 | D | |
| I-70 | D | |
| I-71 | D | |
| I-72 | D | |
| I-73 | D | |
| I-74 | D | |
| I-75 | D | |
| I-76 | D | |
| I-77 | D | |
| P-1 | A | B |
| P-2 | A | C |
| P-3 | A | D |
| P-4 | A | C |
| P-5 | A | D |
| P-6 | A | D |
| P-7 | A | D |
| P-8 | A | C |
| P-9 | A | D |
| P-10 | B | D |
| P-11 | B | D |
| P-12 | B | D |
| P-13 | C | D |
| P-14 | D | |

Certain compounds were tested in the assays. The data are listed in Table 3 below. A: EC50≤0.010 µM; B: 0.010 µM<EC50≤0.1 µM; C: 0.1 µM<EC50≤1.0 µM; and D: EC50>1.0 µM.

TABLE 3

In vitro Data of Certain Exemplary Compounds.

| Compound # | DRE-Luc HepG2 - Agonist: Average EC50 (µM) | DRE-Luc Hepa1.6 - Agonist: Average EC50 (µM) |
|---|---|---|
| I-78 | D | |
| I-79 | D | |
| I-80 | B | |
| I-81 | D | |
| I-82 | D | |
| I-83 | A | C |
| I-84 | B | |
| I-85 | D | |
| I-86 | A | |
| I-87 | A | D |
| I-88 | D | |
| I-89 | A | D |
| I-90 | A | D |
| I-91 | A | B |
| I-92 | A | C |
| I-93 | A | D |
| I-94 | D | |
| I-95 | D | |
| I-96 | A | |
| I-97 | A | B |
| I-98 | C | |
| I-99 | D | |
| I-100 | A | D |
| I-101 | D | |
| I-102 | D | |
| I-103 | D | |
| I-104 | D | |
| I-105 | D | |
| I-106 | C | |
| I-107 | A | D |
| I-108 | C | |
| I-109 | A | D |
| I-110 | D | |
| I-111 | D | |
| I-112 | A | D |
| I-113 | D | |
| I-114 | D | |
| I-115 | D | |
| I-116 | D | |
| I-117 | A | D |
| I-118 | C | |
| I-119 | A | |
| I-120 | A | C |
| I-121 | A | D |
| I-122 | D | |
| I-123 | D | |
| I-124 | D | |
| I-125 | B | D |
| I-126 | D | |
| I-127 | C | |
| I-128 | A | D |
| I-129 | C | |
| I-130 | A | A |
| I-131 | D | |

TABLE 3-continued

In vitro Data of Certain Exemplary Compounds.

| Compound # | DRE-Luc HepG2 - Agonist: Average EC50 (µM) | DRE-Luc Hepa1.6 - Agonist: Average EC50 (µM) |
|---|---|---|
| I-132 | D | |
| I-133 | C | |
| I-134 | D | |
| I-135 | D | |
| I-136 | A | C |
| I-137 | D | |
| I-138 | D | |
| I-139 | C | |
| I-140 | D | |
| I-141 | D | |
| I-142 | D | |
| I-143 | C | D |
| I-144 | B | D |
| I-145 | A | D |
| I-146 | A | D |
| I-147 | C | D |
| I-148 | B | C |
| I-149 | C | C |
| I-150 | D | |
| I-151 | D | |
| I-152 | D | D |
| I-153 | B | D |
| I-154 | A | B |
| I-155 | B | D |
| I-156 | A | A |
| I-157 | C | D |
| I-158 | B | D |
| I-159 | D | D |
| I-160 | A | D |
| I-161 | C | D |
| I-162 | D | D |
| I-163 | A | A |
| I-164 | A | A |
| I-165 | A | A |
| I-166 | A | A |
| I-167 | C | C |
| I-168 | D | D |
| I-169 | C | C |
| I-170 | B | B |
| I-171 | D | D |
| I-172 | B | D |
| I-173 | C | C |
| I-174 | C | C |
| I-175 | C | C |
| I-176 | D | D |
| I-177 | B | A |
| I-178 | D | D |
| I-179 | C | D |

Example 3: Liver and Colon Pharmacodynamics (PD) Assays and Methods

C57BL/6N mice are weighed and randomized into treatment groups with group size of 3-5 mice. On study Day 1, treatment is initiated and necropsies follow on day 1 at 4 and 12 hours post-dose and on Day 2, 24 hours post-dose.

On Day 1, mice are dosed orally with one dose of the AHR agonist compound(s) that are in a suspension and mixed well before dosing. At the designated time, animals are euthanized and plasma and tissue taken for compound levels (PK) and compound effect (PD) on gene expression. Liver samples and proximal colon are weighed and then frozen for subsequent RNA extraction and RT-PCR analysis. AHR activation is determined by measuring Cyp1a1 gene expression relative to a housekeeping gene, such as GAPDH or HPRT. Cyp1a1 expression levels in the liver are compared to Cyp1a1 levels in the colon to determine a colon:liver ratio to determine the level of GI preferred AHR activation.

Figure 2:
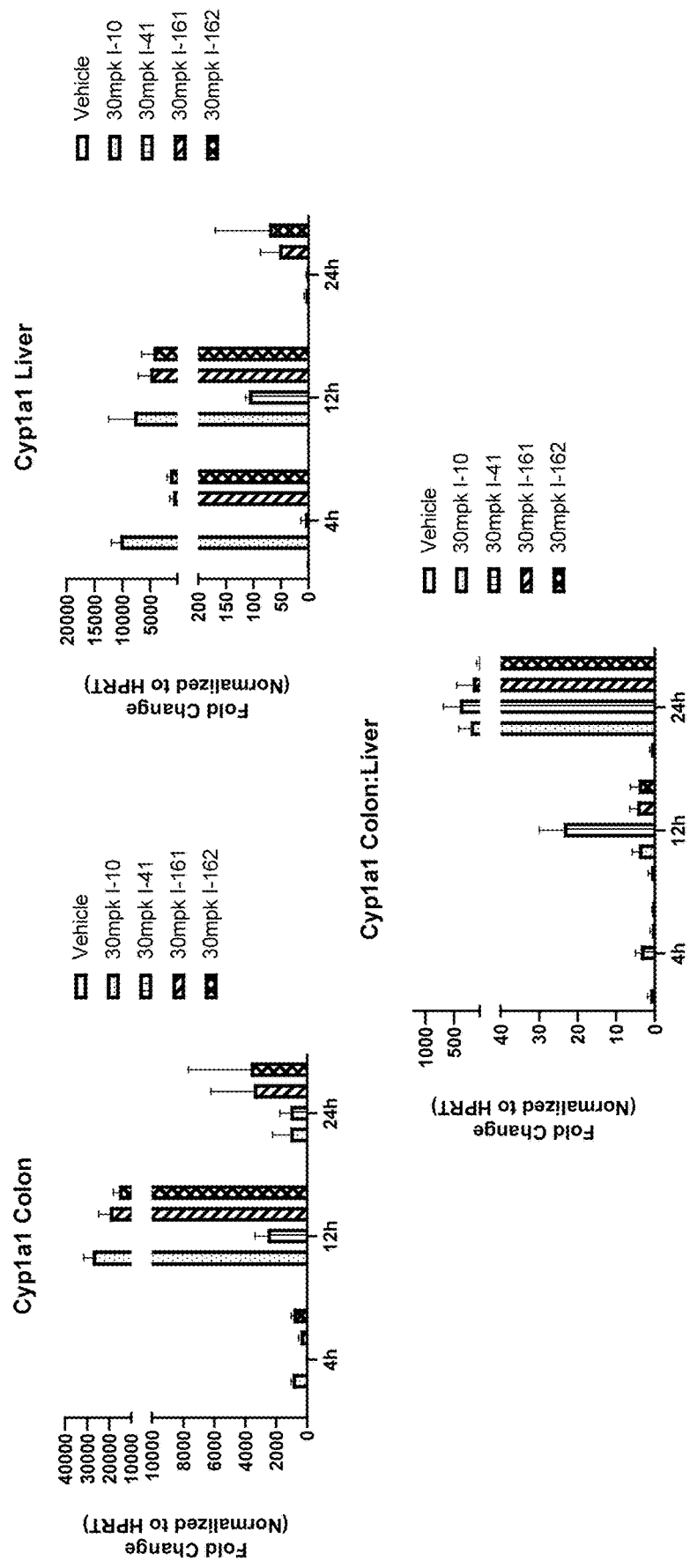
FIG. 2 depicts exemplary pharmacodynamic (PD) data in the liver and colon for AHR agonist compounds I-10, I-41, I-161 (pro-drug form of I-10), and I-162. The ratio of expression in the colon:liver is indicative of "colon-preferred" activity.
Figure 3:
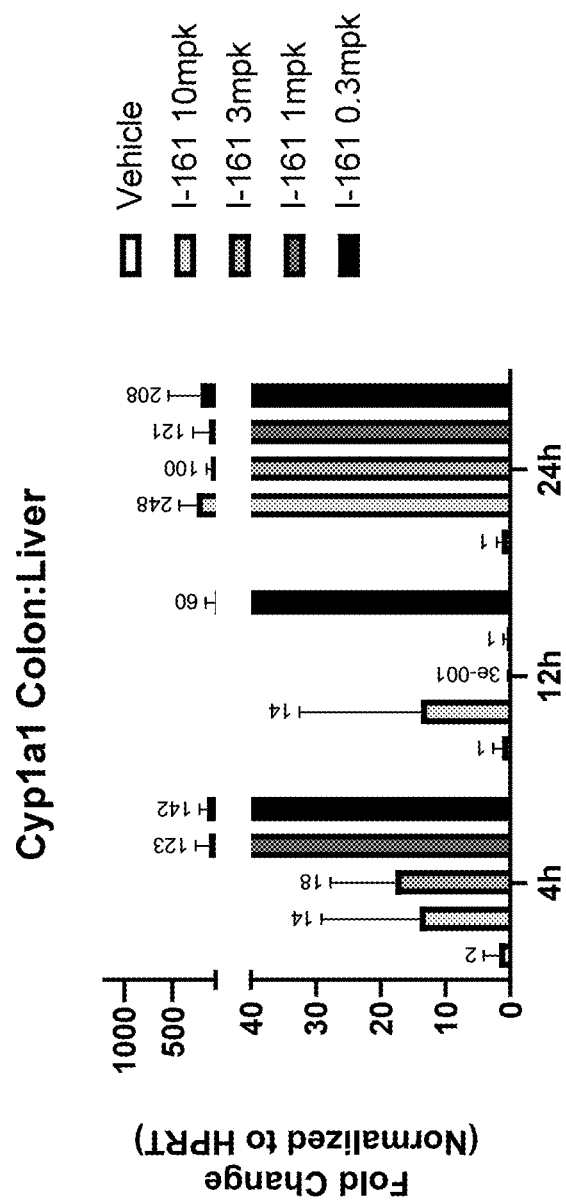
FIG. 3 depicts exemplary pharmacodynamic (PD) data in the liver and colon for AHR agonist compound I-161 at various concentrations and at 4 hours, 12 hours, and 24 hours. The colon:liver ratio data demonstrates Cyp1a1 induction in the colon at low doses of I-161 and colon-preferred activity at 24 hours after a single dose treatment.
Figure 4:
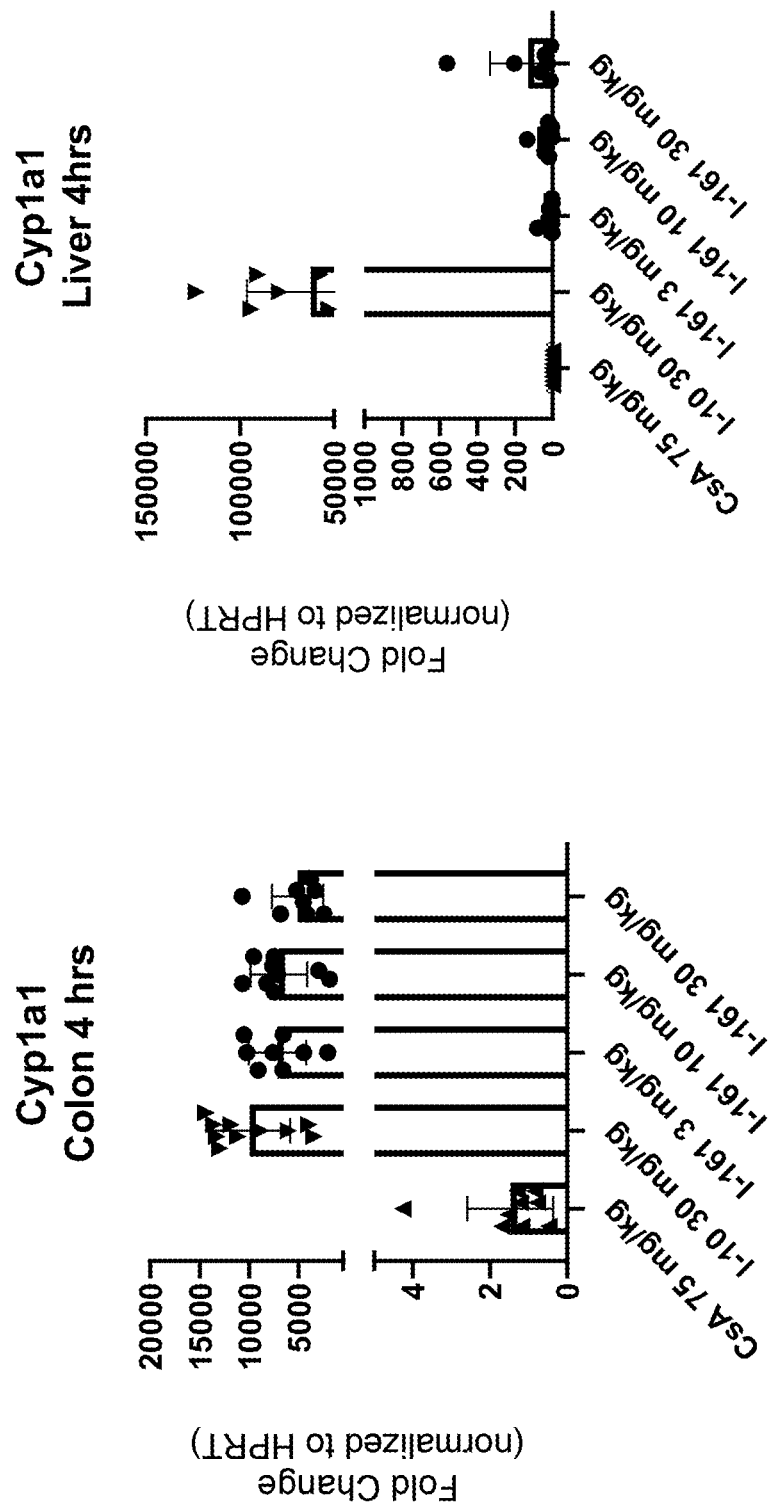
FIG. 4 depicts exemplary pharmacodynamic (PD) data in the liver and colon for AHR agonist compounds I-10 and I-161 at 4 hours. These data show that while Cyp1a1 induction in the colon is comparable with I-10 and I-161, I-161, the pro-drug form of I-10, has significantly less induction in the liver than the active form I-10.0

As shown herein, FIG. 1 depicts exemplary pharmacodynamic (PD) data in the liver and colon for AHR agonist compound P-2 at 4 hours, 12 hours, and 24 hours. FIG. 2 depicts exemplary pharmacodynamic (PD) data in the liver and colon for AHR agonist compounds I-10, I-41, I-161 (pro-drug form of I-10), and I-162. The ratio of expression in the colon:liver is indicative of "GI-preferred" or "colon-preferred" activity. FIG. 3 depicts exemplary pharmacodynamic (PD) data in the liver and colon for AHR agonist compound I-161 at various concentrations and at 4 hours, 12 hours, and 24 hours. The colon:liver ratio data demonstrates Cyp1a1 induction in the colon at low doses of I-161 and colon-preferred activity at 24 hours after a single dose treatment. FIG. 4 depicts exemplary pharmacodynamic (PD) data in the liver and colon for AHR agonist compounds I-10 and I-161 at 4 hours. These data show that while Cyp1a1 induction in the colon is comparable with I-10 and I-161, I-161, the pro-drug form of I-10, has significantly less induction in the liver than the active form I-10.

Example 4: DSS Study Method

On study day-1, C57Bl/6 mice are weighed and randomized into treatment groups based on body weight. On study day 0, treatment groups are given 2.5% DSS in drinking water and treatment is initiated on the same day, with either vehicle or AHR agonist compound(s).

On study day 7, DSS drinking water is replaced with normal drinking water for the remainder of the study. Body weight is measured daily during the entire study.

On study day 10, animals are anesthetized with Isoflurane and bled to exsanguination followed by cervical dislocation. The entire colon is removed and measured for length, weight, and weight per length. Overall efficacy of test AR agonist compounds is based on body weight, colon length, and colon histopathology.

Histopathology data is assessed for appropriate parameters, as determined by a pathologist and the parameters for these DSS studies can include inflammation, erosion, gland loss, edema, hyperplasia, neutrophil count, mucosal thickening, lymphoid aggregate count and lymphoid aggregate size. The different parameter scores can be added for a summed score for the study histopathology.

Figure 5:
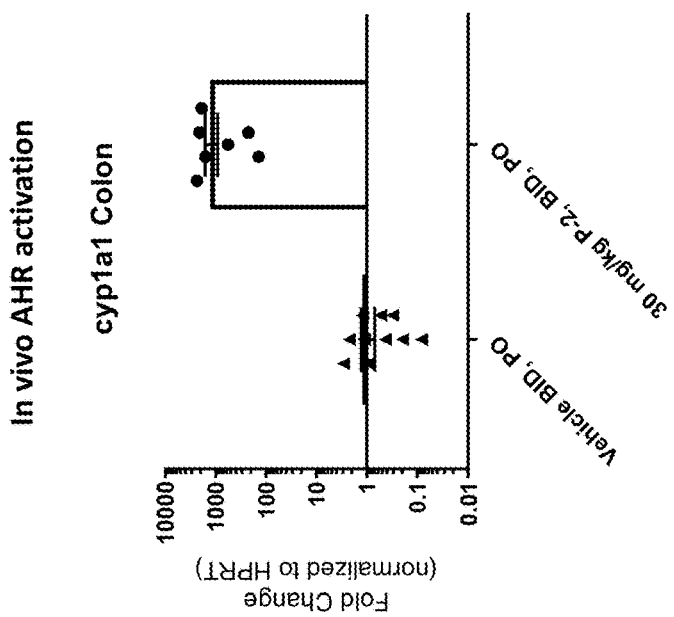
FIG. 5 shows that administration of AHR agonist compound P-2 results in increased colon length and improved content score in a DSS model of Inflammatory Bowel Disease (IBD). In vivo AHR activation by P-2 is also confirmed in this model by the expression of Cyp1a1 in the colon.
Figure 5:
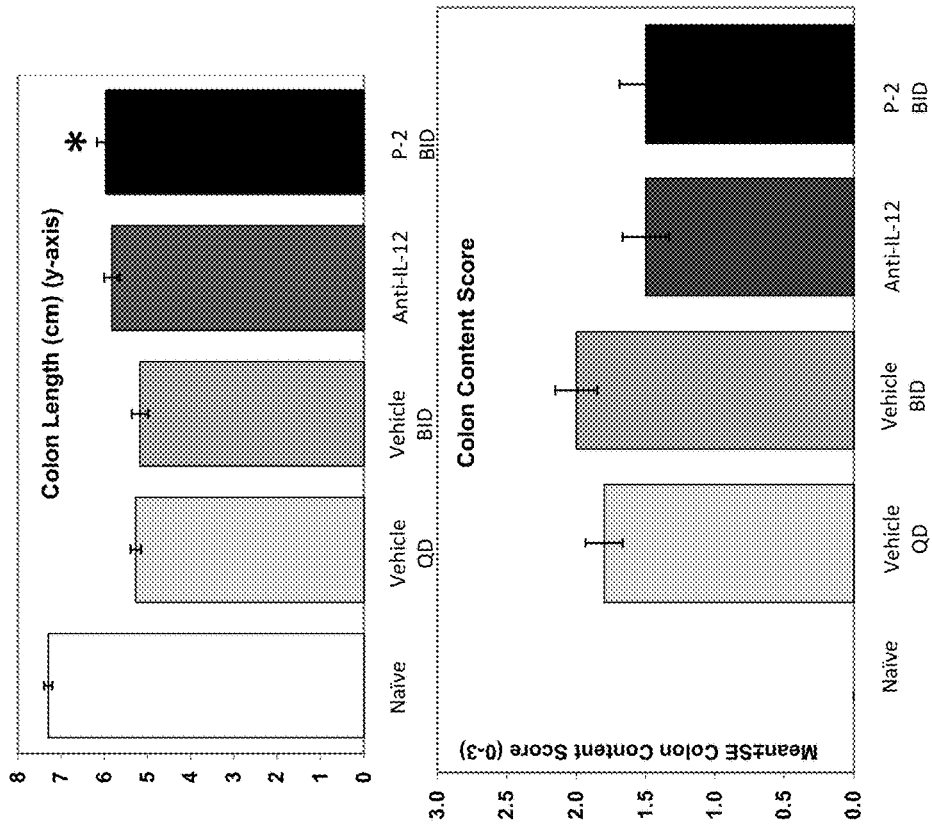
Figure 6:
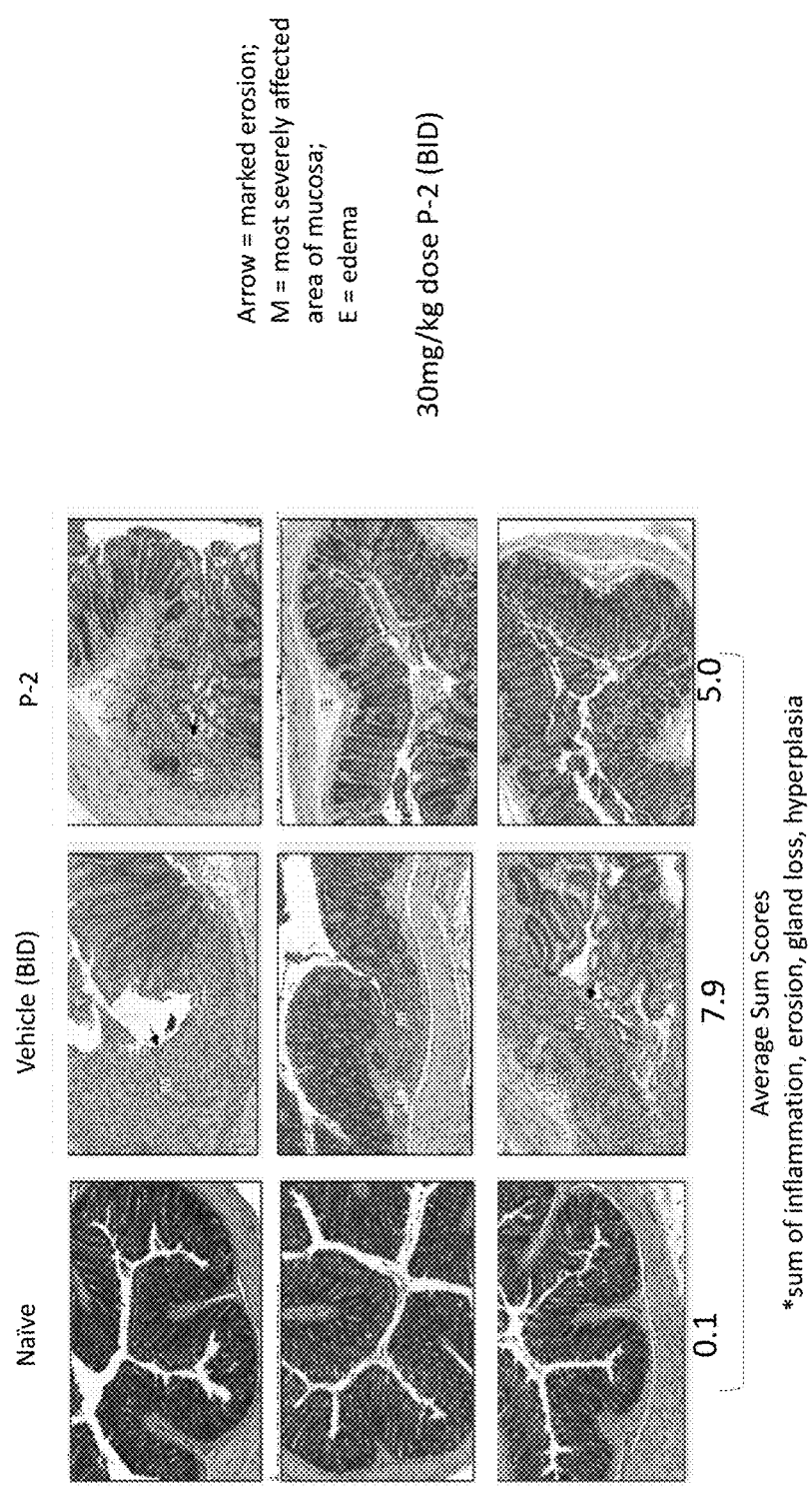
FIG. 6 shows that administration of AHR agonist compound P-2 results in minimal inflammation and mild erosion relative to a vehicle control in a DSS model of Inflammatory Bowel Disease (IBD).
Figure 7:
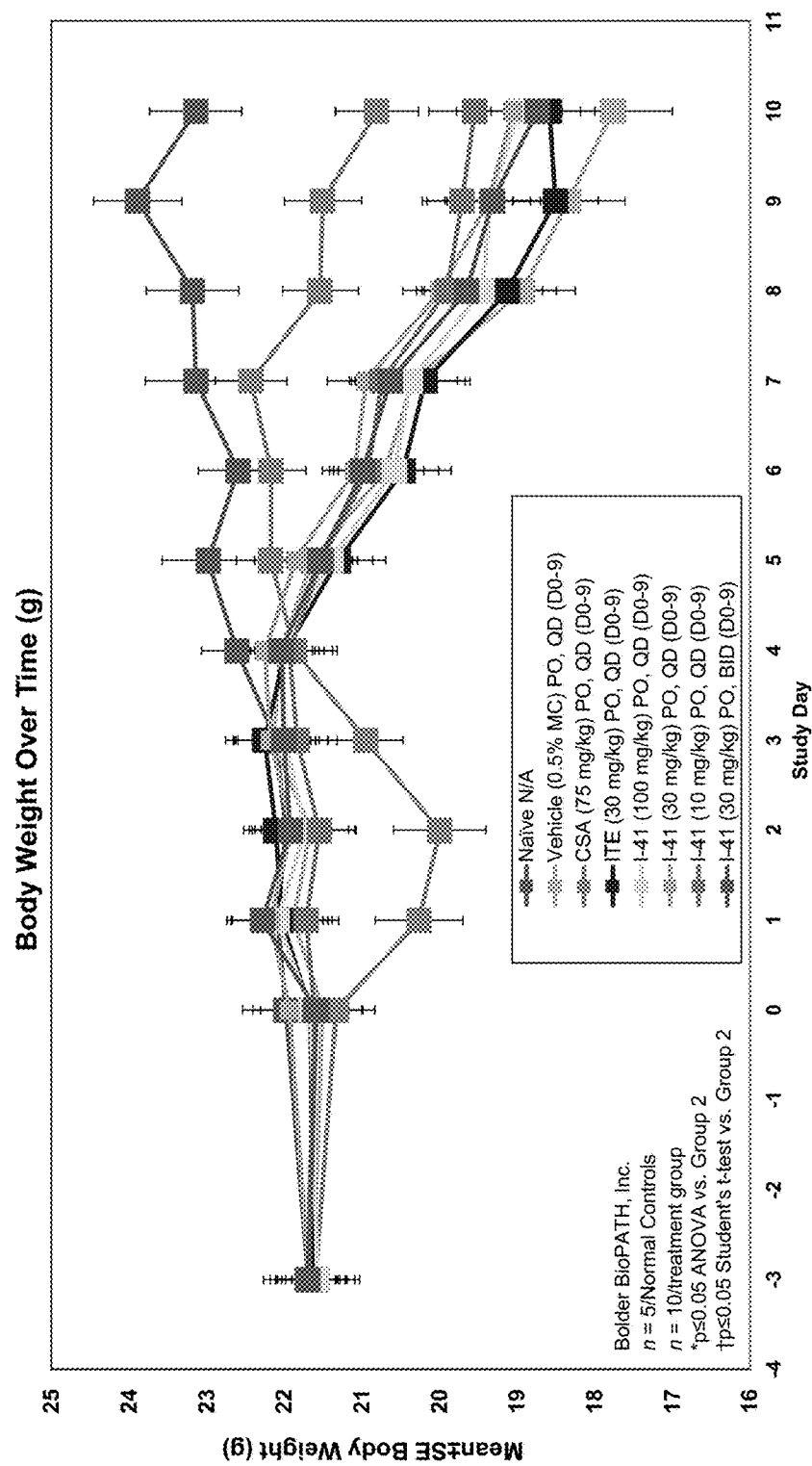
FIG. 7 shows that administration of AHR agonist compound I-41 results in similar body weight changes as ITE administration in a DSS model of IBD.
Figure 8:
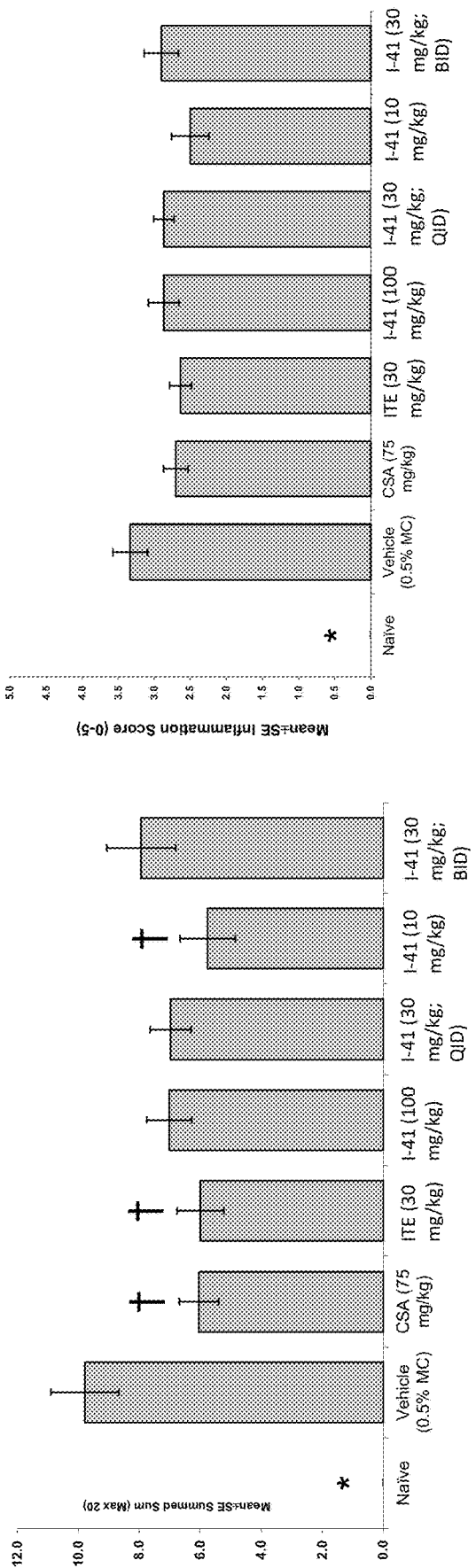
FIG. 8 shows that administration of AHR agonist compound I-41 results in comparable activity in histology evaluation of inflammation as ITE administration in a DSS model of IBD.
Figure 18A:
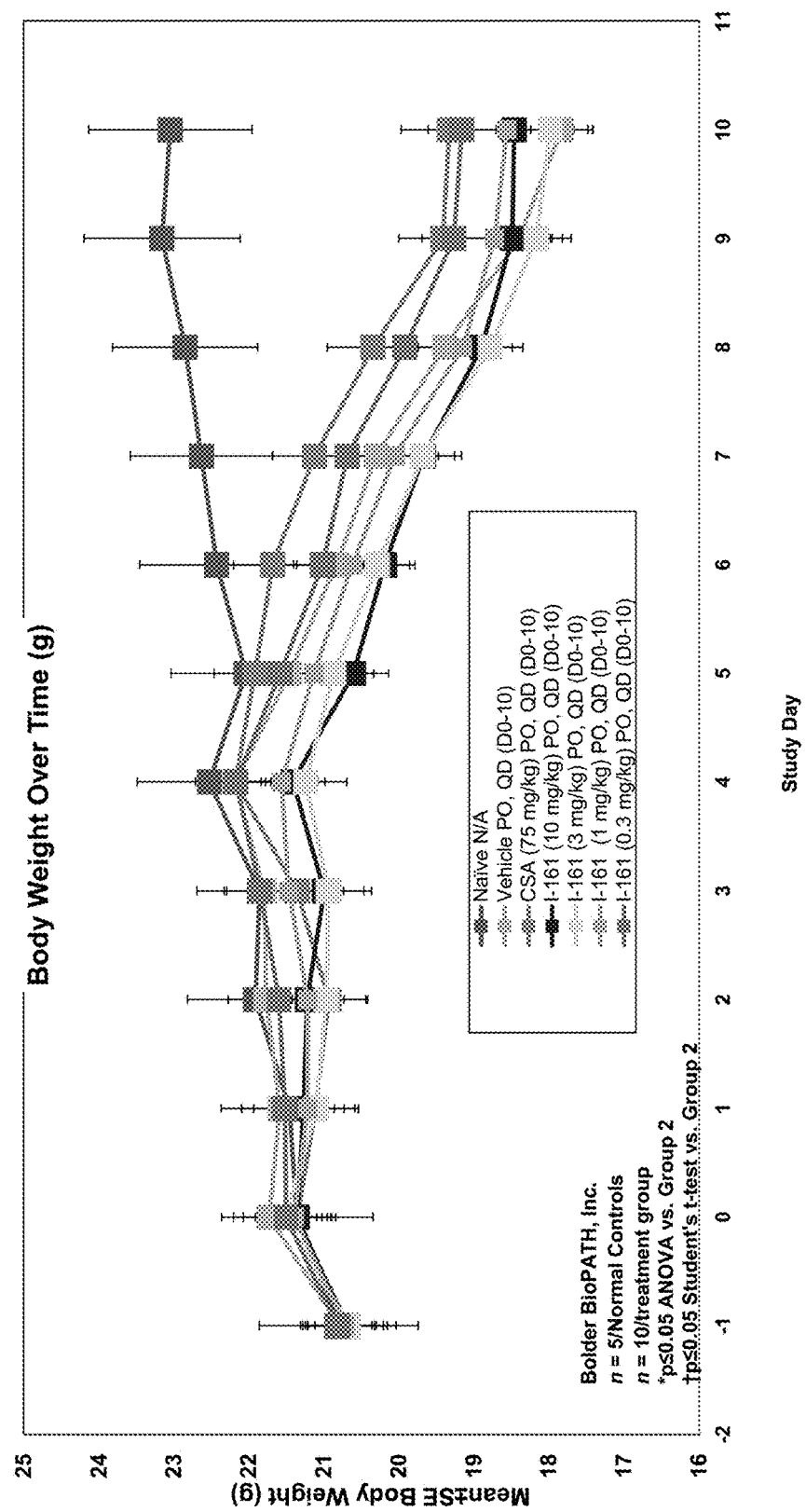
FIGS. 18A-18B show that AHR agonist compound I-161, a GI- or colon-preferred pro-drug of I-10, demonstrates efficacy in a DSS IBD mouse model.
Figure 18B:
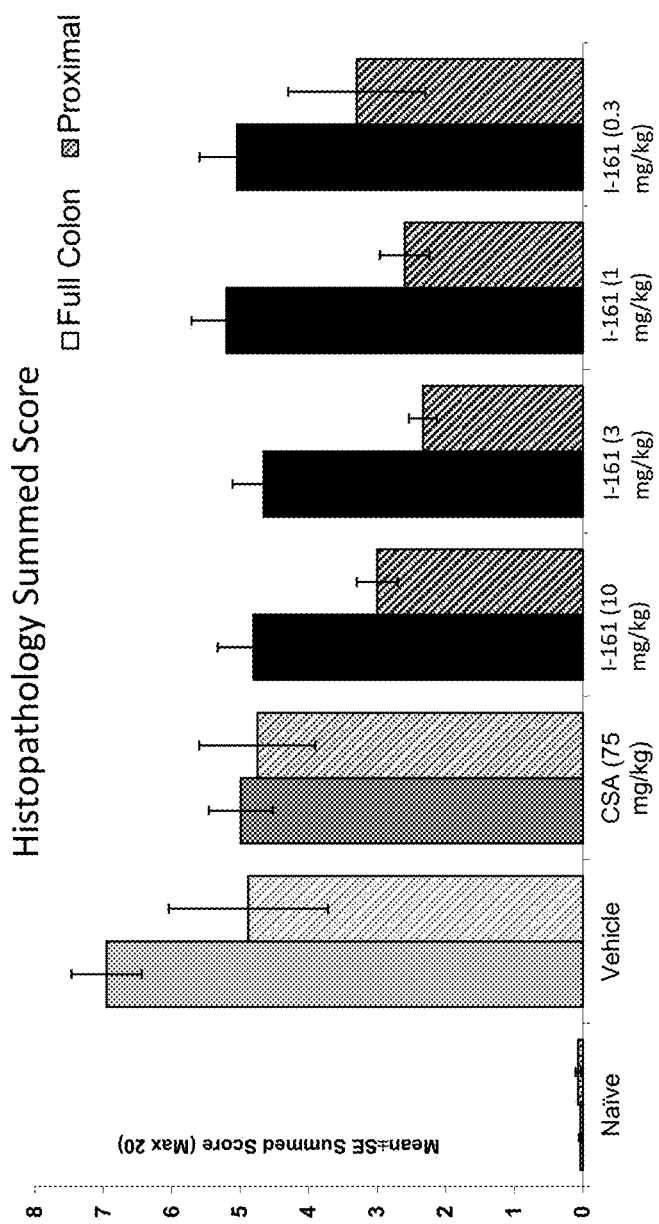
Figure 19:
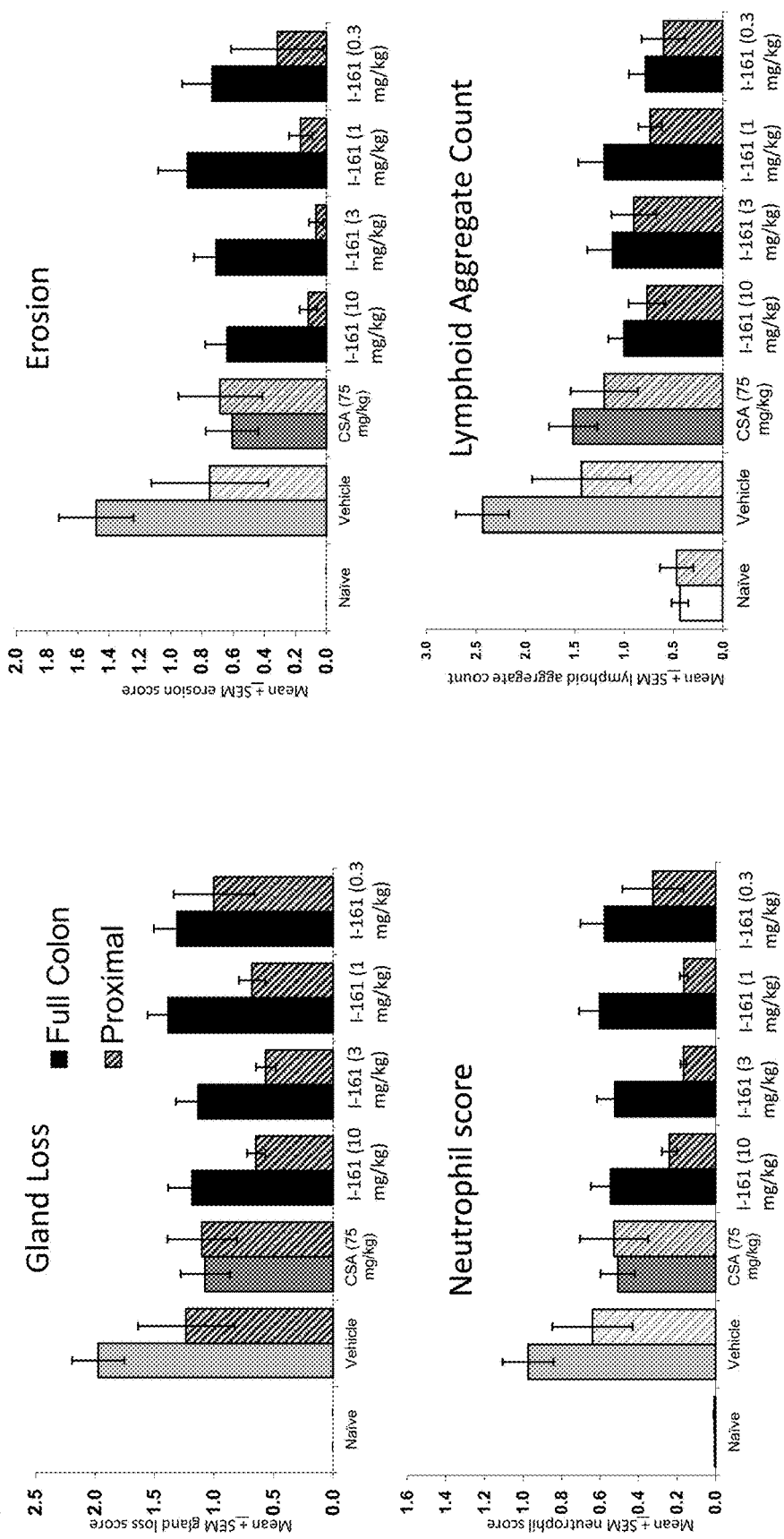
FIG. 19 shows that administration of AHR agonist compound I-161, a GI- or colon-preferred pro-drug of I-10, leads to reduced inflammation and erosion in a DSS IBD model. I-161 also led to reduction in inflammation, edema, hyperplasia, and lymphoid aggregate size.

As shown herein, FIG. 5 shows that administration of AHR agonist compound P-2 results in increased colon length and improved content score in a DSS model of Inflammatory Bowel Disease (IBD). In vivo AHR activation by P-2 is also confirmed in this model by the expression of Cyp1a1 in the colon. FIG. 6 shows that administration of AHR agonist compound P-2 results in minimal inflammation and mild erosion relative to a vehicle control in a DSS model of Inflammatory Bowel Disease (IBD). FIG. 7 shows that administration of AHR agonist compound I-41 results in similar body weight changes as ITE administration in a DSS model of IBD. FIG. 8 shows that administration of AHR agonist compound I-41 results in comparable activity in histology evaluation of inflammation as ITE administration in a DSS model of IBD. FIGS. 18A and 18B show that AHR agonist compound I-161, a GI- or colon-preferred pro-drug of I-10, demonstrates efficacy in a DSS IBD mouse model. I-161 results in similar body weight changes and recovery as administration of Cyclosporine A (CSA, positive control) in a DSS model of IBD (FIG. 18A). I-161 demonstrates activity at all doses that is comparable or better than CSA, and histopathology data shows activity comparable to CSA as well (FIG. 18B). FIG. 19 shows that administration of AHR agonist compound I-161, a GI- or colon-preferred pro-drug of I-10, leads to reduced inflammation and erosion in a DSS IBD model. I-161 also led to reduction in inflammation, edema, hyperplasia, and lymphoid aggregate size.

Example 5: Th17 Assay

On Day 1, naive CD62L+ human T-Cells were plated in a 96 well plate (25,000 cells in 200 uL media). Cells were activated with human CD3/CD28 tetramer (12.5 μL/1×10$^6$ cells) and differentiated with human Th17 cytokines (50 ng/mL IL-6, 20 ng/mL IL-1 beta, 10 ng/mL IL-23, 1 ng/mL TGF-beta, 12 μg/mL anti-human IFN-γ antibody and 10 μg/mL anti-human IL-4 antibody) for 10 days. Media containing cytokine cocktail and CD3/CD28 was refreshed every 2-3 days.

On Day 10, cell supernatant was collected and frozen for cytokine analysis. Cells were stimulated with 1× Cell Stimulation Cocktail (PMA and Ionomycin) for 5 hours. After 5 hours of stimulation, cells were stained for intracellular cytokines (human CD4, IL-17A, IL-22). Samples were run on BD LSR FORTESSA and analyzed in FLOWJO software.

Figure 16:
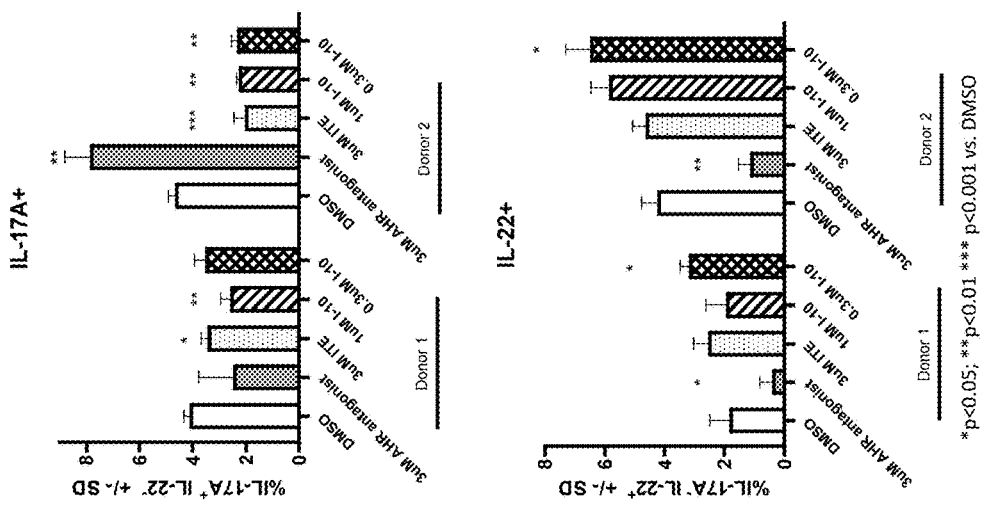
FIG. 16 shows AHR agonist compound I-10 modulates human Th17 cell differentiation in vitro. Addition of I-10 decreases IL-17A+ and increases IL-22+ human T-cells under Th17 polarizing conditions. Addition of an AHR antagonist has the opposite effect.
Figure 16:
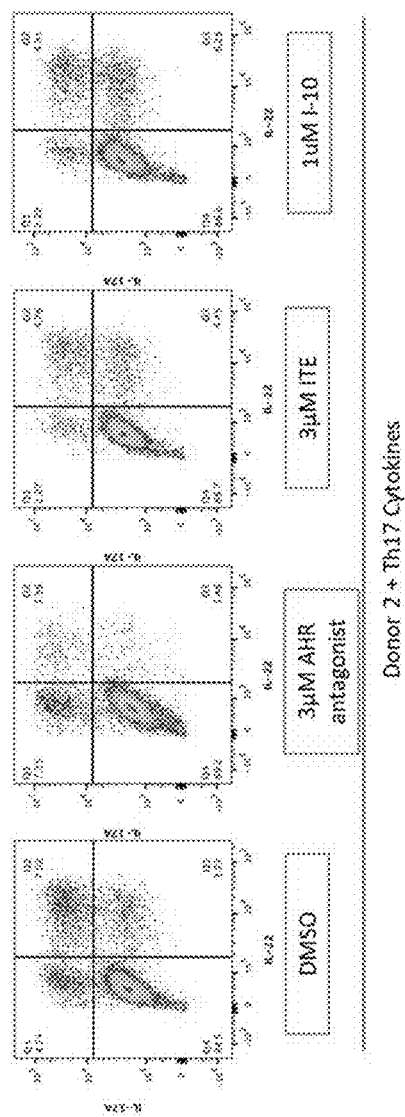

As shown herein, FIG. 16 shows AHR agonist compound I-10 modulates human Th17 cell differentiation in vitro. Addition of I-10 decreases IL-17A+ and increases IL-22+ human T-cells under Th17 polarizing conditions. Addition of an AHR antagonist has the opposite effect.

Example 6: Treg Assay

On day 0, nave T cells from cryopreserved human derived PBMCs were isolated. These cells were plated in 48 well plate at 500,000 cells/mL concentration with human CD3/CD28 activation tetramer (12.5 μL/1×10$^6$ cells) and differentiated into regulatory T cells (Tregs) with 1 ng/mL TGF-β and 5 ng/mL human recombinant IL-2 in the presence of DMSO or different concentrations of AHR agonist compounds.

On day 5, the Tregs were counted and washed. CD25- Effector T cells (Teffs) were isolated from the same human donor and were labeled with Cell Trace Violet. The Tregs and Teffs were cocultured for 4 days in 96 well plate at 1:2 or 1:1 ratio with human CD3/CD28 tetramer (12.5 μL/1×10$^6$ cells).

At the end of a 4 day co-culture, the cells were washed and stained with LiveDead stain. They were run on flow cytometer and analyzed using FLOWJO software.

Figure 14:
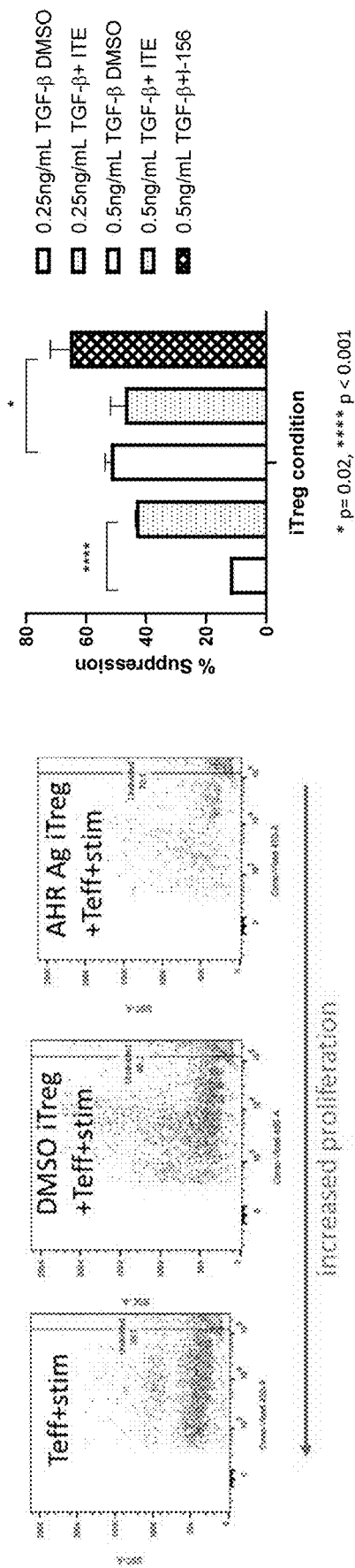
FIG. 14 shows that the presence of AHR agonist compounds during the induction of murine regulatory T cells (Tregs) increase suppressive functions of murine Tregs in vitro.
Figure 15:
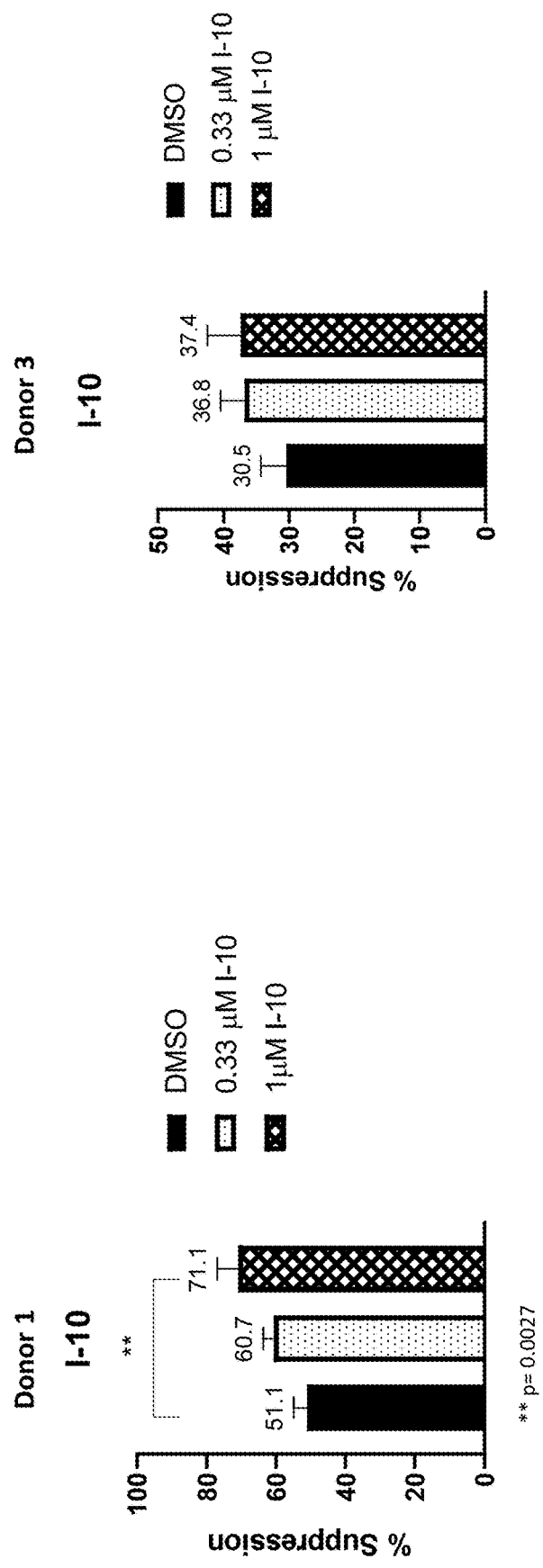
FIG. 15 shows that the presence of AHR agonist compound I-10 during the induction of human regulatory T cells (Tregs) increases suppressive functions of human Tregs in vitro.

As shown herein, FIG. 14 shows that the presence of AHR agonist compounds during the induction of murine regulatory T cells (Tregs) increase suppressive functions of murine Tregs in vitro. FIG. 15 shows that the presence of AHR agonist compound I-10 during the induction of human regulatory T cells (Tregs) increases suppressive functions of human Tregs in vitro.

Example 7: T Cell Transfer IBD Model

On study day 0, donor Balb/C mice are terminated, and spleens obtained for CD4$^+$CD45RB$^{high}$ cell isolation (Using a SCID IBD Cell Separation Protocol). After cells have been sorted and obtained, each recipient SCID animal receives an IP injection of, at a minimum, 4×10$^5$ cells (200 μl/mouse injections).

Also on study day 0, SCID mice are weighed and randomized into treatment groups based on body weight. On study day 14, AHR agonist compound treatments are initiated and dosed orally daily; the control group receiving anti-IL12 (0.5 mg/mouse) is dosed IP once a week.

On study day 49, animals are anesthetized with Isoflurane and bled to exsanguination followed by cervical dislocation. The entire colon is removed, measured, and weighed. Overall efficacy of AHR agonist compounds are based on a ratio of colon weight to length, and colon histopathology and colon cytokines (Th17 panel).

Figure 9:
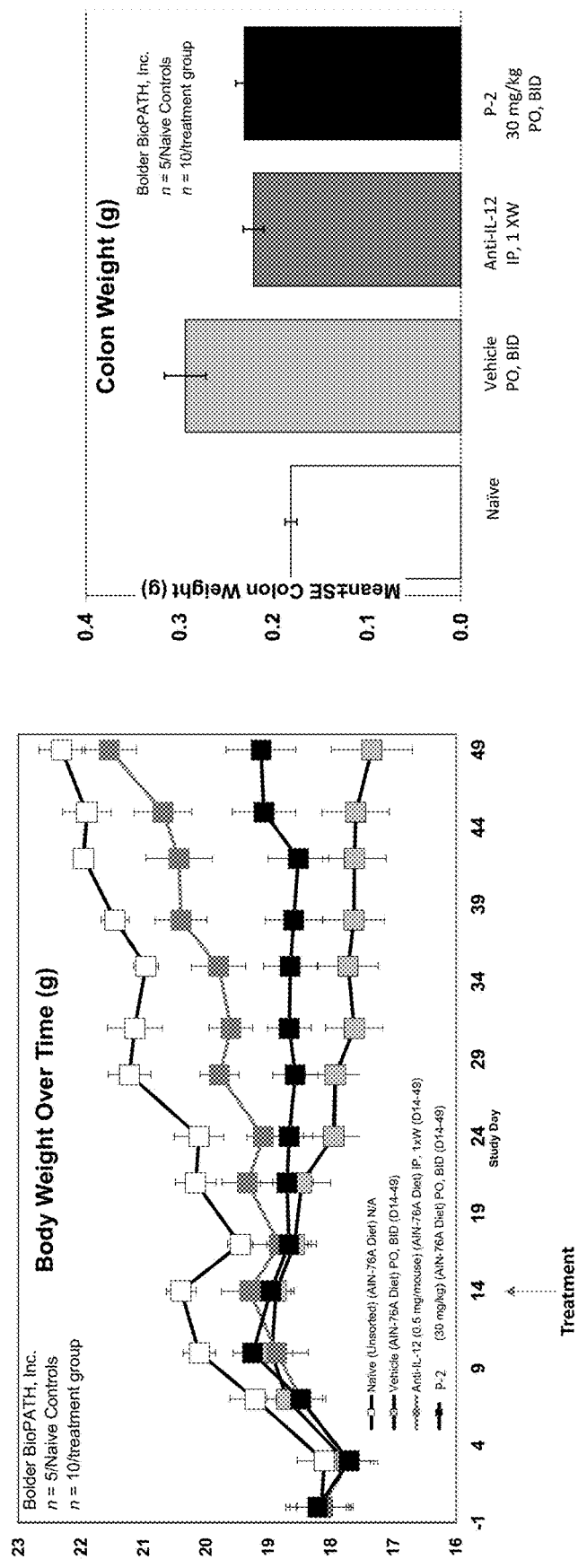
FIG. 9 shows that administration of AHR agonist compound P-2 leads to increased body weight and decreased colon weight in a T-cell transfer IBD model. P-2 led to a 54% reduction in colon weight and weight per length compared to vehicle in this model.
Figure 10:
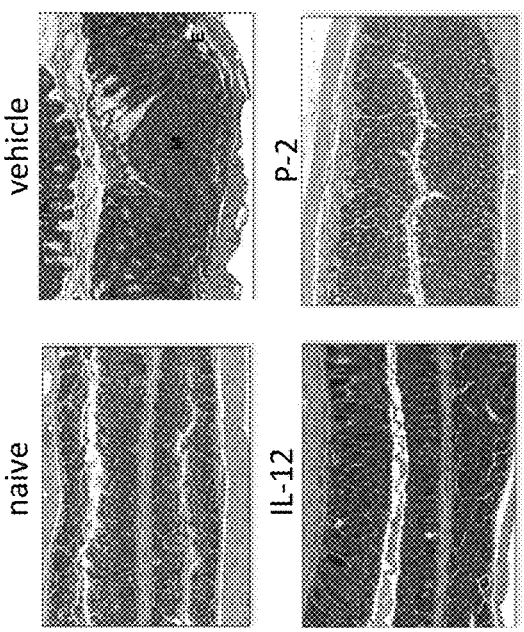
FIG. 10 shows that administration of AHR agonist compound P-2 leads to a significant reduction in inflammation in a T-cell transfer IBD model. In vivo AHR activation by P-2 is also confirmed in this model by the expression of Cyp1a1 in the colon.
Figure 10:
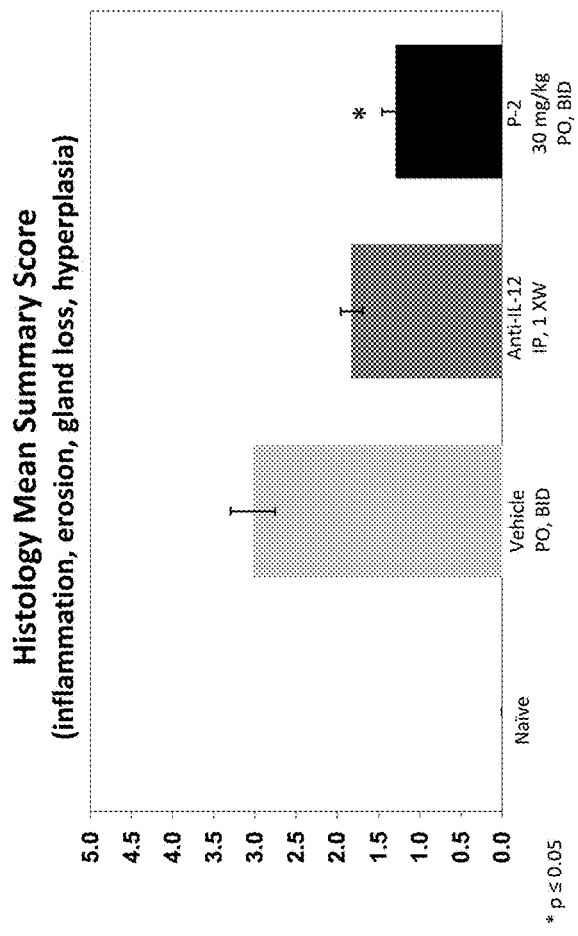
Figure 11:
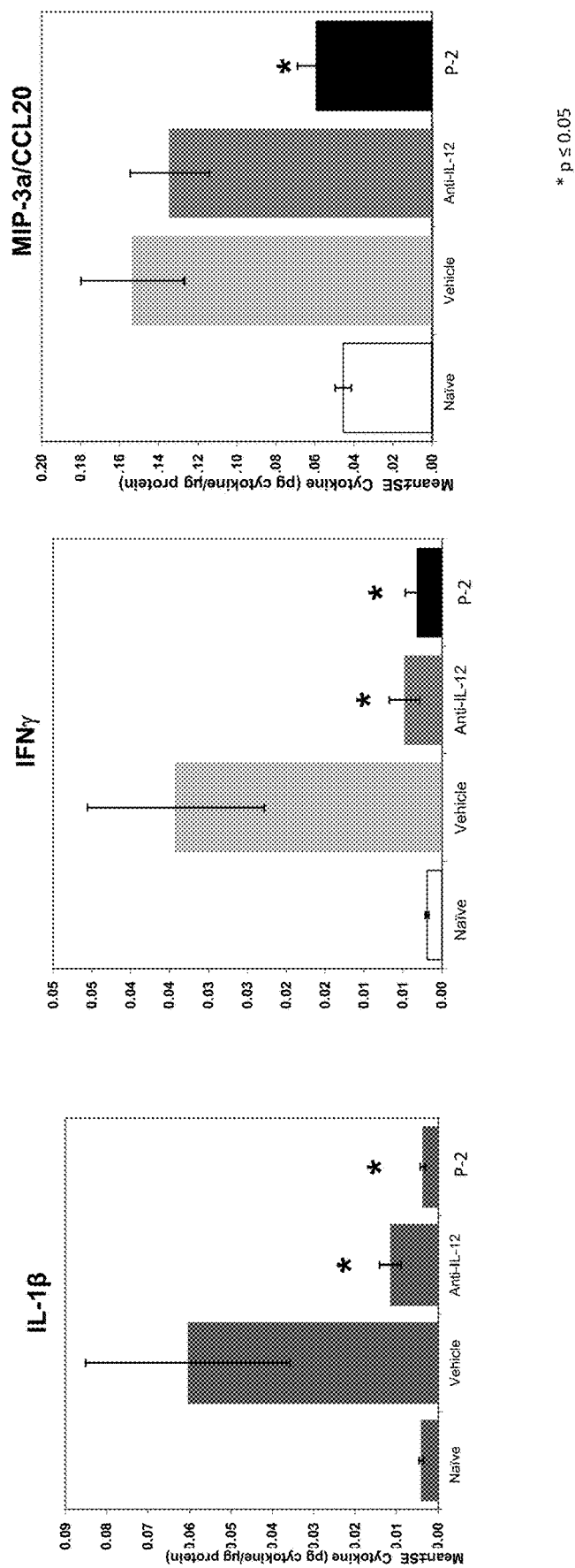
FIG. 11 shows cytokine activity after administration of AHR agonist compound P-2 in a T-cell transfer IBD model. A significant reduction in IFN-γIL-1β, and MIP-3α/CCL20 is observed.
Figure 12:
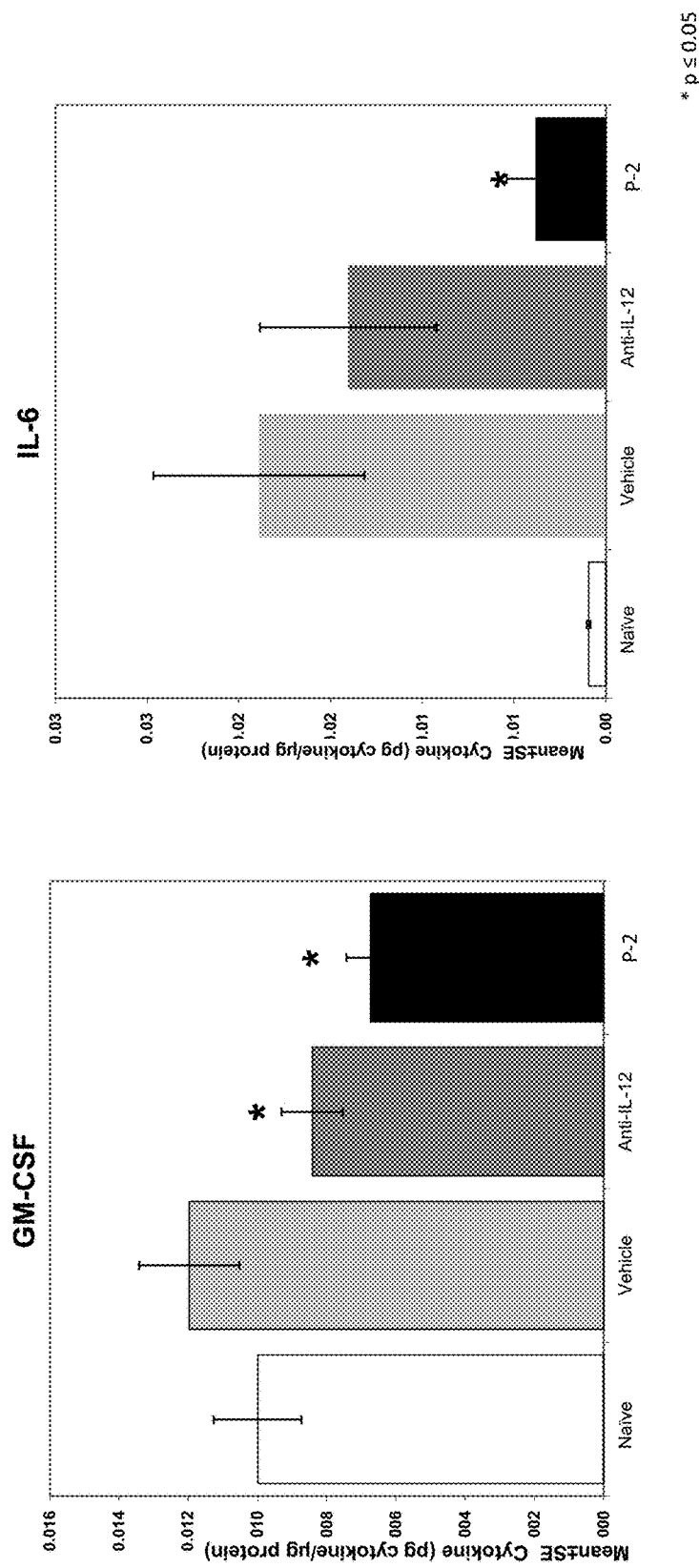
FIG. 12 shows cytokine activity after administration of AHR agonist compound P-2 in a T-cell transfer IBD model. A significant reduction in GM-CSF and IL-6 is observed.
Figure 13:
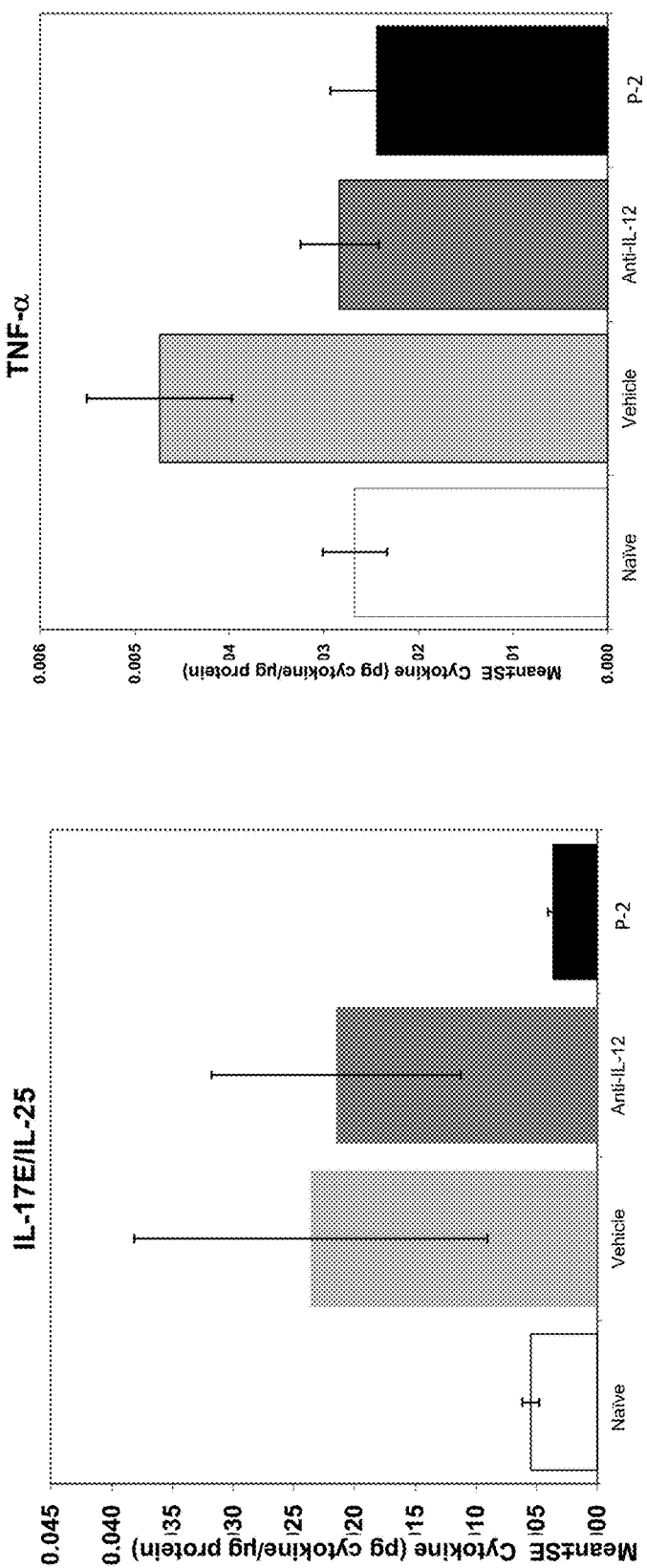
FIG. 13 shows cytokine activity after administration of AHR agonist compound P-2 in a T-cell transfer IBD model. A reduction in IL-17/IL-25 and TNF-α is observed.

As demonstrated herein, FIG. 9 shows that administration of AHR agonist compound P-2 leads to increased body weight and decreased colon weight in a T-cell transfer IBD model. P-2 led to a 54% reduction in colon weight and weight per length compared to vehicle in this model. FIG. 10 shows that administration of AHR agonist compound P-2 leads to a significant reduction in inflammation in a T-cell transfer IBD model. In vivo AHR activation by P-2 is also confirmed in this model by the expression of Cyp1a1 in the colon. FIG. 11 shows cytokine activity after administration of AHR agonist compound P-2 in a T-cell transfer IBD model. A significant reduction in IFN-γ, IL-1β, and MIP-3α/CCL20 is observed. FIG. 12 shows cytokine activity after administration of AHR agonist compound P-2 in a T-cell transfer IBD model. A significant reduction in GM-CSF and IL-6 is observed. FIG. 13 shows cytokine activity after administration of AHR agonist compound P-2 in a T-cell transfer IBD model. A reduction in IL-17/IL-25 and TNF-α is observed.

Example 8: IBD Ex Vivo Treat Methods

The studies described herein are to assess the effect of various AHR agonist compounds in human Crohn's and ulcerative colitis tissue cultures ex vivo. Following this culture, the resulting culture supernatant samples are collected for analysis of cytokine release. Briefly, Crohn's Disease or ulcerative colitis donor samples were obtained with full ethical consent from patients undergoing therapeutic resection for Crohn's disease or ulcerative colitis. A minimum of 18×5 mm$^2$ mucosal biopsies are taken using a scalpel. Three baseline biopsy samples are collected at time 0, and a minimum of 9 biopsies are incubated in 12 well culture plates. Tissues are placed apical (mucosal) side facing upwards on a Netwell filter. The biopsies are then cultured in either control media or media fortified with the appropriate AHR agonist compound in an incubator at 37° C. and high O2 atmospheric conditions (95% O2/5% CO2). To minimize variation, the biopsies are cultured in the presence of the inflammatory stimulant Staphylococcal Enterotoxin B (SEB) to normalize cytokine levels. The positive control BIRB796 (Selleck Chemicals catalogue No: S1574) is purchased as a powder. A 1 mM stock solution is prepared in DMSO and used at 1 μM. At approximately 18 hours post-culture start, media samples are collected, protease inhibitor is added and samples are stored at −80° C. Supernatant is collected at the 18-hour timepoint and divided into aliquots for cytokine analysis: analysis of cytokines, such as TNFα, IFNγ, IL1β, IL17α, IL-22, and IL10) are performed in duplicate after completion of each set of 3 donors.

Figure 17:
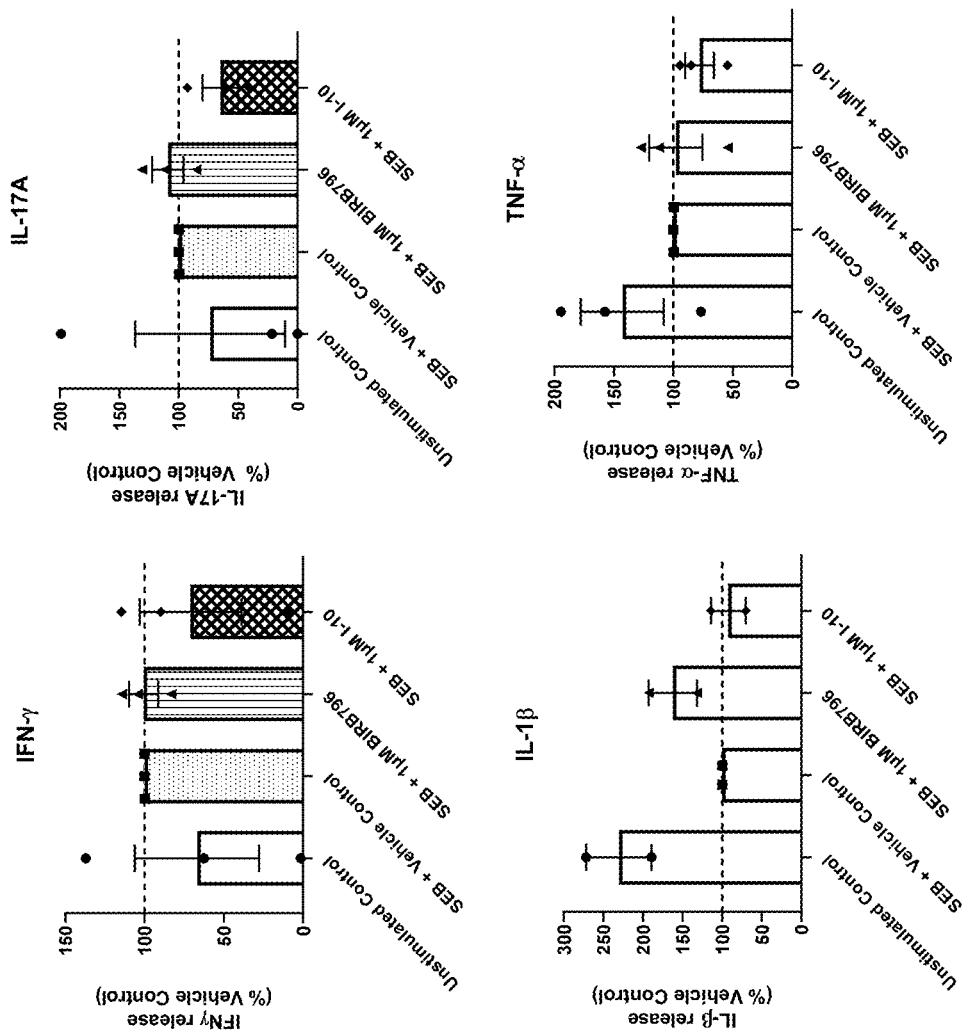
FIG. 17 shows AHR agonist compound I-10 led to decreases in IFN-γIL-17A, IL-1β, and TNF-α in human IBD samples treated ex vivo.

As demonstrated herein, FIG. 17 shows AHR agonist compound I-10 led to decreases in IFN-γIL-17A, IL-1β, and TNF-α in human IBD samples treated ex vivo.

While we have described a number of embodiments of this invention, it is apparent that our basic examples may be altered to provide other embodiments that utilize the compounds and methods of this invention. Therefore, it will be appreciated that the scope of this invention is to be defined

What is claimed is:
1. A compound of Formula (I):

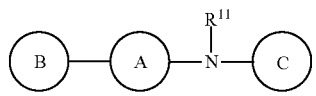

(I)

or a pharmaceutically acceptable salt thereof, wherein:
Ring A is

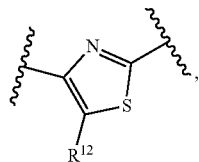

wherein $R^{12}$ is halogen, —CN, —NO$_2$, $R^W$, —C(O)—$R^W$, —C(=N$R^W$)—$R^W$, —N($R^W$)—C(O)—$R^W$, —N($R^W$)—C(=N$R^W$)—$R^W$, —OC(O)—$R^W$, —OC(=N$R^W$)—$R^W$, —S(O)$_2$—$R^W$, —N($R^W$)—S(O)$_2$—$R^W$, —OS(O)$_2$—$R^W$, —S(O)—$R^W$, —N($R^W$)—S(O)—$R^W$, or —OS(O)—$R^W$;
Ring B is

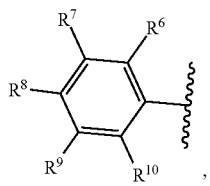

wherein each of $R^6$, $R^7$, $R^8$, and $R^{10}$ is independently halogen, —CN, —NO$_2$, $R^W$, —C(O)—$R^W$, —C(=N$R^W$)—$R^W$, —N($R^W$)—C(O)—$R^W$, —N($R^W$)—C(=N$R^W$)—$R^W$, —OC(O)—$R^W$, —OC(=N$R^W$)—$R^W$, —S(O)$_2$—$R^W$, —N($R^W$)—S(O)$_2$—$R^W$, —OS(O)$_2$—$R^W$, —S(O)—$R^W$, —N($R^W$)—S(O)—$R^W$, or —OS(O)—$R^W$; $R^9$ is —N(R)$_2$,

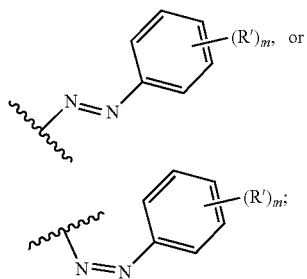

each R' is independently halogen, —CN, —NO$_2$, R, —OR, —SR, —N(R)$_2$, —C(O)OR, or —C(O)N(R)$_2$; and m is 0, 1, 2, 3, 4, or 5;

Ring C is

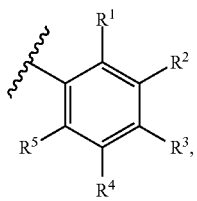

wherein each of $R^1$, $R^3$, $R^4$, and $R^5$ is independently halogen, —CN, —NO$_2$, $R^W$, —C(O)—$R^W$, —C(=N$R^W$)—$R^W$, —N($R^W$)—C(O)—$R^W$, —N($R^W$)—C(=N$R^W$)—$R^W$, —OC(O)—$R^W$, —OC(=N$R^W$)—$R^W$, —N($R^W$)—S(O)$_2$—$R^W$, —OS(O)$_2$—$R^W$, —S(O)$_2$—$R^W$, —S(O)—$R^W$, —N($R^W$)—S(O)—$R^W$, or —OS(O)—$R^W$; and $R^2$ is C$_{1-6}$ aliphatic substituted 1-6 times by halogen; provided that when $R^2$ is CF$_3$, then $R^9$ is not —N(CH$_3$)$_2$ or —N(CH$_2$CH$_3$)$_2$;

$R^{11}$ is —R, —C(O)—$R^W$, —C(=N$R^W$)—$R^W$, —S(O)$_2$—$R^W$, or —S(O)—$R^W$;

$R^W$ is —R, —N(R)$_2$, —NR—OR, —N(R)—N(R)$_2$, —N(OR)—N(R)$_2$, —N(R)—N(OR)R, —OR, —O—N(R)$_2$, or —SR; and R is hydrogen, or optionally substituted C$_{1-6}$ aliphatic, provided that the compound is not

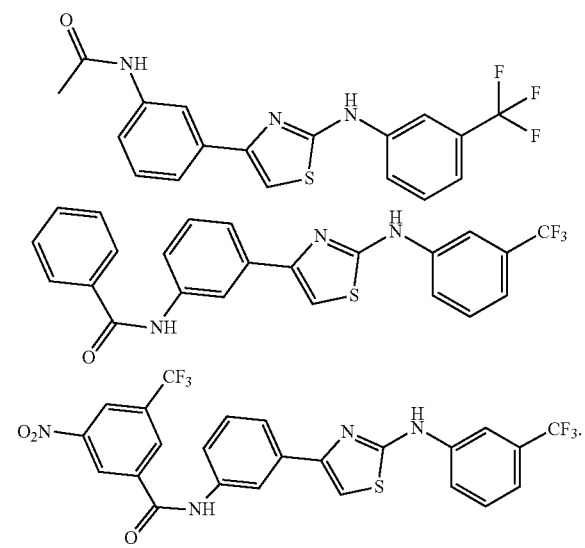

2. The compound of claim 1, or a pharmaceutically acceptable salt thereof, wherein the compound is a compound of Formula (III), (IV), (V), or (VIII):

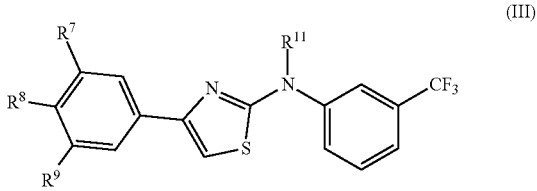

(III)

-continued (IV)

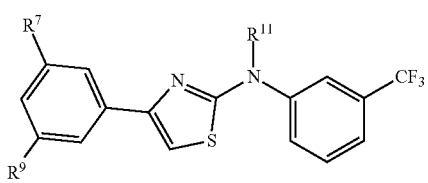

(V)

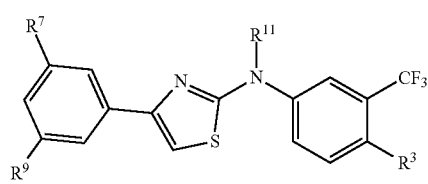

(VIII)

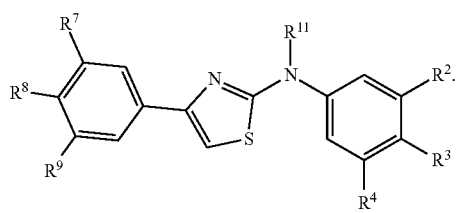

3. The compound of claim 1, or a pharmaceutically acceptable salt thereof, wherein the compound is a compound of Formula (VIII):

(VIII)

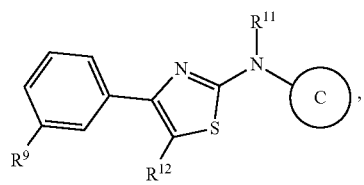

wherein $R^{11}$ is —C(O)—R, —C(O)—N(R)$_2$, —C(O)—NR—OR, —C(O)—N(R)—N(R)$_2$, —C(O)—N(OR)—N(R)$_2$, —C(O)—N(R)—N(OR)R, —C(O)OR, or —C(O)O—N(R)$_2$, except that $R^{11}$ is not —C(O)H.

4. The compound of claim 1, or a pharmaceutically acceptable salt thereof, wherein the compound is a compound of Formula (X):

(X)

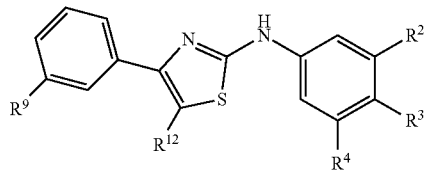

wherein:
$R^9$ is

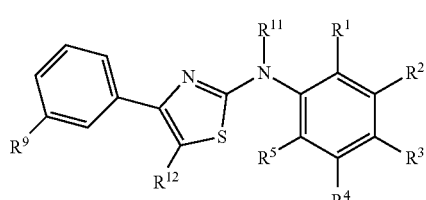

or

5. The compound of claim 4, or a pharmaceutically acceptable salt thereof, wherein the compound is a compound selected from Formulas (X-1) to (X-10):

(X-1)

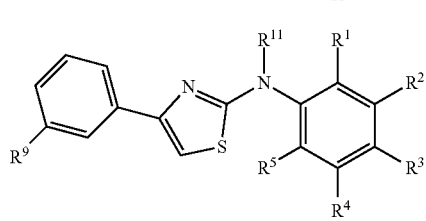

(X-2)

(X-3)

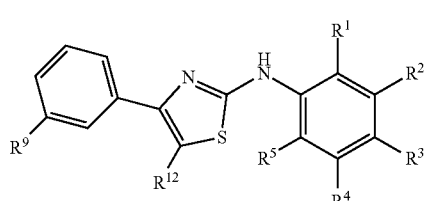

(X-4)

(X-5)

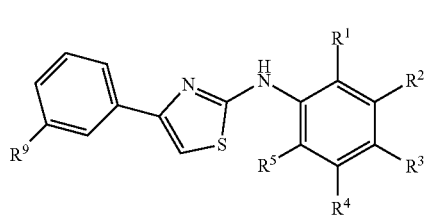

(X-6)

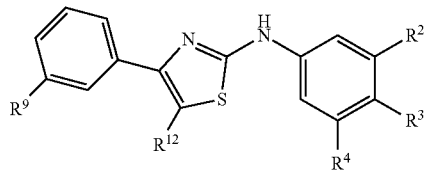

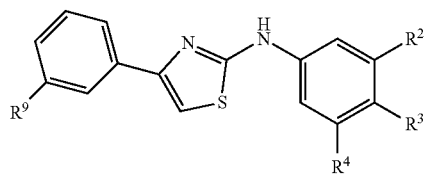
(X-7)
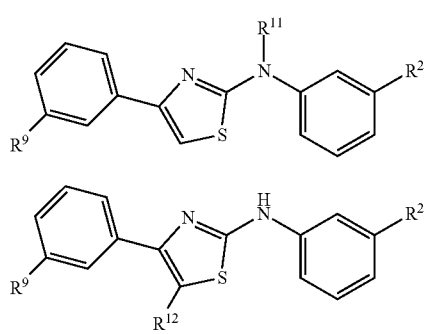
(X-8)
(X-9)
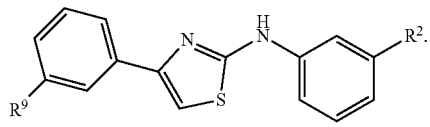
(X-10)
6. The compound of claim 1, or a pharmaceutically acceptable salt thereof, wherein $R^{11}$ is H,
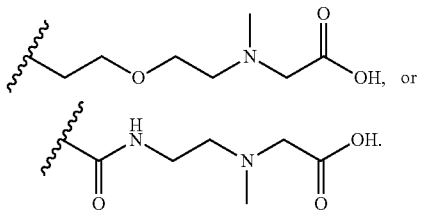
7. A compound selected from:
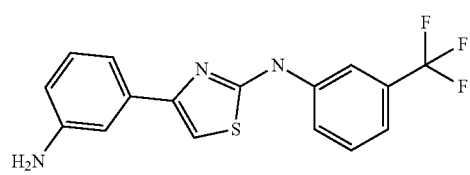
I-10
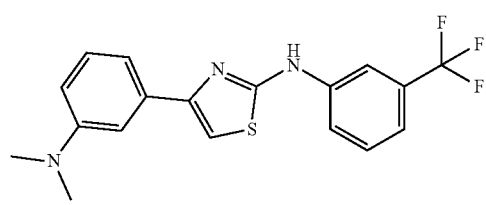
I-30
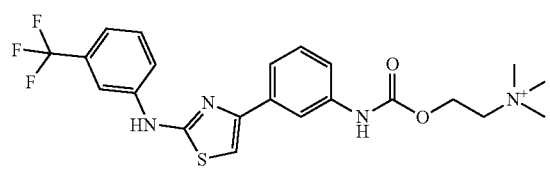
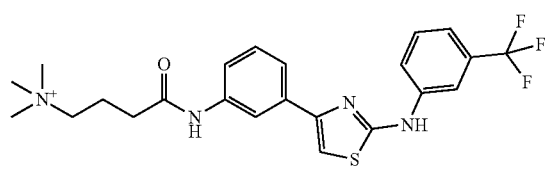
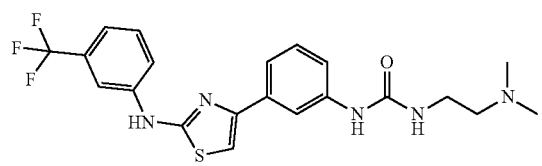
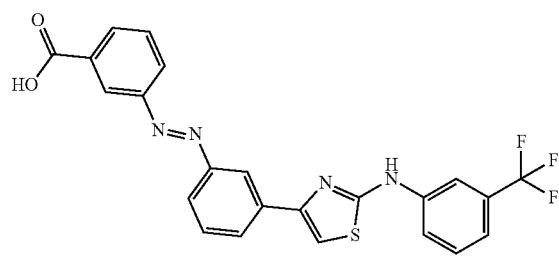
I-161
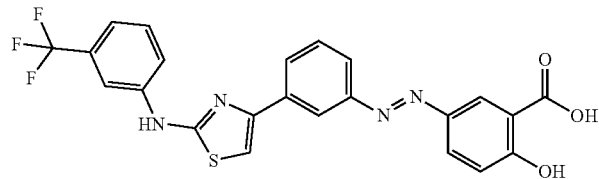
I-162
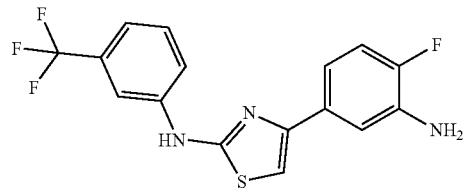
I-163

-continued
I-165
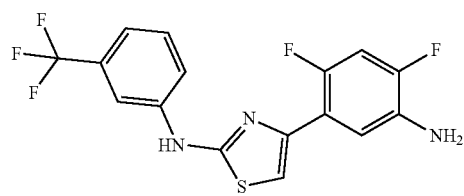
I-166
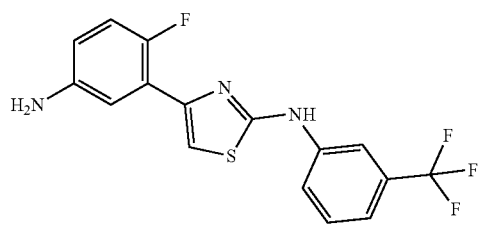
I-173
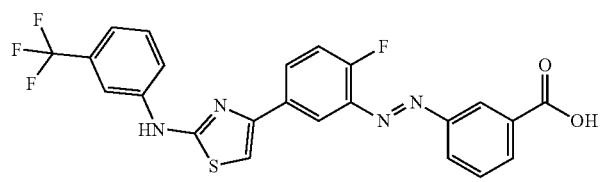
I-174
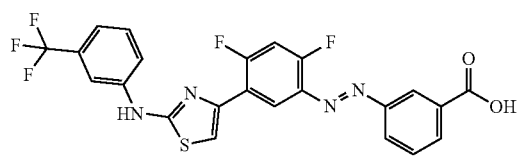
I-176
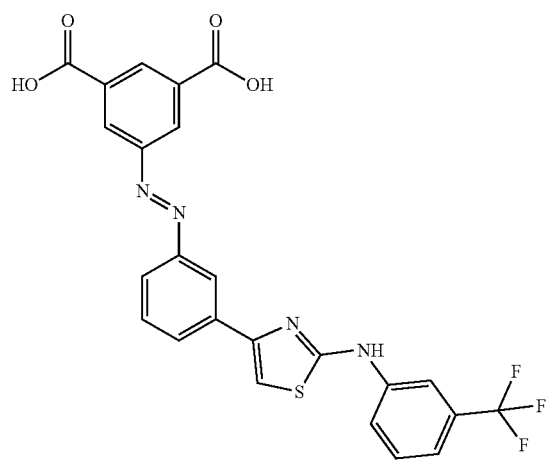
I-178
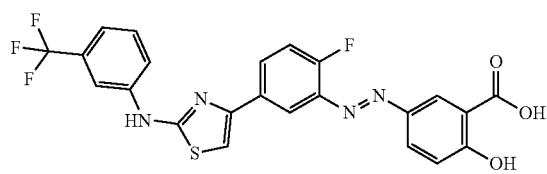
I-179
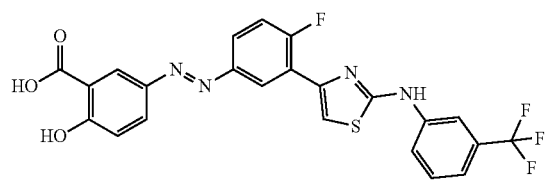
I-180
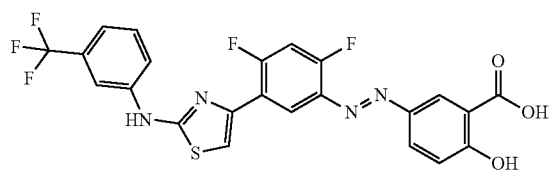
I-184
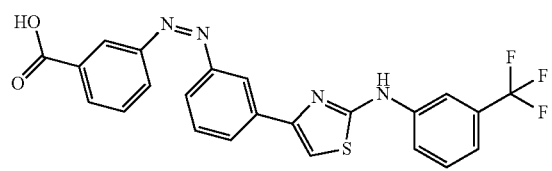
I-185
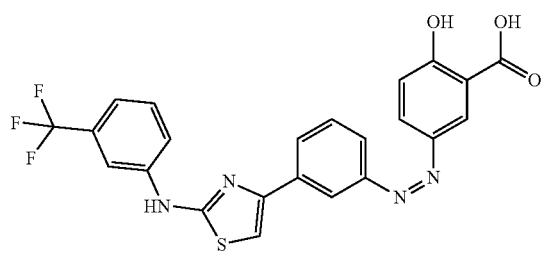

I-188
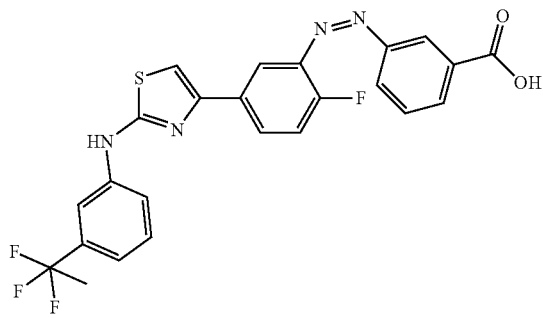

I-190
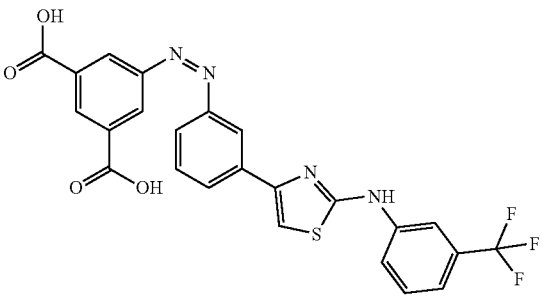

I-191
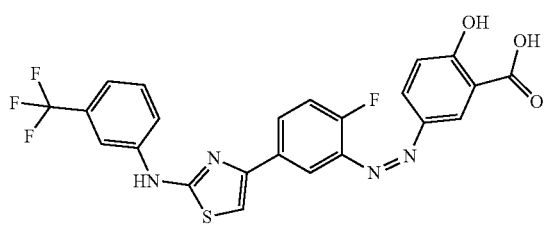

I-192
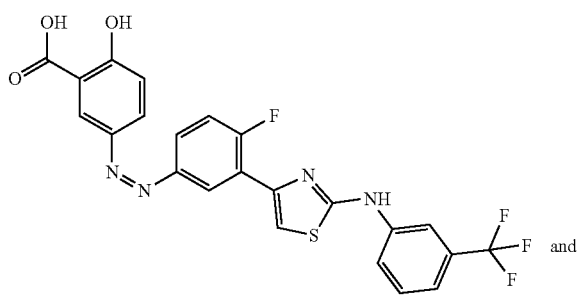

I-193
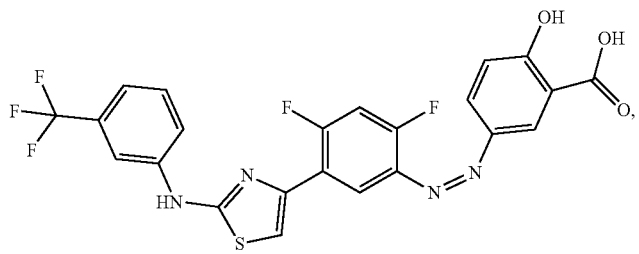

or a pharmaceutically acceptable salt thereof.

8. A pharmaceutical composition comprising the compound of claim 1, or a pharmaceutically acceptable salt thereof, and a pharmaceutically acceptable carrier, adjuvant, or vehicle.

9. The compound of claim 1, or a pharmaceutically acceptable salt thereof, wherein Ring B is

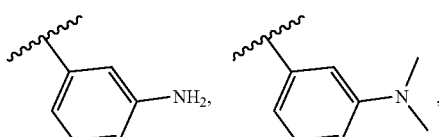

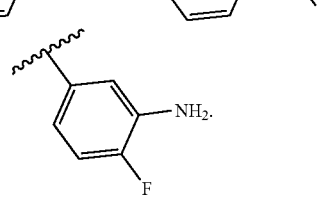

10. The compound of claim 1, or a pharmaceutically acceptable salt thereof, wherein Ring C is

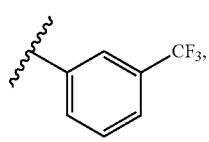 [SMILES: *c1cccc(C(F)(F)F)c1]

11. The compound of claim 1, or a pharmaceutically acceptable salt thereof, wherein Ring B is

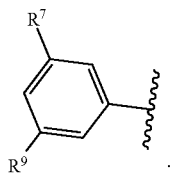

12. The compound of claim 1, or a pharmaceutically acceptable salt thereof, wherein Ring C is

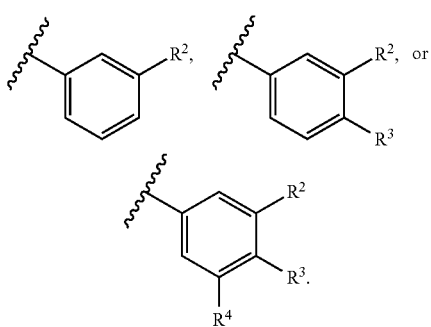

13. The compound of claim 1, or a pharmaceutically acceptable salt thereof, wherein $R^{11}$ is hydrogen.

14. The compound of claim 1, or a pharmaceutically acceptable salt thereof, wherein $R^{12}$ is hydrogen.

15. The compound of claim 1, or a pharmaceutically acceptable salt thereof, wherein the compound is a compound selected from Formulae (X-1) to (X-10):

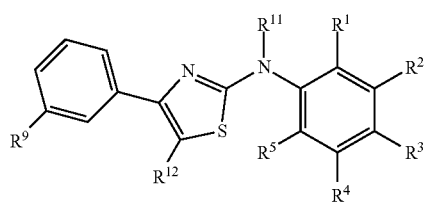

16. The compound of claim 1, or a pharmaceutically acceptable salt thereof, wherein $R^9$ is —$N(R)_2$.

17. The compound of claim 1, or a pharmaceutically acceptable salt thereof, wherein each of $R^1$, $R^3$, $R^4$, and $R^5$ is independently selected from hydrogen, —Cl, —Br, —CN, —$NO_2$, —$NH_2$, —$N(CH_3)_2$, —OH, —$O(CH_2)_2N(CH_3)_2$, —$OCH_3$, —$OCF_3$, —$CF_3$, —$CH_3$, —$C(O)NH_2$, —$C(O)N(CH_3)_2$, —COOH, —C(=NH)$NH_2$, and —$S(O)_2$—$N(CH_3)_2$.

18. The compound of claim 1, or a pharmaceutically acceptable salt thereof, wherein each of $R^7$ and $R^8$ is independently selected from hydrogen, —Cl, —Br, —CN, —$NO_2$, —$NH_2$, —$N(CH_3)_2$, —OH, —$O(CH_2)_2N(CH_3)_2$, —$OCH_3$, —$OCF_3$, —$CF_3$, —$CH_3$, —$C(O)NH_2$, —$C(O)N(CH_3)_2$, —COOH, —C(=NH)$NH_2$, and —$S(O)_2$—$N(CH_3)_2$.

19. The compound of claim 1, or a pharmaceutically acceptable salt thereof, wherein each R is independently hydrogen, unsubstituted —$C_{1-6}$ aliphatic, or —$C_{1-6}$ aliphatic substituted 1-6 times by halogen.

20. The compound of claim 1, or a pharmaceutically acceptable salt thereof, wherein each R is independently hydrogen or unsubstituted —$C_{1-6}$ aliphatic.

* * * * *